(12) United States Patent
Blaschuk et al.

(10) Patent No.: US 7,476,509 B2
(45) Date of Patent: Jan. 13, 2009

(54) COMPOUNDS AND METHODS FOR MODULATING FUNCTIONS OF NONCLASSICAL CADHERINS

(75) Inventors: Orest W Blaschuk, Westmount (CA); Stephanie D Michaud, Hull (CA)

(73) Assignee: Adherex Technologies Inc., Ottawa (CA)

( * ) Notice: Subject to any disclaimer, the term of this patent is extended or adjusted under 35 U.S.C. 154(b) by 124 days.

(21) Appl. No.: 10/714,564

(22) Filed: Nov. 14, 2003

(65) Prior Publication Data

US 2004/0175361 A1    Sep. 9, 2004

Related U.S. Application Data

(60) Provisional application No. 60/426,689, filed on Nov. 14, 2002, provisional application No. 60/426,551, filed on Nov. 14, 2002.

(51) Int. Cl.
*A61K 38/04* (2006.01)
*G01N 33/53* (2006.01)

(52) U.S. Cl. .................. 435/7.1; 530/327; 530/326; 530/329

(58) Field of Classification Search .................. None
See application file for complete search history.

(56) References Cited

U.S. PATENT DOCUMENTS

| | | | |
|---|---|---|---|
| 5,455,228 A * | 10/1995 | Coller et al. | 514/17 |
| 5,585,351 A | 12/1996 | Ranscht | |
| 5,597,725 A | 1/1997 | Suzuki | |
| 5,610,281 A | 3/1997 | Brenner et al. | |
| 5,639,634 A | 6/1997 | Suzuki | |
| 5,643,781 A | 7/1997 | Suzuki | |
| 5,646,250 A | 7/1997 | Suzuki | |
| 5,663,300 A | 9/1997 | Suzuki | |
| 5,708,143 A | 1/1998 | Suzuki | |
| 5,811,514 A | 9/1998 | Bard et al. | |
| 5,869,683 A | 2/1999 | Jonishi et al. | |
| 5,895,748 A | 4/1999 | Johnson et al. | |
| 5,916,771 A | 6/1999 | Hori et al. | |
| 5,997,866 A | 12/1999 | Johnson et al. | |
| 6,031,072 A | 2/2000 | Blaschuk et al. | |
| 6,060,595 A | 5/2000 | Scaglioni et al. | |
| 6,083,713 A | 7/2000 | Manly et al. | |
| 6,110,747 A | 8/2000 | Blaschuk et al. | |
| 6,169,071 B1 | 1/2001 | Blaschuk et al. | |
| 6,203,788 B1 | 3/2001 | Blaschuk et al. | |
| 6,207,639 B1 | 3/2001 | Blaschuk et al. | |
| 6,248,864 B1 | 6/2001 | Blaschuk et al. | |
| 6,277,824 B1 | 8/2001 | Doherty et al. | |
| 6,303,576 B1 | 10/2001 | Blaschuk et al. | |
| 6,310,177 B1 | 10/2001 | Blaschuk et al. | |
| 6,326,352 B1 | 12/2001 | Blaschuk et al. | |
| 6,333,307 B1 | 12/2001 | Blaschuk et al. | |
| 6,346,512 B1 | 2/2002 | Blaschuk et al. | |
| 6,358,920 B1 | 3/2002 | Blaschuk et al. | |
| 6,391,855 B1 | 5/2002 | Blaschuk et al. | |
| 6,417,325 B1 | 7/2002 | Blaschuk et al. | |
| 6,433,149 B1 | 8/2002 | Blaschuk et al. | |
| 6,465,427 B1 | 10/2002 | Blaschuk et al. | |
| 6,472,367 B1 | 10/2002 | Blaschuk et al. | |
| 6,472,368 B1 | 10/2002 | Doherty et al. | |
| 6,562,786 B1 | 5/2003 | Blaschuk et al. | |
| 6,600,013 B1 * | 7/2003 | Ruelle | 530/300 |
| 6,713,450 B2 * | 3/2004 | Frangione et al. | 514/12 |
| 6,936,587 B1 * | 8/2005 | Mazar et al. | 514/16 |

FOREIGN PATENT DOCUMENTS

| | | |
|---|---|---|
| EP | 1074618 | 2/2001 |
| GB | 2 282 379 A | 4/1995 |
| WO | WO 91/04745 | 4/1991 |
| WO | WO 94/11401 | 5/1994 |
| WO | WO 94/21809 * | 9/1994 |
| WO | WO 96/27387 | 9/1996 |
| WO | WO 97/10258 | 3/1997 |
| WO | WO 97/38011 | 10/1997 |
| WO | WO 98/02452 | 1/1998 |
| WO | WO 98/25946 | 6/1998 |
| WO | WO 00/02917 | 1/2000 |
| WO | WO 01/72956 | 10/2001 |
| WO | WO 01/75109 | 10/2001 |

OTHER PUBLICATIONS

Chidgey et al. Changing pattern of desmocollin 3 expression accompanies epidermal organisation during skin development. Dev Dyn. Nov. 1997;210(3):315-27.*

(Continued)

*Primary Examiner*—Maher M Haddad
(74) *Attorney, Agent, or Firm*—Seed IP Law Group PLLC

(57) ABSTRACT

Modulating agents and methods for enhancing or inhibiting nonclassical cadherin-mediated functions, such as atypical or desmosomal cadherin-mediated functions, are provided. The modulating agents comprise at least a tryptophan-containing cell adhesion recognition sequence of an atypical and/or desmosomal cadherin, a conservative analogue or peptidomimetic thereof, or an antibody or fragment thereof that specifically binds to such a cell adhesion recognition sequence. Modulating agents may additionally comprise one or more cell adhesion recognition sequences recognized by cadherins and/or other adhesion molecules. Such modulating agents may, but need not, be linked to a targeting agent, pharmaceutically active substance and/or support material.

5 Claims, 11 Drawing Sheets

OTHER PUBLICATIONS

Albelda et al., "Adhesion molecules and inflammatory injury," *The FASEB Journal* 8(8):504-512, 1994.
Alexander, J.S. et al., "An N-cadherin-like protein contributes to solute barrier maintenance in cultured endothelium," *J. Cell Physiol.* 156(3): 610-618, Sep. 1993.
Bangma et al., "The Value of Screening Tests in the Detection of Prostate Cancer. Part I: Results of a Retrospective Evaluation of 1726 Men," *Urology* 46(6): 773-778, 1995.
Berndorff et al., "Liver-Intestine Cadherin: Molecular Cloning and Characterization of a Novel $Ca^{2+}$-dependent Cell Adhesion Molecule Expressed in Liver and Intestine," *The Journal of Cell Biology* 125(6): 1353-1369, 1994.
Blaschuk and Farookhi, "Estradiol Stimulates Cadherin Expression in Rat Granulosa Cells," *Developmental Biology* 136: 564-567, 1989.
Blaschuk et al., "E-cadherin, estrogens and cancer: is there a connection?," *The Canadian Journal of Oncology* 4(4): 291-301, Nov. 1994.
Blaschuk, O.W. et al., "Identification of a conserved region common to cadherins and influenza strain A hemagglutinins," *J. Mol. Biol.* 211(4): 679-682, Feb. 1990.
Breier et al., "Molecular Cloning and Expression of Murine Vascular Endothelial-Cadherin in Early Stage Development of Cardiovascular System," *Blood* 87(2): 630-641, Jan. 15, 1996.
Bussemakers et al., "The role of OB-cadherin in human prostate cancer," *Proceedings of the American Association for Cancer Research* vol. 39, No. 3405, New Orleans, LA, Mar. 28-Apr. 1, 1998.
Cardarelli, P.M. et al., "The Collagen Receptor α2β1, from MG-63 and HT1080 Cells, Interacts with a Cyclic RGD Peptide," *The Journal of Biological Chemistry* 267(32): 23159-23164, Nov. 15, 1992.
Carmeliet, P. et al., "Angiogenesis in cancer and other diseases," *Nature* 407: 249-257, Sep. 14, 2000.
Carmeliet, P. et al., "Targeted deficiency of cytosolic truncation of the VE-cadherin gene in mice impairs VEGF-mediated endothelial survival and angiogenesis," *Cell* 98(2): 147-157, Jul. 1999.
Caveda, L. et al., "Inhibition of Cultured Cell Growth by Vascular Endothelial Cadherin (Cadherin-5/VE-Cadherin)," *Journal of Clinical Investigation* 98(4): 886-893, Aug. 1996.
Doherty and Walsh, "CAM-FGF Receptor Interactions: A Model for Axonal Growth," *Molecular and Cellular Neuroscience* 8: 99-111, 1996.
Doherty and Walsh, "Signal transduction events underlying neurite outgrowth stimulated by cell adhesion molecules," *Current Opinion in Neurobiology* 4: 49-55, 1994.
Dvorak, H.F., "Vascular Permeabiligy Factor/Vascular Endothelial Growth Factor: A Critical Cytokine in Tumor Angiogenesis and a Potential Target for Diagnosis and Therapy," *Journal of Clinical Oncology* 20(21): 4368-4380, Nov. 1, 2002.
Edgington, "How Sweet It Is: Selectin-Mediating Drugs," *Bio/Technology* 10(4): 383-389, Apr. 1992.
Erez, N. et al., "Induction of apoptosis in cultured endothelial cells by a cadherin antagonist peptide: Involvement of fibroblast growth factor receptor-mediated signaling," *Experimental Cell Research* 294(2): 366-378, Apr. 2004.
Feltes, C.M. et al., "An Alternatively Spliced Cadherin-11 Enhances Human Breast Cancer Cell Invasion," *Cancer Research* 62: 6688-6697, Nov. 15, 2002.
Fredette and Ranscht, "T-Cadherin Expression Delineates Specific Regions of the Developing Motor Axon-Hindlimb Projection Pathway," *The Journal of Neuroscience* 14(12): 7331-7346, Dec. 1994.
Garrod, D.R. et al., "Desmosomal cadherins," *Current Opinion in Cell Biology* 14: 537-545, 2002.
Genbank Database, Accession No. AB008178, Feb. 13, 1999.
Genbank Database, Accession No. AB008180, Feb. 13, 1999.
Genbank Database, Accession No. AB008181, Feb. 13, 1999.
Genbank Database, Accession No. AB008182, Feb. 13, 1999.
Genbank Database, Accession No. AB008183, Feb. 13, 1999.
Genbank Database, Accession No. AB035302, Aug. 8, 2000.
Genbank Database, Accession No. AF029343, Nov. 10, 1997.
Genbank Database, Accession No. AF039747, Jul. 17, 1999.
Genbank Database, Accession No. AF217289, Oct. 17, 2000.
Genbank Database, Accession No. AJ007607, Jan. 16, 2001.
Genbank Database, Accession No. AY192158, Jun. 7, 2003.
Genbank Database, Accession No. AY192159, Jun. 7, 2003.
Genbank Database, Accession No. AY227349, Jun. 5, 2003.
Genbank Database, Accession No. AY227350, Jun. 5, 2003.
Genbank Database, Accession No. D17427, Feb. 1, 2000.
Genbank Database, Accession No. D31784, Jul. 7, 1997.
Genbank Database, Accession No. D42150, Feb. 9, 1999.
Genbank Database, Accession No. D83348, Feb. 6, 1999.
Genbank Database, Accession No. D83542, Oct. 28, 2000.
Genbank Database, Accession No. D86916, Feb. 7, 1999.
Genbank Database, Accession No. D86917, Feb. 7, 1999.
Genbank Database, Accession No. D88349, Feb. 7, 1999.
Genbank Database, Accession No. L11373, Sep. 14, 1995.
Genbank Database, Accession No. L34056, Jun. 29, 1994.
Genbank Database, Accession No. L34057, Jun. 29, 1994.
Genbank Database, Accession No. L34058, Jun. 29, 1994.
Genbank Database, Accession No. L34060, Jun. 29, 1994.
Genbank Database, Accession No. P55287, Oct. 1, 1996.
Genbank Database, Accession No. Q02413, Oct. 1, 1993.
Genbank Database, Accession No. S64273, Jul. 19, 1993.
Genbank Database, Accession No. U59325, Jun. 27, 1996.
Genbank Database, Accession No. X56654, Aug. 3, 1993.
Genbank Database, Accession No. X56807, Apr. 18, 2002.
Genbank Database, Accession No. X59796, Jan. 24, 1995.
Genbank Database, Accession No. X72925, Feb. 24, 1999.
Genbank Database, Accession No. X83228, Jun. 1, 1995.
Genbank Database, Accession No. X83929, Dec. 14, 1995.
Genbank Database, Accession No. Z26317, May 15, 2001.
Genbank Database, Accession No. Z34522, Jun. 22, 1994.
Getsios et al., "Regulated Expression of Cadherin-6 and Cadherin-11 in the Glandular Epithelial and Stromal Cells of the Human Endometrium," *Developmental Dynamics* 211: 238-247, 1998.
Griffiths et al., "Cell adhesion molecules in bladder cancer: soluble serum E-cadherin correlates with predictors of recurrence," *Br. J. Cancer* 74: 579-584, 1996.
Grillner and Matsushima, "The Neural Network Underlying Locomotion in Lamprey-Synaptic and Cellular Mechanisms," *Neuron* 7: 1-15, Jul. 1991.
Hall et al., "Review: A Role for the FGF Receptor in the Axonal Growth Response Stimulated by Cell Adhesion Molecules?," *Cell Adhesion and Communication* 3: 441-450, 1996.
Hanahan, D., "Signaling Vascular Morphogenesis and Maintenance," *Science* 277: 48-50, Jul. 4, 1997.
Hazan, R.B. et al., "N-Cadherin Promotes Adhesion Between Invasive Breast Cancer Cells and the Stroma," *Cell Adhesion and Communication* 4(6): 399-411, 1997.
Huber, P. et al., "Genomic Structure and Chromosomal Mapping of the Mouse VE-Cadherin Gene (*Cdh5*)," *Genomics* 32: 21-28, 1996.
Inoue et al., "Cadherin-6 in the Developing Mouse Brain: Expression Along Restricted Connection Systems and Synaptic Localization Suggest a Potential Role in Neuronal Circuitry," *Developmental Dynamics* 211: 338-351, Apr. 1998.
Iruela-Arispe et al., "Expression of SPARC during Development of the Chicken Chorioallantoic Membrane: Evidence for Regulated Proteolysis in Vivo," *Molecular Biology of the Cell* 6: 327-343, Mar. 1995.
Kahan, B.D., "Immunosuppressive Therapy," *Current Opinion in Immunology* 4(5): 553-560, Oct. 1992.
Kashima, T. et al., "Anomalous Cadherin Expression in Osterosarcoma. Possible Relationships to Metastasis and Morphogenesis," *American Journal of Pathology* 155(5): 1549-1555, Nov. 1999.
Katayama et al., "Soluble E-cadherin fragments increased in circulation of cancer patients," *Br. J. Cancer* 69: 580-585, 1994.
Kawaguchi, J. et al., "Targeted disruption of cadherin-11 leads to a reduction in bone density in calvaria and long bone metaphyses," *J. Bone Mineral Research* 16(7): 1265-1271, Jul. 2001.
Kawamura et al., "cDNA Cloning and Expression of a Novel Human Desmocollin," *The Journal Of Biological Chemistry* 269(42): 26295-26302, Oct. 21, 1994.
Kido et al., "Molecular Properties and Chromosomal Location of Cadherin-8," *Genomics* 48: 186-194, 1998.

Kimura, Y. et al., "Cadherin-11 Expressed in Association with Mesenchymal Morphogenesis in the Head, Somite, and Limb Bud of Early Mouse Embryos," *Developmental Biology 169*: 347-358, 1995.

King et al., "Cloning of the cDNA (DSC1) Coding for Human Type 1 Desmocollin and Its Assignment to Chromosome 18," *Genomics 18*: 185-194, 1993.

King et al., "The Desmocollins of Human Foreskin Epidermis: Identification and Chromosomal Assignment of a Third Gene and Expression Patterns of the Three Isoforms," *J Invest Dermatol 105*: 314-321, 1995.

Klopfenstein et al., "Increased N-cadherin mediated adhesion does not reduce invasion of *Rous sarcoma* virus-transformed astrocycle-like WC5 cells," *Proceedings of the American Association for Cancer Research 34*: 33, #195, Mar. 1993.

Knudsen et al., "Interaction of alpha-actinin with the cadherin/catenin cell-cell adhesion complex via alpha-catenin," *J. Cell Biol. 130*(1):67-77, Jul. 1995.

Koch et al., "Complete amino acid sequence of the epidermal desmoglein precursor polypeptide and identification of a second type of desmoglein gene," *European Journal of Cell Biology 55*: 200-208, 1991.

Kogan et al., "A Single Amino Acid Residue Can Determine the Ligand Specificity of E-selectin," *The Journal of Biological Chemistry 270*(23):14047-14055, Jun. 9, 1995.

Kohmura et al., "Diversity Revealed by a Novel Family of Cadherins Expressed in Neurons at a Synaptic Complex," *Neuron 20*: 1137-1151, Jun. 1998.

Kools, P. et al., "Characterization of three novel human cadherin genes (CDH7, CHD19, CDH20) clustered on chromosome 18q22-q23 and with high homology to chicken cadherin-7," *Genomics 68*(3): 283-295, Sep. 15, 2000.

Kools, P. et al., "The human cadherin-10 gene: complete coding sequence, predominant expression in the brain, and mapping of chromosome 5p13-14," *FEBS Letters 452*: 328-334, 1999.

Kools, P.F.J. et al., "Expression in mesenchymal tumors of alternative cadherin-11 transcripts encoding truncated adhesion molecules: a mechanism for acquiring invasive properties?" *Clinical & Experimental Metastasis 14*(Suppl.1): 52-53, Sep. 1996.

Kreft et al., "LI-Cadherin-mediated Cell-Cell Adhesion Does Not Require Cytoplasmic Interactions," *The Journal of Cell Biology 136*(5): 1109-1121, Mar. 10, 1997.

Lampugnani, M.G. et al., "The Molecular Organization of Endothelial Cell to Cell Junctions: Differential Association of Plankoglobin, β-catenin, and α-catenin with Vascular Endothelial Cadherin (VE-cadherin)," *The Journal of Cell Biology 129*(1): 203-217, Apr. 1995.

Lindahl et al., "Pericyte Loss and Microaneurysm Formation in PDGF-B-Deficient Mice," *Science 277*: 242-245, Jul. 11, 1997.

Loric et al., "Enhanced Detection of Hematogenous Circulating Prostatic Cells in Patients with Prostate Adenocarcinoma by Using Nested Reverse Transcription Polymerase Chain Reaction Assay Based on Prostate-Specific Membrane Antigen," *Clin. Chem. 41*(12): 1698-1704, 1995.

Lutz et al., "Antibody Recognition of Peptide Sequences from the Cell-Cell Adhesion Proteins: N- and E-cadherins," *Peptide Research 9*(5): 233-239, 1996.

Makrigiannakis, A. et al., "N-Cadherin-Mediated Human Granulosa Cell Adhesion Prevents Apoptosis. A Role in Follicular Atresia and Luteolysis?" *American Journal of Pathology 154*(5): 1391-1406, May 1999.

Manabe, T. et al., "Loss of cadherin-11 adhesion receptor enhances plastic changes in hippocampal synapses and modifies behavioral responses," *Mol. Cell Neurosci 15*(6): 534-546, Jun. 2000.

Marcozzi et al., "Coexpression of both types of desmosomal cadherin and plakoglobin confers strong intercellular adhesion," *Journal of Cell Science 111*: 495-509, 1998.

Marin-Padura, I. et al., "Junctional Adhesion Molecule, a Novel Member of the Immunoglobulin Superfamily That Distributes at Intercellular Junctions and Modulates Monocyte Transmigration," *The Journal of Cell Biology 142*(1): 117-127, Jul. 13, 1998.

Matsuoka et al., "Recognition of Ovarian Cancer Antigen CA125 by Murine Monoclonal Antibody Produced by Immunization of Lung Cancer Cells," *Cancer Res. 47*: 6335-6340, Dec. 1, 1987.

Matsuyoshi and Imamura, "Multiple Cadherins Are Expressed in Human Fibroblasts," *Biochemical and Biophysical Research Communications 235*: 355-358, 1997.

Mbalaviele et al., "Cadherin-6 Mediates the Heterotypic Interactions between the Hemopoietic Osteoclast Cell Lineage and Stromal Cells in a Murine Model of Osteoclast Differentiation," *The Journal of Cell Biology 141*(6): 1467-1476, Jun. 15, 1998.

Mulders et al., "Prostate-specific antigen (PSA). A tissue-specific and sensitive tumor marker," *Eur. J. Surg. Oncol. 16*: 37-41, 1990.

Mundy, G.R., "Metastasis to bone: causes, consequences and therapeutic opportunities," *Nature Reviews. Cancer 2*(8): 584-593, Aug. 2002.

Munro and Blaschuk, "A Comprehensive Survey of the Cadherins Expressed in the Testes of Fetal, Immature, and Adult Mice Utilizing the Polymerase Chain Reaction," *Biology Of Reproduction 55*: 822-827, 1996.

Munro and Blashchuk, "The Structure, Function and Regulation of Cadherins," in *Cell Adhesion and Invasion in Cancer Metastasis*, P. Brodt (ed.), RG Landes Co., Austin, Texas, 1996, Chapter 3, pp. 17-34.

Munro et al., "Characterization of Cadherins Expressed by Murine Thymocytes," *Cellular Immunology 169*: 309-312, 1996.

Munro, S.B. et al., "E-Cadherin and OB-Cadherin mRNA in Normal Human Colon and Colon Carcinoma," *Experimental and Molecular Pathology 62*(2): 118-122, Apr. 1995.

Nagafuchi et al., "Transformation of cell adhesion properties by exogenously introduced E-cadherin cDNA," *Nature 329*: 341-343, Sep. 1987.

Nagashima et al., "Invasion properties in malignant gliomas—Expression of N-cadherin mRNA in gliomas," *Proceedings of the American Association for Cancer Proceedings 37*:68, #473, Mar. 1996.

Nakagawa and Takeichi, "Neural crest cell-cell adhesion controlled by sequential and subpopulation-specific expression of novel cadherins," *Development 121*: 1321-1332, 1995.

Navarro et al., "Differential Localization of VE- and N-Cadherins in Human Endothelial Cells: VE-Cadherin Competes with N-Cadherin for Junctional Localization," *The Journal of Cell Biology 140*(6): 1475-1484, Mar. 23, 1998.

Ngo et al., "Computational Complexity, Protein Structure Prediction, and the Levinthal Paradox," *The Protein Folding Problem and Tertiary Structure Prediction*, K. Merz, Jr. and S. Le Grand (eds.), Birkhäuser, Boston, pp. 491-495, 1994.

Nieman, M.T. et al., "N-Cadherin Promotes Motility in Human Breast Cancer Cells Regardless of their E-Cadherin Expression," *The Journal of Cell Biology 147*(3): 631-643, Nov. 1, 1999.

Nollet, F. et al., "Phylogentic analysis of the cadherin superfamily allows identification of six major subfamilies besides several solitary members," *Journal of Molecular Biology 299*(3): 551-572, Jun. 9, 2000.

Okazaki et al., "Molecular Cloning and Characterization of OB-cadherin, a New Member of Cadherin Family Expressed in Osteoblasts," *The Journal of Biological Chemistry 269*(16): 12092-12098, Apr. 22, 1994.

Orlandini and Oliverio, "In Fibroblast *Vegf-D* Expression Is Induced by Cell-Cell Contact Mediated by Cadherin-11," *The Journal of Biological Chemistry 276*(9): 6576-6581, Mar. 2, 2001.

Parker et al., "Desmosomal Glycoproteins II and III. Cadherin-Like Junctional Molecules Generated By Alternative Splicing," *The Journal of Biological Chemistry 266*(16): 10438-10445, Jun. 1991.

Pertz, O. et al., "A new crystal structure, $Ca^{2+}$ dependence and mutational analysis reveal molecular details of E-cadherin homoassociation," *The EMBO Journal 18*(7): 1738-1747, 1999.

Pishvaian, M.J. et al., "Cadherin-11 Is Expressed in Invasive Breast Cancer Cell Lines," *Cancer Research 59*: 947-952, Feb. 15, 1999.

Pouliot et al., "Developmental Regulation of A Cadherin during the Differentiation of Skeletal Myoblasts," *Developmental Biology 141*: 292-298, 1990.

Ransch and Bronner-Fraser, "T-cadherin expression alternates with migrating neural crest cells in the trunk of he avian embryo," *Development 111*: 15-22, Jan. 1991.

Ranscht and Dours-Zimmermann, "T-Cadherin, a Novel Cadherin Cell Adhesion Molecule in the Nervous System Lacks the Conserved Cytoplasmic Region," *Neuron 7*: 391-402, Sep. 1991.

Rodies and Takeichi, "Cadherins in the Developing Central Nervous System: An Adhesive Code for Segmental and Functional Subdivisions," *Developmental Biology 180*: 413-423, 1996.

Rowlands, T.M. et al., "Cadherins: crucial regulators of structure and function in reproductive tissues," *Reviews of Reproduction 5*: 53-61, 2000.

Rozdzinski et al., "Antiinflammatory Effects in Experimental Meningitis of Prokaryotic Peptides that Mimic Selectins," *J. Infect. Dis. 168*:1422-1428, 1993.

Rustin et al., "Defining Response of Ovarian Carcinoma to Initial Chemotherapy According to Serum CA 125," *J. Clin. Oncol. 14*(5): 1545-1551, May 1996.

Sacristán et al., "T-Cadherin 2: Molecular Characterization, Function in Cell Adhesion, and Coexpression With T-Cadherin and N-Cadherin," *Journal of Neuroscience Research 34*: 664-680, 1993.

Saffell et al., "Expression of a Dominant Negative FGF Receptor Inhibits Axonal Growth and FGF Receptor Phosphorylation Stimulated by CAMS," *Neuron 18*: 231-242, 1997.

Sano et al., "Protcadherins: a large family of cadherin-related molecules in central nervous system," *The EMBO Journal 12*(6): 2249-2256, 1993.

Schnädelbach, O. et al., "N-cadherin influences migration of oligodendrocytes on astrocytes monolayers," *Mol. Cell Neurosci. 15*(3): 288-302, Mar. 2000.

Schnädelbach, O. et al., "N-cadherin is involved in axon-oligodendrocyte contact and myelination," *Mol. Cell Neurosci. 17*(6): 1084-1093, Jun. 2001.

Shapiro, L. et al., "Structural basis of cell-cell adhesion by cadherins," *Nature 374*: 327-337, Mar. 23, 1995.

Shibata et al., "Identification of Human Cadherin-14, a Novel Neurally Specific Type II Cadherin, by Protein Interaction Cloning," *The Journal Of Biological Chemistry 272*(8): 5236-5240, Feb. 21, 1997.

Shibata et al., "Simultaneous expression of cadherin-11 in signet-ring cell carcinoma and stormal cells of diffuse-type gastric cancer," *Cancer Letters 99*: 147-153, 1996.

Shimazui et al., "Complex Cadherin Expression in Renal Cell Carcinoma," *Cancer Research 56*: 3234-3237, Jul. 15, 1996.

Shimoyama et al., "Isolation and Sequence Analysis of Human Cadherin-6 Complementary DNA for the Full Coding Sequence and Its Expression in Human Carcinoma Cells," *Cancer Research 55*: 2206-2211, May 15, 1995.

Shimoyama et al., "Molecular Cloning and Characterization of a Novel Human Classic Cadherin Homlgous with Mouse Muscle Cadherin," *The Journal of Biological Chemistry 273*(16): 10011-10018, Apr. 17, 1998.

Shimoyama, Y. et al., "Identification of threee human type-II classic cadherins and frequent heterophilic interactions between different subclasses of type-II classic cadherins," *Biochemical Journal 349*: 159-167, 2000.

Simonneau et al., "Cadherin 11 Expression Marks the Mesenchymal Phenotype: Towards New Functions for Cadherins?," *Cell Adhesion and Communication 3*: 115-130, 1995.

Slootstra et al., "Structural Aspects of Antibody-Antigen Interaction Revealed Through Small Random Peptide Libraries," *Molecular Diversity 1*: 87-96, 1995.

Sugimoto et al., "Molecular Cloning and Characterization of a Newly Identified Member of the Cadherin Family, PB-cadherin," *The Journal Of Biological Chemistry 271*(19): 11548-11556, May 10, 1996.

Suzuki et al., "Diversity of the cadherin family: evidence for eight new cadherins in nervous tissue," *Cell Regulation 2*: 261-270, Apr. 1991.

Taber's Cyclopedic Medical Dictionary, 17th Ed., F.A. Davis Company, Philadelphia, 1993, p. 1016.

Tanihara et al., "Cloning of Five Human Cadherins Clarifies Characteristic Features of Cadherin Extracellular Domain and Provides Further Evidence for Two Structurally Different Types of Cadherin," *Cell Adhesion and Communication 2*: 15-26, 1994.

The Merck Manual of Diagnosis and Therapy, 16th ED., Berkow, R. et al. (eds.), Merck Research Laboratories, Rahway, NJ, 1992, pp. 1264-1265.

Tkachuk et al., "Identification of an atypical lipoprotein-binding protein from human aortic smooth muscle as T-cadherin," *FEBS Letters 421*: 208-212, 1998.

Tselepis, C. et al., "Desmosomal adhesion inhibits invasive behavior," *Proc. Natl. Acad. Sci. USA 95*: 8064-8069, Jul. 1998.

Tsutsui et al., "Expression of Cadherin-Catenin Complexes in Human Leukemia Cell Lines," *Journal of Biochemistry 120*(5): 1034-1039, Nov. 1996.

Valin, J. et al., "Xenopus cadherin-11 is expressed in different populations of migrating neural crest cells," *Mechanisms of Development 75*(1-2): 171-174, Jul. 1998.

Van Den Brüle et al., "Genes Involved in Tumor Invasion and Metastasis are Differentially Modulated by Estradiol and Progestin in Human Breast-Cancer Cells," *Int. J. Cancer 52*: 653-657, Oct. 1992.

Vestal and Ranscht, "Glycosyl Phosphatidylinositol-anchored T-Cadherin Mediates Calcium-dependent, Homophilic Cell Adhesion," *The Journal of Cell Biology 119*(2): 451-461, Oct. 1992.

Ward and Mulligan, "Blocking of Adhesion Molecules In Vivo as Anti-Inflammatory Therapy," *Therapeutic Immunology 1*: 165-171, 1994.

Wheeler et al., "Desmosomal glycoprotein DGI, a component of intercellular desmosome junctions, is related to the cadherin family of cell adhesion molecules," *Proc. Natl. Acad. Sci. USA 88*: 4796-4800, Jun. 1991.

Wheelock, M.J. et al., "Soluble 80-kd Fragment of Cell-CAM 120/80 Disrupts Cell-Cell Adhesion," *Journal of Cellular Biochemistry 34*: 187-202, 1987.

Wilby, M.J. et al., "N-Cadherin inhibits Schwann cell migration on astrocytes," *Mol. Cell Neurosci. 14*(1): 66-84, Jul. 1999.

Williams et al., "Activation of the FGF Receptor Underlies Neurite Outgrowth Stimulated by L1, N-CAM, and N-Cadherin," *Neuron 13*: 583-594, Sep. 1994.

Zanetti, A. et al., "Vascular Endothelial Growth Factor Induces Shc Association With Vascular Endothelial Cadherin. A Potential Feedback Mechanism to Control Vascular Endothelial Growth Factor Receptor-2 Signaling," *Arterioscler Thromb Vasc Biol. 22*: 617-622, Apr. 2002.

\* cited by examiner

```
Obcad   EC1   RSKRGWWNQFFVLEEYTGPDPVLVGRLHSDIDSGDGNIKYILSGEGAGTIFVIDDKSGNIHATKTLDREERAQYTLMAQAVDRDTNRPLEPPSEFIVKVQDINDNPPEF
Cad5    EC1   RQKRDWIWNQMHIDEEKNTSLPHHVGKIKSSVSRKN--AKYLLKGEYVGKVFRVDAETGDVFAIERLDRENISEYHLTAVIVDKDTGENLETPSSFTIKVHDVNDNMPYF
Cad6    EC1   RSKRSMWNQFFLLEEYTGSDYQYVGKLHSDQDRGDGSLKYILSDGAGDLFIINENTGDIQATKRLDREKPVYILRAQAINRRTGRPVEPESEFIIKIHDINDNEPIF
Cad7    EC1   RTKRSWWNQFFVLEEYMGSDPLYVGKLHSDVDKGDGSIKYILSGEGASSIFIIDENTGDIHATKRLDREEQAYYTLRAQAHDRLTNKPVEPESEFVIKIQDINDNEPKF
Cad8    EC1   RSKRGWWNQMFVLEEFSGPEPILVGRLHTDLDPGSKKIKYILSGDGAGTIFIFQINDVTGDIHAIKRLDREEKAEYTLTAQAVDWETSKPLEPPSEFIKVQDINDNAPEF
Cad12   EC1   RVKRGWWNQFFVLEEYVGSEPQYVGKLHSDLDKGEGTVKYTLSGDGAGTVFTIDETTGDIHAIRSLDREEKPFYTLRAQAVDIETRKPLEPESEFTIKVQDINDNEPKF
Cad14   EC1   RPKRGWWNQFFVLEEHMGPDPQYVGKLHSNSDKGDGSVKYILTGEEAGTIFIIDDTTGDIHSTKSLDREQKTHYVLHAQAIDRRTNKPLEPESEFIIKVQDINDNAPKF
PBcad   EC1   RVKRGWWNQFFVVEEYTGTEPLYVGKIHSDSDEGDGTIKYTISGEEGAGTIFLIDELTGDIHATERLDREQKTFYTLRAQARDRATNRLLEPESEFIIKVQDINDSEPRF
```

*Fig. 2*

Human G W V W N Q F F V I E E Y T G P D P V L V G R L H S D I D S G D G N I K Y I L S G E G A G
Mouse G W V W N Q F F V I E E Y T G P D P V L V G R L H S D I D S G D G N I K Y I L S G E G A G Human T I F V I D D K S G N I H A T K T L D R E E R A Q Y T L M A Q A V D R D T N R P L E P P S
Mouse T I F V I D D K S G N I H A T K T L D R E E R A Q Y T L M A Q A V D R D T N R P L E P P S Human E F I V K V Q D I N D N P P E F
Mouse E F I V K V Q D I N D N P P E F

*Fig. 3*

```
Human Dsg1  EWIKFAAACREGEDNSKRNPIAKIHSDCAANQ--QVTYRISGVGIDQPPYGIFVINQKTGEINITSIVDREVTPFFIIYCRALNSMGQDLERPLELRVRVLDINDNPPVF
Bull Dsg1   EWIKFAAACREGEDNSKRNPIAKIHSDCAANQ--QVTYRISGVGIDQPPYGIFVINQKTGEINITSIVDREVTPFFIIYCRALNSLGQDLEKPLELRVRVLDINDNPPVF
Human Dsg2  AWITAPVALREGEDLSKKNPIAKIHSDLAEERGLKITYKYTGKGITEPPFGIFVFNKDTGELNVTSILDREETPFFLLTGYALDARGNNVEKPLELRIKVLDINDNEPVF
Human Dsg3  EWVKFAKPCREGEDNSKRNPIAKITSDYQATQ--KITYRISGVGIDQPPFGIFVVDKNTGDINITAIVDREETPSFLITCRALNAQGLDVEKPLILTVKILDINDNPPVF
Mouse Dsg3  EWVKFAKPCREREDNSRRNPIAKITSDFQKNQ--KITYRISGVGIDQPPFGIFVVDPNNGDINITAIVDREETPSFLITCRALNALGQDVERPLILTVKILDVNDNPPIF
Human Dsg4  EWIKFAAACREGEDNSKRNPIAKIRSDCESNQ--KITYRISGVGIDRPPYGVFTINPRTGEINITSVVDRETPLFLFIYCRALNSRGEDLERPLELRVKVMDINDNAPVF
Mouse Dsg4  EWIKFAAACREGEDNSKRNPIARIRSDCEVSQ--RITYRISGAGIDRPPYGVFTINPRTGEINITSVVDRETPLFLFIHCRALNSRGEDLERPLELRVKVMDVNDNPPVF
Mouse Dsg5  EWIKFAAACREGEDNSKRNPIAKIHSDCAANQ--PVTYRISGVGIDQPPYGIFIINQKTGEINITSIVDREVTPFFIIYCRALNAQGQDLENPLELRVRMDINDNPPVF
Mouse Dsg6  EWIKFAAACREGEDNSKRNPIAKIHSDCAANQ--PVTYRISGVGIDQPPYGIFIINQKTGEINITSIVDREVTPFFIIYCRALNAQGQDLENPLELRVRMDINDNPPVF
Human Dsc1  RWAPIPASLMENSLGPFPQHVQQIQSDAAQNY--TIFYRISISGPGVDKEPFNLFYIEKDTGDIFCTRSIDREKYEQFALYGYATTADGYAPEYPLPLIKIEDDNDNAPYF
Mouse Dsc1  RWAPIPCSLMENSLGPFPQHIQQIQSDAAQNY--TIFYSISGPGVDKEPYNLFYIEKDTGDIYCTRSIDREQYDQFLVYGYATTADGYAPDYPLPLLFKVEDDNDNAPYF
Bull Dsc1   RWAPIPCSLMENSLGPFPQHVQQVQSDAAQNY--TIFYSISGPGVDKEPFNLFFIEKDTGDIFCTRSIDREQYQEFPIYAYATTADGYAPEYPLPVFKVEDDNDNAPYF
Human Dsc2  RWAPIPCSMLENSLGPFPLFLQQVQSDTAQNY--TIYYSIRGPGVDQEPRNLFYYERDTGNLYCTRPVDREQYESFEIIAFATTPDGYTPELPLPLIKIEDENDNYPIF
Dog Dsc2    RWAPIPCSMLENSLGPFPLFLQQIQSDTAQNY--TIFYSIRGPGVDREPKNLFYYERDTGNLFCTRPVDREEYDVFDLIAYASTADGYSADLPLPLPIRVEDENDNPVF
Human Dsc3  RWAPIPCSMQENSLGPFPLFLQQVESDAAQNY--TVFYSISGRGVDKEPLNLFYIERDTGNLYCTRPVDREEYDVFDLIAYASTADGYSADLPLPLPLPIKIEDENDNYPIF
Mouse Dsc3  RWAPIPCSMQENSLGPFPLFLQQVESDAAQNY--TVFYSISGRGADQEPLNWFFIERDTGNLYCTRPVDREEYDVFDLIAYASTADGYSADLPLPLPIRVEDENDNYPLF
Bull Dsc3   RWAPIPCSMQENSLGPFPLFLQQVESDAAQNY--TVFYSISGRGVDKEPLNLFFIERDTGNLYCTQPVDREEYDVFDLIAYASTADGYSADFPLPLPIKIEDENDNHPIF
Human Dsc4  RWAPIPCSMQENSLGPFPLFLQQVESDAAQNY--TVFYSISGRGVDKEPLNLFYIERDTGNLFCTRPVDREEYDVFDLIAYASTADGYSADLPLPLPIRVEDENDNHPVF
```

Fig. 5

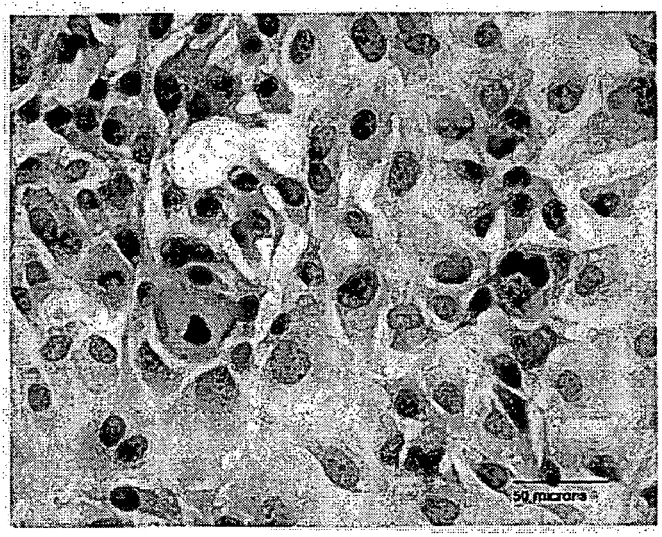
Control
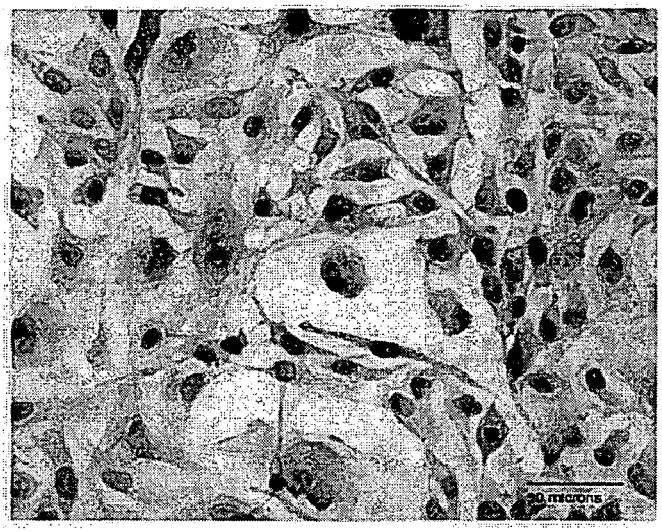
ADH358
Confluent cultures of SKOV3 cells treated with ADH358 (1.0 mg/ml) for 24 h.
*Fig. 6*

```
                        SEQUENCE LISTING

<160> NUMBER OF SEQ ID NOS: 1402

<210> SEQ ID NO 1
<211> LENGTH: 6
<212> TYPE: PRT
<213> ORGANISM: Artificial Sequence
<220> FEATURE:
<223> OTHER INFORMATION: Trp-containing CAR sequence
<220> FEATURE:
<221> NAME/KEY: VARIANT
<222> LOCATION: 1
<223> OTHER INFORMATION: Xaa = Glu or Ala
<220> FEATURE:
<221> NAME/KEY: VARIANT
<222> LOCATION: 3
<223> OTHER INFORMATION: Xaa = Ile or Val
<220> FEATURE:
<221> NAME/KEY: VARIANT
<222> LOCATION: 4
<223> OTHER INFORMATION: Xaa = Lys or Thr
<220> FEATURE:
<221> NAME/KEY: VARIANT
<222> LOCATION: 5
<223> OTHER INFORMATION: Xaa = Phe or Ala
<220> FEATURE:
<221> NAME/KEY: VARIANT
<222> LOCATION: 6
<223> OTHER INFORMATION: Xaa = Ala or Pro

<400> SEQUENCE: 1

Xaa Trp Xaa Xaa Xaa Xaa
 1               5

<210> SEQ ID NO 2
<211> LENGTH: 5
<212> TYPE: PRT
<213> ORGANISM: Artificial Sequence
<220> FEATURE:
<223> OTHER INFORMATION: Trp-containing CAR sequence
```

```
<400> SEQUENCE: 2

Trp Ala Pro Ile Pro
1               5

<210> SEQ ID NO 3
<211> LENGTH: 5
<212> TYPE: PRT
<213> ORGANISM: Unknown
<220> FEATURE:
<223> OTHER INFORMATION: Calcium binding motif
<220> FEATURE:
<221> NAME/KEY: VARIANT
<222> LOCATION: 2
<223> OTHER INFORMATION: Xaa = any amino acid

<400> SEQUENCE: 3

Asp Xaa Asn Asp Asn
1               5

<210> SEQ ID NO 4
<211> LENGTH: 4
<212> TYPE: PRT
<213> ORGANISM: unknown
<220> FEATURE:
<223> OTHER INFORMATION: Calcium binding motif

<400> SEQUENCE: 4

Leu Asp Arg Glu
1

<210> SEQ ID NO 5
<211> LENGTH: 6
<212> TYPE: PRT
<213> ORGANISM: Artificial Sequence
<220> FEATURE:
<223> OTHER INFORMATION: Trp-containing CAR sequence
<220> FEATURE:
<221> NAME/KEY: VARIANT
<222> LOCATION: 1
<223> OTHER INFORMATION: Xaa = Gly, Asp or Ser
<220> FEATURE:
<221> NAME/KEY: VARIANT
<222> LOCATION: 3
<223> OTHER INFORMATION: Xaa = Val, Ile or Met

<400> SEQUENCE: 5

Xaa Trp Xaa Trp Asn Gln
1               5

<210> SEQ ID NO 6
<211> LENGTH: 6
<212> TYPE: PRT
<213> ORGANISM: Artificial Sequence
<220> FEATURE:
<223> OTHER INFORMATION: Trp-containing CAR sequence

<400> SEQUENCE: 6

Ala Trp Val Ile Pro Pro
1               5

<210> SEQ ID NO 7
<211> LENGTH: 4
<212> TYPE: PRT
<213> ORGANISM: unknown
<220> FEATURE:
<223> OTHER INFORMATION: Calcium binding motif
<220> FEATURE:
<221> NAME/KEY: VARIANT
```

-continued

```
<222> LOCATION: 1,3
<223> OTHER INFORMATION: Xaa = any amino acid

<400> SEQUENCE: 7

Xaa Asp Xaa Glu
 1

<210> SEQ ID NO 8
<211> LENGTH: 5
<212> TYPE: PRT
<213> ORGANISM: unknown
<220> FEATURE:
<223> OTHER INFORMATION: Calcium binding motif
<220> FEATURE:
<221> NAME/KEY: VARIANT
<222> LOCATION: 2,3,5
<223> OTHER INFORMATION: Xaa = any amino acid

<400> SEQUENCE: 8

Asp Xaa Xaa Asp Xaa
 1               5

<210> SEQ ID NO 9
<211> LENGTH: 4
<212> TYPE: PRT
<213> ORGANISM: unknown
<220> FEATURE:
<223> OTHER INFORMATION: Calcium binding motif

<400> SEQUENCE: 9

Met Asp Arg Glu
 1

<210> SEQ ID NO 10
<211> LENGTH: 4
<212> TYPE: PRT
<213> ORGANISM: unknown
<220> FEATURE:
<223> OTHER INFORMATION: Calcium binding motif

<400> SEQUENCE: 10

Leu Asp Phe Glu
 1

<210> SEQ ID NO 11
<211> LENGTH: 4
<212> TYPE: PRT
<213> ORGANISM: unknown
<220> FEATURE:
<223> OTHER INFORMATION: Calcium binding motif

<400> SEQUENCE: 11

Leu Asp Tyr Glu
 1

<210> SEQ ID NO 12
<211> LENGTH: 4
<212> TYPE: PRT
<213> ORGANISM: Unknown
<220> FEATURE:
<223> OTHER INFORMATION: Calcium binding motif

<400> SEQUENCE: 12

Ile Asp Arg Glu
 1

<210> SEQ ID NO 13
```

```
<211> LENGTH: 4
<212> TYPE: PRT
<213> ORGANISM: Unknown
<220> FEATURE:
<223> OTHER INFORMATION: Calcium binding motif

<400> SEQUENCE: 13

Val Asp Arg Glu
 1

<210> SEQ ID NO 14
<211> LENGTH: 4
<212> TYPE: PRT
<213> ORGANISM: Unknown
<220> FEATURE:
<223> OTHER INFORMATION: Calcium binding motif

<400> SEQUENCE: 14

Ile Asp Phe Glu
 1

<210> SEQ ID NO 15
<211> LENGTH: 11
<212> TYPE: PRT
<213> ORGANISM: Unknown
<220> FEATURE:
<223> OTHER INFORMATION: Third calcium binding motif found within most
      cadherin repeats
<220> FEATURE:
<221> NAME/KEY: VARIANT
<222> LOCATION: 1
<223> OTHER INFORMATION: Xaa = Leu, Ile or Val
<220> FEATURE:
<221> NAME/KEY: VARIANT
<222> LOCATION: 2
<223> OTHER INFORMATION: Xaa = any amino acid
<220> FEATURE:
<221> NAME/KEY: VARIANT
<222> LOCATION: 3
<223> OTHER INFORMATION: Xaa = Leu, Ile or Val
<220> FEATURE:
<221> NAME/KEY: VARIANT
<222> LOCATION: 4,6
<223> OTHER INFORMATION: Xaa = any amino acid
<220> FEATURE:
<221> NAME/KEY: VARIANT
<222> LOCATION: 9
<223> OTHER INFORMATION: Xaa = Asn or His
<220> FEATURE:
<221> NAME/KEY: VARIANT
<222> LOCATION: 10
<223> OTHER INFORMATION: Xaa = any amino acid

<400> SEQUENCE: 15

Xaa Xaa Xaa Xaa Asp Xaa Asn Asp Xaa Xaa Pro
 1               5                  10

<210> SEQ ID NO 16
<211> LENGTH: 6
<212> TYPE: PRT
<213> ORGANISM: Artificial Sequence
<220> FEATURE:
<223> OTHER INFORMATION: Representative atypical cadherin Trp-containing
      CAR sequence

<400> SEQUENCE: 16

Gly Trp Val Trp Asn Gln
 1               5

<210> SEQ ID NO 17
<211> LENGTH: 6
```

```
<212> TYPE: PRT
<213> ORGANISM: Artificial Sequence
<220> FEATURE:
<223> OTHER INFORMATION: Representative atypical cadherin Trp-containing
      CAR sequence

<400> SEQUENCE: 17

Asp Trp Ile Trp Asn Gln
 1               5

<210> SEQ ID NO 18
<211> LENGTH: 6
<212> TYPE: PRT
<213> ORGANISM: Artificial Sequence
<220> FEATURE:
<223> OTHER INFORMATION: Representative atypical cadherin Trp-containing
      CAR sequence

<400> SEQUENCE: 18

Ser Trp Met Trp Asn Gln
 1               5

<210> SEQ ID NO 19
<211> LENGTH: 6
<212> TYPE: PRT
<213> ORGANISM: Artificial Sequence
<220> FEATURE:
<223> OTHER INFORMATION: Representative atypical cadherin Trp-containing
      CAR sequence

<400> SEQUENCE: 19

Ser Trp Val Trp Asn Gln
 1               5

<210> SEQ ID NO 20
<211> LENGTH: 6
<212> TYPE: PRT
<213> ORGANISM: Artificial Sequence
<220> FEATURE:
<223> OTHER INFORMATION: Representative atypical cadherin Trp-containing
      CAR sequence

<400> SEQUENCE: 20

Gly Trp Met Trp Asn Gln
 1               5

<210> SEQ ID NO 21
<211> LENGTH: 4
<212> TYPE: PRT
<213> ORGANISM: Artificial Sequence
<220> FEATURE:
<223> OTHER INFORMATION: Exemplary Trp-containing CAR sequences for
      atypical cadherins sequence

<400> SEQUENCE: 21

Gly Trp Val Trp
 1

<210> SEQ ID NO 22
<211> LENGTH: 5
<212> TYPE: PRT
<213> ORGANISM: Artificial Sequence
<220> FEATURE:
<223> OTHER INFORMATION: Exemplary Trp-containing CAR sequences for
      atypical cadherins

<400> SEQUENCE: 22

Gly Trp Val Trp Asn
```

-continued

```
<210> SEQ ID NO 23
<211> LENGTH: 4
<212> TYPE: PRT
<213> ORGANISM: Artificial Sequence
<220> FEATURE:
<223> OTHER INFORMATION: Exemplary Trp-containing CAR sequences for
      atypical cadherins

<400> SEQUENCE: 23

Trp Val Trp Asn
1

<210> SEQ ID NO 24
<211> LENGTH: 5
<212> TYPE: PRT
<213> ORGANISM: Artificial Sequence
<220> FEATURE:
<223> OTHER INFORMATION: Exemplary Trp-containing CAR sequences for
      atypical cadherins

<400> SEQUENCE: 24

Trp Val Trp Asn Gln
1               5

<210> SEQ ID NO 25
<211> LENGTH: 4
<212> TYPE: PRT
<213> ORGANISM: Artificial Sequence
<220> FEATURE:
<223> OTHER INFORMATION: Exemplary Trp-containing CAR sequences for
      atypical cadherins

<400> SEQUENCE: 25

Asp Trp Ile Trp
1

<210> SEQ ID NO 26
<211> LENGTH: 5
<212> TYPE: PRT
<213> ORGANISM: Artificial Sequence
<220> FEATURE:
<223> OTHER INFORMATION: Exemplary Trp-containing CAR sequences for
      atypical cadherins

<400> SEQUENCE: 26

Asp Trp Ile Trp Asn
1               5

<210> SEQ ID NO 27
<211> LENGTH: 4
<212> TYPE: PRT
<213> ORGANISM: Artificial Sequence
<220> FEATURE:
<223> OTHER INFORMATION: Exemplary Trp-containing CAR sequences for
      atypical cadherins

<400> SEQUENCE: 27

Trp Ile Trp Asn
1

<210> SEQ ID NO 28
<211> LENGTH: 5
<212> TYPE: PRT
<213> ORGANISM: Artificial Sequence
<220> FEATURE:
<223> OTHER INFORMATION: Exemplary Trp-containing CAR sequences for
``` atypical cadherins

<400> SEQUENCE: 28

Trp Ile Trp Asn Gln
1               5

<210> SEQ ID NO 29
<211> LENGTH: 4
<212> TYPE: PRT
<213> ORGANISM: Artificial Sequence
<220> FEATURE:
<223> OTHER INFORMATION: Exemplary Trp-containing CAR sequences for
      atypical cadherins

<400> SEQUENCE: 29

Ser Trp Met Trp
1

<210> SEQ ID NO 30
<211> LENGTH: 5
<212> TYPE: PRT
<213> ORGANISM: Artificial Sequence
<220> FEATURE:
<223> OTHER INFORMATION: Exemplary Trp-containing CAR sequences for
      atypical cadherins

<400> SEQUENCE: 30

Ser Trp Met Trp Asn
1               5

<210> SEQ ID NO 31
<211> LENGTH: 4
<212> TYPE: PRT
<213> ORGANISM: Artificial Sequence
<220> FEATURE:
<223> OTHER INFORMATION: Exemplary Trp-containing CAR sequences for
      atypical cadherins

<400> SEQUENCE: 31

Trp Met Trp Asn
1

<210> SEQ ID NO 32
<211> LENGTH: 5
<212> TYPE: PRT
<213> ORGANISM: Artificial Sequence
<220> FEATURE:
<223> OTHER INFORMATION: Exemplary Trp-containing CAR sequences for
      atypical cadherins

<400> SEQUENCE: 32

Trp Met Trp Asn Gln
1               5

<210> SEQ ID NO 33
<211> LENGTH: 4
<212> TYPE: PRT
<213> ORGANISM: Artificial Sequence
<220> FEATURE:
<223> OTHER INFORMATION: Exemplary Trp-containing CAR sequences for
      atypical cadherins

<400> SEQUENCE: 33

Ser Trp Val Trp
1

<210> SEQ ID NO 34

```
<211> LENGTH: 5
<212> TYPE: PRT
<213> ORGANISM: Artificial Sequence
<220> FEATURE:
<223> OTHER INFORMATION: Exemplary Trp-containing CAR sequences for
      atypical cadherins

<400> SEQUENCE: 34

Ser Trp Val Trp Asn
1               5

<210> SEQ ID NO 35
<211> LENGTH: 4
<212> TYPE: PRT
<213> ORGANISM: Artificial Sequence
<220> FEATURE:
<223> OTHER INFORMATION: Exemplary Trp-containing CAR sequences for
      atypical cadherins

<400> SEQUENCE: 35

Gly Trp Met Trp
1

<210> SEQ ID NO 36
<211> LENGTH: 5
<212> TYPE: PRT
<213> ORGANISM: Artificial Sequence
<220> FEATURE:
<223> OTHER INFORMATION: Exemplary Trp-containing CAR sequences for
      atypical cadherins

<400> SEQUENCE: 36

Gly Trp Met Trp Asn
1               5

<210> SEQ ID NO 37
<211> LENGTH: 4
<212> TYPE: PRT
<213> ORGANISM: Artificial Sequence
<220> FEATURE:
<223> OTHER INFORMATION: Exemplary Trp-containing CAR sequences for
      atypical cadherins

<400> SEQUENCE: 37

Ala Trp Val Ile
1

<210> SEQ ID NO 38
<211> LENGTH: 5
<212> TYPE: PRT
<213> ORGANISM: Artificial Sequence
<220> FEATURE:
<223> OTHER INFORMATION: Exemplary Trp-containing CAR sequences for
      atypical cadherins

<400> SEQUENCE: 38

Ala Trp Val Ile Pro
1               5

<210> SEQ ID NO 39
<211> LENGTH: 4
<212> TYPE: PRT
<213> ORGANISM: Artificial Sequence
<220> FEATURE:
<223> OTHER INFORMATION: Exemplary Trp-containing CAR sequences for
      atypical cadherins

<400> SEQUENCE: 39
```

```
Trp Val Ile Pro
 1

<210> SEQ ID NO 40
<211> LENGTH: 5
<212> TYPE: PRT
<213> ORGANISM: Artificial Sequence
<220> FEATURE:
<223> OTHER INFORMATION: Exemplary Trp-containing CAR sequences for
      atypical cadherins

<400> SEQUENCE: 40

Trp Val Ile Pro Pro
 1               5

<210> SEQ ID NO 41
<211> LENGTH: 7
<212> TYPE: PRT
<213> ORGANISM: Artificial Sequence
<220> FEATURE:
<223> OTHER INFORMATION: Exemplary Trp-containing CAR sequences for
      atypical cadherins

<400> SEQUENCE: 41

Gly Trp Val Trp Asn Gln Phe
 1               5

<210> SEQ ID NO 42
<211> LENGTH: 8
<212> TYPE: PRT
<213> ORGANISM: Artificial Sequence
<220> FEATURE:
<223> OTHER INFORMATION: Exemplary Trp-containing CAR sequences for
      atypical cadherins

<400> SEQUENCE: 42

Gly Trp Val Trp Asn Gln Phe Phe
 1               5

<210> SEQ ID NO 43
<211> LENGTH: 9
<212> TYPE: PRT
<213> ORGANISM: Artificial Sequence
<220> FEATURE:
<223> OTHER INFORMATION: Exemplary Trp-containing CAR sequences for
      atypical cadherins

<400> SEQUENCE: 43

Gly Trp Val Trp Asn Gln Phe Phe Val
 1               5

<210> SEQ ID NO 44
<211> LENGTH: 6
<212> TYPE: PRT
<213> ORGANISM: Artificial Sequence
<220> FEATURE:
<223> OTHER INFORMATION: Exemplary Trp-containing CAR sequences for
      atypical cadherins

<400> SEQUENCE: 44

Trp Val Trp Asn Gln Phe
 1               5

<210> SEQ ID NO 45
<211> LENGTH: 7
<212> TYPE: PRT
<213> ORGANISM: Artificial Sequence
<220> FEATURE:
```

```
<223> OTHER INFORMATION: Exemplary Trp-containing CAR sequences for
      atypical cadherins

<400> SEQUENCE: 45

Trp Val Trp Asn Gln Phe Phe
1               5

<210> SEQ ID NO 46
<211> LENGTH: 8
<212> TYPE: PRT
<213> ORGANISM: Artificial Sequence
<220> FEATURE:
<223> OTHER INFORMATION: Exemplary Trp-containing CAR sequences for
      atypical cadherins

<400> SEQUENCE: 46

Trp Val Trp Asn Gln Phe Phe Val
1               5

<210> SEQ ID NO 47
<211> LENGTH: 4
<212> TYPE: PRT
<213> ORGANISM: Artificial Sequence
<220> FEATURE:
<223> OTHER INFORMATION: Exemplary Trp-containing CAR sequences for
      atypical cadherins

<400> SEQUENCE: 47

Arg Gly Trp Val
1

<210> SEQ ID NO 48
<211> LENGTH: 5
<212> TYPE: PRT
<213> ORGANISM: Artificial Sequence
<220> FEATURE:
<223> OTHER INFORMATION: Exemplary Trp-containing CAR sequences for
      atypical cadherins

<400> SEQUENCE: 48

Arg Gly Trp Val Trp
1               5

<210> SEQ ID NO 49
<211> LENGTH: 6
<212> TYPE: PRT
<213> ORGANISM: Artificial Sequence
<220> FEATURE:
<223> OTHER INFORMATION: Exemplary Trp-containing CAR sequences for
      atypical cadherins

<400> SEQUENCE: 49

Arg Gly Trp Val Trp Asn
1               5

<210> SEQ ID NO 50
<211> LENGTH: 7
<212> TYPE: PRT
<213> ORGANISM: Artificial Sequence
<220> FEATURE:
<223> OTHER INFORMATION: Exemplary Trp-containing CAR sequences for
      atypical cadherins

<400> SEQUENCE: 50

Arg Gly Trp Val Trp Asn Gln
1               5
```

```
<210> SEQ ID NO 51
<211> LENGTH: 8
<212> TYPE: PRT
<213> ORGANISM: Artificial Sequence
<220> FEATURE:
<223> OTHER INFORMATION: Exemplary Trp-containing CAR sequences for
      atypical cadherins

<400> SEQUENCE: 51

Arg Gly Trp Val Trp Asn Gln Phe
1               5

<210> SEQ ID NO 52
<211> LENGTH: 9
<212> TYPE: PRT
<213> ORGANISM: Artificial Sequence
<220> FEATURE:
<223> OTHER INFORMATION: Exemplary Trp-containing CAR sequences for
      atypical cadherins

<400> SEQUENCE: 52

Arg Gly Trp Val Trp Asn Gln Phe Phe
1               5

<210> SEQ ID NO 53
<211> LENGTH: 10
<212> TYPE: PRT
<213> ORGANISM: Artificial Sequence
<220> FEATURE:
<223> OTHER INFORMATION: Exemplary Trp-containing CAR sequences for
      atypical cadherins

<400> SEQUENCE: 53

Arg Gly Trp Val Trp Asn Gln Phe Phe Val
1               5                   10

<210> SEQ ID NO 54
<211> LENGTH: 4
<212> TYPE: PRT
<213> ORGANISM: Artificial Sequence
<220> FEATURE:
<223> OTHER INFORMATION: Exemplary Trp-containing CAR sequences for
      atypical cadherins

<400> SEQUENCE: 54

Lys Arg Gly Trp
1

<210> SEQ ID NO 55
<211> LENGTH: 5
<212> TYPE: PRT
<213> ORGANISM: Artificial Sequence
<220> FEATURE:
<223> OTHER INFORMATION: Exemplary Trp-containing CAR sequences for
      atypical cadherins

<400> SEQUENCE: 55

Lys Arg Gly Trp Val
1               5

<210> SEQ ID NO 56
<211> LENGTH: 6
<212> TYPE: PRT
<213> ORGANISM: Artificial Sequence
<220> FEATURE:
<223> OTHER INFORMATION: Exemplary Trp-containing CAR sequences for
      atypical cadherins

<400> SEQUENCE: 56
```

```
Lys Arg Gly Trp Val Trp
 1               5

<210> SEQ ID NO 57
<211> LENGTH: 7
<212> TYPE: PRT
<213> ORGANISM: Artificial Sequence
<220> FEATURE:
<223> OTHER INFORMATION: Exemplary Trp-containing CAR sequences for
      atypical cadherins

<400> SEQUENCE: 57

Lys Arg Gly Trp Val Trp Asn
 1               5

<210> SEQ ID NO 58
<211> LENGTH: 8
<212> TYPE: PRT
<213> ORGANISM: Artificial Sequence
<220> FEATURE:
<223> OTHER INFORMATION: Exemplary Trp-containing CAR sequences for
      atypical cadherins

<400> SEQUENCE: 58

Lys Arg Gly Trp Val Trp Asn Gln
 1               5

<210> SEQ ID NO 59
<211> LENGTH: 9
<212> TYPE: PRT
<213> ORGANISM: Artificial Sequence
<220> FEATURE:
<223> OTHER INFORMATION: Exemplary Trp-containing CAR sequences for
      atypical cadherins

<400> SEQUENCE: 59

Lys Arg Gly Trp Val Trp Asn Gln Phe
 1               5

<210> SEQ ID NO 60
<211> LENGTH: 10
<212> TYPE: PRT
<213> ORGANISM: Artificial Sequence
<220> FEATURE:
<223> OTHER INFORMATION: Exemplary Trp-containing CAR sequences for
      atypical cadherins

<400> SEQUENCE: 60

Lys Arg Gly Trp Val Trp Asn Gln Phe Phe
 1               5                  10

<210> SEQ ID NO 61
<211> LENGTH: 11
<212> TYPE: PRT
<213> ORGANISM: Artificial Sequence
<220> FEATURE:
<223> OTHER INFORMATION: Exemplary Trp-containing CAR sequences for
      atypical cadherins

<400> SEQUENCE: 61

Lys Arg Gly Trp Val Trp Asn Gln Phe Phe Val
 1               5                  10

<210> SEQ ID NO 62
<211> LENGTH: 7
<212> TYPE: PRT
<213> ORGANISM: Artificial Sequence
```

```
<220> FEATURE:
<223> OTHER INFORMATION: Exemplary Trp-containing CAR sequences for
      atypical cadherins

<400> SEQUENCE: 62

Asp Trp Ile Trp Asn Gln Met
1               5

<210> SEQ ID NO 63
<211> LENGTH: 8
<212> TYPE: PRT
<213> ORGANISM: Artificial Sequence
<220> FEATURE:
<223> OTHER INFORMATION: Exemplary Trp-containing CAR sequences for
      atypical cadherins

<400> SEQUENCE: 63

Asp Trp Ile Trp Asn Gln Met His
1               5

<210> SEQ ID NO 64
<211> LENGTH: 9
<212> TYPE: PRT
<213> ORGANISM: Artificial Sequence
<220> FEATURE:
<223> OTHER INFORMATION: Exemplary Trp-containing CAR sequences for
      atypical cadherins

<400> SEQUENCE: 64

Asp Trp Ile Trp Asn Gln Met His Ile
1               5

<210> SEQ ID NO 65
<211> LENGTH: 6
<212> TYPE: PRT
<213> ORGANISM: Artificial Sequence
<220> FEATURE:
<223> OTHER INFORMATION: Exemplary Trp-containing CAR sequences for
      atypical cadherins

<400> SEQUENCE: 65

Trp Ile Trp Asn Gln Met
1               5

<210> SEQ ID NO 66
<211> LENGTH: 7
<212> TYPE: PRT
<213> ORGANISM: Artificial Sequence
<220> FEATURE:
<223> OTHER INFORMATION: Exemplary Trp-containing CAR sequences for
      atypical cadherins

<400> SEQUENCE: 66

Trp Ile Trp Asn Gln Met His
1               5

<210> SEQ ID NO 67
<211> LENGTH: 8
<212> TYPE: PRT
<213> ORGANISM: Artificial Sequence
<220> FEATURE:
<223> OTHER INFORMATION: Exemplary Trp-containing CAR sequences for
      atypical cadherins

<400> SEQUENCE: 67

Trp Ile Trp Asn Gln Met His Ile
1               5
```

```
<210> SEQ ID NO 68
<211> LENGTH: 4
<212> TYPE: PRT
<213> ORGANISM: Artificial Sequence
<220> FEATURE:
<223> OTHER INFORMATION: Exemplary Trp-containing CAR sequences for
      atypical cadherins

<400> SEQUENCE: 68

Arg Asp Trp Ile
 1

<210> SEQ ID NO 69
<211> LENGTH: 5
<212> TYPE: PRT
<213> ORGANISM: Artificial Sequence
<220> FEATURE:
<223> OTHER INFORMATION: Exemplary Trp-containing CAR sequences for
      atypical cadherins

<400> SEQUENCE: 69

Arg Asp Trp Ile Trp
 1               5

<210> SEQ ID NO 70
<211> LENGTH: 6
<212> TYPE: PRT
<213> ORGANISM: Artificial Sequence
<220> FEATURE:
<223> OTHER INFORMATION: Exemplary Trp-containing CAR sequences for
      atypical cadherins

<400> SEQUENCE: 70

Arg Asp Trp Ile Trp Asn
 1               5

<210> SEQ ID NO 71
<211> LENGTH: 7
<212> TYPE: PRT
<213> ORGANISM: Artificial Sequence
<220> FEATURE:
<223> OTHER INFORMATION: Exemplary Trp-containing CAR sequences for
      atypical cadherins

<400> SEQUENCE: 71

Arg Asp Trp Ile Trp Asn Gln
 1               5

<210> SEQ ID NO 72
<211> LENGTH: 8
<212> TYPE: PRT
<213> ORGANISM: Artificial Sequence
<220> FEATURE:
<223> OTHER INFORMATION: Exemplary Trp-containing CAR sequences for
      atypical cadherins

<400> SEQUENCE: 72

Arg Asp Trp Ile Trp Asn Gln Met
 1               5

<210> SEQ ID NO 73
<211> LENGTH: 9
<212> TYPE: PRT
<213> ORGANISM: Artificial Sequence
<220> FEATURE:
<223> OTHER INFORMATION: Exemplary Trp-containing CAR sequences for
      atypical cadherins
```

-continued

```
<400> SEQUENCE: 73

Arg Asp Trp Ile Trp Asn Gln Met His
1               5

<210> SEQ ID NO 74
<211> LENGTH: 10
<212> TYPE: PRT
<213> ORGANISM: Artificial Sequence
<220> FEATURE:
<223> OTHER INFORMATION: Exemplary Trp-containing CAR sequences for
      atypical cadherins

<400> SEQUENCE: 74

Arg Asp Trp Ile Trp Asn Gln Met His Ile
1               5                   10

<210> SEQ ID NO 75
<211> LENGTH: 4
<212> TYPE: PRT
<213> ORGANISM: Artificial Sequence
<220> FEATURE:
<223> OTHER INFORMATION: Exemplary Trp-containing CAR sequences for
      atypical cadherins

<400> SEQUENCE: 75

Lys Arg Asp Trp
1

<210> SEQ ID NO 76
<211> LENGTH: 5
<212> TYPE: PRT
<213> ORGANISM: Artificial Sequence
<220> FEATURE:
<223> OTHER INFORMATION: Exemplary Trp-containing CAR sequences for
      atypical cadherins

<400> SEQUENCE: 76

Lys Arg Asp Trp Ile
1               5

<210> SEQ ID NO 77
<211> LENGTH: 6
<212> TYPE: PRT
<213> ORGANISM: Artificial Sequence
<220> FEATURE:
<223> OTHER INFORMATION: Exemplary Trp-containing CAR sequences for
      atypical cadherins

<400> SEQUENCE: 77

Lys Arg Asp Trp Ile Trp
1               5

<210> SEQ ID NO 78
<211> LENGTH: 7
<212> TYPE: PRT
<213> ORGANISM: Artificial Sequence
<220> FEATURE:
<223> OTHER INFORMATION: Exemplary Trp-containing CAR sequences for
      atypical cadherins

<400> SEQUENCE: 78

Lys Arg Asp Trp Ile Trp Asn
1               5

<210> SEQ ID NO 79
<211> LENGTH: 8
<212> TYPE: PRT
```

```
<213> ORGANISM: Artificial Sequence
<220> FEATURE:
<223> OTHER INFORMATION: Exemplary Trp-containing CAR sequences for
      atypical cadherins

<400> SEQUENCE: 79

Lys Arg Asp Trp Ile Trp Asn Gln
1               5

<210> SEQ ID NO 80
<211> LENGTH: 9
<212> TYPE: PRT
<213> ORGANISM: Artificial Sequence
<220> FEATURE:
<223> OTHER INFORMATION: Exemplary Trp-containing CAR sequences for
      atypical cadherins

<400> SEQUENCE: 80

Lys Arg Asp Trp Ile Trp Asn Gln Met
1               5

<210> SEQ ID NO 81
<211> LENGTH: 10
<212> TYPE: PRT
<213> ORGANISM: Artificial Sequence
<220> FEATURE:
<223> OTHER INFORMATION: Exemplary Trp-containing CAR sequences for
      atypical cadherins

<400> SEQUENCE: 81

Lys Arg Asp Trp Ile Trp Asn Gln Met His
1               5                   10

<210> SEQ ID NO 82
<211> LENGTH: 11
<212> TYPE: PRT
<213> ORGANISM: Artificial Sequence
<220> FEATURE:
<223> OTHER INFORMATION: Exemplary Trp-containing CAR sequences for
      atypical cadherins

<400> SEQUENCE: 82

Lys Arg Asp Trp Ile Trp Asn Gln Met His Ile
1               5                   10

<210> SEQ ID NO 83
<211> LENGTH: 7
<212> TYPE: PRT
<213> ORGANISM: Artificial Sequence
<220> FEATURE:
<223> OTHER INFORMATION: Exemplary Trp-containing CAR sequences for
      atypical cadherins

<400> SEQUENCE: 83

Ser Trp Met Trp Asn Gln Phe
1               5

<210> SEQ ID NO 84
<211> LENGTH: 8
<212> TYPE: PRT
<213> ORGANISM: Artificial Sequence
<220> FEATURE:
<223> OTHER INFORMATION: Exemplary Trp-containing CAR sequences for
      atypical cadherins

<400> SEQUENCE: 84

Ser Trp Met Trp Asn Gln Phe Phe
1               5
```

```
<210> SEQ ID NO 85
<211> LENGTH: 9
<212> TYPE: PRT
<213> ORGANISM: Artificial Sequence
<220> FEATURE:
<223> OTHER INFORMATION: Exemplary Trp-containing CAR sequences for
      atypical cadherins

<400> SEQUENCE: 85

Ser Trp Met Trp Asn Gln Phe Phe Leu
1               5

<210> SEQ ID NO 86
<211> LENGTH: 6
<212> TYPE: PRT
<213> ORGANISM: Artificial Sequence
<220> FEATURE:
<223> OTHER INFORMATION: Exemplary Trp-containing CAR sequences for
      atypical cadherins

<400> SEQUENCE: 86

Trp Met Trp Asn Gln Phe
1               5

<210> SEQ ID NO 87
<211> LENGTH: 7
<212> TYPE: PRT
<213> ORGANISM: Artificial Sequence
<220> FEATURE:
<223> OTHER INFORMATION: Exemplary Trp-containing CAR sequences for
      atypical cadherins

<400> SEQUENCE: 87

Trp Met Trp Asn Gln Phe Phe
1               5

<210> SEQ ID NO 88
<211> LENGTH: 8
<212> TYPE: PRT
<213> ORGANISM: Artificial Sequence
<220> FEATURE:
<223> OTHER INFORMATION: Exemplary Trp-containing CAR sequences for
      atypical cadherins

<400> SEQUENCE: 88

Trp Met Trp Asn Gln Phe Phe Leu
1               5

<210> SEQ ID NO 89
<211> LENGTH: 4
<212> TYPE: PRT
<213> ORGANISM: Artificial Sequence
<220> FEATURE:
<223> OTHER INFORMATION: Exemplary Trp-containing CAR sequences for
      atypical cadherins

<400> SEQUENCE: 89

Arg Ser Trp Met
1

<210> SEQ ID NO 90
<211> LENGTH: 5
<212> TYPE: PRT
<213> ORGANISM: Artificial Sequence
<220> FEATURE:
<223> OTHER INFORMATION: Exemplary Trp-containing CAR sequences for
      atypical cadherins
```

```
<400> SEQUENCE: 90

Arg Ser Trp Met Trp
1               5

<210> SEQ ID NO 91
<211> LENGTH: 6
<212> TYPE: PRT
<213> ORGANISM: Artificial Sequence
<220> FEATURE:
<223> OTHER INFORMATION: Exemplary Trp-containing CAR sequences for
      atypical cadherins

<400> SEQUENCE: 91

Arg Ser Trp Met Trp Asn
1               5

<210> SEQ ID NO 92
<211> LENGTH: 7
<212> TYPE: PRT
<213> ORGANISM: Artificial Sequence
<220> FEATURE:
<223> OTHER INFORMATION: Exemplary Trp-containing CAR sequences for
      atypical cadherins

<400> SEQUENCE: 92

Arg Ser Trp Met Trp Asn Gln
1               5

<210> SEQ ID NO 93
<211> LENGTH: 8
<212> TYPE: PRT
<213> ORGANISM: Artificial Sequence
<220> FEATURE:
<223> OTHER INFORMATION: Exemplary Trp-containing CAR sequences for
      atypical cadherins

<400> SEQUENCE: 93

Arg Ser Trp Met Trp Asn Gln Phe
1               5

<210> SEQ ID NO 94
<211> LENGTH: 9
<212> TYPE: PRT
<213> ORGANISM: Artificial Sequence
<220> FEATURE:
<223> OTHER INFORMATION: Exemplary Trp-containing CAR sequences for
      atypical cadherins

<400> SEQUENCE: 94

Arg Ser Trp Met Trp Asn Gln Phe Phe
1               5

<210> SEQ ID NO 95
<211> LENGTH: 10
<212> TYPE: PRT
<213> ORGANISM: Artificial Sequence
<220> FEATURE:
<223> OTHER INFORMATION: Exemplary Trp-containing CAR sequences for
      atypical cadherins

<400> SEQUENCE: 95

Arg Ser Trp Met Trp Asn Gln Phe Phe Leu
1               5                   10

<210> SEQ ID NO 96
<211> LENGTH: 4
```

```
<212> TYPE: PRT
<213> ORGANISM: Artificial Sequence
<220> FEATURE:
<223> OTHER INFORMATION: Exemplary Trp-containing CAR sequences for
      atypical cadherins

<400> SEQUENCE: 96

Lys Arg Ser Trp
 1

<210> SEQ ID NO 97
<211> LENGTH: 5
<212> TYPE: PRT
<213> ORGANISM: Artificial Sequence
<220> FEATURE:
<223> OTHER INFORMATION: Exemplary Trp-containing CAR sequences for
      atypical cadherins

<400> SEQUENCE: 97

Lys Arg Ser Trp Met
 1               5

<210> SEQ ID NO 98
<211> LENGTH: 6
<212> TYPE: PRT
<213> ORGANISM: Artificial Sequence
<220> FEATURE:
<223> OTHER INFORMATION: Exemplary Trp-containing CAR sequences for
      atypical cadherins

<400> SEQUENCE: 98

Lys Arg Ser Trp Met Trp
 1               5

<210> SEQ ID NO 99
<211> LENGTH: 7
<212> TYPE: PRT
<213> ORGANISM: Artificial Sequence
<220> FEATURE:
<223> OTHER INFORMATION: Exemplary Trp-containing CAR sequences for
      atypical cadherins

<400> SEQUENCE: 99

Lys Arg Ser Trp Met Trp Asn
 1               5

<210> SEQ ID NO 100
<211> LENGTH: 8
<212> TYPE: PRT
<213> ORGANISM: Artificial Sequence
<220> FEATURE:
<223> OTHER INFORMATION: Exemplary Trp-containing CAR sequences for
      atypical cadherins

<400> SEQUENCE: 100

Lys Arg Ser Trp Met Trp Asn Gln
 1               5

<210> SEQ ID NO 101
<211> LENGTH: 9
<212> TYPE: PRT
<213> ORGANISM: Artificial Sequence
<220> FEATURE:
<223> OTHER INFORMATION: Exemplary Trp-containing CAR sequences for
      atypical cadherins

<400> SEQUENCE: 101

Lys Arg Ser Trp Met Trp Asn Gln Phe
```

<210> SEQ ID NO 102
<211> LENGTH: 10
<212> TYPE: PRT
<213> ORGANISM: Artificial Sequence
<220> FEATURE:
<223> OTHER INFORMATION: Exemplary Trp-containing CAR sequences for
      atypical cadherins

<400> SEQUENCE: 102

Lys Arg Ser Trp Met Trp Asn Gln Phe Phe
1               5                   10

<210> SEQ ID NO 103
<211> LENGTH: 11
<212> TYPE: PRT
<213> ORGANISM: Artificial Sequence
<220> FEATURE:
<223> OTHER INFORMATION: Exemplary Trp-containing CAR sequences for
      atypical cadherins

<400> SEQUENCE: 103

Lys Arg Ser Trp Met Trp Asn Gln Phe Phe Leu
1               5                   10

<210> SEQ ID NO 104
<211> LENGTH: 7
<212> TYPE: PRT
<213> ORGANISM: Artificial Sequence
<220> FEATURE:
<223> OTHER INFORMATION: Exemplary Trp-containing CAR sequences for
      atypical cadherins

<400> SEQUENCE: 104

Ser Trp Val Trp Asn Gln Phe
1               5

<210> SEQ ID NO 105
<211> LENGTH: 8
<212> TYPE: PRT
<213> ORGANISM: Artificial Sequence
<220> FEATURE:
<223> OTHER INFORMATION: Exemplary Trp-containing CAR sequences for
      atypical cadherins

<400> SEQUENCE: 105

Ser Trp Val Trp Asn Gln Phe Phe
1               5

<210> SEQ ID NO 106
<211> LENGTH: 9
<212> TYPE: PRT
<213> ORGANISM: Artificial Sequence
<220> FEATURE:
<223> OTHER INFORMATION: Exemplary Trp-containing CAR sequences for
      atypical cadherins

<400> SEQUENCE: 106

Ser Trp Val Trp Asn Gln Phe Phe Val
1               5

<210> SEQ ID NO 107
<211> LENGTH: 4
<212> TYPE: PRT
<213> ORGANISM: Artificial Sequence
<220> FEATURE:
<223> OTHER INFORMATION: Exemplary Trp-containing CAR sequences for -continued atypical cadherins

<400> SEQUENCE: 107

Arg Ser Trp Val
1

<210> SEQ ID NO 108
<211> LENGTH: 5
<212> TYPE: PRT
<213> ORGANISM: Artificial Sequence
<220> FEATURE:
<223> OTHER INFORMATION: Exemplary Trp-containing CAR sequences for
      atypical cadherins

<400> SEQUENCE: 108

Arg Ser Trp Val Trp
1               5

<210> SEQ ID NO 109
<211> LENGTH: 6
<212> TYPE: PRT
<213> ORGANISM: Artificial Sequence
<220> FEATURE:
<223> OTHER INFORMATION: Exemplary Trp-containing CAR sequences for
      atypical cadherins

<400> SEQUENCE: 109

Arg Ser Trp Val Trp Asn
1               5

<210> SEQ ID NO 110
<211> LENGTH: 7
<212> TYPE: PRT
<213> ORGANISM: Artificial Sequence
<220> FEATURE:
<223> OTHER INFORMATION: Exemplary Trp-containing CAR sequences for
      atypical cadherins

<400> SEQUENCE: 110

Arg Ser Trp Val Trp Asn Gln
1               5

<210> SEQ ID NO 111
<211> LENGTH: 8
<212> TYPE: PRT
<213> ORGANISM: Artificial Sequence
<220> FEATURE:
<223> OTHER INFORMATION: Exemplary Trp-containing CAR sequences for
      atypical cadherins

<400> SEQUENCE: 111

Arg Ser Trp Val Trp Asn Gln Phe
1               5

<210> SEQ ID NO 112
<211> LENGTH: 9
<212> TYPE: PRT
<213> ORGANISM: Artificial Sequence
<220> FEATURE:
<223> OTHER INFORMATION: Exemplary Trp-containing CAR sequences for
      atypical cadherins

<400> SEQUENCE: 112

Arg Ser Trp Val Trp Asn Gln Phe Phe
1               5

<210> SEQ ID NO 113

```
<211> LENGTH: 10
<212> TYPE: PRT
<213> ORGANISM: Artificial Sequence
<220> FEATURE:
<223> OTHER INFORMATION: Exemplary Trp-containing CAR sequences for
      atypical cadherins

<400> SEQUENCE: 113

Arg Ser Trp Val Trp Asn Gln Phe Phe Val
1               5                   10

<210> SEQ ID NO 114
<211> LENGTH: 5
<212> TYPE: PRT
<213> ORGANISM: Artificial Sequence
<220> FEATURE:
<223> OTHER INFORMATION: Exemplary Trp-containing CAR sequences for
      atypical cadherins

<400> SEQUENCE: 114

Lys Arg Ser Trp Val
1               5

<210> SEQ ID NO 115
<211> LENGTH: 6
<212> TYPE: PRT
<213> ORGANISM: Artificial Sequence
<220> FEATURE:
<223> OTHER INFORMATION: Exemplary Trp-containing CAR sequences for
      atypical cadherins

<400> SEQUENCE: 115

Lys Arg Ser Trp Val Trp
1               5

<210> SEQ ID NO 116
<211> LENGTH: 7
<212> TYPE: PRT
<213> ORGANISM: Artificial Sequence
<220> FEATURE:
<223> OTHER INFORMATION: Exemplary Trp-containing CAR sequences for
      atypical cadherins

<400> SEQUENCE: 116

Lys Arg Ser Trp Val Trp Asn
1               5

<210> SEQ ID NO 117
<211> LENGTH: 8
<212> TYPE: PRT
<213> ORGANISM: Artificial Sequence
<220> FEATURE:
<223> OTHER INFORMATION: Exemplary Trp-containing CAR sequences for
      atypical cadherins

<400> SEQUENCE: 117

Lys Arg Ser Trp Val Trp Asn Gln
1               5

<210> SEQ ID NO 118
<211> LENGTH: 9
<212> TYPE: PRT
<213> ORGANISM: Artificial Sequence
<220> FEATURE:
<223> OTHER INFORMATION: Exemplary Trp-containing CAR sequences for
      atypical cadherins

<400> SEQUENCE: 118
```

```
Lys Arg Ser Trp Val Trp Asn Gln Phe
1               5
```

<210> SEQ ID NO 119
<211> LENGTH: 10
<212> TYPE: PRT
<213> ORGANISM: Artificial Sequence
<220> FEATURE:
<223> OTHER INFORMATION: Exemplary Trp-containing CAR sequences for
      atypical cadherins

<400> SEQUENCE: 119

```
Lys Arg Ser Trp Val Trp Asn Gln Phe Phe
1               5                   10
```

<210> SEQ ID NO 120
<211> LENGTH: 11
<212> TYPE: PRT
<213> ORGANISM: Artificial Sequence
<220> FEATURE:
<223> OTHER INFORMATION: Exemplary Trp-containing CAR sequences for
      atypical cadherins

<400> SEQUENCE: 120

```
Lys Arg Ser Trp Val Trp Asn Gln Phe Phe Val
1               5                   10
```

<210> SEQ ID NO 121
<211> LENGTH: 7
<212> TYPE: PRT
<213> ORGANISM: Artificial Sequence
<220> FEATURE:
<223> OTHER INFORMATION: Exemplary Trp-containing CAR sequences for
      atypical cadherins

<400> SEQUENCE: 121

```
Gly Trp Val Trp Asn Gln Met
1               5
```

<210> SEQ ID NO 122
<211> LENGTH: 8
<212> TYPE: PRT
<213> ORGANISM: Artificial Sequence
<220> FEATURE:
<223> OTHER INFORMATION: Exemplary Trp-containing CAR sequences for
      atypical cadherins

<400> SEQUENCE: 122

```
Gly Trp Val Trp Asn Gln Met Phe
1               5
```

<210> SEQ ID NO 123
<211> LENGTH: 9
<212> TYPE: PRT
<213> ORGANISM: Artificial Sequence
<220> FEATURE:
<223> OTHER INFORMATION: Exemplary Trp-containing CAR sequences for
      atypical cadherins

<400> SEQUENCE: 123

```
Gly Trp Val Trp Asn Gln Met Phe Val
1               5
```

<210> SEQ ID NO 124
<211> LENGTH: 8
<212> TYPE: PRT
<213> ORGANISM: Artificial Sequence
<220> FEATURE:

```
<223> OTHER INFORMATION: Exemplary Trp-containing CAR sequences for
      atypical cadherins

<400> SEQUENCE: 124

Arg Gly Trp Val Trp Asn Gln Met
1               5

<210> SEQ ID NO 125
<211> LENGTH: 9
<212> TYPE: PRT
<213> ORGANISM: Artificial Sequence
<220> FEATURE:
<223> OTHER INFORMATION: Exemplary Trp-containing CAR sequences for
      atypical cadherins

<400> SEQUENCE: 125

Arg Gly Trp Val Trp Asn Gln Met Phe
1               5

<210> SEQ ID NO 126
<211> LENGTH: 10
<212> TYPE: PRT
<213> ORGANISM: Artificial Sequence
<220> FEATURE:
<223> OTHER INFORMATION: Exemplary Trp-containing CAR sequences for
      atypical cadherins

<400> SEQUENCE: 126

Arg Gly Trp Val Trp Asn Gln Met Phe Val
1               5                   10

<210> SEQ ID NO 127
<211> LENGTH: 9
<212> TYPE: PRT
<213> ORGANISM: Artificial Sequence
<220> FEATURE:
<223> OTHER INFORMATION: Exemplary Trp-containing CAR sequences for
      atypical cadherins

<400> SEQUENCE: 127

Lys Arg Gly Trp Val Trp Asn Gln Met
1               5

<210> SEQ ID NO 128
<211> LENGTH: 11
<212> TYPE: PRT
<213> ORGANISM: Artificial Sequence
<220> FEATURE:
<223> OTHER INFORMATION: Exemplary Trp-containing CAR sequences for
      atypical cadherins

<400> SEQUENCE: 128

Lys Arg Gly Trp Val Trp Asn Gln Met Phe Val
1               5                   10

<210> SEQ ID NO 129
<211> LENGTH: 9
<212> TYPE: PRT
<213> ORGANISM: Artificial Sequence
<220> FEATURE:
<223> OTHER INFORMATION: Exemplary Trp-containing CAR sequences for
      atypical cadherins

<400> SEQUENCE: 129

Gly Trp Val Trp Asn Gln Phe Phe Leu
1               5
```

```
<210> SEQ ID NO 130
<211> LENGTH: 10
<212> TYPE: PRT
<213> ORGANISM: Artificial Sequence
<220> FEATURE:
<223> OTHER INFORMATION: Exemplary Trp-containing CAR sequences for
      atypical cadherins

<400> SEQUENCE: 130

Arg Gly Trp Val Trp Asn Gln Phe Phe Leu
1               5                   10

<210> SEQ ID NO 131
<211> LENGTH: 11
<212> TYPE: PRT
<213> ORGANISM: Artificial Sequence
<220> FEATURE:
<223> OTHER INFORMATION: Exemplary Trp-containing CAR sequences for
      atypical cadherins

<400> SEQUENCE: 131

Lys Arg Gly Trp Val Trp Asn Gln Phe Phe Leu
1               5                   10

<210> SEQ ID NO 132
<211> LENGTH: 7
<212> TYPE: PRT
<213> ORGANISM: Artificial Sequence
<220> FEATURE:
<223> OTHER INFORMATION: Exemplary Trp-containing CAR sequences for
      atypical cadherins

<400> SEQUENCE: 132

Ala Trp Val Ile Pro Pro Ile
1               5

<210> SEQ ID NO 133
<211> LENGTH: 8
<212> TYPE: PRT
<213> ORGANISM: Artificial Sequence
<220> FEATURE:
<223> OTHER INFORMATION: Exemplary Trp-containing CAR sequences for
      atypical cadherins

<400> SEQUENCE: 133

Ala Trp Val Ile Pro Pro Ile Ser
1               5

<210> SEQ ID NO 134
<211> LENGTH: 9
<212> TYPE: PRT
<213> ORGANISM: Artificial Sequence
<220> FEATURE:
<223> OTHER INFORMATION: Exemplary Trp-containing CAR sequences for
      atypical cadherins

<400> SEQUENCE: 134

Ala Trp Val Ile Pro Pro Ile Ser Val
1               5

<210> SEQ ID NO 135
<211> LENGTH: 6
<212> TYPE: PRT
<213> ORGANISM: Artificial Sequence
<220> FEATURE:
<223> OTHER INFORMATION: Exemplary Trp-containing CAR sequences for
      atypical cadherins

<400> SEQUENCE: 135
```

```
Trp Val Ile Pro Pro Ile
1               5

<210> SEQ ID NO 136
<211> LENGTH: 7
<212> TYPE: PRT
<213> ORGANISM: Artificial Sequence
<220> FEATURE:
<223> OTHER INFORMATION: Exemplary Trp-containing CAR sequences for
      atypical cadherins

<400> SEQUENCE: 136

Trp Val Ile Pro Pro Ile Ser
1               5

<210> SEQ ID NO 137
<211> LENGTH: 8
<212> TYPE: PRT
<213> ORGANISM: Artificial Sequence
<220> FEATURE:
<223> OTHER INFORMATION: Exemplary Trp-containing CAR sequences for
      atypical cadherins

<400> SEQUENCE: 137

Trp Val Ile Pro Pro Ile Ser Val
1               5

<210> SEQ ID NO 138
<211> LENGTH: 4
<212> TYPE: PRT
<213> ORGANISM: Artificial Sequence
<220> FEATURE:
<223> OTHER INFORMATION: Exemplary Trp-containing CAR sequences for
      atypical cadherins

<400> SEQUENCE: 138

Arg Ala Trp Val
1

<210> SEQ ID NO 139
<211> LENGTH: 5
<212> TYPE: PRT
<213> ORGANISM: Artificial Sequence
<220> FEATURE:
<223> OTHER INFORMATION: Exemplary Trp-containing CAR sequences for
      atypical cadherins

<400> SEQUENCE: 139

Arg Ala Trp Val Ile
1               5

<210> SEQ ID NO 140
<211> LENGTH: 6
<212> TYPE: PRT
<213> ORGANISM: Artificial Sequence
<220> FEATURE:
<223> OTHER INFORMATION: Exemplary Trp-containing CAR sequences for
      atypical cadherins

<400> SEQUENCE: 140

Arg Ala Trp Val Ile Pro
1               5

<210> SEQ ID NO 141
<211> LENGTH: 7
<212> TYPE: PRT
<213> ORGANISM: Artificial Sequence
```

```
<220> FEATURE:
<223> OTHER INFORMATION: Exemplary Trp-containing CAR sequences for
      atypical cadherins

<400> SEQUENCE: 141

Arg Ala Trp Val Ile Pro Pro
 1               5

<210> SEQ ID NO 142
<211> LENGTH: 8
<212> TYPE: PRT
<213> ORGANISM: Artificial Sequence
<220> FEATURE:
<223> OTHER INFORMATION: Exemplary Trp-containing CAR sequences for
      atypical cadherins

<400> SEQUENCE: 142

Arg Ala Trp Val Ile Pro Pro Ile
 1               5

<210> SEQ ID NO 143
<211> LENGTH: 9
<212> TYPE: PRT
<213> ORGANISM: Artificial Sequence
<220> FEATURE:
<223> OTHER INFORMATION: Exemplary Trp-containing CAR sequences for
      atypical cadherins

<400> SEQUENCE: 143

Arg Ala Trp Val Ile Pro Pro Ile Ser
 1               5

<210> SEQ ID NO 144
<211> LENGTH: 10
<212> TYPE: PRT
<213> ORGANISM: Artificial Sequence
<220> FEATURE:
<223> OTHER INFORMATION: Exemplary Trp-containing CAR sequences for
      atypical cadherins

<400> SEQUENCE: 144

Arg Ala Trp Val Ile Pro Pro Ile Ser Val
 1               5                  10

<210> SEQ ID NO 145
<211> LENGTH: 4
<212> TYPE: PRT
<213> ORGANISM: Artificial Sequence
<220> FEATURE:
<223> OTHER INFORMATION: Exemplary Trp-containing CAR sequences for
      atypical cadherins

<400> SEQUENCE: 145

Lys Arg Ala Trp
 1

<210> SEQ ID NO 146
<211> LENGTH: 5
<212> TYPE: PRT
<213> ORGANISM: Artificial Sequence
<220> FEATURE:
<223> OTHER INFORMATION: Exemplary Trp-containing CAR sequences for
      atypical cadherins

<400> SEQUENCE: 146

Lys Arg Ala Trp Val
 1               5
```

<210> SEQ ID NO 147
<211> LENGTH: 6
<212> TYPE: PRT
<213> ORGANISM: Artificial Sequence
<220> FEATURE:
<223> OTHER INFORMATION: Exemplary Trp-containing CAR sequences for
      atypical cadherins

<400> SEQUENCE: 147

Lys Arg Ala Trp Val Ile
1               5

<210> SEQ ID NO 148
<211> LENGTH: 7
<212> TYPE: PRT
<213> ORGANISM: Artificial Sequence
<220> FEATURE:
<223> OTHER INFORMATION: Exemplary Trp-containing CAR sequences for
      atypical cadherins

<400> SEQUENCE: 148

Lys Arg Ala Trp Val Ile Pro
1               5

<210> SEQ ID NO 149
<211> LENGTH: 8
<212> TYPE: PRT
<213> ORGANISM: Artificial Sequence
<220> FEATURE:
<223> OTHER INFORMATION: Exemplary Trp-containing CAR sequences for
      atypical cadherins

<400> SEQUENCE: 149

Lys Arg Ala Trp Val Ile Pro Pro
1               5

<210> SEQ ID NO 150
<211> LENGTH: 9
<212> TYPE: PRT
<213> ORGANISM: Artificial Sequence
<220> FEATURE:
<223> OTHER INFORMATION: Exemplary Trp-containing CAR sequences for
      atypical cadherins

<400> SEQUENCE: 150

Lys Arg Ala Trp Val Ile Pro Pro Ile
1               5

<210> SEQ ID NO 151
<211> LENGTH: 10
<212> TYPE: PRT
<213> ORGANISM: Artificial Sequence
<220> FEATURE:
<223> OTHER INFORMATION: Exemplary Trp-containing CAR sequences for
      atypical cadherins

<400> SEQUENCE: 151

Lys Arg Ala Trp Val Ile Pro Pro Ile Ser
1               5                   10

<210> SEQ ID NO 152
<211> LENGTH: 4
<212> TYPE: PRT
<213> ORGANISM: Artificial Sequence
<220> FEATURE:
<223> OTHER INFORMATION: Exemplary Trp-containing CAR sequences for
      atypical cadherins

```
<400> SEQUENCE: 152

Val Trp Asn Gln
1

<210> SEQ ID NO 153
<211> LENGTH: 5
<212> TYPE: PRT
<213> ORGANISM: Artificial Sequence
<220> FEATURE:
<223> OTHER INFORMATION: Exemplary Trp-containing CAR sequences for
      atypical cadherins

<400> SEQUENCE: 153

Val Trp Asn Gln Met
1               5

<210> SEQ ID NO 154
<211> LENGTH: 5
<212> TYPE: PRT
<213> ORGANISM: Artificial Sequence
<220> FEATURE:
<223> OTHER INFORMATION: Exemplary Trp-containing CAR sequences for
      atypical cadherins

<400> SEQUENCE: 154

Val Trp Asn Gln Phe
1               5

<210> SEQ ID NO 155
<211> LENGTH: 6
<212> TYPE: PRT
<213> ORGANISM: Artificial Sequence
<220> FEATURE:
<223> OTHER INFORMATION: Exemplary Trp-containing CAR sequences for
      atypical cadherins

<400> SEQUENCE: 155

Val Trp Asn Gln Met Phe
1               5

<210> SEQ ID NO 156
<211> LENGTH: 6
<212> TYPE: PRT
<213> ORGANISM: Artificial Sequence
<220> FEATURE:
<223> OTHER INFORMATION: Exemplary Trp-containing CAR sequences for
      atypical cadherins

<400> SEQUENCE: 156

Val Trp Asn Gln Phe Phe
1               5

<210> SEQ ID NO 157
<211> LENGTH: 4
<212> TYPE: PRT
<213> ORGANISM: Artificial Sequence
<220> FEATURE:
<223> OTHER INFORMATION: Exemplary Trp-containing CAR sequences for
      atypical cadherins

<400> SEQUENCE: 157

Trp Asn Gln Met
1

<210> SEQ ID NO 158
<211> LENGTH: 4
<212> TYPE: PRT
```

```
<213> ORGANISM: Artificial Sequence
<220> FEATURE:
<223> OTHER INFORMATION: Exemplary Trp-containing CAR sequences for
      atypical cadherins

<400> SEQUENCE: 158

Trp Asn Gln Phe
 1

<210> SEQ ID NO 159
<211> LENGTH: 5
<212> TYPE: PRT
<213> ORGANISM: Artificial Sequence
<220> FEATURE:
<223> OTHER INFORMATION: Exemplary Trp-containing CAR sequences for
      atypical cadherins

<400> SEQUENCE: 159

Trp Asn Gln Phe Phe
 1               5

<210> SEQ ID NO 160
<211> LENGTH: 4
<212> TYPE: PRT
<213> ORGANISM: Artificial Sequence
<220> FEATURE:
<223> OTHER INFORMATION: Exemplary Trp-containing CAR sequences for
      atypical cadherins

<400> SEQUENCE: 160

Ile Trp Asn Gln
 1

<210> SEQ ID NO 161
<211> LENGTH: 5
<212> TYPE: PRT
<213> ORGANISM: Artificial Sequence
<220> FEATURE:
<223> OTHER INFORMATION: Exemplary Trp-containing CAR sequences for
      atypical cadherins

<400> SEQUENCE: 161

Ile Trp Asn Gln Met
 1               5

<210> SEQ ID NO 162
<211> LENGTH: 6
<212> TYPE: PRT
<213> ORGANISM: Artificial Sequence
<220> FEATURE:
<223> OTHER INFORMATION: Exemplary Trp-containing CAR sequences for
      atypical cadherins

<400> SEQUENCE: 162

Ile Trp Asn Gln Met His
 1               5

<210> SEQ ID NO 163
<211> LENGTH: 5
<212> TYPE: PRT
<213> ORGANISM: Artificial Sequence
<220> FEATURE:
<223> OTHER INFORMATION: Exemplary Trp-containing CAR sequences for
      atypical cadherins

<400> SEQUENCE: 163

Trp Asn Gln Met His
 1               5
```

```
<210> SEQ ID NO 164
<211> LENGTH: 4
<212> TYPE: PRT
<213> ORGANISM: Artificial Sequence
<220> FEATURE:
<223> OTHER INFORMATION: Exemplary Trp-containing CAR sequences for
      atypical cadherins

<400> SEQUENCE: 164

Met Trp Asn Gln
  1

<210> SEQ ID NO 165
<211> LENGTH: 5
<212> TYPE: PRT
<213> ORGANISM: Artificial Sequence
<220> FEATURE:
<223> OTHER INFORMATION: Exemplary Trp-containing CAR sequences for
      atypical cadherins

<400> SEQUENCE: 165

Met Trp Asn Gln Phe
  1               5

<210> SEQ ID NO 166
<211> LENGTH: 6
<212> TYPE: PRT
<213> ORGANISM: Artificial Sequence
<220> FEATURE:
<223> OTHER INFORMATION: Exemplary Trp-containing CAR sequences for
      atypical cadherins

<400> SEQUENCE: 166

Met Trp Asn Gln Phe Phe
  1               5

<210> SEQ ID NO 167
<211> LENGTH: 6
<212> TYPE: PRT
<213> ORGANISM: Artificial Sequence
<220> FEATURE:
<223> OTHER INFORMATION: Consensus sequence shared by certain desmosomal
      cadherin Trp-containing CAR sequence
<220> FEATURE:
<221> NAME/KEY: VARIANT
<222> LOCATION: 1
<223> OTHER INFORMATION: Xaa = Glu, Ala or Arg
<220> FEATURE:
<221> NAME/KEY: VARIANT
<222> LOCATION: 3
<223> OTHER INFORMATION: Xaa = Ile, Val or Ala
<220> FEATURE:
<221> NAME/KEY: VARIANT
<222> LOCATION: 4
<223> OTHER INFORMATION: Xaa = Lys, Thr or Pro
<220> FEATURE:
<221> NAME/KEY: VARIANT
<222> LOCATION: 5
<223> OTHER INFORMATION: Xaa = Phe, Ala or Ile
<220> FEATURE:
<221> NAME/KEY: VARIANT
<222> LOCATION: 6
<223> OTHER INFORMATION: Xaa = Ala or Pro

<400> SEQUENCE: 167

Xaa Trp Xaa Xaa Xaa Xaa
  1               5

<210> SEQ ID NO 168
```

```
<211> LENGTH: 6
<212> TYPE: PRT
<213> ORGANISM: Artificial Sequence
<220> FEATURE:
<223> OTHER INFORMATION: Representative desmosomal cadherin
      Trp-containing CAR sequence

<400> SEQUENCE: 168

Glu Trp Ile Lys Phe Ala
 1               5

<210> SEQ ID NO 169
<211> LENGTH: 6
<212> TYPE: PRT
<213> ORGANISM: Artificial Sequence
<220> FEATURE:
<223> OTHER INFORMATION: Representative desmosomal cadherin
      Trp-containing CAR sequence

<400> SEQUENCE: 169

Ala Trp Ile Thr Ala Pro
 1               5

<210> SEQ ID NO 170
<211> LENGTH: 6
<212> TYPE: PRT
<213> ORGANISM: Artificial Sequence
<220> FEATURE:
<223> OTHER INFORMATION: Representative desmosomal cadherin
      Trp-containing CAR sequence

<400> SEQUENCE: 170

Glu Trp Val Lys Phe Ala
 1               5

<210> SEQ ID NO 171
<211> LENGTH: 4
<212> TYPE: PRT
<213> ORGANISM: Artificial Sequence
<220> FEATURE:
<223> OTHER INFORMATION: Exemplary desmosomal Trp-containing CAR
      sequence

<400> SEQUENCE: 171

Arg Trp Ala Pro
 1

<210> SEQ ID NO 172
<211> LENGTH: 5
<212> TYPE: PRT
<213> ORGANISM: Artificial Sequence
<220> FEATURE:
<223> OTHER INFORMATION: Exemplary desmosomal Trp-containing CAR
      sequence

<400> SEQUENCE: 172

Arg Trp Ala Pro Ile
 1               5

<210> SEQ ID NO 173
<211> LENGTH: 7
<212> TYPE: PRT
<213> ORGANISM: Artificial Sequence
<220> FEATURE:
<223> OTHER INFORMATION: Exemplary desmosomal Trp-containing CAR
      sequence

<400> SEQUENCE: 173
```

```
Arg Trp Ala Pro Ile Pro Cys
1               5

<210> SEQ ID NO 174
<211> LENGTH: 8
<212> TYPE: PRT
<213> ORGANISM: Artificial Sequence
<220> FEATURE:
<223> OTHER INFORMATION: Exemplary desmosomal Trp-containing CAR
      sequence

<400> SEQUENCE: 174

Arg Trp Ala Pro Ile Pro Cys Ser
1               5

<210> SEQ ID NO 175
<211> LENGTH: 9
<212> TYPE: PRT
<213> ORGANISM: Artificial Sequence
<220> FEATURE:
<223> OTHER INFORMATION: Exemplary desmosomal Trp-containing CAR
      sequence

<400> SEQUENCE: 175

Arg Trp Ala Pro Ile Pro Cys Ser Met
1               5

<210> SEQ ID NO 176
<211> LENGTH: 4
<212> TYPE: PRT
<213> ORGANISM: Artificial Sequence
<220> FEATURE:
<223> OTHER INFORMATION: Exemplary desmosomal Trp-containing CAR
      sequence

<400> SEQUENCE: 176

Trp Ala Pro Ile
1

<210> SEQ ID NO 177
<211> LENGTH: 5
<212> TYPE: PRT
<213> ORGANISM: Artificial Sequence
<220> FEATURE:
<223> OTHER INFORMATION: Exemplary desmosomal Trp-containing CAR
      sequence

<400> SEQUENCE: 177

Trp Ala Pro Ile Pro
1               5

<210> SEQ ID NO 178
<211> LENGTH: 6
<212> TYPE: PRT
<213> ORGANISM: Artificial Sequence
<220> FEATURE:
<223> OTHER INFORMATION: Exemplary desmosomal Trp-containing CAR
      sequence

<400> SEQUENCE: 178

Trp Ala Pro Ile Pro Cys
1               5

<210> SEQ ID NO 179
<211> LENGTH: 7
<212> TYPE: PRT
<213> ORGANISM: Artificial Sequence
<220> FEATURE:
```

```
<223> OTHER INFORMATION: Exemplary desmosomal Trp-containing CAR
      sequence

<400> SEQUENCE: 179

Trp Ala Pro Ile Pro Cys Ser
 1               5

<210> SEQ ID NO 180
<211> LENGTH: 8
<212> TYPE: PRT
<213> ORGANISM: Artificial Sequence
<220> FEATURE:
<223> OTHER INFORMATION: Exemplary desmosomal Trp-containing CAR
      sequence

<400> SEQUENCE: 180

Trp Ala Pro Ile Pro Cys Ser Met
 1               5

<210> SEQ ID NO 181
<211> LENGTH: 9
<212> TYPE: PRT
<213> ORGANISM: Artificial Sequence
<220> FEATURE:
<223> OTHER INFORMATION: Exemplary desmosomal Trp-containing CAR
      sequence

<400> SEQUENCE: 181

Arg Trp Ala Pro Ile Pro Cys Ser Leu
 1               5

<210> SEQ ID NO 182
<211> LENGTH: 8
<212> TYPE: PRT
<213> ORGANISM: Artificial Sequence
<220> FEATURE:
<223> OTHER INFORMATION: Exemplary desmosomal Trp-containing CAR
      sequence

<400> SEQUENCE: 182

Trp Ala Pro Ile Pro Cys Ser Leu
 1               5

<210> SEQ ID NO 183
<211> LENGTH: 8
<212> TYPE: PRT
<213> ORGANISM: Artificial Sequence
<220> FEATURE:
<223> OTHER INFORMATION: Exemplary desmosomal Trp-containing CAR
      sequence

<400> SEQUENCE: 183

Arg Trp Ala Pro Ile Pro Cys Ala
 1               5

<210> SEQ ID NO 184
<211> LENGTH: 7
<212> TYPE: PRT
<213> ORGANISM: Artificial Sequence
<220> FEATURE:
<223> OTHER INFORMATION: Exemplary desmosomal Trp-containing CAR
      sequence

<400> SEQUENCE: 184

Trp Ala Pro Ile Pro Cys Ala
 1               5
```

```
<210> SEQ ID NO 185
<211> LENGTH: 9
<212> TYPE: PRT
<213> ORGANISM: Artificial Sequence
<220> FEATURE:
<223> OTHER INFORMATION: Exemplary desmosomal Trp-containing CAR
      sequence

<400> SEQUENCE: 185

Arg Trp Ala Pro Ile Pro Cys Ala Ser
 1               5

<210> SEQ ID NO 186
<211> LENGTH: 8
<212> TYPE: PRT
<213> ORGANISM: Artificial Sequence
<220> FEATURE:
<223> OTHER INFORMATION: Exemplary desmosomal Trp-containing CAR
      sequence

<400> SEQUENCE: 186

Trp Ala Pro Ile Pro Cys Ala Ser
 1               5

<210> SEQ ID NO 187
<211> LENGTH: 4
<212> TYPE: PRT
<213> ORGANISM: Artificial Sequence
<220> FEATURE:
<223> OTHER INFORMATION: Exemplary desmosomal Trp-containing CAR
      sequence

<400> SEQUENCE: 187

Glu Trp Ile Lys
 1

<210> SEQ ID NO 188
<211> LENGTH: 5
<212> TYPE: PRT
<213> ORGANISM: Artificial Sequence
<220> FEATURE:
<223> OTHER INFORMATION: Exemplary desmosomal Trp-containing CAR
      sequence

<400> SEQUENCE: 188

Glu Trp Ile Lys Phe
 1               5

<210> SEQ ID NO 189
<211> LENGTH: 7
<212> TYPE: PRT
<213> ORGANISM: Artificial Sequence
<220> FEATURE:
<223> OTHER INFORMATION: Exemplary desmosomal Trp-containing CAR
      sequence

<400> SEQUENCE: 189

Glu Trp Ile Lys Phe Ala Ala
 1               5

<210> SEQ ID NO 190
<211> LENGTH: 8
<212> TYPE: PRT
<213> ORGANISM: Artificial Sequence
<220> FEATURE:
<223> OTHER INFORMATION: Exemplary desmosomal Trp-containing CAR
      sequence

<400> SEQUENCE: 190
```

```
Glu Trp Ile Lys Phe Ala Ala Ala
1               5
```

<210> SEQ ID NO 191
<211> LENGTH: 9
<212> TYPE: PRT
<213> ORGANISM: Artificial Sequence
<220> FEATURE:
<223> OTHER INFORMATION: Exemplary desmosomal Trp-containing CAR
      sequence

<400> SEQUENCE: 191

```
Glu Trp Ile Lys Phe Ala Ala Ala Cys
1               5
```

<210> SEQ ID NO 192
<211> LENGTH: 4
<212> TYPE: PRT
<213> ORGANISM: Artificial Sequence
<220> FEATURE:
<223> OTHER INFORMATION: Exemplary desmosomal Trp-containing CAR
      sequence

<400> SEQUENCE: 192

```
Trp Ile Lys Phe
1
```

<210> SEQ ID NO 193
<211> LENGTH: 5
<212> TYPE: PRT
<213> ORGANISM: Artificial Sequence
<220> FEATURE:
<223> OTHER INFORMATION: Exemplary desmosomal Trp-containing CAR
      sequence

<400> SEQUENCE: 193

```
Trp Ile Lys Phe Ala
1               5
```

<210> SEQ ID NO 194
<211> LENGTH: 6
<212> TYPE: PRT
<213> ORGANISM: Artificial Sequence
<220> FEATURE:
<223> OTHER INFORMATION: Exemplary desmosomal Trp-containing CAR
      sequence

<400> SEQUENCE: 194

```
Trp Ile Lys Phe Ala Ala
1               5
```

<210> SEQ ID NO 195
<211> LENGTH: 7
<212> TYPE: PRT
<213> ORGANISM: Artificial Sequence
<220> FEATURE:
<223> OTHER INFORMATION: Exemplary desmosomal Trp-containing CAR
      sequence

<400> SEQUENCE: 195

```
Trp Ile Lys Phe Ala Ala Ala
1               5
```

<210> SEQ ID NO 196
<211> LENGTH: 8
<212> TYPE: PRT
<213> ORGANISM: Artificial Sequence

```
<220> FEATURE:
<223> OTHER INFORMATION: Exemplary desmosomal Trp-containing CAR
      sequence

<400> SEQUENCE: 196

Trp Ile Lys Phe Ala Ala Ala Cys
1               5

<210> SEQ ID NO 197
<211> LENGTH: 4
<212> TYPE: PRT
<213> ORGANISM: Artificial Sequence
<220> FEATURE:
<223> OTHER INFORMATION: Exemplary desmosomal Trp-containing CAR
      sequence

<400> SEQUENCE: 197

Glu Trp Val Lys
1

<210> SEQ ID NO 198
<211> LENGTH: 5
<212> TYPE: PRT
<213> ORGANISM: Artificial Sequence
<220> FEATURE:
<223> OTHER INFORMATION: Exemplary desmosomal Trp-containing CAR
      sequence

<400> SEQUENCE: 198

Glu Trp Val Lys Phe
1               5

<210> SEQ ID NO 199
<211> LENGTH: 7
<212> TYPE: PRT
<213> ORGANISM: Artificial Sequence
<220> FEATURE:
<223> OTHER INFORMATION: Exemplary desmosomal Trp-containing CAR
      sequence

<400> SEQUENCE: 199

Glu Trp Val Lys Phe Ala Lys
1               5

<210> SEQ ID NO 200
<211> LENGTH: 8
<212> TYPE: PRT
<213> ORGANISM: Artificial Sequence
<220> FEATURE:
<223> OTHER INFORMATION: Exemplary desmosomal Trp-containing CAR
      sequence

<400> SEQUENCE: 200

Glu Trp Val Lys Phe Ala Lys Pro
1               5

<210> SEQ ID NO 201
<211> LENGTH: 9
<212> TYPE: PRT
<213> ORGANISM: Artificial Sequence
<220> FEATURE:
<223> OTHER INFORMATION: Exemplary desmosomal Trp-containing CAR
      sequence

<400> SEQUENCE: 201

Glu Trp Val Lys Phe Ala Lys Pro Cys
1               5
```

```
<210> SEQ ID NO 202
<211> LENGTH: 4
<212> TYPE: PRT
<213> ORGANISM: Artificial Sequence
<220> FEATURE:
<223> OTHER INFORMATION: Exemplary desmosomal Trp-containing CAR
      sequence

<400> SEQUENCE: 202

Trp Val Lys Phe
 1

<210> SEQ ID NO 203
<211> LENGTH: 5
<212> TYPE: PRT
<213> ORGANISM: Artificial Sequence
<220> FEATURE:
<223> OTHER INFORMATION: Exemplary desmosomal Trp-containing CAR
      sequence

<400> SEQUENCE: 203

Trp Val Lys Phe Ala
 1               5

<210> SEQ ID NO 204
<211> LENGTH: 6
<212> TYPE: PRT
<213> ORGANISM: Artificial Sequence
<220> FEATURE:
<223> OTHER INFORMATION: Exemplary desmosomal Trp-containing CAR
      sequence

<400> SEQUENCE: 204

Trp Val Lys Phe Ala Lys
 1               5

<210> SEQ ID NO 205
<211> LENGTH: 7
<212> TYPE: PRT
<213> ORGANISM: Artificial Sequence
<220> FEATURE:
<223> OTHER INFORMATION: Exemplary desmosomal Trp-containing CAR
      sequence

<400> SEQUENCE: 205

Trp Val Lys Phe Ala Lys Pro
 1               5

<210> SEQ ID NO 206
<211> LENGTH: 8
<212> TYPE: PRT
<213> ORGANISM: Artificial Sequence
<220> FEATURE:
<223> OTHER INFORMATION: Exemplary desmosomal Trp-containing CAR
      sequence

<400> SEQUENCE: 206

Trp Val Lys Phe Ala Lys Pro Cys
 1               5

<210> SEQ ID NO 207
<211> LENGTH: 4
<212> TYPE: PRT
<213> ORGANISM: Artificial Sequence
<220> FEATURE:
<223> OTHER INFORMATION: Exemplary desmosomal Trp-containing CAR
      sequence
```

```
<400> SEQUENCE: 207

Ala Trp Ile Thr
 1

<210> SEQ ID NO 208
<211> LENGTH: 5
<212> TYPE: PRT
<213> ORGANISM: Artificial Sequence
<220> FEATURE:
<223> OTHER INFORMATION: Exemplary desmosomal Trp-containing CAR
      sequence

<400> SEQUENCE: 208

Ala Trp Ile Thr Ala
 1               5

<210> SEQ ID NO 209
<211> LENGTH: 7
<212> TYPE: PRT
<213> ORGANISM: Artificial Sequence
<220> FEATURE:
<223> OTHER INFORMATION: Exemplary desmosomal Trp-containing CAR
      sequence

<400> SEQUENCE: 209

Ala Trp Ile Thr Ala Pro Val
 1               5

<210> SEQ ID NO 210
<211> LENGTH: 8
<212> TYPE: PRT
<213> ORGANISM: Artificial Sequence
<220> FEATURE:
<223> OTHER INFORMATION: Exemplary desmosomal Trp-containing CAR
      sequence

<400> SEQUENCE: 210

Ala Trp Ile Thr Ala Pro Val Ala
 1               5

<210> SEQ ID NO 211
<211> LENGTH: 9
<212> TYPE: PRT
<213> ORGANISM: Artificial Sequence
<220> FEATURE:
<223> OTHER INFORMATION: Exemplary desmosomal Trp-containing CAR
      sequence

<400> SEQUENCE: 211

Ala Trp Ile Thr Ala Pro Val Ala Leu
 1               5

<210> SEQ ID NO 212
<211> LENGTH: 4
<212> TYPE: PRT
<213> ORGANISM: Artificial Sequence
<220> FEATURE:
<223> OTHER INFORMATION: Exemplary desmosomal Trp-containing CAR
      sequence

<400> SEQUENCE: 212

Trp Ile Thr Ala
 1

<210> SEQ ID NO 213
<211> LENGTH: 5
<212> TYPE: PRT
```

```
<213> ORGANISM: Artificial Sequence
<220> FEATURE:
<223> OTHER INFORMATION: Exemplary desmosomal Trp-containing CAR
      sequence

<400> SEQUENCE: 213

Trp Ile Thr Ala Pro
1               5

<210> SEQ ID NO 214
<211> LENGTH: 6
<212> TYPE: PRT
<213> ORGANISM: Artificial Sequence
<220> FEATURE:
<223> OTHER INFORMATION: Exemplary desmosomal Trp-containing CAR
      sequence

<400> SEQUENCE: 214

Trp Ile Thr Ala Pro Val
1               5

<210> SEQ ID NO 215
<211> LENGTH: 7
<212> TYPE: PRT
<213> ORGANISM: Artificial Sequence
<220> FEATURE:
<223> OTHER INFORMATION: Exemplary desmosomal Trp-containing CAR
      sequence

<400> SEQUENCE: 215

Trp Ile Thr Ala Pro Val Ala
1               5

<210> SEQ ID NO 216
<211> LENGTH: 8
<212> TYPE: PRT
<213> ORGANISM: Artificial Sequence
<220> FEATURE:
<223> OTHER INFORMATION: Exemplary desmosomal Trp-containing CAR
      sequence

<400> SEQUENCE: 216

Trp Ile Thr Ala Pro Val Ala Leu
1               5

<210> SEQ ID NO 217
<211> LENGTH: 5
<212> TYPE: PRT
<213> ORGANISM: Artificial Sequence
<220> FEATURE:
<223> OTHER INFORMATION: Exemplary cyclic peptide

<400> SEQUENCE: 217

Cys Gly Trp Val Cys
1               5

<210> SEQ ID NO 218
<211> LENGTH: 6
<212> TYPE: PRT
<213> ORGANISM: Artificial Sequence
<220> FEATURE:
<223> OTHER INFORMATION: Exemplary cyclic peptide

<400> SEQUENCE: 218

Cys Gly Trp Val Trp Cys
1               5
```

```
<210> SEQ ID NO 219
<211> LENGTH: 7
<212> TYPE: PRT
<213> ORGANISM: Artificial Sequence
<220> FEATURE:
<223> OTHER INFORMATION: Exemplary cyclic peptide

<400> SEQUENCE: 219

Cys Gly Trp Val Trp Asn Cys
1               5

<210> SEQ ID NO 220
<211> LENGTH: 8
<212> TYPE: PRT
<213> ORGANISM: Artificial Sequence
<220> FEATURE:
<223> OTHER INFORMATION: Exemplary cyclic peptide

<400> SEQUENCE: 220

Cys Gly Trp Val Trp Asn Gln Cys
1               5

<210> SEQ ID NO 221
<211> LENGTH: 5
<212> TYPE: PRT
<213> ORGANISM: Artificial Sequence
<220> FEATURE:
<223> OTHER INFORMATION: Exemplary cyclic peptide

<400> SEQUENCE: 221

Cys Trp Val Trp Cys
1               5

<210> SEQ ID NO 222
<211> LENGTH: 6
<212> TYPE: PRT
<213> ORGANISM: Artificial Sequence
<220> FEATURE:
<223> OTHER INFORMATION: Exemplary cyclic peptide

<400> SEQUENCE: 222

Cys Trp Val Trp Asn Cys
1               5

<210> SEQ ID NO 223
<211> LENGTH: 7
<212> TYPE: PRT
<213> ORGANISM: Artificial Sequence
<220> FEATURE:
<223> OTHER INFORMATION: Exemplary cyclic peptide

<400> SEQUENCE: 223

Cys Trp Val Trp Asn Gln Cys
1               5

<210> SEQ ID NO 224
<211> LENGTH: 5
<212> TYPE: PRT
<213> ORGANISM: Artificial Sequence
<220> FEATURE:
<223> OTHER INFORMATION: Exemplary cyclic peptide

<400> SEQUENCE: 224

Cys Asp Trp Ile Cys
1               5

<210> SEQ ID NO 225
```

```
<211> LENGTH: 6
<212> TYPE: PRT
<213> ORGANISM: Artificial Sequence
<220> FEATURE:
<223> OTHER INFORMATION: Exemplary cyclic peptide

<400> SEQUENCE: 225

Cys Asp Trp Ile Trp Cys
1               5

<210> SEQ ID NO 226
<211> LENGTH: 7
<212> TYPE: PRT
<213> ORGANISM: Artificial Sequence
<220> FEATURE:
<223> OTHER INFORMATION: Exemplary cyclic peptide

<400> SEQUENCE: 226

Cys Asp Trp Ile Trp Asn Cys
1               5

<210> SEQ ID NO 227
<211> LENGTH: 8
<212> TYPE: PRT
<213> ORGANISM: Artificial Sequence
<220> FEATURE:
<223> OTHER INFORMATION: Exemplary cyclic peptide

<400> SEQUENCE: 227

Cys Asp Trp Ile Trp Asn Gln Cys
1               5

<210> SEQ ID NO 228
<211> LENGTH: 5
<212> TYPE: PRT
<213> ORGANISM: Artificial Sequence
<220> FEATURE:
<223> OTHER INFORMATION: Exemplary cyclic peptide

<400> SEQUENCE: 228

Cys Trp Ile Trp Cys
1               5

<210> SEQ ID NO 229
<211> LENGTH: 6
<212> TYPE: PRT
<213> ORGANISM: Artificial Sequence
<220> FEATURE:
<223> OTHER INFORMATION: Exemplary cyclic peptide

<400> SEQUENCE: 229

Cys Trp Ile Trp Asn Cys
1               5

<210> SEQ ID NO 230
<211> LENGTH: 7
<212> TYPE: PRT
<213> ORGANISM: Artificial Sequence
<220> FEATURE:
<223> OTHER INFORMATION: Exemplary cyclic peptide

<400> SEQUENCE: 230

Cys Trp Ile Trp Asn Gln Cys
1               5

<210> SEQ ID NO 231
<211> LENGTH: 5
```

```
<212> TYPE: PRT
<213> ORGANISM: Artificial Sequence
<220> FEATURE:
<223> OTHER INFORMATION: Exemplary cyclic peptide

<400> SEQUENCE: 231

Cys Ser Trp Met Cys
1               5

<210> SEQ ID NO 232
<211> LENGTH: 6
<212> TYPE: PRT
<213> ORGANISM: Artificial Sequence
<220> FEATURE:
<223> OTHER INFORMATION: Exemplary cyclic peptide

<400> SEQUENCE: 232

Cys Ser Trp Met Trp Cys
1               5

<210> SEQ ID NO 233
<211> LENGTH: 7
<212> TYPE: PRT
<213> ORGANISM: Artificial Sequence
<220> FEATURE:
<223> OTHER INFORMATION: Exemplary cyclic peptide

<400> SEQUENCE: 233

Cys Ser Trp Met Trp Asn Cys
1               5

<210> SEQ ID NO 234
<211> LENGTH: 8
<212> TYPE: PRT
<213> ORGANISM: Artificial Sequence
<220> FEATURE:
<223> OTHER INFORMATION: Exemplary cyclic peptide

<400> SEQUENCE: 234

Cys Ser Trp Met Trp Asn Gln Cys
1               5

<210> SEQ ID NO 235
<211> LENGTH: 5
<212> TYPE: PRT
<213> ORGANISM: Artificial Sequence
<220> FEATURE:
<223> OTHER INFORMATION: Exemplary cyclic peptide

<400> SEQUENCE: 235

Cys Trp Met Trp Cys
1               5

<210> SEQ ID NO 236
<211> LENGTH: 6
<212> TYPE: PRT
<213> ORGANISM: Artificial Sequence
<220> FEATURE:
<223> OTHER INFORMATION: Exemplary cyclic peptide

<400> SEQUENCE: 236

Cys Trp Met Trp Asn Cys
1               5

<210> SEQ ID NO 237
<211> LENGTH: 7
<212> TYPE: PRT
```

```
<213> ORGANISM: Artificial Sequence
<220> FEATURE:
<223> OTHER INFORMATION: Exemplary cyclic peptide

<400> SEQUENCE: 237

Cys Trp Met Trp Asn Gln Cys
 1               5

<210> SEQ ID NO 238
<211> LENGTH: 5
<212> TYPE: PRT
<213> ORGANISM: Artificial Sequence
<220> FEATURE:
<223> OTHER INFORMATION: Exemplary cyclic peptide

<400> SEQUENCE: 238

Cys Ser Trp Val Cys
 1               5

<210> SEQ ID NO 239
<211> LENGTH: 6
<212> TYPE: PRT
<213> ORGANISM: Artificial Sequence
<220> FEATURE:
<223> OTHER INFORMATION: Exemplary cyclic peptide

<400> SEQUENCE: 239

Cys Ser Trp Val Trp Cys
 1               5

<210> SEQ ID NO 240
<211> LENGTH: 7
<212> TYPE: PRT
<213> ORGANISM: Artificial Sequence
<220> FEATURE:
<223> OTHER INFORMATION: Exemplary cyclic peptide

<400> SEQUENCE: 240

Cys Ser Trp Val Trp Asn Cys
 1               5

<210> SEQ ID NO 241
<211> LENGTH: 8
<212> TYPE: PRT
<213> ORGANISM: Artificial Sequence
<220> FEATURE:
<223> OTHER INFORMATION: Exemplary cyclic peptide

<400> SEQUENCE: 241

Cys Ser Trp Val Trp Asn Gln Cys
 1               5

<210> SEQ ID NO 242
<211> LENGTH: 5
<212> TYPE: PRT
<213> ORGANISM: Artificial Sequence
<220> FEATURE:
<223> OTHER INFORMATION: Exemplary cyclic peptide

<400> SEQUENCE: 242

Cys Gly Trp Met Cys
 1               5

<210> SEQ ID NO 243
<211> LENGTH: 6
<212> TYPE: PRT
<213> ORGANISM: Artificial Sequence
```

```
<220> FEATURE:
<223> OTHER INFORMATION: Exemplary cyclic peptide

<400> SEQUENCE: 243

Cys Gly Trp Met Trp Cys
1               5

<210> SEQ ID NO 244
<211> LENGTH: 7
<212> TYPE: PRT
<213> ORGANISM: Artificial Sequence
<220> FEATURE:
<223> OTHER INFORMATION: Exemplary cyclic peptide

<400> SEQUENCE: 244

Cys Gly Trp Met Trp Asn Cys
1               5

<210> SEQ ID NO 245
<211> LENGTH: 8
<212> TYPE: PRT
<213> ORGANISM: Artificial Sequence
<220> FEATURE:
<223> OTHER INFORMATION: Exemplary cyclic peptide

<400> SEQUENCE: 245

Cys Gly Trp Met Trp Asn Gln Cys
1               5

<210> SEQ ID NO 246
<211> LENGTH: 5
<212> TYPE: PRT
<213> ORGANISM: Artificial Sequence
<220> FEATURE:
<223> OTHER INFORMATION: Exemplary cyclic peptide

<400> SEQUENCE: 246

Cys Ala Trp Val Cys
1               5

<210> SEQ ID NO 247
<211> LENGTH: 6
<212> TYPE: PRT
<213> ORGANISM: Artificial Sequence
<220> FEATURE:
<223> OTHER INFORMATION: Exemplary cyclic peptide

<400> SEQUENCE: 247

Cys Ala Trp Val Ile Cys
1               5

<210> SEQ ID NO 248
<211> LENGTH: 7
<212> TYPE: PRT
<213> ORGANISM: Artificial Sequence
<220> FEATURE:
<223> OTHER INFORMATION: Exemplary cyclic peptide

<400> SEQUENCE: 248

Cys Ala Trp Val Ile Pro Cys
1               5

<210> SEQ ID NO 249
<211> LENGTH: 8
<212> TYPE: PRT
<213> ORGANISM: Artificial Sequence
<220> FEATURE:
```

```
<223> OTHER INFORMATION: Exemplary cyclic peptide

<400> SEQUENCE: 249

Cys Ala Trp Val Ile Pro Pro Cys
 1               5

<210> SEQ ID NO 250
<211> LENGTH: 5
<212> TYPE: PRT
<213> ORGANISM: Artificial Sequence
<220> FEATURE:
<223> OTHER INFORMATION: Exemplary cyclic peptide

<400> SEQUENCE: 250

Cys Trp Val Ile Cys
 1               5

<210> SEQ ID NO 251
<211> LENGTH: 6
<212> TYPE: PRT
<213> ORGANISM: Artificial Sequence
<220> FEATURE:
<223> OTHER INFORMATION: Exemplary cyclic peptide

<400> SEQUENCE: 251

Cys Trp Val Ile Pro Cys
 1               5

<210> SEQ ID NO 252
<211> LENGTH: 7
<212> TYPE: PRT
<213> ORGANISM: Artificial Sequence
<220> FEATURE:
<223> OTHER INFORMATION: Exemplary cyclic peptide

<400> SEQUENCE: 252

Cys Trp Val Ile Pro Pro Cys
 1               5

<210> SEQ ID NO 253
<211> LENGTH: 9
<212> TYPE: PRT
<213> ORGANISM: Artificial Sequence
<220> FEATURE:
<223> OTHER INFORMATION: Exemplary cyclic peptide

<400> SEQUENCE: 253

Cys Gly Trp Val Trp Asn Gln Phe Cys
 1               5

<210> SEQ ID NO 254
<211> LENGTH: 10
<212> TYPE: PRT
<213> ORGANISM: Artificial Sequence
<220> FEATURE:
<223> OTHER INFORMATION: Exemplary cyclic peptide

<400> SEQUENCE: 254

Cys Gly Trp Val Trp Asn Gln Phe Phe Cys
 1               5                  10

<210> SEQ ID NO 255
<211> LENGTH: 11
<212> TYPE: PRT
<213> ORGANISM: Artificial Sequence
<220> FEATURE:
<223> OTHER INFORMATION: Exemplary cyclic peptide
```

<400> SEQUENCE: 255

Cys Gly Trp Val Trp Asn Gln Phe Phe Val Cys
1               5                   10

<210> SEQ ID NO 256
<211> LENGTH: 8
<212> TYPE: PRT
<213> ORGANISM: Artificial Sequence
<220> FEATURE:
<223> OTHER INFORMATION: Exemplary cyclic peptide

<400> SEQUENCE: 256

Cys Trp Val Trp Asn Gln Phe Cys
1               5

<210> SEQ ID NO 257
<211> LENGTH: 9
<212> TYPE: PRT
<213> ORGANISM: Artificial Sequence
<220> FEATURE:
<223> OTHER INFORMATION: Exemplary cyclic peptide

<400> SEQUENCE: 257

Cys Trp Val Trp Asn Gln Phe Phe Cys
1               5

<210> SEQ ID NO 258
<211> LENGTH: 10
<212> TYPE: PRT
<213> ORGANISM: Artificial Sequence
<220> FEATURE:
<223> OTHER INFORMATION: Exemplary cyclic peptide

<400> SEQUENCE: 258

Cys Trp Val Trp Asn Gln Phe Phe Val Cys
1               5                   10

<210> SEQ ID NO 259
<211> LENGTH: 5
<212> TYPE: PRT
<213> ORGANISM: Artificial Sequence
<220> FEATURE:
<223> OTHER INFORMATION: Exemplary cyclic peptide

<400> SEQUENCE: 259

Cys Arg Gly Trp Cys
1               5

<210> SEQ ID NO 260
<211> LENGTH: 6
<212> TYPE: PRT
<213> ORGANISM: Artificial Sequence
<220> FEATURE:
<223> OTHER INFORMATION: Exemplary cyclic peptide

<400> SEQUENCE: 260

Cys Arg Gly Trp Val Cys
1               5

<210> SEQ ID NO 261
<211> LENGTH: 7
<212> TYPE: PRT
<213> ORGANISM: Artificial Sequence
<220> FEATURE:
<223> OTHER INFORMATION: Exemplary cyclic peptide

```
<400> SEQUENCE: 261

Cys Arg Gly Trp Val Trp Cys
1               5

<210> SEQ ID NO 262
<211> LENGTH: 8
<212> TYPE: PRT
<213> ORGANISM: Artificial Sequence
<220> FEATURE:
<223> OTHER INFORMATION: Exemplary cyclic peptide

<400> SEQUENCE: 262

Cys Arg Gly Trp Val Trp Asn Cys
1               5

<210> SEQ ID NO 263
<211> LENGTH: 9
<212> TYPE: PRT
<213> ORGANISM: Artificial Sequence
<220> FEATURE:
<223> OTHER INFORMATION: Exemplary cyclic peptide

<400> SEQUENCE: 263

Cys Arg Gly Trp Val Trp Asn Gln Cys
1               5

<210> SEQ ID NO 264
<211> LENGTH: 10
<212> TYPE: PRT
<213> ORGANISM: Artificial Sequence
<220> FEATURE:
<223> OTHER INFORMATION: Exemplary cyclic peptide

<400> SEQUENCE: 264

Cys Arg Gly Trp Val Trp Asn Gln Phe Cys
1               5                   10

<210> SEQ ID NO 265
<211> LENGTH: 11
<212> TYPE: PRT
<213> ORGANISM: Artificial Sequence
<220> FEATURE:
<223> OTHER INFORMATION: Exemplary cyclic peptide

<400> SEQUENCE: 265

Cys Arg Gly Trp Val Trp Asn Gln Phe Phe Cys
1               5                   10

<210> SEQ ID NO 266
<211> LENGTH: 12
<212> TYPE: PRT
<213> ORGANISM: Artificial Sequence
<220> FEATURE:
<223> OTHER INFORMATION: Exemplary cyclic peptide

<400> SEQUENCE: 266

Cys Arg Gly Trp Val Trp Asn Gln Phe Phe Val Cys
1               5                   10

<210> SEQ ID NO 267
<211> LENGTH: 6
<212> TYPE: PRT
<213> ORGANISM: Artificial Sequence
<220> FEATURE:
<223> OTHER INFORMATION: Exemplary cyclic peptide

<400> SEQUENCE: 267
```

Cys Lys Arg Gly Trp Cys
1               5

<210> SEQ ID NO 268
<211> LENGTH: 7
<212> TYPE: PRT
<213> ORGANISM: Artificial Sequence
<220> FEATURE:
<223> OTHER INFORMATION: Exemplary cyclic peptide

<400> SEQUENCE: 268

Cys Lys Arg Gly Trp Val Cys
1               5

<210> SEQ ID NO 269
<211> LENGTH: 8
<212> TYPE: PRT
<213> ORGANISM: Artificial Sequence
<220> FEATURE:
<223> OTHER INFORMATION: Exemplary cyclic peptide

<400> SEQUENCE: 269

Cys Lys Arg Gly Trp Val Trp Cys
1               5

<210> SEQ ID NO 270
<211> LENGTH: 9
<212> TYPE: PRT
<213> ORGANISM: Artificial Sequence
<220> FEATURE:
<223> OTHER INFORMATION: Exemplary cyclic peptide

<400> SEQUENCE: 270

Cys Lys Arg Gly Trp Val Trp Asn Cys
1               5

<210> SEQ ID NO 271
<211> LENGTH: 10
<212> TYPE: PRT
<213> ORGANISM: Artificial Sequence
<220> FEATURE:
<223> OTHER INFORMATION: Exemplary cyclic peptide

<400> SEQUENCE: 271

Cys Lys Arg Gly Trp Val Trp Asn Gln Cys
1               5                   10

<210> SEQ ID NO 272
<211> LENGTH: 11
<212> TYPE: PRT
<213> ORGANISM: Artificial Sequence
<220> FEATURE:
<223> OTHER INFORMATION: Exemplary cyclic peptide

<400> SEQUENCE: 272

Cys Lys Arg Gly Trp Val Trp Asn Gln Phe Cys
1               5                   10

<210> SEQ ID NO 273
<211> LENGTH: 12
<212> TYPE: PRT
<213> ORGANISM: Artificial Sequence
<220> FEATURE:
<223> OTHER INFORMATION: Exemplary cyclic peptide

<400> SEQUENCE: 273

```
Cys Lys Arg Gly Trp Val Trp Asn Gln Phe Phe Cys
 1               5                  10
```

<210> SEQ ID NO 274
<211> LENGTH: 13
<212> TYPE: PRT
<213> ORGANISM: Artificial Sequence
<220> FEATURE:
<223> OTHER INFORMATION: Exemplary cyclic peptide

<400> SEQUENCE: 274

```
Cys Lys Arg Gly Trp Val Trp Asn Gln Phe Phe Val Cys
 1               5                  10
```

<210> SEQ ID NO 275
<211> LENGTH: 9
<212> TYPE: PRT
<213> ORGANISM: Artificial Sequence
<220> FEATURE:
<223> OTHER INFORMATION: Exemplary cyclic peptide

<400> SEQUENCE: 275

```
Cys Asp Trp Ile Trp Asn Gln Met Cys
 1               5
```

<210> SEQ ID NO 276
<211> LENGTH: 10
<212> TYPE: PRT
<213> ORGANISM: Artificial Sequence
<220> FEATURE:
<223> OTHER INFORMATION: Exemplary cyclic peptide

<400> SEQUENCE: 276

```
Cys Asp Trp Ile Trp Asn Gln Met His Cys
 1               5                  10
```

<210> SEQ ID NO 277
<211> LENGTH: 11
<212> TYPE: PRT
<213> ORGANISM: Artificial Sequence
<220> FEATURE:
<223> OTHER INFORMATION: Exemplary cyclic peptide

<400> SEQUENCE: 277

```
Cys Asp Trp Ile Trp Asn Gln Met His Ile Cys
 1               5                  10
```

<210> SEQ ID NO 278
<211> LENGTH: 8
<212> TYPE: PRT
<213> ORGANISM: Artificial Sequence
<220> FEATURE:
<223> OTHER INFORMATION: Exemplary cyclic peptide

<400> SEQUENCE: 278

```
Cys Trp Ile Trp Asn Gln Met Cys
 1               5
```

<210> SEQ ID NO 279
<211> LENGTH: 9
<212> TYPE: PRT
<213> ORGANISM: Artificial Sequence
<220> FEATURE:
<223> OTHER INFORMATION: Exemplary cyclic peptide

<400> SEQUENCE: 279

```
Cys Trp Ile Trp Asn Gln Met His Cys
```

```
<210> SEQ ID NO 280
<211> LENGTH: 10
<212> TYPE: PRT
<213> ORGANISM: Artificial Sequence
<220> FEATURE:
<223> OTHER INFORMATION: Exemplary cyclic peptide

<400> SEQUENCE: 280

Cys Trp Ile Trp Asn Gln Met His Ile Cys
1               5                   10

<210> SEQ ID NO 281
<211> LENGTH: 5
<212> TYPE: PRT
<213> ORGANISM: Artificial Sequence
<220> FEATURE:
<223> OTHER INFORMATION: Exemplary cyclic peptide

<400> SEQUENCE: 281

Cys Arg Asp Trp Cys
1               5

<210> SEQ ID NO 282
<211> LENGTH: 6
<212> TYPE: PRT
<213> ORGANISM: Artificial Sequence
<220> FEATURE:
<223> OTHER INFORMATION: Exemplary cyclic peptide

<400> SEQUENCE: 282

Cys Arg Asp Trp Ile Cys
1               5

<210> SEQ ID NO 283
<211> LENGTH: 7
<212> TYPE: PRT
<213> ORGANISM: Artificial Sequence
<220> FEATURE:
<223> OTHER INFORMATION: Exemplary cyclic peptide

<400> SEQUENCE: 283

Cys Arg Asp Trp Ile Trp Cys
1               5

<210> SEQ ID NO 284
<211> LENGTH: 8
<212> TYPE: PRT
<213> ORGANISM: Artificial Sequence
<220> FEATURE:
<223> OTHER INFORMATION: Exemplary cyclic peptide

<400> SEQUENCE: 284

Cys Arg Asp Trp Ile Trp Asn Cys
1               5

<210> SEQ ID NO 285
<211> LENGTH: 9
<212> TYPE: PRT
<213> ORGANISM: Artificial Sequence
<220> FEATURE:
<223> OTHER INFORMATION: Exemplary cyclic peptide

<400> SEQUENCE: 285

Cys Arg Asp Trp Ile Trp Asn Gln Cys
1               5
```

```
<210> SEQ ID NO 286
<211> LENGTH: 10
<212> TYPE: PRT
<213> ORGANISM: Artificial Sequence
<220> FEATURE:
<223> OTHER INFORMATION: Exemplary cyclic peptide

<400> SEQUENCE: 286

Cys Arg Asp Trp Ile Trp Asn Gln Met Cys
1               5                   10

<210> SEQ ID NO 287
<211> LENGTH: 11
<212> TYPE: PRT
<213> ORGANISM: Artificial Sequence
<220> FEATURE:
<223> OTHER INFORMATION: Exemplary cyclic peptide

<400> SEQUENCE: 287

Cys Arg Asp Trp Ile Trp Asn Gln Met His Cys
1               5                   10

<210> SEQ ID NO 288
<211> LENGTH: 12
<212> TYPE: PRT
<213> ORGANISM: Artificial Sequence
<220> FEATURE:
<223> OTHER INFORMATION: Exemplary cyclic peptide

<400> SEQUENCE: 288

Cys Arg Asp Trp Ile Trp Asn Gln Met His Ile Cys
1               5                   10

<210> SEQ ID NO 289
<211> LENGTH: 6
<212> TYPE: PRT
<213> ORGANISM: Artificial Sequence
<220> FEATURE:
<223> OTHER INFORMATION: Exemplary cyclic peptide

<400> SEQUENCE: 289

Cys Lys Arg Asp Trp Cys
1               5

<210> SEQ ID NO 290
<211> LENGTH: 7
<212> TYPE: PRT
<213> ORGANISM: Artificial Sequence
<220> FEATURE:
<223> OTHER INFORMATION: Exemplary cyclic peptide

<400> SEQUENCE: 290

Cys Lys Arg Asp Trp Ile Cys
1               5

<210> SEQ ID NO 291
<211> LENGTH: 8
<212> TYPE: PRT
<213> ORGANISM: Artificial Sequence
<220> FEATURE:
<223> OTHER INFORMATION: Exemplary cyclic peptide

<400> SEQUENCE: 291

Cys Lys Arg Asp Trp Ile Trp Cys
1               5
```

```
<210> SEQ ID NO 292
<211> LENGTH: 9
<212> TYPE: PRT
<213> ORGANISM: Artificial Sequence
<220> FEATURE:
<223> OTHER INFORMATION: Exemplary cyclic peptide

<400> SEQUENCE: 292

Cys Lys Arg Asp Trp Ile Trp Asn Cys
 1               5

<210> SEQ ID NO 293
<211> LENGTH: 10
<212> TYPE: PRT
<213> ORGANISM: Artificial Sequence
<220> FEATURE:
<223> OTHER INFORMATION: Exemplary cyclic peptide

<400> SEQUENCE: 293

Cys Lys Arg Asp Trp Ile Trp Asn Gln Cys
 1               5                  10

<210> SEQ ID NO 294
<211> LENGTH: 11
<212> TYPE: PRT
<213> ORGANISM: Artificial Sequence
<220> FEATURE:
<223> OTHER INFORMATION: Exemplary cyclic peptide

<400> SEQUENCE: 294

Cys Lys Arg Asp Trp Ile Trp Asn Gln Met Cys
 1               5                  10

<210> SEQ ID NO 295
<211> LENGTH: 12
<212> TYPE: PRT
<213> ORGANISM: Artificial Sequence
<220> FEATURE:
<223> OTHER INFORMATION: Exemplary cyclic peptide

<400> SEQUENCE: 295

Cys Lys Arg Asp Trp Ile Trp Asn Gln Met His Cys
 1               5                  10

<210> SEQ ID NO 296
<211> LENGTH: 13
<212> TYPE: PRT
<213> ORGANISM: Artificial Sequence
<220> FEATURE:
<223> OTHER INFORMATION: Exemplary cyclic peptide

<400> SEQUENCE: 296

Cys Lys Arg Asp Trp Ile Trp Asn Gln Met His Ile Cys
 1               5                  10

<210> SEQ ID NO 297
<211> LENGTH: 9
<212> TYPE: PRT
<213> ORGANISM: Artificial Sequence
<220> FEATURE:
<223> OTHER INFORMATION: Exemplary cyclic peptide

<400> SEQUENCE: 297

Cys Ser Trp Met Trp Asn Gln Phe Cys
 1               5
```

```
<210> SEQ ID NO 298
<211> LENGTH: 10
<212> TYPE: PRT
<213> ORGANISM: Artificial Sequence
<220> FEATURE:
<223> OTHER INFORMATION: Exemplary cyclic peptide

<400> SEQUENCE: 298

Cys Ser Trp Met Trp Asn Gln Phe Phe Cys
 1               5                  10

<210> SEQ ID NO 299
<211> LENGTH: 11
<212> TYPE: PRT
<213> ORGANISM: Artificial Sequence
<220> FEATURE:
<223> OTHER INFORMATION: Exemplary cyclic peptide

<400> SEQUENCE: 299

Cys Ser Trp Met Trp Asn Gln Phe Phe Leu Cys
 1               5                  10

<210> SEQ ID NO 300
<211> LENGTH: 8
<212> TYPE: PRT
<213> ORGANISM: Artificial Sequence
<220> FEATURE:
<223> OTHER INFORMATION: Exemplary cyclic peptide

<400> SEQUENCE: 300

Cys Trp Met Trp Asn Gln Phe Cys
 1               5

<210> SEQ ID NO 301
<211> LENGTH: 9
<212> TYPE: PRT
<213> ORGANISM: Artificial Sequence
<220> FEATURE:
<223> OTHER INFORMATION: Exemplary cyclic peptide

<400> SEQUENCE: 301

Cys Trp Met Trp Asn Gln Phe Phe Cys
 1               5

<210> SEQ ID NO 302
<211> LENGTH: 10
<212> TYPE: PRT
<213> ORGANISM: Artificial Sequence
<220> FEATURE:
<223> OTHER INFORMATION: Exemplary cyclic peptide

<400> SEQUENCE: 302

Cys Trp Met Trp Asn Gln Phe Phe Leu Cys
 1               5                  10

<210> SEQ ID NO 303
<211> LENGTH: 5
<212> TYPE: PRT
<213> ORGANISM: Artificial Sequence
<220> FEATURE:
<223> OTHER INFORMATION: Exemplary cyclic peptide

<400> SEQUENCE: 303

Cys Arg Ser Trp Cys
 1               5

<210> SEQ ID NO 304
```

```
<211> LENGTH: 6
<212> TYPE: PRT
<213> ORGANISM: Artificial Sequence
<220> FEATURE:
<223> OTHER INFORMATION: Exemplary cyclic peptide

<400> SEQUENCE: 304

Cys Arg Ser Trp Met Cys
1               5

<210> SEQ ID NO 305
<211> LENGTH: 7
<212> TYPE: PRT
<213> ORGANISM: Artificial Sequence
<220> FEATURE:
<223> OTHER INFORMATION: Exemplary cyclic peptide

<400> SEQUENCE: 305

Cys Arg Ser Trp Met Trp Cys
1               5

<210> SEQ ID NO 306
<211> LENGTH: 8
<212> TYPE: PRT
<213> ORGANISM: Artificial Sequence
<220> FEATURE:
<223> OTHER INFORMATION: Exemplary cyclic peptide

<400> SEQUENCE: 306

Cys Arg Ser Trp Met Trp Asn Cys
1               5

<210> SEQ ID NO 307
<211> LENGTH: 9
<212> TYPE: PRT
<213> ORGANISM: Artificial Sequence
<220> FEATURE:
<223> OTHER INFORMATION: Exemplary cyclic peptide

<400> SEQUENCE: 307

Cys Arg Ser Trp Met Trp Asn Gln Cys
1               5

<210> SEQ ID NO 308
<211> LENGTH: 10
<212> TYPE: PRT
<213> ORGANISM: Artificial Sequence
<220> FEATURE:
<223> OTHER INFORMATION: Exemplary cyclic peptide

<400> SEQUENCE: 308

Cys Arg Ser Trp Met Trp Asn Gln Phe Cys
1               5                   10

<210> SEQ ID NO 309
<211> LENGTH: 11
<212> TYPE: PRT
<213> ORGANISM: Artificial Sequence
<220> FEATURE:
<223> OTHER INFORMATION: Exemplary cyclic peptide

<400> SEQUENCE: 309

Cys Arg Ser Trp Met Trp Asn Gln Phe Phe Cys
1               5                   10

<210> SEQ ID NO 310
<211> LENGTH: 12
```

```
<212> TYPE: PRT
<213> ORGANISM: Artificial Sequence
<220> FEATURE:
<223> OTHER INFORMATION: Exemplary cyclic peptide

<400> SEQUENCE: 310

Cys Arg Ser Trp Met Trp Asn Gln Phe Phe Leu Cys
 1               5                  10

<210> SEQ ID NO 311
<211> LENGTH: 6
<212> TYPE: PRT
<213> ORGANISM: Artificial Sequence
<220> FEATURE:
<223> OTHER INFORMATION: Exemplary cyclic peptide

<400> SEQUENCE: 311

Cys Lys Arg Ser Trp Cys
 1               5

<210> SEQ ID NO 312
<211> LENGTH: 7
<212> TYPE: PRT
<213> ORGANISM: Artificial Sequence
<220> FEATURE:
<223> OTHER INFORMATION: Exemplary cyclic peptide

<400> SEQUENCE: 312

Cys Lys Arg Ser Trp Met Cys
 1               5

<210> SEQ ID NO 313
<211> LENGTH: 8
<212> TYPE: PRT
<213> ORGANISM: Artificial Sequence
<220> FEATURE:
<223> OTHER INFORMATION: Exemplary cyclic peptide

<400> SEQUENCE: 313

Cys Lys Arg Ser Trp Met Trp Cys
 1               5

<210> SEQ ID NO 314
<211> LENGTH: 9
<212> TYPE: PRT
<213> ORGANISM: Artificial Sequence
<220> FEATURE:
<223> OTHER INFORMATION: Exemplary cyclic peptide

<400> SEQUENCE: 314

Cys Lys Arg Ser Trp Met Trp Asn Cys
 1               5

<210> SEQ ID NO 315
<211> LENGTH: 10
<212> TYPE: PRT
<213> ORGANISM: Artificial Sequence
<220> FEATURE:
<223> OTHER INFORMATION: Exemplary cyclic peptide

<400> SEQUENCE: 315

Cys Lys Arg Ser Trp Met Trp Asn Gln Cys
 1               5                  10

<210> SEQ ID NO 316
<211> LENGTH: 11
<212> TYPE: PRT
```

```
<213> ORGANISM: Artificial Sequence
<220> FEATURE:
<223> OTHER INFORMATION: Exemplary cyclic peptide

<400> SEQUENCE: 316

Cys Lys Arg Ser Trp Met Trp Asn Gln Phe Cys
 1               5                  10

<210> SEQ ID NO 317
<211> LENGTH: 12
<212> TYPE: PRT
<213> ORGANISM: Artificial Sequence
<220> FEATURE:
<223> OTHER INFORMATION: Exemplary cyclic peptide

<400> SEQUENCE: 317

Cys Lys Arg Ser Trp Met Trp Asn Gln Phe Phe Cys
 1               5                  10

<210> SEQ ID NO 318
<211> LENGTH: 13
<212> TYPE: PRT
<213> ORGANISM: Artificial Sequence
<220> FEATURE:
<223> OTHER INFORMATION: Exemplary cyclic peptide

<400> SEQUENCE: 318

Cys Lys Arg Ser Trp Met Trp Asn Gln Phe Phe Leu Cys
 1               5                  10

<210> SEQ ID NO 319
<211> LENGTH: 9
<212> TYPE: PRT
<213> ORGANISM: Artificial Sequence
<220> FEATURE:
<223> OTHER INFORMATION: Exemplary cyclic peptide

<400> SEQUENCE: 319

Cys Ser Trp Val Trp Asn Gln Phe Cys
 1               5

<210> SEQ ID NO 320
<211> LENGTH: 10
<212> TYPE: PRT
<213> ORGANISM: Artificial Sequence
<220> FEATURE:
<223> OTHER INFORMATION: Exemplary cyclic peptide

<400> SEQUENCE: 320

Cys Ser Trp Val Trp Asn Gln Phe Phe Cys
 1               5                  10

<210> SEQ ID NO 321
<211> LENGTH: 11
<212> TYPE: PRT
<213> ORGANISM: Artificial Sequence
<220> FEATURE:
<223> OTHER INFORMATION: Exemplary cyclic peptide

<400> SEQUENCE: 321

Cys Ser Trp Val Trp Asn Gln Phe Phe Val Cys
 1               5                  10

<210> SEQ ID NO 322
<211> LENGTH: 6
<212> TYPE: PRT
<213> ORGANISM: Artificial Sequence
```

```
<220> FEATURE:
<223> OTHER INFORMATION: Exemplary cyclic peptide

<400> SEQUENCE: 322

Cys Arg Ser Trp Val Cys
 1               5

<210> SEQ ID NO 323
<211> LENGTH: 7
<212> TYPE: PRT
<213> ORGANISM: Artificial Sequence
<220> FEATURE:
<223> OTHER INFORMATION: Exemplary cyclic peptide

<400> SEQUENCE: 323

Cys Arg Ser Trp Val Trp Cys
 1               5

<210> SEQ ID NO 324
<211> LENGTH: 8
<212> TYPE: PRT
<213> ORGANISM: Artificial Sequence
<220> FEATURE:
<223> OTHER INFORMATION: Exemplary cyclic peptide

<400> SEQUENCE: 324

Cys Arg Ser Trp Val Trp Asn Cys
 1               5

<210> SEQ ID NO 325
<211> LENGTH: 9
<212> TYPE: PRT
<213> ORGANISM: Artificial Sequence
<220> FEATURE:
<223> OTHER INFORMATION: Exemplary cyclic peptide

<400> SEQUENCE: 325

Cys Arg Ser Trp Val Trp Asn Gln Cys
 1               5

<210> SEQ ID NO 326
<211> LENGTH: 10
<212> TYPE: PRT
<213> ORGANISM: Artificial Sequence
<220> FEATURE:
<223> OTHER INFORMATION: Exemplary cyclic peptide

<400> SEQUENCE: 326

Cys Arg Ser Trp Val Trp Asn Gln Phe Cys
 1               5                  10

<210> SEQ ID NO 327
<211> LENGTH: 11
<212> TYPE: PRT
<213> ORGANISM: Artificial Sequence
<220> FEATURE:
<223> OTHER INFORMATION: Exemplary cyclic peptide

<400> SEQUENCE: 327

Cys Arg Ser Trp Val Trp Asn Gln Phe Phe Cys
 1               5                  10

<210> SEQ ID NO 328
<211> LENGTH: 12
<212> TYPE: PRT
<213> ORGANISM: Artificial Sequence
<220> FEATURE:
```

<223> OTHER INFORMATION: Exemplary cyclic peptide

<400> SEQUENCE: 328

Cys Arg Ser Trp Val Trp Asn Gln Phe Phe Val Cys
1               5                   10

<210> SEQ ID NO 329
<211> LENGTH: 7
<212> TYPE: PRT
<213> ORGANISM: Artificial Sequence
<220> FEATURE:
<223> OTHER INFORMATION: Exemplary cyclic peptide

<400> SEQUENCE: 329

Cys Lys Arg Ser Trp Val Cys
1               5

<210> SEQ ID NO 330
<211> LENGTH: 8
<212> TYPE: PRT
<213> ORGANISM: Artificial Sequence
<220> FEATURE:
<223> OTHER INFORMATION: Exemplary cyclic peptide

<400> SEQUENCE: 330

Cys Lys Arg Ser Trp Val Trp Cys
1               5

<210> SEQ ID NO 331
<211> LENGTH: 9
<212> TYPE: PRT
<213> ORGANISM: Artificial Sequence
<220> FEATURE:
<223> OTHER INFORMATION: Exemplary cyclic peptide

<400> SEQUENCE: 331

Cys Lys Arg Ser Trp Val Trp Asn Cys
1               5

<210> SEQ ID NO 332
<211> LENGTH: 10
<212> TYPE: PRT
<213> ORGANISM: Artificial Sequence
<220> FEATURE:
<223> OTHER INFORMATION: Exemplary cyclic peptide

<400> SEQUENCE: 332

Cys Lys Arg Ser Trp Val Trp Asn Gln Cys
1               5                   10

<210> SEQ ID NO 333
<211> LENGTH: 11
<212> TYPE: PRT
<213> ORGANISM: Artificial Sequence
<220> FEATURE:
<223> OTHER INFORMATION: Exemplary cyclic peptide

<400> SEQUENCE: 333

Cys Lys Arg Ser Trp Val Trp Asn Gln Phe Cys
1               5                   10

<210> SEQ ID NO 334
<211> LENGTH: 12
<212> TYPE: PRT
<213> ORGANISM: Artificial Sequence
<220> FEATURE:
<223> OTHER INFORMATION: Exemplary cyclic peptide

```
<400> SEQUENCE: 334

Cys Lys Arg Ser Trp Val Trp Asn Gln Phe Phe Cys
1               5                   10

<210> SEQ ID NO 335
<211> LENGTH: 13
<212> TYPE: PRT
<213> ORGANISM: Artificial Sequence
<220> FEATURE:
<223> OTHER INFORMATION: Exemplary cyclic peptide

<400> SEQUENCE: 335

Cys Lys Arg Ser Trp Val Trp Asn Gln Phe Phe Val Cys
1               5                   10

<210> SEQ ID NO 336
<211> LENGTH: 9
<212> TYPE: PRT
<213> ORGANISM: Artificial Sequence
<220> FEATURE:
<223> OTHER INFORMATION: Exemplary cyclic peptide

<400> SEQUENCE: 336

Cys Gly Trp Val Trp Asn Gln Met Cys
1               5

<210> SEQ ID NO 337
<211> LENGTH: 10
<212> TYPE: PRT
<213> ORGANISM: Artificial Sequence
<220> FEATURE:
<223> OTHER INFORMATION: Exemplary cyclic peptide

<400> SEQUENCE: 337

Cys Gly Trp Val Trp Asn Gln Met Phe Cys
1               5                   10

<210> SEQ ID NO 338
<211> LENGTH: 11
<212> TYPE: PRT
<213> ORGANISM: Artificial Sequence
<220> FEATURE:
<223> OTHER INFORMATION: Exemplary cyclic peptide

<400> SEQUENCE: 338

Cys Gly Trp Val Trp Asn Gln Met Phe Val Cys
1               5                   10

<210> SEQ ID NO 339
<211> LENGTH: 10
<212> TYPE: PRT
<213> ORGANISM: Artificial Sequence
<220> FEATURE:
<223> OTHER INFORMATION: Exemplary cyclic peptide

<400> SEQUENCE: 339

Cys Arg Gly Trp Val Trp Asn Gln Met Cys
1               5                   10

<210> SEQ ID NO 340
<211> LENGTH: 11
<212> TYPE: PRT
<213> ORGANISM: Artificial Sequence
<220> FEATURE:
<223> OTHER INFORMATION: Exemplary cyclic peptide
```

```
<400> SEQUENCE: 340

Cys Arg Gly Trp Val Trp Asn Gln Met Phe Cys
1               5                   10

<210> SEQ ID NO 341
<211> LENGTH: 12
<212> TYPE: PRT
<213> ORGANISM: Artificial Sequence
<220> FEATURE:
<223> OTHER INFORMATION: Exemplary cyclic peptide

<400> SEQUENCE: 341

Cys Arg Gly Trp Val Trp Asn Gln Met Phe Val Cys
1               5                   10

<210> SEQ ID NO 342
<211> LENGTH: 11
<212> TYPE: PRT
<213> ORGANISM: Artificial Sequence
<220> FEATURE:
<223> OTHER INFORMATION: Exemplary cyclic peptide

<400> SEQUENCE: 342

Cys Lys Arg Gly Trp Val Trp Asn Gln Met Cys
1               5                   10

<210> SEQ ID NO 343
<211> LENGTH: 13
<212> TYPE: PRT
<213> ORGANISM: Artificial Sequence
<220> FEATURE:
<223> OTHER INFORMATION: Exemplary cyclic peptide

<400> SEQUENCE: 343

Cys Lys Arg Gly Trp Val Trp Asn Gln Met Phe Val Cys
1               5                   10

<210> SEQ ID NO 344
<211> LENGTH: 11
<212> TYPE: PRT
<213> ORGANISM: Artificial Sequence
<220> FEATURE:
<223> OTHER INFORMATION: Exemplary cyclic peptide

<400> SEQUENCE: 344

Cys Gly Trp Val Trp Asn Gln Phe Phe Leu Cys
1               5                   10

<210> SEQ ID NO 345
<211> LENGTH: 12
<212> TYPE: PRT
<213> ORGANISM: Artificial Sequence
<220> FEATURE:
<223> OTHER INFORMATION: Exemplary cyclic peptide

<400> SEQUENCE: 345

Cys Arg Gly Trp Val Trp Asn Gln Phe Phe Leu Cys
1               5                   10

<210> SEQ ID NO 346
<211> LENGTH: 13
<212> TYPE: PRT
<213> ORGANISM: Artificial Sequence
<220> FEATURE:
<223> OTHER INFORMATION: Exemplary cyclic peptide

<400> SEQUENCE: 346
```

Cys Lys Arg Gly Trp Val Trp Asn Gln Phe Phe Leu Cys
1               5                   10

<210> SEQ ID NO 347
<211> LENGTH: 9
<212> TYPE: PRT
<213> ORGANISM: Artificial Sequence
<220> FEATURE:
<223> OTHER INFORMATION: Exemplary cyclic peptide

<400> SEQUENCE: 347

Cys Ala Trp Val Ile Pro Pro Ile Cys
1               5

<210> SEQ ID NO 348
<211> LENGTH: 10
<212> TYPE: PRT
<213> ORGANISM: Artificial Sequence
<220> FEATURE:
<223> OTHER INFORMATION: Exemplary cyclic peptide

<400> SEQUENCE: 348

Cys Ala Trp Val Ile Pro Pro Ile Ser Cys
1               5                   10

<210> SEQ ID NO 349
<211> LENGTH: 11
<212> TYPE: PRT
<213> ORGANISM: Artificial Sequence
<220> FEATURE:
<223> OTHER INFORMATION: Exemplary cyclic peptide

<400> SEQUENCE: 349

Cys Ala Trp Val Ile Pro Pro Ile Ser Val Cys
1               5                   10

<210> SEQ ID NO 350
<211> LENGTH: 8
<212> TYPE: PRT
<213> ORGANISM: Artificial Sequence
<220> FEATURE:
<223> OTHER INFORMATION: Exemplary cyclic peptide

<400> SEQUENCE: 350

Cys Trp Val Ile Pro Pro Ile Cys
1               5

<210> SEQ ID NO 351
<211> LENGTH: 9
<212> TYPE: PRT
<213> ORGANISM: Artificial Sequence
<220> FEATURE:
<223> OTHER INFORMATION: Exemplary cyclic peptide

<400> SEQUENCE: 351

Cys Trp Val Ile Pro Pro Ile Ser Cys
1               5

<210> SEQ ID NO 352
<211> LENGTH: 10
<212> TYPE: PRT
<213> ORGANISM: Artificial Sequence
<220> FEATURE:
<223> OTHER INFORMATION: Exemplary cyclic peptide

<400> SEQUENCE: 352

```
Cys Trp Val Ile Pro Pro Ile Ser Val Cys
 1               5                  10
```

<210> SEQ ID NO 353
<211> LENGTH: 5
<212> TYPE: PRT
<213> ORGANISM: Artificial Sequence
<220> FEATURE:
<223> OTHER INFORMATION: Exemplary cyclic peptide

<400> SEQUENCE: 353

```
Cys Arg Ala Trp Cys
 1               5
```

<210> SEQ ID NO 354
<211> LENGTH: 6
<212> TYPE: PRT
<213> ORGANISM: Artificial Sequence
<220> FEATURE:
<223> OTHER INFORMATION: Exemplary cyclic peptide

<400> SEQUENCE: 354

```
Cys Arg Ala Trp Val Cys
 1               5
```

<210> SEQ ID NO 355
<211> LENGTH: 7
<212> TYPE: PRT
<213> ORGANISM: Artificial Sequence
<220> FEATURE:
<223> OTHER INFORMATION: Exemplary cyclic peptide

<400> SEQUENCE: 355

```
Cys Arg Ala Trp Val Ile Cys
 1               5
```

<210> SEQ ID NO 356
<211> LENGTH: 8
<212> TYPE: PRT
<213> ORGANISM: Artificial Sequence
<220> FEATURE:
<223> OTHER INFORMATION: Exemplary cyclic peptide

<400> SEQUENCE: 356

```
Cys Arg Ala Trp Val Ile Pro Cys
 1               5
```

<210> SEQ ID NO 357
<211> LENGTH: 9
<212> TYPE: PRT
<213> ORGANISM: Artificial Sequence
<220> FEATURE:
<223> OTHER INFORMATION: Exemplary cyclic peptide

<400> SEQUENCE: 357

```
Cys Arg Ala Trp Val Ile Pro Pro Cys
 1               5
```

<210> SEQ ID NO 358
<211> LENGTH: 10
<212> TYPE: PRT
<213> ORGANISM: Artificial Sequence
<220> FEATURE:
<223> OTHER INFORMATION: Exemplary cyclic peptide

<400> SEQUENCE: 358

```
Cys Arg Ala Trp Val Ile Pro Pro Ile Cys
```

```
1               5              10
```

<210> SEQ ID NO 359
<211> LENGTH: 11
<212> TYPE: PRT
<213> ORGANISM: Artificial Sequence
<220> FEATURE:
<223> OTHER INFORMATION: Exemplary cyclic peptide

<400> SEQUENCE: 359

```
Cys Arg Ala Trp Val Ile Pro Pro Ile Ser Cys
1               5              10
```

<210> SEQ ID NO 360
<211> LENGTH: 12
<212> TYPE: PRT
<213> ORGANISM: Artificial Sequence
<220> FEATURE:
<223> OTHER INFORMATION: Exemplary cyclic peptide

<400> SEQUENCE: 360

```
Cys Arg Ala Trp Val Ile Pro Pro Ile Ser Val Cys
1               5              10
```

<210> SEQ ID NO 361
<211> LENGTH: 6
<212> TYPE: PRT
<213> ORGANISM: Artificial Sequence
<220> FEATURE:
<223> OTHER INFORMATION: Exemplary cyclic peptide

<400> SEQUENCE: 361

```
Cys Lys Arg Ala Trp Cys
1               5
```

<210> SEQ ID NO 362
<211> LENGTH: 7
<212> TYPE: PRT
<213> ORGANISM: Artificial Sequence
<220> FEATURE:
<223> OTHER INFORMATION: Exemplary cyclic peptide

<400> SEQUENCE: 362

```
Cys Lys Arg Ala Trp Val Cys
1               5
```

<210> SEQ ID NO 363
<211> LENGTH: 8
<212> TYPE: PRT
<213> ORGANISM: Artificial Sequence
<220> FEATURE:
<223> OTHER INFORMATION: Exemplary cyclic peptide

<400> SEQUENCE: 363

```
Cys Lys Arg Ala Trp Val Ile Cys
1               5
```

<210> SEQ ID NO 364
<211> LENGTH: 9
<212> TYPE: PRT
<213> ORGANISM: Artificial Sequence
<220> FEATURE:
<223> OTHER INFORMATION: Exemplary cyclic peptide

<400> SEQUENCE: 364

```
Cys Lys Arg Ala Trp Val Ile Pro Cys
1               5
```

```
<210> SEQ ID NO 365
<211> LENGTH: 10
<212> TYPE: PRT
<213> ORGANISM: Artificial Sequence
<220> FEATURE:
<223> OTHER INFORMATION: Exemplary cyclic peptide

<400> SEQUENCE: 365

Cys Lys Arg Ala Trp Val Ile Pro Pro Cys
 1               5                  10

<210> SEQ ID NO 366
<211> LENGTH: 11
<212> TYPE: PRT
<213> ORGANISM: Artificial Sequence
<220> FEATURE:
<223> OTHER INFORMATION: Exemplary cyclic peptide

<400> SEQUENCE: 366

Cys Lys Arg Ala Trp Val Ile Pro Pro Ile Cys
 1               5                  10

<210> SEQ ID NO 367
<211> LENGTH: 12
<212> TYPE: PRT
<213> ORGANISM: Artificial Sequence
<220> FEATURE:
<223> OTHER INFORMATION: Exemplary cyclic peptide

<400> SEQUENCE: 367

Cys Lys Arg Ala Trp Val Ile Pro Pro Ile Ser Cys
 1               5                  10

<210> SEQ ID NO 368
<211> LENGTH: 5
<212> TYPE: PRT
<213> ORGANISM: Artificial Sequence
<220> FEATURE:
<223> OTHER INFORMATION: Exemplary cyclic peptide

<400> SEQUENCE: 368

Cys Val Trp Asn Cys
 1               5

<210> SEQ ID NO 369
<211> LENGTH: 6
<212> TYPE: PRT
<213> ORGANISM: Artificial Sequence
<220> FEATURE:
<223> OTHER INFORMATION: Exemplary cyclic peptide

<400> SEQUENCE: 369

Cys Val Trp Asn Gln Cys
 1               5

<210> SEQ ID NO 370
<211> LENGTH: 7
<212> TYPE: PRT
<213> ORGANISM: Artificial Sequence
<220> FEATURE:
<223> OTHER INFORMATION: Exemplary cyclic peptide

<400> SEQUENCE: 370

Cys Val Trp Asn Gln Met Cys
 1               5
```

```
<210> SEQ ID NO 371
<211> LENGTH: 7
<212> TYPE: PRT
<213> ORGANISM: Artificial Sequence
<220> FEATURE:
<223> OTHER INFORMATION: Exemplary cyclic peptide

<400> SEQUENCE: 371

Cys Val Trp Asn Gln Phe Cys
 1               5

<210> SEQ ID NO 372
<211> LENGTH: 8
<212> TYPE: PRT
<213> ORGANISM: Artificial Sequence
<220> FEATURE:
<223> OTHER INFORMATION: Exemplary cyclic peptide

<400> SEQUENCE: 372

Cys Val Trp Asn Gln Met Phe Cys
 1               5

<210> SEQ ID NO 373
<211> LENGTH: 8
<212> TYPE: PRT
<213> ORGANISM: Artificial Sequence
<220> FEATURE:
<223> OTHER INFORMATION: Exemplary cyclic peptide

<400> SEQUENCE: 373

Cys Val Trp Asn Gln Phe Phe Cys
 1               5

<210> SEQ ID NO 374
<211> LENGTH: 4
<212> TYPE: PRT
<213> ORGANISM: Artificial Sequence
<220> FEATURE:
<223> OTHER INFORMATION: Exemplary cyclic peptide

<400> SEQUENCE: 374

Cys Trp Asn Gln
 1

<210> SEQ ID NO 375
<211> LENGTH: 6
<212> TYPE: PRT
<213> ORGANISM: Artificial Sequence
<220> FEATURE:
<223> OTHER INFORMATION: Exemplary cyclic peptide

<400> SEQUENCE: 375

Cys Trp Asn Gln Met Cys
 1               5

<210> SEQ ID NO 376
<211> LENGTH: 6
<212> TYPE: PRT
<213> ORGANISM: Artificial Sequence
<220> FEATURE:
<223> OTHER INFORMATION: Exemplary cyclic peptide

<400> SEQUENCE: 376

Cys Trp Asn Gln Phe Cys
 1               5
```

```
<210> SEQ ID NO 377
<211> LENGTH: 7
<212> TYPE: PRT
<213> ORGANISM: Artificial Sequence
<220> FEATURE:
<223> OTHER INFORMATION: Exemplary cyclic peptide

<400> SEQUENCE: 377

Cys Trp Asn Gln Phe Phe Cys
 1               5

<210> SEQ ID NO 378
<211> LENGTH: 5
<212> TYPE: PRT
<213> ORGANISM: Artificial Sequence
<220> FEATURE:
<223> OTHER INFORMATION: Exemplary cyclic peptide

<400> SEQUENCE: 378

Cys Ile Trp Asn Cys
 1               5

<210> SEQ ID NO 379
<211> LENGTH: 6
<212> TYPE: PRT
<213> ORGANISM: Artificial Sequence
<220> FEATURE:
<223> OTHER INFORMATION: Exemplary cyclic peptide

<400> SEQUENCE: 379

Cys Ile Trp Asn Gln Cys
 1               5

<210> SEQ ID NO 380
<211> LENGTH: 7
<212> TYPE: PRT
<213> ORGANISM: Artificial Sequence
<220> FEATURE:
<223> OTHER INFORMATION: Exemplary cyclic peptide

<400> SEQUENCE: 380

Cys Ile Trp Asn Gln Met Cys
 1               5

<210> SEQ ID NO 381
<211> LENGTH: 8
<212> TYPE: PRT
<213> ORGANISM: Artificial Sequence
<220> FEATURE:
<223> OTHER INFORMATION: Exemplary cyclic peptide

<400> SEQUENCE: 381

Cys Ile Trp Asn Gln Met His Cys
 1               5

<210> SEQ ID NO 382
<211> LENGTH: 7
<212> TYPE: PRT
<213> ORGANISM: Artificial Sequence
<220> FEATURE:
<223> OTHER INFORMATION: Exemplary cyclic peptide

<400> SEQUENCE: 382

Cys Trp Asn Gln Met His Cys
 1               5

<210> SEQ ID NO 383
```

```
<211> LENGTH: 5
<212> TYPE: PRT
<213> ORGANISM: Artificial Sequence
<220> FEATURE:
<223> OTHER INFORMATION: Exemplary cyclic peptide

<400> SEQUENCE: 383

Cys Met Trp Asn Cys
 1               5

<210> SEQ ID NO 384
<211> LENGTH: 6
<212> TYPE: PRT
<213> ORGANISM: Artificial Sequence
<220> FEATURE:
<223> OTHER INFORMATION: Exemplary cyclic peptide

<400> SEQUENCE: 384

Cys Met Trp Asn Gln Cys
 1               5

<210> SEQ ID NO 385
<211> LENGTH: 7
<212> TYPE: PRT
<213> ORGANISM: Artificial Sequence
<220> FEATURE:
<223> OTHER INFORMATION: Exemplary cyclic peptide

<400> SEQUENCE: 385

Cys Met Trp Asn Gln Phe Cys
 1               5

<210> SEQ ID NO 386
<211> LENGTH: 8
<212> TYPE: PRT
<213> ORGANISM: Artificial Sequence
<220> FEATURE:
<223> OTHER INFORMATION: Exemplary cyclic peptide

<400> SEQUENCE: 386

Cys Met Trp Asn Gln Phe Phe Cys
 1               5

<210> SEQ ID NO 387
<211> LENGTH: 5
<212> TYPE: PRT
<213> ORGANISM: Artificial Sequence
<220> FEATURE:
<223> OTHER INFORMATION: Exemplary cyclic peptide

<400> SEQUENCE: 387

Lys Gly Trp Val Asp
 1               5

<210> SEQ ID NO 388
<211> LENGTH: 6
<212> TYPE: PRT
<213> ORGANISM: Artificial Sequence
<220> FEATURE:
<223> OTHER INFORMATION: Exemplary cyclic peptide

<400> SEQUENCE: 388

Lys Gly Trp Val Trp Asp
 1               5

<210> SEQ ID NO 389
<211> LENGTH: 7
```

```
<212> TYPE: PRT
<213> ORGANISM: Artificial Sequence
<220> FEATURE:
<223> OTHER INFORMATION: Exemplary cyclic peptide

<400> SEQUENCE: 389

Lys Gly Trp Val Trp Asn Asp
 1               5

<210> SEQ ID NO 390
<211> LENGTH: 8
<212> TYPE: PRT
<213> ORGANISM: Artificial Sequence
<220> FEATURE:
<223> OTHER INFORMATION: Exemplary cyclic peptide

<400> SEQUENCE: 390

Lys Gly Trp Val Trp Asn Gln Asp
 1               5

<210> SEQ ID NO 391
<211> LENGTH: 5
<212> TYPE: PRT
<213> ORGANISM: Artificial Sequence
<220> FEATURE:
<223> OTHER INFORMATION: Exemplary cyclic peptide

<400> SEQUENCE: 391

Lys Trp Val Trp Asp
 1               5

<210> SEQ ID NO 392
<211> LENGTH: 6
<212> TYPE: PRT
<213> ORGANISM: Artificial Sequence
<220> FEATURE:
<223> OTHER INFORMATION: Exemplary cyclic peptide

<400> SEQUENCE: 392

Lys Trp Val Trp Asn Asp
 1               5

<210> SEQ ID NO 393
<211> LENGTH: 7
<212> TYPE: PRT
<213> ORGANISM: Artificial Sequence
<220> FEATURE:
<223> OTHER INFORMATION: Exemplary cyclic peptide

<400> SEQUENCE: 393

Lys Trp Val Trp Asn Gln Asp
 1               5

<210> SEQ ID NO 394
<211> LENGTH: 5
<212> TYPE: PRT
<213> ORGANISM: Artificial Sequence
<220> FEATURE:
<223> OTHER INFORMATION: Exemplary cyclic peptide

<400> SEQUENCE: 394

Lys Asp Trp Ile Asp
 1               5

<210> SEQ ID NO 395
<211> LENGTH: 6
<212> TYPE: PRT
```

```
<213> ORGANISM: Artificial Sequence
<220> FEATURE:
<223> OTHER INFORMATION: Exemplary cyclic peptide

<400> SEQUENCE: 395

Lys Asp Trp Ile Trp Asp
 1               5

<210> SEQ ID NO 396
<211> LENGTH: 7
<212> TYPE: PRT
<213> ORGANISM: Artificial Sequence
<220> FEATURE:
<223> OTHER INFORMATION: Exemplary cyclic peptide

<400> SEQUENCE: 396

Lys Asp Trp Ile Trp Asn Asp
 1               5

<210> SEQ ID NO 397
<211> LENGTH: 8
<212> TYPE: PRT
<213> ORGANISM: Artificial Sequence
<220> FEATURE:
<223> OTHER INFORMATION: Exemplary cyclic peptide

<400> SEQUENCE: 397

Lys Asp Trp Ile Trp Asn Gln Asp
 1               5

<210> SEQ ID NO 398
<211> LENGTH: 5
<212> TYPE: PRT
<213> ORGANISM: Artificial Sequence
<220> FEATURE:
<223> OTHER INFORMATION: Exemplary cyclic peptide

<400> SEQUENCE: 398

Lys Trp Ile Trp Asp
 1               5

<210> SEQ ID NO 399
<211> LENGTH: 6
<212> TYPE: PRT
<213> ORGANISM: Artificial Sequence
<220> FEATURE:
<223> OTHER INFORMATION: Exemplary cyclic peptide

<400> SEQUENCE: 399

Lys Trp Ile Trp Asn Asp
 1               5

<210> SEQ ID NO 400
<211> LENGTH: 7
<212> TYPE: PRT
<213> ORGANISM: Artificial Sequence
<220> FEATURE:
<223> OTHER INFORMATION: Exemplary cyclic peptide

<400> SEQUENCE: 400

Lys Trp Ile Trp Asn Gln Asp
 1               5

<210> SEQ ID NO 401
<211> LENGTH: 5
<212> TYPE: PRT
<213> ORGANISM: Artificial Sequence
```

```
<220> FEATURE:
<223> OTHER INFORMATION: Exemplary cyclic peptide

<400> SEQUENCE: 401

Lys Ser Trp Met Asp
 1               5

<210> SEQ ID NO 402
<211> LENGTH: 6
<212> TYPE: PRT
<213> ORGANISM: Artificial Sequence
<220> FEATURE:
<223> OTHER INFORMATION: Exemplary cyclic peptide

<400> SEQUENCE: 402

Lys Ser Trp Met Trp Asp
 1               5

<210> SEQ ID NO 403
<211> LENGTH: 7
<212> TYPE: PRT
<213> ORGANISM: Artificial Sequence
<220> FEATURE:
<223> OTHER INFORMATION: Exemplary cyclic peptide

<400> SEQUENCE: 403

Lys Ser Trp Met Trp Asn Asp
 1               5

<210> SEQ ID NO 404
<211> LENGTH: 8
<212> TYPE: PRT
<213> ORGANISM: Artificial Sequence
<220> FEATURE:
<223> OTHER INFORMATION: Exemplary cyclic peptide

<400> SEQUENCE: 404

Lys Ser Trp Met Trp Asn Gln Asp
 1               5

<210> SEQ ID NO 405
<211> LENGTH: 5
<212> TYPE: PRT
<213> ORGANISM: Artificial Sequence
<220> FEATURE:
<223> OTHER INFORMATION: Exemplary cyclic peptide

<400> SEQUENCE: 405

Lys Trp Met Trp Asp
 1               5

<210> SEQ ID NO 406
<211> LENGTH: 6
<212> TYPE: PRT
<213> ORGANISM: Artificial Sequence
<220> FEATURE:
<223> OTHER INFORMATION: Exemplary cyclic peptide

<400> SEQUENCE: 406

Lys Trp Met Trp Asn Asp
 1               5

<210> SEQ ID NO 407
<211> LENGTH: 7
<212> TYPE: PRT
<213> ORGANISM: Artificial Sequence
<220> FEATURE:
```

<223> OTHER INFORMATION: Exemplary cyclic peptide

<400> SEQUENCE: 407

Lys Trp Met Trp Asn Gln Asp
1               5

<210> SEQ ID NO 408
<211> LENGTH: 5
<212> TYPE: PRT
<213> ORGANISM: Artificial Sequence
<220> FEATURE:
<223> OTHER INFORMATION: Exemplary cyclic peptide

<400> SEQUENCE: 408

Lys Ser Trp Val Asp
1               5

<210> SEQ ID NO 409
<211> LENGTH: 6
<212> TYPE: PRT
<213> ORGANISM: Artificial Sequence
<220> FEATURE:
<223> OTHER INFORMATION: Exemplary cyclic peptide

<400> SEQUENCE: 409

Lys Ser Trp Val Trp Asp
1               5

<210> SEQ ID NO 410
<211> LENGTH: 7
<212> TYPE: PRT
<213> ORGANISM: Artificial Sequence
<220> FEATURE:
<223> OTHER INFORMATION: Exemplary cyclic peptide

<400> SEQUENCE: 410

Lys Ser Trp Val Trp Asn Asp
1               5

<210> SEQ ID NO 411
<211> LENGTH: 8
<212> TYPE: PRT
<213> ORGANISM: Artificial Sequence
<220> FEATURE:
<223> OTHER INFORMATION: Exemplary cyclic peptide

<400> SEQUENCE: 411

Lys Ser Trp Val Trp Asn Gln Asp
1               5

<210> SEQ ID NO 412
<211> LENGTH: 5
<212> TYPE: PRT
<213> ORGANISM: Artificial Sequence
<220> FEATURE:
<223> OTHER INFORMATION: Exemplary cyclic peptide

<400> SEQUENCE: 412

Lys Gly Trp Met Asp
1               5

<210> SEQ ID NO 413
<211> LENGTH: 6
<212> TYPE: PRT
<213> ORGANISM: Artificial Sequence
<220> FEATURE:
<223> OTHER INFORMATION: Exemplary cyclic peptide

```
<400> SEQUENCE: 413

Lys Gly Trp Met Trp Asp
 1               5

<210> SEQ ID NO 414
<211> LENGTH: 7
<212> TYPE: PRT
<213> ORGANISM: Artificial Sequence
<220> FEATURE:
<223> OTHER INFORMATION: Exemplary cyclic peptide

<400> SEQUENCE: 414

Lys Gly Trp Met Trp Asn Asp
 1               5

<210> SEQ ID NO 415
<211> LENGTH: 8
<212> TYPE: PRT
<213> ORGANISM: Artificial Sequence
<220> FEATURE:
<223> OTHER INFORMATION: Exemplary cyclic peptide

<400> SEQUENCE: 415

Lys Gly Trp Met Trp Asn Gln Asp
 1               5

<210> SEQ ID NO 416
<211> LENGTH: 5
<212> TYPE: PRT
<213> ORGANISM: Artificial Sequence
<220> FEATURE:
<223> OTHER INFORMATION: Exemplary cyclic peptide

<400> SEQUENCE: 416

Lys Ala Trp Val Asp
 1               5

<210> SEQ ID NO 417
<211> LENGTH: 6
<212> TYPE: PRT
<213> ORGANISM: Artificial Sequence
<220> FEATURE:
<223> OTHER INFORMATION: Exemplary cyclic peptide

<400> SEQUENCE: 417

Lys Ala Trp Val Ile Asp
 1               5

<210> SEQ ID NO 418
<211> LENGTH: 7
<212> TYPE: PRT
<213> ORGANISM: Artificial Sequence
<220> FEATURE:
<223> OTHER INFORMATION: Exemplary cyclic peptide

<400> SEQUENCE: 418

Lys Ala Trp Val Ile Pro Asp
 1               5

<210> SEQ ID NO 419
<211> LENGTH: 8
<212> TYPE: PRT
<213> ORGANISM: Artificial Sequence
<220> FEATURE:
<223> OTHER INFORMATION: Exemplary cyclic peptide
```

```
<400> SEQUENCE: 419

Lys Ala Trp Val Ile Pro Pro Asp
1               5

<210> SEQ ID NO 420
<211> LENGTH: 5
<212> TYPE: PRT
<213> ORGANISM: Artificial Sequence
<220> FEATURE:
<223> OTHER INFORMATION: Exemplary cyclic peptide

<400> SEQUENCE: 420

Lys Trp Val Ile Asp
1               5

<210> SEQ ID NO 421
<211> LENGTH: 6
<212> TYPE: PRT
<213> ORGANISM: Artificial Sequence
<220> FEATURE:
<223> OTHER INFORMATION: Exemplary cyclic peptide

<400> SEQUENCE: 421

Lys Trp Val Ile Pro Asp
1               5

<210> SEQ ID NO 422
<211> LENGTH: 7
<212> TYPE: PRT
<213> ORGANISM: Artificial Sequence
<220> FEATURE:
<223> OTHER INFORMATION: Exemplary cyclic peptide

<400> SEQUENCE: 422

Lys Trp Val Ile Pro Pro Asp
1               5

<210> SEQ ID NO 423
<211> LENGTH: 9
<212> TYPE: PRT
<213> ORGANISM: Artificial Sequence
<220> FEATURE:
<223> OTHER INFORMATION: Exemplary cyclic peptide

<400> SEQUENCE: 423

Lys Gly Trp Val Trp Asn Gln Phe Asp
1               5

<210> SEQ ID NO 424
<211> LENGTH: 10
<212> TYPE: PRT
<213> ORGANISM: Artificial Sequence
<220> FEATURE:
<223> OTHER INFORMATION: Exemplary cyclic peptide

<400> SEQUENCE: 424

Lys Gly Trp Val Trp Asn Gln Phe Phe Asp
1               5                   10

<210> SEQ ID NO 425
<211> LENGTH: 11
<212> TYPE: PRT
<213> ORGANISM: Artificial Sequence
<220> FEATURE:
<223> OTHER INFORMATION: Exemplary cyclic peptide

<400> SEQUENCE: 425
```

```
Lys Gly Trp Val Trp Asn Gln Phe Phe Val Asp
 1               5                   10
```

<210> SEQ ID NO 426
<211> LENGTH: 8
<212> TYPE: PRT
<213> ORGANISM: Artificial Sequence
<220> FEATURE:
<223> OTHER INFORMATION: Exemplary cyclic peptide

<400> SEQUENCE: 426

```
Lys Trp Val Trp Asn Gln Phe Asp
 1               5
```

<210> SEQ ID NO 427
<211> LENGTH: 9
<212> TYPE: PRT
<213> ORGANISM: Artificial Sequence
<220> FEATURE:
<223> OTHER INFORMATION: Exemplary cyclic peptide

<400> SEQUENCE: 427

```
Lys Trp Val Trp Asn Gln Phe Phe Asp
 1               5
```

<210> SEQ ID NO 428
<211> LENGTH: 10
<212> TYPE: PRT
<213> ORGANISM: Artificial Sequence
<220> FEATURE:
<223> OTHER INFORMATION: Exemplary cyclic peptide

<400> SEQUENCE: 428

```
Lys Trp Val Trp Asn Gln Phe Phe Val Asp
 1               5                   10
```

<210> SEQ ID NO 429
<211> LENGTH: 5
<212> TYPE: PRT
<213> ORGANISM: Artificial Sequence
<220> FEATURE:
<223> OTHER INFORMATION: Exemplary cyclic peptide

<400> SEQUENCE: 429

```
Lys Arg Gly Trp Asp
 1               5
```

<210> SEQ ID NO 430
<211> LENGTH: 6
<212> TYPE: PRT
<213> ORGANISM: Artificial Sequence
<220> FEATURE:
<223> OTHER INFORMATION: Exemplary cyclic peptide

<400> SEQUENCE: 430

```
Lys Arg Gly Trp Val Asp
 1               5
```

<210> SEQ ID NO 431
<211> LENGTH: 7
<212> TYPE: PRT
<213> ORGANISM: Artificial Sequence
<220> FEATURE:
<223> OTHER INFORMATION: Exemplary cyclic peptide

<400> SEQUENCE: 431

```
Lys Arg Gly Trp Val Trp Asp
 1               5
```

<210> SEQ ID NO 432
<211> LENGTH: 8
<212> TYPE: PRT
<213> ORGANISM: Artificial Sequence
<220> FEATURE:
<223> OTHER INFORMATION: Exemplary cyclic peptide

<400> SEQUENCE: 432

```
Lys Arg Gly Trp Val Trp Asn Asp
 1               5
```

<210> SEQ ID NO 433
<211> LENGTH: 9
<212> TYPE: PRT
<213> ORGANISM: Artificial Sequence
<220> FEATURE:
<223> OTHER INFORMATION: Exemplary cyclic peptide

<400> SEQUENCE: 433

```
Lys Arg Gly Trp Val Trp Asn Gln Asp
 1               5
```

<210> SEQ ID NO 434
<211> LENGTH: 10
<212> TYPE: PRT
<213> ORGANISM: Artificial Sequence
<220> FEATURE:
<223> OTHER INFORMATION: Exemplary cyclic peptide

<400> SEQUENCE: 434

```
Lys Arg Gly Trp Val Trp Asn Gln Phe Asp
 1               5                  10
```

<210> SEQ ID NO 435
<211> LENGTH: 11
<212> TYPE: PRT
<213> ORGANISM: Artificial Sequence
<220> FEATURE:
<223> OTHER INFORMATION: Exemplary cyclic peptide

<400> SEQUENCE: 435

```
Lys Arg Gly Trp Val Trp Asn Gln Phe Phe Asp
 1               5                  10
```

<210> SEQ ID NO 436
<211> LENGTH: 12
<212> TYPE: PRT
<213> ORGANISM: Artificial Sequence
<220> FEATURE:
<223> OTHER INFORMATION: Exemplary cyclic peptide

<400> SEQUENCE: 436

```
Lys Arg Gly Trp Val Trp Asn Gln Phe Phe Val Asp
 1               5                  10
```

<210> SEQ ID NO 437
<211> LENGTH: 8
<212> TYPE: PRT
<213> ORGANISM: Artificial Sequence
<220> FEATURE:
<223> OTHER INFORMATION: Exemplary cyclic peptide

<400> SEQUENCE: 437

```
Asp Trp Ile Trp Asn Gln Met Asp
```

```
1               5

<210> SEQ ID NO 438
<211> LENGTH: 10
<212> TYPE: PRT
<213> ORGANISM: Artificial Sequence
<220> FEATURE:
<223> OTHER INFORMATION: Exemplary cyclic peptide

<400> SEQUENCE: 438

Lys Asp Trp Ile Trp Asn Gln Met His Asp
1               5                   10

<210> SEQ ID NO 439
<211> LENGTH: 11
<212> TYPE: PRT
<213> ORGANISM: Artificial Sequence
<220> FEATURE:
<223> OTHER INFORMATION: Exemplary cyclic peptide

<400> SEQUENCE: 439

Lys Asp Trp Ile Trp Asn Gln Met His Ile Asp
1               5                   10

<210> SEQ ID NO 440
<211> LENGTH: 8
<212> TYPE: PRT
<213> ORGANISM: Artificial Sequence
<220> FEATURE:
<223> OTHER INFORMATION: Exemplary cyclic peptide

<400> SEQUENCE: 440

Lys Trp Ile Trp Asn Gln Met Asp
1               5

<210> SEQ ID NO 441
<211> LENGTH: 9
<212> TYPE: PRT
<213> ORGANISM: Artificial Sequence
<220> FEATURE:
<223> OTHER INFORMATION: Exemplary cyclic peptide

<400> SEQUENCE: 441

Lys Trp Ile Trp Asn Gln Met His Asp
1               5

<210> SEQ ID NO 442
<211> LENGTH: 10
<212> TYPE: PRT
<213> ORGANISM: Artificial Sequence
<220> FEATURE:
<223> OTHER INFORMATION: Exemplary cyclic peptide

<400> SEQUENCE: 442

Lys Trp Ile Trp Asn Gln Met His Ile Asp
1               5                   10

<210> SEQ ID NO 443
<211> LENGTH: 4
<212> TYPE: PRT
<213> ORGANISM: Artificial Sequence
<220> FEATURE:
<223> OTHER INFORMATION: Exemplary cyclic peptide

<400> SEQUENCE: 443

Arg Asp Trp Asp
1
```

```
<210> SEQ ID NO 444
<211> LENGTH: 5
<212> TYPE: PRT
<213> ORGANISM: Artificial Sequence
<220> FEATURE:
<223> OTHER INFORMATION: Exemplary cyclic peptide

<400> SEQUENCE: 444

Arg Asp Trp Ile Asp
1               5

<210> SEQ ID NO 445
<211> LENGTH: 6
<212> TYPE: PRT
<213> ORGANISM: Artificial Sequence
<220> FEATURE:
<223> OTHER INFORMATION: Exemplary cyclic peptide

<400> SEQUENCE: 445

Arg Asp Trp Ile Trp Asp
1               5

<210> SEQ ID NO 446
<211> LENGTH: 7
<212> TYPE: PRT
<213> ORGANISM: Artificial Sequence
<220> FEATURE:
<223> OTHER INFORMATION: Exemplary cyclic peptide

<400> SEQUENCE: 446

Arg Asp Trp Ile Trp Asn Asp
1               5

<210> SEQ ID NO 447
<211> LENGTH: 8
<212> TYPE: PRT
<213> ORGANISM: Artificial Sequence
<220> FEATURE:
<223> OTHER INFORMATION: Exemplary cyclic peptide

<400> SEQUENCE: 447

Arg Asp Trp Ile Trp Asn Gln Asp
1               5

<210> SEQ ID NO 448
<211> LENGTH: 9
<212> TYPE: PRT
<213> ORGANISM: Artificial Sequence
<220> FEATURE:
<223> OTHER INFORMATION: Exemplary cyclic peptide

<400> SEQUENCE: 448

Arg Asp Trp Ile Trp Asn Gln Met Asp
1               5

<210> SEQ ID NO 449
<211> LENGTH: 10
<212> TYPE: PRT
<213> ORGANISM: Artificial Sequence
<220> FEATURE:
<223> OTHER INFORMATION: Exemplary cyclic peptide

<400> SEQUENCE: 449

Arg Asp Trp Ile Trp Asn Gln Met His Asp
1               5                   10
```

```
<210> SEQ ID NO 450
<211> LENGTH: 11
<212> TYPE: PRT
<213> ORGANISM: Artificial Sequence
<220> FEATURE:
<223> OTHER INFORMATION: Exemplary cyclic peptide

<400> SEQUENCE: 450

Arg Asp Trp Ile Trp Asn Gln Met His Ile Asp
 1               5                  10

<210> SEQ ID NO 451
<211> LENGTH: 7
<212> TYPE: PRT
<213> ORGANISM: Artificial Sequence
<220> FEATURE:
<223> OTHER INFORMATION: Exemplary cyclic peptide

<400> SEQUENCE: 451

Lys Arg Asp Trp Ile Trp Asp
 1               5

<210> SEQ ID NO 452
<211> LENGTH: 8
<212> TYPE: PRT
<213> ORGANISM: Artificial Sequence
<220> FEATURE:
<223> OTHER INFORMATION: Exemplary cyclic peptide

<400> SEQUENCE: 452

Lys Arg Asp Trp Ile Trp Asn Asp
 1               5

<210> SEQ ID NO 453
<211> LENGTH: 9
<212> TYPE: PRT
<213> ORGANISM: Artificial Sequence
<220> FEATURE:
<223> OTHER INFORMATION: Exemplary cyclic peptide

<400> SEQUENCE: 453

Lys Arg Asp Trp Ile Trp Asn Gln Asp
 1               5

<210> SEQ ID NO 454
<211> LENGTH: 10
<212> TYPE: PRT
<213> ORGANISM: Artificial Sequence
<220> FEATURE:
<223> OTHER INFORMATION: Exemplary cyclic peptide

<400> SEQUENCE: 454

Lys Arg Asp Trp Ile Trp Asn Gln Met Asp
 1               5                  10

<210> SEQ ID NO 455
<211> LENGTH: 11
<212> TYPE: PRT
<213> ORGANISM: Artificial Sequence
<220> FEATURE:
<223> OTHER INFORMATION: Exemplary cyclic peptide

<400> SEQUENCE: 455

Lys Arg Asp Trp Ile Trp Asn Gln Met His Asp
 1               5                  10
```

```
<210> SEQ ID NO 456
<211> LENGTH: 12
<212> TYPE: PRT
<213> ORGANISM: Artificial Sequence
<220> FEATURE:
<223> OTHER INFORMATION: Exemplary cyclic peptide

<400> SEQUENCE: 456

Lys Arg Asp Trp Ile Trp Asn Gln Met His Ile Asp
 1               5                  10

<210> SEQ ID NO 457
<211> LENGTH: 9
<212> TYPE: PRT
<213> ORGANISM: Artificial Sequence
<220> FEATURE:
<223> OTHER INFORMATION: Exemplary cyclic peptide

<400> SEQUENCE: 457

Lys Ser Trp Met Trp Asn Gln Phe Asp
 1               5

<210> SEQ ID NO 458
<211> LENGTH: 10
<212> TYPE: PRT
<213> ORGANISM: Artificial Sequence
<220> FEATURE:
<223> OTHER INFORMATION: Exemplary cyclic peptide

<400> SEQUENCE: 458

Lys Ser Trp Met Trp Asn Gln Phe Phe Asp
 1               5                  10

<210> SEQ ID NO 459
<211> LENGTH: 11
<212> TYPE: PRT
<213> ORGANISM: Artificial Sequence
<220> FEATURE:
<223> OTHER INFORMATION: Exemplary cyclic peptide

<400> SEQUENCE: 459

Lys Ser Trp Met Trp Asn Gln Phe Phe Leu Asp
 1               5                  10

<210> SEQ ID NO 460
<211> LENGTH: 8
<212> TYPE: PRT
<213> ORGANISM: Artificial Sequence
<220> FEATURE:
<223> OTHER INFORMATION: Exemplary cyclic peptide

<400> SEQUENCE: 460

Lys Trp Met Trp Asn Gln Phe Asp
 1               5

<210> SEQ ID NO 461
<211> LENGTH: 9
<212> TYPE: PRT
<213> ORGANISM: Artificial Sequence
<220> FEATURE:
<223> OTHER INFORMATION: Exemplary cyclic peptide

<400> SEQUENCE: 461

Lys Trp Met Trp Asn Gln Phe Phe Asp
 1               5

<210> SEQ ID NO 462
```

```
<211> LENGTH: 10
<212> TYPE: PRT
<213> ORGANISM: Artificial Sequence
<220> FEATURE:
<223> OTHER INFORMATION: Exemplary cyclic peptide

<400> SEQUENCE: 462

Lys Trp Met Trp Asn Gln Phe Phe Leu Asp
 1               5                  10

<210> SEQ ID NO 463
<211> LENGTH: 4
<212> TYPE: PRT
<213> ORGANISM: Artificial Sequence
<220> FEATURE:
<223> OTHER INFORMATION: Exemplary cyclic peptide

<400> SEQUENCE: 463

Arg Ser Trp Asp
 1

<210> SEQ ID NO 464
<211> LENGTH: 5
<212> TYPE: PRT
<213> ORGANISM: Artificial Sequence
<220> FEATURE:
<223> OTHER INFORMATION: Exemplary cyclic peptide

<400> SEQUENCE: 464

Arg Ser Trp Met Asp
 1               5

<210> SEQ ID NO 465
<211> LENGTH: 6
<212> TYPE: PRT
<213> ORGANISM: Artificial Sequence
<220> FEATURE:
<223> OTHER INFORMATION: Exemplary cyclic peptide

<400> SEQUENCE: 465

Arg Ser Trp Met Trp Asp
 1               5

<210> SEQ ID NO 466
<211> LENGTH: 7
<212> TYPE: PRT
<213> ORGANISM: Artificial Sequence
<220> FEATURE:
<223> OTHER INFORMATION: Exemplary cyclic peptide

<400> SEQUENCE: 466

Arg Ser Trp Met Trp Asn Asp
 1               5

<210> SEQ ID NO 467
<211> LENGTH: 8
<212> TYPE: PRT
<213> ORGANISM: Artificial Sequence
<220> FEATURE:
<223> OTHER INFORMATION: Exemplary cyclic peptide

<400> SEQUENCE: 467

Arg Ser Trp Met Trp Asn Gln Asp
 1               5

<210> SEQ ID NO 468
<211> LENGTH: 9
```

```
<212> TYPE: PRT
<213> ORGANISM: Artificial Sequence
<220> FEATURE:
<223> OTHER INFORMATION: Exemplary cyclic peptide

<400> SEQUENCE: 468

Arg Ser Trp Met Trp Asn Gln Phe Asp
 1               5

<210> SEQ ID NO 469
<211> LENGTH: 10
<212> TYPE: PRT
<213> ORGANISM: Artificial Sequence
<220> FEATURE:
<223> OTHER INFORMATION: Exemplary cyclic peptide

<400> SEQUENCE: 469

Arg Ser Trp Met Trp Asn Gln Phe Phe Asp
 1               5                  10

<210> SEQ ID NO 470
<211> LENGTH: 11
<212> TYPE: PRT
<213> ORGANISM: Artificial Sequence
<220> FEATURE:
<223> OTHER INFORMATION: Exemplary cyclic peptide

<400> SEQUENCE: 470

Arg Ser Trp Met Trp Asn Gln Phe Phe Leu Asp
 1               5                  10

<210> SEQ ID NO 471
<211> LENGTH: 5
<212> TYPE: PRT
<213> ORGANISM: Artificial Sequence
<220> FEATURE:
<223> OTHER INFORMATION: Exemplary cyclic peptide

<400> SEQUENCE: 471

Lys Arg Ser Trp Asp
 1               5

<210> SEQ ID NO 472
<211> LENGTH: 6
<212> TYPE: PRT
<213> ORGANISM: Artificial Sequence
<220> FEATURE:
<223> OTHER INFORMATION: Exemplary cyclic peptide

<400> SEQUENCE: 472

Lys Arg Ser Trp Met Asp
 1               5

<210> SEQ ID NO 473
<211> LENGTH: 7
<212> TYPE: PRT
<213> ORGANISM: Artificial Sequence
<220> FEATURE:
<223> OTHER INFORMATION: Exemplary cyclic peptide

<400> SEQUENCE: 473

Lys Arg Ser Trp Met Trp Asp
 1               5

<210> SEQ ID NO 474
<211> LENGTH: 8
<212> TYPE: PRT
```

```
<213> ORGANISM: Artificial Sequence
<220> FEATURE:
<223> OTHER INFORMATION: Exemplary cyclic peptide

<400> SEQUENCE: 474

Lys Arg Ser Trp Met Trp Asn Asp
 1               5

<210> SEQ ID NO 475
<211> LENGTH: 9
<212> TYPE: PRT
<213> ORGANISM: Artificial Sequence
<220> FEATURE:
<223> OTHER INFORMATION: Exemplary cyclic peptide

<400> SEQUENCE: 475

Lys Arg Ser Trp Met Trp Asn Gln Asp
 1               5

<210> SEQ ID NO 476
<211> LENGTH: 10
<212> TYPE: PRT
<213> ORGANISM: Artificial Sequence
<220> FEATURE:
<223> OTHER INFORMATION: Exemplary cyclic peptide

<400> SEQUENCE: 476

Lys Arg Ser Trp Met Trp Asn Gln Phe Asp
 1               5                  10

<210> SEQ ID NO 477
<211> LENGTH: 11
<212> TYPE: PRT
<213> ORGANISM: Artificial Sequence
<220> FEATURE:
<223> OTHER INFORMATION: Exemplary cyclic peptide

<400> SEQUENCE: 477

Lys Arg Ser Trp Met Trp Asn Gln Phe Phe Asp
 1               5                  10

<210> SEQ ID NO 478
<211> LENGTH: 12
<212> TYPE: PRT
<213> ORGANISM: Artificial Sequence
<220> FEATURE:
<223> OTHER INFORMATION: Exemplary cyclic peptide

<400> SEQUENCE: 478

Lys Arg Ser Trp Met Trp Asn Gln Phe Phe Leu Asp
 1               5                  10

<210> SEQ ID NO 479
<211> LENGTH: 9
<212> TYPE: PRT
<213> ORGANISM: Artificial Sequence
<220> FEATURE:
<223> OTHER INFORMATION: Exemplary cyclic peptide

<400> SEQUENCE: 479

Lys Ser Trp Val Trp Asn Gln Phe Asp
 1               5

<210> SEQ ID NO 480
<211> LENGTH: 10
<212> TYPE: PRT
<213> ORGANISM: Artificial Sequence
```

-continued

```
<220> FEATURE:
<223> OTHER INFORMATION: Exemplary cyclic peptide

<400> SEQUENCE: 480

Lys Ser Trp Val Trp Asn Gln Phe Phe Asp
 1               5                  10

<210> SEQ ID NO 481
<211> LENGTH: 11
<212> TYPE: PRT
<213> ORGANISM: Artificial Sequence
<220> FEATURE:
<223> OTHER INFORMATION: Exemplary cyclic peptide

<400> SEQUENCE: 481

Lys Ser Trp Val Trp Asn Gln Phe Phe Val Asp
 1               5                  10

<210> SEQ ID NO 482
<211> LENGTH: 5
<212> TYPE: PRT
<213> ORGANISM: Artificial Sequence
<220> FEATURE:
<223> OTHER INFORMATION: Exemplary cyclic peptide

<400> SEQUENCE: 482

Arg Ser Trp Val Asp
 1               5

<210> SEQ ID NO 483
<211> LENGTH: 6
<212> TYPE: PRT
<213> ORGANISM: Artificial Sequence
<220> FEATURE:
<223> OTHER INFORMATION: Exemplary cyclic peptide

<400> SEQUENCE: 483

Arg Ser Trp Val Trp Asp
 1               5

<210> SEQ ID NO 484
<211> LENGTH: 7
<212> TYPE: PRT
<213> ORGANISM: Artificial Sequence
<220> FEATURE:
<223> OTHER INFORMATION: Exemplary cyclic peptide

<400> SEQUENCE: 484

Arg Ser Trp Val Trp Asn Asp
 1               5

<210> SEQ ID NO 485
<211> LENGTH: 8
<212> TYPE: PRT
<213> ORGANISM: Artificial Sequence
<220> FEATURE:
<223> OTHER INFORMATION: Exemplary cyclic peptide

<400> SEQUENCE: 485

Arg Ser Trp Val Trp Asn Gln Asp
 1               5

<210> SEQ ID NO 486
<211> LENGTH: 9
<212> TYPE: PRT
<213> ORGANISM: Artificial Sequence
<220> FEATURE:
```

```
<223> OTHER INFORMATION: Exemplary cyclic peptide

<400> SEQUENCE: 486

Arg Ser Trp Val Trp Asn Gln Phe Asp
 1               5

<210> SEQ ID NO 487
<211> LENGTH: 10
<212> TYPE: PRT
<213> ORGANISM: Artificial Sequence
<220> FEATURE:
<223> OTHER INFORMATION: Exemplary cyclic peptide

<400> SEQUENCE: 487

Arg Ser Trp Val Trp Asn Gln Phe Phe Asp
 1               5                  10

<210> SEQ ID NO 488
<211> LENGTH: 11
<212> TYPE: PRT
<213> ORGANISM: Artificial Sequence
<220> FEATURE:
<223> OTHER INFORMATION: Exemplary cyclic peptide

<400> SEQUENCE: 488

Arg Ser Trp Val Trp Asn Gln Phe Phe Val Asp
 1               5                  10

<210> SEQ ID NO 489
<211> LENGTH: 6
<212> TYPE: PRT
<213> ORGANISM: Artificial Sequence
<220> FEATURE:
<223> OTHER INFORMATION: Exemplary cyclic peptide

<400> SEQUENCE: 489

Lys Arg Ser Trp Val Asp
 1               5

<210> SEQ ID NO 490
<211> LENGTH: 7
<212> TYPE: PRT
<213> ORGANISM: Artificial Sequence
<220> FEATURE:
<223> OTHER INFORMATION: Exemplary cyclic peptide

<400> SEQUENCE: 490

Lys Arg Ser Trp Val Trp Asp
 1               5

<210> SEQ ID NO 491
<211> LENGTH: 8
<212> TYPE: PRT
<213> ORGANISM: Artificial Sequence
<220> FEATURE:
<223> OTHER INFORMATION: Exemplary cyclic peptide

<400> SEQUENCE: 491

Lys Arg Ser Trp Val Trp Asn Asp
 1               5

<210> SEQ ID NO 492
<211> LENGTH: 9
<212> TYPE: PRT
<213> ORGANISM: Artificial Sequence
<220> FEATURE:
<223> OTHER INFORMATION: Exemplary cyclic peptide
```

```
<400> SEQUENCE: 492

Lys Arg Ser Trp Val Trp Asn Gln Asp
 1               5

<210> SEQ ID NO 493
<211> LENGTH: 10
<212> TYPE: PRT
<213> ORGANISM: Artificial Sequence
<220> FEATURE:
<223> OTHER INFORMATION: Exemplary cyclic peptide

<400> SEQUENCE: 493

Lys Arg Ser Trp Val Trp Asn Gln Phe Asp
 1               5                  10

<210> SEQ ID NO 494
<211> LENGTH: 11
<212> TYPE: PRT
<213> ORGANISM: Artificial Sequence
<220> FEATURE:
<223> OTHER INFORMATION: Exemplary cyclic peptide

<400> SEQUENCE: 494

Lys Arg Ser Trp Val Trp Asn Gln Phe Phe Asp
 1               5                  10

<210> SEQ ID NO 495
<211> LENGTH: 12
<212> TYPE: PRT
<213> ORGANISM: Artificial Sequence
<220> FEATURE:
<223> OTHER INFORMATION: Exemplary cyclic peptide

<400> SEQUENCE: 495

Lys Arg Ser Trp Val Trp Asn Gln Phe Phe Val Asp
 1               5                  10

<210> SEQ ID NO 496
<211> LENGTH: 9
<212> TYPE: PRT
<213> ORGANISM: Artificial Sequence
<220> FEATURE:
<223> OTHER INFORMATION: Exemplary cyclic peptide

<400> SEQUENCE: 496

Lys Gly Trp Val Trp Asn Gln Met Asp
 1               5

<210> SEQ ID NO 497
<211> LENGTH: 10
<212> TYPE: PRT
<213> ORGANISM: Artificial Sequence
<220> FEATURE:
<223> OTHER INFORMATION: Exemplary cyclic peptide

<400> SEQUENCE: 497

Lys Gly Trp Val Trp Asn Gln Met Phe Asp
 1               5                  10

<210> SEQ ID NO 498
<211> LENGTH: 11
<212> TYPE: PRT
<213> ORGANISM: Artificial Sequence
<220> FEATURE:
<223> OTHER INFORMATION: Exemplary cyclic peptide
```

```
<400> SEQUENCE: 498

Lys Gly Trp Val Trp Asn Gln Met Phe Val Asp
 1               5                  10

<210> SEQ ID NO 499
<211> LENGTH: 9
<212> TYPE: PRT
<213> ORGANISM: Artificial Sequence
<220> FEATURE:
<223> OTHER INFORMATION: Exemplary cyclic peptide

<400> SEQUENCE: 499

Arg Gly Trp Val Trp Asn Gln Met Asp
 1               5

<210> SEQ ID NO 500
<211> LENGTH: 11
<212> TYPE: PRT
<213> ORGANISM: Artificial Sequence
<220> FEATURE:
<223> OTHER INFORMATION: Exemplary cyclic peptide

<400> SEQUENCE: 500

Lys Arg Gly Trp Val Trp Asn Gln Met Phe Asp
 1               5                  10

<210> SEQ ID NO 501
<211> LENGTH: 11
<212> TYPE: PRT
<213> ORGANISM: Artificial Sequence
<220> FEATURE:
<223> OTHER INFORMATION: Exemplary cyclic peptide

<400> SEQUENCE: 501

Arg Gly Trp Val Trp Asn Gln Met Phe Val Asp
 1               5                  10

<210> SEQ ID NO 502
<211> LENGTH: 10
<212> TYPE: PRT
<213> ORGANISM: Artificial Sequence
<220> FEATURE:
<223> OTHER INFORMATION: Exemplary cyclic peptide

<400> SEQUENCE: 502

Lys Arg Gly Trp Val Trp Asn Gln Met Asp
 1               5                  10

<210> SEQ ID NO 503
<211> LENGTH: 12
<212> TYPE: PRT
<213> ORGANISM: Artificial Sequence
<220> FEATURE:
<223> OTHER INFORMATION: Exemplary cyclic peptide

<400> SEQUENCE: 503

Lys Arg Gly Trp Val Trp Asn Gln Met Phe Val Asp
 1               5                  10

<210> SEQ ID NO 504
<211> LENGTH: 11
<212> TYPE: PRT
<213> ORGANISM: Artificial Sequence
<220> FEATURE:
<223> OTHER INFORMATION: Exemplary cyclic peptide

<400> SEQUENCE: 504
```

```
Lys Gly Trp Val Trp Asn Gln Phe Phe Leu Asp
 1               5                   10

<210> SEQ ID NO 505
<211> LENGTH: 11
<212> TYPE: PRT
<213> ORGANISM: Artificial Sequence
<220> FEATURE:
<223> OTHER INFORMATION: Exemplary cyclic peptide

<400> SEQUENCE: 505

Arg Gly Trp Val Trp Asn Gln Phe Phe Leu Asp
 1               5                   10

<210> SEQ ID NO 506
<211> LENGTH: 12
<212> TYPE: PRT
<213> ORGANISM: Artificial Sequence
<220> FEATURE:
<223> OTHER INFORMATION: Exemplary cyclic peptide

<400> SEQUENCE: 506

Lys Arg Gly Trp Val Trp Asn Gln Phe Phe Leu Asp
 1               5                   10

<210> SEQ ID NO 507
<211> LENGTH: 9
<212> TYPE: PRT
<213> ORGANISM: Artificial Sequence
<220> FEATURE:
<223> OTHER INFORMATION: Exemplary cyclic peptide

<400> SEQUENCE: 507

Lys Ala Trp Val Ile Pro Pro Ile Asp
 1               5

<210> SEQ ID NO 508
<211> LENGTH: 10
<212> TYPE: PRT
<213> ORGANISM: Artificial Sequence
<220> FEATURE:
<223> OTHER INFORMATION: Exemplary cyclic peptide

<400> SEQUENCE: 508

Lys Ala Trp Val Ile Pro Pro Ile Ser Asp
 1               5                   10

<210> SEQ ID NO 509
<211> LENGTH: 11
<212> TYPE: PRT
<213> ORGANISM: Artificial Sequence
<220> FEATURE:
<223> OTHER INFORMATION: Exemplary cyclic peptide

<400> SEQUENCE: 509

Lys Ala Trp Val Ile Pro Pro Ile Ser Val Asp
 1               5                   10

<210> SEQ ID NO 510
<211> LENGTH: 8
<212> TYPE: PRT
<213> ORGANISM: Artificial Sequence
<220> FEATURE:
<223> OTHER INFORMATION: Exemplary cyclic peptide

<400> SEQUENCE: 510
```

```
Lys Trp Val Ile Pro Pro Ile Asp
 1               5

<210> SEQ ID NO 511
<211> LENGTH: 9
<212> TYPE: PRT
<213> ORGANISM: Artificial Sequence
<220> FEATURE:
<223> OTHER INFORMATION: Exemplary cyclic peptide

<400> SEQUENCE: 511

Lys Trp Val Ile Pro Pro Ile Ser Asp
 1               5

<210> SEQ ID NO 512
<211> LENGTH: 10
<212> TYPE: PRT
<213> ORGANISM: Artificial Sequence
<220> FEATURE:
<223> OTHER INFORMATION: Exemplary cyclic peptide

<400> SEQUENCE: 512

Lys Trp Val Ile Pro Pro Ile Ser Val Asp
 1               5                  10

<210> SEQ ID NO 513
<211> LENGTH: 4
<212> TYPE: PRT
<213> ORGANISM: Artificial Sequence
<220> FEATURE:
<223> OTHER INFORMATION: Exemplary cyclic peptide

<400> SEQUENCE: 513

Arg Ala Trp Asp
 1

<210> SEQ ID NO 514
<211> LENGTH: 5
<212> TYPE: PRT
<213> ORGANISM: Artificial Sequence
<220> FEATURE:
<223> OTHER INFORMATION: Exemplary cyclic peptide

<400> SEQUENCE: 514

Arg Ala Trp Val Asp
 1               5

<210> SEQ ID NO 515
<211> LENGTH: 6
<212> TYPE: PRT
<213> ORGANISM: Artificial Sequence
<220> FEATURE:
<223> OTHER INFORMATION: Exemplary cyclic peptide

<400> SEQUENCE: 515

Arg Ala Trp Val Ile Asp
 1               5

<210> SEQ ID NO 516
<211> LENGTH: 7
<212> TYPE: PRT
<213> ORGANISM: Artificial Sequence
<220> FEATURE:
<223> OTHER INFORMATION: Exemplary cyclic peptide

<400> SEQUENCE: 516

Arg Ala Trp Val Ile Pro Asp
```

-continued

```
<210> SEQ ID NO 517
<211> LENGTH: 8
<212> TYPE: PRT
<213> ORGANISM: Artificial Sequence
<220> FEATURE:
<223> OTHER INFORMATION: Exemplary cyclic peptide

<400> SEQUENCE: 517

Arg Ala Trp Val Ile Pro Pro Asp
 1               5

<210> SEQ ID NO 518
<211> LENGTH: 9
<212> TYPE: PRT
<213> ORGANISM: Artificial Sequence
<220> FEATURE:
<223> OTHER INFORMATION: Exemplary cyclic peptide

<400> SEQUENCE: 518

Arg Ala Trp Val Ile Pro Pro Ile Asp
 1               5

<210> SEQ ID NO 519
<211> LENGTH: 10
<212> TYPE: PRT
<213> ORGANISM: Artificial Sequence
<220> FEATURE:
<223> OTHER INFORMATION: Exemplary cyclic peptide

<400> SEQUENCE: 519

Arg Ala Trp Val Ile Pro Pro Ile Ser Asp
 1               5                  10

<210> SEQ ID NO 520
<211> LENGTH: 11
<212> TYPE: PRT
<213> ORGANISM: Artificial Sequence
<220> FEATURE:
<223> OTHER INFORMATION: Exemplary cyclic peptide

<400> SEQUENCE: 520

Arg Ala Trp Val Ile Pro Pro Ile Ser Val Asp
 1               5                  10

<210> SEQ ID NO 521
<211> LENGTH: 9
<212> TYPE: PRT
<213> ORGANISM: Artificial Sequence
<220> FEATURE:
<223> OTHER INFORMATION: Exemplary cyclic peptide

<400> SEQUENCE: 521

Lys Arg Ala Trp Val Ile Pro Pro Asp
 1               5

<210> SEQ ID NO 522
<211> LENGTH: 10
<212> TYPE: PRT
<213> ORGANISM: Artificial Sequence
<220> FEATURE:
<223> OTHER INFORMATION: Exemplary cyclic peptide

<400> SEQUENCE: 522

Lys Arg Ala Trp Val Ile Pro Pro Ile Asp
 1               5                  10
```

<210> SEQ ID NO 523
<211> LENGTH: 11
<212> TYPE: PRT
<213> ORGANISM: Artificial Sequence
<220> FEATURE:
<223> OTHER INFORMATION: Exemplary cyclic peptide

<400> SEQUENCE: 523

Lys Arg Ala Trp Val Ile Pro Pro Ile Ser Asp
1               5                   10

<210> SEQ ID NO 524
<211> LENGTH: 5
<212> TYPE: PRT
<213> ORGANISM: Artificial Sequence
<220> FEATURE:
<223> OTHER INFORMATION: Exemplary cyclic peptide

<400> SEQUENCE: 524

Lys Val Trp Asn Asp
1               5

<210> SEQ ID NO 525
<211> LENGTH: 6
<212> TYPE: PRT
<213> ORGANISM: Artificial Sequence
<220> FEATURE:
<223> OTHER INFORMATION: Exemplary cyclic peptide

<400> SEQUENCE: 525

Lys Val Trp Asn Gln Asp
1               5

<210> SEQ ID NO 526
<211> LENGTH: 7
<212> TYPE: PRT
<213> ORGANISM: Artificial Sequence
<220> FEATURE:
<223> OTHER INFORMATION: Exemplary cyclic peptide

<400> SEQUENCE: 526

Lys Val Trp Asn Gln Met Asp
1               5

<210> SEQ ID NO 527
<211> LENGTH: 7
<212> TYPE: PRT
<213> ORGANISM: Artificial Sequence
<220> FEATURE:
<223> OTHER INFORMATION: Exemplary cyclic peptide

<400> SEQUENCE: 527

Lys Val Trp Asn Gln Phe Asp
1               5

<210> SEQ ID NO 528
<211> LENGTH: 8
<212> TYPE: PRT
<213> ORGANISM: Artificial Sequence
<220> FEATURE:
<223> OTHER INFORMATION: Exemplary cyclic peptide

<400> SEQUENCE: 528

Lys Val Trp Asn Gln Met Phe Asp
1               5

```
<210> SEQ ID NO 529
<211> LENGTH: 8
<212> TYPE: PRT
<213> ORGANISM: Artificial Sequence
<220> FEATURE:
<223> OTHER INFORMATION: Exemplary cyclic peptide

<400> SEQUENCE: 529

Lys Val Trp Asn Gln Phe Phe Asp
1               5

<210> SEQ ID NO 530
<211> LENGTH: 5
<212> TYPE: PRT
<213> ORGANISM: Artificial Sequence
<220> FEATURE:
<223> OTHER INFORMATION: Exemplary cyclic peptide

<400> SEQUENCE: 530

Lys Trp Asn Gln Asp
1               5

<210> SEQ ID NO 531
<211> LENGTH: 6
<212> TYPE: PRT
<213> ORGANISM: Artificial Sequence
<220> FEATURE:
<223> OTHER INFORMATION: Exemplary cyclic peptide

<400> SEQUENCE: 531

Lys Trp Asn Gln Met Asp
1               5

<210> SEQ ID NO 532
<211> LENGTH: 6
<212> TYPE: PRT
<213> ORGANISM: Artificial Sequence
<220> FEATURE:
<223> OTHER INFORMATION: Exemplary cyclic peptide

<400> SEQUENCE: 532

Lys Trp Asn Gln Phe Asp
1               5

<210> SEQ ID NO 533
<211> LENGTH: 7
<212> TYPE: PRT
<213> ORGANISM: Artificial Sequence
<220> FEATURE:
<223> OTHER INFORMATION: Exemplary cyclic peptide

<400> SEQUENCE: 533

Lys Trp Asn Gln Phe Phe Asp
1               5

<210> SEQ ID NO 534
<211> LENGTH: 5
<212> TYPE: PRT
<213> ORGANISM: Artificial Sequence
<220> FEATURE:
<223> OTHER INFORMATION: Exemplary cyclic peptide

<400> SEQUENCE: 534

Lys Ile Trp Asn Asp
1               5
```

<210> SEQ ID NO 535
<211> LENGTH: 6
<212> TYPE: PRT
<213> ORGANISM: Artificial Sequence
<220> FEATURE:
<223> OTHER INFORMATION: Exemplary cyclic peptide

<400> SEQUENCE: 535

Lys Ile Trp Asn Gln Asp
 1               5

<210> SEQ ID NO 536
<211> LENGTH: 7
<212> TYPE: PRT
<213> ORGANISM: Artificial Sequence
<220> FEATURE:
<223> OTHER INFORMATION: Exemplary cyclic peptide

<400> SEQUENCE: 536

Lys Ile Trp Asn Gln Met Asp
 1               5

<210> SEQ ID NO 537
<211> LENGTH: 8
<212> TYPE: PRT
<213> ORGANISM: Artificial Sequence
<220> FEATURE:
<223> OTHER INFORMATION: Exemplary cyclic peptide

<400> SEQUENCE: 537

Lys Ile Trp Asn Gln Met His Asp
 1               5

<210> SEQ ID NO 538
<211> LENGTH: 7
<212> TYPE: PRT
<213> ORGANISM: Artificial Sequence
<220> FEATURE:
<223> OTHER INFORMATION: Exemplary cyclic peptide

<400> SEQUENCE: 538

Lys Trp Asn Gln Met His Asp
 1               5

<210> SEQ ID NO 539
<211> LENGTH: 5
<212> TYPE: PRT
<213> ORGANISM: Artificial Sequence
<220> FEATURE:
<223> OTHER INFORMATION: Exemplary cyclic peptide

<400> SEQUENCE: 539

Lys Met Trp Asn Asp
 1               5

<210> SEQ ID NO 540
<211> LENGTH: 6
<212> TYPE: PRT
<213> ORGANISM: Artificial Sequence
<220> FEATURE:
<223> OTHER INFORMATION: Exemplary cyclic peptide

<400> SEQUENCE: 540

Lys Met Trp Asn Gln Asp
 1               5

<210> SEQ ID NO 541

```
<211> LENGTH: 7
<212> TYPE: PRT
<213> ORGANISM: Artificial Sequence
<220> FEATURE:
<223> OTHER INFORMATION: Exemplary cyclic peptide

<400> SEQUENCE: 541

Lys Met Trp Asn Gln Phe Asp
 1               5

<210> SEQ ID NO 542
<211> LENGTH: 8
<212> TYPE: PRT
<213> ORGANISM: Artificial Sequence
<220> FEATURE:
<223> OTHER INFORMATION: Exemplary cyclic peptide

<400> SEQUENCE: 542

Lys Met Trp Asn Gln Phe Phe Asp
 1               5

<210> SEQ ID NO 543
<211> LENGTH: 5
<212> TYPE: PRT
<213> ORGANISM: Artificial Sequence
<220> FEATURE:
<223> OTHER INFORMATION: Exemplary cyclic peptide

<400> SEQUENCE: 543

Lys Gly Trp Val Glu
 1               5

<210> SEQ ID NO 544
<211> LENGTH: 6
<212> TYPE: PRT
<213> ORGANISM: Artificial Sequence
<220> FEATURE:
<223> OTHER INFORMATION: Exemplary cyclic peptide

<400> SEQUENCE: 544

Lys Gly Trp Val Trp Glu
 1               5

<210> SEQ ID NO 545
<211> LENGTH: 7
<212> TYPE: PRT
<213> ORGANISM: Artificial Sequence
<220> FEATURE:
<223> OTHER INFORMATION: Exemplary cyclic peptide

<400> SEQUENCE: 545

Lys Gly Trp Val Trp Asn Glu
 1               5

<210> SEQ ID NO 546
<211> LENGTH: 8
<212> TYPE: PRT
<213> ORGANISM: Artificial Sequence
<220> FEATURE:
<223> OTHER INFORMATION: Exemplary cyclic peptide

<400> SEQUENCE: 546

Lys Gly Trp Val Trp Asn Gln Glu
 1               5

<210> SEQ ID NO 547
<211> LENGTH: 5
```

```
<212> TYPE: PRT
<213> ORGANISM: Artificial Sequence
<220> FEATURE:
<223> OTHER INFORMATION: Exemplary cyclic peptide

<400> SEQUENCE: 547

Lys Trp Val Trp Glu
 1               5

<210> SEQ ID NO 548
<211> LENGTH: 6
<212> TYPE: PRT
<213> ORGANISM: Artificial Sequence
<220> FEATURE:
<223> OTHER INFORMATION: Exemplary cyclic peptide

<400> SEQUENCE: 548

Lys Trp Val Trp Asn Glu
 1               5

<210> SEQ ID NO 549
<211> LENGTH: 7
<212> TYPE: PRT
<213> ORGANISM: Artificial Sequence
<220> FEATURE:
<223> OTHER INFORMATION: Exemplary cyclic peptide

<400> SEQUENCE: 549

Lys Trp Val Trp Asn Gln Glu
 1               5

<210> SEQ ID NO 550
<211> LENGTH: 5
<212> TYPE: PRT
<213> ORGANISM: Artificial Sequence
<220> FEATURE:
<223> OTHER INFORMATION: Exemplary cyclic peptide

<400> SEQUENCE: 550

Lys Asp Trp Ile Glu
 1               5

<210> SEQ ID NO 551
<211> LENGTH: 6
<212> TYPE: PRT
<213> ORGANISM: Artificial Sequence
<220> FEATURE:
<223> OTHER INFORMATION: Exemplary cyclic peptide

<400> SEQUENCE: 551

Lys Asp Trp Ile Trp Glu
 1               5

<210> SEQ ID NO 552
<211> LENGTH: 6
<212> TYPE: PRT
<213> ORGANISM: Artificial Sequence
<220> FEATURE:
<223> OTHER INFORMATION: Exemplary cyclic peptide

<400> SEQUENCE: 552

Lys Asp Trp Ile Trp Asn
 1               5

<210> SEQ ID NO 553
<211> LENGTH: 8
<212> TYPE: PRT
```

```
<213> ORGANISM: Artificial Sequence
<220> FEATURE:
<223> OTHER INFORMATION: Exemplary cyclic peptide

<400> SEQUENCE: 553

Lys Asp Trp Ile Trp Asn Gln Glu
 1               5

<210> SEQ ID NO 554
<211> LENGTH: 5
<212> TYPE: PRT
<213> ORGANISM: Artificial Sequence
<220> FEATURE:
<223> OTHER INFORMATION: Exemplary cyclic peptide

<400> SEQUENCE: 554

Lys Trp Ile Trp Glu
 1               5

<210> SEQ ID NO 555
<211> LENGTH: 6
<212> TYPE: PRT
<213> ORGANISM: Artificial Sequence
<220> FEATURE:
<223> OTHER INFORMATION: Exemplary cyclic peptide

<400> SEQUENCE: 555

Lys Trp Ile Trp Asn Glu
 1               5

<210> SEQ ID NO 556
<211> LENGTH: 7
<212> TYPE: PRT
<213> ORGANISM: Artificial Sequence
<220> FEATURE:
<223> OTHER INFORMATION: Exemplary cyclic peptide

<400> SEQUENCE: 556

Lys Trp Ile Trp Asn Gln Glu
 1               5

<210> SEQ ID NO 557
<211> LENGTH: 5
<212> TYPE: PRT
<213> ORGANISM: Artificial Sequence
<220> FEATURE:
<223> OTHER INFORMATION: Exemplary cyclic peptide

<400> SEQUENCE: 557

Lys Ser Trp Met Glu
 1               5

<210> SEQ ID NO 558
<211> LENGTH: 6
<212> TYPE: PRT
<213> ORGANISM: Artificial Sequence
<220> FEATURE:
<223> OTHER INFORMATION: Exemplary cyclic peptide

<400> SEQUENCE: 558

Lys Ser Trp Met Trp Glu
 1               5

<210> SEQ ID NO 559
<211> LENGTH: 7
<212> TYPE: PRT
<213> ORGANISM: Artificial Sequence
```

```
<220> FEATURE:
<223> OTHER INFORMATION: Exemplary cyclic peptide

<400> SEQUENCE: 559

Lys Ser Trp Met Trp Asn Glu
1               5

<210> SEQ ID NO 560
<211> LENGTH: 8
<212> TYPE: PRT
<213> ORGANISM: Artificial Sequence
<220> FEATURE:
<223> OTHER INFORMATION: Exemplary cyclic peptide

<400> SEQUENCE: 560

Lys Ser Trp Met Trp Asn Gln Glu
1               5

<210> SEQ ID NO 561
<211> LENGTH: 5
<212> TYPE: PRT
<213> ORGANISM: Artificial Sequence
<220> FEATURE:
<223> OTHER INFORMATION: Exemplary cyclic peptide

<400> SEQUENCE: 561

Lys Trp Met Trp Glu
1               5

<210> SEQ ID NO 562
<211> LENGTH: 6
<212> TYPE: PRT
<213> ORGANISM: Artificial Sequence
<220> FEATURE:
<223> OTHER INFORMATION: Exemplary cyclic peptide

<400> SEQUENCE: 562

Lys Trp Met Trp Asn Glu
1               5

<210> SEQ ID NO 563
<211> LENGTH: 7
<212> TYPE: PRT
<213> ORGANISM: Artificial Sequence
<220> FEATURE:
<223> OTHER INFORMATION: Exemplary cyclic peptide

<400> SEQUENCE: 563

Lys Trp Met Trp Asn Gln Glu
1               5

<210> SEQ ID NO 564
<211> LENGTH: 5
<212> TYPE: PRT
<213> ORGANISM: Artificial Sequence
<220> FEATURE:
<223> OTHER INFORMATION: Exemplary cyclic peptide

<400> SEQUENCE: 564

Lys Ser Trp Val Glu
1               5

<210> SEQ ID NO 565
<211> LENGTH: 6
<212> TYPE: PRT
<213> ORGANISM: Artificial Sequence
<220> FEATURE:
```

```
<223> OTHER INFORMATION: Exemplary cyclic peptide

<400> SEQUENCE: 565

Lys Ser Trp Val Trp Glu
 1               5

<210> SEQ ID NO 566
<211> LENGTH: 7
<212> TYPE: PRT
<213> ORGANISM: Artificial Sequence
<220> FEATURE:
<223> OTHER INFORMATION: Exemplary cyclic peptide

<400> SEQUENCE: 566

Lys Ser Trp Val Trp Asn Glu
 1               5

<210> SEQ ID NO 567
<211> LENGTH: 8
<212> TYPE: PRT
<213> ORGANISM: Artificial Sequence
<220> FEATURE:
<223> OTHER INFORMATION: Exemplary cyclic peptide

<400> SEQUENCE: 567

Lys Ser Trp Val Trp Asn Gln Glu
 1               5

<210> SEQ ID NO 568
<211> LENGTH: 5
<212> TYPE: PRT
<213> ORGANISM: Artificial Sequence
<220> FEATURE:
<223> OTHER INFORMATION: Exemplary cyclic peptide

<400> SEQUENCE: 568

Lys Gly Trp Met Glu
 1               5

<210> SEQ ID NO 569
<211> LENGTH: 6
<212> TYPE: PRT
<213> ORGANISM: Artificial Sequence
<220> FEATURE:
<223> OTHER INFORMATION: Exemplary cyclic peptide

<400> SEQUENCE: 569

Lys Gly Trp Met Trp Glu
 1               5

<210> SEQ ID NO 570
<211> LENGTH: 7
<212> TYPE: PRT
<213> ORGANISM: Artificial Sequence
<220> FEATURE:
<223> OTHER INFORMATION: Exemplary cyclic peptide

<400> SEQUENCE: 570

Lys Gly Trp Met Trp Asn Glu
 1               5

<210> SEQ ID NO 571
<211> LENGTH: 8
<212> TYPE: PRT
<213> ORGANISM: Artificial Sequence
<220> FEATURE:
<223> OTHER INFORMATION: Exemplary cyclic peptide
```

-continued

```
<400> SEQUENCE: 571

Lys Gly Trp Met Trp Asn Gln Glu
1               5

<210> SEQ ID NO 572
<211> LENGTH: 5
<212> TYPE: PRT
<213> ORGANISM: Artificial Sequence
<220> FEATURE:
<223> OTHER INFORMATION: Exemplary cyclic peptide

<400> SEQUENCE: 572

Lys Ala Trp Val Glu
1               5

<210> SEQ ID NO 573
<211> LENGTH: 6
<212> TYPE: PRT
<213> ORGANISM: Artificial Sequence
<220> FEATURE:
<223> OTHER INFORMATION: Exemplary cyclic peptide

<400> SEQUENCE: 573

Lys Ala Trp Val Ile Glu
1               5

<210> SEQ ID NO 574
<211> LENGTH: 7
<212> TYPE: PRT
<213> ORGANISM: Artificial Sequence
<220> FEATURE:
<223> OTHER INFORMATION: Exemplary cyclic peptide

<400> SEQUENCE: 574

Lys Ala Trp Val Ile Pro Glu
1               5

<210> SEQ ID NO 575
<211> LENGTH: 8
<212> TYPE: PRT
<213> ORGANISM: Artificial Sequence
<220> FEATURE:
<223> OTHER INFORMATION: Exemplary cyclic peptide

<400> SEQUENCE: 575

Lys Ala Trp Val Ile Pro Pro Glu
1               5

<210> SEQ ID NO 576
<211> LENGTH: 5
<212> TYPE: PRT
<213> ORGANISM: Artificial Sequence
<220> FEATURE:
<223> OTHER INFORMATION: Exemplary cyclic peptide

<400> SEQUENCE: 576

Lys Trp Val Ile Glu
1               5

<210> SEQ ID NO 577
<211> LENGTH: 6
<212> TYPE: PRT
<213> ORGANISM: Artificial Sequence
<220> FEATURE:
<223> OTHER INFORMATION: Exemplary cyclic peptide
```

```
<400> SEQUENCE: 577

Lys Trp Val Ile Pro Glu
  1               5

<210> SEQ ID NO 578
<211> LENGTH: 7
<212> TYPE: PRT
<213> ORGANISM: Artificial Sequence
<220> FEATURE:
<223> OTHER INFORMATION: Exemplary cyclic peptide

<400> SEQUENCE: 578

Lys Trp Val Ile Pro Pro Glu
  1               5

<210> SEQ ID NO 579
<211> LENGTH: 9
<212> TYPE: PRT
<213> ORGANISM: Artificial Sequence
<220> FEATURE:
<223> OTHER INFORMATION: Exemplary cyclic peptide

<400> SEQUENCE: 579

Lys Gly Trp Val Trp Asn Gln Phe Glu
  1               5

<210> SEQ ID NO 580
<211> LENGTH: 10
<212> TYPE: PRT
<213> ORGANISM: Artificial Sequence
<220> FEATURE:
<223> OTHER INFORMATION: Exemplary cyclic peptide

<400> SEQUENCE: 580

Lys Gly Trp Val Trp Asn Gln Phe Phe Glu
  1               5                  10

<210> SEQ ID NO 581
<211> LENGTH: 11
<212> TYPE: PRT
<213> ORGANISM: Artificial Sequence
<220> FEATURE:
<223> OTHER INFORMATION: Exemplary cyclic peptide

<400> SEQUENCE: 581

Lys Gly Trp Val Trp Asn Gln Phe Phe Val Glu
  1               5                  10

<210> SEQ ID NO 582
<211> LENGTH: 8
<212> TYPE: PRT
<213> ORGANISM: Artificial Sequence
<220> FEATURE:
<223> OTHER INFORMATION: Exemplary cyclic peptide

<400> SEQUENCE: 582

Lys Trp Val Trp Asn Gln Phe Glu
  1               5

<210> SEQ ID NO 583
<211> LENGTH: 9
<212> TYPE: PRT
<213> ORGANISM: Artificial Sequence
<220> FEATURE:
<223> OTHER INFORMATION: Exemplary cyclic peptide

<400> SEQUENCE: 583
```

```
Lys Trp Val Trp Asn Gln Phe Phe Glu
  1               5
```

<210> SEQ ID NO 584
<211> LENGTH: 10
<212> TYPE: PRT
<213> ORGANISM: Artificial Sequence
<220> FEATURE:
<223> OTHER INFORMATION: Exemplary cyclic peptide

<400> SEQUENCE: 584

```
Lys Trp Val Trp Asn Gln Phe Phe Val Glu
  1               5                  10
```

<210> SEQ ID NO 585
<211> LENGTH: 5
<212> TYPE: PRT
<213> ORGANISM: Artificial Sequence
<220> FEATURE:
<223> OTHER INFORMATION: Exemplary cyclic peptide

<400> SEQUENCE: 585

```
Lys Arg Gly Trp Glu
  1               5
```

<210> SEQ ID NO 586
<211> LENGTH: 6
<212> TYPE: PRT
<213> ORGANISM: Artificial Sequence
<220> FEATURE:
<223> OTHER INFORMATION: Exemplary cyclic peptide

<400> SEQUENCE: 586

```
Lys Arg Gly Trp Val Glu
  1               5
```

<210> SEQ ID NO 587
<211> LENGTH: 7
<212> TYPE: PRT
<213> ORGANISM: Artificial Sequence
<220> FEATURE:
<223> OTHER INFORMATION: Exemplary cyclic peptide

<400> SEQUENCE: 587

```
Lys Arg Gly Trp Val Trp Glu
  1               5
```

<210> SEQ ID NO 588
<211> LENGTH: 8
<212> TYPE: PRT
<213> ORGANISM: Artificial Sequence
<220> FEATURE:
<223> OTHER INFORMATION: Exemplary cyclic peptide

<400> SEQUENCE: 588

```
Lys Arg Gly Trp Val Trp Asn Glu
  1               5
```

<210> SEQ ID NO 589
<211> LENGTH: 9
<212> TYPE: PRT
<213> ORGANISM: Artificial Sequence
<220> FEATURE:
<223> OTHER INFORMATION: Exemplary cyclic peptide

<400> SEQUENCE: 589

Lys Arg Gly Trp Val Trp Asn Gln Glu
1               5

<210> SEQ ID NO 590
<211> LENGTH: 10
<212> TYPE: PRT
<213> ORGANISM: Artificial Sequence
<220> FEATURE:
<223> OTHER INFORMATION: Exemplary cyclic peptide

<400> SEQUENCE: 590

Lys Arg Gly Trp Val Trp Asn Gln Phe Glu
1               5                   10

<210> SEQ ID NO 591
<211> LENGTH: 11
<212> TYPE: PRT
<213> ORGANISM: Artificial Sequence
<220> FEATURE:
<223> OTHER INFORMATION: Exemplary cyclic peptide

<400> SEQUENCE: 591

Lys Arg Gly Trp Val Trp Asn Gln Phe Phe Glu
1               5                   10

<210> SEQ ID NO 592
<211> LENGTH: 12
<212> TYPE: PRT
<213> ORGANISM: Artificial Sequence
<220> FEATURE:
<223> OTHER INFORMATION: Exemplary cyclic peptide

<400> SEQUENCE: 592

Lys Arg Gly Trp Val Trp Asn Gln Phe Phe Val Glu
1               5                   10

<210> SEQ ID NO 593
<211> LENGTH: 8
<212> TYPE: PRT
<213> ORGANISM: Artificial Sequence
<220> FEATURE:
<223> OTHER INFORMATION: Exemplary cyclic peptide

<400> SEQUENCE: 593

Asp Trp Ile Trp Asn Gln Met Glu
1               5

<210> SEQ ID NO 594
<211> LENGTH: 10
<212> TYPE: PRT
<213> ORGANISM: Artificial Sequence
<220> FEATURE:
<223> OTHER INFORMATION: Exemplary cyclic peptide

<400> SEQUENCE: 594

Lys Asp Trp Ile Trp Asn Gln Met His Glu
1               5                   10

<210> SEQ ID NO 595
<211> LENGTH: 11
<212> TYPE: PRT
<213> ORGANISM: Artificial Sequence
<220> FEATURE:
<223> OTHER INFORMATION: Exemplary cyclic peptide

<400> SEQUENCE: 595

Lys Asp Trp Ile Trp Asn Gln Met His Ile Glu

```
<210> SEQ ID NO 596
<211> LENGTH: 8
<212> TYPE: PRT
<213> ORGANISM: Artificial Sequence
<220> FEATURE:
<223> OTHER INFORMATION: Exemplary cyclic peptide

<400> SEQUENCE: 596

Lys Trp Ile Trp Asn Gln Met Glu
 1               5

<210> SEQ ID NO 597
<211> LENGTH: 9
<212> TYPE: PRT
<213> ORGANISM: Artificial Sequence
<220> FEATURE:
<223> OTHER INFORMATION: Exemplary cyclic peptide

<400> SEQUENCE: 597

Lys Trp Ile Trp Asn Gln Met His Glu
 1               5

<210> SEQ ID NO 598
<211> LENGTH: 10
<212> TYPE: PRT
<213> ORGANISM: Artificial Sequence
<220> FEATURE:
<223> OTHER INFORMATION: Exemplary cyclic peptide

<400> SEQUENCE: 598

Lys Trp Ile Trp Asn Gln Met His Ile Glu
 1               5                  10

<210> SEQ ID NO 599
<211> LENGTH: 4
<212> TYPE: PRT
<213> ORGANISM: Artificial Sequence
<220> FEATURE:
<223> OTHER INFORMATION: Exemplary cyclic peptide

<400> SEQUENCE: 599

Arg Asp Trp Glu
 1

<210> SEQ ID NO 600
<211> LENGTH: 5
<212> TYPE: PRT
<213> ORGANISM: Artificial Sequence
<220> FEATURE:
<223> OTHER INFORMATION: Exemplary cyclic peptide

<400> SEQUENCE: 600

Arg Asp Trp Ile Glu
 1               5

<210> SEQ ID NO 601
<211> LENGTH: 6
<212> TYPE: PRT
<213> ORGANISM: Artificial Sequence
<220> FEATURE:
<223> OTHER INFORMATION: Exemplary cyclic peptide

<400> SEQUENCE: 601

Arg Asp Trp Ile Trp Glu
 1               5
```

```
<210> SEQ ID NO 602
<211> LENGTH: 7
<212> TYPE: PRT
<213> ORGANISM: Artificial Sequence
<220> FEATURE:
<223> OTHER INFORMATION: Exemplary cyclic peptide

<400> SEQUENCE: 602

Arg Asp Trp Ile Trp Asn Glu
 1               5

<210> SEQ ID NO 603
<211> LENGTH: 8
<212> TYPE: PRT
<213> ORGANISM: Artificial Sequence
<220> FEATURE:
<223> OTHER INFORMATION: Exemplary cyclic peptide

<400> SEQUENCE: 603

Arg Asp Trp Ile Trp Asn Gln Glu
 1               5

<210> SEQ ID NO 604
<211> LENGTH: 9
<212> TYPE: PRT
<213> ORGANISM: Artificial Sequence
<220> FEATURE:
<223> OTHER INFORMATION: Exemplary cyclic peptide

<400> SEQUENCE: 604

Arg Asp Trp Ile Trp Asn Gln Met Glu
 1               5

<210> SEQ ID NO 605
<211> LENGTH: 10
<212> TYPE: PRT
<213> ORGANISM: Artificial Sequence
<220> FEATURE:
<223> OTHER INFORMATION: Exemplary cyclic peptide

<400> SEQUENCE: 605

Arg Asp Trp Ile Trp Asn Gln Met His Glu
 1               5                  10

<210> SEQ ID NO 606
<211> LENGTH: 11
<212> TYPE: PRT
<213> ORGANISM: Artificial Sequence
<220> FEATURE:
<223> OTHER INFORMATION: Exemplary cyclic peptide

<400> SEQUENCE: 606

Arg Asp Trp Ile Trp Asn Gln Met His Ile Glu
 1               5                  10

<210> SEQ ID NO 607
<211> LENGTH: 7
<212> TYPE: PRT
<213> ORGANISM: Artificial Sequence
<220> FEATURE:
<223> OTHER INFORMATION: Exemplary cyclic peptide

<400> SEQUENCE: 607

Lys Arg Asp Trp Ile Trp Glu
 1               5
```

```
<210> SEQ ID NO 608
<211> LENGTH: 8
<212> TYPE: PRT
<213> ORGANISM: Artificial Sequence
<220> FEATURE:
<223> OTHER INFORMATION: Exemplary cyclic peptide

<400> SEQUENCE: 608

Lys Arg Asp Trp Ile Trp Asn Glu
1               5

<210> SEQ ID NO 609
<211> LENGTH: 9
<212> TYPE: PRT
<213> ORGANISM: Artificial Sequence
<220> FEATURE:
<223> OTHER INFORMATION: Exemplary cyclic peptide

<400> SEQUENCE: 609

Lys Arg Asp Trp Ile Trp Asn Gln Glu
1               5

<210> SEQ ID NO 610
<211> LENGTH: 10
<212> TYPE: PRT
<213> ORGANISM: Artificial Sequence
<220> FEATURE:
<223> OTHER INFORMATION: Exemplary cyclic peptide

<400> SEQUENCE: 610

Lys Arg Asp Trp Ile Trp Asn Gln Met Glu
1               5                   10

<210> SEQ ID NO 611
<211> LENGTH: 11
<212> TYPE: PRT
<213> ORGANISM: Artificial Sequence
<220> FEATURE:
<223> OTHER INFORMATION: Exemplary cyclic peptide

<400> SEQUENCE: 611

Lys Arg Asp Trp Ile Trp Asn Gln Met His Glu
1               5                   10

<210> SEQ ID NO 612
<211> LENGTH: 12
<212> TYPE: PRT
<213> ORGANISM: Artificial Sequence
<220> FEATURE:
<223> OTHER INFORMATION: Exemplary cyclic peptide

<400> SEQUENCE: 612

Lys Arg Asp Trp Ile Trp Asn Gln Met His Ile Glu
1               5                   10

<210> SEQ ID NO 613
<211> LENGTH: 9
<212> TYPE: PRT
<213> ORGANISM: Artificial Sequence
<220> FEATURE:
<223> OTHER INFORMATION: Exemplary cyclic peptide

<400> SEQUENCE: 613

Lys Ser Trp Met Trp Asn Gln Phe Glu
1               5
```

```
<210> SEQ ID NO 614
<211> LENGTH: 10
<212> TYPE: PRT
<213> ORGANISM: Artificial Sequence
<220> FEATURE:
<223> OTHER INFORMATION: Exemplary cyclic peptide

<400> SEQUENCE: 614

Lys Ser Trp Met Trp Asn Gln Phe Phe Glu
 1               5                  10

<210> SEQ ID NO 615
<211> LENGTH: 11
<212> TYPE: PRT
<213> ORGANISM: Artificial Sequence
<220> FEATURE:
<223> OTHER INFORMATION: Exemplary cyclic peptide

<400> SEQUENCE: 615

Lys Ser Trp Met Trp Asn Gln Phe Phe Leu Glu
 1               5                  10

<210> SEQ ID NO 616
<211> LENGTH: 8
<212> TYPE: PRT
<213> ORGANISM: Artificial Sequence
<220> FEATURE:
<223> OTHER INFORMATION: Exemplary cyclic peptide

<400> SEQUENCE: 616

Lys Trp Met Trp Asn Gln Phe Glu
 1               5

<210> SEQ ID NO 617
<211> LENGTH: 9
<212> TYPE: PRT
<213> ORGANISM: Artificial Sequence
<220> FEATURE:
<223> OTHER INFORMATION: Exemplary cyclic peptide

<400> SEQUENCE: 617

Lys Trp Met Trp Asn Gln Phe Phe Glu
 1               5

<210> SEQ ID NO 618
<211> LENGTH: 10
<212> TYPE: PRT
<213> ORGANISM: Artificial Sequence
<220> FEATURE:
<223> OTHER INFORMATION: Exemplary cyclic peptide

<400> SEQUENCE: 618

Lys Trp Met Trp Asn Gln Phe Phe Leu Glu
 1               5                  10

<210> SEQ ID NO 619
<211> LENGTH: 4
<212> TYPE: PRT
<213> ORGANISM: Artificial Sequence
<220> FEATURE:
<223> OTHER INFORMATION: Exemplary cyclic peptide

<400> SEQUENCE: 619

Arg Ser Trp Glu
 1

<210> SEQ ID NO 620
```

```
<211> LENGTH: 5
<212> TYPE: PRT
<213> ORGANISM: Artificial Sequence
<220> FEATURE:
<223> OTHER INFORMATION: Exemplary cyclic peptide

<400> SEQUENCE: 620

Arg Ser Trp Met Glu
1               5

<210> SEQ ID NO 621
<211> LENGTH: 6
<212> TYPE: PRT
<213> ORGANISM: Artificial Sequence
<220> FEATURE:
<223> OTHER INFORMATION: Exemplary cyclic peptide

<400> SEQUENCE: 621

Arg Ser Trp Met Trp Glu
1               5

<210> SEQ ID NO 622
<211> LENGTH: 7
<212> TYPE: PRT
<213> ORGANISM: Artificial Sequence
<220> FEATURE:
<223> OTHER INFORMATION: Exemplary cyclic peptide

<400> SEQUENCE: 622

Arg Ser Trp Met Trp Asn Glu
1               5

<210> SEQ ID NO 623
<211> LENGTH: 8
<212> TYPE: PRT
<213> ORGANISM: Artificial Sequence
<220> FEATURE:
<223> OTHER INFORMATION: Exemplary cyclic peptide

<400> SEQUENCE: 623

Arg Ser Trp Met Trp Asn Gln Glu
1               5

<210> SEQ ID NO 624
<211> LENGTH: 9
<212> TYPE: PRT
<213> ORGANISM: Artificial Sequence
<220> FEATURE:
<223> OTHER INFORMATION: Exemplary cyclic peptide

<400> SEQUENCE: 624

Arg Ser Trp Met Trp Asn Gln Phe Glu
1               5

<210> SEQ ID NO 625
<211> LENGTH: 10
<212> TYPE: PRT
<213> ORGANISM: Artificial Sequence
<220> FEATURE:
<223> OTHER INFORMATION: Exemplary cyclic peptide

<400> SEQUENCE: 625

Arg Ser Trp Met Trp Asn Gln Phe Phe Glu
1               5                   10

<210> SEQ ID NO 626
<211> LENGTH: 11
```

```
<212> TYPE: PRT
<213> ORGANISM: Artificial Sequence
<220> FEATURE:
<223> OTHER INFORMATION: Exemplary cyclic peptide

<400> SEQUENCE: 626

Arg Ser Trp Met Trp Asn Gln Phe Phe Leu Glu
1               5                   10

<210> SEQ ID NO 627
<211> LENGTH: 5
<212> TYPE: PRT
<213> ORGANISM: Artificial Sequence
<220> FEATURE:
<223> OTHER INFORMATION: Exemplary cyclic peptide

<400> SEQUENCE: 627

Lys Arg Ser Trp Glu
1               5

<210> SEQ ID NO 628
<211> LENGTH: 6
<212> TYPE: PRT
<213> ORGANISM: Artificial Sequence
<220> FEATURE:
<223> OTHER INFORMATION: Exemplary cyclic peptide

<400> SEQUENCE: 628

Lys Arg Ser Trp Met Glu
1               5

<210> SEQ ID NO 629
<211> LENGTH: 7
<212> TYPE: PRT
<213> ORGANISM: Artificial Sequence
<220> FEATURE:
<223> OTHER INFORMATION: Exemplary cyclic peptide

<400> SEQUENCE: 629

Lys Arg Ser Trp Met Trp Glu
1               5

<210> SEQ ID NO 630
<211> LENGTH: 8
<212> TYPE: PRT
<213> ORGANISM: Artificial Sequence
<220> FEATURE:
<223> OTHER INFORMATION: Exemplary cyclic peptide

<400> SEQUENCE: 630

Lys Arg Ser Trp Met Trp Asn Glu
1               5

<210> SEQ ID NO 631
<211> LENGTH: 9
<212> TYPE: PRT
<213> ORGANISM: Artificial Sequence
<220> FEATURE:
<223> OTHER INFORMATION: Exemplary cyclic peptide

<400> SEQUENCE: 631

Lys Arg Ser Trp Met Trp Asn Gln Glu
1               5

<210> SEQ ID NO 632
<211> LENGTH: 10
<212> TYPE: PRT
```

<213> ORGANISM: Artificial Sequence
<220> FEATURE:
<223> OTHER INFORMATION: Exemplary cyclic peptide

<400> SEQUENCE: 632

Lys Arg Ser Trp Met Trp Asn Gln Phe Glu
 1               5                  10

<210> SEQ ID NO 633
<211> LENGTH: 11
<212> TYPE: PRT
<213> ORGANISM: Artificial Sequence
<220> FEATURE:
<223> OTHER INFORMATION: Exemplary cyclic peptide

<400> SEQUENCE: 633

Lys Arg Ser Trp Met Trp Asn Gln Phe Phe Glu
 1               5                  10

<210> SEQ ID NO 634
<211> LENGTH: 12
<212> TYPE: PRT
<213> ORGANISM: Artificial Sequence
<220> FEATURE:
<223> OTHER INFORMATION: Exemplary cyclic peptide

<400> SEQUENCE: 634

Lys Arg Ser Trp Met Trp Asn Gln Phe Phe Leu Glu
 1               5                  10

<210> SEQ ID NO 635
<211> LENGTH: 9
<212> TYPE: PRT
<213> ORGANISM: Artificial Sequence
<220> FEATURE:
<223> OTHER INFORMATION: Exemplary cyclic peptide

<400> SEQUENCE: 635

Lys Ser Trp Val Trp Asn Gln Phe Glu
 1               5

<210> SEQ ID NO 636
<211> LENGTH: 10
<212> TYPE: PRT
<213> ORGANISM: Artificial Sequence
<220> FEATURE:
<223> OTHER INFORMATION: Exemplary cyclic peptide

<400> SEQUENCE: 636

Lys Ser Trp Val Trp Asn Gln Phe Phe Glu
 1               5                  10

<210> SEQ ID NO 637
<211> LENGTH: 11
<212> TYPE: PRT
<213> ORGANISM: Artificial Sequence
<220> FEATURE:
<223> OTHER INFORMATION: Exemplary cyclic peptide

<400> SEQUENCE: 637

Lys Ser Trp Val Trp Asn Gln Phe Phe Val Glu
 1               5                  10

<210> SEQ ID NO 638
<211> LENGTH: 5
<212> TYPE: PRT
<213> ORGANISM: Artificial Sequence

```
<220> FEATURE:
<223> OTHER INFORMATION: Exemplary cyclic peptide

<400> SEQUENCE: 638

Arg Ser Trp Val Glu
 1               5

<210> SEQ ID NO 639
<211> LENGTH: 6
<212> TYPE: PRT
<213> ORGANISM: Artificial Sequence
<220> FEATURE:
<223> OTHER INFORMATION: Exemplary cyclic peptide

<400> SEQUENCE: 639

Arg Ser Trp Val Trp Glu
 1               5

<210> SEQ ID NO 640
<211> LENGTH: 7
<212> TYPE: PRT
<213> ORGANISM: Artificial Sequence
<220> FEATURE:
<223> OTHER INFORMATION: Exemplary cyclic peptide

<400> SEQUENCE: 640

Arg Ser Trp Val Trp Asn Glu
 1               5

<210> SEQ ID NO 641
<211> LENGTH: 8
<212> TYPE: PRT
<213> ORGANISM: Artificial Sequence
<220> FEATURE:
<223> OTHER INFORMATION: Exemplary cyclic peptide

<400> SEQUENCE: 641

Arg Ser Trp Val Trp Asn Gln Glu
 1               5

<210> SEQ ID NO 642
<211> LENGTH: 9
<212> TYPE: PRT
<213> ORGANISM: Artificial Sequence
<220> FEATURE:
<223> OTHER INFORMATION: Exemplary cyclic peptide

<400> SEQUENCE: 642

Arg Ser Trp Val Trp Asn Gln Phe Glu
 1               5

<210> SEQ ID NO 643
<211> LENGTH: 10
<212> TYPE: PRT
<213> ORGANISM: Artificial Sequence
<220> FEATURE:
<223> OTHER INFORMATION: Exemplary cyclic peptide

<400> SEQUENCE: 643

Arg Ser Trp Val Trp Asn Gln Phe Phe Glu
 1               5                   10

<210> SEQ ID NO 644
<211> LENGTH: 11
<212> TYPE: PRT
<213> ORGANISM: Artificial Sequence
<220> FEATURE:
```

-continued

```
<223> OTHER INFORMATION: Exemplary cyclic peptide

<400> SEQUENCE: 644

Arg Ser Trp Val Trp Asn Gln Phe Phe Val Glu
1               5                   10

<210> SEQ ID NO 645
<211> LENGTH: 6
<212> TYPE: PRT
<213> ORGANISM: Artificial Sequence
<220> FEATURE:
<223> OTHER INFORMATION: Exemplary cyclic peptide

<400> SEQUENCE: 645

Lys Arg Ser Trp Val Glu
1               5

<210> SEQ ID NO 646
<211> LENGTH: 7
<212> TYPE: PRT
<213> ORGANISM: Artificial Sequence
<220> FEATURE:
<223> OTHER INFORMATION: Exemplary cyclic peptide

<400> SEQUENCE: 646

Lys Arg Ser Trp Val Trp Glu
1               5

<210> SEQ ID NO 647
<211> LENGTH: 8
<212> TYPE: PRT
<213> ORGANISM: Artificial Sequence
<220> FEATURE:
<223> OTHER INFORMATION: Exemplary cyclic peptide

<400> SEQUENCE: 647

Lys Arg Ser Trp Val Trp Asn Glu
1               5

<210> SEQ ID NO 648
<211> LENGTH: 9
<212> TYPE: PRT
<213> ORGANISM: Artificial Sequence
<220> FEATURE:
<223> OTHER INFORMATION: Exemplary cyclic peptide

<400> SEQUENCE: 648

Lys Arg Ser Trp Val Trp Asn Gln Glu
1               5

<210> SEQ ID NO 649
<211> LENGTH: 10
<212> TYPE: PRT
<213> ORGANISM: Artificial Sequence
<220> FEATURE:
<223> OTHER INFORMATION: Exemplary cyclic peptide

<400> SEQUENCE: 649

Lys Arg Ser Trp Val Trp Asn Gln Phe Glu
1               5                   10

<210> SEQ ID NO 650
<211> LENGTH: 11
<212> TYPE: PRT
<213> ORGANISM: Artificial Sequence
<220> FEATURE:
<223> OTHER INFORMATION: Exemplary cyclic peptide
```

<400> SEQUENCE: 650

Lys Arg Ser Trp Val Trp Asn Gln Phe Phe Glu
1               5                   10

<210> SEQ ID NO 651
<211> LENGTH: 12
<212> TYPE: PRT
<213> ORGANISM: Artificial Sequence
<220> FEATURE:
<223> OTHER INFORMATION: Exemplary cyclic peptide

<400> SEQUENCE: 651

Lys Arg Ser Trp Val Trp Asn Gln Phe Phe Val Glu
1               5                   10

<210> SEQ ID NO 652
<211> LENGTH: 9
<212> TYPE: PRT
<213> ORGANISM: Artificial Sequence
<220> FEATURE:
<223> OTHER INFORMATION: Exemplary cyclic peptide

<400> SEQUENCE: 652

Lys Gly Trp Val Trp Asn Gln Met Glu
1               5

<210> SEQ ID NO 653
<211> LENGTH: 10
<212> TYPE: PRT
<213> ORGANISM: Artificial Sequence
<220> FEATURE:
<223> OTHER INFORMATION: Exemplary cyclic peptide

<400> SEQUENCE: 653

Lys Gly Trp Val Trp Asn Gln Met Phe Glu
1               5                   10

<210> SEQ ID NO 654
<211> LENGTH: 11
<212> TYPE: PRT
<213> ORGANISM: Artificial Sequence
<220> FEATURE:
<223> OTHER INFORMATION: Exemplary cyclic peptide

<400> SEQUENCE: 654

Lys Gly Trp Val Trp Asn Gln Met Phe Val Glu
1               5                   10

<210> SEQ ID NO 655
<211> LENGTH: 9
<212> TYPE: PRT
<213> ORGANISM: Artificial Sequence
<220> FEATURE:
<223> OTHER INFORMATION: Exemplary cyclic peptide

<400> SEQUENCE: 655

Arg Gly Trp Val Trp Asn Gln Met Glu
1               5

<210> SEQ ID NO 656
<211> LENGTH: 11
<212> TYPE: PRT
<213> ORGANISM: Artificial Sequence
<220> FEATURE:
<223> OTHER INFORMATION: Exemplary cyclic peptide

<400> SEQUENCE: 656

Lys Arg Gly Trp Val Trp Asn Gln Met Phe Glu
1               5                   10

<210> SEQ ID NO 657
<211> LENGTH: 11
<212> TYPE: PRT
<213> ORGANISM: Artificial Sequence
<220> FEATURE:
<223> OTHER INFORMATION: Exemplary cyclic peptide

<400> SEQUENCE: 657

Arg Gly Trp Val Trp Asn Gln Met Phe Val Glu
1               5                   10

<210> SEQ ID NO 658
<211> LENGTH: 10
<212> TYPE: PRT
<213> ORGANISM: Artificial Sequence
<220> FEATURE:
<223> OTHER INFORMATION: Exemplary cyclic peptide

<400> SEQUENCE: 658

Lys Arg Gly Trp Val Trp Asn Gln Met Glu
1               5                   10

<210> SEQ ID NO 659
<211> LENGTH: 12
<212> TYPE: PRT
<213> ORGANISM: Artificial Sequence
<220> FEATURE:
<223> OTHER INFORMATION: Exemplary cyclic peptide

<400> SEQUENCE: 659

Lys Arg Gly Trp Val Trp Asn Gln Met Phe Val Glu
1               5                   10

<210> SEQ ID NO 660
<211> LENGTH: 11
<212> TYPE: PRT
<213> ORGANISM: Artificial Sequence
<220> FEATURE:
<223> OTHER INFORMATION: Exemplary cyclic peptide

<400> SEQUENCE: 660

Lys Gly Trp Val Trp Asn Gln Phe Phe Leu Glu
1               5                   10

<210> SEQ ID NO 661
<211> LENGTH: 11
<212> TYPE: PRT
<213> ORGANISM: Artificial Sequence
<220> FEATURE:
<223> OTHER INFORMATION: Exemplary cyclic peptide

<400> SEQUENCE: 661

Arg Gly Trp Val Trp Asn Gln Phe Phe Leu Glu
1               5                   10

<210> SEQ ID NO 662
<211> LENGTH: 12
<212> TYPE: PRT
<213> ORGANISM: Artificial Sequence
<220> FEATURE:
<223> OTHER INFORMATION: Exemplary cyclic peptide

<400> SEQUENCE: 662

Lys Arg Gly Trp Val Trp Asn Gln Phe Phe Leu Glu
1               5                   10

<210> SEQ ID NO 663
<211> LENGTH: 9
<212> TYPE: PRT
<213> ORGANISM: Artificial Sequence
<220> FEATURE:
<223> OTHER INFORMATION: Exemplary cyclic peptide

<400> SEQUENCE: 663

Lys Ala Trp Val Ile Pro Pro Ile Glu
1               5

<210> SEQ ID NO 664
<211> LENGTH: 10
<212> TYPE: PRT
<213> ORGANISM: Artificial Sequence
<220> FEATURE:
<223> OTHER INFORMATION: Exemplary cyclic peptide

<400> SEQUENCE: 664

Lys Ala Trp Val Ile Pro Pro Ile Ser Glu
1               5                   10

<210> SEQ ID NO 665
<211> LENGTH: 11
<212> TYPE: PRT
<213> ORGANISM: Artificial Sequence
<220> FEATURE:
<223> OTHER INFORMATION: Exemplary cyclic peptide

<400> SEQUENCE: 665

Lys Ala Trp Val Ile Pro Pro Ile Ser Val Glu
1               5                   10

<210> SEQ ID NO 666
<211> LENGTH: 8
<212> TYPE: PRT
<213> ORGANISM: Artificial Sequence
<220> FEATURE:
<223> OTHER INFORMATION: Exemplary cyclic peptide

<400> SEQUENCE: 666

Lys Trp Val Ile Pro Pro Ile Glu
1               5

<210> SEQ ID NO 667
<211> LENGTH: 9
<212> TYPE: PRT
<213> ORGANISM: Artificial Sequence
<220> FEATURE:
<223> OTHER INFORMATION: Exemplary cyclic peptide

<400> SEQUENCE: 667

Lys Trp Val Ile Pro Pro Ile Ser Glu
1               5

<210> SEQ ID NO 668
<211> LENGTH: 10
<212> TYPE: PRT
<213> ORGANISM: Artificial Sequence
<220> FEATURE:
<223> OTHER INFORMATION: Exemplary cyclic peptide

<400> SEQUENCE: 668

```
Lys Trp Val Ile Pro Pro Ile Ser Val Glu
1               5                   10
```

<210> SEQ ID NO 669
<211> LENGTH: 4
<212> TYPE: PRT
<213> ORGANISM: Artificial Sequence
<220> FEATURE:
<223> OTHER INFORMATION: Exemplary cyclic peptide

<400> SEQUENCE: 669

```
Arg Ala Trp Glu
1
```

<210> SEQ ID NO 670
<211> LENGTH: 5
<212> TYPE: PRT
<213> ORGANISM: Artificial Sequence
<220> FEATURE:
<223> OTHER INFORMATION: Exemplary cyclic peptide

<400> SEQUENCE: 670

```
Arg Ala Trp Val Glu
1               5
```

<210> SEQ ID NO 671
<211> LENGTH: 6
<212> TYPE: PRT
<213> ORGANISM: Artificial Sequence
<220> FEATURE:
<223> OTHER INFORMATION: Exemplary cyclic peptide

<400> SEQUENCE: 671

```
Arg Ala Trp Val Ile Glu
1               5
```

<210> SEQ ID NO 672
<211> LENGTH: 7
<212> TYPE: PRT
<213> ORGANISM: Artificial Sequence
<220> FEATURE:
<223> OTHER INFORMATION: Exemplary cyclic peptide

<400> SEQUENCE: 672

```
Arg Ala Trp Val Ile Pro Glu
1               5
```

<210> SEQ ID NO 673
<211> LENGTH: 8
<212> TYPE: PRT
<213> ORGANISM: Artificial Sequence
<220> FEATURE:
<223> OTHER INFORMATION: Exemplary cyclic peptide

<400> SEQUENCE: 673

```
Arg Ala Trp Val Ile Pro Pro Glu
1               5
```

<210> SEQ ID NO 674
<211> LENGTH: 9
<212> TYPE: PRT
<213> ORGANISM: Artificial Sequence
<220> FEATURE:
<223> OTHER INFORMATION: Exemplary cyclic peptide

<400> SEQUENCE: 674

```
Arg Ala Trp Val Ile Pro Pro Ile Glu
```

-continued 1               5

<210> SEQ ID NO 675
<211> LENGTH: 10
<212> TYPE: PRT
<213> ORGANISM: Artificial Sequence
<220> FEATURE:
<223> OTHER INFORMATION: Exemplary cyclic peptide

<400> SEQUENCE: 675

Arg Ala Trp Val Ile Pro Pro Ile Ser Glu
1               5                   10

<210> SEQ ID NO 676
<211> LENGTH: 11
<212> TYPE: PRT
<213> ORGANISM: Artificial Sequence
<220> FEATURE:
<223> OTHER INFORMATION: Exemplary cyclic peptide

<400> SEQUENCE: 676

Arg Ala Trp Val Ile Pro Pro Ile Ser Val Glu
1               5                   10

<210> SEQ ID NO 677
<211> LENGTH: 9
<212> TYPE: PRT
<213> ORGANISM: Artificial Sequence
<220> FEATURE:
<223> OTHER INFORMATION: Exemplary cyclic peptide

<400> SEQUENCE: 677

Lys Arg Ala Trp Val Ile Pro Pro Glu
1               5

<210> SEQ ID NO 678
<211> LENGTH: 10
<212> TYPE: PRT
<213> ORGANISM: Artificial Sequence
<220> FEATURE:
<223> OTHER INFORMATION: Exemplary cyclic peptide

<400> SEQUENCE: 678

Lys Arg Ala Trp Val Ile Pro Pro Ile Glu
1               5                   10

<210> SEQ ID NO 679
<211> LENGTH: 5
<212> TYPE: PRT
<213> ORGANISM: Artificial Sequence
<220> FEATURE:
<223> OTHER INFORMATION: Exemplary cyclic peptide

<400> SEQUENCE: 679

Lys Val Trp Asn Glu
1               5

<210> SEQ ID NO 680
<211> LENGTH: 6
<212> TYPE: PRT
<213> ORGANISM: Artificial Sequence
<220> FEATURE:
<223> OTHER INFORMATION: Exemplary cyclic peptide

<400> SEQUENCE: 680

Lys Val Trp Asn Gln Glu
1               5

<210> SEQ ID NO 681
<211> LENGTH: 7
<212> TYPE: PRT
<213> ORGANISM: Artificial Sequence
<220> FEATURE:
<223> OTHER INFORMATION: Exemplary cyclic peptide

<400> SEQUENCE: 681

Lys Val Trp Asn Gln Met Glu
 1               5

<210> SEQ ID NO 682
<211> LENGTH: 7
<212> TYPE: PRT
<213> ORGANISM: Artificial Sequence
<220> FEATURE:
<223> OTHER INFORMATION: Exemplary cyclic peptide

<400> SEQUENCE: 682

Lys Val Trp Asn Gln Phe Glu
 1               5

<210> SEQ ID NO 683
<211> LENGTH: 8
<212> TYPE: PRT
<213> ORGANISM: Artificial Sequence
<220> FEATURE:
<223> OTHER INFORMATION: Exemplary cyclic peptide

<400> SEQUENCE: 683

Lys Val Trp Asn Gln Met Phe Glu
 1               5

<210> SEQ ID NO 684
<211> LENGTH: 8
<212> TYPE: PRT
<213> ORGANISM: Artificial Sequence
<220> FEATURE:
<223> OTHER INFORMATION: Exemplary cyclic peptide

<400> SEQUENCE: 684

Lys Val Trp Asn Gln Phe Phe Glu
 1               5

<210> SEQ ID NO 685
<211> LENGTH: 5
<212> TYPE: PRT
<213> ORGANISM: Artificial Sequence
<220> FEATURE:
<223> OTHER INFORMATION: Exemplary cyclic peptide

<400> SEQUENCE: 685

Lys Trp Asn Gln Glu
 1               5

<210> SEQ ID NO 686
<211> LENGTH: 6
<212> TYPE: PRT
<213> ORGANISM: Artificial Sequence
<220> FEATURE:
<223> OTHER INFORMATION: Exemplary cyclic peptide

<400> SEQUENCE: 686

Lys Trp Asn Gln Met Glu
 1               5

```
<210> SEQ ID NO 687
<211> LENGTH: 6
<212> TYPE: PRT
<213> ORGANISM: Artificial Sequence
<220> FEATURE:
<223> OTHER INFORMATION: Exemplary cyclic peptide

<400> SEQUENCE: 687

Lys Trp Asn Gln Phe Glu
 1               5

<210> SEQ ID NO 688
<211> LENGTH: 7
<212> TYPE: PRT
<213> ORGANISM: Artificial Sequence
<220> FEATURE:
<223> OTHER INFORMATION: Exemplary cyclic peptide

<400> SEQUENCE: 688

Lys Trp Asn Gln Phe Phe Glu
 1               5

<210> SEQ ID NO 689
<211> LENGTH: 5
<212> TYPE: PRT
<213> ORGANISM: Artificial Sequence
<220> FEATURE:
<223> OTHER INFORMATION: Exemplary cyclic peptide

<400> SEQUENCE: 689

Lys Ile Trp Asn Glu
 1               5

<210> SEQ ID NO 690
<211> LENGTH: 6
<212> TYPE: PRT
<213> ORGANISM: Artificial Sequence
<220> FEATURE:
<223> OTHER INFORMATION: Exemplary cyclic peptide

<400> SEQUENCE: 690

Lys Ile Trp Asn Gln Glu
 1               5

<210> SEQ ID NO 691
<211> LENGTH: 7
<212> TYPE: PRT
<213> ORGANISM: Artificial Sequence
<220> FEATURE:
<223> OTHER INFORMATION: Exemplary cyclic peptide

<400> SEQUENCE: 691

Lys Ile Trp Asn Gln Met Glu
 1               5

<210> SEQ ID NO 692
<211> LENGTH: 8
<212> TYPE: PRT
<213> ORGANISM: Artificial Sequence
<220> FEATURE:
<223> OTHER INFORMATION: Exemplary cyclic peptide

<400> SEQUENCE: 692

Lys Ile Trp Asn Gln Met His Glu
 1               5
```

```
<210> SEQ ID NO 693
<211> LENGTH: 7
<212> TYPE: PRT
<213> ORGANISM: Artificial Sequence
<220> FEATURE:
<223> OTHER INFORMATION: Exemplary cyclic peptide

<400> SEQUENCE: 693

Lys Trp Asn Gln Met His Glu
 1               5

<210> SEQ ID NO 694
<211> LENGTH: 5
<212> TYPE: PRT
<213> ORGANISM: Artificial Sequence
<220> FEATURE:
<223> OTHER INFORMATION: Exemplary cyclic peptide

<400> SEQUENCE: 694

Lys Met Trp Asn Glu
 1               5

<210> SEQ ID NO 695
<211> LENGTH: 6
<212> TYPE: PRT
<213> ORGANISM: Artificial Sequence
<220> FEATURE:
<223> OTHER INFORMATION: Exemplary cyclic peptide

<400> SEQUENCE: 695

Lys Met Trp Asn Gln Glu
 1               5

<210> SEQ ID NO 696
<211> LENGTH: 7
<212> TYPE: PRT
<213> ORGANISM: Artificial Sequence
<220> FEATURE:
<223> OTHER INFORMATION: Exemplary cyclic peptide

<400> SEQUENCE: 696

Lys Met Trp Asn Gln Phe Glu
 1               5

<210> SEQ ID NO 697
<211> LENGTH: 8
<212> TYPE: PRT
<213> ORGANISM: Artificial Sequence
<220> FEATURE:
<223> OTHER INFORMATION: Exemplary cyclic peptide

<400> SEQUENCE: 697

Lys Met Trp Asn Gln Phe Phe Glu
 1               5

<210> SEQ ID NO 698
<211> LENGTH: 5
<212> TYPE: PRT
<213> ORGANISM: Artificial Sequence
<220> FEATURE:
<223> OTHER INFORMATION: Exemplary cyclic peptide

<400> SEQUENCE: 698

Asp Gly Trp Val Lys
 1               5

<210> SEQ ID NO 699
```

```
<211> LENGTH: 6
<212> TYPE: PRT
<213> ORGANISM: Artificial Sequence
<220> FEATURE:
<223> OTHER INFORMATION: Exemplary cyclic peptide

<400> SEQUENCE: 699

Asp Gly Trp Val Trp Lys
 1               5

<210> SEQ ID NO 700
<211> LENGTH: 7
<212> TYPE: PRT
<213> ORGANISM: Artificial Sequence
<220> FEATURE:
<223> OTHER INFORMATION: Exemplary cyclic peptide

<400> SEQUENCE: 700

Asp Gly Trp Val Trp Asn Lys
 1               5

<210> SEQ ID NO 701
<211> LENGTH: 8
<212> TYPE: PRT
<213> ORGANISM: Artificial Sequence
<220> FEATURE:
<223> OTHER INFORMATION: Exemplary cyclic peptide

<400> SEQUENCE: 701

Asp Gly Trp Val Trp Asn Gln Lys
 1               5

<210> SEQ ID NO 702
<211> LENGTH: 5
<212> TYPE: PRT
<213> ORGANISM: Artificial Sequence
<220> FEATURE:
<223> OTHER INFORMATION: Exemplary cyclic peptide

<400> SEQUENCE: 702

Asp Trp Val Trp Lys
 1               5

<210> SEQ ID NO 703
<211> LENGTH: 6
<212> TYPE: PRT
<213> ORGANISM: Artificial Sequence
<220> FEATURE:
<223> OTHER INFORMATION: Exemplary cyclic peptide

<400> SEQUENCE: 703

Asp Trp Val Trp Asn Lys
 1               5

<210> SEQ ID NO 704
<211> LENGTH: 7
<212> TYPE: PRT
<213> ORGANISM: Artificial Sequence
<220> FEATURE:
<223> OTHER INFORMATION: Exemplary cyclic peptide

<400> SEQUENCE: 704

Asp Trp Val Trp Asn Gln Lys
 1               5

<210> SEQ ID NO 705
<211> LENGTH: 4
```

```
<212> TYPE: PRT
<213> ORGANISM: Artificial Sequence
<220> FEATURE:
<223> OTHER INFORMATION: Exemplary cyclic peptide

<400> SEQUENCE: 705

Asp Trp Ile Lys
 1

<210> SEQ ID NO 706
<211> LENGTH: 5
<212> TYPE: PRT
<213> ORGANISM: Artificial Sequence
<220> FEATURE:
<223> OTHER INFORMATION: Exemplary cyclic peptide

<400> SEQUENCE: 706

Asp Trp Ile Trp Lys
 1               5

<210> SEQ ID NO 707
<211> LENGTH: 6
<212> TYPE: PRT
<213> ORGANISM: Artificial Sequence
<220> FEATURE:
<223> OTHER INFORMATION: Exemplary cyclic peptide

<400> SEQUENCE: 707

Asp Trp Ile Trp Asn Lys
 1               5

<210> SEQ ID NO 708
<211> LENGTH: 7
<212> TYPE: PRT
<213> ORGANISM: Artificial Sequence
<220> FEATURE:
<223> OTHER INFORMATION: Exemplary cyclic peptide

<400> SEQUENCE: 708

Asp Trp Ile Trp Asn Gln Lys
 1               5

<210> SEQ ID NO 709
<211> LENGTH: 5
<212> TYPE: PRT
<213> ORGANISM: Artificial Sequence
<220> FEATURE:
<223> OTHER INFORMATION: Exemplary cyclic peptide

<400> SEQUENCE: 709

Asp Ser Trp Met Lys
 1               5

<210> SEQ ID NO 710
<211> LENGTH: 6
<212> TYPE: PRT
<213> ORGANISM: Artificial Sequence
<220> FEATURE:
<223> OTHER INFORMATION: Exemplary cyclic peptide

<400> SEQUENCE: 710

Asp Ser Trp Met Trp Lys
 1               5

<210> SEQ ID NO 711
<211> LENGTH: 7
<212> TYPE: PRT
```

```
<213> ORGANISM: Artificial Sequence
<220> FEATURE:
<223> OTHER INFORMATION: Exemplary cyclic peptide

<400> SEQUENCE: 711

Asp Ser Trp Met Trp Asn Lys
 1               5

<210> SEQ ID NO 712
<211> LENGTH: 8
<212> TYPE: PRT
<213> ORGANISM: Artificial Sequence
<220> FEATURE:
<223> OTHER INFORMATION: Exemplary cyclic peptide

<400> SEQUENCE: 712

Asp Ser Trp Met Trp Asn Gln Lys
 1               5

<210> SEQ ID NO 713
<211> LENGTH: 5
<212> TYPE: PRT
<213> ORGANISM: Artificial Sequence
<220> FEATURE:
<223> OTHER INFORMATION: Exemplary cyclic peptide

<400> SEQUENCE: 713

Asp Trp Met Trp Lys
 1               5

<210> SEQ ID NO 714
<211> LENGTH: 6
<212> TYPE: PRT
<213> ORGANISM: Artificial Sequence
<220> FEATURE:
<223> OTHER INFORMATION: Exemplary cyclic peptide

<400> SEQUENCE: 714

Asp Trp Met Trp Asn Lys
 1               5

<210> SEQ ID NO 715
<211> LENGTH: 7
<212> TYPE: PRT
<213> ORGANISM: Artificial Sequence
<220> FEATURE:
<223> OTHER INFORMATION: Exemplary cyclic peptide

<400> SEQUENCE: 715

Asp Trp Met Trp Asn Gln Lys
 1               5

<210> SEQ ID NO 716
<211> LENGTH: 5
<212> TYPE: PRT
<213> ORGANISM: Artificial Sequence
<220> FEATURE:
<223> OTHER INFORMATION: Exemplary cyclic peptide

<400> SEQUENCE: 716

Asp Ser Trp Val Lys
 1               5

<210> SEQ ID NO 717
<211> LENGTH: 6
<212> TYPE: PRT
<213> ORGANISM: Artificial Sequence
```

```
<220> FEATURE:
<223> OTHER INFORMATION: Exemplary cyclic peptide

<400> SEQUENCE: 717

Asp Ser Trp Val Trp Lys
 1               5

<210> SEQ ID NO 718
<211> LENGTH: 7
<212> TYPE: PRT
<213> ORGANISM: Artificial Sequence
<220> FEATURE:
<223> OTHER INFORMATION: Exemplary cyclic peptide

<400> SEQUENCE: 718

Asp Ser Trp Val Trp Asn Lys
 1               5

<210> SEQ ID NO 719
<211> LENGTH: 8
<212> TYPE: PRT
<213> ORGANISM: Artificial Sequence
<220> FEATURE:
<223> OTHER INFORMATION: Exemplary cyclic peptide

<400> SEQUENCE: 719

Asp Ser Trp Val Trp Asn Gln Lys
 1               5

<210> SEQ ID NO 720
<211> LENGTH: 5
<212> TYPE: PRT
<213> ORGANISM: Artificial Sequence
<220> FEATURE:
<223> OTHER INFORMATION: Exemplary cyclic peptide

<400> SEQUENCE: 720

Asp Gly Trp Met Lys
 1               5

<210> SEQ ID NO 721
<211> LENGTH: 6
<212> TYPE: PRT
<213> ORGANISM: Artificial Sequence
<220> FEATURE:
<223> OTHER INFORMATION: Exemplary cyclic peptide

<400> SEQUENCE: 721

Asp Gly Trp Met Trp Lys
 1               5

<210> SEQ ID NO 722
<211> LENGTH: 7
<212> TYPE: PRT
<213> ORGANISM: Artificial Sequence
<220> FEATURE:
<223> OTHER INFORMATION: Exemplary cyclic peptide

<400> SEQUENCE: 722

Asp Gly Trp Met Trp Asn Lys
 1               5

<210> SEQ ID NO 723
<211> LENGTH: 8
<212> TYPE: PRT
<213> ORGANISM: Artificial Sequence
<220> FEATURE:
```

```
<223> OTHER INFORMATION: Exemplary cyclic peptide

<400> SEQUENCE: 723

Asp Gly Trp Met Trp Asn Gln Lys
 1               5

<210> SEQ ID NO 724
<211> LENGTH: 5
<212> TYPE: PRT
<213> ORGANISM: Artificial Sequence
<220> FEATURE:
<223> OTHER INFORMATION: Exemplary cyclic peptide

<400> SEQUENCE: 724

Asp Ala Trp Val Lys
 1               5

<210> SEQ ID NO 725
<211> LENGTH: 6
<212> TYPE: PRT
<213> ORGANISM: Artificial Sequence
<220> FEATURE:
<223> OTHER INFORMATION: Exemplary cyclic peptide

<400> SEQUENCE: 725

Asp Ala Trp Val Ile Lys
 1               5

<210> SEQ ID NO 726
<211> LENGTH: 7
<212> TYPE: PRT
<213> ORGANISM: Artificial Sequence
<220> FEATURE:
<223> OTHER INFORMATION: Exemplary cyclic peptide

<400> SEQUENCE: 726

Asp Ala Trp Val Ile Pro Lys
 1               5

<210> SEQ ID NO 727
<211> LENGTH: 8
<212> TYPE: PRT
<213> ORGANISM: Artificial Sequence
<220> FEATURE:
<223> OTHER INFORMATION: Exemplary cyclic peptide

<400> SEQUENCE: 727

Asp Ala Trp Val Ile Pro Pro Lys
 1               5

<210> SEQ ID NO 728
<211> LENGTH: 5
<212> TYPE: PRT
<213> ORGANISM: Artificial Sequence
<220> FEATURE:
<223> OTHER INFORMATION: Exemplary cyclic peptide

<400> SEQUENCE: 728

Asp Trp Val Ile Lys
 1               5

<210> SEQ ID NO 729
<211> LENGTH: 6
<212> TYPE: PRT
<213> ORGANISM: Artificial Sequence
<220> FEATURE:
<223> OTHER INFORMATION: Exemplary cyclic peptide
```

```
<400> SEQUENCE: 729

Asp Trp Val Ile Pro Lys
 1               5

<210> SEQ ID NO 730
<211> LENGTH: 7
<212> TYPE: PRT
<213> ORGANISM: Artificial Sequence
<220> FEATURE:
<223> OTHER INFORMATION: Exemplary cyclic peptide

<400> SEQUENCE: 730

Asp Trp Val Ile Pro Pro Lys
 1               5

<210> SEQ ID NO 731
<211> LENGTH: 9
<212> TYPE: PRT
<213> ORGANISM: Artificial Sequence
<220> FEATURE:
<223> OTHER INFORMATION: Exemplary cyclic peptide

<400> SEQUENCE: 731

Asp Gly Trp Val Trp Asn Gln Phe Lys
 1               5

<210> SEQ ID NO 732
<211> LENGTH: 10
<212> TYPE: PRT
<213> ORGANISM: Artificial Sequence
<220> FEATURE:
<223> OTHER INFORMATION: Exemplary cyclic peptide

<400> SEQUENCE: 732

Asp Gly Trp Val Trp Asn Gln Phe Phe Lys
 1               5                   10

<210> SEQ ID NO 733
<211> LENGTH: 11
<212> TYPE: PRT
<213> ORGANISM: Artificial Sequence
<220> FEATURE:
<223> OTHER INFORMATION: Exemplary cyclic peptide

<400> SEQUENCE: 733

Asp Gly Trp Val Trp Asn Gln Phe Phe Val Lys
 1               5                   10

<210> SEQ ID NO 734
<211> LENGTH: 8
<212> TYPE: PRT
<213> ORGANISM: Artificial Sequence
<220> FEATURE:
<223> OTHER INFORMATION: Exemplary cyclic peptide

<400> SEQUENCE: 734

Asp Trp Val Trp Asn Gln Phe Lys
 1               5

<210> SEQ ID NO 735
<211> LENGTH: 9
<212> TYPE: PRT
<213> ORGANISM: Artificial Sequence
<220> FEATURE:
<223> OTHER INFORMATION: Exemplary cyclic peptide
```

```
<400> SEQUENCE: 735

Asp Trp Val Trp Asn Gln Phe Phe Lys
 1               5

<210> SEQ ID NO 736
<211> LENGTH: 10
<212> TYPE: PRT
<213> ORGANISM: Artificial Sequence
<220> FEATURE:
<223> OTHER INFORMATION: Exemplary cyclic peptide

<400> SEQUENCE: 736

Asp Trp Val Trp Asn Gln Phe Phe Val Lys
 1               5                  10

<210> SEQ ID NO 737
<211> LENGTH: 5
<212> TYPE: PRT
<213> ORGANISM: Artificial Sequence
<220> FEATURE:
<223> OTHER INFORMATION: Exemplary cyclic peptide

<400> SEQUENCE: 737

Asp Arg Gly Trp Lys
 1               5

<210> SEQ ID NO 738
<211> LENGTH: 6
<212> TYPE: PRT
<213> ORGANISM: Artificial Sequence
<220> FEATURE:
<223> OTHER INFORMATION: Exemplary cyclic peptide

<400> SEQUENCE: 738

Asp Arg Gly Trp Val Lys
 1               5

<210> SEQ ID NO 739
<211> LENGTH: 7
<212> TYPE: PRT
<213> ORGANISM: Artificial Sequence
<220> FEATURE:
<223> OTHER INFORMATION: Exemplary cyclic peptide

<400> SEQUENCE: 739

Asp Arg Gly Trp Val Trp Lys
 1               5

<210> SEQ ID NO 740
<211> LENGTH: 8
<212> TYPE: PRT
<213> ORGANISM: Artificial Sequence
<220> FEATURE:
<223> OTHER INFORMATION: Exemplary cyclic peptide

<400> SEQUENCE: 740

Asp Arg Gly Trp Val Trp Asn Lys
 1               5

<210> SEQ ID NO 741
<211> LENGTH: 9
<212> TYPE: PRT
<213> ORGANISM: Artificial Sequence
<220> FEATURE:
<223> OTHER INFORMATION: Exemplary cyclic peptide

<400> SEQUENCE: 741
```

Asp Arg Gly Trp Val Trp Asn Gln Lys
1               5

<210> SEQ ID NO 742
<211> LENGTH: 10
<212> TYPE: PRT
<213> ORGANISM: Artificial Sequence
<220> FEATURE:
<223> OTHER INFORMATION: Exemplary cyclic peptide

<400> SEQUENCE: 742

Asp Arg Gly Trp Val Trp Asn Gln Phe Lys
1               5                   10

<210> SEQ ID NO 743
<211> LENGTH: 11
<212> TYPE: PRT
<213> ORGANISM: Artificial Sequence
<220> FEATURE:
<223> OTHER INFORMATION: Exemplary cyclic peptide

<400> SEQUENCE: 743

Asp Arg Gly Trp Val Trp Asn Gln Phe Phe Lys
1               5                   10

<210> SEQ ID NO 744
<211> LENGTH: 12
<212> TYPE: PRT
<213> ORGANISM: Artificial Sequence
<220> FEATURE:
<223> OTHER INFORMATION: Exemplary cyclic peptide

<400> SEQUENCE: 744

Asp Arg Gly Trp Val Trp Asn Gln Phe Phe Val Lys
1               5                   10

<210> SEQ ID NO 745
<211> LENGTH: 6
<212> TYPE: PRT
<213> ORGANISM: Artificial Sequence
<220> FEATURE:
<223> OTHER INFORMATION: Exemplary cyclic peptide

<400> SEQUENCE: 745

Asp Lys Arg Gly Trp Lys
1               5

<210> SEQ ID NO 746
<211> LENGTH: 7
<212> TYPE: PRT
<213> ORGANISM: Artificial Sequence
<220> FEATURE:
<223> OTHER INFORMATION: Exemplary cyclic peptide

<400> SEQUENCE: 746

Asp Lys Arg Gly Trp Val Lys
1               5

<210> SEQ ID NO 747
<211> LENGTH: 8
<212> TYPE: PRT
<213> ORGANISM: Artificial Sequence
<220> FEATURE:
<223> OTHER INFORMATION: Exemplary cyclic peptide

<400> SEQUENCE: 747

-continued

```
Asp Lys Arg Gly Trp Val Trp Lys
1               5
```

<210> SEQ ID NO 748
<211> LENGTH: 9
<212> TYPE: PRT
<213> ORGANISM: Artificial Sequence
<220> FEATURE:
<223> OTHER INFORMATION: Exemplary cyclic peptide

<400> SEQUENCE: 748

```
Asp Lys Arg Gly Trp Val Trp Asn Lys
1               5
```

<210> SEQ ID NO 749
<211> LENGTH: 10
<212> TYPE: PRT
<213> ORGANISM: Artificial Sequence
<220> FEATURE:
<223> OTHER INFORMATION: Exemplary cyclic peptide

<400> SEQUENCE: 749

```
Asp Lys Arg Gly Trp Val Trp Asn Gln Lys
1               5                   10
```

<210> SEQ ID NO 750
<211> LENGTH: 11
<212> TYPE: PRT
<213> ORGANISM: Artificial Sequence
<220> FEATURE:
<223> OTHER INFORMATION: Exemplary cyclic peptide

<400> SEQUENCE: 750

```
Asp Lys Arg Gly Trp Val Trp Asn Gln Phe Lys
1               5                   10
```

<210> SEQ ID NO 751
<211> LENGTH: 12
<212> TYPE: PRT
<213> ORGANISM: Artificial Sequence
<220> FEATURE:
<223> OTHER INFORMATION: Exemplary cyclic peptide

<400> SEQUENCE: 751

```
Asp Lys Arg Gly Trp Val Trp Asn Gln Phe Phe Lys
1               5                   10
```

<210> SEQ ID NO 752
<211> LENGTH: 13
<212> TYPE: PRT
<213> ORGANISM: Artificial Sequence
<220> FEATURE:
<223> OTHER INFORMATION: Exemplary cyclic peptide

<400> SEQUENCE: 752

```
Asp Lys Arg Gly Trp Val Trp Asn Gln Phe Phe Val Lys
1               5                   10
```

<210> SEQ ID NO 753
<211> LENGTH: 8
<212> TYPE: PRT
<213> ORGANISM: Artificial Sequence
<220> FEATURE:
<223> OTHER INFORMATION: Exemplary cyclic peptide

<400> SEQUENCE: 753

```
Asp Trp Ile Trp Asn Gln Met Lys
1               5
```

-continued

```
  1               5

<210> SEQ ID NO 754
<211> LENGTH: 9
<212> TYPE: PRT
<213> ORGANISM: Artificial Sequence
<220> FEATURE:
<223> OTHER INFORMATION: Exemplary cyclic peptide

<400> SEQUENCE: 754

Asp Trp Ile Trp Asn Gln Met His Lys
  1               5

<210> SEQ ID NO 755
<211> LENGTH: 10
<212> TYPE: PRT
<213> ORGANISM: Artificial Sequence
<220> FEATURE:
<223> OTHER INFORMATION: Exemplary cyclic peptide

<400> SEQUENCE: 755

Asp Trp Ile Trp Asn Gln Met His Ile Lys
  1               5                  10

<210> SEQ ID NO 756
<211> LENGTH: 5
<212> TYPE: PRT
<213> ORGANISM: Artificial Sequence
<220> FEATURE:
<223> OTHER INFORMATION: Exemplary cyclic peptide

<400> SEQUENCE: 756

Asp Arg Asp Trp Lys
  1               5

<210> SEQ ID NO 757
<211> LENGTH: 6
<212> TYPE: PRT
<213> ORGANISM: Artificial Sequence
<220> FEATURE:
<223> OTHER INFORMATION: Exemplary cyclic peptide

<400> SEQUENCE: 757

Asp Arg Asp Trp Ile Lys
  1               5

<210> SEQ ID NO 758
<211> LENGTH: 7
<212> TYPE: PRT
<213> ORGANISM: Artificial Sequence
<220> FEATURE:
<223> OTHER INFORMATION: Exemplary cyclic peptide

<400> SEQUENCE: 758

Asp Arg Asp Trp Ile Trp Lys
  1               5

<210> SEQ ID NO 759
<211> LENGTH: 8
<212> TYPE: PRT
<213> ORGANISM: Artificial Sequence
<220> FEATURE:
<223> OTHER INFORMATION: Exemplary cyclic peptide

<400> SEQUENCE: 759

Asp Arg Asp Trp Ile Trp Asn Lys
  1               5
```

```
<210> SEQ ID NO 760
<211> LENGTH: 9
<212> TYPE: PRT
<213> ORGANISM: Artificial Sequence
<220> FEATURE:
<223> OTHER INFORMATION: Exemplary cyclic peptide

<400> SEQUENCE: 760

Asp Arg Asp Trp Ile Trp Asn Gln Lys
1               5

<210> SEQ ID NO 761
<211> LENGTH: 10
<212> TYPE: PRT
<213> ORGANISM: Artificial Sequence
<220> FEATURE:
<223> OTHER INFORMATION: Exemplary cyclic peptide

<400> SEQUENCE: 761

Asp Arg Asp Trp Ile Trp Asn Gln Met Lys
1               5                   10

<210> SEQ ID NO 762
<211> LENGTH: 11
<212> TYPE: PRT
<213> ORGANISM: Artificial Sequence
<220> FEATURE:
<223> OTHER INFORMATION: Exemplary cyclic peptide

<400> SEQUENCE: 762

Asp Arg Asp Trp Ile Trp Asn Gln Met His Lys
1               5                   10

<210> SEQ ID NO 763
<211> LENGTH: 12
<212> TYPE: PRT
<213> ORGANISM: Artificial Sequence
<220> FEATURE:
<223> OTHER INFORMATION: Exemplary cyclic peptide

<400> SEQUENCE: 763

Asp Arg Asp Trp Ile Trp Asn Gln Met His Ile Lys
1               5                   10

<210> SEQ ID NO 764
<211> LENGTH: 6
<212> TYPE: PRT
<213> ORGANISM: Artificial Sequence
<220> FEATURE:
<223> OTHER INFORMATION: Exemplary cyclic peptide

<400> SEQUENCE: 764

Asp Lys Arg Asp Trp Lys
1               5

<210> SEQ ID NO 765
<211> LENGTH: 7
<212> TYPE: PRT
<213> ORGANISM: Artificial Sequence
<220> FEATURE:
<223> OTHER INFORMATION: Exemplary cyclic peptide

<400> SEQUENCE: 765

Asp Lys Arg Asp Trp Ile Lys
1               5
```

```
<210> SEQ ID NO 766
<211> LENGTH: 8
<212> TYPE: PRT
<213> ORGANISM: Artificial Sequence
<220> FEATURE:
<223> OTHER INFORMATION: Exemplary cyclic peptide

<400> SEQUENCE: 766

Asp Lys Arg Asp Trp Ile Trp Lys
 1               5

<210> SEQ ID NO 767
<211> LENGTH: 9
<212> TYPE: PRT
<213> ORGANISM: Artificial Sequence
<220> FEATURE:
<223> OTHER INFORMATION: Exemplary cyclic peptide

<400> SEQUENCE: 767

Asp Lys Arg Asp Trp Ile Trp Asn Lys
 1               5

<210> SEQ ID NO 768
<211> LENGTH: 10
<212> TYPE: PRT
<213> ORGANISM: Artificial Sequence
<220> FEATURE:
<223> OTHER INFORMATION: Exemplary cyclic peptide

<400> SEQUENCE: 768

Asp Lys Arg Asp Trp Ile Trp Asn Gln Lys
 1               5                   10

<210> SEQ ID NO 769
<211> LENGTH: 11
<212> TYPE: PRT
<213> ORGANISM: Artificial Sequence
<220> FEATURE:
<223> OTHER INFORMATION: Exemplary cyclic peptide

<400> SEQUENCE: 769

Asp Lys Arg Asp Trp Ile Trp Asn Gln Met Lys
 1               5                   10

<210> SEQ ID NO 770
<211> LENGTH: 12
<212> TYPE: PRT
<213> ORGANISM: Artificial Sequence
<220> FEATURE:
<223> OTHER INFORMATION: Exemplary cyclic peptide

<400> SEQUENCE: 770

Asp Lys Arg Asp Trp Ile Trp Asn Gln Met His Lys
 1               5                   10

<210> SEQ ID NO 771
<211> LENGTH: 13
<212> TYPE: PRT
<213> ORGANISM: Artificial Sequence
<220> FEATURE:
<223> OTHER INFORMATION: Exemplary cyclic peptide

<400> SEQUENCE: 771

Asp Lys Arg Asp Trp Ile Trp Asn Gln Met His Ile Lys
 1               5                   10
```

```
<210> SEQ ID NO 772
<211> LENGTH: 9
<212> TYPE: PRT
<213> ORGANISM: Artificial Sequence
<220> FEATURE:
<223> OTHER INFORMATION: Exemplary cyclic peptide

<400> SEQUENCE: 772

Asp Ser Trp Met Trp Asn Gln Phe Lys
 1               5

<210> SEQ ID NO 773
<211> LENGTH: 10
<212> TYPE: PRT
<213> ORGANISM: Artificial Sequence
<220> FEATURE:
<223> OTHER INFORMATION: Exemplary cyclic peptide

<400> SEQUENCE: 773

Asp Ser Trp Met Trp Asn Gln Phe Phe Lys
 1               5                  10

<210> SEQ ID NO 774
<211> LENGTH: 11
<212> TYPE: PRT
<213> ORGANISM: Artificial Sequence
<220> FEATURE:
<223> OTHER INFORMATION: Exemplary cyclic peptide

<400> SEQUENCE: 774

Asp Ser Trp Met Trp Asn Gln Phe Phe Leu Lys
 1               5                  10

<210> SEQ ID NO 775
<211> LENGTH: 8
<212> TYPE: PRT
<213> ORGANISM: Artificial Sequence
<220> FEATURE:
<223> OTHER INFORMATION: Exemplary cyclic peptide

<400> SEQUENCE: 775

Asp Trp Met Trp Asn Gln Phe Lys
 1               5

<210> SEQ ID NO 776
<211> LENGTH: 9
<212> TYPE: PRT
<213> ORGANISM: Artificial Sequence
<220> FEATURE:
<223> OTHER INFORMATION: Exemplary cyclic peptide

<400> SEQUENCE: 776

Asp Trp Met Trp Asn Gln Phe Phe Lys
 1               5

<210> SEQ ID NO 777
<211> LENGTH: 10
<212> TYPE: PRT
<213> ORGANISM: Artificial Sequence
<220> FEATURE:
<223> OTHER INFORMATION: Exemplary cyclic peptide

<400> SEQUENCE: 777

Asp Trp Met Trp Asn Gln Phe Phe Leu Lys
 1               5                  10

<210> SEQ ID NO 778
```

```
<211> LENGTH: 5
<212> TYPE: PRT
<213> ORGANISM: Artificial Sequence
<220> FEATURE:
<223> OTHER INFORMATION: Exemplary cyclic peptide

<400> SEQUENCE: 778

Asp Arg Ser Trp Lys
 1               5

<210> SEQ ID NO 779
<211> LENGTH: 6
<212> TYPE: PRT
<213> ORGANISM: Artificial Sequence
<220> FEATURE:
<223> OTHER INFORMATION: Exemplary cyclic peptide

<400> SEQUENCE: 779

Asp Arg Ser Trp Met Lys
 1               5

<210> SEQ ID NO 780
<211> LENGTH: 7
<212> TYPE: PRT
<213> ORGANISM: Artificial Sequence
<220> FEATURE:
<223> OTHER INFORMATION: Exemplary cyclic peptide

<400> SEQUENCE: 780

Asp Arg Ser Trp Met Trp Lys
 1               5

<210> SEQ ID NO 781
<211> LENGTH: 8
<212> TYPE: PRT
<213> ORGANISM: Artificial Sequence
<220> FEATURE:
<223> OTHER INFORMATION: Exemplary cyclic peptide

<400> SEQUENCE: 781

Asp Arg Ser Trp Met Trp Asn Lys
 1               5

<210> SEQ ID NO 782
<211> LENGTH: 9
<212> TYPE: PRT
<213> ORGANISM: Artificial Sequence
<220> FEATURE:
<223> OTHER INFORMATION: Exemplary cyclic peptide

<400> SEQUENCE: 782

Asp Arg Ser Trp Met Trp Asn Gln Lys
 1               5

<210> SEQ ID NO 783
<211> LENGTH: 10
<212> TYPE: PRT
<213> ORGANISM: Artificial Sequence
<220> FEATURE:
<223> OTHER INFORMATION: Exemplary cyclic peptide

<400> SEQUENCE: 783

Asp Arg Ser Trp Met Trp Asn Gln Phe Lys
 1               5                  10

<210> SEQ ID NO 784
<211> LENGTH: 11
```

```
<212> TYPE: PRT
<213> ORGANISM: Artificial Sequence
<220> FEATURE:
<223> OTHER INFORMATION: Exemplary cyclic peptide

<400> SEQUENCE: 784

Asp Arg Ser Trp Met Trp Asn Gln Phe Phe Lys
1               5                   10

<210> SEQ ID NO 785
<211> LENGTH: 12
<212> TYPE: PRT
<213> ORGANISM: Artificial Sequence
<220> FEATURE:
<223> OTHER INFORMATION: Exemplary cyclic peptide

<400> SEQUENCE: 785

Asp Arg Ser Trp Met Trp Asn Gln Phe Phe Leu Lys
1               5                   10

<210> SEQ ID NO 786
<211> LENGTH: 6
<212> TYPE: PRT
<213> ORGANISM: Artificial Sequence
<220> FEATURE:
<223> OTHER INFORMATION: Exemplary cyclic peptide

<400> SEQUENCE: 786

Asp Lys Arg Ser Trp Lys
1               5

<210> SEQ ID NO 787
<211> LENGTH: 7
<212> TYPE: PRT
<213> ORGANISM: Artificial Sequence
<220> FEATURE:
<223> OTHER INFORMATION: Exemplary cyclic peptide

<400> SEQUENCE: 787

Asp Lys Arg Ser Trp Met Lys
1               5

<210> SEQ ID NO 788
<211> LENGTH: 8
<212> TYPE: PRT
<213> ORGANISM: Artificial Sequence
<220> FEATURE:
<223> OTHER INFORMATION: Exemplary cyclic peptide

<400> SEQUENCE: 788

Asp Lys Arg Ser Trp Met Trp Lys
1               5

<210> SEQ ID NO 789
<211> LENGTH: 9
<212> TYPE: PRT
<213> ORGANISM: Artificial Sequence
<220> FEATURE:
<223> OTHER INFORMATION: Exemplary cyclic peptide

<400> SEQUENCE: 789

Asp Lys Arg Ser Trp Met Trp Asn Lys
1               5

<210> SEQ ID NO 790
<211> LENGTH: 10
<212> TYPE: PRT
```

```
<213> ORGANISM: Artificial Sequence
<220> FEATURE:
<223> OTHER INFORMATION: Exemplary cyclic peptide

<400> SEQUENCE: 790

Asp Lys Arg Ser Trp Met Trp Asn Gln Lys
1               5                   10

<210> SEQ ID NO 791
<211> LENGTH: 11
<212> TYPE: PRT
<213> ORGANISM: Artificial Sequence
<220> FEATURE:
<223> OTHER INFORMATION: Exemplary cyclic peptide

<400> SEQUENCE: 791

Asp Lys Arg Ser Trp Met Trp Asn Gln Phe Lys
1               5                   10

<210> SEQ ID NO 792
<211> LENGTH: 12
<212> TYPE: PRT
<213> ORGANISM: Artificial Sequence
<220> FEATURE:
<223> OTHER INFORMATION: Exemplary cyclic peptide

<400> SEQUENCE: 792

Asp Lys Arg Ser Trp Met Trp Asn Gln Phe Phe Lys
1               5                   10

<210> SEQ ID NO 793
<211> LENGTH: 9
<212> TYPE: PRT
<213> ORGANISM: Artificial Sequence
<220> FEATURE:
<223> OTHER INFORMATION: Exemplary cyclic peptide

<400> SEQUENCE: 793

Asp Ser Trp Val Trp Asn Gln Phe Lys
1               5

<210> SEQ ID NO 794
<211> LENGTH: 10
<212> TYPE: PRT
<213> ORGANISM: Artificial Sequence
<220> FEATURE:
<223> OTHER INFORMATION: Exemplary cyclic peptide

<400> SEQUENCE: 794

Asp Ser Trp Val Trp Asn Gln Phe Phe Lys
1               5                   10

<210> SEQ ID NO 795
<211> LENGTH: 11
<212> TYPE: PRT
<213> ORGANISM: Artificial Sequence
<220> FEATURE:
<223> OTHER INFORMATION: Exemplary cyclic peptide

<400> SEQUENCE: 795

Asp Ser Trp Val Trp Asn Gln Phe Phe Val Lys
1               5                   10

<210> SEQ ID NO 796
<211> LENGTH: 6
<212> TYPE: PRT
<213> ORGANISM: Artificial Sequence
```

```
<220> FEATURE:
<223> OTHER INFORMATION: Exemplary cyclic peptide

<400> SEQUENCE: 796

Asp Arg Ser Trp Val Lys
1               5

<210> SEQ ID NO 797
<211> LENGTH: 7
<212> TYPE: PRT
<213> ORGANISM: Artificial Sequence
<220> FEATURE:
<223> OTHER INFORMATION: Exemplary cyclic peptide

<400> SEQUENCE: 797

Asp Arg Ser Trp Val Trp Lys
1               5

<210> SEQ ID NO 798
<211> LENGTH: 8
<212> TYPE: PRT
<213> ORGANISM: Artificial Sequence
<220> FEATURE:
<223> OTHER INFORMATION: Exemplary cyclic peptide

<400> SEQUENCE: 798

Asp Arg Ser Trp Val Trp Asn Lys
1               5

<210> SEQ ID NO 799
<211> LENGTH: 9
<212> TYPE: PRT
<213> ORGANISM: Artificial Sequence
<220> FEATURE:
<223> OTHER INFORMATION: Exemplary cyclic peptide

<400> SEQUENCE: 799

Asp Arg Ser Trp Val Trp Asn Gln Lys
1               5

<210> SEQ ID NO 800
<211> LENGTH: 10
<212> TYPE: PRT
<213> ORGANISM: Artificial Sequence
<220> FEATURE:
<223> OTHER INFORMATION: Exemplary cyclic peptide

<400> SEQUENCE: 800

Asp Arg Ser Trp Val Trp Asn Gln Phe Lys
1               5                   10

<210> SEQ ID NO 801
<211> LENGTH: 11
<212> TYPE: PRT
<213> ORGANISM: Artificial Sequence
<220> FEATURE:
<223> OTHER INFORMATION: Exemplary cyclic peptide

<400> SEQUENCE: 801

Asp Arg Ser Trp Val Trp Asn Gln Phe Phe Lys
1               5                   10

<210> SEQ ID NO 802
<211> LENGTH: 12
<212> TYPE: PRT
<213> ORGANISM: Artificial Sequence
<220> FEATURE:
```

<223> OTHER INFORMATION: Exemplary cyclic peptide

<400> SEQUENCE: 802

Asp Arg Ser Trp Val Trp Asn Gln Phe Phe Val Lys
1               5                   10

<210> SEQ ID NO 803
<211> LENGTH: 7
<212> TYPE: PRT
<213> ORGANISM: Artificial Sequence
<220> FEATURE:
<223> OTHER INFORMATION: Exemplary cyclic peptide

<400> SEQUENCE: 803

Asp Lys Arg Ser Trp Val Lys
1               5

<210> SEQ ID NO 804
<211> LENGTH: 8
<212> TYPE: PRT
<213> ORGANISM: Artificial Sequence
<220> FEATURE:
<223> OTHER INFORMATION: Exemplary cyclic peptide

<400> SEQUENCE: 804

Asp Lys Arg Ser Trp Val Trp Lys
1               5

<210> SEQ ID NO 805
<211> LENGTH: 9
<212> TYPE: PRT
<213> ORGANISM: Artificial Sequence
<220> FEATURE:
<223> OTHER INFORMATION: Exemplary cyclic peptide

<400> SEQUENCE: 805

Asp Lys Arg Ser Trp Val Trp Asn Lys
1               5

<210> SEQ ID NO 806
<211> LENGTH: 10
<212> TYPE: PRT
<213> ORGANISM: Artificial Sequence
<220> FEATURE:
<223> OTHER INFORMATION: Exemplary cyclic peptide

<400> SEQUENCE: 806

Asp Lys Arg Ser Trp Val Trp Asn Gln Lys
1               5                   10

<210> SEQ ID NO 807
<211> LENGTH: 11
<212> TYPE: PRT
<213> ORGANISM: Artificial Sequence
<220> FEATURE:
<223> OTHER INFORMATION: Exemplary cyclic peptide

<400> SEQUENCE: 807

Asp Lys Arg Ser Trp Val Trp Asn Gln Phe Lys
1               5                   10

<210> SEQ ID NO 808
<211> LENGTH: 12
<212> TYPE: PRT
<213> ORGANISM: Artificial Sequence
<220> FEATURE:
<223> OTHER INFORMATION: Exemplary cyclic peptide

```
<400> SEQUENCE: 808

Asp Lys Arg Ser Trp Val Trp Asn Gln Phe Phe Lys
 1               5                  10

<210> SEQ ID NO 809
<211> LENGTH: 13
<212> TYPE: PRT
<213> ORGANISM: Artificial Sequence
<220> FEATURE:
<223> OTHER INFORMATION: Exemplary cyclic peptide

<400> SEQUENCE: 809

Asp Lys Arg Ser Trp Val Trp Asn Gln Phe Phe Val Lys
 1               5                  10

<210> SEQ ID NO 810
<211> LENGTH: 9
<212> TYPE: PRT
<213> ORGANISM: Artificial Sequence
<220> FEATURE:
<223> OTHER INFORMATION: Exemplary cyclic peptide

<400> SEQUENCE: 810

Asp Gly Trp Val Trp Asn Gln Met Lys
 1               5

<210> SEQ ID NO 811
<211> LENGTH: 10
<212> TYPE: PRT
<213> ORGANISM: Artificial Sequence
<220> FEATURE:
<223> OTHER INFORMATION: Exemplary cyclic peptide

<400> SEQUENCE: 811

Asp Gly Trp Val Trp Asn Gln Met Phe Lys
 1               5                  10

<210> SEQ ID NO 812
<211> LENGTH: 11
<212> TYPE: PRT
<213> ORGANISM: Artificial Sequence
<220> FEATURE:
<223> OTHER INFORMATION: Exemplary cyclic peptide

<400> SEQUENCE: 812

Asp Gly Trp Val Trp Asn Gln Met Phe Val Lys
 1               5                  10

<210> SEQ ID NO 813
<211> LENGTH: 10
<212> TYPE: PRT
<213> ORGANISM: Artificial Sequence
<220> FEATURE:
<223> OTHER INFORMATION: Exemplary cyclic peptide

<400> SEQUENCE: 813

Asp Arg Gly Trp Val Trp Asn Gln Met Lys
 1               5                  10

<210> SEQ ID NO 814
<211> LENGTH: 11
<212> TYPE: PRT
<213> ORGANISM: Artificial Sequence
<220> FEATURE:
<223> OTHER INFORMATION: Exemplary cyclic peptide
```

```
<400> SEQUENCE: 814

Asp Arg Gly Trp Val Trp Asn Gln Met Phe Lys
 1               5                  10

<210> SEQ ID NO 815
<211> LENGTH: 12
<212> TYPE: PRT
<213> ORGANISM: Artificial Sequence
<220> FEATURE:
<223> OTHER INFORMATION: Exemplary cyclic peptide

<400> SEQUENCE: 815

Asp Arg Gly Trp Val Trp Asn Gln Met Phe Val Lys
 1               5                  10

<210> SEQ ID NO 816
<211> LENGTH: 11
<212> TYPE: PRT
<213> ORGANISM: Artificial Sequence
<220> FEATURE:
<223> OTHER INFORMATION: Exemplary cyclic peptide

<400> SEQUENCE: 816

Asp Lys Arg Gly Trp Val Trp Asn Gln Met Lys
 1               5                  10

<210> SEQ ID NO 817
<211> LENGTH: 13
<212> TYPE: PRT
<213> ORGANISM: Artificial Sequence
<220> FEATURE:
<223> OTHER INFORMATION: Exemplary cyclic peptide

<400> SEQUENCE: 817

Asp Lys Arg Gly Trp Val Trp Asn Gln Met Phe Val Lys
 1               5                  10

<210> SEQ ID NO 818
<211> LENGTH: 11
<212> TYPE: PRT
<213> ORGANISM: Artificial Sequence
<220> FEATURE:
<223> OTHER INFORMATION: Exemplary cyclic peptide

<400> SEQUENCE: 818

Asp Gly Trp Val Trp Asn Gln Phe Phe Leu Lys
 1               5                  10

<210> SEQ ID NO 819
<211> LENGTH: 12
<212> TYPE: PRT
<213> ORGANISM: Artificial Sequence
<220> FEATURE:
<223> OTHER INFORMATION: Exemplary cyclic peptide

<400> SEQUENCE: 819

Asp Arg Gly Trp Val Trp Asn Gln Phe Phe Leu Lys
 1               5                  10

<210> SEQ ID NO 820
<211> LENGTH: 13
<212> TYPE: PRT
<213> ORGANISM: Artificial Sequence
<220> FEATURE:
<223> OTHER INFORMATION: Exemplary cyclic peptide

<400> SEQUENCE: 820
```

Asp Lys Arg Gly Trp Val Trp Asn Gln Phe Phe Leu Lys
1               5                   10

<210> SEQ ID NO 821
<211> LENGTH: 9
<212> TYPE: PRT
<213> ORGANISM: Artificial Sequence
<220> FEATURE:
<223> OTHER INFORMATION: Exemplary cyclic peptide

<400> SEQUENCE: 821

Asp Ala Trp Val Ile Pro Pro Ile Lys
1               5

<210> SEQ ID NO 822
<211> LENGTH: 10
<212> TYPE: PRT
<213> ORGANISM: Artificial Sequence
<220> FEATURE:
<223> OTHER INFORMATION: Exemplary cyclic peptide

<400> SEQUENCE: 822

Asp Ala Trp Val Ile Pro Pro Ile Ser Lys
1               5                   10

<210> SEQ ID NO 823
<211> LENGTH: 11
<212> TYPE: PRT
<213> ORGANISM: Artificial Sequence
<220> FEATURE:
<223> OTHER INFORMATION: Exemplary cyclic peptide

<400> SEQUENCE: 823

Asp Ala Trp Val Ile Pro Pro Ile Ser Val Lys
1               5                   10

<210> SEQ ID NO 824
<211> LENGTH: 8
<212> TYPE: PRT
<213> ORGANISM: Artificial Sequence
<220> FEATURE:
<223> OTHER INFORMATION: Exemplary cyclic peptide

<400> SEQUENCE: 824

Asp Trp Val Ile Pro Pro Ile Lys
1               5

<210> SEQ ID NO 825
<211> LENGTH: 9
<212> TYPE: PRT
<213> ORGANISM: Artificial Sequence
<220> FEATURE:
<223> OTHER INFORMATION: Exemplary cyclic peptide

<400> SEQUENCE: 825

Asp Trp Val Ile Pro Pro Ile Ser Lys
1               5

<210> SEQ ID NO 826
<211> LENGTH: 10
<212> TYPE: PRT
<213> ORGANISM: Artificial Sequence
<220> FEATURE:
<223> OTHER INFORMATION: Exemplary cyclic peptide

<400> SEQUENCE: 826

```
Asp Trp Val Ile Pro Pro Ile Ser Val Lys
 1               5                  10
```

<210> SEQ ID NO 827
<211> LENGTH: 5
<212> TYPE: PRT
<213> ORGANISM: Artificial Sequence
<220> FEATURE:
<223> OTHER INFORMATION: Exemplary cyclic peptide

<400> SEQUENCE: 827

```
Asp Arg Ala Trp Lys
 1               5
```

<210> SEQ ID NO 828
<211> LENGTH: 6
<212> TYPE: PRT
<213> ORGANISM: Artificial Sequence
<220> FEATURE:
<223> OTHER INFORMATION: Exemplary cyclic peptide

<400> SEQUENCE: 828

```
Asp Arg Ala Trp Val Lys
 1               5
```

<210> SEQ ID NO 829
<211> LENGTH: 7
<212> TYPE: PRT
<213> ORGANISM: Artificial Sequence
<220> FEATURE:
<223> OTHER INFORMATION: Exemplary cyclic peptide

<400> SEQUENCE: 829

```
Asp Arg Ala Trp Val Ile Lys
 1               5
```

<210> SEQ ID NO 830
<211> LENGTH: 8
<212> TYPE: PRT
<213> ORGANISM: Artificial Sequence
<220> FEATURE:
<223> OTHER INFORMATION: Exemplary cyclic peptide

<400> SEQUENCE: 830

```
Asp Arg Ala Trp Val Ile Pro Lys
 1               5
```

<210> SEQ ID NO 831
<211> LENGTH: 9
<212> TYPE: PRT
<213> ORGANISM: Artificial Sequence
<220> FEATURE:
<223> OTHER INFORMATION: Exemplary cyclic peptide

<400> SEQUENCE: 831

```
Asp Arg Ala Trp Val Ile Pro Pro Lys
 1               5
```

<210> SEQ ID NO 832
<211> LENGTH: 10
<212> TYPE: PRT
<213> ORGANISM: Artificial Sequence
<220> FEATURE:
<223> OTHER INFORMATION: Exemplary cyclic peptide

<400> SEQUENCE: 832

```
Asp Arg Ala Trp Val Ile Pro Pro Ile Lys
```

-continued

```
  1               5                  10
```

<210> SEQ ID NO 833
<211> LENGTH: 11
<212> TYPE: PRT
<213> ORGANISM: Artificial Sequence
<220> FEATURE:
<223> OTHER INFORMATION: Exemplary cyclic peptide

<400> SEQUENCE: 833

```
Asp Arg Ala Trp Val Ile Pro Pro Ile Ser Lys
  1               5                  10
```

<210> SEQ ID NO 834
<211> LENGTH: 12
<212> TYPE: PRT
<213> ORGANISM: Artificial Sequence
<220> FEATURE:
<223> OTHER INFORMATION: Exemplary cyclic peptide

<400> SEQUENCE: 834

```
Asp Arg Ala Trp Val Ile Pro Pro Ile Ser Val Lys
  1               5                  10
```

<210> SEQ ID NO 835
<211> LENGTH: 6
<212> TYPE: PRT
<213> ORGANISM: Artificial Sequence
<220> FEATURE:
<223> OTHER INFORMATION: Exemplary cyclic peptide

<400> SEQUENCE: 835

```
Asp Lys Arg Ala Trp Lys
  1               5
```

<210> SEQ ID NO 836
<211> LENGTH: 7
<212> TYPE: PRT
<213> ORGANISM: Artificial Sequence
<220> FEATURE:
<223> OTHER INFORMATION: Exemplary cyclic peptide

<400> SEQUENCE: 836

```
Asp Lys Arg Ala Trp Val Lys
  1               5
```

<210> SEQ ID NO 837
<211> LENGTH: 8
<212> TYPE: PRT
<213> ORGANISM: Artificial Sequence
<220> FEATURE:
<223> OTHER INFORMATION: Exemplary cyclic peptide

<400> SEQUENCE: 837

```
Asp Lys Arg Ala Trp Val Ile Lys
  1               5
```

<210> SEQ ID NO 838
<211> LENGTH: 9
<212> TYPE: PRT
<213> ORGANISM: Artificial Sequence
<220> FEATURE:
<223> OTHER INFORMATION: Exemplary cyclic peptide

<400> SEQUENCE: 838

```
Asp Lys Arg Ala Trp Val Ile Pro Lys
  1               5
```

<210> SEQ ID NO 839
<211> LENGTH: 10
<212> TYPE: PRT
<213> ORGANISM: Artificial Sequence
<220> FEATURE:
<223> OTHER INFORMATION: Exemplary cyclic peptide

<400> SEQUENCE: 839

Asp Lys Arg Ala Trp Val Ile Pro Pro Lys
1               5                   10

<210> SEQ ID NO 840
<211> LENGTH: 11
<212> TYPE: PRT
<213> ORGANISM: Artificial Sequence
<220> FEATURE:
<223> OTHER INFORMATION: Exemplary cyclic peptide

<400> SEQUENCE: 840

Asp Lys Arg Ala Trp Val Ile Pro Pro Ile Lys
1               5                   10

<210> SEQ ID NO 841
<211> LENGTH: 12
<212> TYPE: PRT
<213> ORGANISM: Artificial Sequence
<220> FEATURE:
<223> OTHER INFORMATION: Exemplary cyclic peptide

<400> SEQUENCE: 841

Asp Lys Arg Ala Trp Val Ile Pro Pro Ile Ser Lys
1               5                   10

<210> SEQ ID NO 842
<211> LENGTH: 5
<212> TYPE: PRT
<213> ORGANISM: Artificial Sequence
<220> FEATURE:
<223> OTHER INFORMATION: Exemplary cyclic peptide

<400> SEQUENCE: 842

Asp Val Trp Asn Lys
1               5

<210> SEQ ID NO 843
<211> LENGTH: 6
<212> TYPE: PRT
<213> ORGANISM: Artificial Sequence
<220> FEATURE:
<223> OTHER INFORMATION: Exemplary cyclic peptide

<400> SEQUENCE: 843

Asp Val Trp Asn Gln Lys
1               5

<210> SEQ ID NO 844
<211> LENGTH: 7
<212> TYPE: PRT
<213> ORGANISM: Artificial Sequence
<220> FEATURE:
<223> OTHER INFORMATION: Exemplary cyclic peptide

<400> SEQUENCE: 844

Asp Val Trp Asn Gln Met Lys
1               5

```
<210> SEQ ID NO 845
<211> LENGTH: 7
<212> TYPE: PRT
<213> ORGANISM: Artificial Sequence
<220> FEATURE:
<223> OTHER INFORMATION: Exemplary cyclic peptide

<400> SEQUENCE: 845

Asp Val Trp Asn Gln Phe Lys
 1               5

<210> SEQ ID NO 846
<211> LENGTH: 8
<212> TYPE: PRT
<213> ORGANISM: Artificial Sequence
<220> FEATURE:
<223> OTHER INFORMATION: Exemplary cyclic peptide

<400> SEQUENCE: 846

Asp Val Trp Asn Gln Met Phe Lys
 1               5

<210> SEQ ID NO 847
<211> LENGTH: 8
<212> TYPE: PRT
<213> ORGANISM: Artificial Sequence
<220> FEATURE:
<223> OTHER INFORMATION: Exemplary cyclic peptide

<400> SEQUENCE: 847

Asp Val Trp Asn Gln Phe Phe Lys
 1               5

<210> SEQ ID NO 848
<211> LENGTH: 5
<212> TYPE: PRT
<213> ORGANISM: Artificial Sequence
<220> FEATURE:
<223> OTHER INFORMATION: Exemplary cyclic peptide

<400> SEQUENCE: 848

Asp Trp Asn Gln Lys
 1               5

<210> SEQ ID NO 849
<211> LENGTH: 6
<212> TYPE: PRT
<213> ORGANISM: Artificial Sequence
<220> FEATURE:
<223> OTHER INFORMATION: Exemplary cyclic peptide

<400> SEQUENCE: 849

Asp Trp Asn Gln Met Lys
 1               5

<210> SEQ ID NO 850
<211> LENGTH: 6
<212> TYPE: PRT
<213> ORGANISM: Artificial Sequence
<220> FEATURE:
<223> OTHER INFORMATION: Exemplary cyclic peptide

<400> SEQUENCE: 850

Asp Trp Asn Gln Phe Lys
 1               5
```

```
<210> SEQ ID NO 851
<211> LENGTH: 7
<212> TYPE: PRT
<213> ORGANISM: Artificial Sequence
<220> FEATURE:
<223> OTHER INFORMATION: Exemplary cyclic peptide

<400> SEQUENCE: 851

Asp Trp Asn Gln Phe Phe Lys
 1               5

<210> SEQ ID NO 852
<211> LENGTH: 5
<212> TYPE: PRT
<213> ORGANISM: Artificial Sequence
<220> FEATURE:
<223> OTHER INFORMATION: Exemplary cyclic peptide

<400> SEQUENCE: 852

Asp Ile Trp Asn Lys
 1               5

<210> SEQ ID NO 853
<211> LENGTH: 6
<212> TYPE: PRT
<213> ORGANISM: Artificial Sequence
<220> FEATURE:
<223> OTHER INFORMATION: Exemplary cyclic peptide

<400> SEQUENCE: 853

Asp Ile Trp Asn Gln Lys
 1               5

<210> SEQ ID NO 854
<211> LENGTH: 7
<212> TYPE: PRT
<213> ORGANISM: Artificial Sequence
<220> FEATURE:
<223> OTHER INFORMATION: Exemplary cyclic peptide

<400> SEQUENCE: 854

Asp Ile Trp Asn Gln Met Lys
 1               5

<210> SEQ ID NO 855
<211> LENGTH: 8
<212> TYPE: PRT
<213> ORGANISM: Artificial Sequence
<220> FEATURE:
<223> OTHER INFORMATION: Exemplary cyclic peptide

<400> SEQUENCE: 855

Asp Ile Trp Asn Gln Met His Lys
 1               5

<210> SEQ ID NO 856
<211> LENGTH: 7
<212> TYPE: PRT
<213> ORGANISM: Artificial Sequence
<220> FEATURE:
<223> OTHER INFORMATION: Exemplary cyclic peptide

<400> SEQUENCE: 856

Asp Trp Asn Gln Met His Lys
 1               5

<210> SEQ ID NO 857
```

```
<211> LENGTH: 5
<212> TYPE: PRT
<213> ORGANISM: Artificial Sequence
<220> FEATURE:
<223> OTHER INFORMATION: Exemplary cyclic peptide

<400> SEQUENCE: 857

Asp Met Trp Asn Lys
 1               5

<210> SEQ ID NO 858
<211> LENGTH: 6
<212> TYPE: PRT
<213> ORGANISM: Artificial Sequence
<220> FEATURE:
<223> OTHER INFORMATION: Exemplary cyclic peptide

<400> SEQUENCE: 858

Asp Met Trp Asn Gln Lys
 1               5

<210> SEQ ID NO 859
<211> LENGTH: 7
<212> TYPE: PRT
<213> ORGANISM: Artificial Sequence
<220> FEATURE:
<223> OTHER INFORMATION: Exemplary cyclic peptide

<400> SEQUENCE: 859

Asp Met Trp Asn Gln Phe Lys
 1               5

<210> SEQ ID NO 860
<211> LENGTH: 8
<212> TYPE: PRT
<213> ORGANISM: Artificial Sequence
<220> FEATURE:
<223> OTHER INFORMATION: Exemplary cyclic peptide

<400> SEQUENCE: 860

Asp Met Trp Asn Gln Phe Phe Lys
 1               5

<210> SEQ ID NO 861
<211> LENGTH: 5
<212> TYPE: PRT
<213> ORGANISM: Artificial Sequence
<220> FEATURE:
<223> OTHER INFORMATION: Exemplary cyclic peptide

<400> SEQUENCE: 861

Glu Gly Trp Val Lys
 1               5

<210> SEQ ID NO 862
<211> LENGTH: 6
<212> TYPE: PRT
<213> ORGANISM: Artificial Sequence
<220> FEATURE:
<223> OTHER INFORMATION: Exemplary cyclic peptide

<400> SEQUENCE: 862

Glu Gly Trp Val Trp Lys
 1               5

<210> SEQ ID NO 863
<211> LENGTH: 7
```

```
<212> TYPE: PRT
<213> ORGANISM: Artificial Sequence
<220> FEATURE:
<223> OTHER INFORMATION: Exemplary cyclic peptide

<400> SEQUENCE: 863

Glu Gly Trp Val Trp Asn Lys
 1               5

<210> SEQ ID NO 864
<211> LENGTH: 8
<212> TYPE: PRT
<213> ORGANISM: Artificial Sequence
<220> FEATURE:
<223> OTHER INFORMATION: Exemplary cyclic peptide

<400> SEQUENCE: 864

Glu Gly Trp Val Trp Asn Gln Lys
 1               5

<210> SEQ ID NO 865
<211> LENGTH: 5
<212> TYPE: PRT
<213> ORGANISM: Artificial Sequence
<220> FEATURE:
<223> OTHER INFORMATION: Exemplary cyclic peptide

<400> SEQUENCE: 865

Glu Trp Val Trp Lys
 1               5

<210> SEQ ID NO 866
<211> LENGTH: 6
<212> TYPE: PRT
<213> ORGANISM: Artificial Sequence
<220> FEATURE:
<223> OTHER INFORMATION: Exemplary cyclic peptide

<400> SEQUENCE: 866

Glu Trp Val Trp Asn Lys
 1               5

<210> SEQ ID NO 867
<211> LENGTH: 7
<212> TYPE: PRT
<213> ORGANISM: Artificial Sequence
<220> FEATURE:
<223> OTHER INFORMATION: Exemplary cyclic peptide

<400> SEQUENCE: 867

Glu Trp Val Trp Asn Gln Lys
 1               5

<210> SEQ ID NO 868
<211> LENGTH: 5
<212> TYPE: PRT
<213> ORGANISM: Artificial Sequence
<220> FEATURE:
<223> OTHER INFORMATION: Exemplary cyclic peptide

<400> SEQUENCE: 868

Glu Ser Trp Met Lys
 1               5

<210> SEQ ID NO 869
<211> LENGTH: 6
<212> TYPE: PRT
```

```
<213> ORGANISM: Artificial Sequence
<220> FEATURE:
<223> OTHER INFORMATION: Exemplary cyclic peptide

<400> SEQUENCE: 869

Glu Ser Trp Met Trp Lys
 1               5

<210> SEQ ID NO 870
<211> LENGTH: 7
<212> TYPE: PRT
<213> ORGANISM: Artificial Sequence
<220> FEATURE:
<223> OTHER INFORMATION: Exemplary cyclic peptide

<400> SEQUENCE: 870

Glu Ser Trp Met Trp Asn Lys
 1               5

<210> SEQ ID NO 871
<211> LENGTH: 8
<212> TYPE: PRT
<213> ORGANISM: Artificial Sequence
<220> FEATURE:
<223> OTHER INFORMATION: Exemplary cyclic peptide

<400> SEQUENCE: 871

Glu Ser Trp Met Trp Asn Gln Lys
 1               5

<210> SEQ ID NO 872
<211> LENGTH: 5
<212> TYPE: PRT
<213> ORGANISM: Artificial Sequence
<220> FEATURE:
<223> OTHER INFORMATION: Exemplary cyclic peptide

<400> SEQUENCE: 872

Glu Trp Met Trp Lys
 1               5

<210> SEQ ID NO 873
<211> LENGTH: 6
<212> TYPE: PRT
<213> ORGANISM: Artificial Sequence
<220> FEATURE:
<223> OTHER INFORMATION: Exemplary cyclic peptide

<400> SEQUENCE: 873

Glu Trp Met Trp Asn Lys
 1               5

<210> SEQ ID NO 874
<211> LENGTH: 7
<212> TYPE: PRT
<213> ORGANISM: Artificial Sequence
<220> FEATURE:
<223> OTHER INFORMATION: Exemplary cyclic peptide

<400> SEQUENCE: 874

Glu Trp Met Trp Asn Gln Lys
 1               5

<210> SEQ ID NO 875
<211> LENGTH: 5
<212> TYPE: PRT
<213> ORGANISM: Artificial Sequence
```

<220> FEATURE:
<223> OTHER INFORMATION: Exemplary cyclic peptide

<400> SEQUENCE: 875

Glu Ser Trp Val Lys
 1               5

<210> SEQ ID NO 876
<211> LENGTH: 6
<212> TYPE: PRT
<213> ORGANISM: Artificial Sequence
<220> FEATURE:
<223> OTHER INFORMATION: Exemplary cyclic peptide

<400> SEQUENCE: 876

Glu Ser Trp Val Trp Lys
 1               5

<210> SEQ ID NO 877
<211> LENGTH: 7
<212> TYPE: PRT
<213> ORGANISM: Artificial Sequence
<220> FEATURE:
<223> OTHER INFORMATION: Exemplary cyclic peptide

<400> SEQUENCE: 877

Glu Ser Trp Val Trp Asn Lys
 1               5

<210> SEQ ID NO 878
<211> LENGTH: 8
<212> TYPE: PRT
<213> ORGANISM: Artificial Sequence
<220> FEATURE:
<223> OTHER INFORMATION: Exemplary cyclic peptide

<400> SEQUENCE: 878

Glu Ser Trp Val Trp Asn Gln Lys
 1               5

<210> SEQ ID NO 879
<211> LENGTH: 5
<212> TYPE: PRT
<213> ORGANISM: Artificial Sequence
<220> FEATURE:
<223> OTHER INFORMATION: Exemplary cyclic peptide

<400> SEQUENCE: 879

Glu Gly Trp Met Lys
 1               5

<210> SEQ ID NO 880
<211> LENGTH: 6
<212> TYPE: PRT
<213> ORGANISM: Artificial Sequence
<220> FEATURE:
<223> OTHER INFORMATION: Exemplary cyclic peptide

<400> SEQUENCE: 880

Glu Gly Trp Met Trp Lys
 1               5

<210> SEQ ID NO 881
<211> LENGTH: 7
<212> TYPE: PRT
<213> ORGANISM: Artificial Sequence
<220> FEATURE:

-continued

```
<223> OTHER INFORMATION: Exemplary cyclic peptide

<400> SEQUENCE: 881

Glu Gly Trp Met Trp Asn Lys
 1               5

<210> SEQ ID NO 882
<211> LENGTH: 8
<212> TYPE: PRT
<213> ORGANISM: Artificial Sequence
<220> FEATURE:
<223> OTHER INFORMATION: Exemplary cyclic peptide

<400> SEQUENCE: 882

Glu Gly Trp Met Trp Asn Gln Lys
 1               5

<210> SEQ ID NO 883
<211> LENGTH: 5
<212> TYPE: PRT
<213> ORGANISM: Artificial Sequence
<220> FEATURE:
<223> OTHER INFORMATION: Exemplary cyclic peptide

<400> SEQUENCE: 883

Glu Ala Trp Val Lys
 1               5

<210> SEQ ID NO 884
<211> LENGTH: 6
<212> TYPE: PRT
<213> ORGANISM: Artificial Sequence
<220> FEATURE:
<223> OTHER INFORMATION: Exemplary cyclic peptide

<400> SEQUENCE: 884

Glu Ala Trp Val Ile Lys
 1               5

<210> SEQ ID NO 885
<211> LENGTH: 7
<212> TYPE: PRT
<213> ORGANISM: Artificial Sequence
<220> FEATURE:
<223> OTHER INFORMATION: Exemplary cyclic peptide

<400> SEQUENCE: 885

Glu Ala Trp Val Ile Pro Lys
 1               5

<210> SEQ ID NO 886
<211> LENGTH: 8
<212> TYPE: PRT
<213> ORGANISM: Artificial Sequence
<220> FEATURE:
<223> OTHER INFORMATION: Exemplary cyclic peptide

<400> SEQUENCE: 886

Glu Ala Trp Val Ile Pro Pro Lys
 1               5

<210> SEQ ID NO 887
<211> LENGTH: 5
<212> TYPE: PRT
<213> ORGANISM: Artificial Sequence
<220> FEATURE:
<223> OTHER INFORMATION: Exemplary cyclic peptide
```

```
<400> SEQUENCE: 887

Glu Trp Val Ile Lys
 1               5

<210> SEQ ID NO 888
<211> LENGTH: 6
<212> TYPE: PRT
<213> ORGANISM: Artificial Sequence
<220> FEATURE:
<223> OTHER INFORMATION: Exemplary cyclic peptide

<400> SEQUENCE: 888

Glu Trp Val Ile Pro Lys
 1               5

<210> SEQ ID NO 889
<211> LENGTH: 7
<212> TYPE: PRT
<213> ORGANISM: Artificial Sequence
<220> FEATURE:
<223> OTHER INFORMATION: Exemplary cyclic peptide

<400> SEQUENCE: 889

Glu Trp Val Ile Pro Pro Lys
 1               5

<210> SEQ ID NO 890
<211> LENGTH: 9
<212> TYPE: PRT
<213> ORGANISM: Artificial Sequence
<220> FEATURE:
<223> OTHER INFORMATION: Exemplary cyclic peptide

<400> SEQUENCE: 890

Glu Gly Trp Val Trp Asn Gln Phe Lys
 1               5

<210> SEQ ID NO 891
<211> LENGTH: 10
<212> TYPE: PRT
<213> ORGANISM: Artificial Sequence
<220> FEATURE:
<223> OTHER INFORMATION: Exemplary cyclic peptide

<400> SEQUENCE: 891

Glu Gly Trp Val Trp Asn Gln Phe Phe Lys
 1               5                  10

<210> SEQ ID NO 892
<211> LENGTH: 11
<212> TYPE: PRT
<213> ORGANISM: Artificial Sequence
<220> FEATURE:
<223> OTHER INFORMATION: Exemplary cyclic peptide

<400> SEQUENCE: 892

Glu Gly Trp Val Trp Asn Gln Phe Phe Val Lys
 1               5                  10

<210> SEQ ID NO 893
<211> LENGTH: 8
<212> TYPE: PRT
<213> ORGANISM: Artificial Sequence
<220> FEATURE:
<223> OTHER INFORMATION: Exemplary cyclic peptide
```

```
<400> SEQUENCE: 893

Glu Trp Val Trp Asn Gln Phe Lys
1               5

<210> SEQ ID NO 894
<211> LENGTH: 9
<212> TYPE: PRT
<213> ORGANISM: Artificial Sequence
<220> FEATURE:
<223> OTHER INFORMATION: Exemplary cyclic peptide

<400> SEQUENCE: 894

Glu Trp Val Trp Asn Gln Phe Phe Lys
1               5

<210> SEQ ID NO 895
<211> LENGTH: 10
<212> TYPE: PRT
<213> ORGANISM: Artificial Sequence
<220> FEATURE:
<223> OTHER INFORMATION: Exemplary cyclic peptide

<400> SEQUENCE: 895

Glu Trp Val Trp Asn Gln Phe Phe Val Lys
1               5                   10

<210> SEQ ID NO 896
<211> LENGTH: 5
<212> TYPE: PRT
<213> ORGANISM: Artificial Sequence
<220> FEATURE:
<223> OTHER INFORMATION: Exemplary cyclic peptide

<400> SEQUENCE: 896

Glu Arg Gly Trp Lys
1               5

<210> SEQ ID NO 897
<211> LENGTH: 6
<212> TYPE: PRT
<213> ORGANISM: Artificial Sequence
<220> FEATURE:
<223> OTHER INFORMATION: Exemplary cyclic peptide

<400> SEQUENCE: 897

Glu Arg Gly Trp Val Lys
1               5

<210> SEQ ID NO 898
<211> LENGTH: 7
<212> TYPE: PRT
<213> ORGANISM: Artificial Sequence
<220> FEATURE:
<223> OTHER INFORMATION: Exemplary cyclic peptide

<400> SEQUENCE: 898

Glu Arg Gly Trp Val Trp Lys
1               5

<210> SEQ ID NO 899
<211> LENGTH: 8
<212> TYPE: PRT
<213> ORGANISM: Artificial Sequence
<220> FEATURE:
<223> OTHER INFORMATION: Exemplary cyclic peptide

<400> SEQUENCE: 899
```

```
Glu Arg Gly Trp Val Trp Asn Lys
1               5
```

<210> SEQ ID NO 900
<211> LENGTH: 9
<212> TYPE: PRT
<213> ORGANISM: Artificial Sequence
<220> FEATURE:
<223> OTHER INFORMATION: Exemplary cyclic peptide

<400> SEQUENCE: 900

```
Glu Arg Gly Trp Val Trp Asn Gln Lys
1               5
```

<210> SEQ ID NO 901
<211> LENGTH: 10
<212> TYPE: PRT
<213> ORGANISM: Artificial Sequence
<220> FEATURE:
<223> OTHER INFORMATION: Exemplary cyclic peptide

<400> SEQUENCE: 901

```
Glu Arg Gly Trp Val Trp Asn Gln Phe Lys
1               5                   10
```

<210> SEQ ID NO 902
<211> LENGTH: 11
<212> TYPE: PRT
<213> ORGANISM: Artificial Sequence
<220> FEATURE:
<223> OTHER INFORMATION: Exemplary cyclic peptide

<400> SEQUENCE: 902

```
Glu Arg Gly Trp Val Trp Asn Gln Phe Phe Lys
1               5                   10
```

<210> SEQ ID NO 903
<211> LENGTH: 12
<212> TYPE: PRT
<213> ORGANISM: Artificial Sequence
<220> FEATURE:
<223> OTHER INFORMATION: Exemplary cyclic peptide

<400> SEQUENCE: 903

```
Glu Arg Gly Trp Val Trp Asn Gln Phe Phe Val Lys
1               5                   10
```

<210> SEQ ID NO 904
<211> LENGTH: 6
<212> TYPE: PRT
<213> ORGANISM: Artificial Sequence
<220> FEATURE:
<223> OTHER INFORMATION: Exemplary cyclic peptide

<400> SEQUENCE: 904

```
Glu Lys Arg Gly Trp Lys
1               5
```

<210> SEQ ID NO 905
<211> LENGTH: 7
<212> TYPE: PRT
<213> ORGANISM: Artificial Sequence
<220> FEATURE:
<223> OTHER INFORMATION: Exemplary cyclic peptide

<400> SEQUENCE: 905

```
Glu Lys Arg Gly Trp Val Lys
  1               5
```

<210> SEQ ID NO 906
<211> LENGTH: 8
<212> TYPE: PRT
<213> ORGANISM: Artificial Sequence
<220> FEATURE:
<223> OTHER INFORMATION: Exemplary cyclic peptide

<400> SEQUENCE: 906

```
Glu Lys Arg Gly Trp Val Trp Lys
  1               5
```

<210> SEQ ID NO 907
<211> LENGTH: 9
<212> TYPE: PRT
<213> ORGANISM: Artificial Sequence
<220> FEATURE:
<223> OTHER INFORMATION: Exemplary cyclic peptide

<400> SEQUENCE: 907

```
Glu Lys Arg Gly Trp Val Trp Asn Lys
  1               5
```

<210> SEQ ID NO 908
<211> LENGTH: 10
<212> TYPE: PRT
<213> ORGANISM: Artificial Sequence
<220> FEATURE:
<223> OTHER INFORMATION: Exemplary cyclic peptide

<400> SEQUENCE: 908

```
Glu Lys Arg Gly Trp Val Trp Asn Gln Lys
  1               5                  10
```

<210> SEQ ID NO 909
<211> LENGTH: 11
<212> TYPE: PRT
<213> ORGANISM: Artificial Sequence
<220> FEATURE:
<223> OTHER INFORMATION: Exemplary cyclic peptide

<400> SEQUENCE: 909

```
Glu Lys Arg Gly Trp Val Trp Asn Gln Phe Lys
  1               5                  10
```

<210> SEQ ID NO 910
<211> LENGTH: 12
<212> TYPE: PRT
<213> ORGANISM: Artificial Sequence
<220> FEATURE:
<223> OTHER INFORMATION: Exemplary cyclic peptide

<400> SEQUENCE: 910

```
Glu Lys Arg Gly Trp Val Trp Asn Gln Phe Phe Lys
  1               5                  10
```

<210> SEQ ID NO 911
<211> LENGTH: 13
<212> TYPE: PRT
<213> ORGANISM: Artificial Sequence
<220> FEATURE:
<223> OTHER INFORMATION: Exemplary cyclic peptide

<400> SEQUENCE: 911

```
Glu Lys Arg Gly Trp Val Trp Asn Gln Phe Phe Val Lys
```

-continued

<210> SEQ ID NO 912
<211> LENGTH: 5
<212> TYPE: PRT
<213> ORGANISM: Artificial Sequence
<220> FEATURE:
<223> OTHER INFORMATION: Exemplary cyclic peptide

<400> SEQUENCE: 912

Glu Arg Asp Trp Lys
 1               5

<210> SEQ ID NO 913
<211> LENGTH: 6
<212> TYPE: PRT
<213> ORGANISM: Artificial Sequence
<220> FEATURE:
<223> OTHER INFORMATION: Exemplary cyclic peptide

<400> SEQUENCE: 913

Glu Arg Asp Trp Ile Lys
 1               5

<210> SEQ ID NO 914
<211> LENGTH: 7
<212> TYPE: PRT
<213> ORGANISM: Artificial Sequence
<220> FEATURE:
<223> OTHER INFORMATION: Exemplary cyclic peptide

<400> SEQUENCE: 914

Glu Arg Asp Trp Ile Trp Lys
 1               5

<210> SEQ ID NO 915
<211> LENGTH: 8
<212> TYPE: PRT
<213> ORGANISM: Artificial Sequence
<220> FEATURE:
<223> OTHER INFORMATION: Exemplary cyclic peptide

<400> SEQUENCE: 915

Glu Arg Asp Trp Ile Trp Asn Lys
 1               5

<210> SEQ ID NO 916
<211> LENGTH: 9
<212> TYPE: PRT
<213> ORGANISM: Artificial Sequence
<220> FEATURE:
<223> OTHER INFORMATION: Exemplary cyclic peptide

<400> SEQUENCE: 916

Glu Arg Asp Trp Ile Trp Asn Gln Lys
 1               5

<210> SEQ ID NO 917
<211> LENGTH: 10
<212> TYPE: PRT
<213> ORGANISM: Artificial Sequence
<220> FEATURE:
<223> OTHER INFORMATION: Exemplary cyclic peptide

<400> SEQUENCE: 917

Glu Arg Asp Trp Ile Trp Asn Gln Met Lys
 1               5                  10

```
<210> SEQ ID NO 918
<211> LENGTH: 11
<212> TYPE: PRT
<213> ORGANISM: Artificial Sequence
<220> FEATURE:
<223> OTHER INFORMATION: Exemplary cyclic peptide

<400> SEQUENCE: 918

Glu Arg Asp Trp Ile Trp Asn Gln Met His Lys
 1               5                  10

<210> SEQ ID NO 919
<211> LENGTH: 12
<212> TYPE: PRT
<213> ORGANISM: Artificial Sequence
<220> FEATURE:
<223> OTHER INFORMATION: Exemplary cyclic peptide

<400> SEQUENCE: 919

Glu Arg Asp Trp Ile Trp Asn Gln Met His Ile Lys
 1               5                  10

<210> SEQ ID NO 920
<211> LENGTH: 6
<212> TYPE: PRT
<213> ORGANISM: Artificial Sequence
<220> FEATURE:
<223> OTHER INFORMATION: Exemplary cyclic peptide

<400> SEQUENCE: 920

Glu Lys Arg Asp Trp Lys
 1               5

<210> SEQ ID NO 921
<211> LENGTH: 7
<212> TYPE: PRT
<213> ORGANISM: Artificial Sequence
<220> FEATURE:
<223> OTHER INFORMATION: Exemplary cyclic peptide

<400> SEQUENCE: 921

Glu Lys Arg Asp Trp Ile Lys
 1               5

<210> SEQ ID NO 922
<211> LENGTH: 8
<212> TYPE: PRT
<213> ORGANISM: Artificial Sequence
<220> FEATURE:
<223> OTHER INFORMATION: Exemplary cyclic peptide

<400> SEQUENCE: 922

Glu Lys Arg Asp Trp Ile Trp Lys
 1               5

<210> SEQ ID NO 923
<211> LENGTH: 9
<212> TYPE: PRT
<213> ORGANISM: Artificial Sequence
<220> FEATURE:
<223> OTHER INFORMATION: Exemplary cyclic peptide

<400> SEQUENCE: 923

Glu Lys Arg Asp Trp Ile Trp Asn Lys
 1               5
```

```
<210> SEQ ID NO 924
<211> LENGTH: 10
<212> TYPE: PRT
<213> ORGANISM: Artificial Sequence
<220> FEATURE:
<223> OTHER INFORMATION: Exemplary cyclic peptide

<400> SEQUENCE: 924

Glu Lys Arg Asp Trp Ile Trp Asn Gln Lys
 1               5                  10

<210> SEQ ID NO 925
<211> LENGTH: 11
<212> TYPE: PRT
<213> ORGANISM: Artificial Sequence
<220> FEATURE:
<223> OTHER INFORMATION: Exemplary cyclic peptide

<400> SEQUENCE: 925

Glu Lys Arg Asp Trp Ile Trp Asn Gln Met Lys
 1               5                  10

<210> SEQ ID NO 926
<211> LENGTH: 12
<212> TYPE: PRT
<213> ORGANISM: Artificial Sequence
<220> FEATURE:
<223> OTHER INFORMATION: Exemplary cyclic peptide

<400> SEQUENCE: 926

Glu Lys Arg Asp Trp Ile Trp Asn Gln Met His Lys
 1               5                  10

<210> SEQ ID NO 927
<211> LENGTH: 13
<212> TYPE: PRT
<213> ORGANISM: Artificial Sequence
<220> FEATURE:
<223> OTHER INFORMATION: Exemplary cyclic peptide

<400> SEQUENCE: 927

Glu Lys Arg Asp Trp Ile Trp Asn Gln Met His Ile Lys
 1               5                  10

<210> SEQ ID NO 928
<211> LENGTH: 9
<212> TYPE: PRT
<213> ORGANISM: Artificial Sequence
<220> FEATURE:
<223> OTHER INFORMATION: Exemplary cyclic peptide

<400> SEQUENCE: 928

Glu Ser Trp Met Trp Asn Gln Phe Lys
 1               5

<210> SEQ ID NO 929
<211> LENGTH: 10
<212> TYPE: PRT
<213> ORGANISM: Artificial Sequence
<220> FEATURE:
<223> OTHER INFORMATION: Exemplary cyclic peptide

<400> SEQUENCE: 929

Glu Ser Trp Met Trp Asn Gln Phe Phe Lys
 1               5                  10
```

```
<210> SEQ ID NO 930
<211> LENGTH: 11
<212> TYPE: PRT
<213> ORGANISM: Artificial Sequence
<220> FEATURE:
<223> OTHER INFORMATION: Exemplary cyclic peptide

<400> SEQUENCE: 930

Glu Ser Trp Met Trp Asn Gln Phe Phe Leu Lys
 1               5                  10

<210> SEQ ID NO 931
<211> LENGTH: 8
<212> TYPE: PRT
<213> ORGANISM: Artificial Sequence
<220> FEATURE:
<223> OTHER INFORMATION: Exemplary cyclic peptide

<400> SEQUENCE: 931

Glu Trp Met Trp Asn Gln Phe Lys
 1               5

<210> SEQ ID NO 932
<211> LENGTH: 9
<212> TYPE: PRT
<213> ORGANISM: Artificial Sequence
<220> FEATURE:
<223> OTHER INFORMATION: Exemplary cyclic peptide

<400> SEQUENCE: 932

Glu Trp Met Trp Asn Gln Phe Phe Lys
 1               5

<210> SEQ ID NO 933
<211> LENGTH: 10
<212> TYPE: PRT
<213> ORGANISM: Artificial Sequence
<220> FEATURE:
<223> OTHER INFORMATION: Exemplary cyclic peptide

<400> SEQUENCE: 933

Glu Trp Met Trp Asn Gln Phe Phe Leu Lys
 1               5                  10

<210> SEQ ID NO 934
<211> LENGTH: 5
<212> TYPE: PRT
<213> ORGANISM: Artificial Sequence
<220> FEATURE:
<223> OTHER INFORMATION: Exemplary cyclic peptide

<400> SEQUENCE: 934

Glu Arg Ser Trp Lys
 1               5

<210> SEQ ID NO 935
<211> LENGTH: 6
<212> TYPE: PRT
<213> ORGANISM: Artificial Sequence
<220> FEATURE:
<223> OTHER INFORMATION: Exemplary cyclic peptide

<400> SEQUENCE: 935

Glu Arg Ser Trp Met Lys
 1               5

<210> SEQ ID NO 936
```

```
<211> LENGTH: 7
<212> TYPE: PRT
<213> ORGANISM: Artificial Sequence
<220> FEATURE:
<223> OTHER INFORMATION: Exemplary cyclic peptide

<400> SEQUENCE: 936

Glu Arg Ser Trp Met Trp Lys
 1               5

<210> SEQ ID NO 937
<211> LENGTH: 8
<212> TYPE: PRT
<213> ORGANISM: Artificial Sequence
<220> FEATURE:
<223> OTHER INFORMATION: Exemplary cyclic peptide

<400> SEQUENCE: 937

Glu Arg Ser Trp Met Trp Asn Lys
 1               5

<210> SEQ ID NO 938
<211> LENGTH: 9
<212> TYPE: PRT
<213> ORGANISM: Artificial Sequence
<220> FEATURE:
<223> OTHER INFORMATION: Exemplary cyclic peptide

<400> SEQUENCE: 938

Glu Arg Ser Trp Met Trp Asn Gln Lys
 1               5

<210> SEQ ID NO 939
<211> LENGTH: 10
<212> TYPE: PRT
<213> ORGANISM: Artificial Sequence
<220> FEATURE:
<223> OTHER INFORMATION: Exemplary cyclic peptide

<400> SEQUENCE: 939

Glu Arg Ser Trp Met Trp Asn Gln Phe Lys
 1               5                  10

<210> SEQ ID NO 940
<211> LENGTH: 11
<212> TYPE: PRT
<213> ORGANISM: Artificial Sequence
<220> FEATURE:
<223> OTHER INFORMATION: Exemplary cyclic peptide

<400> SEQUENCE: 940

Glu Arg Ser Trp Met Trp Asn Gln Phe Phe Lys
 1               5                  10

<210> SEQ ID NO 941
<211> LENGTH: 12
<212> TYPE: PRT
<213> ORGANISM: Artificial Sequence
<220> FEATURE:
<223> OTHER INFORMATION: Exemplary cyclic peptide

<400> SEQUENCE: 941

Glu Arg Ser Trp Met Trp Asn Gln Phe Phe Leu Lys
 1               5                  10

<210> SEQ ID NO 942
<211> LENGTH: 6
```

```
<212> TYPE: PRT
<213> ORGANISM: Artificial Sequence
<220> FEATURE:
<223> OTHER INFORMATION: Exemplary cyclic peptide

<400> SEQUENCE: 942

Glu Lys Arg Ser Trp Lys
 1               5

<210> SEQ ID NO 943
<211> LENGTH: 7
<212> TYPE: PRT
<213> ORGANISM: Artificial Sequence
<220> FEATURE:
<223> OTHER INFORMATION: Exemplary cyclic peptide

<400> SEQUENCE: 943

Glu Lys Arg Ser Trp Met Lys
 1               5

<210> SEQ ID NO 944
<211> LENGTH: 8
<212> TYPE: PRT
<213> ORGANISM: Artificial Sequence
<220> FEATURE:
<223> OTHER INFORMATION: Exemplary cyclic peptide

<400> SEQUENCE: 944

Glu Lys Arg Ser Trp Met Trp Lys
 1               5

<210> SEQ ID NO 945
<211> LENGTH: 9
<212> TYPE: PRT
<213> ORGANISM: Artificial Sequence
<220> FEATURE:
<223> OTHER INFORMATION: Exemplary cyclic peptide

<400> SEQUENCE: 945

Glu Lys Arg Ser Trp Met Trp Asn Lys
 1               5

<210> SEQ ID NO 946
<211> LENGTH: 10
<212> TYPE: PRT
<213> ORGANISM: Artificial Sequence
<220> FEATURE:
<223> OTHER INFORMATION: Exemplary cyclic peptide

<400> SEQUENCE: 946

Glu Lys Arg Ser Trp Met Trp Asn Gln Lys
 1               5                  10

<210> SEQ ID NO 947
<211> LENGTH: 11
<212> TYPE: PRT
<213> ORGANISM: Artificial Sequence
<220> FEATURE:
<223> OTHER INFORMATION: Exemplary cyclic peptide

<400> SEQUENCE: 947

Glu Lys Arg Ser Trp Met Trp Asn Gln Phe Lys
 1               5                  10

<210> SEQ ID NO 948
<211> LENGTH: 12
<212> TYPE: PRT
```

```
<213> ORGANISM: Artificial Sequence
<220> FEATURE:
<223> OTHER INFORMATION: Exemplary cyclic peptide

<400> SEQUENCE: 948

Glu Lys Arg Ser Trp Met Trp Asn Gln Phe Phe Lys
1               5                   10

<210> SEQ ID NO 949
<211> LENGTH: 9
<212> TYPE: PRT
<213> ORGANISM: Artificial Sequence
<220> FEATURE:
<223> OTHER INFORMATION: Exemplary cyclic peptide

<400> SEQUENCE: 949

Glu Ser Trp Val Trp Asn Gln Phe Lys
1               5

<210> SEQ ID NO 950
<211> LENGTH: 10
<212> TYPE: PRT
<213> ORGANISM: Artificial Sequence
<220> FEATURE:
<223> OTHER INFORMATION: Exemplary cyclic peptide

<400> SEQUENCE: 950

Glu Ser Trp Val Trp Asn Gln Phe Phe Lys
1               5                   10

<210> SEQ ID NO 951
<211> LENGTH: 11
<212> TYPE: PRT
<213> ORGANISM: Artificial Sequence
<220> FEATURE:
<223> OTHER INFORMATION: Exemplary cyclic peptide

<400> SEQUENCE: 951

Glu Ser Trp Val Trp Asn Gln Phe Phe Val Lys
1               5                   10

<210> SEQ ID NO 952
<211> LENGTH: 6
<212> TYPE: PRT
<213> ORGANISM: Artificial Sequence
<220> FEATURE:
<223> OTHER INFORMATION: Exemplary cyclic peptide

<400> SEQUENCE: 952

Glu Arg Ser Trp Val Lys
1               5

<210> SEQ ID NO 953
<211> LENGTH: 7
<212> TYPE: PRT
<213> ORGANISM: Artificial Sequence
<220> FEATURE:
<223> OTHER INFORMATION: Exemplary cyclic peptide

<400> SEQUENCE: 953

Glu Arg Ser Trp Val Trp Lys
1               5

<210> SEQ ID NO 954
<211> LENGTH: 8
<212> TYPE: PRT
<213> ORGANISM: Artificial Sequence
```

```
<220> FEATURE:
<223> OTHER INFORMATION: Exemplary cyclic peptide

<400> SEQUENCE: 954

Glu Arg Ser Trp Val Trp Asn Lys
  1               5

<210> SEQ ID NO 955
<211> LENGTH: 9
<212> TYPE: PRT
<213> ORGANISM: Artificial Sequence
<220> FEATURE:
<223> OTHER INFORMATION: Exemplary cyclic peptide

<400> SEQUENCE: 955

Glu Arg Ser Trp Val Trp Asn Gln Lys
  1               5

<210> SEQ ID NO 956
<211> LENGTH: 10
<212> TYPE: PRT
<213> ORGANISM: Artificial Sequence
<220> FEATURE:
<223> OTHER INFORMATION: Exemplary cyclic peptide

<400> SEQUENCE: 956

Glu Arg Ser Trp Val Trp Asn Gln Phe Lys
  1               5                  10

<210> SEQ ID NO 957
<211> LENGTH: 11
<212> TYPE: PRT
<213> ORGANISM: Artificial Sequence
<220> FEATURE:
<223> OTHER INFORMATION: Exemplary cyclic peptide

<400> SEQUENCE: 957

Glu Arg Ser Trp Val Trp Asn Gln Phe Phe Lys
  1               5                  10

<210> SEQ ID NO 958
<211> LENGTH: 12
<212> TYPE: PRT
<213> ORGANISM: Artificial Sequence
<220> FEATURE:
<223> OTHER INFORMATION: Exemplary cyclic peptide

<400> SEQUENCE: 958

Glu Arg Ser Trp Val Trp Asn Gln Phe Phe Val Lys
  1               5                  10

<210> SEQ ID NO 959
<211> LENGTH: 7
<212> TYPE: PRT
<213> ORGANISM: Artificial Sequence
<220> FEATURE:
<223> OTHER INFORMATION: Exemplary cyclic peptide

<400> SEQUENCE: 959

Glu Lys Arg Ser Trp Val Lys
  1               5

<210> SEQ ID NO 960
<211> LENGTH: 8
<212> TYPE: PRT
<213> ORGANISM: Artificial Sequence
<220> FEATURE:
```

```
<223> OTHER INFORMATION: Exemplary cyclic peptide

<400> SEQUENCE: 960

Glu Lys Arg Ser Trp Val Trp Lys
1               5

<210> SEQ ID NO 961
<211> LENGTH: 9
<212> TYPE: PRT
<213> ORGANISM: Artificial Sequence
<220> FEATURE:
<223> OTHER INFORMATION: Exemplary cyclic peptide

<400> SEQUENCE: 961

Glu Lys Arg Ser Trp Val Trp Asn Lys
1               5

<210> SEQ ID NO 962
<211> LENGTH: 10
<212> TYPE: PRT
<213> ORGANISM: Artificial Sequence
<220> FEATURE:
<223> OTHER INFORMATION: Exemplary cyclic peptide

<400> SEQUENCE: 962

Glu Lys Arg Ser Trp Val Trp Asn Gln Lys
1               5                   10

<210> SEQ ID NO 963
<211> LENGTH: 11
<212> TYPE: PRT
<213> ORGANISM: Artificial Sequence
<220> FEATURE:
<223> OTHER INFORMATION: Exemplary cyclic peptide

<400> SEQUENCE: 963

Glu Lys Arg Ser Trp Val Trp Asn Gln Phe Lys
1               5                   10

<210> SEQ ID NO 964
<211> LENGTH: 12
<212> TYPE: PRT
<213> ORGANISM: Artificial Sequence
<220> FEATURE:
<223> OTHER INFORMATION: Exemplary cyclic peptide

<400> SEQUENCE: 964

Glu Lys Arg Ser Trp Val Trp Asn Gln Phe Phe Lys
1               5                   10

<210> SEQ ID NO 965
<211> LENGTH: 13
<212> TYPE: PRT
<213> ORGANISM: Artificial Sequence
<220> FEATURE:
<223> OTHER INFORMATION: Exemplary cyclic peptide

<400> SEQUENCE: 965

Glu Lys Arg Ser Trp Val Trp Asn Gln Phe Phe Val Lys
1               5                   10

<210> SEQ ID NO 966
<211> LENGTH: 9
<212> TYPE: PRT
<213> ORGANISM: Artificial Sequence
<220> FEATURE:
<223> OTHER INFORMATION: Exemplary cyclic peptide
```

-continued

<400> SEQUENCE: 966

Glu Gly Trp Val Trp Asn Gln Met Lys
1               5

<210> SEQ ID NO 967
<211> LENGTH: 10
<212> TYPE: PRT
<213> ORGANISM: Artificial Sequence
<220> FEATURE:
<223> OTHER INFORMATION: Exemplary cyclic peptide

<400> SEQUENCE: 967

Glu Gly Trp Val Trp Asn Gln Met Phe Lys
1               5                   10

<210> SEQ ID NO 968
<211> LENGTH: 11
<212> TYPE: PRT
<213> ORGANISM: Artificial Sequence
<220> FEATURE:
<223> OTHER INFORMATION: Exemplary cyclic peptide

<400> SEQUENCE: 968

Glu Gly Trp Val Trp Asn Gln Met Phe Val Lys
1               5                   10

<210> SEQ ID NO 969
<211> LENGTH: 10
<212> TYPE: PRT
<213> ORGANISM: Artificial Sequence
<220> FEATURE:
<223> OTHER INFORMATION: Exemplary cyclic peptide

<400> SEQUENCE: 969

Glu Arg Gly Trp Val Trp Asn Gln Met Lys
1               5                   10

<210> SEQ ID NO 970
<211> LENGTH: 11
<212> TYPE: PRT
<213> ORGANISM: Artificial Sequence
<220> FEATURE:
<223> OTHER INFORMATION: Exemplary cyclic peptide

<400> SEQUENCE: 970

Glu Arg Gly Trp Val Trp Asn Gln Met Phe Lys
1               5                   10

<210> SEQ ID NO 971
<211> LENGTH: 12
<212> TYPE: PRT
<213> ORGANISM: Artificial Sequence
<220> FEATURE:
<223> OTHER INFORMATION: Exemplary cyclic peptide

<400> SEQUENCE: 971

Glu Arg Gly Trp Val Trp Asn Gln Met Phe Val Lys
1               5                   10

<210> SEQ ID NO 972
<211> LENGTH: 11
<212> TYPE: PRT
<213> ORGANISM: Artificial Sequence
<220> FEATURE:
<223> OTHER INFORMATION: Exemplary cyclic peptide -continued

```
<400> SEQUENCE: 972

Glu Lys Arg Gly Trp Val Trp Asn Gln Met Lys
 1               5                  10

<210> SEQ ID NO 973
<211> LENGTH: 13
<212> TYPE: PRT
<213> ORGANISM: Artificial Sequence
<220> FEATURE:
<223> OTHER INFORMATION: Exemplary cyclic peptide

<400> SEQUENCE: 973

Glu Lys Arg Gly Trp Val Trp Asn Gln Met Phe Val Lys
 1               5                  10

<210> SEQ ID NO 974
<211> LENGTH: 11
<212> TYPE: PRT
<213> ORGANISM: Artificial Sequence
<220> FEATURE:
<223> OTHER INFORMATION: Exemplary cyclic peptide

<400> SEQUENCE: 974

Glu Gly Trp Val Trp Asn Gln Phe Phe Leu Lys
 1               5                  10

<210> SEQ ID NO 975
<211> LENGTH: 12
<212> TYPE: PRT
<213> ORGANISM: Artificial Sequence
<220> FEATURE:
<223> OTHER INFORMATION: Exemplary cyclic peptide

<400> SEQUENCE: 975

Glu Arg Gly Trp Val Trp Asn Gln Phe Phe Leu Lys
 1               5                  10

<210> SEQ ID NO 976
<211> LENGTH: 13
<212> TYPE: PRT
<213> ORGANISM: Artificial Sequence
<220> FEATURE:
<223> OTHER INFORMATION: Exemplary cyclic peptide

<400> SEQUENCE: 976

Glu Lys Arg Gly Trp Val Trp Asn Gln Phe Phe Leu Lys
 1               5                  10

<210> SEQ ID NO 977
<211> LENGTH: 9
<212> TYPE: PRT
<213> ORGANISM: Artificial Sequence
<220> FEATURE:
<223> OTHER INFORMATION: Exemplary cyclic peptide

<400> SEQUENCE: 977

Glu Ala Trp Val Ile Pro Pro Ile Lys
 1               5

<210> SEQ ID NO 978
<211> LENGTH: 10
<212> TYPE: PRT
<213> ORGANISM: Artificial Sequence
<220> FEATURE:
<223> OTHER INFORMATION: Exemplary cyclic peptide

<400> SEQUENCE: 978
```

```
Glu Ala Trp Val Ile Pro Pro Ile Ser Lys
1               5                   10

<210> SEQ ID NO 979
<211> LENGTH: 11
<212> TYPE: PRT
<213> ORGANISM: Artificial Sequence
<220> FEATURE:
<223> OTHER INFORMATION: Exemplary cyclic peptide

<400> SEQUENCE: 979

Glu Ala Trp Val Ile Pro Pro Ile Ser Val Lys
1               5                   10

<210> SEQ ID NO 980
<211> LENGTH: 8
<212> TYPE: PRT
<213> ORGANISM: Artificial Sequence
<220> FEATURE:
<223> OTHER INFORMATION: Exemplary cyclic peptide

<400> SEQUENCE: 980

Glu Trp Val Ile Pro Pro Ile Lys
1               5

<210> SEQ ID NO 981
<211> LENGTH: 9
<212> TYPE: PRT
<213> ORGANISM: Artificial Sequence
<220> FEATURE:
<223> OTHER INFORMATION: Exemplary cyclic peptide

<400> SEQUENCE: 981

Glu Trp Val Ile Pro Pro Ile Ser Lys
1               5

<210> SEQ ID NO 982
<211> LENGTH: 10
<212> TYPE: PRT
<213> ORGANISM: Artificial Sequence
<220> FEATURE:
<223> OTHER INFORMATION: Exemplary cyclic peptide

<400> SEQUENCE: 982

Glu Trp Val Ile Pro Pro Ile Ser Val Lys
1               5                   10

<210> SEQ ID NO 983
<211> LENGTH: 5
<212> TYPE: PRT
<213> ORGANISM: Artificial Sequence
<220> FEATURE:
<223> OTHER INFORMATION: Exemplary cyclic peptide

<400> SEQUENCE: 983

Glu Arg Ala Trp Lys
1               5

<210> SEQ ID NO 984
<211> LENGTH: 6
<212> TYPE: PRT
<213> ORGANISM: Artificial Sequence
<220> FEATURE:
<223> OTHER INFORMATION: Exemplary cyclic peptide

<400> SEQUENCE: 984
```

```
Glu Arg Ala Trp Val Lys
  1               5

<210> SEQ ID NO 985
<211> LENGTH: 7
<212> TYPE: PRT
<213> ORGANISM: Artificial Sequence
<220> FEATURE:
<223> OTHER INFORMATION: Exemplary cyclic peptide

<400> SEQUENCE: 985

Glu Arg Ala Trp Val Ile Lys
  1               5

<210> SEQ ID NO 986
<211> LENGTH: 8
<212> TYPE: PRT
<213> ORGANISM: Artificial Sequence
<220> FEATURE:
<223> OTHER INFORMATION: Exemplary cyclic peptide

<400> SEQUENCE: 986

Glu Arg Ala Trp Val Ile Pro Lys
  1               5

<210> SEQ ID NO 987
<211> LENGTH: 9
<212> TYPE: PRT
<213> ORGANISM: Artificial Sequence
<220> FEATURE:
<223> OTHER INFORMATION: Exemplary cyclic peptide

<400> SEQUENCE: 987

Glu Arg Ala Trp Val Ile Pro Pro Lys
  1               5

<210> SEQ ID NO 988
<211> LENGTH: 10
<212> TYPE: PRT
<213> ORGANISM: Artificial Sequence
<220> FEATURE:
<223> OTHER INFORMATION: Exemplary cyclic peptide

<400> SEQUENCE: 988

Glu Arg Ala Trp Val Ile Pro Pro Ile Lys
  1               5                  10

<210> SEQ ID NO 989
<211> LENGTH: 11
<212> TYPE: PRT
<213> ORGANISM: Artificial Sequence
<220> FEATURE:
<223> OTHER INFORMATION: Exemplary cyclic peptide

<400> SEQUENCE: 989

Glu Arg Ala Trp Val Ile Pro Pro Ile Ser Lys
  1               5                  10

<210> SEQ ID NO 990
<211> LENGTH: 12
<212> TYPE: PRT
<213> ORGANISM: Artificial Sequence
<220> FEATURE:
<223> OTHER INFORMATION: Exemplary cyclic peptide

<400> SEQUENCE: 990

Glu Arg Ala Trp Val Ile Pro Pro Ile Ser Val Lys
```

```
1               5              10
```

<210> SEQ ID NO 991
<211> LENGTH: 6
<212> TYPE: PRT
<213> ORGANISM: Artificial Sequence
<220> FEATURE:
<223> OTHER INFORMATION: Exemplary cyclic peptide

<400> SEQUENCE: 991

Glu Lys Arg Ala Trp Lys
1               5

<210> SEQ ID NO 992
<211> LENGTH: 7
<212> TYPE: PRT
<213> ORGANISM: Artificial Sequence
<220> FEATURE:
<223> OTHER INFORMATION: Exemplary cyclic peptide

<400> SEQUENCE: 992

Glu Lys Arg Ala Trp Val Lys
1               5

<210> SEQ ID NO 993
<211> LENGTH: 8
<212> TYPE: PRT
<213> ORGANISM: Artificial Sequence
<220> FEATURE:
<223> OTHER INFORMATION: Exemplary cyclic peptide

<400> SEQUENCE: 993

Glu Lys Arg Ala Trp Val Ile Lys
1               5

<210> SEQ ID NO 994
<211> LENGTH: 9
<212> TYPE: PRT
<213> ORGANISM: Artificial Sequence
<220> FEATURE:
<223> OTHER INFORMATION: Exemplary cyclic peptide

<400> SEQUENCE: 994

Glu Lys Arg Ala Trp Val Ile Pro Lys
1               5

<210> SEQ ID NO 995
<211> LENGTH: 10
<212> TYPE: PRT
<213> ORGANISM: Artificial Sequence
<220> FEATURE:
<223> OTHER INFORMATION: Exemplary cyclic peptide

<400> SEQUENCE: 995

Glu Lys Arg Ala Trp Val Ile Pro Pro Lys
1               5              10

<210> SEQ ID NO 996
<211> LENGTH: 11
<212> TYPE: PRT
<213> ORGANISM: Artificial Sequence
<220> FEATURE:
<223> OTHER INFORMATION: Exemplary cyclic peptide

<400> SEQUENCE: 996

Glu Lys Arg Ala Trp Val Ile Pro Pro Ile Lys
1               5              10

```
<210> SEQ ID NO 997
<211> LENGTH: 12
<212> TYPE: PRT
<213> ORGANISM: Artificial Sequence
<220> FEATURE:
<223> OTHER INFORMATION: Exemplary cyclic peptide

<400> SEQUENCE: 997

Glu Lys Arg Ala Trp Val Ile Pro Pro Ile Ser Lys
 1               5                  10

<210> SEQ ID NO 998
<211> LENGTH: 5
<212> TYPE: PRT
<213> ORGANISM: Artificial Sequence
<220> FEATURE:
<223> OTHER INFORMATION: Exemplary cyclic peptide

<400> SEQUENCE: 998

Glu Val Trp Asn Lys
 1               5

<210> SEQ ID NO 999
<211> LENGTH: 6
<212> TYPE: PRT
<213> ORGANISM: Artificial Sequence
<220> FEATURE:
<223> OTHER INFORMATION: Exemplary cyclic peptide

<400> SEQUENCE: 999

Glu Val Trp Asn Gln Lys
 1               5

<210> SEQ ID NO 1000
<211> LENGTH: 7
<212> TYPE: PRT
<213> ORGANISM: Artificial Sequence
<220> FEATURE:
<223> OTHER INFORMATION: Exemplary cyclic peptide

<400> SEQUENCE: 1000

Glu Val Trp Asn Gln Met Lys
 1               5

<210> SEQ ID NO 1001
<211> LENGTH: 7
<212> TYPE: PRT
<213> ORGANISM: Artificial Sequence
<220> FEATURE:
<223> OTHER INFORMATION: Exemplary cyclic peptide

<400> SEQUENCE: 1001

Glu Val Trp Asn Gln Phe Lys
 1               5

<210> SEQ ID NO 1002
<211> LENGTH: 8
<212> TYPE: PRT
<213> ORGANISM: Artificial Sequence
<220> FEATURE:
<223> OTHER INFORMATION: Exemplary cyclic peptide

<400> SEQUENCE: 1002

Glu Val Trp Asn Gln Met Phe Lys
 1               5
```

-continued

```
<210> SEQ ID NO 1003
<211> LENGTH: 8
<212> TYPE: PRT
<213> ORGANISM: Artificial Sequence
<220> FEATURE:
<223> OTHER INFORMATION: Exemplary cyclic peptide

<400> SEQUENCE: 1003

Glu Val Trp Asn Gln Phe Phe Lys
 1               5

<210> SEQ ID NO 1004
<211> LENGTH: 5
<212> TYPE: PRT
<213> ORGANISM: Artificial Sequence
<220> FEATURE:
<223> OTHER INFORMATION: Exemplary cyclic peptide

<400> SEQUENCE: 1004

Glu Trp Asn Gln Lys
 1               5

<210> SEQ ID NO 1005
<211> LENGTH: 6
<212> TYPE: PRT
<213> ORGANISM: Artificial Sequence
<220> FEATURE:
<223> OTHER INFORMATION: Exemplary cyclic peptide

<400> SEQUENCE: 1005

Glu Trp Asn Gln Met Lys
 1               5

<210> SEQ ID NO 1006
<211> LENGTH: 6
<212> TYPE: PRT
<213> ORGANISM: Artificial Sequence
<220> FEATURE:
<223> OTHER INFORMATION: Exemplary cyclic peptide

<400> SEQUENCE: 1006

Glu Trp Asn Gln Phe Lys
 1               5

<210> SEQ ID NO 1007
<211> LENGTH: 7
<212> TYPE: PRT
<213> ORGANISM: Artificial Sequence
<220> FEATURE:
<223> OTHER INFORMATION: Exemplary cyclic peptide

<400> SEQUENCE: 1007

Glu Trp Asn Gln Phe Phe Lys
 1               5

<210> SEQ ID NO 1008
<211> LENGTH: 5
<212> TYPE: PRT
<213> ORGANISM: Artificial Sequence
<220> FEATURE:
<223> OTHER INFORMATION: Exemplary cyclic peptide

<400> SEQUENCE: 1008

Glu Ile Trp Asn Lys
 1               5
```

```
<210> SEQ ID NO 1009
<211> LENGTH: 6
<212> TYPE: PRT
<213> ORGANISM: Artificial Sequence
<220> FEATURE:
<223> OTHER INFORMATION: Exemplary cyclic peptide

<400> SEQUENCE: 1009

Glu Ile Trp Asn Gln Lys
1               5

<210> SEQ ID NO 1010
<211> LENGTH: 7
<212> TYPE: PRT
<213> ORGANISM: Artificial Sequence
<220> FEATURE:
<223> OTHER INFORMATION: Exemplary cyclic peptide

<400> SEQUENCE: 1010

Glu Ile Trp Asn Gln Met Lys
1               5

<210> SEQ ID NO 1011
<211> LENGTH: 8
<212> TYPE: PRT
<213> ORGANISM: Artificial Sequence
<220> FEATURE:
<223> OTHER INFORMATION: Exemplary cyclic peptide

<400> SEQUENCE: 1011

Glu Ile Trp Asn Gln Met His Lys
1               5

<210> SEQ ID NO 1012
<211> LENGTH: 7
<212> TYPE: PRT
<213> ORGANISM: Artificial Sequence
<220> FEATURE:
<223> OTHER INFORMATION: Exemplary cyclic peptide

<400> SEQUENCE: 1012

Glu Trp Asn Gln Met His Lys
1               5

<210> SEQ ID NO 1013
<211> LENGTH: 5
<212> TYPE: PRT
<213> ORGANISM: Artificial Sequence
<220> FEATURE:
<223> OTHER INFORMATION: Exemplary cyclic peptide

<400> SEQUENCE: 1013

Glu Met Trp Asn Lys
1               5

<210> SEQ ID NO 1014
<211> LENGTH: 6
<212> TYPE: PRT
<213> ORGANISM: Artificial Sequence
<220> FEATURE:
<223> OTHER INFORMATION: Exemplary cyclic peptide

<400> SEQUENCE: 1014

Glu Met Trp Asn Gln Lys
1               5

<210> SEQ ID NO 1015
```

```
<211> LENGTH: 7
<212> TYPE: PRT
<213> ORGANISM: Artificial Sequence
<220> FEATURE:
<223> OTHER INFORMATION: Exemplary cyclic peptide

<400> SEQUENCE: 1015

Glu Met Trp Asn Gln Phe Lys
1               5

<210> SEQ ID NO 1016
<211> LENGTH: 8
<212> TYPE: PRT
<213> ORGANISM: Artificial Sequence
<220> FEATURE:
<223> OTHER INFORMATION: Exemplary cyclic peptide

<400> SEQUENCE: 1016

Glu Met Trp Asn Gln Phe Phe Lys
1               5

<210> SEQ ID NO 1017
<211> LENGTH: 5
<212> TYPE: PRT
<213> ORGANISM: Artificial Sequence
<220> FEATURE:
<223> OTHER INFORMATION: Exemplary cyclic peptide

<400> SEQUENCE: 1017

Cys Arg Trp Ala Cys
1               5

<210> SEQ ID NO 1018
<211> LENGTH: 6
<212> TYPE: PRT
<213> ORGANISM: Artificial Sequence
<220> FEATURE:
<223> OTHER INFORMATION: Exemplary cyclic peptide

<400> SEQUENCE: 1018

Cys Arg Trp Ala Pro Cys
1               5

<210> SEQ ID NO 1019
<211> LENGTH: 7
<212> TYPE: PRT
<213> ORGANISM: Artificial Sequence
<220> FEATURE:
<223> OTHER INFORMATION: Exemplary cyclic peptide

<400> SEQUENCE: 1019

Cys Arg Trp Ala Pro Ile Cys
1               5

<210> SEQ ID NO 1020
<211> LENGTH: 8
<212> TYPE: PRT
<213> ORGANISM: Artificial Sequence
<220> FEATURE:
<223> OTHER INFORMATION: Exemplary cyclic peptide

<400> SEQUENCE: 1020

Cys Arg Trp Ala Pro Ile Pro Cys
1               5

<210> SEQ ID NO 1021
<211> LENGTH: 9
```

-continued

```
<212> TYPE: PRT
<213> ORGANISM: Artificial Sequence
<220> FEATURE:
<223> OTHER INFORMATION: Exemplary cyclic peptide

<400> SEQUENCE: 1021

Cys Arg Trp Ala Pro Ile Pro Cys Cys
 1               5

<210> SEQ ID NO 1022
<211> LENGTH: 10
<212> TYPE: PRT
<213> ORGANISM: Artificial Sequence
<220> FEATURE:
<223> OTHER INFORMATION: Exemplary cyclic peptide

<400> SEQUENCE: 1022

Cys Arg Trp Ala Pro Ile Pro Cys Ser Cys
 1               5                  10

<210> SEQ ID NO 1023
<211> LENGTH: 11
<212> TYPE: PRT
<213> ORGANISM: Artificial Sequence
<220> FEATURE:
<223> OTHER INFORMATION: Exemplary cyclic peptide

<400> SEQUENCE: 1023

Cys Arg Trp Ala Pro Ile Pro Cys Ser Met Cys
 1               5                  10

<210> SEQ ID NO 1024
<211> LENGTH: 5
<212> TYPE: PRT
<213> ORGANISM: Artificial Sequence
<220> FEATURE:
<223> OTHER INFORMATION: Exemplary cyclic peptide

<400> SEQUENCE: 1024

Cys Trp Ala Pro Cys
 1               5

<210> SEQ ID NO 1025
<211> LENGTH: 6
<212> TYPE: PRT
<213> ORGANISM: Artificial Sequence
<220> FEATURE:
<223> OTHER INFORMATION: Exemplary cyclic peptide

<400> SEQUENCE: 1025

Cys Trp Ala Pro Ile Cys
 1               5

<210> SEQ ID NO 1026
<211> LENGTH: 7
<212> TYPE: PRT
<213> ORGANISM: Artificial Sequence
<220> FEATURE:
<223> OTHER INFORMATION: Exemplary cyclic peptide

<400> SEQUENCE: 1026

Cys Trp Ala Pro Ile Pro Cys
 1               5

<210> SEQ ID NO 1027
<211> LENGTH: 8
<212> TYPE: PRT
```

```
<213> ORGANISM: Artificial Sequence
<220> FEATURE:
<223> OTHER INFORMATION: Exemplary cyclic peptide

<400> SEQUENCE: 1027

Cys Trp Ala Pro Ile Pro Cys Cys
1               5

<210> SEQ ID NO 1028
<211> LENGTH: 9
<212> TYPE: PRT
<213> ORGANISM: Artificial Sequence
<220> FEATURE:
<223> OTHER INFORMATION: Exemplary cyclic peptide

<400> SEQUENCE: 1028

Cys Trp Ala Pro Ile Pro Cys Ser Cys
1               5

<210> SEQ ID NO 1029
<211> LENGTH: 10
<212> TYPE: PRT
<213> ORGANISM: Artificial Sequence
<220> FEATURE:
<223> OTHER INFORMATION: Exemplary cyclic peptide

<400> SEQUENCE: 1029

Cys Trp Ala Pro Ile Pro Cys Ser Met Cys
1               5                   10

<210> SEQ ID NO 1030
<211> LENGTH: 11
<212> TYPE: PRT
<213> ORGANISM: Artificial Sequence
<220> FEATURE:
<223> OTHER INFORMATION: Exemplary cyclic peptide

<400> SEQUENCE: 1030

Cys Arg Trp Ala Pro Ile Pro Cys Ser Leu Cys
1               5                   10

<210> SEQ ID NO 1031
<211> LENGTH: 10
<212> TYPE: PRT
<213> ORGANISM: Artificial Sequence
<220> FEATURE:
<223> OTHER INFORMATION: Exemplary cyclic peptide

<400> SEQUENCE: 1031

Cys Trp Ala Pro Ile Pro Cys Ser Leu Cys
1               5                   10

<210> SEQ ID NO 1032
<211> LENGTH: 10
<212> TYPE: PRT
<213> ORGANISM: Artificial Sequence
<220> FEATURE:
<223> OTHER INFORMATION: Exemplary cyclic peptide

<400> SEQUENCE: 1032

Cys Arg Trp Ala Pro Ile Pro Cys Ala Cys
1               5                   10

<210> SEQ ID NO 1033
<211> LENGTH: 9
<212> TYPE: PRT
<213> ORGANISM: Artificial Sequence
```

```
<220> FEATURE:
<223> OTHER INFORMATION: Exemplary cyclic peptide

<400> SEQUENCE: 1033

Cys Trp Ala Pro Ile Pro Cys Ala Cys
1               5

<210> SEQ ID NO 1034
<211> LENGTH: 11
<212> TYPE: PRT
<213> ORGANISM: Artificial Sequence
<220> FEATURE:
<223> OTHER INFORMATION: Exemplary cyclic peptide

<400> SEQUENCE: 1034

Cys Arg Trp Ala Pro Ile Pro Cys Ala Ser Cys
1               5                   10

<210> SEQ ID NO 1035
<211> LENGTH: 10
<212> TYPE: PRT
<213> ORGANISM: Artificial Sequence
<220> FEATURE:
<223> OTHER INFORMATION: Exemplary cyclic peptide

<400> SEQUENCE: 1035

Cys Trp Ala Pro Ile Pro Cys Ala Ser Cys
1               5                   10

<210> SEQ ID NO 1036
<211> LENGTH: 5
<212> TYPE: PRT
<213> ORGANISM: Artificial Sequence
<220> FEATURE:
<223> OTHER INFORMATION: Exemplary cyclic peptide

<400> SEQUENCE: 1036

Cys Glu Trp Ile Cys
1               5

<210> SEQ ID NO 1037
<211> LENGTH: 6
<212> TYPE: PRT
<213> ORGANISM: Artificial Sequence
<220> FEATURE:
<223> OTHER INFORMATION: Exemplary cyclic peptide

<400> SEQUENCE: 1037

Cys Glu Trp Ile Lys Cys
1               5

<210> SEQ ID NO 1038
<211> LENGTH: 7
<212> TYPE: PRT
<213> ORGANISM: Artificial Sequence
<220> FEATURE:
<223> OTHER INFORMATION: Exemplary cyclic peptide

<400> SEQUENCE: 1038

Cys Glu Trp Ile Lys Phe Cys
1               5

<210> SEQ ID NO 1039
<211> LENGTH: 8
<212> TYPE: PRT
<213> ORGANISM: Artificial Sequence
<220> FEATURE:
```

```
<223> OTHER INFORMATION: Exemplary cyclic peptide

<400> SEQUENCE: 1039

Cys Glu Trp Ile Lys Phe Ala Cys
1               5

<210> SEQ ID NO 1040
<211> LENGTH: 9
<212> TYPE: PRT
<213> ORGANISM: Artificial Sequence
<220> FEATURE:
<223> OTHER INFORMATION: Exemplary cyclic peptide

<400> SEQUENCE: 1040

Cys Glu Trp Ile Lys Phe Ala Ala Cys
1               5

<210> SEQ ID NO 1041
<211> LENGTH: 10
<212> TYPE: PRT
<213> ORGANISM: Artificial Sequence
<220> FEATURE:
<223> OTHER INFORMATION: Exemplary cyclic peptide

<400> SEQUENCE: 1041

Cys Glu Trp Ile Lys Phe Ala Ala Ala Cys
1               5                   10

<210> SEQ ID NO 1042
<211> LENGTH: 11
<212> TYPE: PRT
<213> ORGANISM: Artificial Sequence
<220> FEATURE:
<223> OTHER INFORMATION: Exemplary cyclic peptide

<400> SEQUENCE: 1042

Cys Glu Trp Ile Lys Phe Ala Ala Ala Cys Cys
1               5                   10

<210> SEQ ID NO 1043
<211> LENGTH: 5
<212> TYPE: PRT
<213> ORGANISM: Artificial Sequence
<220> FEATURE:
<223> OTHER INFORMATION: Exemplary cyclic peptide

<400> SEQUENCE: 1043

Cys Trp Ile Lys Cys
1               5

<210> SEQ ID NO 1044
<211> LENGTH: 6
<212> TYPE: PRT
<213> ORGANISM: Artificial Sequence
<220> FEATURE:
<223> OTHER INFORMATION: Exemplary cyclic peptide

<400> SEQUENCE: 1044

Cys Trp Ile Lys Phe Cys
1               5

<210> SEQ ID NO 1045
<211> LENGTH: 7
<212> TYPE: PRT
<213> ORGANISM: Artificial Sequence
<220> FEATURE:
<223> OTHER INFORMATION: Exemplary cyclic peptide
```

```
<400> SEQUENCE: 1045

Cys Trp Ile Lys Phe Ala Cys
1               5

<210> SEQ ID NO 1046
<211> LENGTH: 8
<212> TYPE: PRT
<213> ORGANISM: Artificial Sequence
<220> FEATURE:
<223> OTHER INFORMATION: Exemplary cyclic peptide

<400> SEQUENCE: 1046

Cys Trp Ile Lys Phe Ala Ala Cys
1               5

<210> SEQ ID NO 1047
<211> LENGTH: 9
<212> TYPE: PRT
<213> ORGANISM: Artificial Sequence
<220> FEATURE:
<223> OTHER INFORMATION: Exemplary cyclic peptide

<400> SEQUENCE: 1047

Cys Trp Ile Lys Phe Ala Ala Ala Cys
1               5

<210> SEQ ID NO 1048
<211> LENGTH: 10
<212> TYPE: PRT
<213> ORGANISM: Artificial Sequence
<220> FEATURE:
<223> OTHER INFORMATION: Exemplary cyclic peptide

<400> SEQUENCE: 1048

Cys Trp Ile Lys Phe Ala Ala Ala Cys Cys
1               5                   10

<210> SEQ ID NO 1049
<211> LENGTH: 5
<212> TYPE: PRT
<213> ORGANISM: Artificial Sequence
<220> FEATURE:
<223> OTHER INFORMATION: Exemplary cyclic peptide

<400> SEQUENCE: 1049

Cys Glu Trp Val Cys
1               5

<210> SEQ ID NO 1050
<211> LENGTH: 6
<212> TYPE: PRT
<213> ORGANISM: Artificial Sequence
<220> FEATURE:
<223> OTHER INFORMATION: Exemplary cyclic peptide

<400> SEQUENCE: 1050

Cys Glu Trp Val Lys Cys
1               5

<210> SEQ ID NO 1051
<211> LENGTH: 7
<212> TYPE: PRT
<213> ORGANISM: Artificial Sequence
<220> FEATURE:
<223> OTHER INFORMATION: Exemplary cyclic peptide
```

```
-continued

<400> SEQUENCE: 1051

Cys Glu Trp Val Lys Phe Cys
 1               5

<210> SEQ ID NO 1052
<211> LENGTH: 8
<212> TYPE: PRT
<213> ORGANISM: Artificial Sequence
<220> FEATURE:
<223> OTHER INFORMATION: Exemplary cyclic peptide

<400> SEQUENCE: 1052

Cys Glu Trp Val Lys Phe Ala Cys
 1               5

<210> SEQ ID NO 1053
<211> LENGTH: 9
<212> TYPE: PRT
<213> ORGANISM: Artificial Sequence
<220> FEATURE:
<223> OTHER INFORMATION: Exemplary cyclic peptide

<400> SEQUENCE: 1053

Cys Glu Trp Val Lys Phe Ala Lys Cys
 1               5

<210> SEQ ID NO 1054
<211> LENGTH: 10
<212> TYPE: PRT
<213> ORGANISM: Artificial Sequence
<220> FEATURE:
<223> OTHER INFORMATION: Exemplary cyclic peptide

<400> SEQUENCE: 1054

Cys Glu Trp Val Lys Phe Ala Lys Pro Cys
 1               5                  10

<210> SEQ ID NO 1055
<211> LENGTH: 11
<212> TYPE: PRT
<213> ORGANISM: Artificial Sequence
<220> FEATURE:
<223> OTHER INFORMATION: Exemplary cyclic peptide

<400> SEQUENCE: 1055

Cys Glu Trp Val Lys Phe Ala Lys Pro Cys Cys
 1               5                  10

<210> SEQ ID NO 1056
<211> LENGTH: 5
<212> TYPE: PRT
<213> ORGANISM: Artificial Sequence
<220> FEATURE:
<223> OTHER INFORMATION: Exemplary cyclic peptide

<400> SEQUENCE: 1056

Cys Trp Val Lys Cys
 1               5

<210> SEQ ID NO 1057
<211> LENGTH: 6
<212> TYPE: PRT
<213> ORGANISM: Artificial Sequence
<220> FEATURE:
<223> OTHER INFORMATION: Exemplary cyclic peptide

<400> SEQUENCE: 1057
```

```
Cys Trp Val Lys Phe Cys
 1               5

<210> SEQ ID NO 1058
<211> LENGTH: 7
<212> TYPE: PRT
<213> ORGANISM: Artificial Sequence
<220> FEATURE:
<223> OTHER INFORMATION: Exemplary cyclic peptide

<400> SEQUENCE: 1058

Cys Trp Val Lys Phe Ala Cys
 1               5

<210> SEQ ID NO 1059
<211> LENGTH: 8
<212> TYPE: PRT
<213> ORGANISM: Artificial Sequence
<220> FEATURE:
<223> OTHER INFORMATION: Exemplary cyclic peptide

<400> SEQUENCE: 1059

Cys Trp Val Lys Phe Ala Lys Cys
 1               5

<210> SEQ ID NO 1060
<211> LENGTH: 9
<212> TYPE: PRT
<213> ORGANISM: Artificial Sequence
<220> FEATURE:
<223> OTHER INFORMATION: Exemplary cyclic peptide

<400> SEQUENCE: 1060

Cys Trp Val Lys Phe Ala Lys Pro Cys
 1               5

<210> SEQ ID NO 1061
<211> LENGTH: 10
<212> TYPE: PRT
<213> ORGANISM: Artificial Sequence
<220> FEATURE:
<223> OTHER INFORMATION: Exemplary cyclic peptide

<400> SEQUENCE: 1061

Cys Trp Val Lys Phe Ala Lys Pro Cys Cys
 1               5                  10

<210> SEQ ID NO 1062
<211> LENGTH: 5
<212> TYPE: PRT
<213> ORGANISM: Artificial Sequence
<220> FEATURE:
<223> OTHER INFORMATION: Exemplary cyclic peptide

<400> SEQUENCE: 1062

Cys Ala Trp Ile Cys
 1               5

<210> SEQ ID NO 1063
<211> LENGTH: 6
<212> TYPE: PRT
<213> ORGANISM: Artificial Sequence
<220> FEATURE:
<223> OTHER INFORMATION: Exemplary cyclic peptide

<400> SEQUENCE: 1063
```

```
Cys Ala Trp Ile Thr Cys
 1               5

<210> SEQ ID NO 1064
<211> LENGTH: 7
<212> TYPE: PRT
<213> ORGANISM: Artificial Sequence
<220> FEATURE:
<223> OTHER INFORMATION: Exemplary cyclic peptide

<400> SEQUENCE: 1064

Cys Ala Trp Ile Thr Ala Cys
 1               5

<210> SEQ ID NO 1065
<211> LENGTH: 8
<212> TYPE: PRT
<213> ORGANISM: Artificial Sequence
<220> FEATURE:
<223> OTHER INFORMATION: Exemplary cyclic peptide

<400> SEQUENCE: 1065

Cys Ala Trp Ile Thr Ala Pro Cys
 1               5

<210> SEQ ID NO 1066
<211> LENGTH: 9
<212> TYPE: PRT
<213> ORGANISM: Artificial Sequence
<220> FEATURE:
<223> OTHER INFORMATION: Exemplary cyclic peptide

<400> SEQUENCE: 1066

Cys Ala Trp Ile Thr Ala Pro Val Cys
 1               5

<210> SEQ ID NO 1067
<211> LENGTH: 10
<212> TYPE: PRT
<213> ORGANISM: Artificial Sequence
<220> FEATURE:
<223> OTHER INFORMATION: Exemplary cyclic peptide

<400> SEQUENCE: 1067

Cys Ala Trp Ile Thr Ala Pro Val Ala Cys
 1               5                   10

<210> SEQ ID NO 1068
<211> LENGTH: 11
<212> TYPE: PRT
<213> ORGANISM: Artificial Sequence
<220> FEATURE:
<223> OTHER INFORMATION: Exemplary cyclic peptide

<400> SEQUENCE: 1068

Cys Ala Trp Ile Thr Ala Pro Val Ala Leu Cys
 1               5                   10

<210> SEQ ID NO 1069
<211> LENGTH: 5
<212> TYPE: PRT
<213> ORGANISM: Artificial Sequence
<220> FEATURE:
<223> OTHER INFORMATION: Exemplary cyclic peptide

<400> SEQUENCE: 1069

Cys Trp Ile Thr Cys
```

-continued

```
                  1               5

<210> SEQ ID NO 1070
<211> LENGTH: 6
<212> TYPE: PRT
<213> ORGANISM: Artificial Sequence
<220> FEATURE:
<223> OTHER INFORMATION: Exemplary cyclic peptide

<400> SEQUENCE: 1070

Cys Trp Ile Thr Ala Cys
  1               5

<210> SEQ ID NO 1071
<211> LENGTH: 6
<212> TYPE: PRT
<213> ORGANISM: Artificial Sequence
<220> FEATURE:
<223> OTHER INFORMATION: Exemplary cyclic peptide

<400> SEQUENCE: 1071

Cys Trp Ile Thr Ala Pro
  1               5

<210> SEQ ID NO 1072
<211> LENGTH: 8
<212> TYPE: PRT
<213> ORGANISM: Artificial Sequence
<220> FEATURE:
<223> OTHER INFORMATION: Exemplary cyclic peptide

<400> SEQUENCE: 1072

Cys Trp Ile Thr Ala Pro Val Cys
  1               5

<210> SEQ ID NO 1073
<211> LENGTH: 9
<212> TYPE: PRT
<213> ORGANISM: Artificial Sequence
<220> FEATURE:
<223> OTHER INFORMATION: Exemplary cyclic peptide

<400> SEQUENCE: 1073

Cys Trp Ile Thr Ala Pro Val Ala Cys
  1               5

<210> SEQ ID NO 1074
<211> LENGTH: 10
<212> TYPE: PRT
<213> ORGANISM: Artificial Sequence
<220> FEATURE:
<223> OTHER INFORMATION: Exemplary cyclic peptide

<400> SEQUENCE: 1074

Cys Trp Ile Thr Ala Pro Val Ala Leu Cys
  1               5                  10

<210> SEQ ID NO 1075
<211> LENGTH: 5
<212> TYPE: PRT
<213> ORGANISM: Artificial Sequence
<220> FEATURE:
<223> OTHER INFORMATION: Exemplary cyclic peptide

<400> SEQUENCE: 1075

Lys Arg Trp Ala Asp
  1               5
```

```
<210> SEQ ID NO 1076
<211> LENGTH: 6
<212> TYPE: PRT
<213> ORGANISM: Artificial Sequence
<220> FEATURE:
<223> OTHER INFORMATION: Exemplary cyclic peptide

<400> SEQUENCE: 1076

Lys Arg Trp Ala Pro Asp
 1               5

<210> SEQ ID NO 1077
<211> LENGTH: 7
<212> TYPE: PRT
<213> ORGANISM: Artificial Sequence
<220> FEATURE:
<223> OTHER INFORMATION: Exemplary cyclic peptide

<400> SEQUENCE: 1077

Lys Arg Trp Ala Pro Ile Asp
 1               5

<210> SEQ ID NO 1078
<211> LENGTH: 7
<212> TYPE: PRT
<213> ORGANISM: Artificial Sequence
<220> FEATURE:
<223> OTHER INFORMATION: Exemplary cyclic peptide

<400> SEQUENCE: 1078

Lys Arg Trp Pro Ile Pro Asp
 1               5

<210> SEQ ID NO 1079
<211> LENGTH: 9
<212> TYPE: PRT
<213> ORGANISM: Artificial Sequence
<220> FEATURE:
<223> OTHER INFORMATION: Exemplary cyclic peptide

<400> SEQUENCE: 1079

Lys Arg Trp Ala Pro Ile Pro Cys Asp
 1               5

<210> SEQ ID NO 1080
<211> LENGTH: 10
<212> TYPE: PRT
<213> ORGANISM: Artificial Sequence
<220> FEATURE:
<223> OTHER INFORMATION: Exemplary cyclic peptide

<400> SEQUENCE: 1080

Lys Arg Trp Ala Pro Ile Pro Cys Ser Asp
 1               5                  10

<210> SEQ ID NO 1081
<211> LENGTH: 11
<212> TYPE: PRT
<213> ORGANISM: Artificial Sequence
<220> FEATURE:
<223> OTHER INFORMATION: Exemplary cyclic peptide

<400> SEQUENCE: 1081

Lys Arg Trp Ala Pro Ile Pro Cys Ser Met Asp
 1               5                  10
```

```
<210> SEQ ID NO 1082
<211> LENGTH: 5
<212> TYPE: PRT
<213> ORGANISM: Artificial Sequence
<220> FEATURE:
<223> OTHER INFORMATION: Exemplary cyclic peptide

<400> SEQUENCE: 1082

Lys Trp Ala Pro Asp
 1               5

<210> SEQ ID NO 1083
<211> LENGTH: 6
<212> TYPE: PRT
<213> ORGANISM: Artificial Sequence
<220> FEATURE:
<223> OTHER INFORMATION: Exemplary cyclic peptide

<400> SEQUENCE: 1083

Lys Trp Ala Pro Ile Asp
 1               5

<210> SEQ ID NO 1084
<211> LENGTH: 7
<212> TYPE: PRT
<213> ORGANISM: Artificial Sequence
<220> FEATURE:
<223> OTHER INFORMATION: Exemplary cyclic peptide

<400> SEQUENCE: 1084

Lys Trp Ala Pro Ile Pro Asp
 1               5

<210> SEQ ID NO 1085
<211> LENGTH: 8
<212> TYPE: PRT
<213> ORGANISM: Artificial Sequence
<220> FEATURE:
<223> OTHER INFORMATION: Exemplary cyclic peptide

<400> SEQUENCE: 1085

Lys Trp Ala Pro Ile Pro Cys Asp
 1               5

<210> SEQ ID NO 1086
<211> LENGTH: 9
<212> TYPE: PRT
<213> ORGANISM: Artificial Sequence
<220> FEATURE:
<223> OTHER INFORMATION: Exemplary cyclic peptide

<400> SEQUENCE: 1086

Lys Trp Ala Pro Ile Pro Cys Ser Asp
 1               5

<210> SEQ ID NO 1087
<211> LENGTH: 10
<212> TYPE: PRT
<213> ORGANISM: Artificial Sequence
<220> FEATURE:
<223> OTHER INFORMATION: Exemplary cyclic peptide

<400> SEQUENCE: 1087

Lys Trp Ala Pro Ile Pro Cys Ser Met Asp
 1               5                  10
```

```
<210> SEQ ID NO 1088
<211> LENGTH: 11
<212> TYPE: PRT
<213> ORGANISM: Artificial Sequence
<220> FEATURE:
<223> OTHER INFORMATION: Exemplary cyclic peptide

<400> SEQUENCE: 1088

Lys Arg Trp Ala Pro Ile Pro Cys Ser Leu Asp
 1               5                  10

<210> SEQ ID NO 1089
<211> LENGTH: 10
<212> TYPE: PRT
<213> ORGANISM: Artificial Sequence
<220> FEATURE:
<223> OTHER INFORMATION: Exemplary cyclic peptide

<400> SEQUENCE: 1089

Lys Trp Ala Pro Ile Pro Cys Ser Leu Asp
 1               5                  10

<210> SEQ ID NO 1090
<211> LENGTH: 10
<212> TYPE: PRT
<213> ORGANISM: Artificial Sequence
<220> FEATURE:
<223> OTHER INFORMATION: Exemplary cyclic peptide

<400> SEQUENCE: 1090

Lys Arg Trp Ala Pro Ile Pro Cys Ala Asp
 1               5                  10

<210> SEQ ID NO 1091
<211> LENGTH: 9
<212> TYPE: PRT
<213> ORGANISM: Artificial Sequence
<220> FEATURE:
<223> OTHER INFORMATION: Exemplary cyclic peptide

<400> SEQUENCE: 1091

Lys Trp Ala Pro Ile Pro Cys Ala Asp
 1               5

<210> SEQ ID NO 1092
<211> LENGTH: 11
<212> TYPE: PRT
<213> ORGANISM: Artificial Sequence
<220> FEATURE:
<223> OTHER INFORMATION: Exemplary cyclic peptide

<400> SEQUENCE: 1092

Lys Arg Trp Ala Pro Ile Pro Cys Ala Ser Asp
 1               5                  10

<210> SEQ ID NO 1093
<211> LENGTH: 10
<212> TYPE: PRT
<213> ORGANISM: Artificial Sequence
<220> FEATURE:
<223> OTHER INFORMATION: Exemplary cyclic peptide

<400> SEQUENCE: 1093

Lys Trp Ala Pro Ile Pro Cys Ala Ser Asp
 1               5                  10

<210> SEQ ID NO 1094
```

```
<211> LENGTH: 5
<212> TYPE: PRT
<213> ORGANISM: Artificial Sequence
<220> FEATURE:
<223> OTHER INFORMATION: Exemplary cyclic peptide

<400> SEQUENCE: 1094

Lys Glu Trp Ile Asp
 1               5

<210> SEQ ID NO 1095
<211> LENGTH: 6
<212> TYPE: PRT
<213> ORGANISM: Artificial Sequence
<220> FEATURE:
<223> OTHER INFORMATION: Exemplary cyclic peptide

<400> SEQUENCE: 1095

Lys Glu Trp Ile Lys Asp
 1               5

<210> SEQ ID NO 1096
<211> LENGTH: 7
<212> TYPE: PRT
<213> ORGANISM: Artificial Sequence
<220> FEATURE:
<223> OTHER INFORMATION: Exemplary cyclic peptide

<400> SEQUENCE: 1096

Lys Glu Trp Ile Lys Phe Asp
 1               5

<210> SEQ ID NO 1097
<211> LENGTH: 8
<212> TYPE: PRT
<213> ORGANISM: Artificial Sequence
<220> FEATURE:
<223> OTHER INFORMATION: Exemplary cyclic peptide

<400> SEQUENCE: 1097

Lys Glu Trp Ile Lys Phe Ala Asp
 1               5

<210> SEQ ID NO 1098
<211> LENGTH: 9
<212> TYPE: PRT
<213> ORGANISM: Artificial Sequence
<220> FEATURE:
<223> OTHER INFORMATION: Exemplary cyclic peptide

<400> SEQUENCE: 1098

Lys Glu Trp Ile Lys Phe Ala Ala Asp
 1               5

<210> SEQ ID NO 1099
<211> LENGTH: 10
<212> TYPE: PRT
<213> ORGANISM: Artificial Sequence
<220> FEATURE:
<223> OTHER INFORMATION: Exemplary cyclic peptide

<400> SEQUENCE: 1099

Lys Glu Trp Ile Lys Phe Ala Ala Ala Asp
 1               5                  10

<210> SEQ ID NO 1100
<211> LENGTH: 11
```

```
<212> TYPE: PRT
<213> ORGANISM: Artificial Sequence
<220> FEATURE:
<223> OTHER INFORMATION: Exemplary cyclic peptide

<400> SEQUENCE: 1100

Lys Glu Trp Ile Lys Phe Ala Ala Ala Cys Asp
1               5                   10

<210> SEQ ID NO 1101
<211> LENGTH: 5
<212> TYPE: PRT
<213> ORGANISM: Artificial Sequence
<220> FEATURE:
<223> OTHER INFORMATION: Exemplary cyclic peptide

<400> SEQUENCE: 1101

Lys Trp Ile Lys Asp
1               5

<210> SEQ ID NO 1102
<211> LENGTH: 6
<212> TYPE: PRT
<213> ORGANISM: Artificial Sequence
<220> FEATURE:
<223> OTHER INFORMATION: Exemplary cyclic peptide

<400> SEQUENCE: 1102

Lys Trp Ile Lys Phe Asp
1               5

<210> SEQ ID NO 1103
<211> LENGTH: 7
<212> TYPE: PRT
<213> ORGANISM: Artificial Sequence
<220> FEATURE:
<223> OTHER INFORMATION: Exemplary cyclic peptide

<400> SEQUENCE: 1103

Lys Trp Ile Lys Phe Ala Asp
1               5

<210> SEQ ID NO 1104
<211> LENGTH: 8
<212> TYPE: PRT
<213> ORGANISM: Artificial Sequence
<220> FEATURE:
<223> OTHER INFORMATION: Exemplary cyclic peptide

<400> SEQUENCE: 1104

Lys Trp Ile Lys Phe Ala Ala Asp
1               5

<210> SEQ ID NO 1105
<211> LENGTH: 9
<212> TYPE: PRT
<213> ORGANISM: Artificial Sequence
<220> FEATURE:
<223> OTHER INFORMATION: Exemplary cyclic peptide

<400> SEQUENCE: 1105

Lys Trp Ile Lys Phe Ala Ala Ala Asp
1               5

<210> SEQ ID NO 1106
<211> LENGTH: 10
<212> TYPE: PRT
```

```
<213> ORGANISM: Artificial Sequence
<220> FEATURE:
<223> OTHER INFORMATION: Exemplary cyclic peptide

<400> SEQUENCE: 1106

Lys Trp Ile Lys Phe Ala Ala Ala Cys Asp
1               5                   10

<210> SEQ ID NO 1107
<211> LENGTH: 5
<212> TYPE: PRT
<213> ORGANISM: Artificial Sequence
<220> FEATURE:
<223> OTHER INFORMATION: Exemplary cyclic peptide

<400> SEQUENCE: 1107

Lys Glu Trp Val Asp
1               5

<210> SEQ ID NO 1108
<211> LENGTH: 6
<212> TYPE: PRT
<213> ORGANISM: Artificial Sequence
<220> FEATURE:
<223> OTHER INFORMATION: Exemplary cyclic peptide

<400> SEQUENCE: 1108

Lys Glu Trp Val Lys Asp
1               5

<210> SEQ ID NO 1109
<211> LENGTH: 7
<212> TYPE: PRT
<213> ORGANISM: Artificial Sequence
<220> FEATURE:
<223> OTHER INFORMATION: Exemplary cyclic peptide

<400> SEQUENCE: 1109

Lys Glu Trp Val Lys Phe Asp
1               5

<210> SEQ ID NO 1110
<211> LENGTH: 8
<212> TYPE: PRT
<213> ORGANISM: Artificial Sequence
<220> FEATURE:
<223> OTHER INFORMATION: Exemplary cyclic peptide

<400> SEQUENCE: 1110

Lys Glu Trp Val Lys Phe Ala Asp
1               5

<210> SEQ ID NO 1111
<211> LENGTH: 9
<212> TYPE: PRT
<213> ORGANISM: Artificial Sequence
<220> FEATURE:
<223> OTHER INFORMATION: Exemplary cyclic peptide

<400> SEQUENCE: 1111

Lys Glu Trp Val Lys Phe Ala Lys Asp
1               5

<210> SEQ ID NO 1112
<211> LENGTH: 10
<212> TYPE: PRT
<213> ORGANISM: Artificial Sequence
```

```
<220> FEATURE:
<223> OTHER INFORMATION: Exemplary cyclic peptide

<400> SEQUENCE: 1112

Lys Glu Trp Val Lys Phe Ala Lys Pro Asp
 1               5                  10

<210> SEQ ID NO 1113
<211> LENGTH: 11
<212> TYPE: PRT
<213> ORGANISM: Artificial Sequence
<220> FEATURE:
<223> OTHER INFORMATION: Exemplary cyclic peptide

<400> SEQUENCE: 1113

Lys Glu Trp Val Lys Phe Ala Lys Pro Cys Asp
 1               5                  10

<210> SEQ ID NO 1114
<211> LENGTH: 5
<212> TYPE: PRT
<213> ORGANISM: Artificial Sequence
<220> FEATURE:
<223> OTHER INFORMATION: Exemplary cyclic peptide

<400> SEQUENCE: 1114

Lys Trp Val Lys Asp
 1               5

<210> SEQ ID NO 1115
<211> LENGTH: 6
<212> TYPE: PRT
<213> ORGANISM: Artificial Sequence
<220> FEATURE:
<223> OTHER INFORMATION: Exemplary cyclic peptide

<400> SEQUENCE: 1115

Lys Trp Val Lys Phe Asp
 1               5

<210> SEQ ID NO 1116
<211> LENGTH: 7
<212> TYPE: PRT
<213> ORGANISM: Artificial Sequence
<220> FEATURE:
<223> OTHER INFORMATION: Exemplary cyclic peptide

<400> SEQUENCE: 1116

Lys Trp Val Lys Phe Ala Asp
 1               5

<210> SEQ ID NO 1117
<211> LENGTH: 8
<212> TYPE: PRT
<213> ORGANISM: Artificial Sequence
<220> FEATURE:
<223> OTHER INFORMATION: Exemplary cyclic peptide

<400> SEQUENCE: 1117

Lys Trp Val Lys Phe Ala Lys Asp
 1               5

<210> SEQ ID NO 1118
<211> LENGTH: 9
<212> TYPE: PRT
<213> ORGANISM: Artificial Sequence
<220> FEATURE:
```

```
<223> OTHER INFORMATION: Exemplary cyclic peptide

<400> SEQUENCE: 1118

Lys Trp Val Lys Phe Ala Lys Pro Asp
 1               5

<210> SEQ ID NO 1119
<211> LENGTH: 10
<212> TYPE: PRT
<213> ORGANISM: Artificial Sequence
<220> FEATURE:
<223> OTHER INFORMATION: Exemplary cyclic peptide

<400> SEQUENCE: 1119

Lys Trp Val Lys Phe Ala Lys Pro Cys Asp
 1               5                  10

<210> SEQ ID NO 1120
<211> LENGTH: 5
<212> TYPE: PRT
<213> ORGANISM: Artificial Sequence
<220> FEATURE:
<223> OTHER INFORMATION: Exemplary cyclic peptide

<400> SEQUENCE: 1120

Lys Ala Trp Ile Asp
 1               5

<210> SEQ ID NO 1121
<211> LENGTH: 6
<212> TYPE: PRT
<213> ORGANISM: Artificial Sequence
<220> FEATURE:
<223> OTHER INFORMATION: Exemplary cyclic peptide

<400> SEQUENCE: 1121

Lys Ala Trp Ile Thr Asp
 1               5

<210> SEQ ID NO 1122
<211> LENGTH: 7
<212> TYPE: PRT
<213> ORGANISM: Artificial Sequence
<220> FEATURE:
<223> OTHER INFORMATION: Exemplary cyclic peptide

<400> SEQUENCE: 1122

Lys Ala Trp Ile Thr Ala Asp
 1               5

<210> SEQ ID NO 1123
<211> LENGTH: 8
<212> TYPE: PRT
<213> ORGANISM: Artificial Sequence
<220> FEATURE:
<223> OTHER INFORMATION: Exemplary cyclic peptide

<400> SEQUENCE: 1123

Lys Ala Trp Ile Thr Ala Pro Asp
 1               5

<210> SEQ ID NO 1124
<211> LENGTH: 9
<212> TYPE: PRT
<213> ORGANISM: Artificial Sequence
<220> FEATURE:
<223> OTHER INFORMATION: Exemplary cyclic peptide
```

```
<400> SEQUENCE: 1124

Lys Ala Trp Ile Thr Ala Pro Val Asp
 1               5

<210> SEQ ID NO 1125
<211> LENGTH: 10
<212> TYPE: PRT
<213> ORGANISM: Artificial Sequence
<220> FEATURE:
<223> OTHER INFORMATION: Exemplary cyclic peptide

<400> SEQUENCE: 1125

Lys Ala Trp Ile Thr Ala Pro Val Ala Asp
 1               5                  10

<210> SEQ ID NO 1126
<211> LENGTH: 11
<212> TYPE: PRT
<213> ORGANISM: Artificial Sequence
<220> FEATURE:
<223> OTHER INFORMATION: Exemplary cyclic peptide

<400> SEQUENCE: 1126

Lys Ala Trp Ile Thr Ala Pro Val Ala Leu Asp
 1               5                  10

<210> SEQ ID NO 1127
<211> LENGTH: 5
<212> TYPE: PRT
<213> ORGANISM: Artificial Sequence
<220> FEATURE:
<223> OTHER INFORMATION: Exemplary cyclic peptide

<400> SEQUENCE: 1127

Lys Trp Ile Thr Asp
 1               5

<210> SEQ ID NO 1128
<211> LENGTH: 6
<212> TYPE: PRT
<213> ORGANISM: Artificial Sequence
<220> FEATURE:
<223> OTHER INFORMATION: Exemplary cyclic peptide

<400> SEQUENCE: 1128

Lys Trp Ile Thr Ala Asp
 1               5

<210> SEQ ID NO 1129
<211> LENGTH: 7
<212> TYPE: PRT
<213> ORGANISM: Artificial Sequence
<220> FEATURE:
<223> OTHER INFORMATION: Exemplary cyclic peptide

<400> SEQUENCE: 1129

Lys Trp Ile Thr Ala Pro Asp
 1               5

<210> SEQ ID NO 1130
<211> LENGTH: 8
<212> TYPE: PRT
<213> ORGANISM: Artificial Sequence
<220> FEATURE:
<223> OTHER INFORMATION: Exemplary cyclic peptide
```

-continued

```
<400> SEQUENCE: 1130

Lys Trp Ile Thr Ala Pro Val Asp
1               5

<210> SEQ ID NO 1131
<211> LENGTH: 9
<212> TYPE: PRT
<213> ORGANISM: Artificial Sequence
<220> FEATURE:
<223> OTHER INFORMATION: Exemplary cyclic peptide

<400> SEQUENCE: 1131

Lys Trp Ile Thr Ala Pro Val Ala Asp
1               5

<210> SEQ ID NO 1132
<211> LENGTH: 10
<212> TYPE: PRT
<213> ORGANISM: Artificial Sequence
<220> FEATURE:
<223> OTHER INFORMATION: Exemplary cyclic peptide

<400> SEQUENCE: 1132

Lys Trp Ile Thr Ala Pro Val Ala Leu Asp
1               5                   10

<210> SEQ ID NO 1133
<211> LENGTH: 5
<212> TYPE: PRT
<213> ORGANISM: Artificial Sequence
<220> FEATURE:
<223> OTHER INFORMATION: Exemplary cyclic peptide

<400> SEQUENCE: 1133

Lys Arg Trp Ala Glu
1               5

<210> SEQ ID NO 1134
<211> LENGTH: 6
<212> TYPE: PRT
<213> ORGANISM: Artificial Sequence
<220> FEATURE:
<223> OTHER INFORMATION: Exemplary cyclic peptide

<400> SEQUENCE: 1134

Lys Arg Trp Ala Pro Glu
1               5

<210> SEQ ID NO 1135
<211> LENGTH: 7
<212> TYPE: PRT
<213> ORGANISM: Artificial Sequence
<220> FEATURE:
<223> OTHER INFORMATION: Exemplary cyclic peptide

<400> SEQUENCE: 1135

Lys Arg Trp Ala Pro Ile Glu
1               5

<210> SEQ ID NO 1136
<211> LENGTH: 8
<212> TYPE: PRT
<213> ORGANISM: Artificial Sequence
<220> FEATURE:
<223> OTHER INFORMATION: Exemplary cyclic peptide

<400> SEQUENCE: 1136
```

```
Lys Arg Trp Ala Pro Ile Pro Glu
 1               5

<210> SEQ ID NO 1137
<211> LENGTH: 9
<212> TYPE: PRT
<213> ORGANISM: Artificial Sequence
<220> FEATURE:
<223> OTHER INFORMATION: Exemplary cyclic peptide

<400> SEQUENCE: 1137

Lys Arg Trp Ala Pro Ile Pro Cys Glu
 1               5

<210> SEQ ID NO 1138
<211> LENGTH: 10
<212> TYPE: PRT
<213> ORGANISM: Artificial Sequence
<220> FEATURE:
<223> OTHER INFORMATION: Exemplary cyclic peptide

<400> SEQUENCE: 1138

Lys Arg Trp Ala Pro Ile Pro Cys Ser Glu
 1               5                  10

<210> SEQ ID NO 1139
<211> LENGTH: 11
<212> TYPE: PRT
<213> ORGANISM: Artificial Sequence
<220> FEATURE:
<223> OTHER INFORMATION: Exemplary cyclic peptide

<400> SEQUENCE: 1139

Lys Arg Trp Ala Pro Ile Pro Cys Ser Met Glu
 1               5                  10

<210> SEQ ID NO 1140
<211> LENGTH: 5
<212> TYPE: PRT
<213> ORGANISM: Artificial Sequence
<220> FEATURE:
<223> OTHER INFORMATION: Exemplary cyclic peptide

<400> SEQUENCE: 1140

Lys Trp Ala Pro Glu
 1               5

<210> SEQ ID NO 1141
<211> LENGTH: 6
<212> TYPE: PRT
<213> ORGANISM: Artificial Sequence
<220> FEATURE:
<223> OTHER INFORMATION: Exemplary cyclic peptide

<400> SEQUENCE: 1141

Lys Trp Ala Pro Ile Glu
 1               5

<210> SEQ ID NO 1142
<211> LENGTH: 7
<212> TYPE: PRT
<213> ORGANISM: Artificial Sequence
<220> FEATURE:
<223> OTHER INFORMATION: Exemplary cyclic peptide

<400> SEQUENCE: 1142
```

Lys Trp Ala Pro Ile Pro Glu
1               5

<210> SEQ ID NO 1143
<211> LENGTH: 8
<212> TYPE: PRT
<213> ORGANISM: Artificial Sequence
<220> FEATURE:
<223> OTHER INFORMATION: Exemplary cyclic peptide

<400> SEQUENCE: 1143

Lys Trp Ala Pro Ile Pro Cys Glu
1               5

<210> SEQ ID NO 1144
<211> LENGTH: 9
<212> TYPE: PRT
<213> ORGANISM: Artificial Sequence
<220> FEATURE:
<223> OTHER INFORMATION: Exemplary cyclic peptide

<400> SEQUENCE: 1144

Lys Trp Ala Pro Ile Pro Cys Ser Glu
1               5

<210> SEQ ID NO 1145
<211> LENGTH: 10
<212> TYPE: PRT
<213> ORGANISM: Artificial Sequence
<220> FEATURE:
<223> OTHER INFORMATION: Exemplary cyclic peptide

<400> SEQUENCE: 1145

Lys Trp Ala Pro Ile Pro Cys Ser Met Glu
1               5                   10

<210> SEQ ID NO 1146
<211> LENGTH: 11
<212> TYPE: PRT
<213> ORGANISM: Artificial Sequence
<220> FEATURE:
<223> OTHER INFORMATION: Exemplary cyclic peptide

<400> SEQUENCE: 1146

Lys Arg Trp Ala Pro Ile Pro Cys Ser Leu Glu
1               5                   10

<210> SEQ ID NO 1147
<211> LENGTH: 10
<212> TYPE: PRT
<213> ORGANISM: Artificial Sequence
<220> FEATURE:
<223> OTHER INFORMATION: Exemplary cyclic peptide

<400> SEQUENCE: 1147

Lys Trp Ala Pro Ile Pro Cys Ser Leu Glu
1               5                   10

<210> SEQ ID NO 1148
<211> LENGTH: 10
<212> TYPE: PRT
<213> ORGANISM: Artificial Sequence
<220> FEATURE:
<223> OTHER INFORMATION: Exemplary cyclic peptide

<400> SEQUENCE: 1148

Lys Arg Trp Ala Pro Ile Pro Cys Ala Glu

```
1               5              10
```

<210> SEQ ID NO 1149
<211> LENGTH: 9
<212> TYPE: PRT
<213> ORGANISM: Artificial Sequence
<220> FEATURE:
<223> OTHER INFORMATION: Exemplary cyclic peptide

<400> SEQUENCE: 1149

```
Lys Trp Ala Pro Ile Pro Cys Ala Glu
 1               5
```

<210> SEQ ID NO 1150
<211> LENGTH: 11
<212> TYPE: PRT
<213> ORGANISM: Artificial Sequence
<220> FEATURE:
<223> OTHER INFORMATION: Exemplary cyclic peptide

<400> SEQUENCE: 1150

```
Lys Arg Trp Ala Pro Ile Pro Cys Ala Ser Glu
 1               5                  10
```

<210> SEQ ID NO 1151
<211> LENGTH: 10
<212> TYPE: PRT
<213> ORGANISM: Artificial Sequence
<220> FEATURE:
<223> OTHER INFORMATION: Exemplary cyclic peptide

<400> SEQUENCE: 1151

```
Lys Trp Ala Pro Ile Pro Cys Ala Ser Glu
 1               5                  10
```

<210> SEQ ID NO 1152
<211> LENGTH: 5
<212> TYPE: PRT
<213> ORGANISM: Artificial Sequence
<220> FEATURE:
<223> OTHER INFORMATION: Exemplary cyclic peptide

<400> SEQUENCE: 1152

```
Lys Glu Trp Ile Glu
 1               5
```

<210> SEQ ID NO 1153
<211> LENGTH: 6
<212> TYPE: PRT
<213> ORGANISM: Artificial Sequence
<220> FEATURE:
<223> OTHER INFORMATION: Exemplary cyclic peptide

<400> SEQUENCE: 1153

```
Lys Glu Trp Ile Lys Glu
 1               5
```

<210> SEQ ID NO 1154
<211> LENGTH: 7
<212> TYPE: PRT
<213> ORGANISM: Artificial Sequence
<220> FEATURE:
<223> OTHER INFORMATION: Exemplary cyclic peptide

<400> SEQUENCE: 1154

```
Lys Glu Trp Ile Lys Phe Glu
 1               5
```

```
<210> SEQ ID NO 1155
<211> LENGTH: 8
<212> TYPE: PRT
<213> ORGANISM: Artificial Sequence
<220> FEATURE:
<223> OTHER INFORMATION: Exemplary cyclic peptide

<400> SEQUENCE: 1155

Lys Glu Trp Ile Lys Phe Ala Glu
 1               5

<210> SEQ ID NO 1156
<211> LENGTH: 9
<212> TYPE: PRT
<213> ORGANISM: Artificial Sequence
<220> FEATURE:
<223> OTHER INFORMATION: Exemplary cyclic peptide

<400> SEQUENCE: 1156

Lys Glu Trp Ile Lys Phe Ala Ala Glu
 1               5

<210> SEQ ID NO 1157
<211> LENGTH: 10
<212> TYPE: PRT
<213> ORGANISM: Artificial Sequence
<220> FEATURE:
<223> OTHER INFORMATION: Exemplary cyclic peptide

<400> SEQUENCE: 1157

Lys Glu Trp Ile Lys Phe Ala Ala Ala Glu
 1               5                  10

<210> SEQ ID NO 1158
<211> LENGTH: 11
<212> TYPE: PRT
<213> ORGANISM: Artificial Sequence
<220> FEATURE:
<223> OTHER INFORMATION: Exemplary cyclic peptide

<400> SEQUENCE: 1158

Lys Glu Trp Ile Lys Phe Ala Ala Ala Cys Glu
 1               5                  10

<210> SEQ ID NO 1159
<211> LENGTH: 5
<212> TYPE: PRT
<213> ORGANISM: Artificial Sequence
<220> FEATURE:
<223> OTHER INFORMATION: Exemplary cyclic peptide

<400> SEQUENCE: 1159

Lys Trp Ile Lys Glu
 1               5

<210> SEQ ID NO 1160
<211> LENGTH: 6
<212> TYPE: PRT
<213> ORGANISM: Artificial Sequence
<220> FEATURE:
<223> OTHER INFORMATION: Exemplary cyclic peptide

<400> SEQUENCE: 1160

Lys Trp Ile Lys Phe Glu
 1               5
```

```
<210> SEQ ID NO 1161
<211> LENGTH: 7
<212> TYPE: PRT
<213> ORGANISM: Artificial Sequence
<220> FEATURE:
<223> OTHER INFORMATION: Exemplary cyclic peptide

<400> SEQUENCE: 1161

Lys Trp Ile Lys Phe Ala Glu
 1               5

<210> SEQ ID NO 1162
<211> LENGTH: 8
<212> TYPE: PRT
<213> ORGANISM: Artificial Sequence
<220> FEATURE:
<223> OTHER INFORMATION: Exemplary cyclic peptide

<400> SEQUENCE: 1162

Lys Trp Ile Lys Phe Ala Ala Glu
 1               5

<210> SEQ ID NO 1163
<211> LENGTH: 9
<212> TYPE: PRT
<213> ORGANISM: Artificial Sequence
<220> FEATURE:
<223> OTHER INFORMATION: Exemplary cyclic peptide

<400> SEQUENCE: 1163

Lys Trp Ile Lys Phe Ala Ala Ala Glu
 1               5

<210> SEQ ID NO 1164
<211> LENGTH: 10
<212> TYPE: PRT
<213> ORGANISM: Artificial Sequence
<220> FEATURE:
<223> OTHER INFORMATION: Exemplary cyclic peptide

<400> SEQUENCE: 1164

Lys Trp Ile Lys Phe Ala Ala Ala Cys Glu
 1               5                  10

<210> SEQ ID NO 1165
<211> LENGTH: 5
<212> TYPE: PRT
<213> ORGANISM: Artificial Sequence
<220> FEATURE:
<223> OTHER INFORMATION: Exemplary cyclic peptide

<400> SEQUENCE: 1165

Lys Glu Trp Val Glu
 1               5

<210> SEQ ID NO 1166
<211> LENGTH: 6
<212> TYPE: PRT
<213> ORGANISM: Artificial Sequence
<220> FEATURE:
<223> OTHER INFORMATION: Exemplary cyclic peptide

<400> SEQUENCE: 1166

Lys Glu Trp Val Lys Glu
 1               5
```

-continued

```
<210> SEQ ID NO 1167
<211> LENGTH: 7
<212> TYPE: PRT
<213> ORGANISM: Artificial Sequence
<220> FEATURE:
<223> OTHER INFORMATION: Exemplary cyclic peptide

<400> SEQUENCE: 1167

Lys Glu Trp Val Lys Phe Glu
 1               5

<210> SEQ ID NO 1168
<211> LENGTH: 8
<212> TYPE: PRT
<213> ORGANISM: Artificial Sequence
<220> FEATURE:
<223> OTHER INFORMATION: Exemplary cyclic peptide

<400> SEQUENCE: 1168

Lys Glu Trp Val Lys Phe Ala Glu
 1               5

<210> SEQ ID NO 1169
<211> LENGTH: 9
<212> TYPE: PRT
<213> ORGANISM: Artificial Sequence
<220> FEATURE:
<223> OTHER INFORMATION: Exemplary cyclic peptide

<400> SEQUENCE: 1169

Lys Glu Trp Val Lys Phe Ala Lys Glu
 1               5

<210> SEQ ID NO 1170
<211> LENGTH: 10
<212> TYPE: PRT
<213> ORGANISM: Artificial Sequence
<220> FEATURE:
<223> OTHER INFORMATION: Exemplary cyclic peptide

<400> SEQUENCE: 1170

Lys Glu Trp Val Lys Phe Ala Lys Pro Glu
 1               5                   10

<210> SEQ ID NO 1171
<211> LENGTH: 11
<212> TYPE: PRT
<213> ORGANISM: Artificial Sequence
<220> FEATURE:
<223> OTHER INFORMATION: Exemplary cyclic peptide

<400> SEQUENCE: 1171

Lys Glu Trp Val Lys Phe Ala Lys Pro Cys Glu
 1               5                   10

<210> SEQ ID NO 1172
<211> LENGTH: 5
<212> TYPE: PRT
<213> ORGANISM: Artificial Sequence
<220> FEATURE:
<223> OTHER INFORMATION: Exemplary cyclic peptide

<400> SEQUENCE: 1172

Lys Trp Val Lys Glu
 1               5

<210> SEQ ID NO 1173
```

```
<211> LENGTH: 6
<212> TYPE: PRT
<213> ORGANISM: Artificial Sequence
<220> FEATURE:
<223> OTHER INFORMATION: Exemplary cyclic peptide

<400> SEQUENCE: 1173

Lys Trp Val Lys Phe Glu
 1               5

<210> SEQ ID NO 1174
<211> LENGTH: 7
<212> TYPE: PRT
<213> ORGANISM: Artificial Sequence
<220> FEATURE:
<223> OTHER INFORMATION: Exemplary cyclic peptide

<400> SEQUENCE: 1174

Lys Trp Val Lys Phe Ala Glu
 1               5

<210> SEQ ID NO 1175
<211> LENGTH: 8
<212> TYPE: PRT
<213> ORGANISM: Artificial Sequence
<220> FEATURE:
<223> OTHER INFORMATION: Exemplary cyclic peptide

<400> SEQUENCE: 1175

Lys Trp Val Lys Phe Ala Lys Glu
 1               5

<210> SEQ ID NO 1176
<211> LENGTH: 9
<212> TYPE: PRT
<213> ORGANISM: Artificial Sequence
<220> FEATURE:
<223> OTHER INFORMATION: Exemplary cyclic peptide

<400> SEQUENCE: 1176

Lys Trp Val Lys Phe Ala Lys Pro Glu
 1               5

<210> SEQ ID NO 1177
<211> LENGTH: 10
<212> TYPE: PRT
<213> ORGANISM: Artificial Sequence
<220> FEATURE:
<223> OTHER INFORMATION: Exemplary cyclic peptide

<400> SEQUENCE: 1177

Lys Trp Val Lys Phe Ala Lys Pro Cys Glu
 1               5                  10

<210> SEQ ID NO 1178
<211> LENGTH: 5
<212> TYPE: PRT
<213> ORGANISM: Artificial Sequence
<220> FEATURE:
<223> OTHER INFORMATION: Exemplary cyclic peptide

<400> SEQUENCE: 1178

Lys Ala Trp Ile Glu
 1               5

<210> SEQ ID NO 1179
<211> LENGTH: 6
```

```
<212> TYPE: PRT
<213> ORGANISM: Artificial Sequence
<220> FEATURE:
<223> OTHER INFORMATION: Exemplary cyclic peptide

<400> SEQUENCE: 1179

Lys Ala Trp Ile Thr Glu
1               5

<210> SEQ ID NO 1180
<211> LENGTH: 7
<212> TYPE: PRT
<213> ORGANISM: Artificial Sequence
<220> FEATURE:
<223> OTHER INFORMATION: Exemplary cyclic peptide

<400> SEQUENCE: 1180

Lys Ala Trp Ile Thr Ala Glu
1               5

<210> SEQ ID NO 1181
<211> LENGTH: 8
<212> TYPE: PRT
<213> ORGANISM: Artificial Sequence
<220> FEATURE:
<223> OTHER INFORMATION: Exemplary cyclic peptide

<400> SEQUENCE: 1181

Lys Ala Trp Ile Thr Ala Pro Glu
1               5

<210> SEQ ID NO 1182
<211> LENGTH: 9
<212> TYPE: PRT
<213> ORGANISM: Artificial Sequence
<220> FEATURE:
<223> OTHER INFORMATION: Exemplary cyclic peptide

<400> SEQUENCE: 1182

Lys Ala Trp Ile Thr Ala Pro Val Glu
1               5

<210> SEQ ID NO 1183
<211> LENGTH: 10
<212> TYPE: PRT
<213> ORGANISM: Artificial Sequence
<220> FEATURE:
<223> OTHER INFORMATION: Exemplary cyclic peptide

<400> SEQUENCE: 1183

Lys Ala Trp Ile Thr Ala Pro Val Ala Glu
1               5                   10

<210> SEQ ID NO 1184
<211> LENGTH: 11
<212> TYPE: PRT
<213> ORGANISM: Artificial Sequence
<220> FEATURE:
<223> OTHER INFORMATION: Exemplary cyclic peptide

<400> SEQUENCE: 1184

Lys Ala Trp Ile Thr Ala Pro Val Ala Leu Glu
1               5                   10

<210> SEQ ID NO 1185
<211> LENGTH: 5
<212> TYPE: PRT
```

```
<213> ORGANISM: Artificial Sequence
<220> FEATURE:
<223> OTHER INFORMATION: Exemplary cyclic peptide

<400> SEQUENCE: 1185

Lys Trp Ile Thr Glu
 1               5

<210> SEQ ID NO 1186
<211> LENGTH: 6
<212> TYPE: PRT
<213> ORGANISM: Artificial Sequence
<220> FEATURE:
<223> OTHER INFORMATION: Exemplary cyclic peptide

<400> SEQUENCE: 1186

Lys Trp Ile Thr Ala Glu
 1               5

<210> SEQ ID NO 1187
<211> LENGTH: 7
<212> TYPE: PRT
<213> ORGANISM: Artificial Sequence
<220> FEATURE:
<223> OTHER INFORMATION: Exemplary cyclic peptide

<400> SEQUENCE: 1187

Lys Trp Ile Thr Ala Pro Glu
 1               5

<210> SEQ ID NO 1188
<211> LENGTH: 8
<212> TYPE: PRT
<213> ORGANISM: Artificial Sequence
<220> FEATURE:
<223> OTHER INFORMATION: Exemplary cyclic peptide

<400> SEQUENCE: 1188

Lys Trp Ile Thr Ala Pro Val Glu
 1               5

<210> SEQ ID NO 1189
<211> LENGTH: 9
<212> TYPE: PRT
<213> ORGANISM: Artificial Sequence
<220> FEATURE:
<223> OTHER INFORMATION: Exemplary cyclic peptide

<400> SEQUENCE: 1189

Lys Trp Ile Thr Ala Pro Val Ala Glu
 1               5

<210> SEQ ID NO 1190
<211> LENGTH: 10
<212> TYPE: PRT
<213> ORGANISM: Artificial Sequence
<220> FEATURE:
<223> OTHER INFORMATION: Exemplary cyclic peptide

<400> SEQUENCE: 1190

Lys Trp Ile Thr Ala Pro Val Ala Leu Glu
 1               5                  10

<210> SEQ ID NO 1191
<211> LENGTH: 5
<212> TYPE: PRT
<213> ORGANISM: Artificial Sequence
```

```
<220> FEATURE:
<223> OTHER INFORMATION: Exemplary cyclic peptide

<400> SEQUENCE: 1191

Asp Arg Trp Ala Lys
 1               5

<210> SEQ ID NO 1192
<211> LENGTH: 6
<212> TYPE: PRT
<213> ORGANISM: Artificial Sequence
<220> FEATURE:
<223> OTHER INFORMATION: Exemplary cyclic peptide

<400> SEQUENCE: 1192

Asp Arg Trp Ala Pro Lys
 1               5

<210> SEQ ID NO 1193
<211> LENGTH: 7
<212> TYPE: PRT
<213> ORGANISM: Artificial Sequence
<220> FEATURE:
<223> OTHER INFORMATION: Exemplary cyclic peptide

<400> SEQUENCE: 1193

Asp Arg Trp Ala Pro Ile Lys
 1               5

<210> SEQ ID NO 1194
<211> LENGTH: 8
<212> TYPE: PRT
<213> ORGANISM: Artificial Sequence
<220> FEATURE:
<223> OTHER INFORMATION: Exemplary cyclic peptide

<400> SEQUENCE: 1194

Asp Arg Trp Ala Pro Ile Pro Lys
 1               5

<210> SEQ ID NO 1195
<211> LENGTH: 9
<212> TYPE: PRT
<213> ORGANISM: Artificial Sequence
<220> FEATURE:
<223> OTHER INFORMATION: Exemplary cyclic peptide

<400> SEQUENCE: 1195

Asp Arg Trp Ala Pro Ile Pro Cys Lys
 1               5

<210> SEQ ID NO 1196
<211> LENGTH: 10
<212> TYPE: PRT
<213> ORGANISM: Artificial Sequence
<220> FEATURE:
<223> OTHER INFORMATION: Exemplary cyclic peptide

<400> SEQUENCE: 1196

Asp Arg Trp Ala Pro Ile Pro Cys Ser Lys
 1               5                  10

<210> SEQ ID NO 1197
<211> LENGTH: 11
<212> TYPE: PRT
<213> ORGANISM: Artificial Sequence
<220> FEATURE:
```

```
<223> OTHER INFORMATION: Exemplary cyclic peptide

<400> SEQUENCE: 1197

Asp Arg Trp Ala Pro Ile Pro Cys Ser Met Lys
 1               5                  10

<210> SEQ ID NO 1198
<211> LENGTH: 5
<212> TYPE: PRT
<213> ORGANISM: Artificial Sequence
<220> FEATURE:
<223> OTHER INFORMATION: Exemplary cyclic peptide

<400> SEQUENCE: 1198

Asp Trp Ala Pro Lys
 1               5

<210> SEQ ID NO 1199
<211> LENGTH: 6
<212> TYPE: PRT
<213> ORGANISM: Artificial Sequence
<220> FEATURE:
<223> OTHER INFORMATION: Exemplary cyclic peptide

<400> SEQUENCE: 1199

Asp Trp Ala Pro Ile Lys
 1               5

<210> SEQ ID NO 1200
<211> LENGTH: 7
<212> TYPE: PRT
<213> ORGANISM: Artificial Sequence
<220> FEATURE:
<223> OTHER INFORMATION: Exemplary cyclic peptide

<400> SEQUENCE: 1200

Asp Trp Ala Pro Ile Pro Lys
 1               5

<210> SEQ ID NO 1201
<211> LENGTH: 8
<212> TYPE: PRT
<213> ORGANISM: Artificial Sequence
<220> FEATURE:
<223> OTHER INFORMATION: Exemplary cyclic peptide

<400> SEQUENCE: 1201

Asp Trp Ala Pro Ile Pro Cys Lys
 1               5

<210> SEQ ID NO 1202
<211> LENGTH: 9
<212> TYPE: PRT
<213> ORGANISM: Artificial Sequence
<220> FEATURE:
<223> OTHER INFORMATION: Exemplary cyclic peptide

<400> SEQUENCE: 1202

Asp Trp Ala Pro Ile Pro Cys Ser Lys
 1               5

<210> SEQ ID NO 1203
<211> LENGTH: 10
<212> TYPE: PRT
<213> ORGANISM: Artificial Sequence
<220> FEATURE:
<223> OTHER INFORMATION: Exemplary cyclic peptide
```

```
<400> SEQUENCE: 1203

Asp Trp Ala Pro Ile Pro Cys Ser Met Lys
 1               5                  10

<210> SEQ ID NO 1204
<211> LENGTH: 11
<212> TYPE: PRT
<213> ORGANISM: Artificial Sequence
<220> FEATURE:
<223> OTHER INFORMATION: Exemplary cyclic peptide

<400> SEQUENCE: 1204

Asp Arg Trp Ala Pro Ile Pro Cys Ser Leu Lys
 1               5                  10

<210> SEQ ID NO 1205
<211> LENGTH: 10
<212> TYPE: PRT
<213> ORGANISM: Artificial Sequence
<220> FEATURE:
<223> OTHER INFORMATION: Exemplary cyclic peptide

<400> SEQUENCE: 1205

Asp Trp Ala Pro Ile Pro Cys Ser Leu Lys
 1               5                  10

<210> SEQ ID NO 1206
<211> LENGTH: 10
<212> TYPE: PRT
<213> ORGANISM: Artificial Sequence
<220> FEATURE:
<223> OTHER INFORMATION: Exemplary cyclic peptide

<400> SEQUENCE: 1206

Asp Arg Trp Ala Pro Ile Pro Cys Ala Lys
 1               5                  10

<210> SEQ ID NO 1207
<211> LENGTH: 9
<212> TYPE: PRT
<213> ORGANISM: Artificial Sequence
<220> FEATURE:
<223> OTHER INFORMATION: Exemplary cyclic peptide

<400> SEQUENCE: 1207

Asp Trp Ala Pro Ile Pro Cys Ala Lys
 1               5

<210> SEQ ID NO 1208
<211> LENGTH: 11
<212> TYPE: PRT
<213> ORGANISM: Artificial Sequence
<220> FEATURE:
<223> OTHER INFORMATION: Exemplary cyclic peptide

<400> SEQUENCE: 1208

Asp Arg Trp Ala Pro Ile Pro Cys Ala Ser Lys
 1               5                  10

<210> SEQ ID NO 1209
<211> LENGTH: 10
<212> TYPE: PRT
<213> ORGANISM: Artificial Sequence
<220> FEATURE:
<223> OTHER INFORMATION: Exemplary cyclic peptide
```

-continued

```
<400> SEQUENCE: 1209

Asp Trp Ala Pro Ile Pro Cys Ala Ser Lys
1               5                   10

<210> SEQ ID NO 1210
<211> LENGTH: 5
<212> TYPE: PRT
<213> ORGANISM: Artificial Sequence
<220> FEATURE:
<223> OTHER INFORMATION: Exemplary cyclic peptide

<400> SEQUENCE: 1210

Asp Glu Trp Ile Lys
1               5

<210> SEQ ID NO 1211
<211> LENGTH: 6
<212> TYPE: PRT
<213> ORGANISM: Artificial Sequence
<220> FEATURE:
<223> OTHER INFORMATION: Exemplary cyclic peptide

<400> SEQUENCE: 1211

Asp Glu Trp Ile Lys Lys
1               5

<210> SEQ ID NO 1212
<211> LENGTH: 7
<212> TYPE: PRT
<213> ORGANISM: Artificial Sequence
<220> FEATURE:
<223> OTHER INFORMATION: Exemplary cyclic peptide

<400> SEQUENCE: 1212

Asp Glu Trp Ile Lys Phe Lys
1               5

<210> SEQ ID NO 1213
<211> LENGTH: 8
<212> TYPE: PRT
<213> ORGANISM: Artificial Sequence
<220> FEATURE:
<223> OTHER INFORMATION: Exemplary cyclic peptide

<400> SEQUENCE: 1213

Asp Glu Trp Ile Lys Phe Ala Lys
1               5

<210> SEQ ID NO 1214
<211> LENGTH: 9
<212> TYPE: PRT
<213> ORGANISM: Artificial Sequence
<220> FEATURE:
<223> OTHER INFORMATION: Exemplary cyclic peptide

<400> SEQUENCE: 1214

Asp Glu Trp Ile Lys Phe Ala Ala Lys
1               5

<210> SEQ ID NO 1215
<211> LENGTH: 10
<212> TYPE: PRT
<213> ORGANISM: Artificial Sequence
<220> FEATURE:
<223> OTHER INFORMATION: Exemplary cyclic peptide

<400> SEQUENCE: 1215
```

Asp Glu Trp Ile Lys Phe Ala Ala Ala Lys
1               5                   10

<210> SEQ ID NO 1216
<211> LENGTH: 11
<212> TYPE: PRT
<213> ORGANISM: Artificial Sequence
<220> FEATURE:
<223> OTHER INFORMATION: Exemplary cyclic peptide

<400> SEQUENCE: 1216

Asp Glu Trp Ile Lys Phe Ala Ala Ala Cys Lys
1               5                   10

<210> SEQ ID NO 1217
<211> LENGTH: 5
<212> TYPE: PRT
<213> ORGANISM: Artificial Sequence
<220> FEATURE:
<223> OTHER INFORMATION: Exemplary cyclic peptide

<400> SEQUENCE: 1217

Asp Trp Ile Lys Lys
1               5

<210> SEQ ID NO 1218
<211> LENGTH: 6
<212> TYPE: PRT
<213> ORGANISM: Artificial Sequence
<220> FEATURE:
<223> OTHER INFORMATION: Exemplary cyclic peptide

<400> SEQUENCE: 1218

Asp Trp Ile Lys Phe Lys
1               5

<210> SEQ ID NO 1219
<211> LENGTH: 7
<212> TYPE: PRT
<213> ORGANISM: Artificial Sequence
<220> FEATURE:
<223> OTHER INFORMATION: Exemplary cyclic peptide

<400> SEQUENCE: 1219

Asp Trp Ile Lys Phe Ala Lys
1               5

<210> SEQ ID NO 1220
<211> LENGTH: 8
<212> TYPE: PRT
<213> ORGANISM: Artificial Sequence
<220> FEATURE:
<223> OTHER INFORMATION: Exemplary cyclic peptide

<400> SEQUENCE: 1220

Asp Trp Ile Lys Phe Ala Ala Lys
1               5

<210> SEQ ID NO 1221
<211> LENGTH: 9
<212> TYPE: PRT
<213> ORGANISM: Artificial Sequence
<220> FEATURE:
<223> OTHER INFORMATION: Exemplary cyclic peptide

<400> SEQUENCE: 1221

```
Asp Trp Ile Lys Phe Ala Ala Ala Lys
 1               5

<210> SEQ ID NO 1222
<211> LENGTH: 10
<212> TYPE: PRT
<213> ORGANISM: Artificial Sequence
<220> FEATURE:
<223> OTHER INFORMATION: Exemplary cyclic peptide

<400> SEQUENCE: 1222

Asp Trp Ile Lys Phe Ala Ala Ala Cys Lys
 1               5                  10

<210> SEQ ID NO 1223
<211> LENGTH: 5
<212> TYPE: PRT
<213> ORGANISM: Artificial Sequence
<220> FEATURE:
<223> OTHER INFORMATION: Exemplary cyclic peptide

<400> SEQUENCE: 1223

Asp Glu Trp Val Lys
 1               5

<210> SEQ ID NO 1224
<211> LENGTH: 6
<212> TYPE: PRT
<213> ORGANISM: Artificial Sequence
<220> FEATURE:
<223> OTHER INFORMATION: Exemplary cyclic peptide

<400> SEQUENCE: 1224

Asp Glu Trp Val Lys Lys
 1               5

<210> SEQ ID NO 1225
<211> LENGTH: 7
<212> TYPE: PRT
<213> ORGANISM: Artificial Sequence
<220> FEATURE:
<223> OTHER INFORMATION: Exemplary cyclic peptide

<400> SEQUENCE: 1225

Asp Glu Trp Val Lys Phe Lys
 1               5

<210> SEQ ID NO 1226
<211> LENGTH: 8
<212> TYPE: PRT
<213> ORGANISM: Artificial Sequence
<220> FEATURE:
<223> OTHER INFORMATION: Exemplary cyclic peptide

<400> SEQUENCE: 1226

Asp Glu Trp Val Lys Phe Ala Lys
 1               5

<210> SEQ ID NO 1227
<211> LENGTH: 9
<212> TYPE: PRT
<213> ORGANISM: Artificial Sequence
<220> FEATURE:
<223> OTHER INFORMATION: Exemplary cyclic peptide

<400> SEQUENCE: 1227

Asp Glu Trp Val Lys Phe Ala Lys Lys
```

-continued

```
1               5
```

<210> SEQ ID NO 1228
<211> LENGTH: 10
<212> TYPE: PRT
<213> ORGANISM: Artificial Sequence
<220> FEATURE:
<223> OTHER INFORMATION: Exemplary cyclic peptide

<400> SEQUENCE: 1228

```
Asp Glu Trp Val Lys Phe Ala Lys Pro Lys
1               5                   10
```

<210> SEQ ID NO 1229
<211> LENGTH: 11
<212> TYPE: PRT
<213> ORGANISM: Artificial Sequence
<220> FEATURE:
<223> OTHER INFORMATION: Exemplary cyclic peptide

<400> SEQUENCE: 1229

```
Asp Glu Trp Val Lys Phe Ala Lys Pro Cys Lys
1               5                   10
```

<210> SEQ ID NO 1230
<211> LENGTH: 5
<212> TYPE: PRT
<213> ORGANISM: Artificial Sequence
<220> FEATURE:
<223> OTHER INFORMATION: Exemplary cyclic peptide

<400> SEQUENCE: 1230

```
Asp Trp Val Lys Lys
1               5
```

<210> SEQ ID NO 1231
<211> LENGTH: 6
<212> TYPE: PRT
<213> ORGANISM: Artificial Sequence
<220> FEATURE:
<223> OTHER INFORMATION: Exemplary cyclic peptide

<400> SEQUENCE: 1231

```
Asp Trp Val Lys Phe Lys
1               5
```

<210> SEQ ID NO 1232
<211> LENGTH: 7
<212> TYPE: PRT
<213> ORGANISM: Artificial Sequence
<220> FEATURE:
<223> OTHER INFORMATION: Exemplary cyclic peptide

<400> SEQUENCE: 1232

```
Asp Trp Val Lys Phe Ala Lys
1               5
```

<210> SEQ ID NO 1233
<211> LENGTH: 8
<212> TYPE: PRT
<213> ORGANISM: Artificial Sequence
<220> FEATURE:
<223> OTHER INFORMATION: Exemplary cyclic peptide

<400> SEQUENCE: 1233

```
Asp Trp Val Lys Phe Ala Lys Lys
1               5
```

```
<210> SEQ ID NO 1234
<211> LENGTH: 9
<212> TYPE: PRT
<213> ORGANISM: Artificial Sequence
<220> FEATURE:
<223> OTHER INFORMATION: Exemplary cyclic peptide

<400> SEQUENCE: 1234

Asp Trp Val Lys Phe Ala Lys Pro Lys
1               5

<210> SEQ ID NO 1235
<211> LENGTH: 10
<212> TYPE: PRT
<213> ORGANISM: Artificial Sequence
<220> FEATURE:
<223> OTHER INFORMATION: Exemplary cyclic peptide

<400> SEQUENCE: 1235

Asp Trp Val Lys Phe Ala Lys Pro Cys Lys
1               5                   10

<210> SEQ ID NO 1236
<211> LENGTH: 5
<212> TYPE: PRT
<213> ORGANISM: Artificial Sequence
<220> FEATURE:
<223> OTHER INFORMATION: Exemplary cyclic peptide

<400> SEQUENCE: 1236

Asp Ala Trp Ile Lys
1               5

<210> SEQ ID NO 1237
<211> LENGTH: 6
<212> TYPE: PRT
<213> ORGANISM: Artificial Sequence
<220> FEATURE:
<223> OTHER INFORMATION: Exemplary cyclic peptide

<400> SEQUENCE: 1237

Asp Ala Trp Ile Thr Lys
1               5

<210> SEQ ID NO 1238
<211> LENGTH: 7
<212> TYPE: PRT
<213> ORGANISM: Artificial Sequence
<220> FEATURE:
<223> OTHER INFORMATION: Exemplary cyclic peptide

<400> SEQUENCE: 1238

Asp Ala Trp Ile Thr Ala Lys
1               5

<210> SEQ ID NO 1239
<211> LENGTH: 8
<212> TYPE: PRT
<213> ORGANISM: Artificial Sequence
<220> FEATURE:
<223> OTHER INFORMATION: Exemplary cyclic peptide

<400> SEQUENCE: 1239

Asp Ala Trp Ile Thr Ala Pro Lys
1               5
```

```
<210> SEQ ID NO 1240
<211> LENGTH: 9
<212> TYPE: PRT
<213> ORGANISM: Artificial Sequence
<220> FEATURE:
<223> OTHER INFORMATION: Exemplary cyclic peptide

<400> SEQUENCE: 1240

Asp Ala Trp Ile Thr Ala Pro Val Lys
 1               5

<210> SEQ ID NO 1241
<211> LENGTH: 10
<212> TYPE: PRT
<213> ORGANISM: Artificial Sequence
<220> FEATURE:
<223> OTHER INFORMATION: Exemplary cyclic peptide

<400> SEQUENCE: 1241

Asp Ala Trp Ile Thr Ala Pro Val Ala Lys
 1               5                  10

<210> SEQ ID NO 1242
<211> LENGTH: 11
<212> TYPE: PRT
<213> ORGANISM: Artificial Sequence
<220> FEATURE:
<223> OTHER INFORMATION: Exemplary cyclic peptide

<400> SEQUENCE: 1242

Asp Ala Trp Ile Thr Ala Pro Val Ala Leu Lys
 1               5                  10

<210> SEQ ID NO 1243
<211> LENGTH: 5
<212> TYPE: PRT
<213> ORGANISM: Artificial Sequence
<220> FEATURE:
<223> OTHER INFORMATION: Exemplary cyclic peptide

<400> SEQUENCE: 1243

Asp Trp Ile Thr Lys
 1               5

<210> SEQ ID NO 1244
<211> LENGTH: 6
<212> TYPE: PRT
<213> ORGANISM: Artificial Sequence
<220> FEATURE:
<223> OTHER INFORMATION: Exemplary cyclic peptide

<400> SEQUENCE: 1244

Asp Trp Ile Thr Ala Lys
 1               5

<210> SEQ ID NO 1245
<211> LENGTH: 7
<212> TYPE: PRT
<213> ORGANISM: Artificial Sequence
<220> FEATURE:
<223> OTHER INFORMATION: Exemplary cyclic peptide

<400> SEQUENCE: 1245

Asp Trp Ile Thr Ala Pro Lys
 1               5
```

```
<210> SEQ ID NO 1246
<211> LENGTH: 8
<212> TYPE: PRT
<213> ORGANISM: Artificial Sequence
<220> FEATURE:
<223> OTHER INFORMATION: Exemplary cyclic peptide

<400> SEQUENCE: 1246

Asp Trp Ile Thr Ala Pro Val Lys
 1               5

<210> SEQ ID NO 1247
<211> LENGTH: 9
<212> TYPE: PRT
<213> ORGANISM: Artificial Sequence
<220> FEATURE:
<223> OTHER INFORMATION: Exemplary cyclic peptide

<400> SEQUENCE: 1247

Asp Trp Ile Thr Ala Pro Val Ala Lys
 1               5

<210> SEQ ID NO 1248
<211> LENGTH: 10
<212> TYPE: PRT
<213> ORGANISM: Artificial Sequence
<220> FEATURE:
<223> OTHER INFORMATION: Exemplary cyclic peptide

<400> SEQUENCE: 1248

Asp Trp Ile Thr Ala Pro Val Ala Leu Lys
 1               5                  10

<210> SEQ ID NO 1249
<211> LENGTH: 5
<212> TYPE: PRT
<213> ORGANISM: Artificial Sequence
<220> FEATURE:
<223> OTHER INFORMATION: Exemplary cyclic peptide

<400> SEQUENCE: 1249

Glu Arg Trp Ala Lys
 1               5

<210> SEQ ID NO 1250
<211> LENGTH: 6
<212> TYPE: PRT
<213> ORGANISM: Artificial Sequence
<220> FEATURE:
<223> OTHER INFORMATION: Exemplary cyclic peptide

<400> SEQUENCE: 1250

Glu Arg Trp Ala Pro Lys
 1               5

<210> SEQ ID NO 1251
<211> LENGTH: 7
<212> TYPE: PRT
<213> ORGANISM: Artificial Sequence
<220> FEATURE:
<223> OTHER INFORMATION: Exemplary cyclic peptide

<400> SEQUENCE: 1251

Glu Arg Trp Ala Pro Ile Lys
 1               5

<210> SEQ ID NO 1252
```

-continued

```
<211> LENGTH: 8
<212> TYPE: PRT
<213> ORGANISM: Artificial Sequence
<220> FEATURE:
<223> OTHER INFORMATION: Exemplary cyclic peptide

<400> SEQUENCE: 1252

Glu Arg Trp Ala Pro Ile Pro Lys
1               5

<210> SEQ ID NO 1253
<211> LENGTH: 9
<212> TYPE: PRT
<213> ORGANISM: Artificial Sequence
<220> FEATURE:
<223> OTHER INFORMATION: Exemplary cyclic peptide

<400> SEQUENCE: 1253

Glu Arg Trp Ala Pro Ile Pro Cys Lys
1               5

<210> SEQ ID NO 1254
<211> LENGTH: 10
<212> TYPE: PRT
<213> ORGANISM: Artificial Sequence
<220> FEATURE:
<223> OTHER INFORMATION: Exemplary cyclic peptide

<400> SEQUENCE: 1254

Glu Arg Trp Ala Pro Ile Pro Cys Ser Lys
1               5                   10

<210> SEQ ID NO 1255
<211> LENGTH: 11
<212> TYPE: PRT
<213> ORGANISM: Artificial Sequence
<220> FEATURE:
<223> OTHER INFORMATION: Exemplary cyclic peptide

<400> SEQUENCE: 1255

Glu Arg Trp Ala Pro Ile Pro Cys Ser Met Lys
1               5                   10

<210> SEQ ID NO 1256
<211> LENGTH: 5
<212> TYPE: PRT
<213> ORGANISM: Artificial Sequence
<220> FEATURE:
<223> OTHER INFORMATION: Exemplary cyclic peptide

<400> SEQUENCE: 1256

Glu Trp Ala Pro Lys
1               5

<210> SEQ ID NO 1257
<211> LENGTH: 6
<212> TYPE: PRT
<213> ORGANISM: Artificial Sequence
<220> FEATURE:
<223> OTHER INFORMATION: Exemplary cyclic peptide

<400> SEQUENCE: 1257

Glu Trp Ala Pro Ile Lys
1               5

<210> SEQ ID NO 1258
<211> LENGTH: 7
```

```
<212> TYPE: PRT
<213> ORGANISM: Artificial Sequence
<220> FEATURE:
<223> OTHER INFORMATION: Exemplary cyclic peptide

<400> SEQUENCE: 1258

Glu Trp Ala Pro Ile Pro Lys
 1               5

<210> SEQ ID NO 1259
<211> LENGTH: 8
<212> TYPE: PRT
<213> ORGANISM: Artificial Sequence
<220> FEATURE:
<223> OTHER INFORMATION: Exemplary cyclic peptide

<400> SEQUENCE: 1259

Glu Trp Ala Pro Ile Pro Cys Lys
 1               5

<210> SEQ ID NO 1260
<211> LENGTH: 9
<212> TYPE: PRT
<213> ORGANISM: Artificial Sequence
<220> FEATURE:
<223> OTHER INFORMATION: Exemplary cyclic peptide

<400> SEQUENCE: 1260

Glu Trp Ala Pro Ile Pro Cys Ser Lys
 1               5

<210> SEQ ID NO 1261
<211> LENGTH: 10
<212> TYPE: PRT
<213> ORGANISM: Artificial Sequence
<220> FEATURE:
<223> OTHER INFORMATION: Exemplary cyclic peptide

<400> SEQUENCE: 1261

Glu Trp Ala Pro Ile Pro Cys Ser Met Lys
 1               5                   10

<210> SEQ ID NO 1262
<211> LENGTH: 11
<212> TYPE: PRT
<213> ORGANISM: Artificial Sequence
<220> FEATURE:
<223> OTHER INFORMATION: Exemplary cyclic peptide

<400> SEQUENCE: 1262

Glu Arg Trp Ala Pro Ile Pro Cys Ser Leu Lys
 1               5                   10

<210> SEQ ID NO 1263
<211> LENGTH: 10
<212> TYPE: PRT
<213> ORGANISM: Artificial Sequence
<220> FEATURE:
<223> OTHER INFORMATION: Exemplary cyclic peptide

<400> SEQUENCE: 1263

Glu Trp Ala Pro Ile Pro Cys Ser Leu Lys
 1               5                   10

<210> SEQ ID NO 1264
<211> LENGTH: 10
<212> TYPE: PRT
```

```
<213> ORGANISM: Artificial Sequence
<220> FEATURE:
<223> OTHER INFORMATION: Exemplary cyclic peptide

<400> SEQUENCE: 1264

Glu Arg Trp Ala Pro Ile Pro Cys Ala Lys
 1               5                  10

<210> SEQ ID NO 1265
<211> LENGTH: 9
<212> TYPE: PRT
<213> ORGANISM: Artificial Sequence
<220> FEATURE:
<223> OTHER INFORMATION: Exemplary cyclic peptide

<400> SEQUENCE: 1265

Glu Trp Ala Pro Ile Pro Cys Ala Lys
 1               5

<210> SEQ ID NO 1266
<211> LENGTH: 11
<212> TYPE: PRT
<213> ORGANISM: Artificial Sequence
<220> FEATURE:
<223> OTHER INFORMATION: Exemplary cyclic peptide

<400> SEQUENCE: 1266

Glu Arg Trp Ala Pro Ile Pro Cys Ala Ser Lys
 1               5                  10

<210> SEQ ID NO 1267
<211> LENGTH: 10
<212> TYPE: PRT
<213> ORGANISM: Artificial Sequence
<220> FEATURE:
<223> OTHER INFORMATION: Exemplary cyclic peptide

<400> SEQUENCE: 1267

Glu Trp Ala Pro Ile Pro Cys Ala Ser Lys
 1               5                  10

<210> SEQ ID NO 1268
<211> LENGTH: 5
<212> TYPE: PRT
<213> ORGANISM: Artificial Sequence
<220> FEATURE:
<223> OTHER INFORMATION: Exemplary cyclic peptide

<400> SEQUENCE: 1268

Glu Glu Trp Ile Lys
 1               5

<210> SEQ ID NO 1269
<211> LENGTH: 6
<212> TYPE: PRT
<213> ORGANISM: Artificial Sequence
<220> FEATURE:
<223> OTHER INFORMATION: Exemplary cyclic peptide

<400> SEQUENCE: 1269

Glu Glu Trp Ile Lys Lys
 1               5

<210> SEQ ID NO 1270
<211> LENGTH: 7
<212> TYPE: PRT
<213> ORGANISM: Artificial Sequence
```

-continued

```
<220> FEATURE:
<223> OTHER INFORMATION: Exemplary cyclic peptide

<400> SEQUENCE: 1270

Glu Glu Trp Ile Lys Phe Lys
 1               5

<210> SEQ ID NO 1271
<211> LENGTH: 8
<212> TYPE: PRT
<213> ORGANISM: Artificial Sequence
<220> FEATURE:
<223> OTHER INFORMATION: Exemplary cyclic peptide

<400> SEQUENCE: 1271

Glu Glu Trp Ile Lys Phe Ala Lys
 1               5

<210> SEQ ID NO 1272
<211> LENGTH: 9
<212> TYPE: PRT
<213> ORGANISM: Artificial Sequence
<220> FEATURE:
<223> OTHER INFORMATION: Exemplary cyclic peptide

<400> SEQUENCE: 1272

Glu Glu Trp Ile Lys Phe Ala Ala Lys
 1               5

<210> SEQ ID NO 1273
<211> LENGTH: 10
<212> TYPE: PRT
<213> ORGANISM: Artificial Sequence
<220> FEATURE:
<223> OTHER INFORMATION: Exemplary cyclic peptide

<400> SEQUENCE: 1273

Glu Glu Trp Ile Lys Phe Ala Ala Ala Lys
 1               5                  10

<210> SEQ ID NO 1274
<211> LENGTH: 11
<212> TYPE: PRT
<213> ORGANISM: Artificial Sequence
<220> FEATURE:
<223> OTHER INFORMATION: Exemplary cyclic peptide

<400> SEQUENCE: 1274

Glu Glu Trp Ile Lys Phe Ala Ala Ala Cys Lys
 1               5                  10

<210> SEQ ID NO 1275
<211> LENGTH: 5
<212> TYPE: PRT
<213> ORGANISM: Artificial Sequence
<220> FEATURE:
<223> OTHER INFORMATION: Exemplary cyclic peptide

<400> SEQUENCE: 1275

Glu Trp Ile Lys Lys
 1               5

<210> SEQ ID NO 1276
<211> LENGTH: 6
<212> TYPE: PRT
<213> ORGANISM: Artificial Sequence
<220> FEATURE:
```

-continued

<223> OTHER INFORMATION: Exemplary cyclic peptide

<400> SEQUENCE: 1276

Glu Trp Ile Lys Phe Lys
1               5

<210> SEQ ID NO 1277
<211> LENGTH: 7
<212> TYPE: PRT
<213> ORGANISM: Artificial Sequence
<220> FEATURE:
<223> OTHER INFORMATION: Exemplary cyclic peptide

<400> SEQUENCE: 1277

Glu Trp Ile Lys Phe Ala Lys
1               5

<210> SEQ ID NO 1278
<211> LENGTH: 8
<212> TYPE: PRT
<213> ORGANISM: Artificial Sequence
<220> FEATURE:
<223> OTHER INFORMATION: Exemplary cyclic peptide

<400> SEQUENCE: 1278

Glu Trp Ile Lys Phe Ala Ala Lys
1               5

<210> SEQ ID NO 1279
<211> LENGTH: 9
<212> TYPE: PRT
<213> ORGANISM: Artificial Sequence
<220> FEATURE:
<223> OTHER INFORMATION: Exemplary cyclic peptide

<400> SEQUENCE: 1279

Glu Trp Ile Lys Phe Ala Ala Ala Lys
1               5

<210> SEQ ID NO 1280
<211> LENGTH: 10
<212> TYPE: PRT
<213> ORGANISM: Artificial Sequence
<220> FEATURE:
<223> OTHER INFORMATION: Exemplary cyclic peptide

<400> SEQUENCE: 1280

Glu Trp Ile Lys Phe Ala Ala Ala Cys Lys
1               5                   10

<210> SEQ ID NO 1281
<211> LENGTH: 5
<212> TYPE: PRT
<213> ORGANISM: Artificial Sequence
<220> FEATURE:
<223> OTHER INFORMATION: Exemplary cyclic peptide

<400> SEQUENCE: 1281

Glu Glu Trp Val Lys
1               5

<210> SEQ ID NO 1282
<211> LENGTH: 6
<212> TYPE: PRT
<213> ORGANISM: Artificial Sequence
<220> FEATURE:
<223> OTHER INFORMATION: Exemplary cyclic peptide -continued

```
<400> SEQUENCE: 1282

Glu Glu Trp Val Lys Lys
1               5

<210> SEQ ID NO 1283
<211> LENGTH: 7
<212> TYPE: PRT
<213> ORGANISM: Artificial Sequence
<220> FEATURE:
<223> OTHER INFORMATION: Exemplary cyclic peptide

<400> SEQUENCE: 1283

Glu Glu Trp Val Lys Phe Lys
1               5

<210> SEQ ID NO 1284
<211> LENGTH: 8
<212> TYPE: PRT
<213> ORGANISM: Artificial Sequence
<220> FEATURE:
<223> OTHER INFORMATION: Exemplary cyclic peptide

<400> SEQUENCE: 1284

Glu Glu Trp Val Lys Phe Ala Lys
1               5

<210> SEQ ID NO 1285
<211> LENGTH: 9
<212> TYPE: PRT
<213> ORGANISM: Artificial Sequence
<220> FEATURE:
<223> OTHER INFORMATION: Exemplary cyclic peptide

<400> SEQUENCE: 1285

Glu Glu Trp Val Lys Phe Ala Lys Lys
1               5

<210> SEQ ID NO 1286
<211> LENGTH: 10
<212> TYPE: PRT
<213> ORGANISM: Artificial Sequence
<220> FEATURE:
<223> OTHER INFORMATION: Exemplary cyclic peptide

<400> SEQUENCE: 1286

Glu Glu Trp Val Lys Phe Ala Lys Pro Lys
1               5                   10

<210> SEQ ID NO 1287
<211> LENGTH: 11
<212> TYPE: PRT
<213> ORGANISM: Artificial Sequence
<220> FEATURE:
<223> OTHER INFORMATION: Exemplary cyclic peptide

<400> SEQUENCE: 1287

Glu Glu Trp Val Lys Phe Ala Lys Pro Cys Lys
1               5                   10

<210> SEQ ID NO 1288
<211> LENGTH: 5
<212> TYPE: PRT
<213> ORGANISM: Artificial Sequence
<220> FEATURE:
<223> OTHER INFORMATION: Exemplary cyclic peptide
```

```
<400> SEQUENCE: 1288

Glu Trp Val Lys Lys
1               5

<210> SEQ ID NO 1289
<211> LENGTH: 6
<212> TYPE: PRT
<213> ORGANISM: Artificial Sequence
<220> FEATURE:
<223> OTHER INFORMATION: Exemplary cyclic peptide

<400> SEQUENCE: 1289

Glu Trp Val Lys Phe Lys
1               5

<210> SEQ ID NO 1290
<211> LENGTH: 8
<212> TYPE: PRT
<213> ORGANISM: Artificial Sequence
<220> FEATURE:
<223> OTHER INFORMATION: Exemplary cyclic peptide

<400> SEQUENCE: 1290

Glu Trp Val Lys Phe Ala Lys Lys
1               5

<210> SEQ ID NO 1291
<211> LENGTH: 9
<212> TYPE: PRT
<213> ORGANISM: Artificial Sequence
<220> FEATURE:
<223> OTHER INFORMATION: Exemplary cyclic peptide

<400> SEQUENCE: 1291

Glu Trp Val Lys Phe Ala Lys Pro Lys
1               5

<210> SEQ ID NO 1292
<211> LENGTH: 10
<212> TYPE: PRT
<213> ORGANISM: Artificial Sequence
<220> FEATURE:
<223> OTHER INFORMATION: Exemplary cyclic peptide

<400> SEQUENCE: 1292

Glu Trp Val Lys Phe Ala Lys Pro Cys Lys
1               5                   10

<210> SEQ ID NO 1293
<211> LENGTH: 5
<212> TYPE: PRT
<213> ORGANISM: Artificial Sequence
<220> FEATURE:
<223> OTHER INFORMATION: Exemplary cyclic peptide

<400> SEQUENCE: 1293

Glu Ala Trp Ile Lys
1               5

<210> SEQ ID NO 1294
<211> LENGTH: 6
<212> TYPE: PRT
<213> ORGANISM: Artificial Sequence
<220> FEATURE:
<223> OTHER INFORMATION: Exemplary cyclic peptide

<400> SEQUENCE: 1294
```

```
Glu Ala Trp Ile Thr Lys
  1               5

<210> SEQ ID NO 1295
<211> LENGTH: 7
<212> TYPE: PRT
<213> ORGANISM: Artificial Sequence
<220> FEATURE:
<223> OTHER INFORMATION: Exemplary cyclic peptide

<400> SEQUENCE: 1295

Glu Ala Trp Ile Thr Ala Lys
  1               5

<210> SEQ ID NO 1296
<211> LENGTH: 8
<212> TYPE: PRT
<213> ORGANISM: Artificial Sequence
<220> FEATURE:
<223> OTHER INFORMATION: Exemplary cyclic peptide

<400> SEQUENCE: 1296

Glu Ala Trp Ile Thr Ala Pro Lys
  1               5

<210> SEQ ID NO 1297
<211> LENGTH: 9
<212> TYPE: PRT
<213> ORGANISM: Artificial Sequence
<220> FEATURE:
<223> OTHER INFORMATION: Exemplary cyclic peptide

<400> SEQUENCE: 1297

Glu Ala Trp Ile Thr Ala Pro Val Lys
  1               5

<210> SEQ ID NO 1298
<211> LENGTH: 10
<212> TYPE: PRT
<213> ORGANISM: Artificial Sequence
<220> FEATURE:
<223> OTHER INFORMATION: Exemplary cyclic peptide

<400> SEQUENCE: 1298

Glu Ala Trp Ile Thr Ala Pro Val Ala Lys
  1               5                  10

<210> SEQ ID NO 1299
<211> LENGTH: 11
<212> TYPE: PRT
<213> ORGANISM: Artificial Sequence
<220> FEATURE:
<223> OTHER INFORMATION: Exemplary cyclic peptide

<400> SEQUENCE: 1299

Glu Ala Trp Ile Thr Ala Pro Val Ala Leu Lys
  1               5                  10

<210> SEQ ID NO 1300
<211> LENGTH: 5
<212> TYPE: PRT
<213> ORGANISM: Artificial Sequence
<220> FEATURE:
<223> OTHER INFORMATION: Exemplary cyclic peptide

<400> SEQUENCE: 1300
```

-continued

Glu Trp Ile Thr Lys
1               5

<210> SEQ ID NO 1301
<211> LENGTH: 6
<212> TYPE: PRT
<213> ORGANISM: Artificial Sequence
<220> FEATURE:
<223> OTHER INFORMATION: Exemplary cyclic peptide

<400> SEQUENCE: 1301

Glu Trp Ile Thr Ala Lys
1               5

<210> SEQ ID NO 1302
<211> LENGTH: 7
<212> TYPE: PRT
<213> ORGANISM: Artificial Sequence
<220> FEATURE:
<223> OTHER INFORMATION: Exemplary cyclic peptide

<400> SEQUENCE: 1302

Glu Trp Ile Thr Ala Pro Lys
1               5

<210> SEQ ID NO 1303
<211> LENGTH: 8
<212> TYPE: PRT
<213> ORGANISM: Artificial Sequence
<220> FEATURE:
<223> OTHER INFORMATION: Exemplary cyclic peptide

<400> SEQUENCE: 1303

Glu Trp Ile Thr Ala Pro Val Lys
1               5

<210> SEQ ID NO 1304
<211> LENGTH: 9
<212> TYPE: PRT
<213> ORGANISM: Artificial Sequence
<220> FEATURE:
<223> OTHER INFORMATION: Exemplary cyclic peptide

<400> SEQUENCE: 1304

Glu Trp Ile Thr Ala Pro Val Ala Lys
1               5

<210> SEQ ID NO 1305
<211> LENGTH: 10
<212> TYPE: PRT
<213> ORGANISM: Artificial Sequence
<220> FEATURE:
<223> OTHER INFORMATION: Exemplary cyclic peptide

<400> SEQUENCE: 1305

Glu Trp Ile Thr Ala Pro Val Ala Leu Lys
1               5                   10

<210> SEQ ID NO 1306
<211> LENGTH: 5
<212> TYPE: PRT
<213> ORGANISM: Artificial Sequence
<220> FEATURE:
<223> OTHER INFORMATION: Preferred CAR sequence for inclusion with a
      modulating agent

<400> SEQUENCE: 1306

```
Tyr Ile Gly Ser Arg
1               5

<210> SEQ ID NO 1307
<211> LENGTH: 10
<212> TYPE: PRT
<213> ORGANISM: Artificial Sequence
<220> FEATURE:
<223> OTHER INFORMATION: Preferred CAR sequence for inclusion with a
      modulating agent

<400> SEQUENCE: 1307

Lys Tyr Ser Phe Asn Tyr Asp Gly Ser Glu
1               5                   10

<210> SEQ ID NO 1308
<211> LENGTH: 9
<212> TYPE: PRT
<213> ORGANISM: Artificial Sequence
<220> FEATURE:
<223> OTHER INFORMATION: Preferred CAR sequence for inclusion with a
      modulating agent

<400> SEQUENCE: 1308

Ser Phe Thr Ile Asp Pro Lys Ser Gly
1               5

<210> SEQ ID NO 1309
<211> LENGTH: 4
<212> TYPE: PRT
<213> ORGANISM: Artificial Sequence
<220> FEATURE:
<223> OTHER INFORMATION: Preferred CAR sequence for inclusion with a
      modulating agent

<400> SEQUENCE: 1309

Leu Tyr His Tyr
1

<210> SEQ ID NO 1310
<211> LENGTH: 8
<212> TYPE: PRT
<213> ORGANISM: Artificial Sequence
<220> FEATURE:
<223> OTHER INFORMATION: Claudin CAR sequence comprising at least four
      consecutive amino acids present within a claudin
      region
<220> FEATURE:
<221> NAME/KEY: VARIANT
<222> LOCATION: 2
<223> OTHER INFORMATION: Xaa = Lys or Arg
<220> FEATURE:
<221> NAME/KEY: VARIANT
<222> LOCATION: 3
<223> OTHER INFORMATION: Xaa = any amino acid
<220> FEATURE:
<221> NAME/KEY: VARIANT
<222> LOCATION: 4
<223> OTHER INFORMATION: Xaa = any amino acid
<220> FEATURE:
<221> NAME/KEY: VARIANT
<222> LOCATION: 5
<223> OTHER INFORMATION: Xaa = Ser or Ala
<220> FEATURE:
<221> NAME/KEY: VARIANT
<222> LOCATION: 6
<223> OTHER INFORMATION: Xaa = Tyr or Phe
<220> FEATURE:
<221> NAME/KEY: VARIANT
<222> LOCATION: 7
<223> OTHER INFORMATION: Xaa = any amino acid
```

```
<400> SEQUENCE: 1310

Trp Xaa Xaa Xaa Xaa Xaa Xaa Gly
 1               5

<210> SEQ ID NO 1311
<211> LENGTH: 9
<212> TYPE: PRT
<213> ORGANISM: Artificial Sequence
<220> FEATURE:
<223> OTHER INFORMATION: Atypical cadherin CAR sequence comprising at
      least three consecutive amino acids present within an
      atypical cadherin region
<220> FEATURE:
<221> NAME/KEY: VARIANT
<222> LOCATION: 1,3
<223> OTHER INFORMATION: Xaa = any amino acid
<220> FEATURE:
<221> NAME/KEY: VARIANT
<222> LOCATION: 4
<223> OTHER INFORMATION: Xaa = Ile, Leu or Val
<220> FEATURE:
<221> NAME/KEY: VARIANT
<222> LOCATION: 5
<223> OTHER INFORMATION: Xaa = Asp, Asn or Glu
<220> FEATURE:
<221> NAME/KEY: VARIANT
<222> LOCATION: 6,7
<223> OTHER INFORMATION: Xaa = any amino acid
<220> FEATURE:
<221> NAME/KEY: VARIANT
<222> LOCATION: 8
<223> OTHER INFORMATION: Xaa = Ser, Thr or Asn

<400> SEQUENCE: 1311

Xaa Phe Xaa Xaa Xaa Xaa Xaa Xaa Gly
 1               5

<210> SEQ ID NO 1312
<211> LENGTH: 4
<212> TYPE: PRT
<213> ORGANISM: Artificial Sequence
<220> FEATURE:
<223> OTHER INFORMATION: Representative claudin CAR sequence

<400> SEQUENCE: 1312

Ile Tyr Ser Tyr
 1

<210> SEQ ID NO 1313
<211> LENGTH: 4
<212> TYPE: PRT
<213> ORGANISM: Artificial Sequence
<220> FEATURE:
<223> OTHER INFORMATION: Representative claudin CAR sequence

<400> SEQUENCE: 1313

Thr Ser Ser Tyr
 1

<210> SEQ ID NO 1314
<211> LENGTH: 4
<212> TYPE: PRT
<213> ORGANISM: Artificial Sequence
<220> FEATURE:
<223> OTHER INFORMATION: Representative claudin CAR sequence

<400> SEQUENCE: 1314

Val Thr Ala Phe
 1
```

```
<210> SEQ ID NO 1315
<211> LENGTH: 4
<212> TYPE: PRT
<213> ORGANISM: Artificial Sequence
<220> FEATURE:
<223> OTHER INFORMATION: Representative claudin CAR sequence

<400> SEQUENCE: 1315

Val Ser Ala Phe
 1

<210> SEQ ID NO 1316
<211> LENGTH: 14
<212> TYPE: PRT
<213> ORGANISM: Artificial Sequence
<220> FEATURE:
<223> OTHER INFORMATION: Trp-containing CAR sequence in the cyclic
      peptides that may be linked in tandem.

<400> SEQUENCE: 1316

Cys Gly Trp Val Met Asn Gln Gly Trp Val Met Asn Gln Cys
 1               5                  10

<210> SEQ ID NO 1317
<211> LENGTH: 14
<212> TYPE: PRT
<213> ORGANISM: Artificial Sequence
<220> FEATURE:
<223> OTHER INFORMATION: Trp-containing CAR sequence in the cyclic
      peptides that may be linked in tandem.

<400> SEQUENCE: 1317

Cys Arg Trp Ala Pro Ile Pro Arg Trp Ala Pro Ile Pro Cys
 1               5                  10

<210> SEQ ID NO 1318
<211> LENGTH: 14
<212> TYPE: PRT
<213> ORGANISM: Artificial Sequence
<220> FEATURE:
<223> OTHER INFORMATION: Trp-containing CAR sequence in the cyclic
      peptides that may be linked in tandem.

<400> SEQUENCE: 1318

Cys Gly Trp Val Met Asn Gln Gln Asn Met Val Trp Gly Cys
 1               5                  10

<210> SEQ ID NO 1319
<211> LENGTH: 14
<212> TYPE: PRT
<213> ORGANISM: Artificial Sequence
<220> FEATURE:
<223> OTHER INFORMATION: Trp-containing CAR sequence in the cyclic
      peptides that may be linked in tandem.

<400> SEQUENCE: 1319

Cys Gln Asn Met Val Trp Gly Gly Trp Val Met Asn Gln Cys
 1               5                  10

<210> SEQ ID NO 1320
<211> LENGTH: 14
<212> TYPE: PRT
<213> ORGANISM: Artificial Sequence
<220> FEATURE:
<223> OTHER INFORMATION: Trp-containing CAR sequence in the cyclic
      peptides that may be linked in tandem.

<400> SEQUENCE: 1320
```

Cys Arg Trp Ala Pro Ile Pro Pro Ile Pro Ala Trp Arg Cys
1               5                   10

<210> SEQ ID NO 1321
<211> LENGTH: 14
<212> TYPE: PRT
<213> ORGANISM: Artificial Sequence
<220> FEATURE:
<223> OTHER INFORMATION: Trp-containing CAR sequence in the cyclic
      peptides that may be linked in tandem.

<400> SEQUENCE: 1321

Cys Pro Ile Pro Ala Trp Arg Arg Trp Ala Pro Ile Pro Cys
1               5                   10

<210> SEQ ID NO 1322
<211> LENGTH: 5
<212> TYPE: PRT
<213> ORGANISM: Artificial Sequence
<220> FEATURE:
<223> OTHER INFORMATION: Peptide used in cyclization

<400> SEQUENCE: 1322

Cys Gly Trp Val Cys
1               5

<210> SEQ ID NO 1323
<211> LENGTH: 8
<212> TYPE: PRT
<213> ORGANISM: Artificial Sequence
<220> FEATURE:
<223> OTHER INFORMATION: Peptide used in cyclization

<400> SEQUENCE: 1323

Cys Gly Trp Val Trp Asn Gln Cys
1               5

<210> SEQ ID NO 1324
<211> LENGTH: 7
<212> TYPE: PRT
<213> ORGANISM: Artificial Sequence
<220> FEATURE:
<223> OTHER INFORMATION: Peptide used in cyclization

<400> SEQUENCE: 1324

Cys Gly Trp Val Trp Asn Cys
1               5

<210> SEQ ID NO 1325
<211> LENGTH: 6
<212> TYPE: PRT
<213> ORGANISM: Artificial Sequence
<220> FEATURE:
<223> OTHER INFORMATION: Peptide used in cyclization

<400> SEQUENCE: 1325

Cys Arg Gly Trp Val Cys
1               5

<210> SEQ ID NO 1326
<211> LENGTH: 7
<212> TYPE: PRT
<213> ORGANISM: Artificial Sequence
<220> FEATURE:
<223> OTHER INFORMATION: Peptide used in cyclization

<400> SEQUENCE: 1326

```
Cys Arg Gly Trp Val Trp Cys
 1               5
```

<210> SEQ ID NO 1327
<211> LENGTH: 6
<212> TYPE: PRT
<213> ORGANISM: Artificial Sequence
<220> FEATURE:
<223> OTHER INFORMATION: Peptide used in cyclization

<400> SEQUENCE: 1327

```
Cys Gly Trp Val Cys Asn
 1               5
```

<210> SEQ ID NO 1328
<211> LENGTH: 4
<212> TYPE: PRT
<213> ORGANISM: Artificial Sequence
<220> FEATURE:
<223> OTHER INFORMATION: Peptide used in cyclization

<400> SEQUENCE: 1328

```
Cys Gly Trp Val
 1
```

<210> SEQ ID NO 1329
<211> LENGTH: 10
<212> TYPE: PRT
<213> ORGANISM: Artificial Sequence
<220> FEATURE:
<223> OTHER INFORMATION: Peptide used in cyclization

<400> SEQUENCE: 1329

```
Cys Arg Gly Trp Val Trp Asn Gln Phe Cys
 1               5                  10
```

<210> SEQ ID NO 1330
<211> LENGTH: 11
<212> TYPE: PRT
<213> ORGANISM: Artificial Sequence
<220> FEATURE:
<223> OTHER INFORMATION: Peptide used in cyclization

<400> SEQUENCE: 1330

```
Cys Arg Gly Trp Val Trp Asn Gln Phe Phe Cys
 1               5                  10
```

<210> SEQ ID NO 1331
<211> LENGTH: 10
<212> TYPE: PRT
<213> ORGANISM: Artificial Sequence
<220> FEATURE:
<223> OTHER INFORMATION: Peptide used in cyclization
<220> FEATURE:
<221> NAME/KEY: MOD_RES
<222> LOCATION: 2
<223> OTHER INFORMATION: Xaa = beta,beta-tetramethylene cysteine

<400> SEQUENCE: 1331

```
Ile Xaa Gly Trp Val Trp Asn Gln Cys Glu
 1               5                  10
```

<210> SEQ ID NO 1332
<211> LENGTH: 9
<212> TYPE: PRT
<213> ORGANISM: Artificial Sequence
<220> FEATURE:

<223> OTHER INFORMATION: Peptide used in cyclization
<220> FEATURE:
<221> NAME/KEY: MOD_RES
<222> LOCATION: 2
<223> OTHER INFORMATION: Xaa = beta,beta -pentamethylene cysteine

<400> SEQUENCE: 1332

Ile Xaa Gly Trp Val Trp Asn Gln Cys
1               5

<210> SEQ ID NO 1333
<211> LENGTH: 8
<212> TYPE: PRT
<213> ORGANISM: Artificial Sequence
<220> FEATURE:
<223> OTHER INFORMATION: Peptide used in cyclization

<400> SEQUENCE: 1333

Gly Trp Val Trp Asn Gln Pro Cys
1               5

<210> SEQ ID NO 1334
<211> LENGTH: 6
<212> TYPE: PRT
<213> ORGANISM: Artificial Sequence
<220> FEATURE:
<223> OTHER INFORMATION: Peptide used in cyclization

<400> SEQUENCE: 1334

Cys Arg Trp Ala Pro Cys
1               5

<210> SEQ ID NO 1335
<211> LENGTH: 8
<212> TYPE: PRT
<213> ORGANISM: Artificial Sequence
<220> FEATURE:
<223> OTHER INFORMATION: Peptide used in cyclization

<400> SEQUENCE: 1335

Cys Arg Trp Ala Pro Ile Pro Cys
1               5

<210> SEQ ID NO 1336
<211> LENGTH: 7
<212> TYPE: PRT
<213> ORGANISM: Artificial Sequence
<220> FEATURE:
<223> OTHER INFORMATION: Peptide used in cyclization

<400> SEQUENCE: 1336

Cys Arg Trp Ala Pro Ile Cys
1               5

<210> SEQ ID NO 1337
<211> LENGTH: 9
<212> TYPE: PRT
<213> ORGANISM: Artificial Sequence
<220> FEATURE:
<223> OTHER INFORMATION: Peptide used in cyclization

<400> SEQUENCE: 1337

Cys Arg Trp Ala Pro Ile Pro Cys Cys
1               5

<210> SEQ ID NO 1338
<211> LENGTH: 11

```
<212> TYPE: PRT
<213> ORGANISM: Artificial Sequence
<220> FEATURE:
<223> OTHER INFORMATION: Peptide used in cyclization

<400> SEQUENCE: 1338

Cys Arg Trp Ala Pro Ile Pro Cys Ser Cys Met
1               5                   10

<210> SEQ ID NO 1339
<211> LENGTH: 6
<212> TYPE: PRT
<213> ORGANISM: Artificial Sequence
<220> FEATURE:
<223> OTHER INFORMATION: Peptide used in cyclization

<400> SEQUENCE: 1339

Cys Arg Trp Ala Cys Asn
1               5

<210> SEQ ID NO 1340
<211> LENGTH: 5
<212> TYPE: PRT
<213> ORGANISM: Artificial Sequence
<220> FEATURE:
<223> OTHER INFORMATION: Peptide used in cyclization
<220> FEATURE:
<221> NAME/KEY: MOD_RES
<222> LOCATION: 5
<223> OTHER INFORMATION: Xaa = penicillamine

<400> SEQUENCE: 1340

Cys Arg Trp Ala Xaa
1               5

<210> SEQ ID NO 1341
<211> LENGTH: 10
<212> TYPE: PRT
<213> ORGANISM: Artificial Sequence
<220> FEATURE:
<223> OTHER INFORMATION: Peptide used in cyclization

<400> SEQUENCE: 1341

Cys Arg Trp Ala Pro Ile Pro Cys Ser Cys
1               5                   10

<210> SEQ ID NO 1342
<211> LENGTH: 11
<212> TYPE: PRT
<213> ORGANISM: Artificial Sequence
<220> FEATURE:
<223> OTHER INFORMATION: Peptide used in cyclization

<400> SEQUENCE: 1342

Cys Arg Trp Ala Pro Ile Pro Cys Ser Met Cys
1               5                   10

<210> SEQ ID NO 1343
<211> LENGTH: 10
<212> TYPE: PRT
<213> ORGANISM: Artificial Sequence
<220> FEATURE:
<223> OTHER INFORMATION: Peptide used in cyclization
<220> FEATURE:
<221> NAME/KEY: MOD_RES
<222> LOCATION: 2
<223> OTHER INFORMATION: Xaa = beta,beta-tetramethylene cysteine

<400> SEQUENCE: 1343
```

```
Ile Xaa Arg Trp Ala Pro Ile Pro Cys Glu
 1               5                  10

<210> SEQ ID NO 1344
<211> LENGTH: 9
<212> TYPE: PRT
<213> ORGANISM: Artificial Sequence
<220> FEATURE:
<223> OTHER INFORMATION: Peptide used in cyclization
<220> FEATURE:
<221> NAME/KEY: MOD_RES
<222> LOCATION: 2
<223> OTHER INFORMATION: Xaa = beta,beta-pentamethylene cysteine

<400> SEQUENCE: 1344

Ile Xaa Arg Trp Ala Pro Ile Pro Cys
 1               5

<210> SEQ ID NO 1345
<211> LENGTH: 8
<212> TYPE: PRT
<213> ORGANISM: Artificial Sequence
<220> FEATURE:
<223> OTHER INFORMATION: Peptide used in cyclization

<400> SEQUENCE: 1345

Arg Trp Ala Pro Ile Pro Cys Cys
 1               5

<210> SEQ ID NO 1346
<211> LENGTH: 8
<212> TYPE: PRT
<213> ORGANISM: Artificial Sequence
<220> FEATURE:
<223> OTHER INFORMATION: Peptide used in cyclization

<400> SEQUENCE: 1346

Lys Arg Trp Ala Pro Ile Pro Asp
 1               5

<210> SEQ ID NO 1347
<211> LENGTH: 4
<212> TYPE: PRT
<213> ORGANISM: Artificial Sequence
<220> FEATURE:
<223> OTHER INFORMATION: Peptide used in cyclization process

<400> SEQUENCE: 1347

Glu Asp Ala Cys
 1

<210> SEQ ID NO 1348
<211> LENGTH: 4
<212> TYPE: PRT
<213> ORGANISM: Artificial Sequence
<220> FEATURE:
<223> OTHER INFORMATION: Peptide used in cyclization process

<400> SEQUENCE: 1348

Asp Cys Cys Ile
 1

<210> SEQ ID NO 1349
<211> LENGTH: 6
<212> TYPE: PRT
<213> ORGANISM: Artificial Sequence
<220> FEATURE:
```

```
<223> OTHER INFORMATION: Modulating agent

<400> SEQUENCE: 1349

Ser His Ala Val Ser Ser
1               5

<210> SEQ ID NO 1350
<211> LENGTH: 6
<212> TYPE: PRT
<213> ORGANISM: Artificial Sequence
<220> FEATURE:
<223> OTHER INFORMATION: Modulating agent

<400> SEQUENCE: 1350

Ala His Ala Val Asp Ile
1               5

<210> SEQ ID NO 1351
<211> LENGTH: 15
<212> TYPE: PRT
<213> ORGANISM: Artificial Sequence
<220> FEATURE:
<223> OTHER INFORMATION: N-cadherin CAR sequence

<400> SEQUENCE: 1351

Phe His Leu Arg Ala His Ala Val Asp Ile Asn Gly Asn Gln Val
1               5                   10                  15

<210> SEQ ID NO 1352
<211> LENGTH: 48
<212> TYPE: PRT
<213> ORGANISM: Artificial Sequence
<220> FEATURE:
<223> OTHER INFORMATION: Occludin CAR sequence

<400> SEQUENCE: 1352

Gly Val Asn Pro Thr Ala Gln Ser Ser Gly Ser Leu Tyr Gly Ser Gln
1               5                   10                  15

Ile Tyr Ala Leu Cys Asn Gln Phe Tyr Thr Pro Ala Ala Thr Gly Leu
            20                  25                  30

Tyr Val Asp Gln Tyr Leu Tyr His Tyr Cys Val Val Asp Pro Gln Glu
        35                  40                  45

<210> SEQ ID NO 1353
<211> LENGTH: 6
<212> TYPE: PRT
<213> ORGANISM: Artificial Sequence
<220> FEATURE:
<223> OTHER INFORMATION: Trp-containing cell adhesion recognition
      sequence

<400> SEQUENCE: 1353

Gly Trp Val Trp Asn Gln
1               5

<210> SEQ ID NO 1354
<211> LENGTH: 6
<212> TYPE: PRT
<213> ORGANISM: Artificial Sequence
<220> FEATURE:
<223> OTHER INFORMATION: Trp-containing cell adhesion recognition
      sequence

<400> SEQUENCE: 1354

Asp Trp Ile Trp Asn Gln
1               5
```

```
<210> SEQ ID NO 1355
<211> LENGTH: 6
<212> TYPE: PRT
<213> ORGANISM: Artificial Sequence
<220> FEATURE:
<223> OTHER INFORMATION: Trp-containing cell adhesion recognition
      sequence

<400> SEQUENCE: 1355

Ser Trp Met Trp Asn Gln
 1               5

<210> SEQ ID NO 1356
<211> LENGTH: 4
<212> TYPE: PRT
<213> ORGANISM: Artificial Sequence
<220> FEATURE:
<223> OTHER INFORMATION: Trp-containing cell adhesion recognition
      sequence

<400> SEQUENCE: 1356

Trp Val Asn Gln
 1

<210> SEQ ID NO 1357
<211> LENGTH: 6
<212> TYPE: PRT
<213> ORGANISM: Artificial Sequence
<220> FEATURE:
<223> OTHER INFORMATION: Trp-containing cell adhesion recognition
      sequence

<400> SEQUENCE: 1357

Gly Trp Met Trp Asn Gln
 1               5

<210> SEQ ID NO 1358
<211> LENGTH: 4
<212> TYPE: PRT
<213> ORGANISM: Artificial Sequence
<220> FEATURE:
<223> OTHER INFORMATION: Calcium binding motif

<400> SEQUENCE: 1358

Asp Val Asn Glu
 1

<210> SEQ ID NO 1359
<211> LENGTH: 5
<212> TYPE: PRT
<213> ORGANISM: Artificial Sequence
<220> FEATURE:
<223> OTHER INFORMATION: Calcium binding motif

<400> SEQUENCE: 1359

Asp Ile Asn Asp Asn
 1               5

<210> SEQ ID NO 1360
<211> LENGTH: 5
<212> TYPE: PRT
<213> ORGANISM: Artificial Sequence
<220> FEATURE:
<223> OTHER INFORMATION: Calcium binding motif

<400> SEQUENCE: 1360
```

-continued

```
Asp Val Asn Asp Asn
 1               5

<210> SEQ ID NO 1361
<211> LENGTH: 4
<212> TYPE: PRT
<213> ORGANISM: Artificial Sequence
<220> FEATURE:
<223> OTHER INFORMATION: Calcium binding motif

<400> SEQUENCE: 1361

Val Asp Phe Glu
 1

<210> SEQ ID NO 1362
<211> LENGTH: 4
<212> TYPE: PRT
<213> ORGANISM: Artificial Sequence
<220> FEATURE:
<223> OTHER INFORMATION: Calcium binding motif

<400> SEQUENCE: 1362

Asp Ala Asp Glu
 1

<210> SEQ ID NO 1363
<211> LENGTH: 4
<212> TYPE: PRT
<213> ORGANISM: Artificial Sequence
<220> FEATURE:
<223> OTHER INFORMATION: Calcium binding motif

<400> SEQUENCE: 1363

Asp Val Asp Glu
 1

<210> SEQ ID NO 1364
<211> LENGTH: 5
<212> TYPE: PRT
<213> ORGANISM: Artificial Sequence
<220> FEATURE:
<223> OTHER INFORMATION: Calcium binding motif

<400> SEQUENCE: 1364

Asp Glu Asn Asp Asn
 1               5

<210> SEQ ID NO 1365
<211> LENGTH: 5
<212> TYPE: PRT
<213> ORGANISM: Artificial Sequence
<220> FEATURE:
<223> OTHER INFORMATION: Calcium binding motif

<400> SEQUENCE: 1365

Asp Val Asn Asp Glu
 1               5

<210> SEQ ID NO 1366
<211> LENGTH: 4
<212> TYPE: PRT
<213> ORGANISM: Artificial Sequence
<220> FEATURE:
<223> OTHER INFORMATION: Calcium binding motif

<400> SEQUENCE: 1366

Leu Asn Tyr Glu
```

-continued

```
<210> SEQ ID NO 1367
<211> LENGTH: 5
<212> TYPE: PRT
<213> ORGANISM: Artificial Sequence
<220> FEATURE:
<223> OTHER INFORMATION: Calcium binding motif

<400> SEQUENCE: 1367

Asp Gln Asn Asp Asn
 1               5

<210> SEQ ID NO 1368
<211> LENGTH: 4
<212> TYPE: PRT
<213> ORGANISM: Artificial Sequence
<220> FEATURE:
<223> OTHER INFORMATION: Calcium binding motif

<400> SEQUENCE: 1368

Asp Thr Asn Glu
 1

<210> SEQ ID NO 1369
<211> LENGTH: 4
<212> TYPE: PRT
<213> ORGANISM: Artificial Sequence
<220> FEATURE:
<223> OTHER INFORMATION: Calcium binding motif

<400> SEQUENCE: 1369

Glu Val Asn Glu
 1

<210> SEQ ID NO 1370
<211> LENGTH: 4
<212> TYPE: PRT
<213> ORGANISM: Artificial Sequence
<220> FEATURE:
<223> OTHER INFORMATION: Calcium binding motif

<400> SEQUENCE: 1370

Asp Ile Asn Asp
 1

<210> SEQ ID NO 1371
<211> LENGTH: 110
<212> TYPE: PRT
<213> ORGANISM: unknown
<220> FEATURE:
<223> OTHER INFORMATION: Obcad sequence

<400> SEQUENCE: 1371

Arg Ser Lys Arg Gly Trp Val Trp Asn Gln Phe Phe Val Ile Glu Glu
 1               5                  10                  15

Tyr Thr Gly Pro Asp Pro Val Leu Val Gly Arg Leu His Ser Asp Ile
                20                  25                  30

Asp Ser Gly Asp Gly Asn Ile Lys Tyr Ile Leu Ser Gly Glu Gly Ala
            35                  40                  45

Gly Thr Ile Phe Val Ile Asp Asp Lys Ser Gly Asn Ile His Ala Thr
        50                  55                  60

Lys Thr Leu Asp Arg Glu Glu Arg Ala Gln Tyr Thr Leu Met Ala Gln
65                  70                  75                  80
```

-continued

Ala Val Asp Arg Asp Thr Asn Arg Pro Leu Glu Pro Pro Ser Glu Phe
            85                  90                  95

Ile Val Lys Val Gln Asp Ile Asn Asp Asn Pro Pro Glu Phe
            100                 105                 110

<210> SEQ ID NO 1372
<211> LENGTH: 108
<212> TYPE: PRT
<213> ORGANISM: Unknown
<220> FEATURE:
<223> OTHER INFORMATION: Cad5 sequence

<400> SEQUENCE: 1372

Arg Gln Lys Arg Asp Trp Ile Trp Asn Gln Met His Ile Asp Glu Glu
1               5                   10                  15

Lys Asn Thr Ser Leu Pro His His Val Gly Lys Ile Lys Ser Ser Val
            20                  25                  30

Ser Arg Lys Asn Ala Lys Tyr Leu Leu Lys Gly Glu Tyr Val Gly Lys
        35                  40                  45

Val Phe Arg Val Asp Ala Glu Thr Gly Asp Val Phe Ala Ile Glu Arg
    50                  55                  60

Leu Asp Arg Glu Asn Ile Ser Glu Tyr His Leu Thr Ala Val Ile Val
65                  70                  75                  80

Asp Lys Asp Thr Gly Glu Asn Leu Glu Thr Pro Ser Ser Phe Thr Ile
                85                  90                  95

Lys Val His Asp Val Asn Asp Asn Trp Pro Val Phe
            100                 105

<210> SEQ ID NO 1373
<211> LENGTH: 110
<212> TYPE: PRT
<213> ORGANISM: unknown
<220> FEATURE:
<223> OTHER INFORMATION: Cad6 sequence

<400> SEQUENCE: 1373

Arg Ser Lys Arg Ser Trp Met Trp Asn Gln Phe Phe Leu Leu Glu Glu
1               5                   10                  15

Tyr Thr Gly Ser Asp Tyr Gln Tyr Val Gly Lys Leu His Ser Asp Gln
            20                  25                  30

Asp Arg Gly Asp Gly Ser Leu Lys Tyr Ile Leu Ser Gly Asp Gly Ala
        35                  40                  45

Gly Asp Leu Phe Ile Ile Asn Glu Asn Thr Gly Asp Ile Gln Ala Thr
    50                  55                  60

Lys Arg Leu Asp Arg Glu Glu Lys Pro Val Tyr Ile Leu Arg Ala Gln
65                  70                  75                  80

Ala Ile Asn Arg Arg Thr Gly Arg Pro Val Glu Pro Glu Ser Glu Phe
                85                  90                  95

Ile Ile Lys Ile His Asp Ile Asn Asp Asn Glu Pro Ile Phe
            100                 105                 110

<210> SEQ ID NO 1374
<211> LENGTH: 110
<212> TYPE: PRT
<213> ORGANISM: unknown
<220> FEATURE:
<223> OTHER INFORMATION: Cad7 sequence

<400> SEQUENCE: 1374

Arg Thr Lys Arg Ser Trp Val Trp Asn Gln Phe Phe Val Leu Glu Glu

-continued

```
              1               5                  10                 15
Tyr Met Gly Ser Asp Pro Leu Tyr Val Gly Lys Leu His Ser Asp Val
                    20                  25                 30

Asp Lys Gly Asp Gly Ser Ile Lys Tyr Ile Leu Ser Gly Glu Gly Ala
            35                  40                 45

Ser Ser Ile Phe Ile Ile Asp Glu Asn Thr Gly Asp Ile His Ala Thr
    50                  55                 60

Lys Arg Leu Asp Arg Glu Glu Gln Ala Tyr Tyr Thr Leu Arg Ala Gln
65                  70                  75                     80

Ala His Asp Arg Leu Thr Asn Lys Pro Val Glu Pro Glu Ser Glu Phe
                85                  90                 95

Val Ile Lys Ile Gln Asp Ile Asn Asp Asn Glu Pro Lys Phe
                100                 105                110
```

<210> SEQ ID NO 1375
<211> LENGTH: 110
<212> TYPE: PRT
<213> ORGANISM: unknown
<220> FEATURE:
<223> OTHER INFORMATION: Cad8 sequence

<400> SEQUENCE: 1375

```
Arg Ser Lys Arg Gly Trp Val Trp Asn Gln Met Phe Val Leu Glu Glu
1               5                  10                 15

Phe Ser Gly Pro Glu Pro Ile Leu Val Gly Arg Leu His Thr Asp Leu
                20                  25                 30

Asp Pro Gly Ser Lys Lys Ile Lys Tyr Ile Leu Ser Gly Asp Gly Ala
            35                  40                 45

Gly Thr Ile Phe Gln Ile Asn Asp Val Thr Gly Asp Ile His Ala Ile
    50                  55                 60

Lys Arg Leu Asp Arg Glu Glu Lys Ala Glu Tyr Thr Leu Thr Ala Gln
65                  70                  75                     80

Ala Val Asp Trp Glu Thr Ser Lys Pro Leu Glu Pro Pro Ser Glu Phe
                85                  90                 95

Ile Ile Lys Val Gln Asp Ile Asn Asp Asn Ala Pro Glu Phe
                100                 105                110
```

<210> SEQ ID NO 1376
<211> LENGTH: 110
<212> TYPE: PRT
<213> ORGANISM: unknown
<220> FEATURE:
<223> OTHER INFORMATION: Cad12 sequence

<400> SEQUENCE: 1376

```
Arg Val Lys Arg Gly Trp Val Trp Asn Gln Phe Phe Val Leu Glu Glu
1               5                  10                 15

Tyr Val Gly Ser Glu Pro Gln Tyr Val Gly Lys Leu His Ser Asp Leu
                20                  25                 30

Asp Lys Gly Glu Gly Thr Val Lys Tyr Thr Leu Ser Gly Asp Gly Ala
            35                  40                 45

Gly Thr Val Phe Thr Ile Asp Glu Thr Thr Gly Asp Ile His Ala Ile
    50                  55                 60

Arg Ser Leu Asp Arg Glu Glu Lys Pro Phe Tyr Thr Leu Arg Ala Gln
65                  70                  75                     80

Ala Val Asp Ile Glu Thr Arg Lys Pro Leu Glu Pro Glu Ser Glu Phe
                85                  90                 95
```

```
Ile Ile Lys Val Gln Asp Ile Asn Asp Asn Glu Pro Lys Phe
            100                 105                 110

<210> SEQ ID NO 1377
<211> LENGTH: 110
<212> TYPE: PRT
<213> ORGANISM: unknown
<220> FEATURE:
<223> OTHER INFORMATION: Cad14 sequence

<400> SEQUENCE: 1377

Arg Pro Lys Arg Gly Trp Val Trp Asn Gln Phe Phe Val Leu Glu Glu
  1               5                  10                  15

His Met Gly Pro Asp Pro Gln Tyr Val Gly Lys Leu His Ser Asn Ser
              20                  25                  30

Asp Lys Gly Asp Gly Ser Val Lys Tyr Ile Leu Thr Gly Glu Gly Ala
          35                  40                  45

Gly Thr Ile Phe Ile Ile Asp Asp Thr Thr Gly Asp Ile His Ser Thr
      50                  55                  60

Lys Ser Leu Asp Arg Glu Gln Lys Thr His Tyr Val Leu His Ala Gln
 65                  70                  75                  80

Ala Ile Asp Arg Arg Thr Asn Lys Pro Leu Glu Pro Glu Ser Glu Phe
                 85                  90                  95

Ile Ile Lys Val Gln Asp Ile Asn Asp Asn Ala Pro Lys Phe
            100                 105                 110

<210> SEQ ID NO 1378
<211> LENGTH: 110
<212> TYPE: PRT
<213> ORGANISM: unknown
<220> FEATURE:
<223> OTHER INFORMATION: PBcad sequence

<400> SEQUENCE: 1378

Arg Val Lys Arg Gly Trp Val Trp Asn Gln Phe Phe Val Val Glu Glu
  1               5                  10                  15

Tyr Thr Gly Thr Glu Pro Leu Tyr Val Gly Lys Ile His Ser Asp Ser
              20                  25                  30

Asp Glu Gly Asp Gly Thr Ile Lys Tyr Thr Ile Ser Gly Glu Gly Ala
          35                  40                  45

Gly Thr Ile Phe Leu Ile Asp Glu Leu Thr Gly Asp Ile His Ala Thr
      50                  55                  60

Glu Arg Leu Asp Arg Glu Gln Lys Thr Phe Tyr Thr Leu Arg Ala Gln
 65                  70                  75                  80

Ala Arg Asp Arg Ala Thr Asn Arg Leu Leu Glu Pro Glu Ser Glu Phe
                 85                  90                  95

Ile Ile Lys Val Gln Asp Ile Asn Asp Ser Glu Pro Arg Phe
            100                 105                 110

<210> SEQ ID NO 1379
<211> LENGTH: 106
<212> TYPE: PRT
<213> ORGANISM: Homo sapiens

<400> SEQUENCE: 1379

Gly Trp Val Trp Asn Gln Phe Phe Val Ile Glu Glu Tyr Thr Gly Pro
  1               5                  10                  15

Asp Pro Val Leu Val Gly Arg Leu His Ser Asp Ile Asp Ser Gly Asp
              20                  25                  30
```

-continued

```
Gly Asn Ile Lys Tyr Ile Leu Ser Gly Glu Gly Ala Gly Thr Ile Phe
            35                  40                  45

Val Ile Asp Asp Lys Ser Gly Asn Ile His Ala Thr Lys Thr Leu Asp
 50                  55                  60

Arg Glu Glu Arg Ala Gln Tyr Thr Leu Met Ala Gln Ala Val Asp Arg
 65                  70                  75                  80

Asp Thr Asn Arg Pro Leu Glu Pro Pro Ser Glu Phe Ile Val Lys Val
                 85                  90                  95

Gln Asp Ile Asn Asp Asn Pro Pro Glu Phe
                100                 105

<210> SEQ ID NO 1380
<211> LENGTH: 106
<212> TYPE: PRT
<213> ORGANISM: Mus musculus

<400> SEQUENCE: 1380

Gly Trp Val Trp Asn Gln Phe Phe Val Ile Glu Glu Tyr Thr Gly Pro
 1               5                  10                  15

Asp Pro Val Leu Val Gly Arg Leu His Ser Asp Ile Asp Ser Gly Asp
                 20                  25                  30

Gly Asn Ile Lys Tyr Ile Leu Ser Gly Glu Gly Ala Gly Thr Ile Phe
            35                  40                  45

Val Ile Asp Asp Lys Ser Gly Asn Ile His Ala Thr Lys Thr Leu Asp
 50                  55                  60

Arg Glu Glu Arg Ala Gln Tyr Thr Leu Met Ala Gln Ala Val Asp Arg
 65                  70                  75                  80

Asp Thr Asn Arg Pro Leu Glu Pro Pro Ser Glu Phe Ile Val Lys Val
                 85                  90                  95

Gln Asp Ile Asn Asp Asn Pro Pro Glu Phe
                100                 105

<210> SEQ ID NO 1381
<211> LENGTH: 4
<212> TYPE: PRT
<213> ORGANISM: Artificial Sequence
<220> FEATURE:
<223> OTHER INFORMATION: Calcium binding motif

<400> SEQUENCE: 1381

Val Asp Tyr Glu
 1

<210> SEQ ID NO 1382
<211> LENGTH: 5
<212> TYPE: PRT
<213> ORGANISM: Artificial Sequence
<220> FEATURE:
<223> OTHER INFORMATION: Calcium binding motif

<400> SEQUENCE: 1382

Asp Asp Asn Asp Asn
 1               5

<210> SEQ ID NO 1383
<211> LENGTH: 5
<212> TYPE: PRT
<213> ORGANISM: Artificial Sequence
<220> FEATURE:
<223> OTHER INFORMATION: Calcium binding motif

<400> SEQUENCE: 1383
```

Asp Tyr Asn Asp Asn
1               5

<210> SEQ ID NO 1384
<211> LENGTH: 5
<212> TYPE: PRT
<213> ORGANISM: Artificial Sequence
<220> FEATURE:
<223> OTHER INFORMATION: Calcium binding motif

<400> SEQUENCE: 1384

Asp Ser Asn Asp Asn
1               5

<210> SEQ ID NO 1385
<211> LENGTH: 108
<212> TYPE: PRT
<213> ORGANISM: Homo sapiens

<400> SEQUENCE: 1385

Glu Trp Ile Lys Phe Ala Ala Ala Cys Arg Glu Gly Glu Asp Asn Ser
1               5                   10                  15

Lys Arg Asn Pro Ile Ala Lys Ile His Ser Asp Cys Ala Ala Asn Gln
            20                  25                  30

Gln Val Thr Tyr Arg Ile Ser Gly Val Gly Ile Asp Gln Pro Pro Tyr
        35                  40                  45

Gly Ile Phe Val Ile Asn Gln Lys Thr Gly Glu Ile Asn Ile Thr Ser
    50                  55                  60

Ile Val Asp Arg Glu Val Thr Pro Phe Phe Ile Ile Tyr Cys Arg Ala
65                  70                  75                  80

Leu Asn Ser Met Gly Gln Asp Leu Glu Arg Pro Leu Glu Leu Arg Val
                85                  90                  95

Arg Val Leu Asp Ile Asn Asp Asn Pro Pro Val Phe
            100                 105

<210> SEQ ID NO 1386
<211> LENGTH: 108
<212> TYPE: PRT
<213> ORGANISM: Bos tarus

<400> SEQUENCE: 1386

Glu Trp Ile Lys Phe Ala Ala Ala Cys Arg Glu Gly Glu Asp Asn Ser
1               5                   10                  15

Lys Arg Asn Pro Ile Ala Lys Ile His Ser Asp Cys Ala Ala Asn Gln
            20                  25                  30

Gln Val Thr Tyr Arg Ile Ser Gly Val Gly Ile Asp Gln Pro Pro Tyr
        35                  40                  45

Gly Ile Phe Val Ile Asn Gln Lys Thr Gly Glu Ile Asn Ile Thr Ser
    50                  55                  60

Ile Val Asp Arg Glu Val Thr Pro Phe Phe Ile Ile Tyr Cys Arg Ala
65                  70                  75                  80

Leu Asn Ser Leu Gly Gln Asp Leu Glu Lys Pro Leu Glu Leu Arg Val
                85                  90                  95

Arg Val Leu Asp Ile Asn Asp Asn Pro Pro Val Phe
            100                 105

<210> SEQ ID NO 1387
<211> LENGTH: 110
<212> TYPE: PRT

<213> ORGANISM: Homo sapiens

<400> SEQUENCE: 1387

```
Ala Trp Ile Thr Ala Pro Val Ala Leu Arg Glu Gly Glu Asp Leu Ser
 1               5                  10                  15

Lys Lys Asn Pro Ile Ala Lys Ile His Ser Asp Leu Ala Glu Glu Arg
            20                  25                  30

Gly Leu Lys Ile Thr Tyr Lys Tyr Thr Gly Lys Gly Ile Thr Glu Pro
        35                  40                  45

Pro Phe Gly Ile Phe Val Phe Asn Lys Asp Thr Gly Glu Leu Asn Val
    50                  55                  60

Thr Ser Ile Leu Asp Arg Glu Glu Thr Pro Phe Phe Leu Leu Thr Gly
65                  70                  75                  80

Tyr Ala Leu Asp Ala Arg Gly Asn Asn Val Glu Lys Pro Leu Glu Leu
                85                  90                  95

Arg Ile Lys Val Leu Asp Ile Asn Asp Asn Glu Pro Val Phe
            100                 105                 110
```

<210> SEQ ID NO 1388
<211> LENGTH: 108
<212> TYPE: PRT
<213> ORGANISM: Homo sapiens

<400> SEQUENCE: 1388

```
Glu Trp Val Lys Phe Ala Lys Pro Cys Arg Glu Gly Glu Asp Asn Ser
 1               5                  10                  15

Lys Arg Asn Pro Ile Ala Lys Ile Thr Ser Asp Tyr Gln Ala Thr Gln
            20                  25                  30

Lys Ile Thr Tyr Arg Ile Ser Gly Val Gly Ile Asp Gln Pro Pro Phe
        35                  40                  45

Gly Ile Phe Val Val Asp Lys Asn Thr Gly Asp Ile Asn Ile Thr Ala
    50                  55                  60

Ile Val Asp Arg Glu Glu Thr Pro Ser Phe Leu Ile Thr Cys Arg Ala
65                  70                  75                  80

Leu Asn Ala Gln Gly Leu Asp Val Glu Lys Pro Leu Ile Leu Thr Val
                85                  90                  95

Lys Ile Leu Asp Ile Asn Asp Asn Pro Pro Val Phe
            100                 105
```

<210> SEQ ID NO 1389
<211> LENGTH: 108
<212> TYPE: PRT
<213> ORGANISM: Mus musculus

<400> SEQUENCE: 1389

```
Glu Trp Val Lys Phe Ala Lys Pro Cys Arg Glu Arg Glu Asp Asn Ser
 1               5                  10                  15

Arg Arg Asn Pro Ile Ala Lys Ile Thr Ser Asp Phe Gln Lys Asn Gln
            20                  25                  30

Lys Ile Thr Tyr Arg Ile Ser Gly Val Gly Ile Asp Gln Pro Pro Phe
        35                  40                  45

Gly Ile Phe Val Val Asp Pro Asn Gly Asp Ile Asn Ile Thr Ala
    50                  55                  60

Ile Val Asp Arg Glu Glu Thr Pro Ser Phe Leu Ile Thr Cys Arg Ala
65                  70                  75                  80

Leu Asn Ala Leu Gly Gln Asp Val Glu Arg Pro Leu Ile Leu Thr Val
                85                  90                  95
```

```
Lys Ile Leu Asp Val Asn Asp Asn Pro Pro Ile Phe
            100                 105
```

```
<210> SEQ ID NO 1390
<211> LENGTH: 108
<212> TYPE: PRT
<213> ORGANISM: Homo sapiens

<400> SEQUENCE: 1390

Glu Trp Ile Lys Phe Ala Ala Ala Cys Arg Glu Gly Glu Asp Asn Ser
 1               5                  10                  15

Lys Arg Asn Pro Ile Ala Lys Ile Arg Ser Asp Cys Glu Ser Asn Gln
            20                  25                  30

Lys Ile Thr Tyr Arg Ile Ser Gly Val Gly Ile Asp Arg Pro Pro Tyr
        35                  40                  45

Gly Val Phe Thr Ile Asn Pro Arg Thr Gly Glu Ile Asn Ile Thr Ser
    50                  55                  60

Val Val Asp Arg Glu Ile Thr Pro Leu Phe Leu Ile Tyr Cys Arg Ala
65                  70                  75                  80

Leu Asn Ser Arg Gly Glu Asp Leu Glu Arg Pro Leu Glu Leu Arg Val
                85                  90                  95

Lys Val Met Asp Ile Asn Asp Asn Ala Pro Val Phe
            100                 105
```

```
<210> SEQ ID NO 1391
<211> LENGTH: 108
<212> TYPE: PRT
<213> ORGANISM: Mus musculus

<400> SEQUENCE: 1391

Glu Trp Ile Lys Phe Ala Ala Ala Cys Arg Glu Gly Glu Asp Asn Ser
 1               5                  10                  15

Lys Arg Asn Pro Ile Ala Arg Ile Arg Ser Asp Cys Glu Val Ser Gln
            20                  25                  30

Arg Ile Thr Tyr Arg Ile Ser Gly Ala Gly Ile Asp Arg Pro Pro Tyr
        35                  40                  45

Gly Val Phe Thr Ile Asn Pro Arg Thr Gly Glu Ile Asn Ile Thr Ser
    50                  55                  60

Val Val Asp Arg Glu Ile Thr Pro Leu Phe Leu Ile His Cys Arg Ala
65                  70                  75                  80

Leu Asn Ser Arg Gly Glu Asp Leu Glu Arg Pro Leu Glu Leu Arg Val
                85                  90                  95

Lys Val Met Asp Val Asn Asp Asn Pro Pro Val Phe
            100                 105
```

```
<210> SEQ ID NO 1392
<211> LENGTH: 108
<212> TYPE: PRT
<213> ORGANISM: Mus musculus

<400> SEQUENCE: 1392

Glu Trp Ile Lys Phe Ala Ala Ala Cys Arg Glu Gly Glu Asp Asn Ser
 1               5                  10                  15

Lys Arg Asn Pro Ile Ala Lys Ile His Ser Asp Cys Ala Ala Asn Gln
            20                  25                  30

Pro Val Thr Tyr Arg Ile Ser Gly Val Gly Ile Asp Gln Pro Pro Tyr
        35                  40                  45
```

```
Gly Ile Phe Ile Ile Asn Gln Lys Thr Gly Glu Ile Asn Ile Thr Ser
    50                  55                  60

Ile Val Asp Arg Glu Val Thr Pro Phe Phe Ile Ile Tyr Cys Arg Ala
65                  70                  75                  80

Leu Asn Ala Gln Gly Gln Asp Leu Glu Asn Pro Leu Glu Leu Arg Val
                85                  90                  95

Arg Val Met Asp Ile Asn Asp Asn Pro Pro Val Phe
            100                 105
```

<210> SEQ ID NO 1393
<211> LENGTH: 108
<212> TYPE: PRT
<213> ORGANISM: Mus musculus

<400> SEQUENCE: 1393

```
Glu Trp Ile Lys Phe Ala Ala Ala Cys Arg Glu Gly Glu Asp Asn Ser
1               5                   10                  15

Lys Arg Asn Pro Ile Ala Lys Ile His Ser Asp Cys Ala Ala Asn Gln
                20                  25                  30

Pro Val Thr Tyr Arg Ile Ser Gly Val Gly Ile Asp Gln Pro Pro Tyr
            35                  40                  45

Gly Ile Phe Ile Ile Asn Gln Lys Thr Gly Glu Ile Asn Ile Thr Ser
    50                  55                  60

Ile Val Asp Arg Glu Val Thr Pro Phe Phe Ile Ile Tyr Cys Arg Ala
65                  70                  75                  80

Leu Asn Ala Gln Gly Gln Asp Leu Glu Asn Pro Leu Glu Leu Arg Val
                85                  90                  95

Arg Val Met Asp Ile Asn Asp Asn Pro Pro Val Phe
            100                 105
```

<210> SEQ ID NO 1394
<211> LENGTH: 108
<212> TYPE: PRT
<213> ORGANISM: Homo sapiens

<400> SEQUENCE: 1394

```
Arg Trp Ala Pro Ile Pro Ala Ser Leu Met Glu Asn Ser Leu Gly Pro
1               5                   10                  15

Phe Pro Gln His Val Gln Gln Ile Gln Ser Asp Ala Ala Gln Asn Tyr
                20                  25                  30

Thr Ile Phe Tyr Ser Ile Ser Gly Pro Gly Val Asp Lys Glu Pro Phe
            35                  40                  45

Asn Leu Phe Tyr Ile Glu Lys Asp Thr Gly Asp Ile Phe Cys Thr Arg
    50                  55                  60

Ser Ile Asp Arg Glu Lys Tyr Glu Gln Phe Ala Leu Tyr Gly Tyr Ala
65                  70                  75                  80

Thr Thr Ala Asp Gly Tyr Ala Pro Glu Tyr Pro Leu Pro Leu Ile Ile
                85                  90                  95

Lys Ile Glu Asp Asp Asn Asp Asn Ala Pro Tyr Phe
            100                 105
```

<210> SEQ ID NO 1395
<211> LENGTH: 108
<212> TYPE: PRT
<213> ORGANISM: Mus musculus

<400> SEQUENCE: 1395

```
Arg Trp Ala Pro Ile Pro Cys Ser Leu Met Glu Asn Ser Leu Gly Pro
```

```
            1               5                   10                  15
Phe Pro Gln His Ile Gln Gln Ile Gln Ser Asp Ala Ala Gln Asn Tyr
                 20                  25                  30

Thr Ile Phe Tyr Ser Ile Ser Gly Pro Gly Val Asp Lys Glu Pro Tyr
             35                  40                  45

Asn Leu Phe Tyr Ile Glu Lys Asp Thr Gly Asp Ile Tyr Cys Thr Arg
         50                  55                  60

Ser Ile Asp Arg Glu Gln Tyr Asp Gln Phe Leu Val Tyr Gly Tyr Ala
 65                  70                  75                  80

Thr Thr Ala Asp Gly Tyr Ala Pro Asp Tyr Pro Leu Pro Leu Leu Phe
                 85                  90                  95

Lys Val Glu Asp Asp Asn Asp Asn Ala Pro Tyr Phe
             100                 105

<210> SEQ ID NO 1396
<211> LENGTH: 108
<212> TYPE: PRT
<213> ORGANISM: Bos tarus

<400> SEQUENCE: 1396

Arg Trp Ala Pro Ile Pro Cys Ser Leu Met Glu Asn Ser Leu Gly Pro
 1               5                  10                  15

Phe Pro Gln His Val Gln Gln Val Gln Ser Asp Ala Ala Gln Asn Tyr
                 20                  25                  30

Thr Ile Phe Tyr Ser Ile Ser Gly Pro Gly Val Asp Lys Glu Pro Phe
             35                  40                  45

Asn Leu Phe Phe Ile Glu Lys Asp Thr Gly Asp Ile Phe Cys Thr Arg
         50                  55                  60

Ser Ile Asp Arg Glu Gln Tyr Gln Glu Phe Pro Ile Tyr Ala Tyr Ala
 65                  70                  75                  80

Thr Thr Ala Asp Gly Tyr Ala Pro Glu Tyr Pro Leu Pro Leu Val Phe
                 85                  90                  95

Lys Val Glu Asp Asp Asn Asp Asn Ala Pro Tyr Phe
             100                 105

<210> SEQ ID NO 1397
<211> LENGTH: 108
<212> TYPE: PRT
<213> ORGANISM: Homo sapiens

<400> SEQUENCE: 1397

Arg Trp Ala Pro Ile Pro Cys Ser Met Leu Glu Asn Ser Leu Gly Pro
 1               5                  10                  15

Phe Pro Leu Phe Leu Gln Gln Val Gln Ser Asp Thr Ala Gln Asn Tyr
                 20                  25                  30

Thr Ile Tyr Tyr Ser Ile Arg Gly Pro Gly Val Asp Gln Glu Pro Arg
             35                  40                  45

Asn Leu Phe Tyr Val Glu Arg Asp Thr Gly Asn Leu Tyr Cys Thr Arg
         50                  55                  60

Pro Val Asp Arg Glu Gln Tyr Glu Ser Phe Glu Ile Ile Ala Phe Ala
 65                  70                  75                  80

Thr Thr Pro Asp Gly Tyr Thr Pro Glu Leu Pro Leu Pro Leu Ile Ile
                 85                  90                  95

Lys Ile Glu Asp Glu Asn Asp Asn Tyr Pro Ile Phe
             100                 105
```

```
<210> SEQ ID NO 1398
<211> LENGTH: 108
<212> TYPE: PRT
<213> ORGANISM: Canis familiaris

<400> SEQUENCE: 1398

Arg Trp Ala Pro Ile Pro Cys Ser Met Gln Glu Asn Ser Leu Gly Pro
1               5                   10                  15

Phe Pro Leu Phe Leu Gln Gln Ile Gln Ser Asp Thr Ala Gln Asn Tyr
            20                  25                  30

Thr Ile Phe Tyr Ser Ile Arg Gly Pro Gly Val Asp Arg Glu Pro Lys
        35                  40                  45

Asn Leu Phe Tyr Val Glu Arg Asp Thr Gly Asn Leu Phe Cys Thr Arg
    50                  55                  60

Pro Val Asp Arg Glu Glu Tyr Glu Ser Phe Glu Leu Ile Ala Phe Ala
65                  70                  75                  80

Thr Thr Pro Asp Gly Tyr Thr Pro Glu Leu Pro Leu Pro Leu Val Ile
                85                  90                  95

Arg Ile Glu Asp Glu Asn Asp Asn Tyr Pro Ile Phe
            100                 105

<210> SEQ ID NO 1399
<211> LENGTH: 108
<212> TYPE: PRT
<213> ORGANISM: Homo sapiens

<400> SEQUENCE: 1399

Arg Trp Ala Pro Ile Pro Cys Ser Met Gln Glu Asn Ser Leu Gly Pro
1               5                   10                  15

Phe Pro Leu Phe Leu Gln Gln Val Glu Ser Asp Ala Ala Gln Asn Tyr
            20                  25                  30

Thr Val Phe Tyr Ser Ile Ser Gly Arg Gly Val Asp Lys Glu Pro Leu
        35                  40                  45

Asn Leu Phe Tyr Ile Glu Arg Asp Thr Gly Asn Leu Phe Cys Thr Arg
    50                  55                  60

Pro Val Asp Arg Glu Glu Tyr Asp Val Phe Asp Leu Ile Ala Tyr Ala
65                  70                  75                  80

Ser Thr Ala Asp Gly Tyr Ser Ala Asp Leu Pro Leu Pro Leu Pro Ile
                85                  90                  95

Arg Val Glu Asp Glu Asn Asp Asn His Pro Val Phe
            100                 105

<210> SEQ ID NO 1400
<211> LENGTH: 108
<212> TYPE: PRT
<213> ORGANISM: Mus musculus

<400> SEQUENCE: 1400

Arg Trp Ala Pro Ile Pro Cys Ser Met Gln Glu Asn Ser Leu Gly Pro
1               5                   10                  15

Phe Pro Leu Phe Leu Gln Gln Val Gln Ser Asp Ala Ala Gln Asn Tyr
            20                  25                  30

Thr Val Phe Tyr Ser Ile Ser Gly Arg Gly Ala Asp Gln Glu Pro Leu
        35                  40                  45

Asn Trp Phe Phe Ile Glu Arg Asp Thr Gly Asn Leu Tyr Cys Thr Arg
    50                  55                  60

Pro Val Asp Arg Glu Glu Tyr Asp Val Phe Asp Leu Ile Ala Tyr Ala
65                  70                  75                  80
```

```
Ser Thr Ala Asp Gly Tyr Ser Ala Asp Leu Pro Leu Pro Leu Pro Ile
                85                  90                  95

Lys Ile Glu Asp Glu Asn Asp Asn Tyr Pro Leu Phe
            100                 105

<210> SEQ ID NO 1401
<211> LENGTH: 108
<212> TYPE: PRT
<213> ORGANISM: Bos tarus

<400> SEQUENCE: 1401

Arg Trp Ala Pro Ile Pro Cys Ser Met Gln Glu Asn Ser Leu Gly Pro
 1               5                  10                  15

Phe Pro Leu Phe Leu Gln Gln Val Gln Ser Asp Ala Ala Gln Asn Tyr
                20                  25                  30

Thr Ile Phe Tyr Ser Ile Ser Gly Arg Gly Val Asp Lys Glu Pro Leu
            35                  40                  45

Asn Leu Phe Phe Ile Glu Arg Asp Thr Gly Asn Leu Tyr Cys Thr Gln
        50                  55                  60

Pro Val Asp Arg Glu Glu Tyr Asp Val Phe Asp Leu Ile Ala Tyr Ala
 65                  70                  75                  80

Ser Thr Ala Asp Gly Tyr Ser Ala Asp Phe Pro Leu Pro Leu Pro Ile
                85                  90                  95

Arg Val Glu Asp Glu Asn Asp Asn His Pro Ile Phe
            100                 105

<210> SEQ ID NO 1402
<211> LENGTH: 108
<212> TYPE: PRT
<213> ORGANISM: Homo sapiens

<400> SEQUENCE: 1402

Arg Trp Ala Pro Ile Pro Cys Ser Met Gln Glu Asn Ser Leu Gly Pro
 1               5                  10                  15

Phe Pro Leu Phe Leu Gln Gln Val Glu Ser Asp Ala Ala Gln Asn Tyr
                20                  25                  30

Thr Val Phe Tyr Ser Ile Ser Gly Arg Gly Val Asp Lys Glu Pro Leu
            35                  40                  45

Asn Leu Phe Tyr Ile Glu Arg Asp Thr Gly Asn Leu Phe Cys Thr Arg
        50                  55                  60

Pro Val Asp Arg Glu Glu Tyr Asp Val Phe Asp Leu Ile Ala Tyr Ala
 65                  70                  75                  80

Ser Thr Ala Asp Gly Tyr Ser Ala Asp Leu Pro Leu Pro Leu Pro Ile
                85                  90                  95

Arg Val Glu Asp Glu Asn Asp Asn His Pro Val Phe
            100                 105
```

COMPOUNDS AND METHODS FOR MODULATING FUNCTIONS OF NONCLASSICAL CADHERINS

CROSS-REFERENCE TO RELATED APPLICATIONS

This application claims the benefit of U.S. Provisional Patent Applications No. 60/426,689, filed Nov. 14, 2002, and No. 60/426,551, filed Nov. 14, 2002, where these provisional applications are incorporated herein by reference their entireties.

BACKGROUND OF THE INVENTION

1. Field of the Invention

The present invention relates generally to methods for modulating nonclassical cadherin-mediated functions, and more particularly to the use of modulating agents derived from nonclassical cadherin cell adhesion recognition sequences, or antibodies that specifically recognize such sequences, for inhibiting or enhancing functions mediated by nonclassical cadherins.

2. Description of the Related Art

Cadherins are a rapidly expanding superfamily of calcium-dependent cell adhesion molecules (CAMs) (for review, see Munro et al., In: *Cell Adhesion and Invasion in Cancer Metastasis*, P. Brodt, ed., pp. 17-34, RG Landes Co., Austin Tex., 1996). All cadherins appear to be membrane glycoproteins that generally promote cell adhesion through homophilic interactions (a cadherin on the surface of one cell binds to an identical cadherin on the surface of another cell), although cadherins also appear to be capable of forming heterotypic complexes with one another under certain circumstances and with lower affinity.

There are many different types of cadherins. The most extensively studied group of cadherins is known as the classical, or type I, cadherins. Classical cadherins have been shown to regulate epithelial, endothelial, neural and cancer cell adhesion, with different cadherins expressed on different cell types. All classical cadherins have a similar structure. As illustrated in FIG. 1A, classical cadherins are composed of five extracellular domains (EC1-EC5), a single hydrophobic domain (TM) that transverses the plasma membrane (PM), and two cytoplasmic domains (CP1 and CP2). The calcium binding motifs DXNDN (SEQ ID NO: 3), DXD and LDRE (SEQ ID NO: 4) are interspersed throughout the extracellular domains, and each 110 amino acid region that contains such motifs is considered a cadherin repeat. The first extracellular domain (EC1) contains the cell adhesion recognition (CAR) sequence, HAV (His-Ala-Val), along with flanking sequences on either side of the CAR sequence that play a role in conferring specificity. Synthetic peptides containing the HAV sequence and antibodies directed against such peptides have been shown to inhibit classical cadherin-dependent processes (Munro et al., supra; Blaschuk et al., *J. Mol. Biol.* 211:679-82, 1990; Blaschuk et al., *Develop. Biol.* 139:227-29, 1990; Alexander et al., *J. Cell. Physiol.* 156:610-18, 1993).

Cadherins that contain calcium binding motifs within extracellular domain cadherin repeats, but do not contain the CAR sequence HAV, are considered to be nonclassical cadherins. To date, nine groups of nonclassical cadherins have been identified (types II-X). These cadherins are also membrane glycoproteins. Type II, or atypical, cadherins include OB-cadherin (cadherin-11; see Getsios et al., *Developmental Dynamics* 211:238-247, 1998; Simonneau et al., *Cell Adhesion and Communication* 3:115-130, 1995; Okazaki et al., *J. Biological Chemistry* 269:12092-12098, 1994), cadherin-5 (VE-cadherin; see Navarro et al., *J. Cell Biology* 140:1475-1484, 1998), cadherin-6 (K-cadherin; see Shimoyama et al., *Cancer Research* 55:2206-2211, 1995; Shimazui et al., *Cancer Research* 56:3234-3237, 1996; Inoue et al., *Developmental Dynamics* 211:338-351, 1998; Getsios et al., *Developmental Dynamics* 211:238-247, 1998), cadherin-7 (see Nakagawa et al., *Development* 121:1321-1332, 1995), cadherin-8 (see Suzuki et al., *Cell Regulation* 2:261-270, 1991), cadherin-9 (T1-cadherin, see Shimoyama et al., *Biochem. J.* 349: 159-67, 2000), cadherin-10 (T2-cadherin, see Kools et al., *FEBS Lett* 452: 328-34, 1999) cadherin-12 (Br-cadherin; see Tanihara et al., *Cell Adhesion and Communication* 2:15-26, 1994), cadherin-14 (also referred to as cadherin-18, see Shibata et al., *J. Biological Chemistry* 272:5236-5240, 1997), EY-cadherin (a mouse orthologue of human cadherin-14), cadherin-15 (M-cadherin; see Shimoyama et al., *J. Biological Chemistry* 273:10011-10018, 1998), cadherin-19 (see Kools et al., *Genomics* 68: 283-95, 2000), cadherin-20 (Kools et al., *Genomics* 68: 283-95, 2000), F-cadherin (likely a Xenopus F-cadherin), mouse cadherin-7 (likely a mouse orthologue of human cadherin-20), and PB-cadherin (see Sugimoto et al., *J. Biological Chemistry* 271:1154 8-11556, 1996). For a general review of atypical cadherins as well as other types of cadherins, see Nollet et al., *J. Mol. Biol.* 299: 551-72, 2000; Redies and Takeichi, Developmental Biology 180:413-423, 1996, Suzuki et al., *Cell Regulation* 2:261-270, 1991.

Types III-X include LI-cadherin (type III; see Berndorff et al., *J. Cell Biology* 125:1353-1369, 1994), T-cadherin (type IV; see Ranscht, U.S. Pat. No. 5,585,351; Tkachuk et al., *FEBS Lett.* 421:208-212, 1998; Ranscht et al., *Neuron* 7:391-402, 1991; Sacristan et al., *J. Neuroscience Research* 34:664-680, 1993; Vestal and Ranscht, *J. Cell Biology* 119:451-461, 1992; Fredette and Ranscht, *J. Neuroscience* 14:7331-7346, 1994; Ranscht and Bronner-Fraser, *Development* 111:15-22, 1991), protocadherins (type V; e.g., protocadherins 42, 43 and 68; see Sano et al., *EMBO J.* 12:2249-2256, 1993; GenBank Accession Number AF029343), desmocollins (type VI; e.g., desmocollins 1, 2, 3 and 4; see King et al., *Genomics* 18:185-194, 1993; Parker et al., *J. Biol. Chem.* 266:10438-10445, 1991; King et al., *J. Invest. Dermatol.* 105:314-321, 1995; Kawamura et al., *J. Biol. Chem.* 269:26295-26302, 1994), desmogleins (type VII; e.g., desmogleins 1 and 2; see Wheeler et al., *Proc. Natl. Acad. Sci. USA* 88:4796-4800; Koch et al., *Eur. J. Cell. Biol.* 55:200-208, 1991), and cadherin-related neuronal receptors (type X; see Kohmura et al., *Neuron* 20:1137-1151, 1998).

The structures of atypical, or type II cadherins are similar to those of the type I cadherins, but they do not contain the CAR sequence, HAV. The structures of representative atypical cadherins are shown in FIGS. 1B-1J. The functions mediated by the atypical cadherins are diverse. OB-cadherin, which is also known as cadherin-11, is an atypical cadherin (Getsios et al., *Developmental Dynamics* 211:238-247, 1998; Okazaki et al., *J. Biol. Chem.* 269:12092-98, 1994; Suzuki et al., *Cell Regulation* 2:261-70, 1991; Munro et al., supra). This cadherin can promote cell adhesion through homophilic interactions. Recent studies have shown that OB-cadherin is not expressed by well-differentiated, poorly invasive cancer cells, whereas it is expressed by invasive cancer cells (Shimazui et al., *Cancer Res.* 56:3234-37, 1996; Shibata et al., *Cancer Letters* 99:147-53, 1996). OB-cadherin levels are also high in stromal cells and osteoblasts (Shibata et al., *Cancer Letters* 99:147-53, 1996; Simonneau et al., *Cell Adhes. Commun.* 3:115-30, 1995; Matsuyoshi and Imamura, Biochem. Biophys. Res. Commun. 23:355-58, 1997; Okazaki et al., *J. Biol. Chem.* 269:12092-98, 1994). Collectively, these observations have led to the hypothesis that OB-cadherin may mediate the interaction between malignant tumor cells and other cell types, such as stromal cells and osteoblasts, thus facilitating tumor cell invasion and metastasis.

OB-cadherin is expressed in certain specific cell types. In some invasive cancer cells, OB-cadherin is not only found at sites of cell-cell contact, but also in lamellopodia-like projections which do not interact with other cells. These observations suggest that OB-cadherin may also play a role in modulating cell-substrate interactions. In adipocytes, OB-cadherin is the only known expressed cadherin. OB-cadherin is therefore likely to mediate adhesion between adipocytes, and it is likely to be an important regulator of adipogenesis. Another cell type that expresses OB-cadherin is the pericyte (also known as the peri-endothelial cell). Pericytes are contractile cells that are similar to smooth muscle cells. They encircle the endothelial cells of blood vessels. Pericytes are involved in maintaining the structural integrity of blood vessels (Hanahan, *Science* 277:48-50, 1997; Lindahl et al., *Science* 277: 242-245, 1997). Loss of pericytes causes blood vessels to regress.

Other atypical cadherins appear to have different functions. For example, cadherin-5 (also referred to VE-cadherin) appears to be involved in modulating endothelial cell adhesion, vascular endothelial growth factor (VEGF)-mediated endothelial cell survival and angiogenesis (Carmeliet et al., *Cell* 98: 147-57, 1999; and Lampugnani et al., *J. Cell Biol.* 129: 203-17, 1995) and cadherin-6 (also referred to as K-cadherin) may be involved in embryonic kidney cell adhesion and is up-regulated in kidney cancer. Cadherin-15 also appears to play a role in the terminal differentiation of muscle cells.

In addition, desmosomal cadherins, including desmogleins and desmocollins, are known to be important in mediating cell adhesion, including epithelial cell adhesion and keratinocyte adhesion. As there is a need in the art for the development of methods to enhance drug penetration through the skin and into tumors, desmosomal cadherins represent attractive targets for this and other areas of therapeutic importance.

Notwithstanding these recent advances, nonclassical cadherin function remains poorly understood at the biological and molecular levels. Accordingly, there is a need in the art for identifying sequences involved in modulating nonclassical cadherin-dependent functions, such as cell adhesion, and for the development of methods employing such sequences to inhibit processes such as cancer cell adhesion, invasion and metastasis. The present invention fulfills these needs and further provides other related advantages.

BRIEF SUMMARY OF THE INVENTION

The present invention provides cell adhesion modulating agents and methods for modulating nonclassical cadherin-mediated cell adhesion.

In one aspect, the present invention provides a cell adhesion modulating agent capable of modulating atypical cadherin-mediated cell adhesion. Such an agent may comprise a Trp-containing CAR sequence (e.g., Trp-Asn-Gln, Gly/Asp/Ser-Trp-Val/Ile/Met-Trp-Asn-Gln (SEQ ID NO: 5) and Ala-Trp-Val-Ile-Pro-Pro (SEQ ID NO: 6)) of an atypical cadherin, a conservative (or nonconservative) analogue, a peptidomimetic of the Trp-containing CAR sequence, or an antibody or antigen-binding fragment thereof that specifically binds to the Trp-containing CAR sequence. In some embodiments, the modulating agent contains at least 3, 4, 5, 6, 7, 8, or 9 amino acids and/or at most 10-50 consecutive amino acid residues (including all integer values therebetween, such as 10, 11, 12, 13, 14, 15, 20, 25, 30, 35, 40, 45, and 50) of a naturally occurring atypical cadherin molecule (i.e., a cadherin molecule that is present in nature and has not been intentionally modified by man in laboratory). In certain embodiments, the cell adhesion modulating agent comprises a Trp-containing CAR sequence present within a linear peptide or within the ring of a cyclic peptide. The linear peptide may contain at least 3, 4, 5, 6, 7, 8 or 9 amino acids and/or at most 10-100 amino acids including all integer values therebetween (e.g., 10, 15, 20, 25, 30, 40, 50, 60, 80 and 100). The size of the cyclic peptide ring in a modulating agent may be at least 3, 4, 5, 6, 7, 8 or 9 amino acids and/or at most 10-100 amino acids including all integer values therebetween (e.g., 10, 15, 20, 25, 30, 40, 50, 60, 80 and 100). Such a peptide may comprise an N-terminal or C-terminal modification, such as N-acetylation.

In another aspect, the present invention provides a cell adhesion modulating agent capable of modulating desmosomal cadherin-mediated cell adhesion. Such an agent may comprise a Trp-containing CAR sequence (e.g., Glu/Ala-Trp-Ile/Val-Lys/Thr-Phe/Ala-Ala/Pro, SEQ ID NO: 1 and Arg-Trp-Ala-Pro-Ile-Pro, SEQ ID NO:2) of a desmosomal cadherin, a conservative (or nonconservative) analogue, a peptidomimetic of the Trp-containing CAR sequence, or an antibody or antigen-binding fragment thereof that specifically binds to the Trp-containing CAR sequence. In some embodiments, the modulating agent contains at least 3, 4, 5, 6, 7, 8, or 9 amino acids and/or at most 10-50 consecutive amino acid residues (including all integer values therebetween, such as 10, 11, 12, 13, 14, 15, 20, 25, 30, 35, 40, 45, and 50) of a naturally occurring desmosomal cadherin molecule (i.e., a desmosomal cadherin molecule that is present in nature and has not been intentionally modified by man in laboratory). In certain embodiments, the cell adhesion modulating agent comprises a Trp-containing CAR sequence present within a linear peptide or within the ring of a cyclic peptide. The linear peptide may contain at least 3, 4, 5, 6, 7, 8 or 9 amino acids and/or at most 10-100 amino acids including all integer values therebetween (e.g., 10, 15, 20, 25, 30, 40, 50, 60, 80 and 100). The size of the cyclic peptide ring in a modulating agent may be at least 3, 4, 5, 6, 7, 8 or 9 amino acids and/or at most 10-100 amino acids including all integer values therebetween (e.g., 10, 15, 20, 25, 30, 40, 50, 60, 80 and 100). Such a peptide may comprise an N-terminal or C-terminal modification, such as N-acetylation.

The cell adhesion modulating agent described above may be linked to one or more of heterologous compounds such as a pharmaceutically active substance, a targeting agent, a detectable marker, or a solid support. In addition, the modulating agent may further comprise (a) a CAR sequence other than a Trp-containing CAR sequence directly linked to, or separated by a linker from, the Trp-containing CAR sequence, (b) an antibody or antigen-binding fragments thereof that specifically binds to a CAR sequence other than the Trp-containing CAR sequence, or both (a) and (b).

In another aspect, the present invention provides a composition comprising a cell adhesion modulating agent as described above in combination with a physiologically acceptable carrier.

The present invention also provides methods for modulating cell adhesion that comprises contacting a cell (e.g., epithelial cells, cardiac muscle cells, vascular smooth muscle cells, endothelial cells, neural cells, osteoblast cells and tumor cells) that expresses a nonclassical cadherin, such as an atypical cadherin or a desmosomal cadherin, with the cell adhesion modulating agent as described above and thereby modulating cell adhesion. In certain embodiments, the desmosomal cadherin is desmoglein 1, desmoglein 2, desmoglein 3, desmoglein 4, desmoglein 5, desmoglein 6, desmocollin 1, desmocollin 2, desmocollin 3, and desmocollin 4.

In certain embodiments, the modulating agent inhibits (reduces) cadherin-mediated cell adhesion. In other embodiments, such a modulating agent enhances cadherin-mediated cell adhesion.

The present invention also provides methods for reducing the progression of a cancer in a mammal that comprises administering to a mammal having a cancer a modulating agent and thereby reducing the progression of the cancer in the mammal.

The present invention also provides methods for reducing unwanted cellular adhesion in a mammal that comprises administering to a mammal with unwanted cellular adhesion a modulating agent that inhibits cadherin-mediated cell adhesion and thereby reducing unwanted cellular adhesion.

The present invention also provides methods for enhancing the delivery of a pharmaceutically active substance through the skin of a mammal that comprises contacting epithelial cells of a mammal with a pharmaceutically active substance and a modulating agent that inhibits cadherin-mediated cell adhesion and thereby enhancing the delivery of the substance through the skin. The contacting step is performed under conditions and for a time sufficient to allow passage of the substance across the epithelial cells.

The present invention also provides a method for enhancing the delivery of a pharmaceutically active substance to a tumor in a mammal that comprises contacting the tumor with a pharmaceutically active substance and a modulating agent that inhibits cadherin mediated cell adhesion and thereby enhancing the delivery of the substance to the tumor. The contacting step is performed under conditions and for a time sufficient to allow passage of the substance into the cells of the tumor.

The present invention also provides a method for inhibiting (lessening or reducing) cancer metastasis comprising administrating to a mammal having a cancer with a modulating agent, thereby inhibiting metastasis of the cancer.

The present invention also provides a method for modulating apoptosis in a cadherin-expressing cell that comprises contacting a cadherin-expressing cell with a modulating agent that inhibits cadherin-mediated cell adhesion, thereby modulating apoptosis in the cell.

The present invention also provides a method for inhibiting (reducing) angiogenesis in a mammal that comprises administering to a mammal a modulating agent that inhibits cadherin mediated cell adhesion, thereby inhibiting angiogenesis in the mammal.

The present invention also provides a method for enhancing the delivery of a pharmaceutically active substance to the central nervous system of a mammal, comprising administering to a mammal a modulating agent that inhibits cadherin mediated cell adhesion, thereby enhancing the delivery of a pharmaceutically active substance.

The present invention also provides a method for ameliorating a demyelinating neurological disease in a mammal, comprising administering to a mammal with a demyelinating neurological disease a modulating agent that inhibits cadherin mediated cell adhesion, thereby ameliorating the demyelinating neurological disease.

The present invention also provides a method for modulating the immune system of a mammal, comprising administering to a mammal a modulating agent that inhibit cadherin mediated cell adhesion, thereby modulating the immune system of the mammal.

The present invention also provides a method for preventing pregnancy in a mammal, comprising administering to a mammal a modulating agent that inhibit cadherin mediated cell adhesion, thereby preventing pregnancy in the mammal.

The present invention also provides a method for increasing vasopermeability in a mammal, comprising administering to a mammal a modulating agent that inhibits cadherin mediated cell adhesion, thereby increasing vasopermeability in the mammal.

The present invention also provides a method for inhibiting (reducing) synaptic stability in a mammal that comprises administering to a mammal a modulating agent that inhibits cadherin mediated cell adhesion, thereby inhibiting synaptic stability in the mammal.

The present invention also provides a method for facilitating blood sampling in a mammal that comprises contacting epithelial cells of a mammal with a cell adhesion modulating agent that inhibits cadherin mediated cell adhesion, thereby facilitating blood sampling in the mammal. The contacting step is performed under conditions and for a time sufficient to allow passage of one or more blood components across the epithelial cells.

The present invention also provides a method for stimulating blood vessel regression that comprises administering to a mammal a cell adhesion modulating agent that inhibit cadherin mediated cell adhesion, thereby stimulating blood vessel regression.

The present invention also provides a method for reducing aggregation of cultured cells (e.g., stem cells) that comprises contacting cultured stem cells with a cell adhesion modulating agent that inhibits cadherin mediated cell adhesion, thereby reducing cell aggregation.

The present invention also provides a method for increasing blood flow to a tumor in a mammal that comprises administering to a mammal the cell adhesion modulating agent that inhibits endothelial cell adhesion, thereby increasing blood flow to a tumor in the mammal.

The present invention also provides a method of disrupting neovasculature in a mammal that comprises administering to a mammal a cell adhesion modulating agent that inhibits cadherin mediated cell adhesion, thereby disrupting neovasculature.

The present invention also provides a method for inhibiting (reducing) endometriosis in a mammal that comprises administering to a mammal a cell adhesion modulating agent that inhibits cadherin mediated cell adhesion, thereby inhibiting endometriosis.

The present invention also provides a method for enhancing inhaled compound delivery in a mammal that comprising contacting lung epithelial cells of a mammal with a cell adhesion modulating agent that inhibits cadherin mediated cell adhesion, thereby enhancing inhaled compound delivery.

The present invention also provides a method for facilitating wound healing in a mammal that comprises contacting a wound in a mammal with a cell adhesion modulating agent that enhances cadherin-mediated cell adhesion, thereby facilitating wound healing.

The present invention also provides a method for enhancing adhesion of a foreign tissue implanted within a mammal that comprises contacting a site of implantation of a foreign tissue in a mammal with a cell adhesion modulating agent that enhances cadherin-mediated cell adhesion, thereby enhancing adhesion of the foreign tissue.

The present invention also provides a method for enhancing and/or directing neurite outgrowth that comprises contacting a neuron with a cell adhesion modulating agent that enhances cadherin-mediated cell adhesion, thereby enhancing and directing neurite outgrowth, wherein the modulating agent enhances cadherin-mediated cell adhesion.

The present invention also provides a method for treating an autoimmune blistering disorder in a mammal, comprising administering to a mammal with an autoimmune blistering disorder a modulating agent that enhances desmosomal cadherin-mediated cell adhesion, thereby treating the disorder. In certain embodiments, the modulating agent is administered topically to a blister. In some embodiments, the modulating agent is linked to a support molecule or a solid support. The autoimmune blistering disorder includes but is not limited to permphigus, vulgaris, pemphigus foliaceus, and intercellular IgA dermatosis.

The present invention also provides a method for removing autoantibodies from a mammal by contacting blood from said mammal with a filter or a solid support having immoblizied thereon Trp-containing CAR sequences of the present invention.

The present invention also provides a method of ameliorating a spinal cord injury in a mammal that comprises administering to a mammal having a spinal cord injury a cell adhesion modulating agent that enhances cadherin-mediated cell adhesion, thereby ameliorating the spinal cord injury.

In one aspect, the present invention provides a kit for enhancing transdermal delivery of a pharmaceutically active substance, comprising: instructions for using the same, a skin patch and a cell adhesion modulating agent.

In another aspect, the present invention provides a method for screening a candidate compound for the ability to modulate cell adhesion that comprises comparing a three-dimensional structure of a candidate compound to a three-dimensional structure of a Trp-containing CAR sequence, therefrom evaluating the ability of the candidate compound to modulate cell adhesion. For such a method, the similarity between the structure of the candidate compound and the structure of the peptide is indicative of the ability of the candidate compound to modulate cell adhesion.

The present invention also provides a method for identifying a compound that modulates cell adhesion that comprises: (a) determining a level of similarity between a three-dimensional structure of a candidate compound and a three-dimensional structure of a Trp-containing CAR sequence; and (b) identifying an alteration in the structure of the candidate compound that results in a three-dimensional structure with an increased similarity to the three-dimensional structure of the peptide; therefrom identifying a compound that has the ability to modulate cell adhesion.

The present invention also provides a method for evaluating a peptidomimetic for the ability to modulate cell adhesion that comprises (a) culturing neurons on a monolayer of cells that express a cadherin in the presence and absence of a peptidomimetic, under conditions and for a time sufficient to allow neurite outgrowth, wherein the peptidomimetic has a three-dimensional structure that is substantially similar to a three-dimensional structure of a Trp-containing CAR sequence; (b) determining a mean neurite length for said neurons; and (c) comparing the mean neurite length for neurons cultured in the presence of peptidomimetic to the neurite length for neurons cultured in the absence of the peptidomimetic, therefrom determining whether the peptidomimetic modulates cell adhesion.

The present invention also provides a method for evaluating a peptidomimetic for the ability to modulate cell adhesion that comprises: (a) culturing cells that express a cadherin in the presence and absence of a peptidomimetic, under conditions and for a time sufficient to allow cell adhesion, wherein the peptidomimetic has a three-dimensional structure that is substantially similar to a three-dimensional structure of a Trp-containing CAR squence; and (b) evaluating the extent of cell adhesion among said cells either visually or by computer, and therefrom identifying a peptidomimetic capable of modulating cell adhesion.

The present invention also provides a method for evaluating a peptidomimetic for the ability to modulate cell adhesion that comprises: (a) contacting an epithelial surface of skin with a test marker in the presence and absence of a peptidomimetic, wherein the peptidomimetic has a three-dimensional structure that is substantially similar to a three-dimensional structure of a Trp-containg CAR sequence; and (b) comparing the amount of test marker that passes through said skin in the presence of the peptidomimetic to the amount that passes through skin in the absence of the peptidomimetic, therefrom determining whether the peptidomimetic modulates cell adhesion.

The present invention also provides a method for evaluating the ability of a peptidomimetic to modulate cell adhesion that comprises: (a) contacting a blood vessel with a peptidomimetic, wherein the peptidomimetic has a three-dimensional structure that is substantially similar to a three-dimensional structure of a peptide having a Trp-containing CAR sequence; and (b) comparing the extent of angiogenesis of the blood vessel to a predetermined extent of angiogenesis observed for a blood vessel in the absence of the peptidomimetic, therefrom determining whether the peptidomimetic modulates cell adhesion.

The present invention further provides a process for manufacturing a compound that modulates cell adhesion that comprises the steps of performing the methods for identifying a compound that modulates cell adhesion as described above and producing the identified compound.

In a related aspect, the present invention provides a process for manufacturing a peptidomimetic that modulates cell adhesion comprising the steps of performing any one of the methods for evaluating the ability of a peptidomimetic to modulating cell adhesion as described above; and producing the peptidomimetic if the peptidomemitic has the ability to modulate cell adhesion.

In other embodiments of the invention, there are provided methods for modulating the behavior, e.g., cell adhesion, proliferation, migration and/or survival, of vascular smooth muscle cells (VSMC) or pericytes, comprising contacting a cadherin expressing VSMC or pericyte cell with, or administering to a mammal, a cell adhesion modulating agent as described herein.

In a related embodiment, there are provided methods for regulating the overgrowth and/or migration of VSMCs or pericytes, comprising contacting a cadherin expressing cell with, or administering to a mammal, a cell adhesion modulating agent as described herein, wherein the modulating agent is preferably an inhibitor of cadherin-mediated cell adhesion. Particularly illustrative uses according to this embodiment relate to preventing the formation or advance of restenosis, vein bypass graft failure, allograft vasculopathy, dialysis graft failure, thin cap fibroatheroma, and other vessel stenoses. Related embodiments include the treatment of essential and secondary hypertension, atheroma, arteriosclerosis, or other indications in which endothelial injury or trauma has occurred.

In another related embodiment, there are provided methods for maintaining vessel luminal area following vascular trauma, comprising contacting a cadherin expressing cell with, or administering to a mammal, a cell adhesion modulating agent as provided herein, wherein the modulating agent is preferably an inhibitor of cadherin-mediated cell adhesion.

In another related embodiment, there are provided methods for treating a traumatized vessel, comprising contacting a cadherin expressing cell with, or administering to a mammal, a cell adhesion modulating agent as provided herein, wherein the modulating agent is preferably an inhibitor of cadherin-mediated cell adhesion. Particularly illustrative uses according to this embodiment include the treatment of trauma that may occur during stent placement, organ transplant, vein bypass, angioplasty, dialysis graft placement, and the like.

In still other embodiments, one or more modulating agents are provided as an active component of a medical device (e.g. a balloon, stent, shunt, catheter, stent graft, vascular graft, vascular patch, filter, adventitial wrap, intraluminal paving system, cerebral stent, cerebral aneurysm filter coil, myocardical plug, pacemaker lead, dialysis access graft, heart valve, etc.). For example, the modulating agents of the invention may be linked to, coated on, or dispersed within essentially any medical device using known techniques in order to provide or deliver modulating agent in a desired physiological and/or anatomical context.

In these and other embodiments, the modulating agents of the present invention may be delivered to a cadherin expressing cell, or a subject, by essentially any delivery approach suitable to a given indication and compatible with the delivery of modulating agents provided herein. In one embodiment, administration of a modulating agent provided herein is accomplished via a catheter. In another embodiment, administration of an agent is accomplished using an infusion needle.

There are also provided according to the invention methods for enhancing the survival of neurons and/or suppressing neural injury, for example as a result of stroke or other type of brain ischemia, comprising contacting a cadherin expressing neural cell with, or administering to a mammal, a cell adhesion modulating agent as described above, wherein the modulating agent preferably is one that enhances cadherin-mediated cell adhesion.

Related embodiments of the invention are provided for treatment for stroke recovery, reversing or establishing plateau in dementias, treatment for trauma to the CNS, spine and peripheral nerves, as well as treatment of neuropathies.

In another embodiment, there are provided methods for enhancing neurite outgrowth comprising contacting a cadherin expressing neural cell with, or administering to a mammal, a cell adhesion modulating agent as described above, wherein the modulating agent is preferably one that enhances cadherin-mediated cell adhesion.

In another embodiment, there are provided methods for facilitating the removal of hair follicles from skin, e.g., viable or intact hair follicles, comprising contacting a cadherin expressing cell with, or administering to a mammal, a cell adhesion modulating agent of the invention. Certain aspects of this embodiment find particular utility in removing unwanted hair follicles and/or in the re-transplantation of hair follicles at a site of the body different from that in which they originated.

In other embodiments, methods are provided for stimulating angiogenesis comprising contacting a cadherin expressing cell with, or administering to a mammal, a modulating agent provided herein, wherein the modulating agent enhances cadherin-mediated cell adhesion.

In still other embodiments, there are provided methods for modulating endothelial cell behavior, e.g., endothelial cell migration, proliferation, survival and/or adhesion comprising contacting a cadherin expressing cell with, or administering to a mammal, a modulating agent provided herein.

Within further embodiments, methods are provided for modulating endothelial cell adhesion, comprising contacting a cadherin-expressing endothelial cell with, or administering to a mammal, a cell adhesion modulating agent as described herein. In certain preferred embodiments, the modulating agent inhibits N-cadherin mediated cell adhesion, resulting in the reduction of unwanted endothelial cell adhesion in the mammal.

Within further aspects, methods are provided for increasing vasopermeability in a mammal, comprising contacting a cadherin-expressing endothelial cell with, or administering to a mammal, a cell adhesion modulating agent as described above, wherein the modulating agent is preferably one that inhibits cadherin-mediated cell adhesion.

Methods are also provided, within further aspects, for disrupting neovasculature in a mammal, comprising contacting a cadherin expressing cell with, or administering to a mammal, a modulating agent as described above, wherein the modulating agent inhibits cadherin-mediated cell adhesion.

Within further aspects, methods are provided for inhibiting the development of endometriosis in a mammal, comprising contacting a cadherin expressing cell with, or administering to a mammal, a modulating agent as described above, wherein the agent is preferably one that inhibits cadherin-mediated cell adhesion.

In another embodiment, method are provided for modulating adipogenesis (a process dependent on angiogenesis) comprising contacting a cadherin-expressing cell with, or administering to a mammal, a modulating agent described herein, wherein the modulating agent is preferably one that inhibits cadherin-mediated cell adhesion.

In another embodiment, methods are provided for modulating tumor blood flow, comprising contacting a cadherin-expressing endothelial cell with, or administering to a mammal, a modulating agent described herein. Depending on the application, in certain embodiments, the modulating agent is preferably one that enhances cadherin-mediated cell adhesion while in others the modulating agent is preferably one that inhibits cadherin-mediated cell adhesion.

In still further embodiments, methods are provided for the treatment of disease conditions that are dependent on angiogenesis and neovascularization. Disruption of neovasculature is therapeutic for conditions in which the presence of newly formed blood vessels is related to the underlying disorder, its symptoms or its complications. For example, disorders that may be treated include, but are not limited to, benign prostatic hyperplasia, diabetic retinopathy, vascular restenosis, arteriovenous malformations, meningioma, hemangioma, neovascular glaucoma, psoriasis, angiofiboma, arthritis, atherosclerotic plaques, corneal graft neovascularization, hemophilic joints, hypertrophic scars, hemorrhagic telangiectasia, pyogenic granuloma, retrolental fibroplasias, scleroderma trachoma, vascular adhesions, synovitis, dermatitis, endometriosis, macular degeneration and exudative macular degeneration. These methods comprise contacting cadherin-expressing cells with, or administering to a mammal, a modulating agent described herein, wherein the modulating agent preferably is one that inhibits cadherin-mediated cell adhesion.

In yet another embodiment, methods are provided for modulating tumor permeability barriers to drugs, such as chemotherapeutic agents, comprising contacting a cadherin-expressing cell with, or administering to a mammal, a modulating agent described herein.

In another embodiment, methods are provided for the modulation of bone adhesion, for example in the context of bone grafts, comprising contacting a cadherin-expressing cell with, or administering to a mammal, a modulating agent described herein, preferably a modulating agent that enhances cadherin-mediated cell adhesion. Modulating agents according to the invention may be effective, for example, in promoting bone adhesion to grafts.

It is appreciated that to successfully perform various methods of the present invention, an effective amount of the modulating agents are used under conditions and for a time sufficient to achieve the desired results. Determining the effective amount, the appropriate conditions and the sufficient time period may either be within the ordinary skill in the art, and/or accomplished in view of the teachings provided herein.

BRIEF DESCRIPTION OF THE SEVERAL VIEWS OF THE DRAWINGS

FIG. 2 provides partial amino acid sequences of the extracellular domains of representative mammalian atypical cadherins (SEQ ID NOS: 1371-1378). Representative Trp-containing CAR sequences are shown in bold and underlined.

FIG. 3 provides the amino acid sequences of representative mammalian OB-cadherin EC1 domains: human OB-cadherin (SEQ ID NO: 1379) and mouse OB-cadherin (SEQ ID NO: 1380).

FIG. 5 provides the amino acid sequences of representative mammalian desmosomal cadherin EC1 domains as indicated (SEQ ID NOS: 1385-1402). Amino acids are represented by their IUPAC codes and "-" represents a gap. The desmosomal cadherin Trp-containing CAR sequence is indicated in bold.

FIG. 6 demostrates the cell adhesion modulating effects of the desmosomal Trp-containing CAR sequence ADH358 (H-RWAPIP-NH2 (SEQ ID NO: 2); Desmocollin derived peptide) on SKOV3 Human Ovarian Cancer Cells

DETAILED DESCRIPTION OF THE INVENTION

Figure 1A:
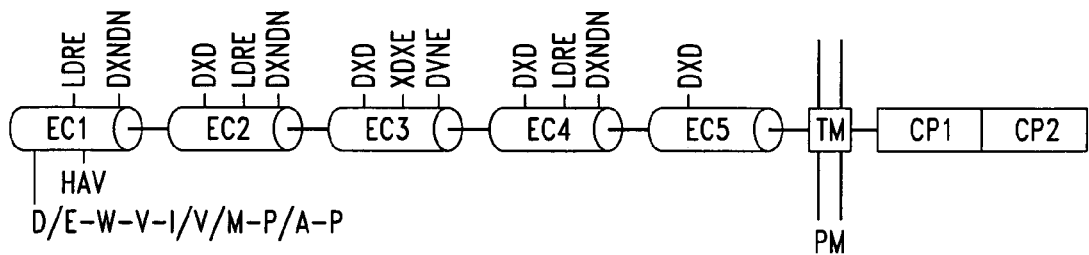
FIGS. 1A-1J are diagrams depicting the structure of classical (FIG. 1A) and representative atypical cadherins, including OB-cadherin, cadherin-5, cadherin 6, cadherin-7, cadherin-8, cadherin 12, cadherin-14, cadherin-15 and PB-cadherin (FIGS. 1B to 1J). The extracellular domains are designated EC1-EC5. The hydrophobic domain that transverses the plasma membrane (PM) is represented by TM, and the varying number of cytoplasmic domains are represented by CP. The calcium binding motifs for classical cadherins are shown in FIG. 1A by DXNDN (SEQ ID NO: 3), DXD and LDRE (SEQ ID NO: 4), and the calcium binding motifs for other cadherins are also indicated above the extracellular domains. Below the extracellular domains, exemplary Trp-containing CAR sequences consisting of six amino acids are shown.

As noted above, the present invention provides methods for modulating cadherin-mediated functions, such as cell adhesion. The present invention is based upon the identification of previously unknown cell adhesion recognition (CAR) sequences, Trp-containing CAR sequences, present in atypical cadherins and desmosomal cadherins. A modulating agent may generally comprise one or more atypical or desmosomal cadherin Trp-containing CAR sequences (or analogues or mimetics thereof), with or without one or more additional CAR sequences, as described below. The Trp-containing CAR sequences may be present within a linear or cyclic peptide portion of the modulating agent. Alternatively, a modulating agent may comprise a substance (such as an antibody or antigen-binding fragment thereof) that specifically binds to an atypical or desmosomal cadherin Trp-containing CAR sequence.

In general, to modulate an atypical or desmosomal cadherin-mediated function, a cell that expresses an atypical or desmosomal cadherin is contacted with a modulating agent either in vivo or in vitro. Within certain aspects, the methods provided herein inhibit (reduce) an atypical or desmosomal cadherin-mediated function. Such methods include, for example, methods for treating diseases or other conditions characterized by undesirable cell adhesion or for facilitating drug delivery to a specific tissue or tumor. Certain methods may inhibit cell adhesion (e.g., cancer cell adhesion), as well as cancer invasion, metastasis and angiogenesis. Alternatively, a modulating agent may, such as when linked to a matrix or to another modulating agent via a linker, be used to enhance an atypical or desmosomal cadherin-mediated function, such as cell adhesion. Such conjugates may be used, for example, to facilitate wound healing or the adhesion of implants.

Cell Adhesion Modulating Agents

As noted above, the term "cell adhesion modulating agent," as used herein, generally refers to a compound that comprises (a) a Trp-containing CAR sequence of a nonclassical cadherin, such as an atypical cadherin or a desmosomal cadherin, (b) a conservative analogue of the above sequence, (c) a peptidomimetic of the above sequence, or (d) an antibody or antigen-binding fragment thereof that specifically binds to the above sequence.

A modulating agent may comprise entirely one or more of the above elements, or may additionally comprise further peptide and/or non-peptide regions. Additional peptide regions may be derived from a nonclassical cadherin (preferably an extracellular domain that comprises a Trp-containing CAR sequence) and/or may be heterologous.

A modulating agent is further capable of modulating a function mediated by a nonclassical cadherin. Such activity may generally be assessed using, for example, representative assays provided herein. Certain modulating agents inhibit (reduce) an interaction between nonclassical cadherin molecules and/or between a nonclassical cadherin and a different adhesion molecule. Alternatively, to enhance adhesion of nonclassical cadherin-expressing cells, a modulating agent may comprise an antibody or antigen-binding fragment thereof and/or multiple peptides or mimetics linked to a support material. Such modulating agents may function as a biological glue to bind non-classical cadherin-expressing cells, and should result in a detectable enhancement of cell adhesion.

Figure 1B:
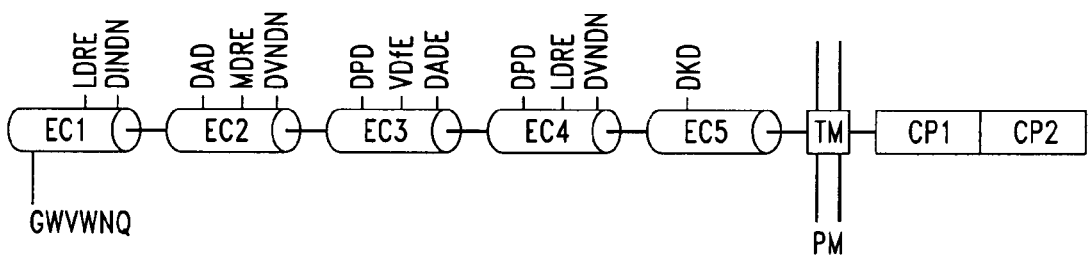
Figure 1C:
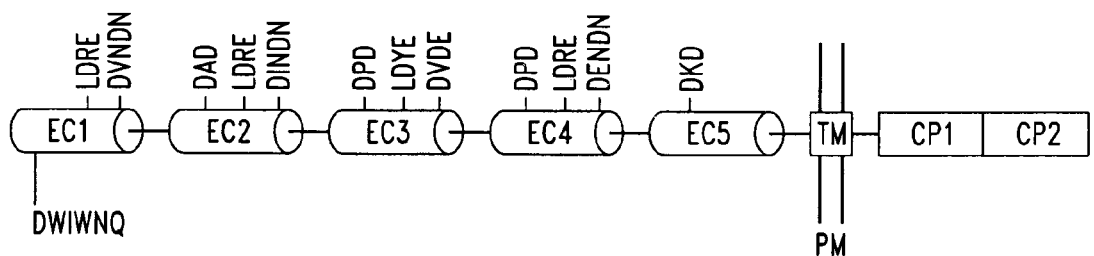
Figure 1D:
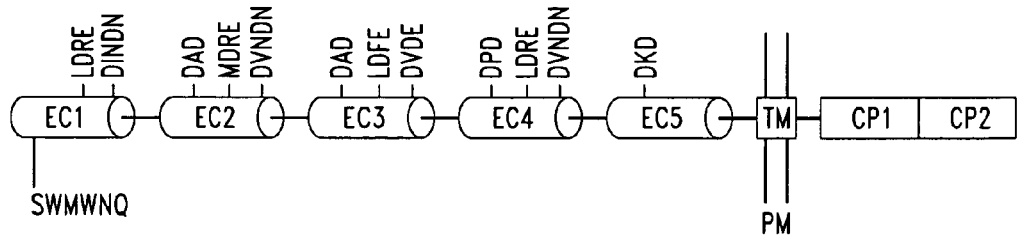
Figure 1E:
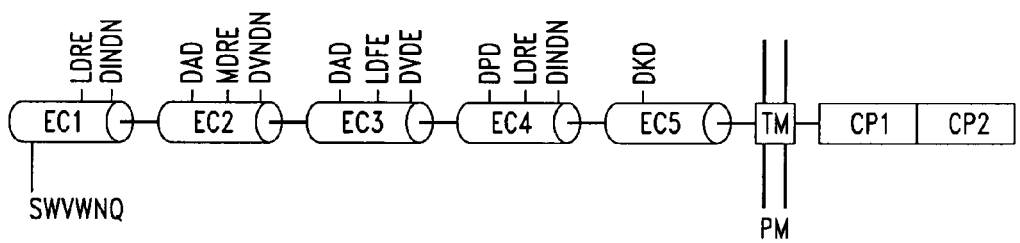
Figure 1F:
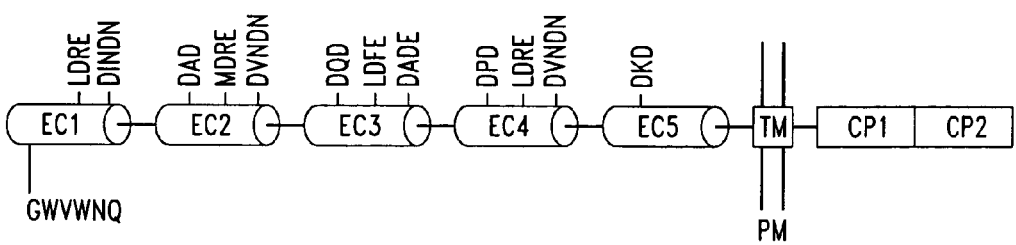
Figure 1G:
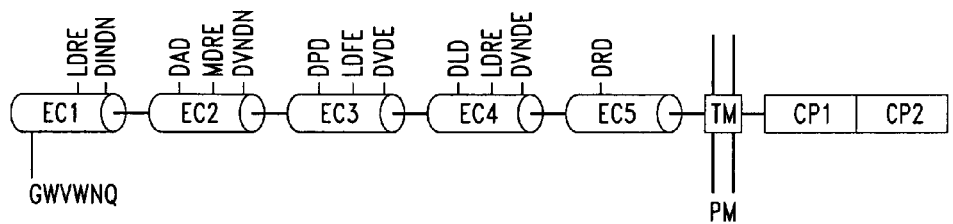
Figure 1H:
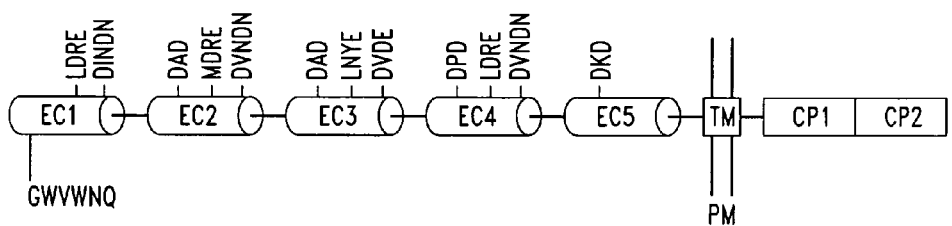
Figure 1I:
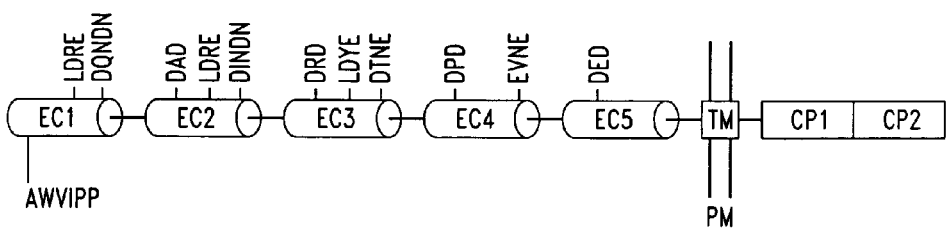
Figure 1J:
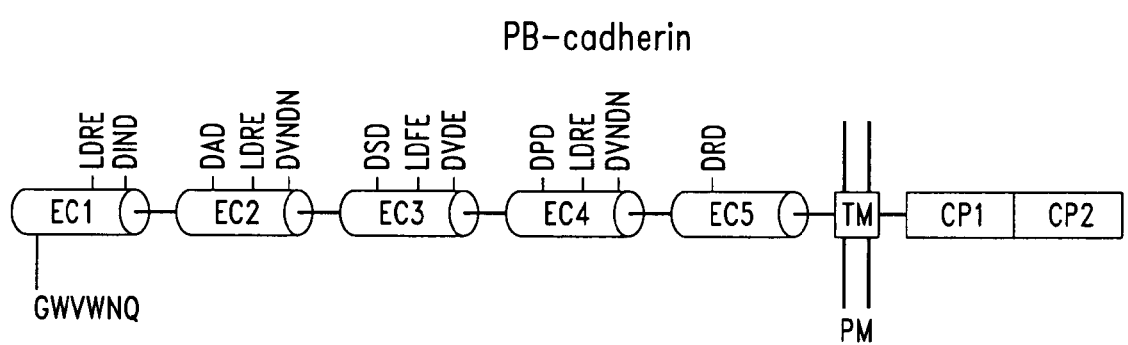
Figure 4A:
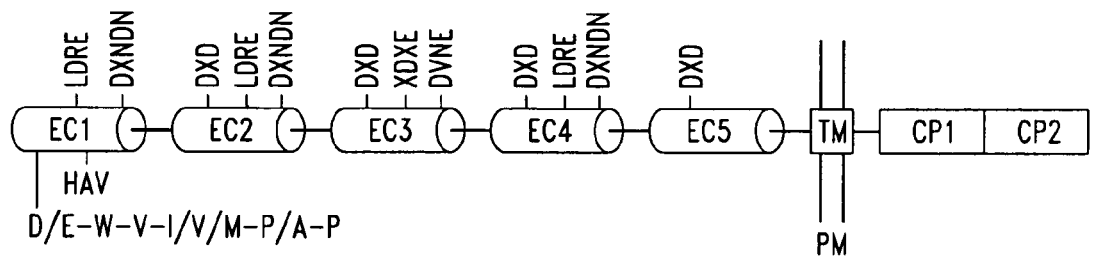
FIGS. 4A-4I are diagrams depicting the structure of classical cadherins (FIG. 4A), representative atypical cadherins (FIGS. 4B to 4C), and representative desmosomal cadherins, including desmoglein 1, desmoglein 2, desmoglein 3, desmoglein 4, desmocollin 1, desmocollin 2, desmocollin 3 and desmocollin 4 (FIG. 4D-4I). The extracellular domains are designated EC1-EC5. The hydrophobic domain that transverses the plasma membrane (PM) is represented by TM, and the varying number of cytoplasmic domains are represented by CP. The calcium binding motifs for classical cadherins are shown in FIG. 4A by DXNDN (SEQ ID NO: 3), DXD and LDRE (SEQ ID NO: 4), and the calcium binding motifs for other cadherins are also indicated above the extracellular domains. Below the extracellular domains, exemplary Trp-containing CAR sequences consisting of six amino acids are shown.
Figure 4B:
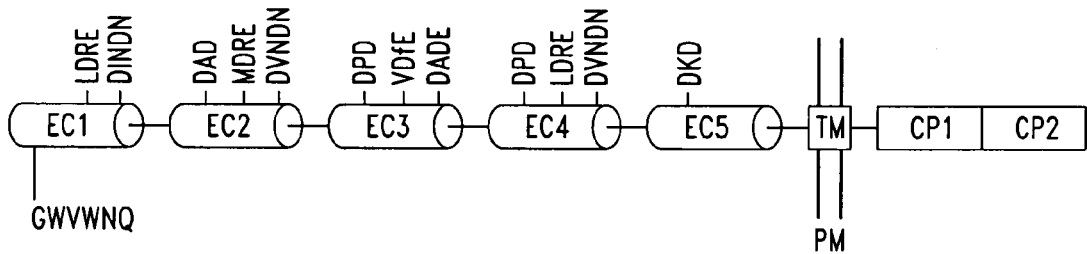
Figure 4C:
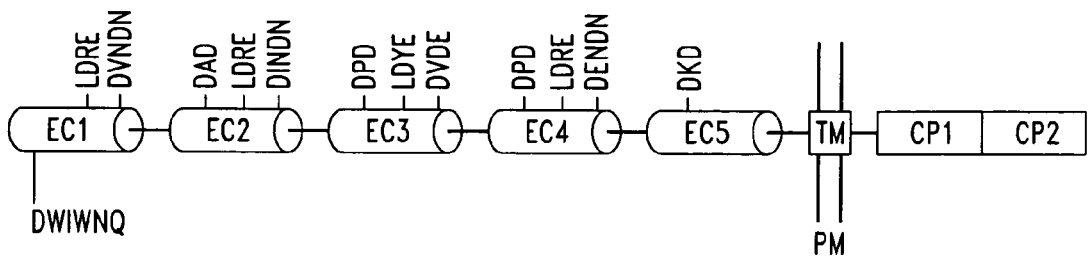
Figure 4D:
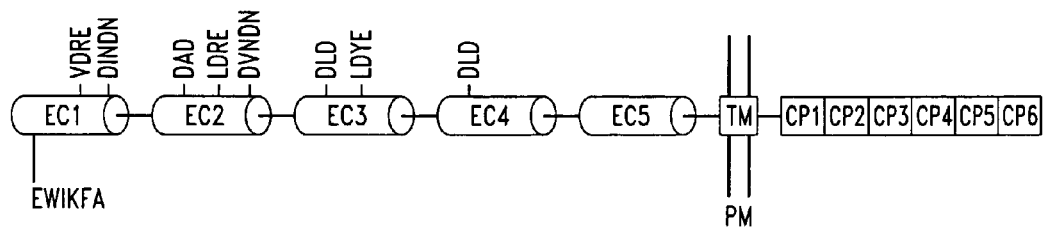
Figure 4E:
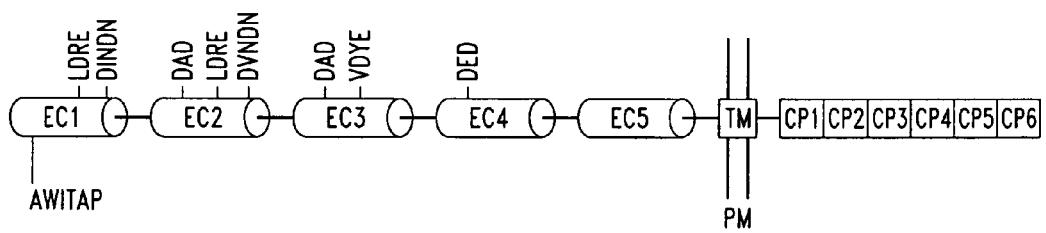
Figure 4F:
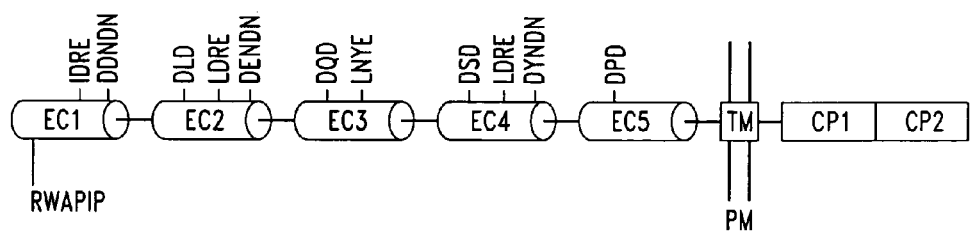
Figure 4G:
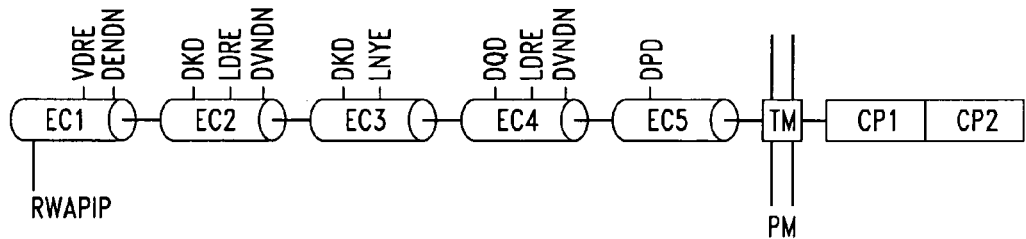
Figure 4H:
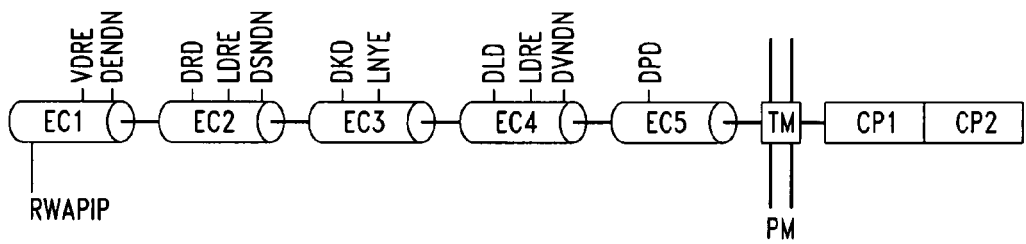
Figure 4I:
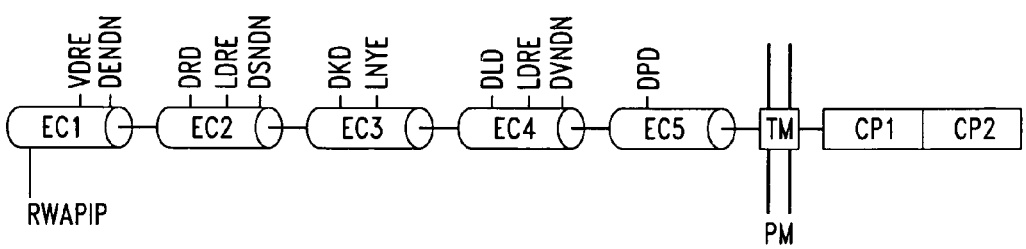

The term "non-classical cadherin," as used herein, refers to a polypeptide that contains characteristic cadherin repeats, but does not contain the classical cadherin CAR sequence His-Ala-Val (HAV). As used herein, a "cadherin repeat" refers to an amino acid sequence that is approximately 110 amino acid residues in length (generally 100 to 120 residues, preferably 105 to 115 residues), comprises an extracellular domain, and contains three calcium binding motifs (DXD, XDXE (SEQ ID NO: 7) and DXXDX (SEQ ID NO: 8)) in the same order and in approximately the same position (see, e.g., FIGS. 1A-1J). The presence of an extracellular domain may generally be determined using well known techniques, such as the presence of one or more of: a hydrophilic sequence, a region that is recognized by an antibody, a region that is cleaved by trypsin and/or a potential glycosylation site with the glycosylation motif Asn-X-Ser/Thr. The second calcium binding motif commonly has the sequence LDRE (SEQ ID NO: 4), although variants of this sequence with conservative substitutions are also observed, including MDRE (SEQ ID NO: 9), LDFE (SEQ ID NO: 10), LDYE (SEQ ID NO: 11), IDRE (SEQ ID NO: 12), VDRE (SEQ ID NO: 13) and IDFE (SEQ ID NO: 14). Within most cadherin repeats, the third calcium binding motif has the sequence [L,I,V]-X-[L,I,V]-X-D-X-N-D-[N,H]-X-P (SEQ ID NO: 15), wherein residues indicated in brackets may be any one of the recited residues. A preferred third calcium binding motif has the sequence DXNDN (SEQ ID NO: 3), although one or both of the D residues may be replaced by an E. Homology among cadherin repeats is generally at least 20%, preferably at least 30%, as determined by the ALIGN algorithm (Myers and Miller, *CABIOS* 4:11-17, 1988). Most cadherins comprise at least five cadherin repeats, along with a hydrophobic domain that transverses the plasma membrane and, optionally, one or more cytoplasmic domains. Occasionally, however, a cadherin may substitute an extracellular domain that contains fewer than three calcium binding motifs for one or more of the cadherin repeats. For example, the second extracellular domain of LI-cadherin comprises only the first calcium binding motif (DXD).

The term "atypical cadherin," as used herein, refers to a polypeptide that has a similar domain structure as those of classical cadherin molecules, but does not have the HAV CAR sequence in its EC1 domain. More specifically, an atypical cadherin has five characteristic cadherin repeats as described above, a transmembrane domain, and two cytoplasmic domains (i.e., a membrane-proximal cytoplasmic domain and a catenin-binding sequence). In general, an atypical cadherin has a lower sequence similarity (e.g., about 43-50% sequence similarity determined by the use of the HOMOLOGIES program, which relies on a similarity weight table described by Gribskow and Burgess, *Nucl. Acids Res.* 14: 6745-63, 1986) with a classical cadherin in the EC1 domain than those among classical cadherins in the same domain (e.g., above about 60% sequence similarity). An exception to the above description is cadherin-15, which has about 62% sequence similarity to E-cadherin in the EC1 domain. A typical cadherins include cadherin-5, cadherin-6, cadherin-7, cadherin-8, cadherin-9, cadherin-10, cadherin-11, cadherin-12, cadherin-14, cadherin-15, cadherin-19, cadherin-20, and PB cadherin. A typical cadherins also include future discovered cadherins that fit the above definition of "atypical cadherins." The structures of certain representative atypical cadherins are shown in FIGS. 1B-1J.

A Trp-containing CAR sequence of an atypical cadherin, as used herein, is an amino acid sequence that comprises a Trp residue, is present within a naturally occurring atypical cadherin, and is capable of detectably modulating an atypical cadherin-mediated function, such as cell adhesion, as described herein. In other words, contacting an atypical cadherin-expressing cell with a peptide comprising a Trp-containing CAR sequence results in a detectable change in an atypical cadherin-mediated function using at least one of the representative assays provided herein. Trp-containing CAR sequences are generally recognized in vivo by an atypical cadherin or other adhesion molecule (i.e., a molecule that mediates cell adhesion via a receptor on the cell surface), and are necessary for maximal heterophilic and/or homophilic interaction. Trp-containing CAR sequences may be of any length, but generally comprise at least 3, 4, 5, 6, 7, 8, or 9 amino acid residues and/or at most 10-50 amino acid residues (including all the integer values therebetween).

It has been found, within the context of the present invention, that certain atypical cadherin Trp-containing CAR sequences share the consensus sequence:

Gly/Asp/Ser-Trp-Val/Ile/Met-Trp-Asn-Gln (SEQ ID NO: 5)

Within the consensus sequence, "Gly/Asp/Ser" indicates an amino acid that is Gly, Asp or Ser; and "Val/Ile/Met" indicates an amino acid that is Val, Ile or Met. Representative atypical cadherin Trp-containing CAR sequences are provided within Table I. Trp-containing CAR sequences specifically provided herein further include portions of such representative Trp-containing CAR sequences, as well as polypeptides that comprise at least a portion of such sequences. Additional atypical cadherin Trp-containing CAR sequences may be identified based on sequence homology to the atypical cadherin Trp-containing CAR sequences provided herein, and based on the ability of a peptide comprising such a sequence to modulate an atypical cadherin-mediated function within a representative assay described herein. Within certain embodiments, a modulating agent comprises at least three, four, five and six consecutive residues of an atypical cadherin Trp-containing CAR sequence that satisfies the above consensus sequence.

TABLE I

Representative Atypical Cadherin Trp-Containing CAR Sequences

| Cadherin | CAR Sequence |
|---|---|
| Human OB-cadherin | GWVWNQ (SEQ ID NO: 16) |
| Human cadherin-5 | DWIWNQ (SEQ ID NO: 17) |
| Human cadherin-6 | SWMWNQ (SEQ ID NO: 18) |
| Human cadherin-7 | SWVWNQ (SEQ ID NO: 19) |
| Human cadherin-8 | GWVWNQ (SEQ ID NO: 16) |
| Human cadherin-9 | GWMWNQ (SEQ ID NO: 20) |
| Human cadherin-10 | GWMWNQ (SEQ ID NO: 20) |
| Human cadherin-11 | SWVWNQ (SEQ ID NO: 19) |
| Human cadherin-12 | GWVWNQ (SEQ ID NO: 16) |
| Human cadherin-14 | GWVWNQ (SEQ ID NO: 16) |
| Human cadherin-19 | GWVWNQ (SEQ ID NO: 16) |
| Human cadherin-20 | SWVWNQ (SEQ ID NO: 19) |
| CONSENSUS | GWVWNQ (SEQ ID NO: 16) |
|  | S M |
|  | D I |

Atypical cadherin Trp-containing CAR sequences are generally physically located within the extracellular domain of a cadherin molecule in or near the binding site of an adhesion molecule (i.e., within 10 amino acids, and preferably within 5 amino acids). The location of a binding site may generally be determined using well known techniques, such as evaluating the ability of a portion of the atypical cadherin to bind to the same atypical cadherin or to another adhesion molecule. Any standard binding assay may be employed for such an evaluation. Recognition of a Trp-containing CAR sequence by the atypical cadherin or other adhesion molecule results in a measurable effect on an adhesion molecule function, such as cell adhesion. Peptides comprising a Trp-containing CAR sequence generally inhibit such a function unless linked, as described herein, to form an enhancer of adhesion molecule function.

Exemplary Trp-containing CAR sequences for atypical cadherins include, but are not limited to GWV, GWVW (SEQ ID NO: 21), GWVWN (SEQ ID NO: 22), GWVWNQ (SEQ ID NO: 16), WVW, WVWN (SEQ ID NO: 23), WVWNQ (SEQ ID NO: 24), DWI, DWIW (SEQ ID NO: 25), DWIWN (SEQ ID NO: 26), DWIWNQ (SEQ ID NO: 17), WIW, WIWN (SEQ ID NO: 27), WIWNQ (SEQ ID NO: 28), SWM, SWMW (SEQ ID NO: 29), SWMWN (SEQ ID NO: 30), SWMWNQ (SEQ ID NO: 18), WMW, WMWN (SEQ ID NO: 31), WMWNQ (SEQ ID NO: 32), SWV, SWVW (SEQ ID NO: 33), SWVWN (SEQ ID NO: 34), SWVWNQ (SEQ ID NO: 19), GWM, GWMW (SEQ ID NO: 35), GWMWN (SEQ ID NO: 36), GWMWNQ (SEQ ID NO: 20), AWV, AWVI (SEQ ID NO: 37), AWVIP (SEQ ID NO: 38), AWVIPP (SEQ ID NO: 6), WVI, WVIP (SEQ ID NO: 39), WVIPP (SEQ ID NO: 40), GWVWNQF (SEQ ID NO: 41), GWVWNQFF (SEQ ID NO: 42), GWVWNQFFV (SEQ ID NO: 43), WVWNQF (SEQ ID NO: 44), WVWNQFF (SEQ ID NO: 45), WVWNQFFV (SEQ ID NO: 46), RGW, RGWV (SEQ ID NO: 47), RGWVW (SEQ ID NO: 48), RGWVWN (SEQ ID NO: 49), RGWVWNQ (SEQ ID NO: 50), RGWVWNQF (SEQ ID NO: 51), RGWVWNQFF (SEQ ID NO: 52), RGWVWNQFFV (SEQ ID NO: 53), KRGW (SEQ ID NO: 54), KRGWV (SEQ ID NO: 55), KRGWVW (SEQ ID NO: 56), KRGWVWN (SEQ ID NO: 57), KRGWVWNQ (SEQ ID NO: 58), KRGWVWNQF (SEQ ID NO: 59), KRGWVWNQFF (SEQ ID NO: 60), KRGWVWNQFFV (SEQ ID NO: 61), DWIWNQM (SEQ ID NO: 62), DWIWNQMH (SEQ ID NO: 63), DWIWNQMHI (SEQ ID NO: 64), WIWNQM (SEQ ID NO: 65), WIWNQMH (SEQ ID NO: 66), WIWNQMHI (SEQ ID NO: 67), RDW, RDWI (SEQ ID NO: 68), RDWIW (SEQ ID NO: 69), RDWIWN (SEQ ID NO: 70), RDWIWNQ (SEQ ID NO: 71), RDWIWNQM (SEQ ID NO: 72), RDWIWNQMH (SEQ ID NO: 73), RDWIWNQMHI (SEQ ID NO: 74), KRDW (SEQ ID NO: 75), KRDWI (SEQ ID NO: 76), KRDWIW (SEQ ID NO: 77), KRDWIWN (SEQ ID NO: 78), KRDWIWNQ (SEQ ID NO: 79), KRDWIWNQM (SEQ ID NO: 80), KRDWIWNQMH (SEQ ID NO: 81), KRDWIWNQMHI (SEQ ID NO: 82), SWMWNQF (SEQ ID NO: 83), SWMWNQFF (SEQ ID NO: 84), SWMWNQFFL (SEQ ID NO: 85), WMWNQF (SEQ ID NO: 86), WMWNQFF (SEQ ID NO: 87), WMWNQFFL (SEQ ID NO: 88), RSW, RSWM (SEQ ID NO: 89), RSWMW (SEQ ID NO:90), RSWMWN (SEQ ID NO: 91), RSWMWNQ (SEQ ID NO: 92), RSWMWNQF (SEQ ID NO: 93), RSWMWNQFF (SEQ ID NO: 94), RSWMWNQFFL (SEQ ID NO: 95), KRSW (SEQ ID NO: 96), KRSWM (SEQ ID NO: 97), KRSWMW (SEQ ID NO: 98), KRSWMWN (SEQ ID NO: 99), KRSWMWNQ (SEQ ID NO: 100), KRSWMWNQF (SEQ ID NO: 101), KRSWMWNQFF (SEQ ID NO: 102), KRSWMWNQFFL (SEQ ID NO: 103), SWVWNQF (SEQ ID NO: 104), SWVWNQFF (SEQ ID NO: 105), SWVWNQFFV (SEQ ID NO: 106), WVWNQF (SEQ ID NO: 44), WVWNQFF (SEQ ID NO: 45), WVWNQFFV (SEQ ID NO: 46), RSWV (SEQ ID NO: 107), RSWVW (SEQ ID NO: 108), RSWVWN (SEQ ID NO: 109), RSWVWNQ (SEQ ID NO: 110), RSWVWNQF (SEQ ID NO: 111), RSWVWNQFF (SEQ ID NO: 112), RSWVWNQFFV (SEQ ID NO: 113), KRSWV (SEQ ID NO: 114), KRSWVW (SEQ ID NO: 115), KRSWVWN (SEQ ID NO: 116), KRSWVWNQ (SEQ ID NO: 117), KRSWVWNQF (SEQ ID NO: 118), KRSWVWNQFF (SEQ ID NO: 119), KRSWVWNQFFV (SEQ ID NO: 120), GWVWNQM (SEQ ID NO: 121), GWVWNQMF (SEQ ID NO: 122), GWVWNQMFV (SEQ ID NO: 123), RGWVWNQM (SEQ ID NO: 124), RGWVWNQMF (SEQ ID NO: 125), RGWVWNQMFV (SEQ ID NO: 126), KRGWVWNQM (SEQ ID NO: 127), KRGWVWNQMFV (SEQ ID NO: 128), GWVWNQFFL (SEQ ID NO: 129), RGWVWNQFFL (SEQ ID NO: 130), KRGWVWNQFFL (SEQ ID NO: 131), AWVIPPI (SEQ ID NO: 132), AWVIPPIS (SEQ ID NO: 133), AWVIPPISV (SEQ ID NO: 134), WVIPPI (SEQ ID NO: 135), WVIPPIS (SEQ ID NO: 136), WVIPPISV (SEQ ID NO: 137), RAW, RAWV (SEQ ID NO: 138), RAWVI (SEQ ID NO: 139), RAWVIP (SEQ ID NO: 140), RAWVIPP (SEQ ID NO: 141), RAWVIPPI (SEQ ID NO: 142), RAWVIPPIS (SEQ ID NO: 143), RAWVIPPISV (SEQ ID NO: 144), KRAW (SEQ ID NO: 145), KRAWV (SEQ ID NO: 146), KRAWVI (SEQ ID NO: 147), KRAWVIP (SEQ ID NO: 148), KRAWVIPP (SEQ ID NO: 149), KRAWVIPPI (SEQ ID NO: 150), KRAWVIPPIS (SEQ ID NO: 151), VWN, VWNQ (SEQ ID NO: 152), VWNQM (SEQ ID NO: 153), VWNQF (SEQ ID NO: 154), VWNQMF (SEQ ID NO: 155), VWNQFF (SEQ ID NO: 156), WNQ, WNQM (SEQ ID NO: 157), WNQF (SEQ ID NO: 158), WNQFF (SEQ ID NO: 159), IWN, IWNQ (SEQ ID NO: 160), IWNQM (SEQ ID NO: 161), IWNQMH (SEQ ID NO: 162), WNQM (SEQ ID NO: 157), WNQMH (SEQ ID NO: 163), MWN, MWNQ (SEQ ID NO: 164), MWNQF (SEQ ID NO: 165), and MWNQFF (SEQ ID NO: 166).

The present invention further contemplates atypical cadherin Trp-containing CAR sequences from organisms other than human. Such Trp-containing CAR sequences may be identified based upon sequence similarity to the sequences provided herein, and the ability to modulate an atypical cadherin-mediated function, such as cell adhesion, may be confirmed as described herein.

It will be apparent that certain of the peptide sequences provided above may modulate a function mediated by multiple atypical cadherins. In general, peptides comprising a greater number of consecutive residues derived from a particular atypical cadherin have a greater specificity for that cadherin. In addition, further flanking sequences may be included to enhance specificity. Such flanking sequences may be identified based on the sequences provided in FIG. 2, or based on published sequences. To achieve specificity (i.e., modulation of a particular atypical cadherin function that is enhanced relative to the modulation of a function mediated by a different cadherin), the addition of 2 to 5 flanking residues (preferably at least one residue on either side of the Trp-containing CAR sequence) is generally sufficient. Specificity may be evaluated using assays for the ability to inhibit functions mediated by particular cadherins, as described herein.

The term "desmosomal cadherin" refers to a nonclassical cadherin that is present within the intercellular junction known as the desmosome. Desmosomal cadherins include desmogleins and desmocollins (see e.g., King et al., *Genomics* 18:185-194, 1993; Parker et al., *J. Biol. Chem.* 266:10438-10445, 1991; King et al., *J. Invest. Dermatol.* 105:314-321, 1995; Kawamura et al., *J. Biol. Chem.* 269:26295-26302, 1994; Wheeler et al., *Proc. Natl. Acad. Sci. USA* 88:4796-4800; and Koch et al., *Eur. J. Cell. Biol.* 55:200-208, 1991). Desmogleins and desmocollins are expressed by cells that possess desmosomes, such as epithelial cells, cardiac muscle cells and meningeal cells. These cadherins are involved in intercellular adhesion of such cells, and may function in a heterotypic manner, whereby a desmocollin isoform and a desmoglein isoform are both required for adhesion. Desmogleins and desmocollins are involved in a number of autoimmune blistering disorders, such as pemphigus vulgaris, pemphigus foliaceus and intercellular IgA dermatosis, and have been shown to have reduced expression in some human carcinomas. The partial sequences of extracellular domains of known desmosomal cadherins are shown in FIG. 2.

A Trp-containing CAR sequence of a desmosomal cadherin, as used herein, is an amino acid sequence that comprises a Trp residue, is present within a naturally occurring desmosomal cadherin, and is capable of detectably modulating a desmosomal cadherin-mediated function, such as cell adhesion, as described herein. In other words, contacting a desmosomal cadherin-expressing cell with a peptide comprising a Trp-containing CAR sequence results in a detectable change in a desmosomal cadherin-mediated function using at least one of the representative assays provided herein. Trp-containing CAR sequences are generally recognized in vivo by a desmosomal cadherin or other adhesion molecule (i.e., a molecule that mediates cell adhesion via a receptor on the cell surface), and are necessary for maximal heterophilic and/or homophilic interaction. Trp-containing CAR sequences may be of any length, but generally comprise at least 3, 4, 5, 6, 7, 8, or 9 amino acid residues and/or at most 10-50 amino acid residues (including all the integer values therebetween).

It has been found, within the context of the present invention, that certain desmosomal cadherin Trp-containing CAR sequences share the consensus sequence:

Glu/Ala/Arg-Trp-Ile/Val/Ala-Lys/Thr/Pro-Phe/Ala/Ile-Ala/Pro (SEQ ID NO:167)

Within the consensus sequence, "Glu/Ala/Arg" is Glu, Ala or Arg, "Ile/Val/Ala" is Ile, Val or Ala, "Lys/Thr/Pro" is Lys, Thr or Pro, "Phe/Ala/Ile" is Phe, Ala or Ile, and "Ala/Pro" is Ala or Pro.

In certain embodiments, desmosomal cadherin Trp-containing CAR sequences comprise the sequence Glu/Ala-Trp-Ile/Val-Lys/Thr-Phe/Ala-Ala/Pro (SEQ ID NO:1) or a portion thereof, where "Glu/Ala" is Glu or Ala, "Ile/Val" is Ile or Val, "Lys/Thr" is Lys or Thr, "Phe/Ala" is Phe or Ala, and "Ala/Pro" is Ala or Pro. In some other embodiments, desmosomal cadherin Trp-containing CAR sequences comprise the sequence Arg-Trp-Ala-Pro-Ile-Pro (SEQ ID NO:2) or a portion thereof.

Representative desmosomal cadherin Trp-containing CAR sequences are provided within Table I. Trp-containing CAR sequences specifically provided herein further include portions of such representative Trp-containing CAR sequences, as well as longer polypeptides that comprise at least a portion of such sequences. Additional desmosomal cadherin Trp-containing CAR sequences may be identified based on sequence homology to the desmosomal cadherin Trp-containing CAR sequences provided herein, and based on the ability of a peptide comprising such a sequence to modulate a desmosomal cadherin-mediated function within a representative assay described herein. Within certain embodiments, a modulating agent comprises at least three, four, five and six consecutive residues of a desmosomal cadherin Trp-containing CAR sequence that satisfies the above consensus sequence.

TABLE II

Representative Desmosomal Cadherin Trp-Containing CAR Sequences

| Cadherin | CAR Sequence |
| --- | --- |
| Human desmoglein 1 | EWIKFA (SEQ ID NO: 168) |
| Bull desmoglein 1 | EWIKFA (SEQ ID NO: 168) |
| Human desmoglein 2 | AWITAP (SEQ ID NO: 169) |

TABLE II-continued

Representative Desmosomal Cadherin Trp-Containing CAR Sequences

| Cadherin | CAR Sequence |
| --- | --- |
| Human desmoglein 3 | EWVKFA (SEQ ID NO: 170) |
| Mouse desmoglein 3 | EWVKFA (SEQ ID NO: 170) |
| Human desmoglein 4 | EWIKFA (SEQ ID NO: 168) |
| Mouse desmoglein 4 | EWIKFA (SEQ ID NO: 168) |
| Mouse desmoglein 5 | EWIKFA (SEQ ID NO: 168) |
| Mouse desmoglein 6 | EWIKFA (SEQ ID NO: 168) |
| Human desmocollin 1 | RWAPTP (SEQ ID NO: 2) |
| Mouse desmocollin 1 | RWAPIP (SEQ ID NO: 2) |
| Bull desmocollin 1 | RWAPIP (SEQ ID NO: 2) |
| Human desmocollin 2 | RWAPIP (SEQ ID NO: 2) |
| Dog desmocollin 2 | RWAPIP (SEQ ID NO: 2) |
| Human desmocollin 3 | RWAPTP (SEQ ID NO: 2) |
| Mouse desmocollin 3 | RWAPIP (SEQ ID NO: 2) |
| Bull desmocollin 3 | RWAPIP (SEQ ID NO: 2) |
| Human desmocollin 4 | RWAPIP (SEQ ID NO: 2) |
| CONSENSUS | RWAPIP (SEQ ID NO: 2) E IKFA A VTA |

Desmosomal cadherin Trp-containing CAR sequences are generally physically located within the extracellular domain of a cadherin molecule in or near the binding site of an adhesion molecule (i.e., within 10 amino acids, and preferably within 5 amino acids). The location of a binding site may generally be determined using well-known techniques, such as evaluating the ability of a portion of the desmosomal cadherin to bind to the same desmosomal cadherin or to another adhesion molecule. Any standard binding assay may be employed for such an evaluation. Recognition of a Trp-containing CAR sequence by the desmosomal cadherin or other adhesion molecule results in a measurable effect on an adhesion molecule function, such as cell adhesion. Peptides comprising a Trp-containing CAR sequence generally inhibit such a function unless linked, as described herein, to form an enhancer of adhesion molecule function.

Exemplary desmosomal Trp-containing CAR sequences include, but are not limited to RWA, RWAP (SEQ ID NO: 171), RWAPI (SEQ ID NO: 172), RWAPIP (SEQ ID NO: 2), RWAPIPC (SEQ ID NO: 173), RWAPIPCS (SEQ ID NO: 174), RWAPIPCSM (SEQ ID NO: 175), WAP, WAPI (SEQ ID NO: 176), WAPIP (SEQ ID NO: 177), WAPIPC (SEQ ID NO: 178), WAPIPCS (SEQ ID NO 179), WAPIPCSM (SEQ ID NO: 180), RWAPIPCSL (SEQ ID NO: 181), WAPIPCSL (SEQ ID NO: 182), RWAPIPCA (SEQ ID NO: 183), WAPIPCA (SEQ ID NO: 184), RWAPIPCAS (SEQ ID NO: 185), WAPIPCAS (SEQ ID NO: 186), EWI, EWIK (SEQ ID NO: 187), EWIKF (SEQ ID NO: 188), EWIKFA (SEQ ID NO: 168), EWIKFAA (SEQ ID NO: 189), EWIKFAAA (SEQ ID NO: 190), EWIKFAAAC (SEQ ID NO: 191), WIK, WIKF (SEQ ID NO: 192), WIKFA (SEQ ID NO: 193), WIKFAA (SEQ ID NO: 194), WIKFAAA (SEQ ID NO: 195), WIKFAAAC (SEQ ID NO: 196), EWV, EWVK (SEQ ID NO: 197), EWVKF (SEQ ID NO: 198), EWVKFA (SEQ ID NO: 170), EWVKFAK (SEQ ID NO: 199), EWVKFAKP (SEQ ID NO: 200), EWVKFAKPC (SEQ ID NO: 201), WVK, WVKF (SEQ ID NO: 202), WVKFA (SEQ ID NO: 203), WVKFAK (SEQ ID NO: 204), WVKFAKP (SEQ ID NO: 205), WVKFAKPC (SEQ ID NO: 206), AWI, AWIT (SEQ ID NO: 207), AWITA (SEQ ID NO: 208), AWITAP (SEQ ID NO: 169), AWITAPV (SEQ ID NO: 209), AWITAPVA (SEQ ID NO: 210), AWITAPVAL (SEQ ID NO: 211), WIT, WITA (SEQ ID NO: 212), WITAP (SEQ ID NO:

213), WITAPV (SEQ ID NO: 214), WITAPVA (SEQ ID NO: 215), and WITAPVAL (SEQ ID NO: 216).

The present invention further contemplates desmosomal cadherin Trp-containing CAR sequences from organisms other than human. Such Trp-containing CAR sequences may be identified based upon sequence similarity to the sequences provided herein, and the ability to modulate a desmosomal cadherin-mediated function, such as cell adhesion, may be confirmed as described herein.

It will be apparent that certain of the peptide sequences provided above may modulate a function mediated by multiple desmosomal cadherins. In general, peptides comprising a greater number of consecutive residues derived from a particular desmosomal cadherin have a greater specificity for that cadherin. In addition, further flanking sequences may be included to enhance specificity. Such flanking sequences may be identified based on the sequences provided in FIG. 2, or based on published sequences. To achieve specificity (i.e., modulation of a particular desmosomal cadherin function that is enhanced relative to the modulation of a function mediated by a different cadherin), the addition of 2 to 5 flanking residues (preferably at least one residue on either side of the Trp-containing CAR sequence) is generally sufficient. Specificity may be evaluated using assays for the ability to inhibit functions mediated by particular cadherins, as described herein.

Modulating agents, or peptide portions thereof, may generally comprise from about 3 to about 100 amino acid residues. In certain embodiments, the modulating agents contain at least 3, 4, 5, 6, 7, 8, or 9 amino acids and/or at most 10-100 amino acid residues including all the integer values therebetween. In some embodiments where non-peptide linkers are employed, each Trp-containing CAR sequence or its conservative analogue thereof may be present within a peptide that contains at least 3, 4, 5, 6, 7, 8, or 9 amino acids an/or at most 10-50 amino acids, including all integer values therebetween, e.g., 10, 15, 20, 25, 30, 35, 40, 45, or 50 amino acid residues. In certain preferred embodiments, modulating agents or peptide portions thereof contain at least 3, 4, 5, 6, 7, 8, or 9 amino acids and/or at most 10-50 amino acids including all integer values therebetween, e.g., 10, 15, 20, 25, 30, 35, 40, 45, and 50 consecutive residues from a naturally occurring (used interchangeably with "native") cadherin molecule.

As noted above, modulating agents as described herein may comprise an analogue or mimetic of a non-classical cadherin Trp-containing CAR sequence. An analogue generally retains at least 50% identity to a native nonclassical cadherin Trp-containing CAR sequence and at least 50% of a nonclassical cadherin-mediated function as described herein. In this context, the percent identity of two amino acid sequences or of two nucleic acids is determined using BLAST programs of Altschul et al. (*J. Mol. Biol.* 215: 403-10, 1990) with their default parameters. These programs implement the algorithm of Karlin and Altschul (*Proc. Natl. Acad. Sci. USA* 87:2264-8, 1990) modified as in Karlin and Altschul (*Proc. Natl. Acad. Sci. USA* 90:5873-7, 1993). BLAST programs are available, for example, at the web site http://www.ncbi.nim.nih.gov.

The analogues of the present invention preferably contain at least three, four or five consecutive residues of a nonclassical cadherin Trp-containing CAR sequence. An analogue may contain any of a variety of amino acid substitutions, additions, deletions and/or modifications (e.g., side chain modifications).

A "conservative analogue" of a Trp-containing CAR sequence is a Trp-containing CAR sequence with one, two, three or more conservative amino acid substitutions and without any non-conservative amino acid substitutions.

A "conservative substitution" is one in which an amino acid is substituted for another amino acid that has similar properties, such that one skilled in the art of peptide chemistry would expect the secondary structure and hydropathic nature of the polypeptide to be substantially unchanged. Amino acid substitutions may generally be made on the basis of similarity in polarity, charge, solubility, hydrophobicity, hydrophilicity and/or the amphipathic nature of the residues. For example, negatively charged amino acids include aspartic acid and glutamic acid; positively charged amino acids include lysine and arginine; and amino acids with uncharged polar head groups having similar hydrophilicity values include leucine, isoleucine and valine; glycine and alanine; asparagine and glutamine; and serine, threonine, phenylalanine and tyrosine. Other groups of amino acids that may represent conservative changes include: (1) ala, pro, gly, glu, asp, gln, asn, ser, thr; (2) cys, ser, tyr, thr; (3) val, ile, leu, met, ala, phe; (4) lys, arg, his; and (5) phe, tyr, trp, his.

A "non-conservative analogue" of a Trp-containing CAR sequence is a Trp-containing CAR sequence with at least one amino acid substitution (i.e., non-conservative amino acid substitution) other than a conservative amino acid substitution as is defined above, at least one amino acid deletion, and/or at least one amino acid insertion.

A "peptidomimetic" is a compound in which at least a portion of a Trp-containing CAR sequence is replaced with a non-peptide structure, but the three-dimensional structure of the Trp-containing CAR sequence remains substantially the same as that of the Trp-containing CAR sequence. In other words, one, two, three, four, five or six amino acid residues within the Trp-containing CAR sequence may be replaced by one or more chemical structures so that at least one peptide bond in the Trp-containing CAR sequence is eliminated. A peptidomimetic of the present invention is also capable of modulating a function mediated by a nonclassical cadherin.

Modulating agents, or peptide portions thereof, may be linear or cyclic peptides. In certain embodiments, the linear or cyclic peptides may contain least one terminal amino acid residue that is modified (e.g., the N-terminal amino group is modified by, for example, acetylation or alkoxybenzylation and/or an amide or ester is formed at the C-terminus).

The term "cyclic peptide," as used herein, refers to a peptide or salt thereof that comprises (1) an intramolecular covalent bond between two non-adjacent residues and (2) at least one nonclassical cadherin Trp-containing CAR sequence or an analogue thereof. The intramolecular bond may be a backbone to backbone, side-chain to backbone or side-chain to side-chain bond (i.e., terminal functional groups of a linear peptide and/or side chain functional groups of a terminal or interior residue may be linked to achieve cyclization). Preferred intramolecular bonds include, but are not limited to, disulfide, amide and thioether bonds. One or more of any of the above nonclassical cadherin Trp-containing CAR sequences, or an analogue or mimetic thereof, may be incorporated into a cyclic peptide, with or without one or more other adhesion molecule binding sites. Additional adhesion molecule binding sites are described in greater detail below.

The size of a cyclic peptide ring may contain at least 3, 4, 5, 6, 7, 8, or 9 amino acid residues and/or contain at most 10-100 amino acid residues including all the integer values therebetween. Additional residue(s) may be present on the N-terminal and/or C-terminal side of a nonclassical cadherin Trp-containing CAR sequence, and may be derived from sequences that flank a nonclassical cadherin Trp-containing CAR sequence, with or without amino acid substitutions and/or other modifications. Alternatively, additional residues present on one or both sides of the Trp-containing CAR sequence(s) may be unrelated to an endogenous sequence (e.g., residues that facilitate cyclization, purification or other manipulation and/or residues having a targeting or other function).

In certain preferred embodiments, an atypical cadherin modulating agent comprises a cyclic peptide of which the cyclic peptide ring comprises the sequence G/S/D-W-V/M/I-W-N-Q (SEQ ID NO:5), the sequence AWVIPP (SEQ ID NO:6), or a portion thereof. Exemplary cyclic peptides have the following formula:

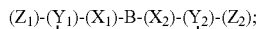

$(Z_1)-(Y_1)-(X_1)-B-(X_2)-(Y_2)-(Z_2);$

In this formula, B represents an amino acid sequence selected from the following sequences: DWIWNQ (SEQ ID NO: 17), SWMWNQ (SEQ ID NO: 18), SWVWNQ (SEQ ID NO: 19), GWVWNQ (SEQ ID NO: 16), AWVIPP (SEQ ID NO: 6), GWVWN (SEQ ID NO: 22), DWIWN (SEQ ID NO: 26), SWMWN (SEQ ID NO: 30), SWVWN (SEQ ID NO: 34), GWVWN (SEQ ID NO: 22), AWVIP (SEQ ID NO: 38), GWVW (SEQ ID NO: 21), DWIW (SEQ ID NO: 25), SWMW (SEQ ID NO: 29), SWVW (SEQ ID NO: 33), GWVW (SEQ ID NO: 21), AWVI (SEQ ID NO: 37), GWV, DWI, SWM, SWV, GWV, AWV, VWN, VWNQ (SEQ ID NO: 152), VWNQM (SEQ ID NO: 153), VWNQF (SEQ ID NO: 154), VWNQMF (SEQ ID NO: 155), VWNQFF (SEQ ID NO: 156), WNQ, WNQM (SEQ ID NO: 157), WNQF (SEQ ID NO: 158), WNQFF (SEQ ID NO: 159), IWN, IWNQ (SEQ ID NO: 160), IWNQM (SEQ ID NO: 161), IWNQMH (SEQ ID NO: 162), WNQM (SEQ ID NO: 157), WNQMH (SEQ ID NO: 163), MWN, MWNQ (SEQ ID NO: 164), MWNQF (SEQ ID NO: 165), and MWNQFF (SEQ ID NO: 166). $X_1$ and $X_2$ are optional, and if present, are amino acid residues or combinations of amino acid residues linked by peptide bonds. $X_1$ and $X_2$ may be identical to, or different from, each other. In general, $X_1$ and $X_2$ independently range in size from 0 to 10 residues, such that the sum of residues contained within $X_1$ and $X_2$ ranges from 1 to 12. $Y_1$ and $Y_2$ are amino acid residues, and a covalent bond is formed between residues $Y_1$ and $Y_2$. $Y_1$ and $Y_2$ may be identical to, or different from, each other. $Z_1$ and $Z_2$ are optional, and if present, are amino acid residues or combinations of amino acid residues linked by peptide bonds. $Z_1$ and $Z_2$ may be identical to, or different from, each other.

Cyclic peptides may be used as atypical cadherin modulating agents without modification, or may be incorporated into a modulating agent. Exemplary cyclic peptides include, but are not limited to, the following sequences where the underlines represent the amino acid residues within cyclic peptide rings: GWV, GWVW (SEQ ID NO: 21), GWVWN (SEQ ID NO: 22), GWVWNQ (SEQ ID NO: 16), WVW, WVWN (SEQ ID NO: 23), WVWNQ (SEQ ID NO: 24), DWI, DWIW (SEQ ID NO: 25), DWIWN (SEQ ID NO: 26), DWIWNQ (SEQ ID NO: 17), WIW, WIWN (SEQ ID NO: 27), WIWNQ (SEQ ID NO: 28), SWM, SWMW (SEQ ID NO: 29), SWMWN (SEQ ID NO: 30), SWMWNQ (SEQ ID NO: 18), WMW, WMWN (SEQ ID NO: 31), WMWNQ (SEQ ID NO: 32), SWV, SWVW (SEQ ID NO: 33), SWVWN (SEQ ID NO: 34), SWVWNQ (SEQ ID NO: 19), GWM, GWMW (SEQ ID NO: 35), GWMWN (SEQ ID NO: 36), GWMWNQ (SEQ ID NO: 20), AWV, AWVI (SEQ ID NO: 37), AWVIP (SEQ ID NO: 38), AWVIPP (SEQ ID NO: 6), WVI, WVIP (SEQ ID NO: 39), WVIPP (SEQ ID NO: 40), GWVWNQF (SEQ ID NO: 41), GWVWNQFF (SEQ ID NO: 42), GWVWNQFFV (SEQ ID NO: 43), WVWNQF (SEQ ID NO: 44), WVWNQFF (SEQ ID NO: 45), WVWNQFFV (SEQ ID NO: 46), RGW, RGWV (SEQ ID NO: 47), RGWVW (SEQ ID NO: 48), RGWVWN (SEQ ID NO: 49), RGWVWNQ (SEQ ID NO: 50), RGWVWNQF (SEQ ID NO: 51), RGWVWNQFF (SEQ ID NO: 52), RGWVWNQFFV (SEQ ID NO: 53), KRGW (SEQ ID NO: 54), KRGWV (SEQ ID NO: 55), KRGWVW (SEQ ID NO: 56), KRGWVWN (SEQ ID NO: 57), KRGWVWNQ (SEQ ID NO: 58), KRGWVWNQF (SEQ ID NO: 59), KRGWVWNQFF (SEQ ID NO: 60), KRGWVWNQFFV (SEQ ID NO: 61), DWIWNQM (SEQ ID NO: 62), DWIWNQMH (SEQ ID NO: 63), DWIWNQMHI (SEQ ID NO: 64), WIWNQM (SEQ ID NO: 65), WIWNQMH (SEQ ID NO: 66), WIWNQMHI (SEQ ID NO: 67), RDW, RDWI (SEQ ID NO: 68), RDWIW (SEQ ID NO: 69), RDWIWN (SEQ ID NO: 70), RDWIWNQ (SEQ ID NO: 71), RDWIWNQM (SEQ ID NO: 72), RDWIWNQMH (SEQ ID NO: 73), RDWIWNQMHI (SEQ ID NO: 74), KRDW (SEQ ID NO: 75), KRDWI (SEQ ID NO: 76), KRDWIW (SEQ ID NO: 77), KRDWIWN (SEQ ID NO: 78), KRDWIWNQ (SEQ ID NO: 79), KRDWIWNQM (SEQ ID NO: 80), KRDWIWNQMH (SEQ ID NO: 81), KRDWIWNQMHI (SEQ ID NO: 82), SWMWNQF (SEQ ID NO: 83), SWMWNQFF (SEQ ID NO: 84), SWMWNQFFL (SEQ ID NO: 85), WMWNQF (SEQ ID NO: 86), WMWNQFF (SEQ ID NO: 87), WMWNQFFL (SEQ ID NO: 88), RSW, RSWM (SEQ ID NO: 89), RSWMW (SEQ ID NO: 90), RSWMWN (SEQ ID NO: 91), RSWMWNQ (SEQ ID NO: 92), RSWMWNQF (SEQ ID NO: 93), RSWMWNQFF (SEQ ID NO: 94), RSWMWNQFFL (SEQ ID NO: 95), KRSW (SEQ ID NO: 96), KRSWM (SEQ ID NO: 97), KRSWMW (SEQ ID NO: 98), KRSWMWN (SEQ ID NO: 99), KRSWMWNQ (SEQ ID NO: 100), KRSWMWNQF (SEQ ID NO: 101), KRSWMWNQFF (SEQ ID NO: 102), KRSWMWNQFFL (SEQ ID NO: 103), SWVWNQF (SEQ ID NO: 104), SWVWNQFF (SEQ ID NO: 105), SWVWNQFFV (SEQ ID NO: 106), WVWNQF (SEQ ID NO: 44), WVWNQFF (SEQ ID NO: 45), WVWNQFFV (SEQ ID NO: 46), RSWV (SEQ ID NO: 107), RSWVW (SEQ ID NO: 108), RSWVWN (SEQ ID NO: 109), RSWVWNQ (SEQ ID NO: 110), RSWVWNQF (SEQ ID NO: 111), RSWVWNQFF (SEQ ID NO: 112), RSWVWNQFFV (SEQ ID NO: 113), KRSWV (SEQ ID NO: 114), KRSWVW (SEQ ID NO: 115), KRSWVWN (SEQ ID NO: 116), KRSWVWNQ (SEQ ID NO: 117), KRSWVWNQF (SEQ ID NO: 118), KRSWVWNQFF (SEQ ID NO: 119), KRSWVWNQFFV (SEQ ID NO: 120), GWVWNQM (SEQ ID NO: 121), GWVWNQMF (SEQ ID NO: 122), GWVWNQMFV (SEQ ID NO: 123), RGWVWNQM (SEQ ID NO: 124), RGWVWNQMF (SEQ ID NO: 125), RGWVWNQMFV (SEQ ID NO: 126), KRGWVWNQM (SEQ ID NO: 127), KRGWVWNQMFV (SEQ ID NO: 128), GWVWNQFFL (SEQ ID NO: 129), RGWVWNQFFL (SEQ ID NO: 130), KRGWVWNQFFL (SEQ ID NO: 131), AWVIPPI (SEQ ID NO: 132), AWVIPPIS (SEQ ID NO: 133), AWVIPPISV (SEQ ID NO: 134), WVIPPI (SEQ ID NO: 135), WVIPPIS (SEQ ID NO: 136), WVIPPISV (SEQ ID NO: 137), RAW, RAWV (SEQ ID NO: 138), RAWVI (SEQ ID NO: 139), RAWVIP (SEQ ID NO: 140), RAWVIPP (SEQ ID NO: 141), RAWVIPPI (SEQ ID NO: 142), RAWVIPPIS (SEQ ID NO: 143), RAWVIPPISV (SEQ ID NO: 144), KRAW (SEQ ID NO: 145), KRAWV (SEQ ID NO: 146), KRAWVI (SEQ ID NO: 147), KRAWVIP (SEQ ID NO: 148), KRAWVIPP (SEQ ID NO: 149), KRAWVIPPI (SEQ ID NO: 150), KRAWVIPPIS (SEQ ID NO: 151), VWN, VWNQ (SEQ ID NO: 152), VWNQM (SEQ ID NO: 153), VWNQF (SEQ ID NO: 154), VWNQMF (SEQ ID NO: 155), VWNQFF (SEQ ID NO: 156), WNQ, WNQM (SEQ ID NO: 157), WNQF (SEQ ID NO: 158), WNQFF (SEQ ID NO: 159), IWN, IWNQ (SEQ ID NO: 160), IWNQM (SEQ ID NO: 161), IWNQMH (SEQ ID NO: 162), WNQM (SEQ ID NO: 157), WNQMH (SEQ ID NO: 163), MWN, MWNQ (SEQ ID NO: 164), MWNQF (SEQ ID NO: 165), and MWNQFF (SEQ ID NO: 166).

Additional exemplary cyclic peptides include the following sequences where the underlines represent the amino acid residues within cyclic peptide rings: CGWVC (SEQ ID NO: 217), CGWVWC (SEQ ID NO: 218), CGWVWNC (SEQ ID NO: 219), CGWVWNQC (SEQ ID NO: 220), CWVWC (SEQ ID NO: 221), CWVWNC (SEQ ID NO: 222), CWVWNQC (SEQ ID NO: 223), CDWIC (SEQ ID NO: 224), CDWIWC (SEQ ID NO: 225), CDWIWNC (SEQ ID NO: 226), CDWIWNQC (SEQ ID NO: 227), CWIWC (SEQ ID NO: 228), CWIWNC (SEQ ID NO: 229), CWIWNQC (SEQ ID NO: 230), CSWMC (SEQ ID NO: 231), CSWMWC (SEQ ID NO: 232), CSWMWNC (SEQ ID NO: 233), CSWMWNQC (SEQ ID NO: 234), CWMWC (SEQ ID NO: 235), CWMWNC (SEQ ID NO: 236), CWMWNQC (SEQ ID NO: 237), CSWVC (SEQ ID NO: 238), CSWVWC (SEQ ID NO: 239), CSWVWNC (SEQ ID NO: 240), CSWVWNQC (SEQ ID NO: 241), CGWMC (SEQ ID NO: 242), CGWMWC (SEQ ID NO: 243), CGWMWNC (SEQ ID NO: 244), CGWMWNQC (SEQ ID NO: 245), CAWVC (SEQ ID NO: 246), CAWVIC (SEQ ID NO: 247), CAWVIPC (SEQ ID NO: 248), CAWVIPPC (SEQ ID NO: 249), CWVIC (SEQ ID NO: 250), CWVIPC (SEQ ID NO: 251), CWVIPPC (SEQ ID NO: 252), CGWVWNQFC (SEQ ID NO: 253), CGWVWNQFFC (SEQ ID NO: 254), CGWVWNQFFVC (SEQ ID NO: 255), CWVWNQFC (SEQ ID NO: 256), CWVWNQFFC (SEQ ID NO: 257), CWVWNQFFVC (SEQ ID NO: 258), CRGWC (SEQ ID NO: 259), CRGWVC (SEQ ID NO: 260), CRGWVWC (SEQ ID NO: 261), CRGWVWNC (SEQ ID NO: 262), CRGWVWNQC (SEQ ID NO: 263), CRGWVWNQFC (SEQ ID NO: 264), CRGWVWNQFFC (SEQ ID NO: 265), CRGWVWNQFFVC (SEQ ID NO: 266), CKRGWC (SEQ ID NO: 267), CKRGWVC (SEQ ID NO: 268), CKRGWVWC (SEQ ID NO: 269), CKRGWVWNC (SEQ ID NO: 270), CKRGWVWNQC (SEQ ID NO: 271), CKRGWVWNQFC (SEQ ID NO: 272), CKRGWVWNQFFC (SEQ ID NO: 273), CKRGWVWNQFFVC (SEQ ID NO: 274), CDWIWNQMC (SEQ ID NO: 275), CDWIWNQMHC (SEQ ID NO: 276), CDWIWNQMHIC (SEQ ID NO: 277), CWIWNQMC (SEQ ID NO: 278), CWIWNQMHC (SEQ ID NO: 279), CWIWNQMHIC (SEQ ID NO: 280), CRDWC (SEQ ID NO: 281), CRDWIC (SEQ ID NO: 282), CRDWIWC (SEQ ID NO: 283), CRDWIWNC (SEQ ID NO: 284), CRDWIWNQC (SEQ ID NO: 285), CRDWIWNQMC (SEQ ID NO: 286), CRDWIWNQMHC (SEQ ID NO: 287), CRDWIWNQMHIC (SEQ ID NO: 288), CKRDWC (SEQ ID NO: 289), CKRDWIC (SEQ ID NO: 290), CKRDWIWC (SEQ ID NO: 291), CKRDWIWNC (SEQ ID NO: 292), CKRDWIWNQC (SEQ ID NO: 293), CKRDWIWNQMC (SEQ ID NO: 294), CKRDWIWNQMHC (SEQ ID NO: 295), CKRDWIWNQMHIC (SEQ ID NO: 296), CSWMWNQFC (SEQ ID NO: 297), CSWMWNQFFC (SEQ ID NO: 298), CSWMWNQFFLC (SEQ ID NO: 299), CWMWNQFC (SEQ ID NO: 300), CWMWNQFFC (SEQ ID NO: 301), CWMWNQFFLC (SEQ ID NO: 302), CRSWC (SEQ ID NO: 303), CRSWMC (SEQ ID NO: 304), CRSWMWC (SEQ ID NO: 305), CRSWMWNC (SEQ ID NO: 306), CRSWMWNQC (SEQ ID NO: 307), CRSWMWNQFC (SEQ ID NO: 308), CRSWMWNQFFC (SEQ ID NO: 309), CRSWMWNQFFLC (SEQ ID NO: 310), CKRSWC (SEQ ID NO: 311), CKRSWMC (SEQ ID NO: 312), CKRSWMWC (SEQ ID NO: 313), CKRSWMWNC (SEQ ID NO: 314), CKRSWMWNQC (SEQ ID NO: 315), CKRSWMWNQFC (SEQ ID NO: 316), CKRSWMWNQFFC (SEQ ID NO: 317), CKRSWMWNQFFLC (SEQ ID NO:318), CSWVWNQFC (SEQ ID NO: 319), CSWVWNQFFC (SEQ ID NO:320), CSWVWNQFFVC (SEQ ID NO:321), CWVWNQFC (SEQ ID NO: 256), CWVWNQFFC (SEQ ID NO: 257), CWVWNQFFVC (SEQ ID NO: 258), CRSWVC (SEQ ID NO: 322), CRSWVWC (SEQ ID NO: 323), CRSWVWNC (SEQ ID NO: 324), CRSWVWNQC (SEQ ID NO: 325), CRSWVWNQFC (SEQ ID NO: 326), CRSWVWNQFFC (SEQ ID NO: 327), CRSWVWNQFFVC (SEQ ID NO: 328), CKRSWVC (SEQ ID NO: 329), CKRSWVWC (SEQ ID NO: 330), CKRSWVWNC (SEQ ID NO: 331), CKRSWVWNQC (SEQ ID NO: 332), CKRSWVWNQFC (SEQ ID NO: 333), CKRSWVWNQFFC (SEQ ID NO: 334), CKRSWVWNQFFVC (SEQ ID NO: 335), CGWVWNQMC (SEQ ID NO: 336), CGWVWNQMFC (SEQ ID NO: 337), CGWVWNQMFVC (SEQ ID NO: 338), CRGWVWNQMC (SEQ ID NO: 339), CRGWVWNQMFC (SEQ ID NO: 340), CRGWVWNQMFVC (SEQ ID NO: 341), CKRGWVWNQMC (SEQ ID NO: 342), CKRGWVWNQMFVC (SEQ ID NO: 343), CGWVWNQFFLC (SEQ ID NO: 344), CRGWVWNQFFLC (SEQ ID NO: 345), CKRGWVWNQFFLC (SEQ ID NO: 346), CAWVIPPIC (SEQ ID NO: 347), CAWVIPPISC (SEQ ID NO: 348), CAWVIPPISVC (SEQ ID NO: 349), CWVIPPIC (SEQ ID NO: 350), CWVIPPISC (SEQ ID NO: 351, CWVIPPISVC (SEQ ID NO: 352), CRAWC (SEQ ID NO: 353), CRAWVC (SEQ ID NO: 354), CRAWVIC (SEQ ID NO: 355), CRAWVIPC (SEQ ID NO: 356), CRAWVIPPC (SEQ ID NO: 357), CRAWVIPPIC (SEQ ID NO: 358), CRAWVIPPISC (SEQ ID NO: 359), CRAWVIPPISVC (SEQ ID NO: 360), CKRAWC (SEQ ID NO: 361), CKRAWVC (SEQ ID NO: 362), CKRAWVIC (SEQ ID NO: 363), CKRAWVIPC (SEQ ID NO: 364), CKRAWVIPPC (SEQ ID NO: 365), CKRAWVIPPIC (SEQ ID NO: 366), CKRAWVIPPISC (SEQ ID NO: 367), CVWNC (SEQ ID NO: 368), CVWNQC (SEQ ID NO: 369), CVWNQMC (SEQ ID NO: 370), CVWNQFC (SEQ ID NO: 371), CVWNQMFC (SEQ ID NO: 372), CVWNQFFC (SEQ ID NO: 373), CWNQ (SEQ ID NO: 374), CWNQMC (SEQ ID NO: 375), CWNQFC (SEQ ID NO: 376), CWNQFFC (SEQ ID NO: 377), CIWNC (SEQ ID NO: 378), CIWNQC (SEQ ID NO: 379), CIWNQMC (SEQ ID NO: 380), CIWNQMHC (SEQ ID NO: 381), CWNQMC (SEQ ID NO: 375), CWNQMHC (SEQ ID NO: 382), CMWNC (SEQ ID NO: 383), CMWNQC (SEQ ID NO: 384), CMWNQFC (SEQ ID NO: 385), and CMWNQFFC (SEQ ID NO: 386).

Additional exemplary cyclic peptides also include the following sequences where the underlines represent the amino acid residues within cyclic peptide rings: KGWVD (SEQ ID NO: 387), KGWVWD (SEQ ID NO: 388), KGWVWND (SEQ ID NO: 389), KGWVWNQD (SEQ ID NO: 390), KWVWD (SEQ ID NO: 391), KWVWND (SEQ ID NO: 392), KWVWNQD (SEQ ID NO: 393), KDWID (SEQ ID NO: 394), KDWIWD (SEQ ID NO: 395), KDWIWND (SEQ ID NO: 396), KDWIWNQD (SEQ ID NO: 397), KWIWD (SEQ ID NO: 398), KWIWND (SEQ ID NO: 399), KWIWNQD (SEQ ID NO: 400), KSWMD (SEQ ID NO:

401), KSWMWD (SEQ ID NO: 402), KSWMWND (SEQ ID NO: 403), KSWMWNQD (SEQ ID NO: 404), KWMWD (SEQ ID NO: 405), KWMWND (SEQ ID NO: 406), KWMWNQD (SEQ ID NO: 407), KSWVD (SEQ ID NO: 408), KSWVWD (SEQ ID NO: 409), KSWVWND (SEQ ID NO: 410), KSWVWNQD (SEQ ID NO: 411), KGWMD (SEQ ID NO: 412), KGWMWD (SEQ ID NO: 413), KGWMWND (SEQ ID NO: 414), KGWMWNQD (SEQ ID NO: 415), KAWVD (SEQ ID NO: 416), KAWVID (SEQ ID NO: 417), KAWVIPD (SEQ ID NO: 418), KAWVIPPD (SEQ ID NO: 419), KWVID (SEQ ID NO: 420), KWVIPD (SEQ ID NO: 421), KWVIPPD (SEQ ID NO: 422), KGWVWNQFD (SEQ ID NO: 423), KGWVWNQFFD (SEQ ID NO: 424), KGWVWNQFFVD (SEQ ID NO: 425), KWVWNQFD (SEQ ID NO: 426), KWVWNQFFD (SEQ ID NO: 427), KWVWNQFFVD (SEQ ID NO: 428), KRGWD (SEQ ID NO: 429), KRGWVD (SEQ ID NO: 430), KRGWVWD (SEQ ID NO: 431), KRGWVWND (SEQ ID NO: 432), KRGWVWNQD (SEQ ID NO: 433), KRGWVWNQFD (SEQ ID NO: 434), KRGWVWNQFFD (SEQ ID NO: 435), KRGWVWNQFFVD (SEQ ID NO: 436), KRGWD (SEQ ID NO: 429), KRGWVD (SEQ ID NO: 430), KRGWVWD (SEQ ID NO: 431), KRGWVWND (SEQ ID NO: 432), KRGWVWNQD (SEQ ID NO: 433), KRGWVWNQFD (SEQ ID NO: 434), KRGWVWNQFFD (SEQ ID NO: 435), KRGWVWNQFFVD (SEQ ID NO: 436), DWIWNQMD (SEQ ID NO: 437), KDWIWNQMHD (SEQ ID NO: 438), KDWIWNQMHID (SEQ ID NO: 439), KWIWNQMD (SEQ ID NO: 440), KWIWNQMHD (SEQ ID NO: 441), KWIWNQMHID (SEQ ID NO: 442), RDWD (SEQ ID NO: 443), RDWID (SEQ ID NO: 444), RDWIWD (SEQ ID NO: 445), RDWIWND (SEQ ID NO: 446), RDWIWNQD (SEQ ID NO: 447), RDWIWNQMD (SEQ ID NO: 448), RDWIWNQMHD (SEQ ID NO: 449), RDWIWNQMHID (SEQ ID NO: 450), RDWD (SEQ ID NO: 443), RDWID (SEQ ID NO: 444), KRDWIWD (SEQ ID NO: 451), KRDWIWND (SEQ ID NO: 452), KRDWIWNQD (SEQ ID NO: 453), KRDWIWNQMD (SEQ ID NO: 454), KRDWIWNQMHD (SEQ ID NO: 455), KRDWIWNQMHID (SEQ ID NO: 456), KSWMWNQFD (SEQ ID NO: 457), KSWMWNQFFD (SEQ ID NO: 458), KSWMWNQFFLD (SEQ ID NO: 459), KWMWNQFD (SEQ ID NO: 460), KWMWNQFFD (SEQ ID NO: 461), KWMWNQFFLD (SEQ ID NO: 462), RSWD (SEQ ID NO: 463), RSWMD (SEQ ID NO: 464), RSWMWD (SEQ ID NO:465), RSWMWND (SEQ ID NO: 466), RSWMWNQD (SEQ ID NO: 467), RSWMWNQFD (SEQ ID NO: 468), RSWMWNQFFD (SEQ ID NO: 469), RSWMWNQFFLD (SEQ ID NO: 470), KRSWD (SEQ ID NO: 471), KRSWMD (SEQ ID NO: 472), KRSWMWD (SEQ ID NO: 473), KRSWMWND (SEQ ID NO: 474), KRSWMWNQD (SEQ ID NO: 475), KRSWMWNQFD (SEQ ID NO: 476), KRSWMWNQFFD (SEQ ID NO: 477), KRSWMWNQFFLD (SEQ ID NO: 478), KSWVWNQFD (SEQ ID NO: 479), KSWVWNQFFD (SEQ ID NO: 480), KSWVWNQFFVD (SEQ ID NO: 481), KWVWNQFD (SEQ ID NO: 426), KWVWNQFFD (SEQ ID NO: 427), KWVWNQFFVD (SEQ ID NO: 428), RSWVD (SEQ ID NO: 482), RSWVWD (SEQ ID NO: 483), RSWVWND (SEQ ID NO: 484), RSWVWNQD (SEQ ID NO: 485), RSWVWNQFD (SEQ ID NO: 486), RSWVWNQFFD (SEQ ID NO: 487), RSWVWNQFFVD (SEQ ID NO: 488), KRSWVD (SEQ ID NO: 489), KRSWVWD (SEQ ID NO: 490), KRSWVWND (SEQ ID NO: 491), KRSWVWNQD (SEQ ID NO: 492), KRSWVWNQFD (SEQ ID NO: 493), KRSWVWNQFFD (SEQ ID NO: 494), KRSWVWNQFFVD (SEQ ID NO: 495), KGWVWNQMD (SEQ ID NO: 496), KGWVWNQMFD (SEQ ID NO: 497), KGWVWNQMFVD (SEQ ID NO: 498), RGWVWNQMD (SEQ ID NO: 499), KRGWVWNQMFD (SEQ ID NO: 500), RGWVWNQMFVD (SEQ ID NO: 501), KRGWVWNQMD (SEQ ID NO: 502), KRGWVWNQMFVD (SEQ ID NO: 503), KGWVWNQFFLD (SEQ ID NO: 504), RGWVWNQFFLD (SEQ ID NO: 505), KRGWVWNQFFLD (SEQ ID NO: 506), KAWVIPPID (SEQ ID NO: 507), KAWVIPPISD (SEQ ID NO: 508), KAWVIPPISVD (SEQ ID NO: 509), KWVIPPID (SEQ ID NO: 510), KWVIPPISD (SEQ ID NO: 511), KWVIPPISVD (SEQ ID NO: 512), RAWD (SEQ ID NO: 513), RAWVD (SEQ ID NO: 514), RAWVID (SEQ ID NO: 515), RAWVIPD (SEQ ID NO: 516), RAWVIPPD (SEQ ID NO: 517), RAWVIPPID (SEQ ID NO: 518), RAWVIPPISD (SEQ ID NO: 519), RAWVIPPISVD (SEQ ID NO: 520), RAWD (SEQ ID NO: 513), RAWVD (SEQ ID NO: 514), RAWVID (SEQ ID NO: 515), RAWVIPD (SEQ ID NO: 516), KRAWVIPPD (SEQ ID NO: 521), KRAWVIPPID (SEQ ID NO: 522), KRAWVIPPISD (SEQ ID NO: 523), KVWND (SEQ ID NO: 524), KVWNQD (SEQ ID NO: 525), KVWNQMD (SEQ ID NO: 526), KVWNQFD (SEQ ID NO: 527), KVWNQMFD (SEQ ID NO: 528), KVWNQFFD (SEQ ID NO: 529), KWNQD (SEQ ID NO: 530), KWNQMD (SEQ ID NO: 531), KWNQFD (SEQ ID NO: 532), KWNQFFD (SEQ ID NO: 533), KIWND (SEQ ID NO: 534), KIWNQD (SEQ ID NO: 535), KIWNQMD (SEQ ID NO: 536), KIWNQMHD (SEQ ID NO: 537), KWNQMD (SEQ ID NO: 531), KWNQMHD (SEQ ID NO: 538), KMWND (SEQ ID NO: 539), KMWNQD (SEQ ID NO: 540), KMWNQFD (SEQ ID NO: 541), and KMWNQFFD (SEQ ID NO: 542).

Additional exemplary cyclic peptides also include the following sequences where the underlines represent the amino acid residues within cyclic peptide rings: KGWVE (SEQ ID NO: 543), KGWVWE (SEQ ID NO: 544), KGWVWNE (SEQ ID NO: 545), KGWVWNQE (SEQ ID NO: 546), KWVWE (SEQ ID NO: 547), KWVWNE (SEQ ID NO: 548), KWVWNQE (SEQ ID NO: 549), KDWIE (SEQ ID NO: 550), KDWIWE (SEQ ID NO: 551), KDWIWN (SEQ ID NO: 552), KDWIWNQE (SEQ ID NO: 553), KWIWE (SEQ ID NO: 554), KWIWNE (SEQ ID NO: 555), KWIWNQE (SEQ ID NO: 556), KSWME (SEQ ID NO: 557), KSWMWE (SEQ ID NO: 558), KSWMWNE (SEQ ID NO: 559), KSWMWNQE (SEQ ID NO: 560), KWMWE (SEQ ID NO: 561), KWMWNE (SEQ ID NO: 562), KWMWNQE (SEQ ID NO: 563), KSWVE (SEQ ID NO: 564), KSWVWE (SEQ ID NO: 565), KSWVWNE (SEQ ID NO: 566), KSWVWNQE (SEQ ID NO: 567), KGWME (SEQ ID NO: 568), KGWMWE (SEQ ID NO: 569), KGWMWNE (SEQ ID NO: 570), KGWMWNQE (SEQ ID NO: 571), KAWVE (SEQ ID NO: 572), KAWVIE (SEQ ID NO: 573), KAWVIPE (SEQ ID NO: 574), KAWVIPPE (SEQ ID NO: 575), KWVIE (SEQ ID NO: 576), KWVIPE (SEQ ID NO: 577), KWVIPPE (SEQ ID NO: 578), KGWVWNQFE (SEQ ID NO: 579), KGWVWNQFFE (SEQ ID NO: 580), KGWVWNQFFVE (SEQ ID NO: 581), KWVWNQFE (SEQ ID NO: 582), KWVWNQFFE (SEQ ID NO: 583), KWVWNQFFVE (SEQ ID NO: 584), KRGWE (SEQ ID NO: 585), KRGWVE (SEQ ID NO: 586), KRGWVWE (SEQ ID NO: 587), KRGWVWNE (SEQ ID NO: 588), KRGWVWNQE (SEQ ID NO: 589), KRGWVWNQFE (SEQ ID NO: 590), KRGWVWNQFFE (SEQ ID NO: 591), KRGWVWNQFFVE (SEQ ID NO: 592), KRGWE (SEQ ID NO: 585), KRGWVE (SEQ ID NO: 586), KRGWVWE (SEQ ID NO: 587), KRGWVWNE (SEQ ID NO: 588), KRGWVWNQE (SEQ ID NO: 589), KRGWVWNQFE (SEQ ID NO: 590), KRGVVWNQFFE (SEQ ID NO: 591), KRGVVWNQFFVE (SEQ ID NO: 592), DWIWNQME (SEQ ID NO: 593), KDWIWNQMHE (SEQ ID NO: 594), KDWIWNQMHIE (SEQ ID NO: 595), KWIWNQME (SEQ ID NO: 596), KWIWNQMHE (SEQ ID NO: 597), KWIWNQMHIE (SEQ ID NO: 598), RDWE (SEQ ID NO: 599), RDWIE (SEQ ID NO: 600), RDWIWE (SEQ ID NO: 601), RDWIWNE (SEQ ID NO: 602), RDWIWNQE (SEQ ID NO: 603), RDWIWNQME (SEQ ID NO: 604), RDWIWNQMHE (SEQ ID NO: 605), RDWIWNQMHIE (SEQ ID NO: 606), RDWE (SEQ ID NO: 599), RDWIE (SEQ ID NO: 600), KRDWIWE (SEQ ID NO: 607), KRDWIWNE (SEQ ID NO: 608), KRDWIWNQE (SEQ ID NO: 609), KRDWIWNQME (SEQ ID NO: 610), KRDWIWNQMHE (SEQ ID NO: 611), KRDWIWNQMHIE (SEQ ID NO: 612), KSWMWNQFE (SEQ ID NO: 613), KSWMWNQFFE (SEQ ID NO: 614), KSWMWNQFFLE (SEQ ID NO: 615), KWMWNQFE (SEQ ID NO: 616), KWMWNQFFE (SEQ ID NO: 617), KWMWNQFFLE (SEQ ID NO: 618), RSWE (SEQ ID NO: 619), RSWME (SEQ ID NO; 620), RSWMWE (SEQ ID NO: 621), RSWMWNE (SEQ ID NO: 622), RSWMWNQE (SEQ ID NO: 623), RSWMWNQFE (SEQ ID NO: 624), RSWMWNQFFE (SEQ ID NO: 625), RSWMWNQFFLE (SEQ ID NO: 626), KRSWE (SEQ ID NO: 627), KRSWME (SEQ ID NO; 628), KRSWMWE (SEQ ID NO: 629), KRSWMWNE (SEQ ID NO: 630), KRSWMWNQE (SEQ ID NO: 631), KRSWMWNQFE (SEQ ID NO: 632), KRSWMWNQFFE (SEQ ID NO: 633), KRSWMWNQFFLE (SEQ ID NO: 634), KSWVWNQFE (SEQ ID NO: 635), KSWVWNQFFE (SEQ ID NO: 636), KSWVWNQFFVE (SEQ ID NO: 637), KWVWNQFE (SEQ ID NO: 582), KWVWNQFFE (SEQ ID NO: 583), KWVWNQFFVE (SEQ ID NO: 584), RSWVE (SEQ ID NO: 638), RSWVWE (SEQ ID NO: 639), RSWVWNE (SEQ ID NO: 640), RSWVWNQE (SEQ ID NO: 641), RSWVWNQFE (SEQ ID NO: 642), RSWVWNQFFE (SEQ ID NO: 643), RSWVWNQFFVE (SEQ ID NO: 644), KRSWVE (SEQ ID NO: 645), KRSWVWE (SEQ ID NO: 646), KRSWVWNE (SEQ ID NO: 647), KRSWVWNQE (SEQ ID NO: 648), KRSWVWNQFE (SEQ ID NO: 649), KRSWVWNQFFE (SEQ ID NO: 650), KRSWVWNQFFVE (SEQ ID NO: 651), KGWVWNQME (SEQ ID NO: 652), KGWVWNQMFE (SEQ ID NO: 653), KGWVWNQMFVE (SEQ ID NO: 654), RGWVWNQME (SEQ ID NO: 655), KRGWVWNQMFE (SEQ ID NO: 656), RGWVWNQMFVE (SEQ ID NO: 657), KRGWVWNQME (SEQ ID NO: 658), KRGWVWNQMFVE (SEQ ID NO: 659), KGWVWNQFFLE (SEQ ID NO: 660), RGWVWNQFFLE (SEQ ID NO: 661), KRGWVWNQFFLE (SEQ ID NO: 662), KAWVIPPIE (SEQ ID NO: 663), KAWVIPPISE (SEQ ID NO: 664), KAWVIPPISVE (SEQ ID NO: 665), KWVIPPIE (SEQ ID NO: 666), KWVIPPISE (SEQ ID NO: 667), KWVIPPISVE (SEQ ID NO: 668), RAWE (SEQ ID NO: 669), RAWVE (SEQ ID NO: 670), RAWVIE (SEQ ID NO: 671), RAWVIPE (SEQ ID NO: 672), RAWVIPPE (SEQ ID NO: 673), RAWVIPPIE (SEQ ID NO: 674), RAWVIPPISE (SEQ ID NO: 675), RAWVIPPISVE (SEQ ID NO: 676), RAWE (SEQ ID NO: 669), RAWVE (SEQ ID NO: 670), RAWVIE (SEQ ID NO: 671), RAWVIPE (SEQ ID NO: 672), KRAWVIPPE (SEQ ID NO: 677), KRAWVIPPIE (SEQ ID NO: 678), KRAWVIPPISD (SEQ ID NO: 523), KVWNE (SEQ ID NO: 679), KVWNQE (SEQ ID NO: 680), KVWNQME (SEQ ID NO: 681), KVWNQFE (SEQ ID NO: 682), KVWNQMFE (SEQ ID NO: 683), KVWNQFFE (SEQ ID NO: 684), KWNQE (SEQ ID NO: 685), KWNQME (SEQ ID NO: 686), KWNQFE (SEQ ID NO: 687), KWNQFFE (SEQ ID NO: 688), KIWNE (SEQ ID NO: 689), KIWNQE (SEQ ID NO: 690), KIWNQME (SEQ ID NO: 691), KIWNQMHE (SEQ ID NO: 692), KWNQME (SEQ ID NO: 686), KWNQMHE (SEQ ID NO: 693), KMWNE (SEQ ID NO: 694), KMWNQE (SEQ ID NO: 695), KMWNQFE (SEQ ID NO: 696), and KMWNQFFE (SEQ ID NO: 697).

Additional exemplary cyclic peptides also include the following sequences where the underlines represent the amino acid residues within cyclic peptide rings: DGWVK (SEQ ID NO: 698), DGWVWK (SEQ ID NO: 699), DGWVWNK (SEQ ID NO: 700), DGWVWNQK (SEQ ID NO: 701), DWVWK (SEQ ID NO: 702), DWVWNK (SEQ ID NO: 703), DWVWNQK (SEQ ID NO: 704), DWIK (SEQ ID NO: 705), DWIWK (SEQ ID NO: 706), DWIWNK (SEQ ID NO: 707), DWIWNQK (SEQ ID NO: 708), DWIWK (SEQ ID NO: 706), DWIWNK (SEQ ID NO: 707), DWIWNQK (SEQ ID NO: 708), DSWMK (SEQ ID NO: 709), DSWMWK (SEQ ID NO: 710), DSWMWNK (SEQ ID NO: 711), DSWMWNQK (SEQ ID NO: 712), DWMWK (SEQ ID NO: 713), DWMWNK (SEQ ID NO: 714), DWMWNQK (SEQ ID NO: 715), DSWVK (SEQ ID NO: 716), DSWVWK (SEQ ID NO: 717), DSWVWNK (SEQ ID NO: 718), DSWVWNQK (SEQ ID NO: 719), DGWMK (SEQ ID NO: 720), DGWMWK (SEQ ID NO: 721), DGWMWNK (SEQ ID NO: 722), DGWMWNQK (SEQ ID NO: 723), DAWVK (SEQ ID NO: 724), DAWVIK (SEQ ID NO: 725), DAWVIPK (SEQ ID NO: 726), DAWVIPPK (SEQ ID NO: 727), DWVIK (SEQ ID NO: 728), DWVIPK (SEQ ID NO: 729), DWVIPPK (SEQ ID NO: 730), DGWVWNQFK (SEQ ID NO: 731), DGWVWNQFFK (SEQ ID NO: 732), DGWVWNQFFVK (SEQ ID NO: 733), DWVWNQFK (SEQ ID NO: 734), DWVWNQFFK (SEQ ID NO: 735), DWVWNQFFVK (SEQ ID NO: 736), DRGWK (SEQ ID NO: 737), DRGWVK (SEQ ID NO: 738), DRGWVWK (SEQ IDN 0: 739), DRGWVWNK (SEQ ID NO: 740), DRGWVWNQK (SEQ ID NO: 741), DRGWVWNQFK (SEQ ID NO: 742), DRGWVWNQFFK (SEQ ID NO: 743), DRGWVWNQFFVK (SEQ ID NO: 744), DKRGWK (SEQ ID NO: 745), DKRGWVK (SEQ ID NO: 746), DKRGWVWK (SEQ ID NO: 747), DKRGWVWNK (SEQ ID NO: 748), DKRGWVWNQK (SEQ ID NO: 749), DKRGWVWNQFK (SEQ ID NO: 750), DKRGWVWNQFFK (SEQ ID NO: 751), DKRGWVWNQFFVK (SEQ ID NO: 752), DWIWNQMK (SEQ ID NO: 753), DWIWNQMHK (SEQ ID NO: 754), DWIWNQMHIK (SEQ ID NO: 755), DWIWNQMK (SEQ ID NO: 753), DWIWNQMHK (SEQ ID NO: 754), DWIWNQMHIK (SEQ ID NO: 755), DRDWK (SEQ ID NO: 756), DRDWIK (SEQ ID NO: 757), DRDWIWK (SEQ ID NO: 758), DRDWIWNK (SEQ ID NO: 759), DRDWIWNQK (SEQ ID NO: 760), DRDWIWNQMK (SEQ ID NO: 761), DRDWIWNQMHK (SEQ ID NO: 762), DRDWIWNQMHIK (SEQ ID NO: 763), DKRDWK (SEQ ID NO: 764), DKRDWIK (SEQ ID NO: 765), DKRDWIWK (SEQ ID NO: 766), DKRDWIWNK (SEQ ID NO: 767), DKRDWIWNQK (SEQ ID NO: 768), DKRDWIWNQMK (SEQ ID NO: 769), DKRDWIWNQMHK (SEQ ID NO: 770), DKRDWIWNQMHIK (SEQ ID NO: 771), DSWMWNQFK (SEQ ID NO: 772), DSWMWNQFFK (SEQ ID NO: 773), DSWMWNQFFLK (SEQ ID NO: 774), DWMWNQFK (SEQ ID NO: 775), DWMWNQFFK (SEQ ID NO: 776), DWMWNQFFLK (SEQ ID NO: 777), DRSWK (SEQ ID NO: 778), DRSWMK (SEQ ID NO: 779), DRSWMWK (SEQ ID NO: 780), DRSWMWNK (SEQ ID NO: 781), DRSWMWNQK (SEQ ID NO: 782), DRSWMWNQFK (SEQ ID NO: 783), DRSWMWNQFFK (SEQ ID NO: 784), DRSWMWNQFFLK (SEQ ID NO: 785), DKRSWK (SEQ ID NO: 786), DKRSWMK (SEQ ID NO: 787), DKRSWMWK (SEQ ID NO: 788), DKRSWMWNK (SEQ ID NO: 789), DKRSWMWNQK (SEQ ID NO: 790), DKRSWMWNQFK (SEQ ID NO: 791), DKRSWMWNQFFK (SEQ ID NO: 792), DKRSWMWNQFFK (SEQ ID NO: 792), DSWVWNQFK (SEQ ID NO: 793), DSWVWNQFFK (SEQ ID NO: 794), DSWVWNQFFVK (SEQ ID NO: 795), DWVWNQFK (SEQ ID NO: 734), DWVWNQFFK (SEQ ID NO: 735), DWVWNQFFVK (SEQ ID NO: 736), DRSWVK (SEQ ID NO: 796), DRSWVWK (SEQ ID NO: 797), DRSWVWNK (SEQ ID NO: 798), DRSWVWNQK (SEQ ID NO: 799), DRSWVWNQFK (SEQ ID NO: 800), DRSWVWNQFFK (SEQ ID NO: 801), DRSWVWNQFFVK (SEQ ID NO: 802), DKRSWVK (SEQ ID NO: 803), DKRSWVWK (SEQ ID NO: 804), DKRSWVWNK (SEQ ID NO: 805), DKRSWVWNQK (SEQ ID NO: 806), DKRSWVWNQFK (SEQ ID NO: 807), DKRSWVWNQFFK (SEQ ID NO: 808), DKRSWVWNQFFVK (SEQ ID NO: 809), DGWVWNQMK (SEQ ID NO: 810), DGWVWNQMFK (SEQ ID NO: 811), DGWVWNQMFVK (SEQ ID NO: 812), DRGWVWNQMK (SEQ ID NO: 813), DRGWVWNQMFK (SEQ ID NO: 814), DRGWVWNQMFVK (SEQ ID NO: 815), DKRGWVWNQMK (SEQ ID NO: 816), DKRGWVWNQMFVK (SEQ ID NO: 817), DGWVWNQFFLK (SEQ ID NO: 818), DRGWVWNQFFLK (SEQ ID NO: 819), DKRGWVWNQFFLK (SEQ ID NO: 820), DAWVIPPIK (SEQ ID NO: 821), DAWVIPPISK (SEQ ID NO: 822), DAWVIPPISVK (SEQ ID NO: 823), DWVIPPIK (SEQ ID NO: 824), DWVIPPISK (SEQ ID NO: 825), DWVIPPISVK (SEQ ID NO: 826), DRAWK (SEQ ID NO: 827), DRAWVK (SEQ ID NO: 828), DRAWVIK (SEQ ID NO: 829), DRAWVIPK (SEQ ID NO: 830), DRAWVIPPK (SEQ ID NO: 831), DRAWVIPPIK (SEQ ID NO: 832), DRAWVIPPISK (SEQ ID NO: 833), DRAWVIPPISVK (SEQ ID NO: 834), DKRAWK (SEQ ID NO: 835), DKRAWVK (SEQ ID NO: 836), DKRAWVIK (SEQ ID NO: 837), DKRAWVIPK (SEQ ID NO: 838), DKRAWVIPPK (SEQ ID NO: 839), DKRAWVIPPIK (SEQ ID NO: 840), DKRAWVIPPISK (SEQ ID NO: 841), DVWNK (SEQ ID NO: 842), DVWNQK (SEQ ID NO: 843), DVWNQMK (SEQ ID NO: 844), DVWNQFK (SEQ ID NO: 845), DVWNQMFK (SEQ ID NO: 846), DVWNQFFK (SEQ ID NO: 847), DWNQK (SEQ ID NO: 848), DWNQMK (SEQ ID NO: 849), DWNQFK (SEQ ID NO: 850), DWNQFFK (SEQ ID NO: 851), DIWNK (SEQ ID NO: 852), DIWNQK (SEQ ID NO: 853), DIWNQMK (SEQ ID NO: 854), DIWNQMHK (SEQ ID NO: 855), DWNQMK (SEQ ID NO: 849), DWNQMHK (SEQ ID NO: 856), DMWNK (SEQ ID NO: 857), DMWNQK (SEQ ID NO: 858), DMWNQFK (SEQ ID NO: 859), and DMWNQFFK (SEQ ID NO: 860).

Additional exemplary cyclic peptides also include the following sequences where the underlines represent the amino acid residues within cyclic peptide rings: EGWVK (SEQ ID NO: 861), EGWVWK (SEQ ID NO: 862), EGWVWNK (SEQ ID NO: 863), EGWVWNQK (SEQ ID NO: 864), EWVWK (SEQ ID NO: 865), EWVWNK (SEQ ID NO: 866), EWVWNQK (SEQ ID NO: 867), ESWMK (SEQ ID NO: 868), ESWMWK (SEQ ID NO: 869), ESWMWNK (SEQ ID NO: 870), ESWMWNQK (SEQ ID NO: 871), EWMWK (SEQ ID NO: 872), EWMWNK (SEQ ID NO: 873), EWMWNQK (SEQ ID NO: 874), ESWVK (SEQ ID NO: 875), ESWVWK (SEQ ID NO: 876), ESWVWNK (SEQ ID NO: 877), ESWVWNQK (SEQ ID NO: 878), EGWMK (SEQ ID NO: 879), EGWMWK (SEQ ID NO: 880), EGWMWNK (SEQ ID NO: 881), EGWMWNQK (SEQ ID NO: 882), EAWVK (SEQ ID NO: 883), EAWVIK (SEQ ID NO: 884), EAWVIPK (SEQ ID NO: 885), EAWVIPPK (SEQ ID NO: 886), EWVIK (SEQ ID NO: 887), EWVIPK (SEQ ID NO: 888), EWVIPPK (SEQ ID NO: 889), EGWVWNQFK (SEQ ID NO: 890), EGWVWNQFFK (SEQ ID NO: 891), EGWVWNQFFVK (SEQ ID NO: 892), EWVWNQFK (SEQ ID NO: 893), EWVWNQFFK (SEQ ID NO: 894), EWVWNQFFVK (SEQ ID NO: 895), ERGWK (SEQ ID NO: 896), ERGWVK (SEQ ID NO: 897), ERGWVWK (SEQ ID NO: 898), ERGWVWNK (SEQ ID NO: 899), ERGWVWNQK (SEQ ID NO: 900), ERGWVWNQFK (SEQ ID NO: 901), ERGWVWNQFFK (SEQ ID NO: 902), ERGWVWNQFFVK (SEQ ID NO: 903), EKRGWK (SEQ ID NO: 904), EKRGWVK (SEQ ID NO: 905), EKRGWVWK (SEQ ID NO: 906), EKRGWVWNK (SEQ ID NO: 907), EKRGWVWNQK (SEQ ID NO: 908), EKRGWVWNQFK (SEQ ID NO: 909), EKRGWVWNQFFK (SEQ ID NO: 910), EKRGWVWNQFFVK (SEQ ID NO: 911), ERDWK (SEQ ID NO: 912), ERDWIK (SEQ ID NO: 913), ERDWIWK (SEQ ID NO: 914), ERDWIWNK (SEQ ID NO: 915), ERDWIWNQK (SEQ ID NO: 916), ERDWIWNQMK (SEQ ID NO: 917), ERDWIWNQMHK (SEQ ID NO: 918), ERDWIWNQMHIK (SEQ ID NO: 919), EKRDWK (SEQ ID NO: 920), EKRDWIK (SEQ ID NO: 921), EKRDWIWK (SEQ ID NO: 922), EKRDWIWNK (SEQ ID NO: 923), EKRDWIWNQK (SEQ ID NO: 924), EKRDWIWNQMK (SEQ ID NO: 925), EKRDWIWNQMHK (SEQ ID NO: 926), EKRDWIWNQMHIK (SEQ ID NO: 927), ESWMWNQFK (SEQ ID NO: 928), ESWMWNQFFK (SEQ ID NO: 929), ESWMWNQFFLK (SEQ ID NO: 930), EWMWNQFK (SEQ ID NO: 931), EWMWNQFFK (SEQ ID NO: 932), EWMWNQFFLK (SEQ ID NO: 933), ERSWK (SEQ ID NO: 934), ERSWMK (SEQ ID NO: 935), ERSWMWK (SEQ ID NO: 936), ERSWMWNK (SEQ ID NO: 937), ERSWMWNQK (SEQ ID NO: 938), ERSWMWNQFK (SEQ ID NO: 939), ERSWMWNQFFK (SEQ ID NO: 940), ERSWMWNQFFLK (SEQ ID NO: 941), EKRSWK (SEQ ID NO: 942), EKRSWMK (SEQ ID NO: 943), EKRSWMWK (SEQ ID NO: 944), EKRSWMWNK (SEQ ID NO: 945), EKRSWMWNQK (SEQ ID NO: 946), EKRSWMWNQFK (SEQ ID NO: 947), EKRSWMWNQFFK (SEQ ID NO: 948), EKRSWMWNQFFK (SEQ ID NO: 948), ESWVWNQFK (SEQ ID NO: 949), ESWVWNQFFK (SEQ ID NO: 950), ESWVWNQFFVK (SEQ ID NO: 951), EWVWNQFK (SEQ ID NO: 893), EWVWNQFFK (SEQ ID NO: 894), EWVWNQFFVK (SEQ ID NO: 895), ERSWVK (SEQ ID NO: 952), ERSWVWK (SEQ ID NO: 953), ERSWVWNK (SEQ ID NO: 954), ERSWVWNQK (SEQ ID NO: 955), ERSWVWNQFK (SEQ ID NO: 956), ERSWVWNQFFK (SEQ ID NO: 957), ERSWVWNQFFVK (SEQ ID NO: 958), EKRSWVK (SEQ ID NO: 959), EKRSWVWK (SEQ ID NO: 960), EKRSWVWNK (SEQ ID NO: 961), EKRSWVWNQK (SEQ ID NO: 962), EKRSWVWNQFK (SEQ ID NO: 963), EKRSWVWNQFFK (SEQ ID NO: 964), EKRSWVWNQFFVK (SEQ ID NO: 965), EGWVWNQMK (SEQ ID NO: 966), EGWVWNQMFK (SEQ ID NO: 967), EGWVWNQMFVK (SEQ ID NO: 968), ERGWVWNQMK (SEQ ID NO; 969), ERGWVWNQMFK (SEQ ID NO: 970), ERGWVWNQMFVK (SEQ ID NO: 971), EKRGWVWNQMK (SEQ ID NO: 972), EKRGWVWNQMFVK (SEQ ID NO: 973), EGWVWNQFFLK (SEQ ID NO: 974), ERGWVWNQFFLK (SEQ ID NO: 975), EKRGWVWNQFFLK (SEQ ID NO: 976), EAWVIPPIK (SEQ ID NO: 977), EAWVIPPISK (SEQ ID NO: 978), EAWVIPPISVK (SEQ ID NO: 979), EWVIPPIK (SEQ ID NO: 980), EWVIPPISK (SEQ ID NO: 981), EWVIPPISVK (SEQ ID NO: 982), ERAWK (SEQ ID NO: 983), ERAWVK (SEQ ID NO: 984), ERAWVIK (SEQ ID NO: 985), ERAWVIPK (SEQ ID NO: 986), ERAWVIPPK (SEQ ID NO: 987), ERAWVIPPIK (SEQ ID NO: 988), ERAWVIPPISK (SEQ ID NO: 989), ERAWVIPPISVK (SEQ ID NO: 990), EKRAWK (SEQ ID NO: 991), EKRAWVK (SEQ ID NO: 992), EKRAWVIK (SEQ ID NO: 993), EKRAWVIPK (SEQ ID NO: 994), EKRAWVIPPK (SEQ ID NO: 995), EKRAWVIPPIK (SEQ ID NO: 996), EKRAWVIPPISK (SEQ ID NO: 997), EVWNK (SEQ ID NO: 998), EVWNQK (SEQ ID NO: 999), EVWNQMK (SEQ ID NO: 1000), EVWNQFK (SEQ ID NO: 1001), EVWNQMFK (SEQ ID NO: 1002), EVWNQFFK (SEQ ID NO: 1003), EWNQK (SEQ ID NO: 1004), EWNQMK (SEQ ID NO: 1005), EWNQFK (SEQ ID NO: 1006), EWNQFFK (SEQ ID NO: 1007), EIWNK (SEQ ID NO: 1008), EIWNQK (SEQ ID NO: 1009), EIWNQMK (SEQ ID NO: 1010), EIWNQMHK (SEQ ID NO: 1011), EWNQMK (SEQ ID NO: 1005), EWNQMHK (SEQ ID NO: 1012), EMWNK (SEQ ID NO: 1013), EMWNQK (SEQ ID NO: 1014), EMWNQFK (SEQ ID NO: 1015), and EMWNQFFK (SEQ ID NO: 1016).

In certain preferred embodiments, a desmosomal cadherin modulating agent comprises a cyclic peptide of which the cyclic peptide ring comprises the sequence E/A/R-W-I/V/A-K/T/P-F/A/I-A/P (SEQ ID NO: 167) (e.g., E/A-W-I/V-K/T-F/A-A/P (SEQ ID NO: 1) and RWAPIP (SEQ ID NO: 2)) or a portion thereof. Exemplary cyclic peptides have one of the following structures:

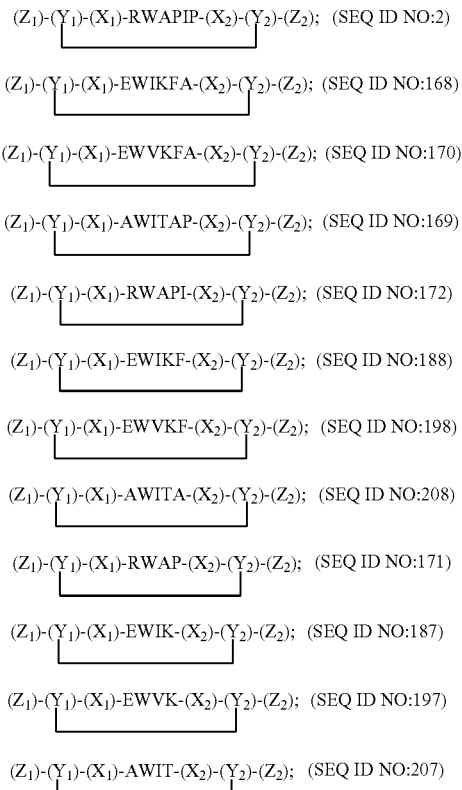

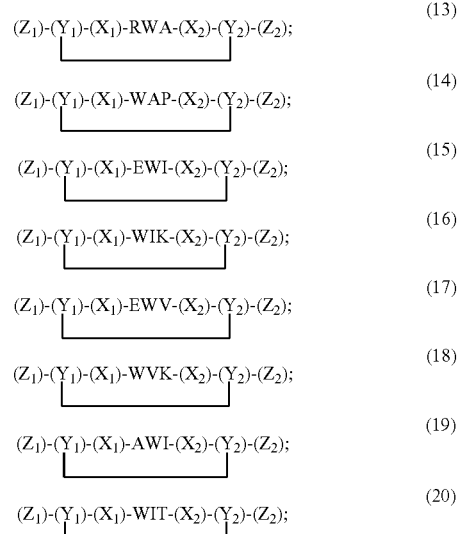

In these structures, $X_1$ and $X_2$ are optional, and if present, are amino acid residues or combinations of amino acid residues linked by peptide bonds. $X_1$ and $X_2$ may be identical to, or different from, each other. In general, $X_1$ and $X_2$ independently range in size from 0 to 10 residues, such that the sum of residues contained within $X_1$ and $X_2$ ranges from 1 to 12. $Y_1$ and $Y_2$ are amino acid residues, and a covalent bond is formed between residues $Y_1$ and $Y_2$. $Y_1$ and $Y_2$ may be identical to, or different from, each other. $Z_1$ and $Z_2$ are optional, and if present, are amino acid residues or combinations of amino acid residues linked by peptide bonds. $Z_1$ and $Z_2$ may be identical to, or different from, each other.

Cyclic peptides may be used as desmosomal cadherin modulating agents without modification, or may be incorporated into a modulating agent. Exemplary cyclic peptides include, but are not limited to, the following sequences where the underlines represent the amino acid residues within cyclic peptide rings: RWA, RWAP (SEQ ID NO: 171), RWAPI (SEQ ID NO: 172), RWAPIP (SEQ ID NO: 2), RWAPIPC (SEQ ID NO: 173), RWAPIPCS (SEQ ID NO: 174), RWAPIPCSM (SEQ ID NO: 175), WAP, WAPI (SEQ ID NO: 176), WAPIP (SEQ ID NO: 177), WAPIPC (SEQ ID NO: 178), WAPIPCS (SEQ ID NO: 179), WAPIPCSM (SEQ ID NO: 180), RWAPIPCSL (SEQ ID NO: 181), WAPIPCSL (SEQ ID NO: 182), RWAPIPCA (SEQ ID NO: 183), WAPIPCA (SEQ ID NO: 184), RWAPIPCAS (SEQ ID NO: 185), WAPIPCAS (SEQ ID NO: 186), EWI, EWIK (SEQ ID NO: 187), EWIKF (SEQ ID NO: 188), EWIKFA (SEQ ID NO: 168), EWIKFAA (SEQ ID NO: 189), EWIKFAAA (SEQ ID NO: 190), EWIKFAAAC (SEQ ID NO: 191), WIK, WIKF (SEQ ID NO: 192), WIKFA (SEQ ID NO: 193), WIKFAA (SEQ ID NO: 194), WIKFAAA (SEQ ID NO: 195), WIKFAAAC (SEQ ID NO: 196), EWV, EWVK (SEQ ID NO: 197), EWVKF (SEQ ID NO: 198), EWVKFA (SEQ ID NO: 170), EWVKFAK (SEQ ID NO: 199), EWVKFAKP (SEQ ID NO: 200), EWVKFAKPC (SEQ ID NO: 201), WVK, WVKF (SEQ ID NO: 202), WVKFA (SEQ ID NO: 203), WVKFAK (SEQ ID NO: 204), WVKFAKP (SEQ ID NO: 205), WVKFAKPC (SEQ ID NO: 206), AWI, AWIT (SEQ ID NO: 207), AWITA (SEQ ID NO: 208), AWITAP (SEQ ID NO: 169), AWITAPV (SEQ ID NO: 209), AWITAPVA (SEQ ID NO: 210), AWITAPVAL (SEQ ID NO:

211), WIT, WITA (SEQ ID NO: 212), WITAP (SEQ ID NO: 213), WITAPV (SEQ ID NO: 214), WITAPVA (SEQ ID NO: 215), and WITAPVAL (SEQ ID NO: 216).

Additional exemplary cyclic peptides include the following sequences where the underlines represent the amino acid residues within cyclic peptide rings: CRWAC (SEQ ID NO: 1017), CRWAPC (SEQ ID NO: 1018), CRWAPIC (SEQ ID NO: 1019), CRWAPIPC (SEQ ID NO: 1020), CRWAPIPCC (SEQ ID NO: 1021), CRWAPIPCSC (SEQ ID NO: 1022), CRWAPIPCSMC (SEQ ID NO: 1023), CWAPC (SEQ ID NO: 1024), CWAPIC (SEQ ID NO: 1025), CWAPIPC (SEQ ID NO: 1026), CWAPIPCC (SEQ ID NO: 1027), CWAPIPCSC (SEQ ID NO: 1028), CWAPIPCSMC (SEQ ID NO: 1029), CRWAPIPCSLC (SEQ ID NO: 1030), CWAPIPCSLC (SEQ ID NO: 1031), CRWAPIPCAC (SEQ ID NO: 1032), CWAPIPCAC (SEQ ID NO: 1033), CRWAPIPCASC (SEQ ID NO: 1034), CWAPIPCASC (SEQ ID NO: 1035), CEWIC (SEQ ID NO: 1036), CEWIKC (SEQ ID NO: 1037), CEWIKFC (SEQ ID NO: 1038), CEWIKFAC (SEQ ID NO: 1039), CEWIKFAAC (SEQ ID NO: 1040), CEWIKFAAAC (SEQ ID NO: 1041), CEWIKFAAACC (SEQ ID NO: 1042), CWIKC (SEQ ID NO: 1043), CWIKFC (SEQ ID NO: 1044), CWIKFAC (SEQ ID NO: 1045), CWIKFAAC (SEQ ID NO: 1046), CWIKFAAAC (SEQ ID NO: 1047), CWIKFAAACC (SEQ ID NO: 1048), CEWVC (SEQ ID NO: 1049), CEWVKC (SEQ ID NO: 1050), CEWVKFC (SEQ ID NO: 1051), CEWVKFAC (SEQ ID NO: 1052), CEWVKFAKC (SEQ ID NO: 1053), CEWVKFAKPC (SEQ ID NO: 1054), CEWVKFAKPCC (SEQ ID NO: 1055), CWVKC (SEQ ID NO: 1056), CWVKFC (SEQ ID NO: 1057), CWVKFAC (SEQ ID NO: 1058), CWVKFAKC (SEQ ID NO: 1059), CWVKFAKPC (SEQ ID NO: 1060), CWVKFAKPCC (SEQ ID NO: 1061), CAWIC (SEQ ID NO: 1062), CAWITC (SEQ ID NO: 1063), CAWITAC (SEQ ID NO: 1064), CAWITAPC (SEQ ID NO: 1065), CAWITAPVC (SEQ ID NO: 1066), CAWITAPVAC (SEQ ID NO: 1067), CAWITAPVALC (SEQ ID NO: 1068), CWITC (SEQ ID NO: 1069), CWITAC (SEQ ID NO: 1070), CWITAP (SEQ ID NO: 1071), CWITAPVC (SEQ ID NO: 1072), CWITAPVAC (SEQ ID NO: 1073), and CWITAPVALC (SEQ ID NO: 1074).

Additional exemplary cyclic peptides also include the following sequences where the underlines represent the amino acid residues within cyclic peptide rings: KRWAD (SEQ ID NO: 1075), KRWAPD (SEQ ID NO: 1076), KRWAPID (SEQ ID NO: 1077), KRWPIPD (SEQ ID NO: 1078), KRWAPIPCD (SEQ ID NO: 1079), KRWAPIPCSD (SEQ ID NO: 1080), KRWAPIPCSMD (SEQ ID NO: 1081), KWAPD (SEQ ID NO: 1082), KWAPID (SEQ ID NO: 1083), KWAPIPD (SEQ ID NO; 1084), KWAPIPCD (SEQ ID NO: 1085), KWAPIPCSD (SEQ ID NO: 1086), KWAPIPCSMD (SEQ ID NO: 1087), KRWAPIPCSLD (SEQ ID NO; 1088), KWAPIPCSLD (SEQ ID NO: 1089), KRWAPIPCAD (SEQ ID NO: 1090), KWAPIPCAD (SEQ ID NO: 1091), KRWAPIPCASD (SEQ ID NO: 1092), KWAPIPCASD (SEQ ID NO: 1093), KEWID (SEQ ID NO: 1094), KEWIKD (SEQ ID NO: 1095), KEWIKFD (SEQ ID NO: 1096), KEWIKFAD (SEQ ID NO: 1097), KEWIKFAAD (SEQ ID NO: 1098), KEWIKFAAAD (SEQ ID NO: 1099), KEWIKFAAACD (SEQ ID NO: 1100), KWIKD (SEQ ID NO: 1101), KWIKFD (SEQ ID NO: 1102), KWIKFAD (SEQ ID NO: 1103), KWIKFAAD (SEQ ID NO: 1104), KWIKFAAAD (SEQ ID NO: 1105), KWIKFAAACD (SEQ ID NO: 1106), KEWVD (SEQ ID NO: 1107), KEWVKD (SEQ ID NO: 1108), KEWVKFD (SEQ ID NO: 1109), KEWVKFAD (SEQ ID NO: 1110), KEWVKFAKD (SEQ ID NO: 1111), KEWVKFAKPD (SEQ ID NO: 1112), KEWVKFAKPCD (SEQ ID NO: 1113), KWVKD (SEQ ID NO: 1114), KWVKFD (SEQ ID NO: 1115), KWVKFAD (SEQ ID NO: 1116), KWVKFAKD (SEQ ID NO: 1117), KWVKFAKPD (SEQ ID NO: 1118), KWVKFAKPCD (SEQ ID NO: 1119), KAWID (SEQ ID NO: 1120), KAWITD (SEQ ID NO: 1121), KAWITAD (SEQ ID NO: 1122), KAWITAPD (SEQ ID NO: 1123), KAWITAPVD (SEQ ID NO: 1124), KAWITAPVAD (SEQ ID NO: 1125), KAWITAPVALD (SEQ ID NO: 1126), KWITD (SEQ ID NO: 1127), KWITAD (SEQ ID NO: 1128), KWITAPD (SEQ ID NO: 1129), KWITAPVD (SEQ ID NO: 1130), KWITAPVAD (SEQ ID NO: 1131), and KWITAPVALD (SEQ ID NO: 1132).

Additional exemplary cyclic peptides also include the following sequences where the underlines represent the amino acid residues within cyclic peptide rings: KRWAE (SEQ ID NO: 1133), KRWAPE (SEQ ID NO: 1134), KRWAPIE (SEQ ID NO: 1135), KRWAPIPE (SEQ ID NO: 1136), KRWAPIPCE (SEQ ID NO: 1137), KRWAPIPCSE (SEQ ID NO: 1138), KRWAPIPCSME (SEQ ID NO; 1139), KWAPE (SEQ ID NO: 1140), KWAPIE (SEQ ID NO: 1141), KWAPIPE (SEQ ID NO: 1142), KWAPIPCE (SEQ ID NO: 1143), KWAPIPCSE (SEQ ID NO; 1144), KWAPIPCSME (SEQ ID NO: 1145), KRWAPIPCSLE (SEQ ID NO: 1146), KWAPIPCSLE (SEQ ID NO: 1147), KRWAPIPCAE (SEQ ID NO: 1148), KWAPIPCAE (SEQ ID NO: 1149), KRWAPIPCASE (SEQ ID NO: 1150), KWAPIPCASE (SEQ ID NO: 1151), KEWIE (SEQ ID NO: 1152), KEWIKE (SEQ ID NO: 1153), KEWIKFE (SEQ ID NO: 1154), KEWIKFAE (SEQ ID NO: 1155), KEWIKFAAE (SEQ ID NO: 1156), KEWIKFAAAE (SEQ ID NO: 1157), KEWIKFAAACE (SEQ ID NO: 1158), KWIKE (SEQ ID NO: 1159), KWIKFE (SEQ ID NO: 1160), KWIKFAE (SEQ ID NO: 1161), KWIKFAAE (SEQ ID NO: 1162), KWIKFAAAE (SEQ ID NO: 1163), KWIKFAAACE (SEQ ID NO: 1164), KEWVE (SEQ ID NO: 1165), KEWVKE (SEQ ID NO: 1166), KEWVKFE (SEQ ID NO: 1167), KEWVKFAE (SEQ ID NO: 1168), KEWVKFAKE (SEQ ID NO: 1169), KEWVKFAKPE (SEQ ID NO: 1170), KEWVKFAKPCE (SEQ ID NO: 1171), KWVKE (SEQ ID NO: 1172), KWVKFE (SEQ ID NO: 1173), KWVKFAE (SEQ ID NO: 1174), KWVKFAKE (SEQ ID NO: 1175), KWVKFAKPE (SEQ ID NO: 1176), KWVKFAKPCE (SEQ ID NO: 1177), KAWIE (SEQ ID NO: 1178), KAWITE (SEQ ID NO: 1179), KAWITAE (SEQ ID NO: 1180), KAWITAPE (SEQ ID NO: 1181), KAWITAPVE (SEQ ID NO: 1182), KAWITAPVAE (SEQ ID NO: 1183), KAWITAPVALE (SEQ ID NO: 1184), KWITE (SEQ ID NO: 1185), KWITAE (SEQ ID NO: 1186), KWITAPE (SEQ ID NO: 1187), KWITAPVE (SEQ ID NO: 1188), KWITAPVAE (SEQ ID NO: 1189), and KWITAPVALE (SEQ ID NO: 1190).

Additional exemplary cyclic peptides also include the following sequences where the underlines represent the amino acid residues within cyclic peptide rings: DRWAK (SEQ ID NO: 1191), DRWAPK (SEQ ID NO: 1192), DRWAPIK (SEQ ID NO: 1193), DRWAPIPK (SEQ ID NO: 1194), DRWAPIPCK (SEQ ID NO: 1195), DRWAPIPCSK (SEQ ID NO: 1196), DRWAPIPCSMK (SEQ ID NO: 1197), DWAPK (SEQ ID NO: 1198), DWAPIK (SEQ ID NO: 1199), DWAPIPK (SEQ ID NO: 1200), DWAPIPCK (SEQ ID NO: 1201), DWAPIPCSK (SEQ ID NO: 1202), DWAPIPCSMK (SEQ ID NO: 1203), DRWAPIPCSLK (SEQ ID NO: 1204), DWAPIPCSLK (SEQ ID NO; 1205), DRWAPIPCAK (SEQ ID NO: 1206), DWAPIPCAK (SEQ ID NO: 1207), DRWAPIPCASK (SEQ ID NO: 1208), DWAPIPCASK (SEQ ID NO: 1209), DEWIK (SEQ ID NO: 1210), DEWIKK (SEQ ID NO: 1211), DEWIKFK (SEQ ID NO: 1212), DEWIKFAK (SEQ ID NO: 1213), DEWIKFMK (SEQ ID NO: 1214), DEWIKFAAAK (SEQ ID NO: 1215), DEWIKFAAACK (SEQ ID NO: 1216), DWIKK (SEQ ID NO: 1217), DWIKFK (SEQ ID NO: 1218), DWIKFAK (SEQ ID NO: 1219), DWIKFAAK (SEQ ID NO: 1220), DWIKFAAAK (SEQ ID NO: 1221), DWIKFAAACK (SEQ ID NO; 1222), DEWVK (SEQ ID NO: 1223), DEWVKK (SEQ ID NO; 1224), DEWVKFK (SEQ ID NO: 1225), DEWVKFAK (SEQ ID NO: 1226), DEWVKFAKK (SEQ ID NO: 1227), DEWVKFAKPK (SEQ ID NO 1228), DEWVKFAKPCK (SEQ ID NO: 1229), DWVKK (SEQ ID NO: 1230), DWVKFK (SEQ ID NO: 1231), DWVKFAK (SEQ ID NO: 1232), DWVKFAKK (SEQ ID NO: 1233), DWVKFAKPK (SEQ ID NO: 1234), DWVKFAKPCK (SEQ ID NO; 1235), DAWIK (SEQ ID NO; 1236), DAWITK (SEQ ID NO: 1237), DAWITAK (SEQ ID NO: 1238), DAWITAPK (SEQ ID NO: 1239), DAWITAPVK (SEQ ID NO: 1240), DAWITAPVAK (SEQ ID NO: 1241), DAWITAPVALK (SEQ ID NO; 1242), DWITK (SEQ ID NO: 1243), DWITAK (SEQ ID NO: 1244), DWITAPK (SEQ ID NO: 1245), DWITAPVK (SEQ ID NO: 1246), DWITAPVAK (SEQ ID NO: 1247), and DWITAPVALK (SEQ ID NO: 1248).

Additional exemplary cyclic peptides also include the following sequences where the underlines represent the amino acid residues within cyclic peptide rings: ERWAK (SEQ ID NO: 1249), ERWAPK (SEQ ID NO: 1250), ERWAPIK (SEQ ID NO: 1251), ERWAPIPK (SEQ ID NO: 1252), ERWAPIPCK (SEQ ID NO: 1253), ERWAPIPCSK (SEQ ID NO: 1254), ERWAPIPCSMK (SEQ ID NO: 1255), EWAPK (SEQ ID NO: 1256), EWAPIK (SEQ ID NO; 1257), EWAPIPK (SEQ ID NO; 1258), EWAPIPCK (SEQ ID NO; 1259), EWAPIPCSK (SEQ ID NO: 1260), EWAPIPCSMK (SEQ ID NO: 1261), ERWAPIPCSLK (SEQ ID NO: 1262), EWAPIPCSLK (SEQ ID NO: 1263), ERWAPIPCAK (SEQ ID NO: 1264), EWAPIPCAK (SEQ ID NO 1265), ERWAPIPCASK (SEQ ID NO: 1266), EWAPIPCASK (SEQ ID NO: 1267), EEWIK (SEQ ID NO: 1268), EEWIKK (SEQ ID NO: 1269), EEWIKFK (SEQ ID NO: 1270), EEWIKFAK (SEQ ID NO: 1271), EEWIKFAAK (SEQ ID NO: 1272), EEWIKFAAAK (SEQ ID NO: 1273), EEWIKFAAACK (SEQ ID NO: 1274), EWIKK (SEQ ID NO: 1275), EWIKFK (SEQ ID NO: 1276), EWIKFAK (SEQ ID NO; 1277), EWIKFAAK (SEQ ID NO: 1278), EWIKFAAAK (SEQ ID NO; 1279), EWIKFAAACK (SEQ ID NO: 1280), EEWVK (SEQ ID NO: 1281), EEWVKK (SEQ ID NO: 1282), EEWVKFK (SEQ ID NO: 1283), EEWVKFAK (SEQ ID NO: 1284), EEWVKFAKK (SEQ ID NO: 1285), EEWVKFAKPK (SEQ ID NO: 1286), EEWVKFAKPCK (SEQ ID NO: 1287), EWVKK (SEQ ID NO: 1288), EWVKFK (SEQ ID NO: 1289), EWVKFAK (SEQ ID NO: 199), EWVKFAKK (SEQ ID NO: 1290), EWVKFAKPK (SEQ ID NO: 1291), EWVKFAKPCK (SEQ ID NO: 1292), EAWIK (SEQ ID NO: 1293), EAWITK (SEQ ID NO: 1294), EAWITAK (SEQ ID NO: 1295), EAWITAPK (SEQ ID NO: 1296), EAWITAPVK (SEQ ID NO: 1297), EAWITAPVAK (SEQ ID NO: 1298), EAWITAPVALK (SEQ ID NO: 1299), EWITK (SEQ ID NO: 1300), EWITAK (SEQ ID NO: 1301), EWITAPK (SEQ ID NO: 1302), EWITAPVK (SEQ ID NO: 1303), EWITAPVAK (SEQ ID NO: 1304), and EWITAPVALK (SEQ ID NO; 1305).

A modulating agent that contains sequences that flank the Trp-containing CAR sequence on one or both sides may be specific for cell adhesion mediated by one or more specific cadherins, resulting in tissue and/or cell-type specificity. Suitable flanking sequences for conferring specificity include, but are not limited to, endogenous sequences present in one or more naturally occurring cadherins. Modulating agents having a desired specificity may be identified using the representative screens provided herein.

In certain embodiments, a modulating agent may comprise multiple CAR sequences (including CAR sequences other than a Trp-containing CAR sequence). The total number of CAR sequences (including both Trp-containing CAR sequence and CAR sequences other than Trp-containing CAR sequences) present within a modulating agent may range from 1 to a large number, such as 100 or 50, preferably from 1 to 10, and more preferably from 1 to 5 (including all integer values in between). CAR sequences that may be included within a modulating agent are any sequences that are an extracellular portion of an adhesion molecule and involved in interaction of the adhesion molecule with another adhesion molecule. As used herein, a "modulating molecule" (also referred to as "cell adhesion modulating molecule") is a molecule that mediates cell adhesion via a receptor on the cell's surface. Adhesion molecules include members of the cadherin gene superfamily; integrins; members of the immunoglobulin supergene family, such as N-CAM and JAM; and other transmembrane proteins, such as occludin and claudins, as well as extracellular matrix proteins such as laminin, fibronectin, collagens, vitronectin, entactin and tenascin. Within certain embodiments, preferred CAR sequences for inclusion within a modulating agent include (a) Arg-Gly-Asp (RGD), which is bound by integrins (see Cardarelli et al., J. Biol. Chem. 267:23159-64, 1992); (b) Tyr-Ile-Gly-Ser-Arg (YIGSR) (SEQ ID NO: 1306), which is bound by α6 β1 integrin; (c) KYSFNYDGSE (SEQ ID NO: 1307), which is bound by N-CAM; (d) the junctional adhesion molecule (JAM; see Martin-Padura et al., J. Cell. Biol. 142:117-127, 1998) CAR sequence SFTIDPKSG (SEQ ID NO: 1308) or DPK; (e) the occludin CAR sequence LYHY (SEQ ID NO: 1309) (f) claudin CAR sequences comprising at least four consecutive amino acids present within a claudin region that has the formula: Trp-Lys/Arg-Aaa-Baa-Ser/Ala-Tyr/Phe-Caa-Gly (SEQ ID NO: 1310), wherein Aaa, Baa and Caa indicate amino acid residues that may be identical to, or different from, one another; Lys/Arg is an amino acid that is lysine or arginine; Ser/Ala is an amino acid that is serine or alanine; and Tyr/Phe is an amino acid that is tyrosine or phenylalanine; (g) classical cadherin CAR sequence, HAV; and (h) atypical cadherin CAR sequences comprising at least three consecutive amino acids present within an atypical cadherin region that has the formula: Aaa-Phe-Baa-Ile/Leu/Val-Asp/Asn/Glu-Caa-Daa-Ser/Thr/Asn-Gly (SEQ ID NO: 1311), wherein Aaa, Baa, Caa and Daa are amino acid residues that may be identical to, or different from, one another; Ile/Leu/Val is an amino acid that is selected from the group consisting of isoleucine, leucine and valine, Asp/Asn/Glu is an amino acid that is selected from the group consisting of aspartate, asparagine and glutamate; and Ser/Thr/Asn is an amino acid that is selected from the group consisting of serine, threonine or asparagine. Representative claudin CAR sequences include IYSY (SEQ ID NO: 1312), TSSY (SEQ ID NO: 1313), VTAF (SEQ ID NO: 1314) and VSAF (SEQ ID NO: 1315). Representative atypical cadherin CAR sequences include the VE-cadherin (cadherin-5) CAR sequence DAE and the OB-cadherin (cadherin-11) CAR sequence DDK. Additional embodiments of the present invention may employ antibodies or Fab fragments directed against one or more of the CAR sequences described herein.

These and other representative CAR sequences useful in conjunction with the Trp-containing CAR sequences described herein can be found, for example, in U.S. Pat. No. 6,031,072, U.S. Pat. No. 6,169,071, U.S. Pat. No. 6,207,639, U.S. Pat. No. 6,562,786, U.S. Pat. No. 6,346,512, U.S. Pat.

No. 6,333,307, U.S. Pat. No. 6,417,325, U.S. Pat. No. 6,465,427, U.S. Pat. No. 6,326,352, U.S. Pat. No. 6,203,788, U.S. Pat. No. 6,277,824, U.S. Pat. No. 6,472,368, U.S. Pat. No. 6,248,864, U.S. Pat. No. 6,110,747, U.S. Pat. No. 6,310,177, U.S. Pat. No. 6,472,367, U.S. Pat. No. 6,358,920, U.S. Pat. No. 6,433,149, U.S. Pat. No. 6,303,576, and U.S. Pat. No. 6,391,855, the disclosures of which are incorporated herein by reference in their entireties.

Linkers may, but need not, be used to separate CAR sequences and/or antibody sequences within a modulating agent. Linkers may also, or alternatively, be used to attach one or more modulating agents to a support molecule or material, as described below. A linker may be any molecule (including peptide and/or non-peptide sequences as well as single amino acids or other molecules), that does not contain a CAR sequence and that can be covalently linked to at least two peptide sequences. Exemplary linkers include, but are not limited to, $(H_2N(CH_2)_nCO_2H)_m$ or derivatives thereof (where n ranges from 1 to 10 and integer values therebetween, and m ranges from 1 to 4000 and integer values therebetween), glycine ($H_2NCH_2CO_2H$), aminopropanoic acid, aminobutanoic acid, aminopentanoic acid, amino hexanoic acid, 2,3-diaminopropanoic acid, lysine or ornithine, or multimers of the above compounds. Peptide and non-peptide linkers may generally be incorporated into a modulating agent using any appropriate method known in the art.

Using a linker, peptides comprising Trp-containing CAR and other peptide or protein sequences may be joined head-to-tail (i.e., the linker may be covalently attached to the carboxyl or amino group of each peptide sequence), head-to-side chain and/or tail-to-side chain. Modulating agents comprising one or more linkers may form linear or branched structures. Within one embodiment, modulating agents having a branched structure comprise three different CAR sequences, such as HAV, RGD, YIGSR (SEQ ID NO: 1306) and a Trp-containing CAR sequence. Within another embodiment, modulating agents having a branched structure may comprise HAV, RGD, YIGSR (SEQ ID NO: 1306), a Trp-containing CAR sequence and KYSFNYDGSE (SEQ ID NO: 1307). In a third embodiment, modulating agents having a branched structure comprise a Trp-containing CAR sequence, one or more desmocollin (Dsc) CAR sequences, one or more Desmoglein (Dsg) CAR sequence and LYHY (SEQ ID NO: 1309).

In certain embodiments, modulating agents comprise two, three, four, or more Trp-containing CAR sequences, which may be adjacent to one another (i.e., without intervening sequences) or separated by peptide and/or non-peptide linkers. At least one of the Trp-containing CAR sequences of the modulating agents is within a cyclic peptide ring. In certain embodiments, all the multiple Trp-containing CAR sequences in the modulating agents are within cyclic peptide rings. The cyclic peptide rings may contain at most 100, 80, 60, 50, 40, 30, 25, 20, or 15 amino acid residues. These Trp-containing CAR sequences in the cyclic peptides may be linked in tandem (e.g., CGWVMNQGWVMNQC (SEQ ID NO: 1316) or CRWAPIPRWAPIPC (SEQ ID NO: 1317)). Alternatively, at least some of the Trp-containing CAR sequences may be linked with each other in a trans configuration (e.g., CGWVMNQQNMVWGC (SEQ ID NO: 1318), CQNMVWGGWVMNQC (SEQ ID NO: 1319), CRWAPIPPIPAWRC (SEQ ID NO: 1320) or CPIPAWRRWAPIPC (SEQ ID NO: 1321)). The linkers that separate Trp-containing CAR sequences in certain embodiments may comprise one or more amino acid residues that flank (i.e., are adjacent to) the Trp-containing CAR sequence on either side of the sequence in a naturally occurring cadherin molecule. Within one such embodiment, the cyclic peptide contains two Trp-containing CAR sequences. The two Trp-containing CAR sequences may be linked in a cis configuration (i.e., in tandem) or in a trans configuration.

Whether a modulating agent that comprises multiple Trp-containing CAR sequences inhibits or enhances cell adhesion may depend on whether multiple Trp-containing CAR sequences are capable of adopting the natural structure of the Trp-containing CAR sequences (i.e., the structure of the Trp-containing CAR sequence in a naturally occurring cadherin molecule) to facilitate binding among cadherin molecules. For instance, certain modulating agents having two or more Trp-containing CAR sequences may adopt a structure that would allow for the presentation of two or more Trp-containing CAR sequences in their natural configurations (used interchangeably with "conformations"). Such presentation allows the modulating agents to stimultaneously interact with two or more cadherin molecules in the cell membrane and therefore promote dimerization or the formation of multimers of these cadherin molecules. In contrast, some other modulating agents incapable of adopting a structure that allow for the presentation of more than one Trp-containing CAR sequence in its natural configuration would be expected to inhibit, rather than facilitate, the interaction among cadherin molecules.

The configuration of a candidate modulating agent may be determined by any appropriate methods known in the art, including NMR techniques and computational techniques (see, Bowen et al., *J. Clin. Pharmacol.* 33:1149-64, 1993; Lesyng and McCammon, *Pharmacol. Ther.* 60:149-67, 1993; Nikiforovich, *Int. J. Pept Protein Res.* 44:513-31, 1994; Shoichet and Kuntz, *Protein Eng.* 6: 723-32, 1993; DesJarlais and Dixon, *J. Comput Aided Mol. Des.* 8: 231-42, 1994; Oshiro et al., *J. Comput. Aided Mol. Des.* 9:113-30, 1995). In addition, molecular modeling of a modulating agent may also be used to facilitate the determination as to whether two or more Trp-containing CAR sequences in the modulating agent have the potential to simultaneously interact with two or more cadherin molecules. Such molecular modeling may be facilitated by the use of known crystal structures of the amino-terminal domain (i.e., EC1) of various cadherin molecules.

The modulating agents that comprise multiple Trp-containing CAR sequences of a nonclassical cadherin, such as an atypical or desmosomal cadherin, may additionally comprise a CAR sequence for one or more different adhesion molecules (including, but not limited to, other CAMs) and/or one or more antibodies or fragments thereof that bind to such sequences. Linkers may, but need not, be used to separate such CAR sequence(s) and/or antibody sequence(s) from the Trp-containing CAR sequence(s) and/or each other. Such modulating agents may be used within methods in which it is desirable to simultaneously disrupt cell adhesion mediated by multiple adhesion molecules. Within certain preferred embodiments, the second CAR sequence is derived from fibronectin and is recognized by an integrin (i.e., RGD; see Cardarelli et al., *J. Biol. Chem.* 267:23159-23164, 1992), or is the classical cadherin CAR sequence HAV, or is an occludin CAR sequence (e.g., LYHY (SEQ ID NO: 1309), or is any other atypical cadherin CAR sequence. One or more antibodies, or fragments thereof, may similarly be used within such embodiments.

As described above, modulating agents that enhance cell adhesion may contain multiple Trp-containing CAR sequences, and/or antibodies that specifically bind to such sequences, joined directly or by linkers with each other. Enhancement of cell adhesion may also be achieved by attachment of multiple modulating agents to a support molecule or material, as discussed further below. Such modulating agents may additionally comprise one or more CAR sequences for one or more different adhesion molecules (including, but not limited to, other CAMs) and/or one or more antibodies or fragments thereof that bind to such sequences, to enhance cell adhesion mediated by multiple adhesion molecules.

As noted above, modulating agents may be polypeptides or salts thereof, containing only amino acid residues linked by peptide bonds, or may contain non-peptide regions, such as linkers. Peptide regions of a modulating agent may comprise residues of L-amino acids, D-amino acids, or any combination thereof. Amino acids may be from natural or non-natural sources, provided that at least one amino group and at least one carboxyl group are present in the molecule; α- and β-amino acids are generally preferred. The 20 L-amino acids commonly found in proteins are identified herein by the conventional three-letter or one-letter abbreviations, and the corresponding D-amino acids are designated by a lower case one letter symbol.

A modulating agent may also contain rare amino acids (such as 4-hydroxyproline or hydroxylysine), organic acids or amides and/or derivatives of common amino acids, such as amino acids having the C-terminal carboxylate esterified (e.g., benzyl, methyl or ethyl ester) or amidated and/or having modifications of the N-terminal amino group (e.g., acetylation or alkoxycarbonylation), with or without any of a wide variety of side-chain modifications and/or substitutions (e.g., methylation, benzylation, t-butylation, tosylation, alkoxycarbonylation, and the like). Preferred derivatives include amino acids having a C-terminal amide group. Residues other than common amino acids that may be present with a modulating agent include, but are not limited to, 2-mercaptoaniline, 2-mercaptoproline, ornithine, diaminobutyric acid, α-aminoadipic acid, m-aminomethylbenzoic acid and α,β-diaminopropionic acid.

Peptide modulating agents (and peptide portions of modulating agents) as described herein may be synthesized by methods well known in the art, including chemical synthesis and recombinant DNA methods. Chemical synthesis may be performed using solution or solid phase peptide synthesis techniques, in which a peptide linkage occurs through the direct condensation of the α-amino group of one amino acid with the α-carboxy group of the other amino acid with the elimination of a water molecule. Peptide bond synthesis by direct condensation, as formulated above, requires suppression of the reactive character of the amino group of the first and of the carboxyl group of the second amino acid. The masking substituents must permit their ready removal, without inducing breakdown of the labile peptide molecule.

In solution phase synthesis, a wide variety of coupling methods and protecting groups may be used (see Gross and Meienhofer, eds., "The Peptides: Analysis, Synthesis, Biology," Vol. 1-4 (Academic Press, 1979); Bodansky and Bodansky, "The Practice of Peptide Synthesis," 2d ed. (Springer Verlag, 1994)). In addition, intermediate purification and linear scale up are possible. Those of ordinary skill in the art will appreciate that solution synthesis requires consideration of main chain and side chain protecting groups and activation method. In addition, careful segment selection is necessary to minimize racemization during segment condensation. Solubility considerations are also a factor.

Solid phase peptide synthesis uses an insoluble polymer for support during organic synthesis. The polymer-supported peptide chain permits the use of simple washing and filtration steps instead of laborious purifications at intermediate steps. Solid-phase peptide synthesis may generally be performed according to the method of Merrifield et al., *J. Am. Chem. Soc.* 85:2149, 1963, which involves assembling a linear peptide chain on a resin support using protected amino acids. Solid phase peptide synthesis typically utilizes either the Boc or Fmoc strategy. The Boc strategy uses a 1% cross-linked polystyrene resin. The standard protecting group for α-amino functions is the tert-butyloxycarbonyl (Boc) group. This group can be removed with dilute solutions of strong acids such as 25% trifluoroacetic acid (TFA). The next Boc-amino acid is typically coupled to the amino acyl resin using dicyclohexylcarbodiimide (DCC). Following completion of the assembly, the peptide-resin is treated with anhydrous HF to cleave the benzyl ester link and liberate the free peptide. Side-chain functional groups are usually blocked during synthesis by benzyl-derived blocking groups, which are also cleaved by HF. The free peptide is then extracted from the resin with a suitable solvent, purified and characterized. Newly synthesized peptides can be purified, for example, by gel filtration, HPLC, partition chromatography and/or ion-exchange chromatography, and may be characterized by, for example, mass spectrometry or amino acid sequence analysis. In the Boc strategy, C-terminal amidated peptides can be obtained using benzhydrylamine or methylbenzhydrylamine resins, which yield peptide amides directly upon cleavage with HF.

In the procedures discussed above, the selectivity of the side-chain blocking groups and of the peptide-resin link depends upon the differences in the rate of acidolytic cleavage. Orthoganol systems have been introduced in which the side-chain blocking groups and the peptide-resin link are completely stable to the reagent used to remove the α-protecting group at each step of the synthesis. The most common of these methods involves the 9-fluorenylmethyloxycarbonyl (Fmoc) approach. Within this method, the side-chain protecting groups and the peptide-resin link are completely stable to the secondary amines used for cleaving the N-α-Fmoc group. The side-chain protection and the peptide-resin link are cleaved by mild acidolysis. The repeated contact with base makes the Merrifield resin unsuitable for Fmoc chemistry, and p-alkoxybenzyl esters linked to the resin are generally used. Deprotection and cleavage are generally accomplished using TFA.

Those of ordinary skill in the art will recognize that, in solid phase synthesis, deprotection and coupling reactions must go to completion and the side-chain blocking groups must be stable throughout the entire synthesis. In addition, solid phase synthesis is generally most suitable when peptides are to be made on a small scale.

Acetylation of the N-terminus can be accomplished by reacting the final peptide with acetic anhydride before cleavage from the resin. C-amidation is accomplished using an appropriate resin such as methylbenzhydrylamine resin using the Boc technology.

Following synthesis of a linear peptide, with or without N-acetylation and/or C-amidation, cyclization may be achieved if desired by any of a variety of techniques well known in the art. Within one embodiment, a bond may be generated between reactive amino acid side chains. For example, a disulfide bridge may be formed from a linear peptide comprising two thiol-containing residues by oxidizing the peptide using any of a variety of methods. Within one such method, air oxidation of thiols can generate disulfide linkages over a period of several days using either basic or neutral aqueous media. The peptide is used in high dilution to minimize aggregation and intermolecular side reactions. This method suffers from the disadvantage of being slow but has the advantage of only producing $H_2O$ as a side product. Alternatively, strong oxidizing agents such as $I_2$ and $K_3Fe(CN)_6$ can be used to form disulfide linkages. Those of ordinary skill in the art will recognize that care must be taken not to oxidize the sensitive side chains of Met, Tyr, Trp or His. Cyclic peptides produced by this method require purification using standard techniques, but this oxidation is applicable at acid pHs. Oxidizing agents also allow concurrent deprotection/oxidation of suitable S-protected linear precursors to avoid premature, nonspecific oxidation of free cysteine.

DMSO, unlike $I_2$ and $K_3Fe(CN)_6$, is a mild oxidizing agent which does not cause oxidative side reactions of the nucleophilic amino acids mentioned above. DMSO is miscible with $H_2O$ at all concentrations, and oxidations can be performed at acidic to neutral pHs with harmless byproducts. Methyltrichlorosilane-diphenylsulfoxide may alternatively be used as an oxidizing agent, for concurrent deprotection/oxidation of S-Acm, S-Tacm or S-t-Bu of cysteine without affecting other nucleophilic amino acids. There are no polymeric products resulting from intermolecular disulfide bond formation. Suitable thiol-containing residues for use in such oxidation methods include, but are not limited to, cysteine, β,β-dimethyl cysteine (penicillamine or Pen), β,β-tetramethylene cysteine (Tmc), β,β-pentamethylene cysteine (Pmc), β-mercaptopropionic acid (Mpr), β,β-pentamethylene-β-mercaptopropionic acid (Pmp), 2-mercaptobenzene, 2-mercaptoaniline and 2-mercaptoproline.

Peptides containing such residues are illustrated by the following representative formulas, in which the atypical cadherin is OB-cadherin, the underlined portion is cyclized, N-acetyl groups are indicated by N-Ac and C-terminal amide groups are represented by —$NH_2$:

| | | |
|---|---|---|
| i) | N-Ac-Cys-Gly-Trp-Val-Cys-$NH_2$ | (SEQ ID NO: 1322) |
| ii) | N-Ac-Cys-Gly-Trp-Val-Trp-Asn-Gln-Cys-$NH_2$ | (SEQ ID NO: 1323) |
| iii) | N-Ac-Cys-Gly-Trp-Val-Trp-Asn-Cys-$NH_2$ | (SEQ ID NO: 1324) |
| iv) | N-Ac-Cys-Arg-Gly-Trp-Val-Cys-$NH_2$ | (SEQ ID NO: 1325) |
| v) | N-Ac-Cys-Arg-Gly-Trp-Val-Trp-Cys-$NH_2$ | (SEQ ID NO: 1326) |
| vi) | N-Ac-Cys-Gly-Trp-Val-Cys-Asn-OH | (SEQ ID NO: 1327) |
| vii) | H-Cys-Gly-Trp-Val-Cys-Asn-$NH_2$ | (SEQ ID NO: 1327) |
| viii) | N-Ac-Cys-Gly-Trp-Val-Pen-$NH_2$ | (SEQ ID NO: 1328) |
| ix) | N-Ac-Cys-Arg-Gly-Trp-Val-Trp-Asn-Gln-Phe-Cys-$NH_2$ | (SEQ ID NO: 1329) |
| x) | N-Ac-Cys-Arg-Gly-Trp-Val-Trp-Asn-Gln-Phe-Phe-Cys-$NH_2$ | (SEQ ID NO: 1330) |
| xi) | N-Ac-Ile-Tmc-Gly-Trp-Val-Trp-Asn-Gln-Cys-Glu-$NH_2$ | (SEQ ID NO: 1331) |
| xii) | N-Ac-Ile-Pmc-Gly-Trp-Val-Trp-Asn-Gln-Cys-$NH_2$ | (SEQ ID NO: 1332) |
| xiii) | Mpr-Gly-Trp-Val-Trp-Asn-Gln-Pro-Cys-$NH_2$ | (SEQ ID NO: 1333) |
| xiv) | Pmp-Gly-Trp-Val-Trp-Asn-Gln-Pro-Cys-$NH_2$ | (SEQ ID NO: 1333) |

Peptides containing such residues are illustrated by the following representative formulas, in which the desmosomal cadherin is human desmocollin 2, the underlined portion is cyclized, N-acetyl groups are indicated by N-Ac and C-terminal amide groups are represented by —NH₂:

| | | |
|---|---|---|
| i) | N-Ac-<u>Cys-Arg-Trp-Ala-Pro-Cys</u>-NH₂ | (SEQ ID NO: 1334) |
| ii) | N-Ac-<u>Cys-Arg-Trp-Ala-Pro-Ile-Pro-Cys</u>-NH₂ | (SEQ ID NO: 1335) |
| iii) | N-Ac-<u>Cys-Arg-Trp-Ala-Pro-Ile-Cys</u>-NH₂ | (SEQ ID NO: 1336) |
| iv) | N-Ac-<u>Cys-Arg-Trp-Ala-Pro-Ile-Pro-Cys-Cys</u>-NH₂ | (SEQ ID NO: 1337) |
| v) | N-Ac-<u>Cys-Arg-Trp-Ala-Pro-Ile-Pro-Cys-Ser-Cys</u>-Met-NH₂ | (SEQ ID NO: 1338) |
| vi) | N-Ac-<u>Cys-Arg-Trp-Ala-Cys</u>-Asn-OH | (SEQ ID NO: 1339) |
| vii) | H-<u>Cys-Arg-Trp-Ala-Cys</u>-Asn-NH₂ | (SEQ ID NO: 1339) |
| viii) | N-Ac-<u>Cys-Arg-Trp-Ala-Pen</u>-NH₂ | (SEQ ID NO: 1340) |
| ix) | N-Ac-<u>Cys-Arg-Trp-Ala-Pro-Ile-Pro-Cys-Ser-Cys</u>-NH₂ | (SEQ ID NO: 1341) |
| x) | N-Ac-<u>Cys-Arg-Trp-Ala-Pro-Ile-Pro-Cys-Ser-Met-Cys</u>-NH₂ | (SEQ ID NO: 1342) |
| xi) | N-Ac-Ile-<u>Tmc-Arg-Trp-Ala-Pro-Ile-Pro-Cys</u>-Glu-NH₂ | (SEQ ID NO: 1343) |
| xii) | N-Ac-Ile-<u>Pmc-Arg-Trp-Ala-Pro-Ile-Pro-Cys</u>-NH₂ | (SEQ ID NO: 1344) |
| xiii) | <u>Mpr-Arg-Trp-Ala-Pro-Ile-Pro-Cys-Cys</u>-NH₂ | (SEQ ID NO: 1345) |
| xiv) | <u>Pmp-Arg-Trp-Ala-Pro-Ile-Pro-Cys-Cys</u>-NH₂ | (SEQ ID NO: 1345) |

It will be readily apparent to those of ordinary skill in the art that, within each of these representative formulas, any of the above thiol-containing residues may be employed in place of one or both of the thiol-containing residues recited. Similar formulas comprising different atypical and/or desmosomal cadherin Trp-containing CAR sequences may be generated by those of ordinary skill in the art, based on the Trp-containing CAR sequences provided herein.

Within another embodiment, cyclization may be achieved by amide bond formation. For example, a peptide bond may be formed between terminal functional groups (i.e., the amino and carboxy termini of a linear peptide prior to cyclization). One such cyclic peptide comprising an OB-cadherin Trp-containing CAR sequence is <u>GWVWNQ</u> (SEQ ID NO: 16) with or without an N-terminal acetyl group and/or a C-terminal amide. Within another such embodiment, the cyclic peptide comprises a D-amino acid. Alternatively, cyclization may be accomplished by linking one terminus and a residue side chain or using two side chains, as in <u>KGWVD</u>(SEQ ID NO:387) or <u>KGWVWNQD</u>(SEQ ID NO:390), with or without an N-terminal acetyl group and/or a C-terminal amide. Residues capable of forming a lactam bond include lysine, ornithine (Orn), α-amino adipic acid, m-aminomethylbenzoic acid, α,β-diaminopropionic acid, glutamate or aspartate.

Another such cyclic peptide comprising a desmocollin 2 Trp-containing CAR sequence is <u>RWAPIP</u> (SEQ ID NO: 2) with or without an N-terminal acetyl group and/or a C-terminal amide. Within another such embodiment, the cyclic peptide comprises a D-amino acid. Alternatively, cyclization may be accomplished by linking one terminus and a residue side chain or using two side chains, as in <u>KRWAD</u> (SEQ ID NO: 1075) or <u>KRWAPIPD</u> (SEQ ID NO: 1346), with or without an N-terminal acetyl group and/or a C-terminal amide. Residues capable of forming a lactam bond include lysine ornithine (Orn), α-amino adipic acid, m-aminomethylbenzoic acid, α,β-diaminopropionic acid, glutamate or aspartate.

Methods for forming amide bonds are well known in the art and are based on well established principles of chemical reactivity. Within one such method, carbodiimide-mediated lactam formation can be accomplished by reaction of the carboxylic acid with DCC, DIC, EDAC (SEQ ID NO: 1347) or DCCI (SEQ ID NO: 1348), resulting in the formation of an O-acylurea that can be reacted immediately with the free amino group to complete the cyclization. The formation of the inactive N-acylurea, resulting from O→N migration, can be circumvented by converting the O-acylurea to an active ester by reaction with an N-hydroxy compound such as 1-hydroxybenzotriazole, 1-hydroxysuccinimide, 1-hydroxynorbornene carboxamide or ethyl 2-hydroximino-2-cyanoacetate. In addition to minimizing O→N migration, these additives also serve as catalysts during cyclization and assist in lowering racemization. Alternatively, cyclization can be performed using the azide method, in which a reactive azide intermediate is generated from an alkyl ester via a hydrazide. Hydrazinolysis of the terminal ester necessitates the use of a t-butyl group for the protection of side chain carboxyl functions in the acylating component. This limitation can be overcome by using diphenylphosphoryl acid (DPPA), which furnishes an azide directly upon reaction with a carboxyl group. The slow reactivity of azides and the formation of isocyanates by their disproportionation restrict the usefulness of this method. The mixed anhydride method of lactam formation is widely used because of the facile removal of reaction by-products. The anhydride is formed upon reaction of the carboxylate anion with an alkyl chloroformate or pivaloyl chloride. The attack of the amino component is then guided to the carbonyl carbon of the acylating component by the electron donating effect of the alkoxy group or by the steric bulk of the pivaloyl chloride t-butyl group, which obstructs attack on the wrong carbonyl group. Mixed anhydrides with phosphoric acid derivatives have also been successfully used. Alternatively, cyclization can be accomplished using activated esters. The presence of electron withdrawing substituents on the alkoxy carbon of esters increases their susceptibility to aminolysis. The high reactivity of esters of p-nitrophenol, N-hydroxy compounds and polyhalogenated phenols has made these "active esters" useful in the synthesis of amide bonds. The last few years have witnessed the development of benzotriazolyloxytris-(dimethylamino)phosphonium hexafluorophosphonate (BOP) and its congeners as advantageous coupling reagents. Their performance is generally superior to that of the well established carbodiimide amide bond formation reactions.

Within a further embodiment, a thioether linkage may be formed between the side chain of a thiol-containing residue and an appropriately derivatized α-amino acid. By way of example, a lysine side chain can be coupled to bromoacetic acid through the carbodiimide coupling method (DCC, EDAC (SEQ ID NO: 1347)) and then reacted with the side chain of any of the thiol containing residues mentioned above to form a thioether linkage. In order to form dithioethers, any two thiol containing side-chains can be reacted with dibromoethane and diisopropylamine in DMF. Examples of thiol-containing linkages are shown below:

i.

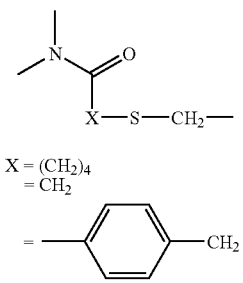

ii.

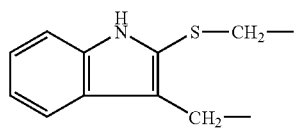

For longer modulating agents, recombinant methods are preferred for synthesis. Within such methods, all or part of a modulating agent can be synthesized in living cells, using any of a variety of expression vectors known to those of ordinary skill in the art to be appropriate for the particular host cell. Suitable host cells may include bacteria, yeast cells, mammalian cells, insect cells, plant cells, algae and other animal cells (e.g., hybridoma, CHO, myeloma). The DNA sequences expressed in this manner may encode portions of a nonclassical cadherin or other adhesion molecule, or may encode a peptide comprising a nonclassical cadherin analogue or an antibody fragment that specifically binds to a nonclassical cadherin Trp-containing CAR sequence. Such DNA sequences may be prepared based on known cDNA or genomic sequences, or from sequences isolated by screening an appropriate library with probes designed based on the sequences of known nonclassical cadherins. Such screens may generally be performed as described in Sambrook et al., *Molecular Cloning: A Laboratory Manual*, Cold Spring Harbor Laboratories, Cold Spring Harbor, N.Y., 1989 (and references cited therein). Polymerase chain reaction (PCR) may also be employed, using oligonucleotide primers in methods well known in the art, to isolate nucleic acid molecules encoding all or a portion of an endogenous adhesion molecule. To generate a nucleic acid molecule encoding a desired modulating agent, an endogenous cadherin sequence may be modified using well known techniques. For example, portions encoding one or more CAR sequences may be joined, with or without separation by nucleic acid regions encoding linkers, as discussed above. Alternatively, portions of the desired nucleic acid sequences may be synthesized using well-known techniques, and then ligated together to form a sequence encoding the modulating agent.

As noted above, polynucleotides may also function as modulating agents. In general, such polynucleotides should be formulated to permit expression of a polypeptide modulating agent following administration to a mammal. Such formulations are particularly useful for therapeutic purposes, as described below. Those of ordinary skill in the art will appreciate that there are many ways to achieve expression of a polynucleotide within a mammal, and any suitable method may be employed. For example, a polynucleotide may be incorporated into a viral vector such as, but not limited to, adenovirus, adeno-associated virus, retrovirus, or vaccinia or other pox virus (e.g., avian pox virus). Techniques for incorporating DNA into such vectors are well known to those of ordinary skill in the art. A retroviral vector may additionally transfer or incorporate a gene for a selectable marker (to aid in the identification or selection of transfected cells) and/or a targeting moiety, such as a gene that encodes a ligand for a receptor on a specific target cell, to render the vector target specific. Targeting may also be accomplished using an antibody, by methods known to those of ordinary skill in the art. Other formulations for polynucleotides for therapeutic purposes include colloidal dispersion systems, such as macromolecule complexes, nanocapsules, microspheres, beads, and lipid-based systems including oil-in-water emulsions, micelles, mixed micelles, and liposomes. A preferred colloidal system for use as a delivery vehicle in vitro and in vivo is a liposome (i.e., an artificial membrane vesicle). The preparation and use of such systems is well known in the art.

As noted above, the modulating agent of the present invention may comprise a peptidomimetic instead of (or in addition to) a Trp-containing CAR sequence. A "peptidomimetic" is a compound in which at least a portion of a Trp-containing CAR sequence is replaced with a non-peptide structure, but the three-dimensional structure of the Trp-containing CAR sequence remains substantially the same as that of the Trp-containing CAR sequence. In other words, one, two, three, four, five or six amino acid residues within the Trp-containing CAR sequence may be replaced by one or more chemical structures so that at least one peptide bond in the Trp-containing CAR sequence is eliminated. A peptidomimetic of the present invention also has a cell adhesion modulating activity assayed detectable by at least one of the assays described below.

Peptidomimetics generally have improved oral availability, which makes them especially suited to treatment of conditions such as cancer. It should be noted that peptidomimetics may or may not have similar two-dimensional chemical structures, but share common three-dimensional structural features and geometry. Each peptidomimetic may further have one or more unique additional binding elements. The present invention provides methods for designing, screening and/or identifying peptidomimetics.

In certain embodiments, the pharmacophore of one or more Trp-containing CAR sequences described above is first mapped to facilitate the designing of peptidomimetics. The term "pharmacophore" refers to the collection of functional groups on a compound that are arranged in three-dimensional space in a manner complementary to the target protein, and that are responsible for biological activity as a result of compound binding to the target protein. Useful three-dimensional pharmacophore models may be derived from either crystallographic or nuclear magnetic resonance (NMR) structures of the target. Alternatively, ligand structure-activity relationships may be used to map the binding site of the ligand. More specifically, structure-activity relationships of structurally diverse and conformationally informative molecules are used to propose a pharmacophore. Such relationships establish the required groups for the activities of the ligands. Conformationally constrained compounds that are also active may help establish the bioactive conformation of all the ligands. The molecules are superimposed, in their proposed bioactive conformations, over the atoms of the pharmacophore or their projected binding points on the macromolecule (i.e., receptor). The union of the volumes occupied by the active compounds as superimposed suggests the regions that can be occupied by any newly designed active ligand. In addition, regions occupied by compounds that meet the pharmacophore requirements but are inactive define "forbidden regions" that, if occupied, destroy activity.

The three-dimensional structures of Trp-containing CAR sequences may generally be determined using nuclear magnetic resonance (NMR) techniques that are well known in the art. NMR data acquisition is preferably carried out in aqueous systems that closely mimic physiological conditions to ensure that a relevant structure is obtained. Briefly, NMR techniques use the magnetic properties of certain atomic nuclei (such as $^1H$, $^{13}C$, $^{15}N$ and $^{31}P$), which have a magnetic moment or spin, to probe the chemical environment of such nuclei. The NMR data can be used to determine distances between atoms in the molecule, which can be used to derive a three-dimensional model or the molecule.

For determining three-dimensional structures of Trp-containing CAR sequences (and candidate peptidomimetics, as discussed below) proton NMR is preferably used. More specifically, when a molecule is placed in a strong magnetic field, the two spin states of the hydrogen atoms are no longer degenerate. The spin aligned parallel to the field will have a lower energy and the spin aligned antiparallel to the field will have a higher energy. At equilibrium, the spin of the hydrogen atoms will be populated according to the Boltzmann distribution equation. This equilibrium of spin populations can be perturbed to an excited state by applying radio frequency (RF) pulses. When the nuclei revert to the equilibrium state, they emit RF radiation that can be measured. The exact frequency of the emitted radiation from each nucleus depends on the molecular environment of the nucleus and is different for each atom (except for those atoms that have the same molecular environment). These different frequencies are obtained relative to a reference signal and are called chemical shifts. The nature, duration and combination of applied RF pulses can be varied greatly and different molecular properties can be probed by those of ordinary skill in the art, by selecting an appropriate combination of pulses.

For three-dimensional structure determinations, one-dimensional NMR spectra are generally insufficient, as limited information pertaining to conformation may be obtained. One-dimensional NMR is generally used to verify connectivity within a molecule and yields incomplete data concerning the orientation of side chains within a peptide. Two-dimensional NMR spectra are much more useful in this respect and allow for unambiguous determination of side-chain-to-side-chain interactions and the conformation of the peptide backbone.

Two-dimensional NMR spectra are generally presented as a contour plot in which the diagonal corresponds to a one-dimensional NMR spectrum and the cross peaks off the diagonal result from interactions between hydrogen atoms that are directly scalar coupled. Two-dimensional experiments generally contain a preparation period, an evolution period where spins are "labeled" as they process in the XY plane according to their chemical shift, a mixing period, during which correlations are made with other spins and a detection period in which a free induction decay is recorded.

Two-dimensional NMR methods are distinguished by the nature of the correlation that is probed during the mixing period. A DQF-COSY (double quantum filtered correlation spectroscopy) analysis gives peaks between hydrogen atoms that are covalently connected through one or two other atoms. Nuclear Overhauser effect spectroscopy (NOESY) gives peaks between pairs of hydrogen atoms that are close together in space, even if connected by way of a large number of intervening atoms. In total correlation spectroscopy (TOCSY), correlations are observed between all protons that share coupling partners, whether or not they are directly coupled to each other. Rotating-frame Overhauser Spectroscopy (ROESY) experiments may be thought of as the rotating frame analogue of NOESY, and yields peaks between pairs of hydrogen atoms that are close together in space. One or more such methods may be used, in conjunction with the necessary water-suppression techniques such as WATERGATE and water flip-back, to determine the three-dimensional structure of a Trp-containing CAR sequence or candidate peptidomimetic under aqueous conditions. Such techniques are well known and are necessary to suppress the resonance of the solvent (HDO) during acquisition of NMR data.

By way of example, both TOCSY and NOESY may be applied to representative Trp-containing CAR sequences for the purpose of determining the conformation and the assignment. The water solvent resonance may be suppressed by application of the WATERGATE procedure. A water flipback pulse may also be applied at the end of the mixing period for both TOCSY and NOESY experiments to maintain the water signal at equilibrium and to minimize the loss of amide proton resonances due to their rapid exchange at the near neutral pH conditions (i.e., pH 6.8) used in the experiment. NMR data may be processed using spectrometer software using a squared cosine window function along both directions. Baseline corrections may be applied to the NOESY, ROESY and TOCSY spectra using the standard Bruker polynomial method.

NOESY data may be acquired at several mixing times ranging from 80 ms to 250 ms. The shorter mixing time NOESY may be acquired to ensure that no diffusion effects were present in the NOESY spectrum acquired at the longer mixing times. The interproton distances may generally be determined from the 250 ms NOESY. The sequence-specific assignment of the proton resonances may be determined by standard methods (see Wuthrich, *NMR of Proteins and Nucleic Acids*, Wiley & Sons, New York, 1986), making use of both the results of the TOCSY and NOESY data. The spin systems of Ala3 and Val4 may be assigned based on the presence of strong NOEs between the amide protons and the respective side chains in conjunction with the relevant TOCSY data.

For conformational calculations, the NOE cross peaks may be initially converted to a uniform distance upper and lower bounds of 1.8-5.0 angstroms regardless of the NOE intensities. The NOE distances may be refined iteratively through a comparison of computed and experimental NOEs at the various mixing times. This refinement may be much in the spirit of the PEPFLEX-II procedure (Wang et al., Techniques in Protein Chemistry IV, 1993, Evaluation of NMR Based Structure Determination for Flexible Peptides: Application to Desmopressin p. 569), although preferably initial NOE-based distances with very loose upper bounds (e.g., 5 angstroms) are used to permit the generation of a more complete set of conformations in agreement with experimental data. Dihedral-angle constraints may be derived from the values of the $^3JC\alpha H$ coupling constants. A tolerance value of 40 degrees may be added to each of the dihedral angle constraints to account for the conformational flexibility of the peptide. Distance geometry calculations may be carried out utilizing fixed bond lengths and bond angles provided in the ECEPP/2 database (Ni et al., *Biochemistry* 31:11551-11557, 2989). The ω-angles are generally fixed at 180 degrees, but all other dihedral angles may be varied during structure optimization.

Structures with the lowest constraint violations may be subjected to energy minimization using a distance-restrained Monte Carlo method (Ripoll and Ni, *Biopolymers* 32:359-365, 1992; Ni, *J. Magn. Reson.* B106:147-155, 1995), and modified to include the ECEPP/3 force field (Ni et al., *J. Mol. Biol.* 252:656-671, 1995). All ionizable groups may be treated as charged during constrained Monte Carlo minimization of the ECEPP/3 energy. Electrostatic interactions among all charges may be screened by use of a distance-dependent dielectric to account for the absence of solvent effects in conformational energy calculations. In addition, hydrogen-bonding interactions can be reduced to 25% of the full scale, while van der Waals and electrostatic terms are kept to full strengths. These special treatments help to ensure that the conformational search is guided primarily by the experimental NMR constraints and that the computed conformations are less biased by the empirical conformational energy parameters (Warder et al., *FEBS Lett.* 411:19-26, 1997).

Low-energy conformations of the peptide from Monte Carlo calculations may be used in NOE simulations to identify proximate protons with no observable NOEs and sets of distance upper bounds that warrant recalibration. The refined set of NOE distances including distance lower bounds derived from absent NOEs are used in the next cycles of Monte Carlo calculations, until the resulting conformations produced simulate NOE spectra close to those observed experimentally (Ning et al., *Biopolymers* 34:1125-1137, 1994; Ni et al., *J. Mol. Biol.* 252:656-671, 1995). Theoretical NOE spectra may be calculated using a tumbling correlation time of 1.5 ns based on the molecular weight of the peptide and the experimental temperature (Cantor, C. R. and Schimmel, P. R. (1980) *Biophysical Chemistry*, W. H. Freeman & Co., San Francisco). All candidate peptide conformations are included with equal weights in an ensemble-averaged relaxation matrix analysis of interconverting conformations (Ni and Zhu *J. Magn. Reson.* B102:180-184, 1994). NOE simulations may also incorporate parameters to account for the local motions of the methyl groups and the effects of incomplete relaxation decay of the proton demagnitizations (Ning et al., *Biopolymers* 34:1125-1137, 1994). The computed NOE intensities are converted to the two-dimensional FID's (Ni, *J. Magn. Reson.* B106:147-155, 1995) using the chemical shift of assignments, estimated linewidths and coupling constants for all resolved proton resonances. Calculated FIDs may be converted to simulated NOESY spectra using identical processing procedures as used for the experimental NOE data sets.

As noted above, the peptidomimetics of the present invention have a three-dimensional structure that is substantially similar to a three-dimensional structure of a Trp-containing CAR sequence as described above. In general, two three-dimensional structures are said to be substantially structurally similar to each other if their pharmacophore atomic coordinates have a root-mean square deviation (RMSD) less than or equal to 1 angstrom, as calculated using the Molecular Similarity module within the QUANTA program (QUANTA, available from Molecular Simulations Inc., San Diego, Calif.). All peptidomimetics provided herein have at least one low-energy three-dimensional structure that is substantially similar to at least one low-energy three-dimensional structure of a Trp-containing CAR sequence as described above.

Low energy conformations may be identified by conformational energy calculations using, for example, the CHARMM program (Brooks et al., *J. Comput. Chem.* 4:187-217, 1983). The energy terms include bonded and non-bonded terms, including bond length energy, angle energy, dihedral angle energy, Van der Waals energy and electrostatic energy. It will be apparent that the conformational energy can be also calculated using any of a variety of other commercially available quantum mechanic or molecular mechanic programs. A low energy structure has a conformational energy that is within 50 kcal/mol of the global minimum.

The low energy conformation(s) of candidate peptidomimetics are compared to the low energy solution conformations of the Trp-containing CAR sequence (as determined by NMR) to determine how closely the conformation of the candidate mimics that of the Trp-containing CAR sequence. In such comparisons, particular attention should be given to the locations and orientations of the elements corresponding to the crucial side chains. If at least one of the candidate low energy conformations is substantially similar to a solution conformation of a Trp-containing CAR sequence (i.e., differs with a root-mean square deviation (RMSD) of 1 angstrom or less), the candidate compound is considered a peptidomimetic. Within such analyses, low energy conformations of candidate peptidomimetics in solution may be studied using, for example, the CHARMM molecular mechanics and molecular dynamics program (Brooks et al., *J. Comput. Chem.* 4:187-217, 1983), with the TIP3P water model (Jorgensen et al., *J. Chem Phys.* 79:926-935, 1983) used to represent water molecules. The CHARM22 force field may be used to represent the designed peptidomimetics.

By way of example, low energy conformations may be identified using a combination of two procedures. The first procedure involves a simulated annealing molecular dynamics simulation approach. In this procedure, the system (which includes the designed peptidomimetics and water molecules) is heated up to above room temperature, preferably around 600K, and simulated for a period of 100 picoseconds (ps) or longer; then gradually reduced to 500K and simulated for a period of 100 ps or longer; then gradually reduced to 400K and simulated for a period of 100 ps or longer; gradually reduced to 300K and simulated for a period of 500 ps or longer. The trajectories are recorded for analysis. This simulated annealing procedure is known for its ability for efficient conformational search.

The second procedure involves the use of the self-guided molecular dynamics (SGMD) method (Wu and Wang, *J. Physical Chemistry* 102:7238-7250, 1998). The SGMD method has been demonstrated to have an extremely enhanced conformational searching capability. Using the SGMD method, simulation may be performed at 300 K for 1000 ps or longer and the trajectories recorded for analysis.

Conformational analysis may be carried out using the QUANTA molecular modeling package. First, cluster analysis may be performed using the trajectories generated from molecular dynamic simulations. From each cluster, the lowest energy conformation may be selected as the representative conformation for this cluster and may be compared to other conformational clusters. Upon cluster analysis, major conformational clusters may be identified and compared to the solution conformations of the Trp-containing CAR sequence(s).

The conformational comparison may be carried out using the Molecular Similarity module within the QUANTA program.

Similarity in structure may also be evaluated by visual comparison of the three-dimensional structures displayed in a graphical format, or by any of a variety of computational comparisons. For example, an atom equivalency may be defined in three-dimensional structures of the peptidomimetic and a Trp-containing CAR sequence, and a fitting operation used to establish the level of similarity. As used herein, an "atom equivalency" is a set of conserved atoms in the two structures. A "fitting operation" may be any process by which a candidate compound structure is translated and rotated to obtain an optimum fit with the structure of the Trp-containing CAR sequence. A fitting operation may be a rigid fitting operation (e.g., the three-dimensional structure of the Trp-containing CAR sequence can be kept rigid and the three-dimensional structure of the peptidomimetic can be translated and rotated to obtain an optimum fit with the Trp-containing CAR sequence). Alternatively, the fitting operation may use a least squares fitting algorithm that computes the optimum translation and rotation to be applied to the moving compound structure, such that the root mean square difference of the fit over the specified pairs of equivalent atoms is a minimum. Preferably, atom equivalencies may be established by the user and the fitting operation is performed using any of a variety of available software applications (e.g., QUANTA, available from Molecular Simulations Inc., San Diego, Calif.). Three-dimensional structures of candidate compounds for use in establishing substantial similarity may be determined experimentally (e.g., using NMR techniques as described herein or x-ray crystallography), or may be computer-generated using, for example, methods provided herein.

Certain peptidomimetics may be designed, based on the structure of a Trp-containing CAR sequence. For example, such peptidomimetics may mimic the local topography about the cleavable amide bonds (amide bond isosteres). These mimetics often match the peptide backbone atom-for-atom, while retaining functionality that makes important contacts with the binding sites. Amide bond mimetics may also include the incorporation of unusual amino acids or dipeptide surrogates (see FIG. 5, and other examples in Gillespie et al., *Biopolymers* 43:191-217, 1997). The conformationally rigid substructural elements found in these types of mimetics are believed to result in binding with highly favorable entropic driving forces, as compared to the more conformationally flexible peptide linkages. Backbone modifications can also impart metabolic stability towards peptidase cleavage relative to the parent peptide. Other peptidomimetics may be secondary structure mimics.

To design a peptidomimetic, heuristic rules that have been developed through experience may be used to systematically modify a Trp-containing CAR sequence. Within such modification, empirical data of various kinds are generally collected throughout an iterative refinement process. As noted above, optimal efficiency in peptidomimetic design requires a three-dimensional structure of the pharmacophore.

Peptidomimetics can also be designed based on a visual comparison of the pharmacophore of a Trp-containing CAR sequence with a three-dimensional structure of a candidate compound, using knowledge of the structure-activity relationships of the Trp-containing CAR sequence. Structure-activity studies should establish important binding elements in the Trp-containing CAR sequences, which in turn should be retained in the designed peptidomimetics.

As an alternative to design by visual inspection, libraries may be made using combinatorial chemical techniques.

Combinatorial chemical technology enables the parallel synthesis of organic compounds through the systematic addition of defined chemical components using highly reliable chemical reactions and robotic instrumentation. Large libraries of compounds result from the combination of all possible reactions that can be done at one site with all the possible reactions that can be done at a second, third or greater number of sites. Combinatorial chemical methods can potentially generate tens to hundreds of millions of new chemical compounds as mixtures, attached to a solid support, or as individual compounds. Methods for constructing peptidomimetic synthetic combinatorial libraries are known in the art and discussed in many journal articles (e.g., Eichler et al., *Medicinal Research Review* 15: 481-96, 1995; Al-Obeidi et al., *Molecular Biotechnology* 9: 205-23, 1998; Hruby et al., *Current Opinion in Chemical Biology* 1: 114-9, 1997; and Ripka and Rich, *Current Opinion in Chemical Biology* 2: 441-52, 1998).

Pharmacophores can be used to facilitate the screening of such chemical libraries. For example, instead of producing all possible members of every library (resulting in an unwieldy number of compounds), library synthesis can focus on the library members with the greatest probability of interacting with the target. The integrated application of structure-based design and combinatorial chemical technologies can produce synergistic improvements in the efficiency of drug discovery.

Further peptidomimetics are compounds that appear to be unrelated to the original peptide, but contain functional groups positioned on a nonpeptide scaffold that serve as topographical mimics. This type of peptidomimetic may be identified using library screens of large chemical databases. Such screens use the three-dimensional conformation of a pharmacophore to search such databases in three-dimensional space. A single three-dimensional structure may be used as a pharmacophore model in such a search. Alternatively, a pharmacophore model may be generated by considering the crucial chemical structural features present within multiple three-dimensional structures.

Any of a variety of databases of three-dimensional structures may be used for such searches. A database of three-dimensional structures may be prepared by generating three-dimensional structures of a database of compounds, and storing the three-dimensional structures in the form of data storage material encoded with machine-readable data. The three-dimensional structures can be displayed on a machine capable of displaying a graphical three-dimensional representation and programmed with instructions for using the data. Within preferred embodiments, three-dimensional structures are supplied as a set of coordinates that define the three-dimensional structure.

Preferably, the 3D-database contains at least 100,000 compounds, with small, non-peptidyl molecules having relatively simple chemical structures particularly preferred. It is also important that the 3D co-ordinates of the compounds in the database be accurately and correctly represented. The National Cancer Institute (NCI) 3D-database (Milne et al., *J. Chem. Inf. Comput. Sci.* 34:1219-1224, 1994) and the Available Chemicals Directory (ACD; available from MDL Information Systems, San Leandro, Calif.) are two excellent databases that can be used to generate a database of three-dimensional structures, using molecular modeling, as discussed above. For flexible molecules, which can have several low-energy conformations, it is desirable to store and search multiple conformations. The Chem-X program (Oxford Molecular Group PLC; Oxford UK) is capable of searching thousands or even millions of conformations for a flexible compound. This capability of Chem-X provides a real advantage in dealing with compounds that can adopt multiple conformations. Using this approach, hundreds of millions of conformations can be searched in a 3D-pharmacophore searching process.

The Available Chemical Database may also be screened for appropriate peptidomimetics. To facilitate pharmacophore searching, the entire ACD database is converted into 3-D conformations, which can be searched using the Chem-X program.

A pharmacophore search typically involves three steps. The first step is the generation of a pharmacophore query. Such queries may be developed from an evaluation of critical distances in the three dimensional structure of a Trp-containing CAR sequence. Using the pharmacophore query of interest, a distance bit screening is performed on the database to identify compounds that fulfill the required geometrical constraints. In other words, compounds that satisfy the specified critical pair-wise distances are identified. After a compound passed the distance bit screening step, the program next checks whether the compound meets the substructural requirements as specified in the pharmacophore query. After a compound passes this sub-structural check, it is finally subjected to a conformational analysis. In this step, conformations are generated and evaluated with regard to geometric requirements specified in the pharmacophore query. Compounds that have at least one conformation satisfying the geometric requirements, are considered as 'hits' and are recorded in a result database.

In some embodiments, computer modeling without the identification of a pharmacophore may also be used to search for appropriate peptidomimetics. For instance, computer program DOCK, which uses spheres to describe the active site of a molecule ("receptor") known from, for example, X-ray crystallography. The "negative" image of this receptor site is then used to test out compounds from a database (e.g., Cambridge Crystallographic Database, Maybridge Structural Database, and ChemDiv Database). Using a score to rank these molecules docked onto the receptor site, compounds that fit well onto the receptor site may be obtained.

Another computer program CAVEAT may also be used to peptidomimetic searches. For every molecule in a database, the program stores the intramolecular bonds as vectors. The resulting new database of vectors is then searched for vector matching. In other words, this approach starts with the crystal structure of a ligand in complex with a receptor and then search for new templates based on the spatial arrangements of the bonds of this known ligand.

While compounds (i.e., hits) selected from databases satisfy the requirements for three-dimensional similarity, it will be apparent to those of ordinary skill in the art that further biological testing may be used to select compounds with optimal activity. It will further be apparent that other criteria may be considered when selecting specific compounds for particular applications, such as the simplicity of the chemical structure, low molecular weight, chemical structure diversity and water solubility. The application of such criteria is well understood by medicinal, computational and structural chemists.

It will be apparent that a compound structure may be optimized using screens as provided herein. Within such screens, the effect of specific alterations of a candidate compound on three-dimensional structure may be evaluated to optimize three-dimensional similarity to a Trp-containing CAR sequence. Such alterations include, for example, changes in hydrophobicity, steric bulk, electrostatic properties, size and bond angle.

Biological testing of candidate compounds may be used to confirm peptidomimetic activity. In general, peptidomimetics should function in a substantially similar manner as a structurally similar Trp-containing CAR sequence. In other words, a peptidomimetic of a Trp-containing CAR sequence should bind to a nonclassical cadherin with an affinity that is at least half the affinity of the Trp-containing CAR sequence, as measured using standard binding assays. Further, a peptidomimetic of the Trp-containing CAR sequence should modulate a nonclassical cadherin-mediated function using a representative assay provided herein at a level that is at least half the level of modulation achieved using the Trp-containing CAR sequence.

Once an active peptidomimetic has been identified, related analogues may be identified using two-dimensional similarity searching. Such searching may be performed, for example, using the program ISIS Base (Molecular Design Limited). Two-dimensional similarity searching permits the identification of other available, closely related compounds, which may be readily screened to optimize biological activity. The active peptidomimetic and its related analogues may be prepared or produced by any methods or chemical reactions known in the art.

As noted above, a modulating agent may additionally, or alternatively, comprise a substance such as an antibody or antigen-binding fragment thereof, that specifically binds to a nonclassical cadherin Trp-containing CAR sequence, such as an atypical or desmosomal cadherin Trp-containing CAR sequence. As used herein, a substance is said to "specifically bind" to an cadherin Trp-containing CAR sequence (with or without flanking amino acids) if it reacts at a detectable level with a peptide containing that sequence, and does not react detectably with peptides containing a different CAR sequence or a sequence in which the order of amino acid residues in the cadherin Trp-containing CAR sequence and/or flanking sequence is altered. Such antibody binding properties may generally be assessed using an ELISA, which may be readily performed by those of ordinary skill in the art and is described, for example, by Newton et al., *Develop. Dynamics* 197:1-13, 1993. In certain embodiments, the dissociation constant of the interaction between an antibody molecule and a Trp-containing CAR sequence is at most $10^{-7}$ M. In other embodiments, the dissociation constant is at most $10^{-8}$ M.

Polyclonal and monoclonal antibodies may be raised against a cadherin Trp-containing CAR sequence using conventional techniques. See, e.g., Harlow and Lane, *Antibodies: A Laboratory Manual*, Cold Spring Harbor Laboratory, 1988. In one such technique, an immunogen comprising the Trp-containing CAR sequence is initially injected into any of a wide variety of mammals (e.g., mice, rats, rabbits, sheep or goats). The smaller immunogens (i.e., less than about 20 amino acids) should be joined to a carrier protein, such as bovine serum albumin or keyhole limpet hemocyanin. Following one or more injections, the animals are bled periodically. Polyclonal antibodies specific for the Trp-containing CAR sequence may then be purified from such antisera by, for example, affinity chromatography using the modulating agent or antigenic portion thereof coupled to a suitable solid support.

Monoclonal antibodies specific for a cadherin sequence may be prepared, for example, using the technique of Kohler and Milstein, *Eur. J. Immunol.* 6:511-519, 1976, and improvements thereto. Briefly, these methods involve the preparation of immortal cell lines capable of producing antibodies having the desired specificity from spleen cells obtained from an animal immunized as described above. The spleen cells are immortalized by, for example, fusion with a myeloma cell fusion partner, preferably one that is syngeneic with the immunized animal. Single colonies are selected and their culture supernatants tested for binding activity against the modulating agent or antigenic portion thereof. Hybridomas having high reactivity and specificity are preferred.

Monoclonal antibodies may be isolated from the supernatants of growing hybridoma colonies, with or without the use of various techniques known in the art to enhance the yield. Contaminants may be removed from the antibodies by conventional techniques, such as chromatography, gel filtration, precipitation and extraction. Antibodies having the desired activity may generally be identified using immunofluorescence analyses of tissue sections, cell or other samples where the target cadherin is localized.

Within certain embodiments, the use of antigen-binding fragments of antibodies may be preferred. Such fragments include Fab fragments, which may be prepared using standard techniques. Briefly, immunoglobulins may be purified from rabbit serum by affinity chromatography on Protein A bead columns (Harlow and Lane, *Antibodies: A Laboratory Manual*, Cold Spring Harbor Laboratory, 1988; see especially page 309) and digested by papain to yield Fab and Fc fragments. The Fab and Fc fragments may be separated by affinity chromatography on protein A bead columns (Harlow and Lane, 1988, pages 628-29).

Evaluation of Modulating Agent Activity

Modulating agents as described above are capable of modulating one or more cadherin-mediated functions. An initial screen for such activity may be performed by evaluating the ability of a modulating agent to bind to a nonclassical cadherin, preferably an atypical or desmosomal cadherin, using any binding assay known to those of ordinary skill in the art. For example, a Pharmacia Biosensor machine may be used, as discussed in Jonsson et al., *Biotechniques* 11:520-27, 1991. For example, a modulating agent may comprise a Trp-containing CAR sequence that binds to a cadherin. A specific example of a technology that measures the interaction of peptides with molecules can be found in Williams et al., *J. Biol. Chem.* 272, 22349-22354, 1997. Alternatively, real-time BIA (Biomolecular Interaction Analysis) uses the optical phenomenon surface plasmon resonance to monitor biomolecular interactions. The detection depends upon changes in the mass concentration of macromolecules at the biospecific interface, which in turn depends upon the immobilization of test molecule (for example, fc-VE-cadherin; referred to as the ligand) or peptide (referred to as the ligand) to the surface of a Biosensor chip, followed by binding of the interacting molecule (referred to as the analyte) to the ligand. Binding to the chip is measured in real-time in arbitrary units of resonance (RU).

For example, surface plasmon resonance experiments may be performed using a BIAcore X™ Biosensor (Pharmacia Ltd., BIAcore, Uppsala, Sweden). Parallel flow cells of CM 5 sensor chips may be derivatized, using the amine coupling method, with streptavidin (200 µg/ml) in 10 mM Sodium Acetate, pH 4.0, according to the manufacturer's protocol. Approximately 2100-2600 resonance units (RU) of target protein/ligand (for example, fc-VE-cadherin) may be immobilized, corresponding to a concentration of about 2.1-2.6 ng/mm$^2$. Any non-specifically bound target protein is removed. To determine binding, test analytes (e.g., peptides) may be placed in running buffer and passed simultaneously over test and control flow cells. After a period of free buffer flow, any analyte remaining bound to the surface may be removed with, for example, a pulse of 0.1% SDS bringing the signal back to baseline. Specific binding to the derivatized sensor chips may be determined automatically by the system by subtraction of test from control flow cell responses. In general, a modulating agent binds a nonclassical cadherin at a detectable level within such as assay. The detection depends upon changes in the mass concentration of macromolecules at the biospecific interface, which in turn depends upon the immobilization of test molecule or peptide (referred to as the ligand) to the surface of a Biosensor chip, followed by binding of the interacting molecule (referred to as the analyte) to the ligand. Binding to the chip is measured in real-time in arbitrary units of resonance (RU).

To determine binding, test analytes (e.g., peptides containing the atypical or desmosomal cadherin Trp-containing CAR sequence) may be placed in running buffer and passed simultaneously over test and control flow cells. After a period of free buffer flow, any analyte remaining bound to the surface may be removed with, for example, a pulse of 0.1% SDS bringing the signal back to baseline. Specific binding to the derivatized sensor chips may be determined automatically by the system by subtraction of test from control flow cell responses. In general, a modulating agent binds to a cadherin at a detectable level within such as assay. The level of binding is preferably at least that observed for the full length cadherin under similar conditions.

The ability to modulate a nonclassical cadherin-mediated function may be evaluated using any of a variety of in vitro assays designed to measure the effect of the peptide on a response that is generally mediated by the nonclassical cadherin. As noted above, modulating agents may be capable of enhancing or inhibiting a nonclassical cadherin-mediated function.

Certain nonclassical cadherins are associated with adhesion of particular cell types (e.g., cancer cells). The ability of an agent to modulate cell adhesion may generally be evaluated in vitro by assaying the effect on adhesion between appropriate cells. In general, a modulating agent is an inhibitor of cell adhesion if contact of the test cells with the modulating agent results in a discernible disruption of cell adhesion. Modulating agents that enhance cell adhesion (e.g., agents comprising multiple cadherin Trp-containing CAR sequences and/or cadherin Trp-containing CAR sequences linked to a support material) are considered to be modulators of cell adhesion if they are capable of promoting cell adhesion, as judged by plating assays to assess cell adhesion to a modulating agent attached to a support material, such as tissue culture plastic.

Within certain cell adhesion assays, the addition of a modulating agent to cells that express a cadherin results in disruption of cell adhesion. An "atypical cadherin-expressing cell," as used herein, may be any type of cell that expresses an atypical cadherin at a detectable level, using standard techniques such as immunocytochemical protocols (e.g., Blaschuk and Farookhi, *Dev. Biol.* 136:564-567, 1989). A "desmosomal cadherin-expressing cell," as used herein, may be any type of cell that expresses a desmosomal cadherin at a detectable level, using standard techniques such as immunocytochemical protocols (e.g., Blaschuk and Farookhi, *Dev. Biol.* 136:564-567, 1989). For example, such cells may be plated under standard conditions that, in the absence of modulating agent, permit cell adhesion. In the presence of modulating agent (e.g., 1 mg/mL), disruption of cell adhesion may be determined visually within 24 hours, by observing retraction of the cells from one another.

In certain embodiments, suitable cells for use within such assays may be any of a variety of cells that express the atypical cadherin of interest. Certain cells express one or more cadherins endogenously. For example, OB-cadherin-expressing cells include stromal, osteoblast and/or cancer cells. Cadherin-5 is expressed by endothelial cells, and cadherin-6 expression is associated with, for example, kidney tumor cells. Accordingly, such cell types may be used to assess the effect of modulating agents directed against OB-cadherin, cadherin-5 or cadherin-6 Trp-containing CAR sequences. It will be apparent that other cells may also be used within such assays, provided that the cells express the atypical cadherin of interest.

In other embodiments, suitable cells for use within such assays may be any of a variety of cells that express the desmosomal cadherin of interest. Certain cells express one or more cadherins endogenously. In general, MDCK cells or keratinocytes may be used to evaluate desmocollin- or desmoglein-mediated cell adhesion. It will be apparent that other cells may also be used within such assays, provided that the cells express the desmosomal cadherin of interest.

Alternatively, cells that do not naturally express a cadherin may be used within such assays. Such cells may be stably transfected with a polynucleotide (e.g., a cDNA) encoding a cadherin of interest, such that the cadherin is expressed on the surface of the cell. For example, as noted above, both a desmoglein and a desmocollin may be required for optimal cell adhesion, and such assays may be performed using cells transformed with polynucleotides encoding both of these desmosomal cadherins. Expression of the cadherin may be confirmed by assessing adhesion of the transfected cells, in conjunction with immunocytochemical techniques using antibodies directed against the cadherin of interest. The stably transfected cells that aggregate, as judged by light microscopy, following transfection express sufficient levels of the cadherin. Preferred cells for use in such assays include L cells, which do not detectably adhere and do not express any cadherin (Nagafuchi et al., *Nature* 329:341-343, 1987). Following transfection of L cells with a cDNA encoding a cadherin, aggregation is observed. Modulating agents that detectably inhibit such aggregation may be used to modulate functions mediated by the cadherin. Such assays have been used for numerous nonclassical cadherins, including OB-cadherin (Okazaki et al., *J. Biol. Chem.* 269:12092-98, 1994), cadherin-5 (Breier et al., *Blood* 87:630-641, 1996), cadherin-6 (Mbalaviele et al., *J. Cell. Biol.* 141:1467-1476, 1998), cadherin-8 (Kido et al., *Genomics* 48:186-194, 1998), cadherin-15 (Shimoyama et al., *J. Biol. Chem.* 273:10011-10018, 1998), PB-cadherin (Sugimoto et al., *J. Biol. Chem.* 271:11548-11556, 1996), LI-cadherin (Kreft et al., *J. Cell. Biol.* 136:1109-1121, 1997), protocadherin 42 and 43 (Sano et al., *EMBO J.* 12:2249-2256, 1993) and desmosomal cadherins (Marcozzi et al., *J. Cell. Sci.* 111:495-509, 1998; Tselepis et al., *Proc. Natl. Acad. Sci. USA* 95:8064-8069, 1998). It will be apparent to those of ordinary skill in the art that assays may be performed in a similar manner for other nonclassical cadherins.

Transfection of cells for use in cell adhesion assays may be performed using standard techniques and published cadherin sequences. For example, sequences of atypical cadherins may be found within references cited herein and in the GenBank database. GenBank accession numbers for certain atypical cadherins include: X59796 (human cadherin-5); D31784 (human cadherin-6); D42150 (chicken cadherin-7); L34060 (human cadherin-8); AB035302 (human cadherin-9); AF039747 (human cadherin-10); L34056 (human OB cadherin); L34057 (human cadherin-12); U59325 (human cadherin-14); D83542 (human cadherin-15); HSAJ7607 (human cadherin-19); AF217289 (human cadherin-20); and D83348 and D88349 (rat PB-cadherin). Sequences of desmosomal cadherins may similarly be found within references cited herein and in the GenBank database. GenBank accession numbers for certain desmosomal cadherins include: X56654 (human desmoglein 1); Z26317 and S64273 (human desmoglein 2); M76482 (human desmoglein 3); AY227350 (human desmoglein 4); AY227349 (mouse desmoglein 4); AY192158 (mouse desmoglein 5); AY192159 (mouse desmoglein 6); X72925 and Z34522 (human desmocollin 1); X56807 (human desmocollin 2); X83929 (human desmocollin 3); and D17427 (human desmocollin 4). Sequences for these and other atypical and desmosomal cadherins are readily available from public sequence databases, such as Genbank.

By way of example, an assay for evaluating a modulating agent for the ability to inhibit an OB-cadherin mediated function may employ MDA-231 human breast cancer cells. According to a representative procedure, the cells may be plated at 10-20,000 cells per 35 mm tissue culture flasks containing DMEM with 5% FCS and sub-cultured periodically (Sommers et al., *Cell Growth Diffn* 2:365-72, 1991). Cells may be harvested and replated in 35 mm tissue culture flasks containing 1 mm coverslips and incubated until 50-65% confluent (24-36 hours). At this time, coverslips may be transferred to a 24-well plate, washed once with fresh DMEM and exposed to modulating agent at a concentration of, for example, 1 mg/mL for 24 hours. Fresh modulating agent may then be added, and the cells left for an additional 24 hours. Cells may be fixed with 2% paraformaldehyde for 30 minutes and then washed three times with PBS. Coverslips can be mounted and viewed by phase contrast microscopy.

By way of another example, an assay for evaluating a modulating agent for the ability to inhibit a desmosomal cadherin mediated function may evaluate the effect of a modulating agent on the electrical resistance across a monolayer of cells. For example, Madin Darby canine kidney (MDCK) cells can be exposed to the modulating agent dissolved in medium (e.g., at a final concentration of 0.5 mg/ml for a period of 24 hours). The effect on electrical resistance can be measured using standard techniques. This assay evaluates the effect of a modulating agent on tight junction formation in epithelial cells. In general, the presence of 500 µg/mL modulating agent should result in a statistically significant decrease in electrical resistance after 24 hours.

In the absence of modulating agent, MDA-231 cells display an epithelial-like morphology and are well attached to the substratum. MDA-231 cells that are treated with a modulating agent that disrupts OB-cadherin mediated cell adhesion may assume a round shape and become loosely attached to the substratum within 48 hours of treatment with 1 mg/mL of modulating agent.

It will be apparent that similar assays may be performed to assess a modulating agent for the ability to inhibit cell adhesion mediated by other cadherins, using cells appropriate for the cadherin of interest. In general, a modulating agent that is derived from a particular cadherin Trp-containing CAR sequence (i.e., comprises such a Trp-containing CAR sequence, or an analog or mimetic thereof, or an antibody that specifically recognizes such a Trp-containing CAR sequence) and that modulates adhesion of a cell that expresses the same cadherin is considered to modulate a function mediated by the cadherin.

Other assays may be used to assess the effect of a modulating agent on specific cadherin-mediated functions. For example, modulating agents that inhibit interactions of certain nonclassical cadherins (e.g., desmogleins and desmocollins) may enhance skin permeability. This ability may be assessed by evaluating, for example, the effect of a modulating agent on permeability of adherent epithelial cell layers (e.g., human skin). Such skin may be derived from a natural source or may be synthetic. Human abdominal skin for use in such assays may generally be obtained from humans at autopsy within 24 hours of death. Briefly, a modulating agent (e.g., 500 μg/ml) and a test marker (e.g., the fluorescent markers Oregon Green™ and Rhodamine Green™ Dextran) may be dissolved in a sterile buffer (e.g., phosphate buffer, pH 7.2), and the ability of the marker to penetrate through the skin and into a receptor fluid (e.g., phosphate buffer) may be measured using a Franz Cell apparatus (Franz, *Curr. Prob. Dermatol.* 7:58-68, 1978; Franz, *J. Invest. Dermatol.* 64:190-195, 1975). The penetration of the markers through the skin may be assessed at, for example, 6, 12, 24, 36, and 48 hours after the start of the experiment. In general, a modulating agent that enhances the permeability of human skin results in a statistically significant increase in the amount of marker in the receptor compartment after 6-48 hours in the presence of 500 μg/mL modulating agent.

Certain other atypical and desmosomal cadherins (e.g., cadherin-6, cadherin-7, cadherin-8, cadherin-10, cadherin-11), as well as the desmogleins and desmocollins, may be involved in mediating neurite outgrowth, synapse formation and maintenance, as well as the establishment of neuronal circuits. Agents that modulate such a function may be evaluated using a neurite outgrowth assay. Within one such assay, neurons may be cultured on a monolayer of cells (e.g., 3T3 cells) that express an atypical cadherin. Neurons grown on such cells (under suitable conditions and for a sufficient period of time) extend neurites that are typically, on average, twice as long as neurites extended from neurons cultured on 3T3 cells that do not express the atypical cadherin. Briefly, monolayers of control 3T3 fibroblasts and 3T3 fibroblasts that express an atypical cadherin may be established by overnight culture of 80,000 cells in individual wells of an 8-chamber well tissue culture slide. 3000 cerebellar neurons isolated from post-natal day 3 mouse brains may be cultured for 18 hours on the various monolayers in control media (SATO/2% FCS), or media supplemented with various concentrations of the modulating agent or control peptide. The cultures may then be fixed and stained for GAP43 which specifically binds to the neurons and their neurites. The length of the longest neurite on each GAP43 positive neuron may be measured by computer assisted morphometry.

A modulating agent may inhibit or enhance such neurite outgrowth. Under the conditions described above, the presence of 500 μg/mL of a modulating agent that disrupts neural cell adhesion should result in a decrease in the mean neurite length by at least 50%, relative to the length in the absence of modulating agent or in the presence of a negative control peptide. Alternatively, the presence of 10 μg/mL of a modulating agent that stimulates neurite outgrowth should result in an increase in the mean neurite length by at least 50%.

Transfection of cells for use in a neurite outgrowth assay may be performed using standard techniques and published cadherin sequences. For example, sequences of atypical cadherins may be found within references cited herein and in the GenBank database. GenBank accession numbers for these cadherins are recited above.

Certain modulating agents (e.g., peptides that contain VE-cadherin and/or OB-cadherin Trp-containing CAR sequences, or analogues or mimetics thereof) may inhibit angiogenesis. The effect of a particular modulating agent on angiogenesis may generally be determined by evaluating the effect of the agent on blood vessel formation. Such a determination may generally be performed, for example, using a chick chorioallantoic membrane assay (Iruela-Arispe et al., *Molecular Biology of the Cell* 6:327-343, 1995). Briefly, a modulating agent may be embedded in a mesh composed of vitrogen at one or more concentrations (e.g., ranging from about 1 to 100 μg/mesh). The mesh(es) may then be applied to chick chorioallantoic membranes. After 24 hours, the effect of the modulating agent may be determined using computer assisted morphometric analysis. A modulating agent should inhibit angiogenesis by at least 25% at a concentration of 33 μg/mesh.

A myoblast fusion assay may be used as a functional assay for agents that modulate cadherin-15 function. Cadherin-15 has been shown to mediate the fusion of muscle cells into mature muscle fibers in vitro. Briefly, to perform such an assay, myoblasts may be grown in a dish, differentiation is induced, and modulating agent is added. The effect on fusion is then evaluated. In general, a modulating agent that inhibits cadherin-15 function results in a statistically significant decrease in myoblast fusion in the presence of 1 mg/mL modulating agent. Such assays may be performed as described by Pouliot et al., *Dev. Biol.* 141:292-298, 1990.

Modulating Agent Modification and Formulations

A modulating agent as described herein may, but need not, be linked to one or more additional molecules. In particular, as discussed below, it may be beneficial for certain applications to link multiple modulating agents (which may, but need not, be identical) to a support material, such as a single molecule (e.g., keyhole limpet hemocyanin) or a solid support, such as a polymeric matrix (which may be formulated as a membrane or microstructure, such as an ultra thin film), a container surface (e.g., the surface of a tissue culture plate or the interior surface of a bioreactor), or a bead or other particle, which may be prepared from a variety of materials including glass, plastic or ceramics. For certain applications, biodegradable support materials are preferred, such as cellulose and derivatives thereof, collagen, spider silk or any of a variety of polyesters (e.g., those derived from hydroxy acids and/or lactones) or sutures (see U.S. Pat. No. 5,245,012). Within certain embodiments, modulating agents and molecules comprising other CAR sequence(s) (e.g., an HAV or RGD sequence) may be attached to a support such as a polymeric matrix, preferably in an alternating pattern.

Suitable methods for linking a modulating agent to a support material will depend upon the composition of the support and the intended use, and will be readily apparent to those of ordinary skill in the art. Attachment may generally be achieved through noncovalent association, such as adsorption or affinity or, preferably, via covalent attachment (which may be a direct linkage between a modulating agent and functional groups on the support, or may be a linkage by way of a cross-linking agent). Attachment of a modulating agent by adsorption may be achieved by contact, in a suitable buffer, with a solid support for a suitable amount of time. The contact time varies with temperature, but is generally between about 5 seconds and 1 day, and typically between about 10 seconds and 1 hour.

Covalent attachment of a modulating agent to a molecule or solid support may generally be achieved by first reacting the support material with a bifunctional reagent that will also react with a functional group, such as a hydroxyl or amino group, on the modulating agent. For example, a modulating agent may be bound to an appropriate polymeric support or coating using benzoquinone, by condensation of an aldehyde group on the support with an amine and an active hydrogen on the modulating agent or by condensation of an amino group on the support with a carboxylic acid on the modulating agent. A preferred method of generating a linkage is via amino groups using glutaraldehyde. A modulating agent may be linked to cellulose via ester linkages. Similarly, amide linkages may be suitable for linkage to other molecules such as keyhole limpet hemocyanin or other support materials.

Multiple modulating agents and/or molecules comprising other CAR sequences may be attached, for example, by random coupling, in which equimolar amounts of such molecules are mixed with a matrix support and allowed to couple at random.

Although modulating agents as described herein may preferentially bind to specific tissues or cells, and thus may be sufficient to target a desired site in vivo, it may be beneficial for certain applications to include an additional targeting agent. Accordingly, a targeting agent may also, or alternatively, be linked to a modulating agent to facilitate targeting to one or more specific tissues. As used herein, a "targeting agent," may be any substance (such as a compound or cell) that, when linked to a modulating agent enhances the transport of the modulating agent to a target tissue, thereby increasing the local concentration of the modulating agent. Targeting agents include antibodies or fragments thereof, receptors, ligands and other molecules that bind to cells of, or in the vicinity of, the target tissue. Known targeting agents include serum hormones, antibodies against cell surface antigens, lectins, adhesion molecules, tumor cell surface binding ligands, steroids, cholesterol, lymphokines, fibrinolytic enzymes and those drugs and proteins that bind to a desired target site. Among the many monoclonal antibodies that may serve as targeting agents are anti-TAC, or other interleukin-2 receptor antibodies; 9.2.27 and NR-ML-05, reactive with the 250 kilodalton human melanoma-associated proteoglycan; and NR-LU-10, reactive with a pancarcinoma glycoprotein. An antibody targeting agent may be an intact (whole) molecule, a fragment thereof, or a functional equivalent thereof. Examples of antibody fragments are F(ab')2, -Fab', Fab and F[v] fragments, which may be produced by conventional methods or by genetic or protein engineering. Linkage is generally covalent and may be achieved by, for example, direct condensation or other reactions, or by way of bi- or multi-functional linkers.

For certain embodiments, it may be beneficial to also, or alternatively, link a drug to a modulating agent. As used herein, the term "drug" (used interchangeably with "pharmaceutically active substance", "pharmaceutically active agent", or "pharmaceutically active compound") refers to any bioactive agent intended for administration to a mammal to prevent or treat a disease or other undesirable condition. Drugs include hormones, growth factors, proteins, peptides and other compounds. The use of certain specific drugs within the context of the present invention is discussed below.

Modulating agents as described herein may be present within a pharmaceutical composition. A pharmaceutical composition comprises one or more modulating agents in combination with one or more pharmaceutically or physiologically acceptable carriers, diluents or excipients. Such compositions may comprise buffers (e.g., neutral buffered saline or phosphate buffered saline), carbohydrates (e.g., glucose, mannose, sucrose or dextrans), mannitol, proteins, polypeptides or amino acids such as glycine, antioxidants, chelating agents such as EDTA or glutathione, adjuvants (e.g., aluminum hydroxide) and/or preservatives. Within yet other embodiments, compositions of the present invention may be formulated as a lyophilizate. One or more modulating agents (alone or in combination with a targeting agent and/or drug) may, but need not, be encapsulated within liposomes using well known technology. Compositions of the present invention may be formulated for any appropriate manner of administration, including for example, topical, oral, nasal, intravenous, intracranial, intraperitoneal, subcutaneous, or intramuscular administration.

For certain embodiments, as discussed below, a pharmaceutical composition may further comprise a modulator of cell adhesion that is mediated by one or more molecules other than a nonclassical cadherin. Such modulators may generally be prepared as described above, using one or more Trp-containing CAR sequences and/or antibodies thereto. Such compositions are particularly useful for situations in which it is desirable to inhibit cell adhesion mediated by multiple cell adhesion molecules, such as other members of the cadherin gene superfamily such as the classical cadherins (e.g., N-cadherin and E-cadherin); integrins; occludin; claudins; N-CAM, JAM and/or extracellular matrix proteins such as laminin, fibronectin, collagens, vitronectin, entactin and tenascin.

A pharmaceutical composition may also, or alternatively, contain one or more drugs, which may be linked to a modulating agent or may be free within the composition. Virtually any drug may be administered in combination with a modulating agent as described herein, for a variety of purposes as described below. Examples of types of drugs that may be administered with a modulating agent include analgesics, anesthetics, antianginals, antifungals, antibiotics, anticancer drugs (e.g., taxol or mitomycin C), antiinflammatories (e.g., ibuprofen and indomethacin), anthelmintics, antidepressants, antidotes, antiemetics, antihistamines, antihypertensives, antimalarials, antimicrotubule agents (e.g., coichicine or vinca alkaloids), antimigraine agents, antimicrobials, antiphsychotics, antipyretics, antiseptics, anti-signaling agents (e.g., protein kinase C inhibitors or inhibitors of intracellular calcium mobilization), antiarthritics, antithrombin agents, antituberculotics, antitussives, antivirals, appetite suppressants, cardioactive drugs, chemical dependency drugs, cathartics, chemotherapeutic agents, coronary, cerebral or peripheral vasodilators, contraceptive agents, depressants, diuretics, expectorants, growth factors, hormonal agents, hypnotics, immunosuppression agents, narcotic antagonists, parasympathomimetics, sedatives, stimulants, sympathomimetics, toxins (e.g., cholera toxin), tranquilizers and urinary antiinfectives.

For imaging purposes, any of a variety of diagnostic agents may be incorporated into a pharmaceutical composition, either linked to a modulating agent or free within the composition. Diagnostic agents include any substance administered to illuminate a physiological function within a patient, while leaving other physiological functions generally unaffected. Diagnostic agents include metals, radioactive isotopes and radioopaque agents (e.g., gallium, technetium, indium, strontium, iodine, barium, bromine and phosphorus-containing compounds), radiolucent agents, contrast agents, dyes (e.g., fluorescent dyes and chromophores) and enzymes that catalyze a colorimetric or fluorometric reaction. In general, such agents may be attached using a variety of techniques as described above, and may be present in any orientation.

The compositions described herein may be administered as part of a sustained release formulation (i.e., a formulation such as a capsule or sponge that effects a slow release of modulating agent following administration). Such formulations may generally be prepared using well known technology and administered by, for example, oral, rectal or subcutaneous implantation, or by implantation at the desired target site. Sustained-release formulations may contain a modulating agent dispersed in a carrier matrix and/or contained within a reservoir surrounded by a rate controlling membrane (see, e.g., European Patent Application 710,491 A). Carriers for use within such formulations are biocompatible, and may also be biodegradable; preferably the formulation provides a relatively constant level of modulating agent release. The amount of modulating agent contained within a sustained release formulation depends upon the site of implantation, the rate and expected duration of release and the nature of the condition to be treated or prevented.

Pharmaceutical compositions of the present invention may be administered in a manner appropriate to the disease to be treated (or prevented). Appropriate dosages and a suitable duration and frequency of administration will be determined by such factors as the condition of the patient, the type and severity of the patient's disease and the method of administration. In general, an appropriate dosage and treatment regimen provides the modulating agent(s) in an amount sufficient to provide therapeutic and/or prophylactic benefit. Within particularly preferred embodiments of the invention, a modulating agent or pharmaceutical composition as described herein may be administered at a dosage ranging from 0.001 to 50 mg/kg body weight, preferably from 0.1 to 20 mg/kg, on a regimen of single or multiple daily doses. For topical administration, a cream typically comprises an amount of modulating agent ranging from 0.00001% to 1%, preferably 0.0001% to 0.002%. Fluid compositions typically contain about 10 ng/ml to 5 mg/ml, preferably from about 10 µg to 2 mg/mL modulating agent. Appropriate dosages may generally be determined using experimental models and/or clinical trials. In general, the use of the minimum dosage that is sufficient to provide effective therapy is preferred. Patients may generally be monitored for therapeutic effectiveness using assays suitable for the condition being treated or prevented, which will be familiar to those of ordinary skill in the art.

Modulating Agent Methods of Use

In general, the modulating agents and compositions described herein may be used for modulating a function, such as cell adhesion, of nonclassical cadherin-expressing cells. Such modulation may be performed in vitro and/or in vivo, preferably in a mammal such as a human, using any method that contacts the nonclassical cadherin-expressing cell with the modulating agent. As noted above, modulating agents for purposes that involve the disruption of nonclassical cadherin-mediated cell adhesion may comprise a nonclassical cadherin Trp-containing CAR sequence, multiple nonclassical cadherin Trp-containing CAR sequences in close proximity and/or a substance (such as an antibody or an antigen-binding fragment thereof) that recognizes a nonclassical cadherin Trp-containing CAR sequence. When it is desirable to also disrupt cell adhesion mediated by other adhesion molecules, a modulating agent may additionally comprise one or more CAR sequences bound by such adhesion molecules (and/or antibodies or fragments thereof that bind such sequences), preferably separated from each other and from the nonclassical cadherin Trp-containing CAR sequence by linkers. As noted above, such linkers may or may not comprise one or more amino acids. For enhancing cell adhesion, a modulating agent may contain multiple nonclassical cadherin Trp-containing CAR sequences derived from either a particular nonclassical cadherin or antibodies (or fragments), which may or may not be separated by linkers. Alternatively, or in addition, the multiple nonclassical cadherin Trp-containing CAR sequences may be linked to a single molecule or to a support material as described above. When it is desirable to also enhance cell adhesion mediated by other adhesion molecules, a modulating agent may additionally comprise one or more CAR sequences bound by such adhesion molecules (and/or antibodies or fragments thereof that bind such sequences), preferably separated from each other and from the nonclassical cadherin Trp-containing CAR sequence by linker.

Certain methods involving the disruption of cell adhesion as described herein have an advantage over prior techniques in that they block tumor cell adhesion. As described in greater detail below, modulating agents as described herein may also be used to disrupt or enhance cell adhesion in a variety of other contexts. Within each of the methods described herein, one or more modulating agents may generally be administered alone, or within a pharmaceutical composition. In each specific method described herein, as noted above, a targeting agent may be employed to increase the local concentration of modulating agent at the target site.

Within one aspect, methods are provided in which cell adhesion is diminished. In one such aspect, the present invention provides methods for reducing unwanted cellular adhesion in a mammal by administering a modulating agent as described herein. Unwanted cellular adhesion can occur, for example, between tumor cells, between tumor cells and normal cells or between normal cells as a result of surgery, injury, chemotherapy, disease, inflammation or other condition jeopardizing cell viability or function. Certain preferred modulating agents for use within such methods comprise one or more of the Trp-containing CAR sequences provided herein. In one particularly preferred embodiment, a modulating agent is further capable of disrupting cell adhesion mediated by multiple adhesion molecules. Such an agent may comprise, in addition to one or more nonclassical cadherin Trp-containing CAR sequences, CAR sequences such as the classical cadherin CAR sequence HAV sequence, an RGD sequence, which is bound by integrins, the occludin CAR sequence LYHY (SEQ ID NO: 1309); and/or the putative claudin CAR sequence IYSY (SEQ ID NO: 1312), preferably separated from the cadherin Trp-containing CAR sequence via a linker. Alternatively, separate modulators of cell adhesion mediated by other adhesion molecules may be administered in conjunction with the modulating agent(s), either within the same pharmaceutical composition or separately.

Topical administration of the modulating agent(s) is generally preferred, but other means may also be employed. Preferably, a fluid composition for topical administration (comprising, for example, physiological saline) comprises an amount of modulating agent as described above, and more preferably from 10 µg/mL to 1 mg/mL. Creams may generally be formulated as described above. Topical administration in the surgical field may be given once at the end of surgery by irrigation of the wound or as an intermittent or continuous irrigation with the use of surgical drains in the post-operative period or by the use of drains specifically inserted in an area of inflammation, injury or disease in cases where surgery does not need to be performed. Alternatively, parenteral or transcutaneous administration may be used to achieve similar results.

Certain modulating agents as provided herein may be used to facilitate transdermal drug delivery. Transdermal delivery of drugs is a convenient and non-invasive method that can be used to maintain relatively constant blood levels of a drug. In general, to facilitate drug delivery via the skin, it is necessary to perturb adhesion between the epithelial cells (keratinocytes) of the skin and the endothelial cells of the microvasculature. Using currently available techniques, only small, uncharged molecules may be delivered across skin in vivo. The methods described herein are not subject to the same degree of limitation. Accordingly, a wide variety of drugs may be transported across the epithelial cell layers of the skin and endothelial cells of the skin microvasculature, for systemic or topical administration. Such drugs may be delivered to melanomas or may enter the blood stream of the mammal for delivery to other sites within the body.

To enhance the delivery of a drug through the skin, a modulating agent as described herein and a drug are contacted with the skin surface. Certain preferred modulating agents for use within such methods comprise a Trp-containing CAR sequence (or an analogue or mimetic thereof) of Dsg, Dsc, and cadherin-5. Multifunctional modulating agents comprising multiple nonclassical cadherin Trp-containing CAR sequences may also be used. Such modulating agents may also, or alternatively, comprise the classical cadherin CAR sequence HAV, the fibronectin CAR sequence RGD, which is recognized by integrins, JAM CAR sequence, claudin CAR sequence, and/or the occludin CAR sequence LYHY (SEQ ID NO: 1309). Alternatively, a separate modulator of cell adhesion may be administered in conjunction with the modulating agent(s), either within the same pharmaceutical composition or separately. Certain additional embodiments of the invention may employ antibodies or Fab fragments directed against one or more such CAR sequences.

Contact may be achieved by direct application of the modulating agent, generally within a composition formulated as a cream or gel, or using any of a variety of skin contact devices for transdermal application (such as those described in European Patent Application No. 566,816 A; U.S. Pat. Nos. 5,613,958; and 5,505,956). A skin patch provides a convenient method of administration (particularly for slow-release formulations). Such patches may contain a reservoir of modulating agent and drug separated from the skin by a membrane through which the drug diffuses. Within other patch designs, the modulating agent and drug may be dissolved or suspended in a polymer or adhesive matrix that is then placed in direct contact with the patient's skin. The modulating agent and drug may then diffuse from the matrix into the skin. Modulating agent(s) and drug(s) may be contained within the same composition or skin patch, or may be separately administered, although administration at the same time and site is preferred. In general, the amount of modulating agent administered via the skin varies with the nature of the condition to be treated or prevented, but may vary as described above. Such levels may be achieved by appropriate adjustments to the device used, or by applying a cream formulated as described above. Transfer of the drug across the skin and to the target tissue may be predicted based on in vitro studies using, for example, a Franz cell apparatus, and evaluated in vivo by appropriate means that will be apparent to those of ordinary skill in the art. As an example, monitoring of the serum level of the administered drug over time provides an easy measure of the drug transfer across the skin.

Transdermal drug delivery as described herein is particularly useful in situations in which a constant rate of drug delivery is desired, to avoid fluctuating blood levels of a drug. For example, morphine is an analgesic commonly used immediately following surgery. When given intermittently in a parenteral form (intramuscular, intravenous), the patient usually feels sleepy during the first hour, is well during the next 2 hours and is in pain during the last hour because the blood level goes up quickly after the injection and goes down below the desirable level before the 4 hour interval prescribed for re-injection is reached. Transdermal administration as described herein permits the maintenance of constant levels for long periods of time (e.g., days), which allows adequate pain control and mental alertness at the same time. Insulin provides another such example. Many diabetic patients need to maintain a constant baseline level of insulin which is different from their needs at the time of meals. The baseline level may be maintained using transdermal administration of insulin, as described herein. Antibiotics may also be administered at a constant rate, maintaining adequate bactericidal blood levels, while avoiding the high levels that are often responsible for the toxicity (e.g., levels of gentamycin that are too high typically result in renal toxicity).

Drug delivery by the methods of the present invention also provide a more convenient method of drug administration. For example, it is often particularly difficult to administer parenteral drugs to newborns and infants because of the difficulty associated with finding veins of acceptable caliber to catheterize. However, newborns and infants often have a relatively large skin surface as compared to adults. Transdermal drug delivery permits easier management of such patients and allows certain types of care that can presently be given only in hospitals to be given at home. Other patients who typically have similar difficulties with venous catheterization are patients undergoing chemotherapy or patients on dialysis. In addition, for patients undergoing prolonged therapy, transdermal administration as described herein is more convenient than parenteral administration.

Transdermal administration as described herein also allows the gastrointestinal tract to be bypassed in situations where parenteral uses would not be practical. For example, there is a growing need for methods suitable for administration of therapeutic small peptides and proteins, which are typically digested within the gastrointestinal tract. The methods described herein permit administration of such compounds and allow easy administration over long periods of time. Patients who have problems with absorption through their gastrointestinal tract because of prolonged ileus or specific gastrointestinal diseases limiting drug absorption may also benefit from drugs formulated for transdermal application as described herein.

Further, there are many clinical situations where it is difficult to maintain compliance. For example, patients with mental problems (e.g., patients with Alzheimer's disease or psychosis) are easier to manage if a constant delivery rate of drug is provided without having to rely on their ability to take their medication at specific times of the day. Also patients who simply forget to take their drugs as prescribed are less likely to do so if they merely have to put on a skin patch periodically (e.g., every 3 days). Patients with diseases that are without symptoms, like patients with hypertension, are especially at risk of forgetting to take their medication as prescribed.

For patients taking multiple drugs, devices for transdermal application such as skin patches may be formulated with combinations of drugs that are frequently used together. For example, many heart failure patients are given digoxin in combination with furosemide. The combination of both drugs into a single skin patch facilitates administration, reduces the risk of errors (taking the correct pills at the appropriate time is often confusing to older people), reduces the psychological strain of taking "so many pills," reduces skipped dosage because of irregular activities and improves compliance.

The methods described herein are particularly applicable to humans, but also have a variety of veterinary uses, such as the administration of growth factors or hormones (e.g., for fertility control) to an animal.

As noted above, a wide variety of drugs may be administered according to the methods provided herein. Some examples of drug categories that may be administered transdermally include anti-inflammatory drugs (e.g., in arthritis and in other condition) such as all NSAID, indomethacin, prednisone, etc.; analgesics (especially when oral absorption is not possible, such as after surgery, and when parenteral administration is not convenient or desirable), including morphine, codeine, Demerol, acetaminophen and combinations of these (e.g., codeine plus acetaminophen); antibiotics such as Vancomycin (which is not absorbed by the GI tract and is frequently given intravenously) or a combination of INH and Rifampicin (e.g., for tuberculosis); anticoagulants such as heparin (which is not well absorbed by the GI tract and is generally given parenterally, resulting in fluctuation in the blood levels with an increased risk of bleeding at high levels and risks of inefficacy at lower levels) and Warfarin (which is absorbed by the GI tract but cannot be administered immediately after abdominal surgery because of the normal ileus following the procedure); antidepressants (e.g., in situations where compliance is an issue as in Alzheimer's disease or when maintaining stable blood levels results in a significant reduction of anti-cholinergic side effects and better tolerance by patients), such as amitriptylin, imipramin, prozac, etc.; antihypertensive drugs (e.g., to improve compliance and reduce side effects associated with fluctuating blood levels), such as diuretics and beta-blockers (which can be administered by the same patch; e.g., furosemide and propanolol); antipsychotics (e.g., to facilitate compliance and make it easier for care giver and family members to make sure that the drug is received), such as haloperidol and chlorpromazine; and anxiolytics or sedatives (e.g., to avoid the reduction of alertness related to high blood levels after oral administration and allow a continual benefit throughout the day by maintaining therapeutic levels constant).

Numerous other drugs may be administered as described herein, including naturally occurring and synthetic hormones, growth factors, proteins and peptides. For example, insulin and human growth hormone, growth factors like erythropoietin, interleukins and inteferons may be delivered via the skin.

Kits for administering a drug via the skin of a mammal are also provided within the present invention. Such kits generally comprise a device for transdermal application (e.g., a skin patch) in combination with, or impregnated with, one or more modulating agents. A drug may additionally be included within such kits.

Within a related aspect, modulating agents as described herein may be used to increase the permeability of endothelial cell barriers and epithelial cell layers, thereby facilitating sampling of the blood compartment by passive diffusion. Such methods permit the detection and/or measurement of the levels of specific molecules circulating in the blood. In general, to sample the blood compartment, it is necessary to perturb adhesion between the epithelial cells (keratinocytes) of the skin and the endothelial cells of the microvasculature. Using currently available techniques, only small, uncharged molecules may be detected across skin in vivo. The methods described herein are not subject to the same degree of limitation. Accordingly, a wide variety of blood components may be sampled across endothelial cell barriers and epithelial cell layers. Such sampling may be achieved across any such barriers and cell layers, including skin and gums.

For example, application of one or more modulating agents to the skin, via a skin patch as described herein, permits the patch to function like a sponge to accumulate a small quantity of fluid containing a representative sample of the serum. The patch is then removed after a specified amount of time and analyzed by suitable techniques for the compound of interest (e.g., a medication, hormone, growth factor, metabolite or marker). Alternatively, a patch may be impregnated with reagents to permit a color change if a specific substance (e.g., an enzyme) is detected. Substances that can be detected in this manner include, but are not limited to, illegal drugs such as cocaine, HIV enzymes, glucose and PSA. This technology is of particular benefit for home testing kits.

To facilitate sampling of blood in a patient, a modulating agent as described above for enhancing drug delivery is contacted with the skin surface. Modulating agent(s) and reagents for assaying blood components may, but need not, be contained within the same composition or skin patch. In general, the amount of modulating agent administered via the skin may vary as described above. Such levels may be achieved by appropriate adjustments to the device used, or by applying a cream formulated as described above. Transfer of the blood component across the skin may be predicted based on in vitro studies using, for example, a Franz cell apparatus, and evaluated in vivo by appropriate means that will be apparent to those of ordinary skill in the art.

Kits for sampling blood component via, for example, the skin or gums of a mammal, are also provided within the present invention. Such kits generally comprise a device for transdermal application (i.e., skin patch) in combination with, or impregnated with, one or more modulating agents. A reagent for detection of a blood component may additionally be included within such kits.

Within a further aspect, methods are provided for enhancing delivery of a drug to a tumor in a mammal, comprising administering a modulating agent in combination with a drug to a tumor-bearing mammal. Modulating agents for use within such methods include those designed to disrupt functions mediated by desmosomal cadherins, occludin, claudins, JAM, OB-cadherin, cadherin-5, and cadherin-6, and may further disrupt E-cadherin and/or N-cadherin mediated cell adhesion. For example, such a modulating agent may comprise a Trp-containing CAR sequence (or analogue or mimetic thereof) derived from one or more of the above nonclassical and classical cadherins, as described above. A modulating agent may further comprise an E- and/or N-cadherin HAV-containing CAR sequence (e.g., SHAVSS, (SEQ ID NO: 1349) AHAVDI (SEQ ID NO; 1350), respectively or an analogue of such a sequence). Multi-functional modulating agents that comprise desmosomal cadherin Trp-containing CAR sequences with either flanking E-cadherin-specific sequences or flanking N-cadherin-specific sequences joined via a linker are also preferred. Preferably, the peptide portion(s) of a modulating agent comprises 6-16 amino acids, since longer peptides are difficult to dissolve in aqueous solution and are more likely to be degraded by peptidases.

In one particularly preferred embodiment, a modulating agent is capable of disrupting cell adhesion mediated by multiple adhesion molecules. For example, a single branched modulating agent (or multiple agents linked to a single molecule or support material) may disrupt adhesion mediated by an atypical or desmosomal cadherin, as well as E-cadherin, N-cadherin, occludin, claudin, JAM and integrin mediated cell adhesion. Such agents serve as multifunctional disrupters of cell adhesion. Alternatively, a separate modulator may be administered in conjunction with the modulating agent(s), either within the same pharmaceutical composition or separately. Preferred antibody modulating agents include Fab fragments directed against an atypical or desmosomal cadherin Trp-containing CAR sequence, Fab fragments directed against the classical cadherin CAR sequence HAV, Fab fragments directed against the occludin CAR sequence, etc as described above. A Fab fragment may be incorporated into a modulating agent or may be present within a separate modulator that is administered concurrently.

Preferably, the modulating agent and the drug are formulated within the same composition or drug delivery device prior to administration. In general, a modulating agent may enhance drug delivery to any tumor (e.g., breast tumor, stomach tumor, ovarian tumor or kidney tumor), and the method of administration may be chosen based on the type of target tumor. For example, injection or topical administration as described above may be preferred for melanomas and other accessible tumors (e.g., metastases from primary ovarian tumors may be treated by flushing the peritoneal cavity with the composition). Other tumors (e.g., breast tumors) may be treated by injection of the modulating agent and the drug (such as mitomycin C) into the site of the tumor. In other instances, the composition may be administered systemically, and targeted to the tumor using any of a variety of specific targeting agents. Suitable drugs may be identified by those of ordinary skill in the art based upon the type of cancer to be treated (e.g., taxol for breast cancer). In general, the amount of modulating agent administered varies with the method of administration and the nature of the tumor, within the typical ranges provided above, preferably ranging from about 1 μg/mL to about 2 mg/mL, and more preferably from about 10 μg/mL to 1 mg/mL. Transfer of the drug to the target tumor may be evaluated by appropriate means that will be apparent to those of ordinary skill in the art. Drugs may also be labeled (e.g., using radionuclides) to permit direct observation of transfer to the target tumor using standard imaging techniques.

Within a related aspect, the present invention provides methods for treating and/or inhibiting (lessening or reducing) cancer in a mammal. Cancer tumors are solid masses of cells which require nourishment via blood vessels. The formation of new capillaries is a prerequisite for tumor growth and the emergence of metastases. Administration of modulating agents as described herein may disrupt the growth of such blood vessels, thereby providing effective therapy for the cancer (e.g., reduce or inhibit cancer progression, including tumor growth).

Within a related aspect, the present invention provides methods for treating and/or inhibiting (lessening or reducing) cancer metastasis in a mammal. Cancer metastasis refers to a multi-step process that comprises cancer cell invasion (i.e., penetration of cancer cells through the membranes that separate cancer cells from healthy tissues and blood vessels), dispersal of tumor cells to other organs or parts of the body, and the growth of secondary tumors in those sites. Modulating agents may also be used to treat non-solid tumors, such as leukemias.

Modulating agents for use within such methods, particularly in the treatment of solid tumors, include those designed to disrupt functions mediated by OB-cadherin, cadherin-5, and cadherin-6, desmosomal cadherins, occludin, claudin, JAM, and may further disrupt E-cadherin, N-cadherin and/or integrin mediated cell adhesion. For example, such a modulating agent may comprise a Trp-containing CAR sequence (or analogue or mimetic thereof), optionally in combination with a sequence such as HAV, SHAVSS (SEQ ID NO: 1349), AHAVDI (SEQ ID NO; 1350), RGD, YIGSR (SEQ ID NO: 1306) and/or a CAR sequence from a cell adhesion molecule such as occludin, claudin, JAM and/or NCAM, or a derivative of such a sequence. Preferably, the peptide portion(s) of such modulating agents comprise 6-16 amino acids.

Within certain embodiments, preferred CAR sequences used in combination with Trp-containing CAR sequences of the present invention include (a) Arg-Gly-Asp (RGD), which is bound by integrins (see Cardarelli et al., *J. Biol. Chem.* 267:23159-64, 1992); (b) Tyr-Ile-Gly-Ser-Arg (YIGSR) (SEQ ID NO: 1306), which is bound by α6β1 integrin; (c) KYSFNYDGSE (SEQ ID NO: 1307), which is bound by N-CAM; (d) the junctional adhesion molecule (JAM; see Martin-Padura et al., *J. Cell. Biol.* 142:117-127, 1998) CAR sequence SFTIDPKSG (SEQ ID NO: 1308) or DPK; (e) the occludin CAR sequence LYHY (SEQ ID NO: 1309); (f) claudin CAR sequences comprising at least four consecutive amino acids present within a claudin region that has the formula: Trp-Lys/Arg-Aaa-Baa-Ser/Ala-Tyr/Phe-Caa-Gly (SEQ ID NO: 1310), wherein Aaa, Baa and Caa indicate amino acid residues that may be identical to, or different from, one another; Lys/Arg is an amino acid that is lysine or arginine; Ser/Ala is an amino acid that is serine or alanine; and Tyr/Phe is an amino acid that is tyrosine or phenylalanine; and (g) nonclassical cadherin CAR sequences comprising at least three consecutive amino acids present within a nonclassical cadherin region that has the formula: Aaa-Phe-Baa-Ile/Leu/Val-Asp/Asn/Glu-Caa-Daa-Ser/Thr/Asn-Gly (SEQ ID NO: 1311), wherein Aaa, Baa, Caa and Daa are amino acid residues that may be identical to, or different from, one another; Ile/Leu/Val is an amino acid that is selected from the group consisting of isoleucine, leucine and valine, Asp/Asn/Glu is an amino acid that is selected from the group consisting of aspartate, asparagine and glutamate; and Ser/Thr/Asn is an amino acid that is selected from the group consisting of serine, threonine or asparagine. Representative claudin CAR sequences include IYSY (SEQ ID NO: 1312), TSSY (SEQ ID NO: 1313), VTAF (SEQ ID NO: 1314) and VSAF (SEQ ID NO: 1315). Representative nonclassical cadherin CAR sequences include the VE-cadherin (cadherin-5) CAR sequence DAE- and the OB-cadherin (cadherin-11) CAR sequence DDK.

Certain of these and other representative CAR sequences useful in conjunction with the Trp-containing CAR sequences described herein can be found, for example, in U.S. Pat. Nos. 6,031,072, 6,169,071, 6,207,639, 6,562,786, 6,346,512, 6,333,307, 6,417,325, 6,465,427, 6,326,352, 6,203,788, 6,277,824, 6,472,368, 6,248,864, 6,110,747, 6,310,177, 6,472,367, 6,358,920, 6,433,149, 6,303,576, and 6,391,855, the disclosures of which are incorporated herein by reference in their entireties.

Preferred antibody modulating agents include, but are not limited to, Fab fragments directed against an atypical and/or desmosomal cadherin Trp-containing CAR sequence, optionally used in combination with one or more Fab fragments directed against a CAR sequence for a distinct cell adhesion molecule, such as a CAR sequence from an integrin, a classical cadherin, an N-CAM, a JAM, an occludin, a claudin, etc., as described above.

A modulating agent may be administered alone (e.g., via the skin) or within a pharmaceutical composition. For melanomas and certain other accessible tumors, injection or topical administration as described above may be preferred. For ovarian cancers, flushing the peritoneal cavity with a composition comprising one or more modulating agents may prevent metastasis of ovarian tumor cells. Other tumors (e.g., bladder tumors, bronchial tumors or tracheal tumors) may be treated by injection of the modulating agent into the cavity. In other instances, the composition may be administered systemically, and targeted to the tumor using any of a variety of specific targeting agents, as described above. Preferably, the tumor is a breast tumor, stomach tumor or kidney tumor. In general, the amount of modulating agent administered varies depending upon the method of administration and the nature of the cancer, but may vary within the ranges identified above. The effectiveness of the cancer treatment or inhibition of metastasis may be evaluated using well known clinical observations, such as monitoring the level of serum tumor markers (e.g., CEA or PSA).

The addition of a targeting agent as described above may be beneficial, particularly when the administration is systemic. Suitable modes of administration and dosages depend upon the condition to be prevented or treated but, in general, administration by injection is appropriate. Dosages may vary as described above. The effectiveness of the inhibition may be evaluated grossly by assessing the inability of the tumors to maintain their growth and microscopically by observing an absence of nerves at the periphery of the tumor.

Within further aspects, the present invention provides methods for inhibiting angiogenesis (i.e., the growth of blood vessels from pre-existing blood vessels) in a mammal. Inhibition of angiogenesis may be beneficial, for example, in patients afflicted with diseases such as cancer or arthritis. Preferred modulating agents for inhibition of angiogenesis include those that modulate functions mediated by cadherin-5, such as those that comprises a cadherin-5 Trp-containing CAR sequence or analogue or mimetic thereof, or antibodies directed thereto. In addition, a modulating agent for use in inhibiting angiogenesis may comprise the sequence RGD, which is recognized by integrins, an OB-cadherin CAR sequence (e.g., DDK), the classical cadherin CAR sequence HAV, claudin CAR sequence, JAM CAR sequence, and/or the occludin CAR sequence LYHY (SEQ ID NO: 1309), separated from the cadherin-5 Trp-containing CAR sequence via a linker. Alternatively, a separate modulator of classical cadherin-, integrin-, claudin-, JAM- or occludin-mediated cell adhesion may be administered in conjunction with the modulating agent(s), either within the same pharmaceutical composition or separately. The ability of a modulating agent to inhibit angiogenesis may be evaluated as described above.

The addition of a targeting agent as described above may be beneficial, particularly when the administration is systemic. Suitable modes of administration and dosages depend upon the condition to be prevented or treated but, in general, administration by injection is appropriate. Dosages may vary as described above. The effectiveness of the inhibition may be evaluated grossly by assessing the inability of the tumors to maintain their growth and microscopically by observing an absence of nerves at the periphery of the tumor.

In yet another related aspect, the present invention provides methods for modulating (enhancing, inducing, inhibiting or reducing) apoptosis in a nonclassical cadherin-expressing cell. In general, patients afflicted with cancer may benefit from the treatment of a modulating agent that induces or enhances apoptosis whereas a modulating agent that inhibits or reduces apoptosis may be used to prevent cell deaths (such as neuron death caused by lack of blood flowing to the brain as a result of stroke). Modulating agents for use within such methods may modulate functions mediated by any atypical or desmosomal cadherin(s). Such agents may comprise, for example, a Trp-containing CAR sequence of such a cadherin, or an analogue or mimetic thereof. In addition, such agents may comprise one or more CAR sequences for a distinct cell adhesion molecule, such as a CAR sequence for an integrin, a classical cadherin, an N-CAM, a JAM, an occludin, a claudin, etc., as described above.

Preferred antibody modulating agents include Fab fragments directed against an atypical and/or desmosomal cadherin Trp-containing CAR sequence, optionally used in combination with one or more Fab fragments directed against a CAR sequence for a distinct cell adhesion molecule, such as a CAR sequence for an integrin, a classical cadherin, an N-CAM, a JAM, an occludin, a claudin, etc., as described above. The Fab fragments may be either incorporated into a modulating agent or within a separate modulator that is administered concurrently. Administration may be topical, via injection or by other means, and the addition of a targeting agent may be beneficial, particularly when the administration is systemic. Suitable modes of administration and dosages depend upon the location and nature of the cells for which induction of apoptosis is desired but, in general, dosages may vary as described above. A biopsy may be performed to evaluate the level of induction of apoptosis.

Within a related aspect, the present invention provides methods for treating obesity in a mammal, by using modulating agents that disrupt OB-cadherin function to inhibit adipocyte adhesion and/or using modulating agents that disrupt VE-cadherin function to inhibit endothelial cell adhesion (as obesity is an angiogenesis dependent disease). Alternatively, modulating agents that inhibit angiogenesis as described herein may be used to inhibit fat cell growth. Modulating agents as described herein may be administered alone, or in combination with other agents, which may comprise, for example, cadherin-5 and cadherin-11 Trp-containing CAR sequences, as well as CAR sequences from one or more distinct cell adhesion molecule, such as a CAR sequence from an integrin, a classical cadherin, an N-CAM, a JAM, an occludin, a claudin, etc., as described above, or an analogue of such a sequence. Preferably the peptide portion(s) of such modulating agents comprise 6-16 amino acids. The use of Fab fragments directed against an OB-cadherin or cadherin-5 Trp-containing CAR sequence is also preferred, as well as CAR sequences from an integrin, a classical cadherin, an N-CAM, a JAM, an occludin, a claudin, etc., as described above, or an analogue of such a sequence. A modulating agent may be administered alone (e.g., via the skin) or within a pharmaceutical composition. Injection or topical administration as described above may be preferred. In other instances, the composition may be administered systemically.

In another embodiment, methods are provided for causing the regression of blood vessels for the treatment of conditions such as cancer, psoriasis, arthritis, and age-related macular degeneration. Cancer tumors are solid masses of cells, growing out of control, which require nourishment via blood vessels. The formation of new capillaries is a prerequisite for tumor growth and the emergence of metastases. Administration of the modulating agents described herein may disrupt blood vessels and cause them to regress, thereby providing effective therapy for patients afflicted with diseases such as cancer. Certain preferred modulating agents for use within such methods comprise, in addition to an atypical cadherin Trp-containing CAR sequence (preferably an OB-cadherin or cadherin-5 Trp-containing CAR sequence), CAR sequences from one or more distinct cell adhesion molecule, such as a CAR sequence from an integrin, a classical cadherin, an N-CAM, a JAM, an occludin, a claudin, etc., as described above, or an analogue of such a sequence. Preferably, the peptide portion(s) of such modulating agents comprise 6-16 amino acids. Preferred antibody modulating agents include Fab fragments directed against the atypical cadherin Trp-containing CAR sequence, with or without Fab fragments directed against one or more CAR sequences from a distinct cell adhesion molecule, such as a CAR sequence from an integrin, a classical cadherin, an N-CAM, a JAM, an occludin, a claudin, etc., as described above, or an analogue of such a sequence. The Fab fragments may be either incorporated into a modulating agent or within a separate modulator that is administered concurrently. Administration may be topical, via injection or by other means, and the addition of a targeting agent may be beneficial, particularly when the administration is systemic. Suitable modes of administration and dosages depend upon the location and nature of the pericytes for which disruption of cell adhesion is desired but, in general, dosages may vary as described above. The effectiveness of the cancer treatment or inhibition of metastasis may be evaluated using well known clinical observations such as the level of serum markers (e.g., CEA or PSA). The addition of a targeting agent may be beneficial, particularly when the administration is systemic. Suitable modes of administration and dosages depend upon the condition to be prevented or treated but, in general, administration by injection is appropriate. Dosages may vary as described above. The effectiveness of the inhibition may be evaluated grossly by assessing the inability of the tumor to maintain growth and microscopically by an absence of nerves at the periphery of the tumor.

Within another aspect, the present invention provides methods for enhancing drug delivery to the central nervous system (CNS) of a mammal. The blood/brain barrier is largely impermeable to most neuroactive agents, and delivery of drugs to the brain of a mammal often requires invasive procedures. Using a modulating agent as described herein, however, delivery may be by, for example, systemic administration of a modulating agent-drug-targeting agent combination, injection of a modulating agent (alone or in combination with a drug and/or targeting agent) into the carotid artery or application of a skin patch comprising a modulating agent to the head of the patient. Modulating agents for enhancing drug delivery to the central nervous system include those agents that disrupt functions mediated by OB-cadherin or cadherin-5. Certain preferred modulating agents for use within such methods are relatively small cyclic peptides (e.g., a ring size of 4-10 residues; preferably 5-7 residues). Also preferred are multi-functional modulating agents comprising one or more of an atypical cadherin Trp-containing CAR sequence and an N-cadherin CAR sequence, the putative claudin CAR sequence IYSY (SEQ ID NO: 1312), an occludin CAR sequence LYHY (SEQ ID NO: 1309) and/or a JAM CAR sequence, preferably joined by a linker. Alternatively, a separate modulator of, for example, N-cadherin, claudin, JAM and/or occludin-mediated cell adhesion may be administered in conjunction with the modulating agent(s), either within the same pharmaceutical composition or separately. Modulating agents may further comprise antibodies or Fab fragments directed against CAR sequences of other cell adhesion molecule, such as a CAR sequence from an integrin, a classical cadherin, an N-CAM, a JAM, an occludin, a claudin, etc., as described above, or an analogue of such a sequence. In one embodiment, Fab fragments directed against the N-cadherin CAR sequence FHLRAHAVDINGNQV-NH$_2$ (SEQ ID NO: 1351) and the occludin CAR sequence: GVNPTAQSSGSLYGSQIYALCNQFYT-PAATGLYVDQYLYHYCVVDPQE (SEQ ID NO: 1352) may also be employed, as can Fab fragments directed against a N-CAM, CAR sequence of other cell adhesion molecules, such as an integrin, a classical cadherin, an a JAM, a claudin, etc., as described above, or an analogue of such a sequence.

The Fabs may either be incorporated into the modulating agent or administered concurrently as a separate modulator. In general, the amount of modulating agent administered varies with the method of administration and the nature of the condition to be treated or prevented, but typically varies as described above. Transfer of the drug to the central nervous system may be evaluated by appropriate means that will be apparent to those of ordinary skill in the art, such as magnetic resonance imaging (MRI) or PET scan (positron emitted tomography).

The present invention also provides, within further aspects, methods for enhancing and/or directing neurological growth. In one such aspect, neurite outgrowth may be enhanced and/or directed by contacting a neuron with one or more modulating agents. Modulating agents for enhancing and/or directing neurological growth include those agents that modulate functions mediated by one or more of cadherin-6, cadherin-7, cadherin-8, cadherin-10, cadherin-11. Preferred modulating agents for use within such methods are linked to a polymeric matrix or other support and/or contain multiple CAR sequences separated by one or more linkers. In addition, a modulating agent comprising the classical cadherin CAR sequence HAV, integrin CAR sequences RGD and/or YIGSR (SEQ ID NO: 1306), and/or the N-CAM CAR sequence KYSFNYDGSE (SEQ ID NO: 1307) may further facilitate neurite outgrowth. Modulating agents comprising antibodies, or fragments thereof, may be used within this aspect of the present invention without the use of linkers or support materials. In addition, Fab fragments directed against the N-CAM CAR sequence KYSFNYDGSE (SEQ ID NO; 1307) or the N-cadherin CAR sequence FHLRAHAVDINGNQV-NH$_2$ (SEQ ID NO: 1351) may be employed, either incorporated into the modulating agent or administered concurrently as a separate modulator.

The method of achieving contact and the amount of modulating agent used will depend upon the location of the neuron and the extent and nature of the outgrowth desired. For example, a neuron may be contacted (e.g., via implantation) with modulating agent(s) linked to a support material such as a suture, fiber nerve guide or other prosthetic device such that the neurite outgrowth is directed along the support material. Alternatively, a tubular nerve guide may be employed, in which the lumen of the nerve guide contains a composition comprising the modulating agent(s). In vivo, such nerve guides or other supported modulating agents may be implanted using well known techniques to, for example, facilitate the growth of severed neuronal connections and/or to treat spinal cord injuries. It will be apparent to those of ordinary skill in the art that the structure and composition of the support should be appropriate for the particular injury being treated. In vitro, a polymeric matrix may similarly be used to direct the growth of neurons onto patterned surfaces as described, for example, in U.S. Pat. No. 5,510,628.

Within another aspect, one or more modulating agents may be used for therapy of a demyelinating neurological disease in a mammal. There are a number of demyelinating diseases, such as multiple sclerosis, characterized by oligodendrocyte death. Modulating agents for treating and/or preventing such diseases include those agents that disrupt functions mediated by one or more of cadherin-6, cadherin-7, cadherin-8, cadherin-10, cadherin-11. Modulating agents may further comprise the classical cadherin CAR sequence HAV, RGD and/or YIGSR (SEQ ID NO: 1306), which are bound by integrins, and/or the N-CAM CAR sequence KYSFNYDGSE (SEQ ID NO: 1307). Such agents, when implanted with Schwann cells into the central nervous system, may facilitate Schwann cell migration and permit the practice of Schwann cell replacement therapy.

Multiple sclerosis (MS) patients suitable for treatment may be identified by criteria that establish a diagnosis of clinically definite or clinically probable MS (see Poser et al., *Ann. Neurol.* 13:227, 1983). Candidate patients for preventive therapy may be identified by the presence of genetic factors, such as HLA-type DR2a and DR2b, or by the presence of early disease of the relapsing remitting type.

Schwann cell grafts may be implanted directly into the brain along with the modulating agent(s) using standard techniques. Suitable amounts of modulating agent generally range as described above, preferably from about 10 μg/mL to about 1 mg/mL. Alternatively, a modulating agent may be implanted with oligodendrocyte progenitor cells (OPs) derived from donors not afflicted with the demyelinating disease. The myelinating cell of the CNS is the oligodendrocyte. Although mature oligodendrocytes and immature cells of the oligodendrocyte lineage, such as the oligodendrocyte type 2 astrocyte progenitor, have been used for transplantation, OPs are more widely used. OPs are highly motile and are able to migrate from transplant sites to lesioned areas where they differentiate into mature myelin-forming oligodendrocytes and contribute to repair of demyelinated axons (see e.g., Groves et al., *Nature* 362:453-55, 1993; Baron-Van Evercooren et al., *Glia* 16:147-64, 1996). OPs can be isolated using routine techniques known in the art (see e.g., Milner and French-Constant, *Development* 120:3497-3506, 1994), from many regions of the CNS including brain, cerebellum, spinal cord, optic nerve and olfactory bulb. Substantially greater yields of OP's are obtained from embryonic or neonatal rather than adult tissue. OPs may be isolated from human embryonic spinal cord and cultures of neurospheres established. Human fetal tissue is a potential valuable and renewable source of donor OP's for future, long range transplantation therapies of demyelinating diseases such as MS.

OPs can be expanded in vitro if cultured as "homotypic aggregates" or "spheres" (Avellana-Adalid et al, *J. Neurosci. Res.* 45:558-70, 1996). Spheres (sometimes called "oligospheres" or "neurospheres") are formed when OPs are grown in suspension in the presence of growth factors such as PDGF and FGF. OPs can be harvested from spheres by mechanical dissociation and used for subsequent transplantation or establishment of new spheres in culture. Alternatively, the spheres themselves may be transplanted, providing a "focal reservoir" of OPs (Avellana-Adalid et al., *J. Neurosci. Res.* 45:558-70, 1996).

An alternative source of OP may be spheres derived from CNS stem cells. Recently, Reynolds and Weiss, *Dev. Biol.* 165:1-13, 1996 have described spheres formed from EGF-responsive cells derived from embryonic neuroepithelium, which appear to retain the pluripotentiality exhibited by neuroepithelium in vivo. Cells dissociated from these spheres are able to differentiate into neurons, oligodendrocytes and astrocytes when plated on adhesive substrates in the absence of EGF, suggesting that EGF-responsive cells derived from undifferentiated embryonic neuroepithelium may represent CNS stem cells (Reynolds and Weiss, *Dev. Biol.* 165:1-13, 1996). Spheres derived from CNS stem cells provide an alternative source of OP that may be manipulated in vitro for transplantation in vivo. Spheres composed of CNS stem cells may further provide a microenvironment conducive to increased survival, migration, and differentiation of the OPs in vivo.

The use of neurospheres for the treatment of MS may be facilitated by modulating agents that enhance cell migration from the spheres. In the absence of modulating agent, the cells within the spheres adhere tightly to one another and migration out of the spheres is hindered. Modulating agents that disrupt cadherin mediated cell adhesion as described herein, when injected with neurospheres into the central nervous system, may improve cell migration and increase the efficacy of OP replacement therapy. Neurosphere grafts may be implanted directly into the central nervous system along with the modulating agent(s) using standard techniques.

Alternatively, a modulating agent may be administered alone or within a pharmaceutical composition. The duration and frequency of administration will be determined by such factors as the condition of the patient, and the type and severity of the patient's disease. Within particularly preferred embodiments of the invention, the modulating agent or pharmaceutical composition may be administered at a dosage ranging from 0.1 mg/kg to 20 mg/kg although appropriate dosages may be determined by clinical trials. Methods of administration include injection, intravenous or intrathecal (i.e., directly in cerebrospinal fluid). A modulating agent or pharmaceutical composition may further comprise a drug (e.g., an immunomodulatory drug).

Effective treatment of multiple sclerosis may be evidenced by any of the following criteria: EDSS (extended disability status scale), appearance of exacerbations or MRI (magnetic resonance imaging). The EDSS is a means to grade clinical impairment due to MS (Kurtzke, *Neurology* 33:1444, 1983), and a decrease of one full step defines an effective treatment in the context of the present invention (Kurtzke, *Ann. Neurol.* 36:573-79, 1994). Exacerbations are defined as the appearance of a new symptom that is attributable to MS and accompanied by an appropriate new neurologic abnormality (Sipe et al., *Neurology* 34:1368, 1984). Therapy is deemed to be effective if there is a statistically significant difference in the rate or proportion of exacerbation-free patients between the treated group and the placebo group or a statistically significant difference in the time to first exacerbation or duration and severity in the treated group compared to control group. MRI can be used to measure active lesions using gadolinium-DTPA-enhanced imaging (McDonald et al. *Ann. Neurol.* 36:14, 1994) or the location and extent of lesions using $T_2$-weighted techniques. The presence, location and extent of MS lesions may be determined by radiologists using standard techniques. Improvement due to therapy is established when there is a statistically significant improvement in an individual patient compared to baseline or in a treated group versus a placebo group.

Efficacy of the modulating agent in the context of prevention may be judged based on clinical measurements such as the relapse rate and EDSS. Other criteria include a change in area and volume of T2 images on MRI, and the number and volume of lesions determined by gadolinium enhanced images.

The present invention also provides methods for increasing vasopermeability in a mammal by administering one or more modulating agents or pharmaceutical compositions. Modulating agents as described herein that decrease OB-cadherin and/or cadherin-5 mediate cell adhesion may be used to increase vascular permeability. Certain preferred modulating agents for use within such methods further inhibit N-cadherin, JAM, claudin and/or occludin mediated adhesion. Such agents may comprise, in addition to an OB-cadherin and/or cadherin-5 Trp-containing CAR sequence, a sequence such as LYHY (SEQ ID NO: 1309) (the occludin CAR sequence), IYSY (SEQ ID NO: 1312) (the putative claudin CAR sequence), JAM, HAV (the classical cadherin CAR sequence) and RGD, or an analogue of such a sequence. Preferably, the peptide portion(s) of such modulating agents comprise 6-16 amino acids. Preferred antibody modulating agents include Fab fragments directed against one or more of the OB-cadherin, cadherin-5, classical cadherin, claudin, JAM, fibronectin and/or occludin CAR sequences. The Fab fragments may be either incorporated into a modulating agent or within a separate modulator that is administered concurrently.

Treatment with a modulating agent may be appropriate, for example, prior to administration of an anti-tumor therapeutic or diagnostic agent (e.g., a monoclonal antibody or other macromolecule), an antimicrobial agent or an anti-inflammatory agent, in order to increase the concentration of such agents in the vicinity of the target tumor, organism or inflammation without increasing the overall dose to the patient. Modulating agents for use within such methods may be linked to a targeting agent to further increase the local concentration of modulating agent, although systemic administration of a vasoactive agent even in the absence of a targeting agent increases the perfusion of certain tumors relative to other tissues. Suitable targeting agents include antibodies and other molecules that specifically bind to tumor cells or to components of structurally abnormal blood vessels. For example, a targeting agent may be an antibody that binds to a fibrin degradation product or a cell enzyme such as a peroxidase that is released by granulocytes or other cells in necrotic or inflamed tissues.

Administration via intravenous injection or transdermal administration is generally preferred. Effective dosages are generally sufficient to increase localization of a subsequently administered diagnostic or therapeutic agent to an extent that improves the clinical efficacy of therapy of accuracy of diagnosis to a statistically significant degree. Comparison may be made between treated and untreated tumor host animals to whom equivalent doses of the diagnostic or therapeutic agent are administered. In general, dosages range as described above.

In certain other aspects, the present invention provides methods for enhancing adhesion of atypical and/or desmosomal cadherin-expressing cells. Within certain embodiments, a modulating agent may be linked to a solid support, resulting in a matrix that comprises multiple modulating agents. Within one such embodiment, the support is a polymeric matrix to which modulating agents and molecules comprising other CAR sequence(s) are attached (e.g., modulating agents and molecules comprising either HAV or RGD sequences may be attached to the same matrix, preferably in an alternating pattern). Such matrices may be used in contexts in which it is desirable to enhance adhesion mediated by multiple cell adhesion molecules. Alternatively, the modulating agent itself may comprise multiple cadherin Trp-containing CAR sequences or antibodies (or fragments thereof), which may or may not be separated by linkers as described above. Either way, the modulating agent(s) function as a "biological glue" to bind multiple cadherin-expressing cells within a variety of contexts.

Within one such aspect, modulating agents comprising the atypical and/or desmosomal cadherin Trp-containing CAR sequence and/or multiple modulating agents linked to a single molecule or support material may be used to facilitate wound healing and/or reduce scar tissue in a mammal. Peptides that may be linked to a support, and/or to one another via a linker, to generate a suitable modulating agent include, but are not limited to, one or more cadherin Trp-containing CAR sequences, or analogues or mimetics thereof. Suitable atypical Trp-containing CAR sequences include desmosomal, OB-cadherin and cadherin-5 Trp-containing CAR sequences. Such nonclassical Trp-containing CAR sequences may be used in combination with one or more classical cadherin CAR sequences, including HAV, SHAVSS (SEQ ID NO; 1349), AHAVDI (SEQ ID NO: 1350), or an analogue of such a sequence, as well as RGD. Preferred antibody modulating agents include Fab fragments directed against desmosomal and atypical cadherin Trp-containing CAR sequences, as well as the classical cadherin CAR sequence HAV. Modulating agents that are linked to a biocompatible and biodegradable matrix such as cellulose or collagen are particularly preferred. For use within such methods, a modulating agent should have a free amino or hydroxyl group. The modulating agents are generally administered topically to the wound, where they may facilitate closure of the wound and may augment, or even replace, stitches. Similarly, administration of matrix-linked modulating agents may facilitate cell adhesion in foreign tissue implants (e.g., skin grafting and prosthetic implants) and may prolong the duration and usefulness of collagen injection. In general, the amount of matrix-linked modulating agent administered to a wound, graft or implant site varies with the severity of the wound and/or the nature of the wound, graft, or implant, but may vary as discussed above. Multifunctional modulating agents comprising an atypical and/or desmosomal cadherin Trp-containing CAR sequence, a classical cadherin CAR sequence (HAV), and/or the CAR sequence bound by certain integrins (RGD) may also be used as potent stimulators of wound healing and/or to reduce scar tissue. Alternatively, one or more separate modulators of classical cadherin- or integrin-mediated cell adhesion may be administered in conjunction with the modulating agent(s), either within the same pharmaceutical composition or separately.

Within another aspect, one or more modulating agents may be linked to the interior surface of a tissue culture plate or other cell culture support, such as for use in a bioreactor. Such linkage may be performed by any suitable technique, as described above. Modulating agents linked in this fashion may generally be used to immobilize cadherin-expressing cells. For example, dishes or plates coated with one or more modulating agents may be used to immobilize cadherin-expressing cells within a variety of assays and screens. Within bioreactors (i.e., systems for large scale production of cells or organoids), modulating agents may generally be used to improve cell attachment and stabilize cell growth. Modulating agents may also be used within bioreactors to support the formation and function of highly differentiated organoids derived, for example, from dispersed populations of fetal mammalian cells. Bioreactors containing biomatrices of modulating agent(s) may also be used to facilitate the production of specific proteins.

Modulating agents as described herein may be used within a variety of bioreactor configurations. In general, a bioreactor is designed with an interior surface area sufficient to support large numbers of adherent cells. This surface area can be provided using membranes, tubes, microtiter wells, columns, hollow fibers, roller bottles, plates, dishes, beads or a combination thereof. A bioreactor may be compartmentalized. The support material within a bioreactor may be any suitable material known in the art; preferably, the support material does not dissolve or swell in water. Preferred support materials include, but are not limited to, synthetic polymers such as acrylics, vinyls, polyethylene, polypropylene, polytetrafluoroethylene, nylons, polyurethanes, polyamides, polysulfones and poly(ethylene terephthalate); ceramics; glass and silica.

Within a further aspect, modulating agents as described herein may be used for controlled inhibition (reduction) of synaptic stability, resulting in increased synaptic plasticity. Within this aspect, administration of one or more modulating agents that inhibit nonclassical cadherin-mediated cell adhesion may be advantageous for repair processes within the brain, as well as learning and memory, in which neural plasticity is a key early event in the remodeling of synapses. In addition, a preferred modulating agent may comprise one or more additional CAR sequences, such as HAV, RGD and/or the N-CAM CAR sequence KYSFNYDGSE (SEQ ID NO: 1307), or an antibody or Fab fragment directed thereto. As noted above, such additional sequence(s) may be separated from the Trp-containing CAR sequence via a linker. Alternatively, a separate modulator of cell adhesion mediated by a different adhesion molecule may be administered in conjunction with the modulating agent(s), either within the same pharmaceutical composition or separately. For such aspects, administration may be via encapsulation into a delivery vehicle such as a liposome, using standard techniques, and injection into, for example, the carotid artery. Alternatively, a modulating agent may be linked to a disrupter of the blood-brain barrier. In general dosages range as described above.

Within further aspects, modulating agents as described herein may be used for modulating the immune system of a mammal in any of several ways. Cadherins are expressed on immature B and T cells (thymocytes and bone marrow pre-B cells), as well as on specific subsets of activated B and T lymphocytes and some hematological malignancies. Modulating agents may generally be used to modulate specific steps within cellular interactions during an immune response or during the dissemination of malignant lymphocytes.

For example, a modulating agent as described herein may be used to treat diseases associated with excessive generation of otherwise normal T cells. Without wishing to be bound by any particular theory, it is believed that the interaction of cadherins on maturing T cells and B cell subsets contributes to protection of these cells from programmed cell death. A modulating agent may decrease such interactions, leading to the induction of programmed cell death. Accordingly, modulating agents may be used to treat certain types of diabetes and rheumatoid arthritis, particularly in young children where the cadherin expression on thymic pre-T cells is greatest.

Modulating agents may also be administered to patients afflicted with certain skin disorders (such as cutaneous lymphomas), acute B cell leukemia and excessive immune reactions involving the humoral immune system and generation of immunoglobulins, such as allergic responses and antibody-mediated graft rejection. In addition, patients with circulating cadherin-positive malignant cells (e.g., during regimes where chemotherapy or radiation therapy is eliminating a major portion of the malignant cells in bone marrow and other lymphoid tissue) may benefit from treatment with a modulating agent. Such treatment may also benefit patients undergoing transplantation with peripheral blood stem cells.

Preferred modulating agents for use within such methods include those that disrupt OB-cadherin, cadherin-5, cadherin-6, cadherin-8, cadherin-9 and/or cadherin-10 mediated cell adhesion. In addition, a preferred modulating agent may comprise one or more additional CAR sequences, such as HAV, RGD, LYHY (SEQ ID NO: 1309) and/or KYSFNYDGSE (SEQ ID NO: 1307), or an antibody or Fab fragment directed thereto. As noted above, such additional sequence(s) may be separated from a Trp-containing CAR sequence via a linker. Alternatively, a separate modulator of classical cadherin-, occludin-, integrin- and/or N-CAM-mediated cell adhesion may be administered in conjunction with the modulating agent(s), either within the same pharmaceutical composition or separately.

Within the above methods, the modulating agent(s) are preferably administered systemically (usually by injection) or topically. A modulating agent may be linked to a targeting agent. For example, targeting to the bone marrow may be beneficial. A suitable dosage is sufficient to effect a statistically significant reduction in the population of B and/or T cells that express cadherin and/or an improvement in the clinical manifestation of the disease being treated. Typical dosages generally range as described above.

Within further aspects, the present invention provides methods and kits for preventing pregnancy in a mammal. In general, disruption of OB-cadherin function prevents the adhesion of trophoblasts and their subsequent fusion to form syncitiotrophoblasts, whereas disruption of cadherin-5 function prevents angiogenesis. In one embodiment, one or more modulating agents may be incorporated into any of a variety of well known contraceptive devices, such as sponges suitable for intravaginal insertion (see, e.g., U.S. Pat. No. 5,417,224) or capsules for subdermal implantation. Other modes of administration are possible, however, including transdermal administration, for modulating agents linked to an appropriate targeting agent. Preferred modulating agents for use within such methods include those comprising an OB-cadherin and/or cadherin-5 Trp-containing CAR sequence, or analogue or mimetic thereof, or an antibody or Fab fragment directed thereto. In addition, a preferred modulating agent may comprise additional CAR sequences, such a CAR sequence from an integrin, a classical cadherin, an N-CAM, a JAM, an occludin, a claudin, etc., as described above, or an analogue of such a sequence.

As noted above, such additional sequences may be separated from the Trp-containing CAR sequence via a linker. Alternatively, a separate modulator of classical cadherin-and/or integrin-mediated cell adhesion may be administered in conjunction with the modulating agent(s), either within the same pharmaceutical composition or separately.

Suitable methods for incorporation into a contraceptive device depend upon the type of device and are well known in the art. Such devices facilitate administration of the modulating agent(s) to the uterine region and may provide a sustained release of the modulating agent(s). In general, modulating agent(s) may be administered via such a contraceptive device at a dosage ranging from 0.1 to 50 mg/kg, although appropriate dosages may be determined by monitoring hCG levels in the urine. hCG is produced by the placenta, and levels of this hormone rise in the urine of pregnant women. The urine hCG levels can be assessed by radio-immunoassay using well known techniques. Kits for preventing pregnancy generally comprise a contraceptive device impregnated with one or more modulating agents.

Alternatively, a sustained release formulation of one or more modulating agents may be implanted, typically subdermally, in a mammal for the prevention of pregnancy. Such implantation may be performed using well known techniques. Preferably, the implanted formulation provides a dosage as described above, although the minimum effective dosage may be determined by those of ordinary skill in the art using, for example, an evaluation of hCG levels in the urine of women.

Other aspects of the present invention provide methods that employ antibodies raised against the Trp-containing CAR sequences for diagnostic and assay purposes. Assays typically involve using an antibody to detect the presence or absence of an cadherin (free or on the surface of a cell), or proteolytic fragments containing one or more EC domains in a suitable biological sample, such as tumor or normal tissue biopsies, blood, lymph node, serum or urine samples, or other tissue, homogenate, or extract thereof obtained from a patient.

There are a variety of assay formats known to those of ordinary skill in the art for using an antibody to detect a target molecule in a sample. See, e.g., Harlow and Lane, *Antibodies: A Laboratory Manual*, Cold Spring Harbor Laboratory, 1988. For example, the assay may be performed in a Western blot format, wherein a protein preparation from the biological sample is submitted to gel electrophoresis, transferred to a suitable membrane and allowed to react with the antibody. The presence of the antibody on the membrane may then be detected using a suitable detection reagent, as described below.

In another embodiment, the assay involves the use of antibody immobilized on a solid support to bind to the target cadherin, or a proteolytic fragment containing an extracellular domain and encompassing a Trp-containing CAR sequence, and remove it from the remainder of the sample. The bound cadherin may then be detected using a second antibody or reagent that contains a reporter group. Alternatively, a competitive assay may be utilized, in which a cadherin is labeled with a reporter group and allowed to bind to the immobilized antibody after incubation of the antibody with the sample. The extent to which components of the sample inhibit the binding of the labeled cadherin to the antibody is indicative of the reactivity of the sample with the immobilized antibody, and as a result, indicative of the level of the cadherin in the sample.

The solid support may be any material known to those of ordinary skill in the art to which the antibody may be attached, such as a test well in a microtiter plate, a nitrocellulose filter or another suitable membrane. Alternatively, the support may be a bead or disc, such as glass, fiberglass, latex or a plastic such as polystyrene or polyvinylchloride. The antibody may be immobilized on the solid support using a variety of techniques known to those in the art, which are amply described in the patent and scientific literature.

In certain embodiments, the assay for detection of an atypical and/or desmosomal cadherin in a sample is a two-antibody sandwich assay. This assay may be performed by first contacting an antibody that has been immobilized on a solid support, commonly the well of a microtiter plate, with the biological sample, such that the cadherin within the sample is allowed to bind to the immobilized antibody (a 30 minute incubation time at room temperature is generally sufficient). Unbound sample is then removed from the immobilized cadherin-antibody complexes and a second antibody (containing a reporter group such as an enzyme, dye, radionuclide, luminescent group, fluorescent group or biotin) capable of binding to a different site on the cadherin is added. The amount of second antibody that remains bound to the solid support is then determined using a method appropriate for the specific reporter group. The method employed for detecting the reporter group depends upon the nature of the reporter group. For radioactive groups, scintillation counting or autoradiographic methods are generally appropriate. Spectroscopic methods may be used to detect dyes, luminescent groups and fluorescent groups. Biotin may be detected using avidin, coupled to a different reporter group (commonly a radioactive or fluorescent group or an enzyme). Enzyme reporter groups may generally be detected by the addition of substrate (generally for a specific period of time), followed by spectroscopic or other analysis of the reaction products. Standards and standard additions may be used to determine the level of cadherin in a sample, using well known techniques.

The present invention also provides kits for use in such immunoassays. Such kits generally comprise one or more antibodies, as described above. In addition, one or more additional compartments or containers of a kit generally enclose elements, such as reagents, buffers and/or wash solutions, to be used in the immunoassay.

Within further aspects, modulating agents or antibodies (or fragments thereof) may be used to facilitate cell identification and sorting in vitro or imaging in vivo, permitting the selection of cells expressing the atypical or desmosomoal cadherin (or different atypical cadherin levels). Preferably, the modulating agent(s) or antibodies for use in such methods are linked to a detectable marker. Suitable markers are well known in the art and include radionuclides, luminescent groups, fluorescent groups, enzymes, dyes, constant immunoglobulin domains and biotin. Within one preferred embodiment, a modulating agent linked to a fluorescent marker, such as fluorescein, is contacted with the cells, which are then analyzed by fluorescence activated cell sorting (FACS).

Antibodies or fragments thereof may also be used within screens of combinatorial or other nonpeptide-based libraries to identify other compounds capable of modulating cadherin-mediated cell adhesion. Such screens may generally be performed using an ELISA or other method well known to those of ordinary skill in the art that detect compounds with a shape and structure similar to that of the modulating agent. In general, such screens may involve contacting an expression library producing test compounds with an antibody, and detecting the level of antibody bound to the candidate compounds. Compounds for which the antibody has a higher affinity may be further characterized as described herein, to evaluate the ability to modulate OB-cadherin-mediated cell adhesion.

Within one aspect, the present invention provides methods for reducing aggregation of cultured cells (e.g., cultured stem cells) by contacting the cells with a cell adhesion modulating agent that inhibits cadherin-mediated cell adhesion. Stem cell therapy offers an opportunity to treat many degenerative diseases caused by the premature death of malfunction of specific cell types and the body's failure to replace or restore them. Possible therapeutic uses of stem cells include immunological conditioning of patients for organ transplants, treatment of autoimmune diseases such as muscular dystrophy, multiple sclerosis and rheumatoid arthritis, repair of damaged tissues such as stroke, spinal injury and burn, treatment of neurodegenerative disease like Lou Gehrig's disease, and neurological conditions such as Parkinson's Huntington's and Alzheimer's diseases, treatment of leukemia, sickle cell anemia, heart disease, and diabetes. For most stem cell therapy, embryonic stem cells or adult stem cells may be cultured in vitro, induced to differentiate to the desired cell type and transplant to a patient. For successful culture of stem cells, aggregation among these cells needs to be minimized.

To reduce aggregation of stem cells, a modulating agent as described herein may be used. In certain embodiments, such an agent comprises a Trp-containing CAR sequence (e.g., Trp-Asn-Gln, Gly/Asp/Ser-Trp-Val/Ile/Met-Trp-Asn-Gln (SEQ ID NO: 5) and/or Ala-Trp-Val-Ile-Pro-Pro (SEQ ID NO: 6)) of an atypical cadherin, a conservative (or nonconservative) analogue, a peptidomimetic of the Trp-containing CAR sequence, or an antibody or antigen-binding fragment thereof that specifically binds to the Trp-containing CAR sequence. In other embodiments, such an agent may comprise a Trp-containing CAR sequence (e.g., Glu/Ala-Trp-Ile/Val-Lys/Thr-Phe/Ala-Ala/Pro, SEQ ID NO:1 and Arg-Trp-Ala-Pro-Ile-Pro, SEQ ID NO:2) of a desmosomal cadherin, a conservative (or nonconservative) analogue, a peptidomimetic of the Trp-containing CAR sequence, or an antibody or antigen-binding fragment thereof that specifically binds to the Trp-containing CAR sequence.

Modulating agents may alternatively, or in addition, comprise a conservative analogue or a peptidomimetic of one of the foregoing sequences. In addition, a modulating agent may comprise the sequence RGD, which is bound by integrins, the sequence LYHY (SEQ ID NO: 1309), which is bound by occludin, a JAM CAR sequence, a claudin CAR sequence, an NCAM CAR sequence and/or one or more of HAV and/or a non-classical cadherin CAR sequence. Antibodies or Fab fragments directed against such CAR sequences may also be employed. Preferably, such sequences are separated from the Trp-containing CAR sequence via a linker. Alternatively, a separate modulator of cell adhesion (e.g., integrin- and/or occludin-mediated) may be administered in conjunction with the modulating agent(s), either within the same pharmaceutical composition or separately.

The modulating agent of the present invention may be used at various stages of stem cell culture. For instance, it may be used to reduce cell adhesion of stem cells when they are isolated from their source tissue. Alternatively, it may be added to culture media when excessive cell aggregation occurs. It may also be continuously present in culture media to minimize cell aggregation. The concentration of the modulating agent may be optimized by adjusting the amount of the modulating agent to the level at which cell aggregation is reduced with respect to cultured stem cells in the absence of the modulating agent, and other aspects of the cell culture (e.g., cell viability rate and cell reproduction rate) is not adversely affected.

Although the above description focuses on the reduction of stem cell aggregation using the modulating agents of the present invention, one of ordinary skill in the art appreciates that such agents may be used in in vitro culture of other types of animal cells to minimize cell aggregation.

Within another related aspect, methods are provided for enhancing delivery of inhaled compounds (e.g., drugs) in a mammal, comprising contacting lung epithelial cells of a mammal with a cell adhesion modulating agent that inhibits cadherin-mediated cell adhesion. Lung is another site for the delivery of drugs, which provide rapid absorption, especially for the delivery of high molecular weight pharmaceutical agents (see, U.S. Pat. No. 6,294,153). The delivery of drugs may be further facilitated by the use of cell adhesion modulating agent that inhibits cadherin-mediated cell adhesion.

To enhance the delivery of an inhaled compound, a modulating agent as described herein and an inhaled compound are contacted with lung epithelial cells. In certain embodiments, such an agent comprises a Trp-containing CAR sequence (e.g., Trp-Asn-Gln, Gly/Asp/Ser-Trp-Val/Ile/Met-Trp-Asn-Gln (SEQ ID NO: 5) and/or Ala-Trp-Val-Ile-Pro-Pro (SEQ ID NO: 6)) of an atypical cadherin, a conservative (or nonconservative) analogue, a peptidomimetic of the Trp-containing CAR sequence, or an antibody or antigen-binding fragment thereof that specifically binds to the Trp-containing CAR sequence. In other embodiments, such an agent may comprise a Trp-containing CAR sequence (e.g., Glu/Ala-Trp-Ile/Val-Lys/Thr-Phe/Ala-Ala/Pro, SEQ ID NO:1 and Arg-Trp-Ala-Pro-Ile-Pro, SEQ ID NO:2) of a desmosomal cadherin, a conservative (or nonconservative) analogue, a peptidomimetic of the Trp-containing CAR sequence, or an antibody or antigen-binding fragment thereof that specifically binds to the Trp-containing CAR sequence. Modulating agents may alternatively, or in addition, comprise a conservative analogue or a peptidomimetic of one of the foregoing sequences. In addition, a modulating agent may comprise the sequence RGD, which is bound by integrins, the sequence LYHY (SEQ ID NO: 1309), which is bound by occludin, a JAM CAR sequence, a claudin CAR sequence and/or one or more of classical cadherin HAV and/or a non-classical cadherin CAR sequence, or an antibody or Fab fragment directed thereto. Preferably, such sequences are separated from the Trp-containing CAR sequence via a linker. Alternatively, a separate modulator of cell adhesion (e.g., integrin- and/or occludin-mediated) may be administered in conjunction with the modulating agent(s), either within the same pharmaceutical composition or separately.

Contact of a cell adhesion modulating agent with lung epithelial cells may be achieved by a device such as an inhaler, a nebulizer or the like. The modulating agent and the compound to be inhaled may be contained within the same composition and administered together. Alternatively, they may be separately administered, although administration at the same time is preferred. In general, the amount of modulating agent administrated via the lung varies with the nature of the condition to be treated or prevented, but may vary. Such levels may be achieved by appropriate adjustment to the device used. Transfer of the drug to the lung may be evaluated by appropriate means that will be apparent to those of ordinary skill in the art, such as monitoring the serum level of the administered drug.

Similar to the enhanced transdermal drug delivery, a wide variety of drugs may be administered according to the methods provided herein. Exemplary drugs include heparin, hirulog, hirugen, huridine, interferons, interleukins, cytokins, antibodies, immunoglobins, chemotherapeutic agents, vaccines, glycoproteins, bacterial toxoids, calcitonins, hormones (e.g., insulin), DNA, RNA, antisense oligonucleotides, narcotics, hypnotics, steroids and non-steroidal anti-inflammatory drugs.

Treatment with the modulating agents provided herein may serve to increase blood flow to a tumor. Such treatment may be appropriate, for example, prior to administration of an anti-tumor therapeutic or diagnostic agent (e.g., a monoclonal antibody or other macromolecule), an antimicrobial agent or an anti-inflammatory agent, in order to increase the concentration of such agents in the vicinity of the target tumor, organism or inflammation without increasing the overall dose to the patient. Modulating agents for use within such methods may be linked to a targeting agent to further increase the local concentration of modulating agent, although systemic administration of a vasoactive agent even in the absence of a targeting agent increases the perfusion of certain tumors relative to other tissues.

Suitable targeting agents include antibodies and other molecules that specifically bind to tumor cells or to components of structurally abnormal blood vessels. For example, a targeting agent may be an antibody that binds to a fibrin degradation product or a cell enzyme such as a peroxidase that is released by granulocytes or other cells in necrotic or inflamed tissues.

Administration via intravenous injection or transdermal administration is generally preferred. Effective dosages are generally sufficient to increase localization of a subsequently administered diagnostic or therapeutic agent to an extent that improves the clinical efficacy of therapy of accuracy of diagnosis to a statistically significant degree. Comparison may be made between treated and untreated tumor host animals to whom equivalent doses of the diagnostic or therapeutic agent are administered. In general, dosages range as described above.

Within further aspects, the present invention provides methods for disrupting neovasculature (i.e., newly formed blood vessels). Such methods may be used to disrupt normal or pathological neovasculature in a variety of contexts. Disruption of neovasculature is therapeutic for conditions in which the presence of newly formed blood vessels is related to the underlying disorder, its symptoms or its complications. For example, disorders that may be treated include, but are not limited to, benign prostatic hyperplasia, diabetic retinopathy, vascular restenosis, arteriovenous malformations, meningioma, hemangioma, neovascular glaucoma, psoriasis, angiofiboma, arthritis, atherosclerotic plaques, corneal graft neovascularization, hemophilic joints, hypertrophic scars, hemorrhagic telangiectasia, pyogenic granuloma, retrolental fibroplasias, scleroderma trachoma, vascular adhesions, synovitis, dermatitis, endometriosis, macular degeneration and exudative macular degeneration. Preferred modulating agents for use within such methods include those capable of modulating VE-CAD and/or OB-CAD. Certain other preferred modulating agents comprise a Trp-containing CAR sequence (e.g., Trp-Asn-Gln, Gly/Asp/Ser-Trp-Val/Ile/Met-Trp-Asn-Gln (SEQ ID NO: 5) and/or Ala-Trp-Val-Ile-Pro-Pro (SEQ ID NO: 6)) of an atypical cadherin, a conservative (or nonconservative) analogue, a peptidomimetic of the Trp-containing CAR sequence, or an antibody or antigen-binding fragment thereof that specifically binds to the Trp-containing CAR sequence. Modulating agents may alternatively, or in addition, comprise a conservative analogue or a peptidomimetic of one of the foregoing sequences. In addition, a modulating agent may comprise the sequence RGD, which is bound by integrins, the sequence LYHY (SEQ ID NO: 1309), which is bound by occludin, a JAM CAR sequence, a claudin CAR sequence, one or more HAV CAR sequences, etc., as discussed above, or an antibody directed thereto. Preferably, such sequences are separated from the Trp-containing CAR sequence via a linker. Alternatively, a separate modulator of cell adhesion (e.g., integrin- and/or occludin-mediated) may be administered in conjunction with the modulating agent(s), either within the same pharmaceutical composition or separately.

The following examples are offered by way of illustration and not by way of limitation.

EXAMPLES

Example 1

Preparation of Representative Cyclic Peptides

This Example illustrates the solid phase synthesis of representative cyclic peptides as cell adhesion modulating agents.

The peptides are assembled on methylbenzhydrylamine resin (MBHA resin) for the C-terminal amide peptides. The traditional Merrifield resins are used for any C-terminal acid peptides. Bags of a polypropylene mesh material are filled with the resin and soaked in dichloromethane. The resin packets are washed three times with 5% diisopropylethylamine in dichloromethane and then washed with dichloromethane. The packets are then sorted and placed into a Nalgene bottle containing a solution of the amino acid of interest in dichloromethane. An equal amount of diisopropylcarbodiimide (DIC) in dichloromethane is added to activate the coupling reaction. The bottle is shaken for one hour to ensure completion of the reaction. The reaction mixture is discarded and the packets washed with DMF. The N-α-Boc is removed by acidolysis using a 55% TFA in dichloromethane for 30 minutes leaving the TFA salt of the α-amino group. The bags are washed and the synthesis completed by repeating the same procedure while substituting for the corresponding amino acid at the coupling step. Acetylation of the N-terminal is performed by reacting the peptide resins with a solution of acetic anhydride in dichloromethane in the presence of diisopropylethylamine. The peptide is then side-chain deprotected and cleaved from the resin at 0° C. with liquid HF in the presence of anisole as a carbocation scavenger.

The crude peptides are purified by reversed-phase high-performance liquid chromatography. Purified linear precursors of the cyclic peptides are solubilized in 75% acetic acid at a concentration of 2-10 mg/mL. A 10% solution of iodine in methanol is added dropwise until a persistent coloration is obtained. A 5% ascorbic acid solution in water is then added to the mixture until discoloration. The disulfide bridge containing compounds are then purified by HPLC and characterized by analytical HPLC and by mass spectral analysis.

Example 2

Disruption of Human Breast Cancer Cell Adhesion

This Example illustrates the detection of the ability of a candidate cell adhesion modulating agent to disrupt human breast epithelial cell adhesion.

MDA-MB-231 human breast cancer cells (Lombardi Cancer Research Center, Washington, D.C.) are used in these experiments. They express cadherin-11 (also known as OB-cadherin) but not N-cadherin or E-cadherin. The cells are plated (~50,000 cells) on glass coverslips and cultured for 24 hours in DMEM containing 5% serum. A candidate cell adhesion modulating agent is dissolved in sterile water (the concentration may be, for example, 10 mg/ml), and 100 μl of the resulting stock solution is added to 1 ml of DMEM containing 5% serum. Control cells have 100 μl of water added to the medium. Cells are monitored by phase contrast microscopy. After 24 hours cells are fixed in formaldehyde. Water should have no effect on cell morphology; the cells treated with water remain flattened and well-attached to the substratum. However, if the candidate cell adhesion modulating agent has a cell adhesion disrupting activity, the cells treated with the candidate modulating agent would round up from each other and not be well-attached to the substratum.

Example 3

Disruption of Endothelial Cell Adhesion

This Example illustrates the detection of the ability of a candidate cell adhesion modulating agent to disrupt endothelial cell adhesion.

Human umbilical vein endothelial cells are cultured using standard procedures (see Ichikawa et al., *Amer. J. Physiol.* 273 (Gastrointest. Liver Physiol. 36):3642-6347, 1997). Cells are maintained in EGM (Clonetics, San Diego, Calif.) and used at P2 for all experiments. Endothelial identity is established by Dil-LDL and factor VIII staining.

The cells are cultured on glass coverslips. Monolayers are exposed to a candidate cell adhesion modulating agent at a concentration of, for example, 75 μg/mL for 60 minutes. The cells are then fixed with 95% ethanol for 30 minutes at 4° C., followed by acetone for one minute and left to air dry at room temperature. Primary antibody for VE-cadherin (Immunotech, Marseilles, France; 1:250) is added for one hour at 37° C. Coverslips are then washed with 0.1% milk/PBS solution three times for five minutes each. Secondary antibody (1:250), goat anti-rabbit FITC (Zymed, San Francisco, Calif.) is incubated at 37° C. for one hour. Coverslips are again washed with 0.1% milk/PBS solution three times for five minutes each. Coverslips are mounted with anti-quenching solution (1 mg/mL phenylenediamine (Sigma, St. Louis, Mo.) in 50% glycerol, 50% PBS). The control cells (i.e., cells without the treatment of the candidate cell adhesion modulating agent) should remain flattened and well-attached to the substratum. However, if the candidate cell adhesion modulating agent has a cell adhesion disrupting activity, the cells treated with the candidate modulating agent would round up from each other and not be well-attached to the substratum.

Example 4

BiaCore

The binding of representative peptide modulating agents to Fc-Dsg1 and Fc-Dsg2 chimeras with or without 3 mM $CaCl_2$ are assayed using a BIAcore X™ Biosensor (Pharmacia Ltd., Sweden). Protein A was immobilized on the flow cells of a CM 5 sensor chip using a standard amine coupling method. The surfaces were activated with a 7-min injection of NHS/EDC, followed by a 7-min injection of protein A in 10 mM acetate pH 5.0 at a concentration of 50 μg/mL and blocked with a 7-min injection of 8M ethanolamine, pH 8.2. This immobilization procedure resulted in the immobilization of ~8,000 RU of protein A on the CM5 chip surface. Next, Fc-Dsg1 and Fc-Dsg2 were injected over protein A surface to be each captured on the sensor chip. These capturing steps resulted in surface densities of 2900 and 3600 RU for Fc-Dsg1 and Fc-Dsg2, respectively.

To test compound binding to these surfaces, candidate modulating agents are solublized and each injected in a three-fold dilution series over the cadherin surfaces using six concentrations. Binding responses are measured and fit to simple binding isotherms to obtain affinities.

Example 5

Effects of ADH358 (H-RWAPIP-NH2; Desmocollin Derived Peptide) on SKOV3 Human Ovarian Cancer Cells We investigated the effects of the linear peptide ADH358 (H-RWAPIP-NH2 (SEQ ID NO: 2); Desmocollin derived peptide) on confluent cultures of SKOV3 cells. SKOV3 human ovarian cancer cells express desmosomes (which are composed of desmocollins and desmogleins). SKOV3 human ovarian cancer cells were obtained from Dr. Riaz Farookhi, McGill University, Montreal, Canada. The cells were cultured in minimum essential medium (MEM) supplemented with 10% fetal calf serum, non-essential amino acids, fungizone, penicillin-streptomycin, and gentamicin in a humidified atmosphere (5% $CO_2$) at 37° C. All culture reagents were purchased from GIBCO (Burlington, ON). ADH358 (1 mg/ml of culture medium) was added to confluent cultures of SKOV3 cells. After 24 hours of treatment, the cells were fixed with 4% paraformaldehyde, followed by 3 washes with phosphate buffered saline, and then stained with hematoxylin. Control cultures were grown in the absence of peptide.

Microscopic examination of SKOV3 confluent cultures treated with ADH358 for 24 h revealed that the peptide caused disruption of the confluent SKOV3 monolayers within 24 hours of addition to the tissue culture medium (FIG. 6). The peptide caused the SKOV3 cells to detach from one another and adopt an elongated, fibroblast-like morphology. These observations indicate that Trp containing peptides can disrupt cell adhesion.

All of the above U.S. patents, U.S. patent application publications, U.S. patent applications, foreign patents, foreign patent applications and non-patent publications referred to in this specification and/or listed in the Application Data Sheet, are incorporated herein by reference, in their entirety.

From the foregoing it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. A cell adhesion modulating agent ranging in size from 6 to 15 amino acid residues that
   (a) inhibits desmosomal cadherin-mediated cell adhesion; and
   (b) consists essentially of the amino acid sequence Arg-Trp-Ala-Pro-Ile-Pro (SEQ ID NO: 2).

2. The cell adhesion modulating agent of claim 1 wherein the sequence consisting essentially of the amino acid sequence Arg-Trp-Ala-Pro-Ile-Pro (SEQ ID NO: 2) is C-terminal carboxylate esterified or amidated.

3. The cell adhesion modulating agent of claim 1 wherein the sequence consisting essentially of the amino acid sequence Arg-Trp-Ala-Pro-Ile-Pro (SEQ ID NO: 2) is N-acetylated.

4. The cell adhesion modulating agent of claim 1 linked to a solid support.

5. A composition comprising a cell adhesion modulating agent of claim 1 in combination with a physiologically acceptable carrier.

* * * * *